US009840478B2

(12) United States Patent
Williams et al.

(10) Patent No.: US 9,840,478 B2
(45) Date of Patent: Dec. 12, 2017

(54) PIPERAZINE DERIVATIVES AS HIV PROTEASE INHIBITORS

(71) Applicants: MERCK SHARP & DOHME CORP., Rahway, NJ (US); MSD R&D (CHINA) CO., LTD., Shanghai (CN)

(72) Inventors: Peter D. Williams, Harleysville, PA (US); John A. McCauley, Maple Glen, PA (US); David Jonathan Bennett, Winchester, MA (US); Christopher J. Bungard, Lansdale, PA (US); Lehua Chang, Ramsey, NJ (US); Michael P. Dwyer, Scotch Plains, NJ (US); M. Katharine Holloway, Lansdale, PA (US); Kartik M. Keertikar, East Windsor, NJ (US); H. Marie Loughran, Perkasie, PA (US); Jessie J. Manikowski, Worcester, PA (US); Gregori J. Morriello, Randolph, NJ (US); Dong-Ming Shen, Edison, NJ (US); Edward C. Sherer, Hillsborough, NJ (US); Jurgen Schultz, Scotland (GB); Sherman T. Waddell, Westfield, NJ (US); Catherine M. Wiscount, Allentown, PA (US); Nicolas Zorn, Durmenach (FR); Xin-Jie Chu, Shanghai (CN); Satyanarayana Tummanapalli, The Galen (SG); Vijayasaradhi Sivalenka, The Galen (SG); Bin Hu, Shanghai (CN); Tao Ji, Shanghai (CN); Bin Zhong, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/908,421

(22) PCT Filed: Jul. 29, 2014

(86) PCT No.: PCT/US2014/048581
§ 371 (c)(1),
(2) Date: Jan. 28, 2016

(87) PCT Pub. No.: WO2015/017393
PCT Pub. Date: Feb. 5, 2015

(65) Prior Publication Data
US 2016/0159752 A1    Jun. 9, 2016

(30) Foreign Application Priority Data
Jul. 31, 2013 (WO) ............... PCT/CN2013/000899

(51) Int. Cl.
C07D 241/04     (2006.01)
C07D 401/14     (2006.01)
C07D 405/14     (2006.01)
C07D 409/14     (2006.01)
C07D 413/14     (2006.01)
C07D 401/06     (2006.01)
C07D 401/12     (2006.01)
C07D 405/12     (2006.01)
C07D 409/12     (2006.01)
C07D 417/14     (2006.01)

(52) U.S. Cl.
CPC ......... *C07D 241/04* (2013.01); *C07D 401/06* (2013.01); *C07D 401/12* (2013.01); *C07D 401/14* (2013.01); *C07D 405/12* (2013.01); *C07D 405/14* (2013.01); *C07D 409/12* (2013.01); *C07D 409/14* (2013.01); *C07D 413/14* (2013.01); *C07D 417/14* (2013.01)

(58) Field of Classification Search
CPC .................................................... C07D 241/04
See application file for complete search history.

(56) References Cited

U.S. PATENT DOCUMENTS

| 5,196,438 | A  | 3/1993  | Martin et al. |
| 5,413,999 | A  | 5/1995  | Vacca et al. |
| 5,484,801 | A  | 1/1996  | Al-Razzak et al. |
| 5,484,926 | A  | 1/1996  | Dressman et al. |
| 5,585,397 | A  | 12/1996 | Tung et al. |
| 5,852,195 | A  | 12/1998 | Romines et al. |
| 5,981,520 | A  | 11/1999 | Shue et al. |
| 6,531,476 | B1 | 3/2003  | Heymans et al. |
| 7,727,991 | B2 | 6/2010  | Sharma et al. |

(Continued)

FOREIGN PATENT DOCUMENTS

| WO | 9309096       | 5/1993  |
| WO | 0138332 A1    | 5/2001  |
| WO | 0230930 A2    | 4/2002  |
| WO | 02088115 A1   | 11/2002 |
| WO | 2009042093 A1 | 4/2009  |
| WO | 2009042094 A2 | 4/2009  |
| WO | 2010138338 A1 | 12/2010 |

(Continued)

OTHER PUBLICATIONS

Patterson, Daniel E., et al, "Developement of a Practical Large-Scale Synthesis of Denagliptin Tosylate", Organic Process Research & Dev., 2009, pp. 900-906, vol. 13, US.

(Continued)

*Primary Examiner* — James D Anderson
(74) *Attorney, Agent, or Firm* — Carol S. Quagliato; Catherine D. Fitch

(57) ABSTRACT

The present invention is directed to piperazine derivatives, pharmaceutical compositions comprising the same, and their use in the inhibition of HIV protease, the inhibition of HIV replication, the prophylaxis of infection by HIV, the treatment of infection by HIV, and the prophylaxis, treatment, and delay in the onset or progression of AIDS.

13 Claims, No Drawings

(56) References Cited

U.S. PATENT DOCUMENTS

2010/0121048 A1    5/2010    Kuroita et al.
2014/0018325 A1    1/2014    Boyd et al.

FOREIGN PATENT DOCUMENTS

| WO | 2011060396 A1 | 5/2011 |
| WO | 2012055034 A1 | 5/2012 |
| WO | 2013059928 A1 | 5/2013 |
| WO | 2014043019 A1 | 3/2014 |
| WO | 2015095265 A1 | 6/2015 |
| WO | 2015095276 A1 | 6/2015 |
| WO | 2015134366 A1 | 9/2015 |
| WO | 2015135091 A1 | 9/2015 |
| WO | 2015138220 A1 | 9/2015 |

OTHER PUBLICATIONS

Toh, Hiroyuki, et al., "Close Structural Resemblance Between Putative Polymerase of a *Drosophila* Transposable Genetic Element 17.5 and Pol Gene Product of Moloney Murine Leukaemia Virus", The EMBO Journal, 1985, pp. 1267-1272, vol. 4, No. 5, US.

Pearl, Laurence H., et al., "A Structural Model for the Retroviral Proteases", Nature, 1987, pp. 351-354, vol. 329, US.

Ratner, Lee, et al., "Complete Nucleotide Sequence of AIDS Virus, HTLV-III", Nature, 1985, pp. 277-284, vol. 313, US.

Power, Michael, et al., "Nucleotide Sequence of SRV-1, a Type D Simian", Science, 1986, pp. -1572, vol. 231, US.

Kohl, Nancy E., et al., "Active Human immunodeficiency Virus Protease is Required for Viral Infectivity", Proc. Natl. Acad. Sci., 1988, pp. 4686-4690, vol. 85, US.

Gulick, Roy M., et al., "Treatment With Indinavir, Zidovudine, and Lamivudine in Adults With Human Immunodeficiency Virus Infection and Prior Antiretroviral Therapy", New England Journal of Medicine, 1997, pp. 734-739, vol. 337, US.

Hammer, Scott M., et al., "A Controlled Trial of Two Nucleoside Analogues Plus Indinavir in Persons With Human Immunodeficiency Virus Infection and CD4 Cell Counts of 200 Per Cubic Millimeter or Less", The New England Journal of Medicine, 1997, pp. 725-733, vol. 337, No. 11, US.

Liu, Tao, et al., "Design, Synthesis and Biological Evaluation of Novel Piperazine Derivatives as CCR5 Antagonists", PLoS One, 2013, pp. 1-7, vol. 8, Issue 1.

McCombie, Stuart W., et al., "Piperazine-Based CCR5 Antagonists asHIV-1 Inhibitors. III: Synthesis, Antiviral and Pharmacokinetic Profiles of Symmetrical Heteroaryl Carboxamides", Bioorganic & Medicinal Chemistry Letters, 2003, pp. 567-571, 13.

PIPERAZINE DERIVATIVES AS HIV PROTEASE INHIBITORS

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., *Proc. Nat'l Acad. Sci.* 1988, 85: 4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, an endonuclease, HIV protease and gag, which encodes the core proteins of the virion (Toh et al., *EMBO J.* 1985, 4: 1267; Power et al., *Science* 1986, 231: 1567; Pearl et al., *Nature* 1987, 329: 351].

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 1997, 337: 725-733 and Gulick et al., *New England J. Med.* 1997, 337: 734-739.

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Furthermore, the currently available protease inhibitors are rapidly metabolized and cleared from the bloodstream, requiring frequent dosing and use of a boosting agent. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

SUMMARY OF THE INVENTION

The present invention is directed to piperazine derivatives, pharmaceutical compositions comprising the same, and their use in the inhibition of HIV protease, the inhibition of HIV replication, the prophylaxis of infection by HIV, the treatment of infection by HIV, and the prophylaxis, treatment, and delay in the onset or progression of AIDS.

DETAILED DESCRIPTION OF THE INVENTION

In a first embodiment ("Embodiment 1"), the invention encompasses a genus of compounds of Formula I

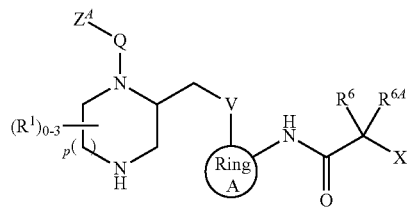

or a pharmaceutically acceptable salt thereof, wherein:
Ring A is selected from $C_{3-7}$ cycloalkyl or

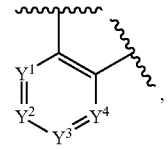

wherein $C_{3-7}$ cycloalkyl is optionally substituted with 1 to 4 substituents independently selected from halogen and OH;
p is an integer equal to 1 or 2;
Q is —N(H)—S(O)$_2$—, —N(C$_{1-4}$alkyl)S(O)$_2$—, —S(O)$_2$—, —C(O)—, —O—C$_{1-6}$alkylenyl-C(O)— or —CH$_2$—, wherein the double asterisk () is the point of attachment of Q to the nitrogen atom in the piperazine or 1,4-diazepane ring depicted in Formula I;
V is CH$_2$ or O;
$Y^1$, $Y^2$, $Y^3$ and $Y^4$ are independently selected from C(R) and N;
X is selected from H, OR$^8$ and NR$^7$R$^8$;
each R is independently selected from H, halo, hydroxy, $C_{1-4}$alkyl, $C_{1-4}$alkoxy, $C_{1-4}$alkoxyC$_{1-4}$alkyl, $C_{1-4}$ alkyl-S(O)$_k$—, CF$_3$, CN, benzyl, or two R groups on adjacent atoms may be joined together with the atoms to which they are attached to form a fused phenyl, pyridine, pyridazine, pyrimidine, pyrazine, or triazine, each of which is optionally substituted with 1 to 4 substituents independently selected from the group consisting of: halo, $C_{1-4}$alkyl, $C_{1-4}$alkoxy, $C_{1-4}$alkoxyC$_{1-4}$ alkyl, CF$_3$ and CN;
each k is independently 0, 1 or 2;
$Z^A$ is selected from the group consisting of:
(1) hydrogen,
(2) $C_{1-10}$ alkyl,
(3) $C_{2-10}$alkenyl,
(4) $C_{3-7}$ cycloalkyl, (5) ArylA,
(6) HetA and
(7) HetB,
wherein said $C_{1-10}$ alkyl, $C_{2-10}$alkenyl and $C_{3-7}$ cycloalky are optionally substituted with 1 to 6 substituents as allowed by valence independently selected from the group consisting of: fluoro, hydroxy, carbamoyl, $C_{3-6}$ cycloalkyl, C(O)O—$C_{1-6}$ alkyl, C(O)OH, C(O)—$C_{1-6}$ alkyl, N(H)—$C_{1-6}$ alkyl, N(—$C_{1-6}$ alkyl)$_2$, ArylA, ArylA-O—, HetA, HetA-O—, HetB and HetB-O—;

each $R^1$ is independently selected from $C_{1-6}$alkyl and $C_{3-6}$cycloalkyl, each optionally substituted with 1 to 3 substituents independently selected from halogen, OC(O)NH$_2$, OC(O)N(H)—$C_{1-6}$ alkyl or OC(O)N(—$C_{1-6}$ alkyl)$_2$, or two $R^1$ groups on adjacent carbon atoms or the same carbon atom may be joined together with the atoms to which they are attached to form a fused 3- to 6-membered nonaromatic cyclic ring;

$R^6$ is selected from:

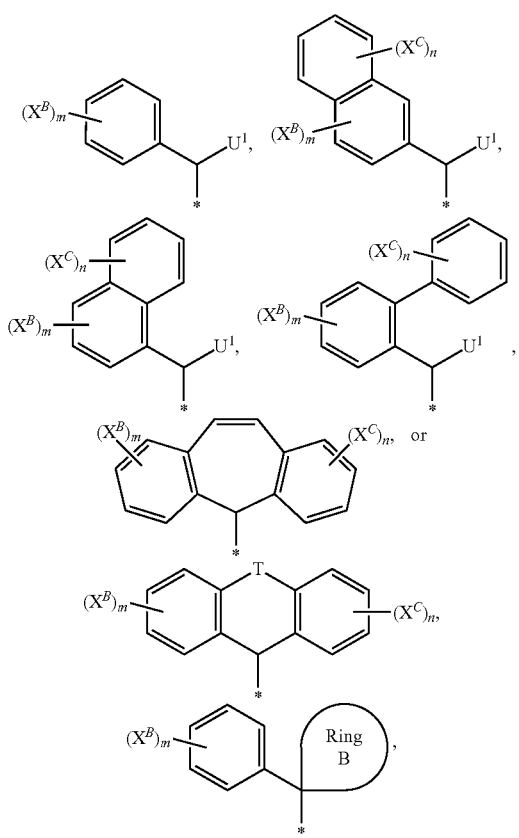

wherein the asterisk (*) denotes the point of attachment to the rest of the compound and $U^1$ is selected from (1) H, (2) $C_{1-10}$alkyl, wherein said $C_{1-10}$alkyl is optionally substituted with 1 to 4 substituents independently selected from halogen, $C_{1-4}$alkyl, $C_{1-4}$haloalkyl, hydroxy and $C_{1-4}$alkoxy, (3) $C_{3-7}$ cycloalkyl, wherein said $C_{3-7}$ cycloalkyl is optionally substituted with 1 to 4 substituents independently selected from halogen, $C_{1-4}$alkyl, $C_{1-4}$haloalkyl, hydroxy and $C_{1-4}$alkoxy, (4) ArylA, (5) HetA, (6) HetB, (7) $C_{1-10}$alkyl substituted with ArylA, (8) $C_{1-10}$alkyl substituted with HetA, and (9) $C_{1-10}$alkyl substituted with HetB; and Ring B is selected from $C_{3-7}$ cycloalky and HetB, wherein $C_{3-7}$ cycloalkyl is optionally substituted with 1 to 4 substituents independently selected from halogen, OH, $C_{1-4}$alkyl and $C_{1-4}$alkoxyl;

$R^{6A}$ is selected from H or $C_{1-6}$ alkyl;

each $X^A$, each $X^B$, each $X^C$, each $X^D$, each $Y^B$ and each $Y^C$ are independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) NO$_2$,
(15) NH$_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) C(O)NH$_2$,
(25) C(O)N(H)—$C_{1-6}$ alkyl,
(26) C(O)N(—$C_1$-6 alkyl)$_2$,
(27) C(O)N(H)C(O)—$C_{1-6}$ alkyl,
(28) C(O)N(H)CH(O)
(29) SO$_2$H,
(30) SO$_2$—$C_{1-6}$ alkyl;
(31) phenyl, benzyl or phenoxy, each optionally substituted with 1 to 5 substituents selected from halogen and $C_{1-6}$ alkyl,
(32) HetA, —O-HetA or CH$_2$-HetA, optionally substituted with 1 to 5 substituents selected from halogen and $C_{1-6}$ alkyl,
(33) trimethylsilyl, and
(34) $C_{2-6}$alkenyl,
wherein $C_{1-6}$ alkyl in each instance of (1), (3) (5), (6), (9), (10), (16), (17), (18), (21), (23), (25), (26), (27), (30), (31) and (32) above is optionally substituted with 1 to 6 substituents as allowed by valence selected from the group consisting of:
(a) $C_{1-6}$ haloalkyl,
(b) OH
(c) O—$C_{1-6}$ alkyl,
(d) O—$C_{1-6}$ haloalkyl,
(e) O—$C_{3-6}$ cycloalkyl,
(f) SH,
(g) S—$C_{1-6}$ alkyl,
(h) halo,
(i) CN,
(j) NO$_2$,
(k) NH$_2$,
(l) N(H)—$C_{1-6}$ alkyl,
(m) N(—$C_{1-6}$ alkyl)$_2$,
(n) C(O)—$C_{1-6}$ alkyl,
(o) C(O)OH,
(p) C(O)O—$C_{1-6}$ alkyl, and
(q) SO$_2$—$C_{1-6}$ alkyl;

T is O, S, S(O), or $SO_2$;

m is an integer equal to 0, 1, 2, or 3;

n is an integer equal to 0, 1, 2, or 3;

$R^7$ is H, $C_{1-6}$ alkyl, $C_{3-6}$ cycloalkyl, $C_{1-6}$ alkyl substituted with $C_{3-6}$ cycloalkyl, C(O)—$R^K$ or $SO_2$—$R^K$;

$R^8$ is H, $C_{1-6}$ alkyl, $C_{1-6}$ haloalkyl and $C_{3-6}$ cycloalkyl;

$R^K$ is:
  (1) $C_{1-6}$ alkyl,
  (2) $C_{1-6}$ fluoroalkyl
  (3) $C_{3-6}$ cycloalkyl,
  (4) $C_{1-6}$ alkyl substituted with $C_{3-6}$ cycloalkyl,
  (5) O—$C_{1-6}$ alkyl,
  (6) O—$C_{1-6}$ alkyl substituted with O—$C_{1-6}$ alkyl,
  (7) O—$C_{1-6}$ fluoroalkyl,
  (8) C(O)O—$C_{1-6}$ alkyl,
  (9) $C_{1-6}$ alkyl substituted with C(O)O—$C_{1-6}$ alkyl,
  (10) $C_{1-6}$ alkyl substituted with C(O)OH,
  (11) $C_{1-6}$ alkyl substituted with C(O)—$C_{1-6}$ alkyl,
  (12) N(H)—$C_{1-6}$ alkyl,
  (13) N(—$C_{1-6}$ alkyl)$_2$,
  (14) $C_{1-6}$ alkyl substituted with $NH_2$, N(H)—$C_{1-6}$ alkyl, or N(—$C_{1-6}$ alkyl)$_2$,
  (15) ArylA,
  (16) $C_{1-6}$ alkyl substituted with ArylA,
  (17) O—$C_{1-6}$ alkyl substituted with ArylA,
  (18) HetA,
  (19) $C_{1-6}$ alkyl substituted with HetA,
  (20) O—$C_{1-6}$ alkyl substituted with HetA,
  (21) HetB,
  (22) O-HetB, or
  (23) O—$C_{1-6}$ alkyl substituted with HetB;

each ArylA is an aryl which is independently phenyl or naphthyl, wherein the phenyl or naphthyl is optionally substituted with from 1 to 4 $Y^B$;

each HetA is a heteroaromatic ring system which is independently (i) a 5- or 6-membered monocyclic heteroaromatic ring containing from 1 to 3 heteroatoms independently selected from N, O and S, or (ii) is a 9-, 10- or 11-membered bicyclic heteroaromatic ring containing from 1 to 4 heteroatoms independently selected from N, O and S; wherein the monocylcic ring (i) or the bicyclic ring (ii) is optionally substituted with from 1 to 4 $Y^C$; and each HetB is independently a 4- to 7-membered monocyclic, or 9-, 10- or 11-membered bicyclic, saturated or unsaturated, non-aromatic heterocyclic ring system containing at least one carbon atom and from 1 to 4 heteroatoms independently selected from N, O and S, where each S is optionally oxidized to S(O) or $S(O)_2$, and wherein the saturated or unsaturated heterocyclic ring is optionally substituted with from 1 to 4 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)NH_2$, C(O)N(H)—$C_{1-6}$ alkyl, C(O)N(—$C_{1-6}$ alkyl)$_2$, C(O)H, C(O)—$C_{1-6}$ alkyl, $CO_2H$, $CO_2$—$C_{1-6}$ alkyl, $N(H)SO_2$—$C_{1-6}$ alkyl, N(H)C(O)—$C_{1-6}$ alkyl, $SO_2H$, $SO_2$—$C_{1-6}$ alkyl, C(O)N(H)—$C_{1-6}$ haloalkyl, C(O)N(—$C_{1-6}$ alkyl)(—$C_{1-6}$ haloalkyl), C(O)N(—$C_{1-6}$ haloalkyl)$_2$, C(O)—$C_{1-6}$ haloalkyl, $CO_2$—$C_{1-6}$ haloalkyl, $N(H)SO_2$—$C_{1-6}$ haloalkyl, N(H)C(O)—$C_{1-6}$ haloalkyl, or $SO_2$—$C_{1-6}$ haloalkyl.

Within the first embodiment, the invention encompasses a second embodiment ("Embodiment 2") of compounds of Formula Ia

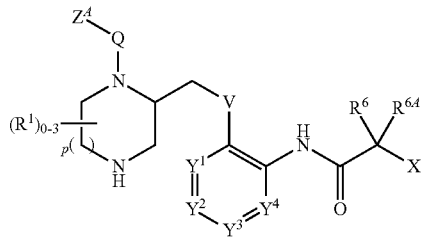

or a pharmaceutically acceptable salt thereof, wherein the variables shown in Formula Ia are defined as in Embodiment 1.

Within the second embodiment, the invention encompasses a third embodiment ("Embodiment 3") of compound of Formula Ib

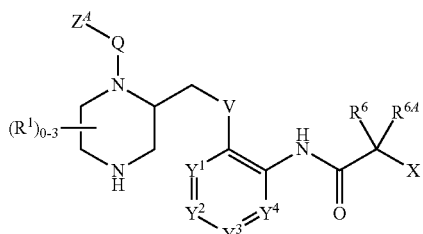

or a pharmaceutically acceptable salt thereof, wherein the variables shown in Formula Ib are defined as in Embodiment 1.

Also within the first embodiment, the invention encompasses a fourth embodiment ("Embodiment 4") of compounds of Formula I wherein $R^6$ is selected from:

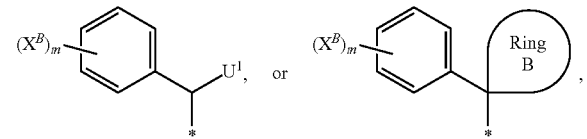

wherein the asterisk (*) denotes the point of attachment to the rest of the compound and $U^1$ is selected from (1) H, (2) $C_{1-10}$alkyl, wherein said $C_{1-10}$alkyl is optionally substituted with 1 to 4 substituents independently selected from halogen, hydroxy and $C_{1-4}$alkoxy, (3) $C_{3-7}$ cycloalkyl, wherein said $C_{3-7}$ cycloalkyl is optionally substituted with 1 to 4 substituents independently selected from halogen, $C_{1-4}$alkyl, $C_{1-4}$haloalkyl, hydroxy and $C_{1-4}$alkoxy, (4) ArylA, (5) HetA, (6) HetB, (7) $C_{1-10}$alkyl substituted with ArylA, (8) $C_{1-10}$alkyl substituted with HetA, and (9) $C_{1-10}$alkyl substituted with HetB; and Ring B is selected from $C_{3-7}$ cycloalky and HetB, wherein $C_{3-7}$ cycloalkyl is optionally substituted with 1 to 4 substituents independently selected from halogen, OH, $C_{1-4}$alkyl, $C_{1-4}$fluorolkyl and $C_{1-4}$alkoxy, wherein all other variables shown in Formula I are defined as in Embodiment 1.

Within the fourth embodiment, the invention encompasses a fifth embodiment ("Embodiment 5") of compounds of Formula I wherein $R^6$ is:

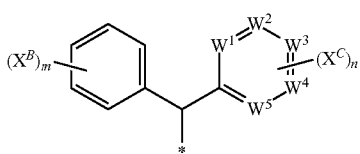

wherein $W^1$ to $W^5$ are independently CH or N, with the proviso that no more that three are N, and $R^{6A}$ is H, wherein all other variables shown in Formula I are defined as in Embodiment 1.

Also within the first embodiment, the invention encompasses a sixth embodiment ("Embodiment 6") of compounds of Formula I wherein Q is —S(O)2-, wherein all other variables shown in Formula I are defined as in Embodiment 1.

Also within the first embodiment, the invention encompasses a seventh embodiment ("Embodiment 7") of compounds of Formula I wherein Q is —C(O)—, wherein all other variables shown in Formula I are defined as in Embodiment 1.

Also within the first embodiment, the invention encompasses an eight embodiment ("Embodiment 8") of compounds of Formula Ic

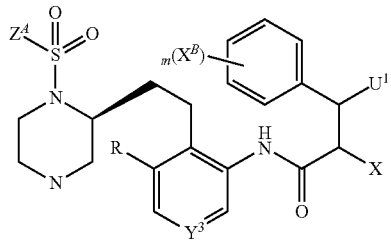

Ic or a pharmaceutically acceptable salt thereof, wherein the variables shown in Formula Ic are defined as in Embodiment 1.

Within the eighth embodiment, the invention encompasses a ninth embodiment ("Embodiment 9") of compounds of Formula Ic wherein:
R is H or fluoro,
$Y^3$ is CH or N,
$X^B$ is selected from F, Cl, —OCH$_3$, —CF$_3$ and —OCF$_3$,
$U^1$ is selected from: 1-methylethyl, tetrahydro-2H-pyran-4-yl,

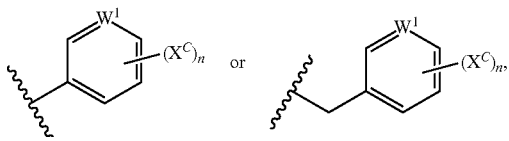

wherein $W^1$ is CH or N, and $X^C$ is selected from F, Cl, —OCH$_3$, —CF$_3$ and —OCF$_3$, and
m and n are independently 0, 1 or 2, wherein all other variables shown in Formula Ic are defined as in Embodiment 1.

Within the eighth embodiment, the invention encompasses a tenth embodiment ("Embodiment 10") of compounds of Formula Ic wherein X is selected from: H, —OH, —NH$_2$ and —N(H)—C(O)—OC$_{1-4}$alkyl, wherein all other variables shown in Formula Ic are defined as in Embodiment 1.

Within the eighth, ninth and tenth embodiment, the invention encompasses an eleventh embodiment ("Embodiment 11") of compounds of Formula Ic, wherein $U^1$ is

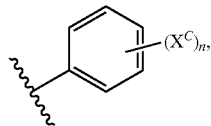

one $X^B$ group is present and substituted at the 4-position, one or two $X^C$ groups are present and substituted at the 3- or 3,5-positions respectively, and the $X^B$ group is a different group with respect to either $X^C$ group, wherein all other variables may be defined as in the eighth, ninth or tenth embodiments.

Within the first through eleventh embodiments, the invention encompasses a twelfth embodiment ("Embodiment 12") of compounds of Formulas I, Ia, Ib or Ic as the case may be, wherein $Z^A$ is $C_{1-6}$ alkyl, optionally substituted with 1 to 3 fluoro groups, wherein all other variables may be defined as in any of the first through eleventh embodiments. Within the twelfth embodiment, the invention encompasses a thirteenth embodiment ("Embodiment 13") of compounds of Formula Ic wherein $Z^A$ is methyl, wherein all other variables may be defined as in any of the first through eleventh embodiments.

Within the first through eleventh embodiments, the invention encompasses a fourteenth embodiment ("Embodiment 14") of compounds of Formulas I, Ia, Ib or Ic as the case may be, wherein $Z^A$ is ArylA or ArylA-methyl-, wherein all other variables may be defined as in any of the first through eleventh embodiments. Within the fourteenth embodiment, the invention encompasses a fifteenth embodiment ("Embodiment 15") wherein $Z^A$ is phenyl or benzyl, each optionally substituted with 1 to 3 substituents independently selected from methyl, formyl, —CF$_3$, —OCF$_3$, —N(H)$_2$, —N(H)(C$_{1-4}$alkyl), —N(C$_{1-4}$alkyl)$_2$, —N(H)—C(O)—C$_{1-4}$alkyl, —N(H)—S(O)$_2$—C$_{1-4}$alkyl, —C(O)—O—C$_{1-4}$alkyl and —S(O)$_2$—C$_{1-4}$alkyl, wherein each C$_{1-4}$alkyl in the aforementioned list is optionally substituted with 1 to 3 halo groups, wherein all other variables may be defined as in any of the first through eleventh embodiments.

Within the first through eleventh embodiments, the invention encompasses a sixteenth embodiment ("Embodiment 16") of compounds of Formulas I, Ia, Ib or Ic as the case may be, wherein $Z^A$ is $C_{3-6}$ cycloalkyl or $C_{3-6}$ cycloalkyl-methyl, wherein all other variables may be defined as in any of the first through eleventh embodiments. Within the sixteenth embodiment, the invention encompasses a seventeenth embodiment ("Embodiment 17") wherein $Z^A$ is cyclopropyl or cyclopropylmethyl, wherein all other variables may be defined as in any of the first through eleventh embodiments.

Within the first through eleventh embodiments, the invention encompasses a eighteenth embodiment ("Embodiment 18") of compounds of Formulas I, Ia, Ib or Ic as the case may be, wherein $Z^A$ is HetA, wherein all other variables may be defined as in any of the first through eleventh embodiments. Within the eighteenth embodiment, the invention encompasses a nineteenth embodiment ("Embodiment 19") wherein $Z^A$ is selected from pyridine, pyrrole, furan, thiophene, pyrazole, imidazole, thiazole, oxazole, isoxazole, pyrazine, pyrimidine, pyrdazine, triazole, oxadiazole, thiadiazole, dithiazole, or a benzo analog of any of the foregoing, each optionally substituted with 1 to 3 substituents independently selected from methyl, formyl, —CF$_3$, —OCF$_3$, —N(H)$_2$, —N(H)(C$_{1-4}$alkyl), —N(C$_{1-4}$alkyl)$_2$, —N(H)—C(O)—C$_{1-4}$alkyl, —N(H)—S(O)$_2$—C$_{1-4}$alkyl, —C(O)—O—C$_{1-4}$alkyl and —S(O)$_2$—C$_{1-4}$alkyl, wherein each C$_{1-4}$alkyl in the aforementioned list is optionally substituted with 1 to 3 halo groups, wherein all other variables may be defined as in any of the first through eleventh embodiments.

Within the first through eleventh embodiments, the invention encompasses a twentieth embodiment ("Embodiment 20") of compounds of Formulas I, Ia, Ib or Ic as the case may be, wherein Z$^A$ is HetB, wherein all other variables may be defined as in any of the first through eleventh embodiments. Within the twentieth embodiment, the invention encompasses a twenty-first embodiment ("Embodiment 21") wherein Z$^A$ is selected from pyrrolidine, piperidine, piperazine and morpholine, or a benzo analog of any of the foregoing, each optionally substituted with 1 to 3 substituents independently selected from fluoro, C$_{1-4}$alkyl, formyl, —OC$_{1-4}$alkyl, —N(H)$_2$, —N(H)(C$_{1-4}$alkyl), —N(C$_{1-4}$alkyl)$_2$, —N(H)—C(O)—C$_{1-4}$alkyl, —N(H)—S(O)$_2$—C$_{1-4}$alkyl, —C(O)—O—C$_{1-4}$alkyl and —S(O)$_2$—C$_{1-4}$alkyl, wherein each C$_{1-4}$alkyl in the aforementioned list is optionally substituted with 1 to 3 halo groups, wherein all other variables may be defined as in any of the first through eleventh embodiments.

Also within the first embodiment, the invention encompasses a twenty-second embodiment ("Embodiment 22") of compounds of Formula I wherein R$^6$ is

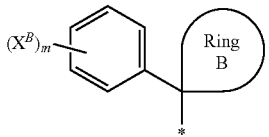

wherein Ring B is selected from tetrahydropyran or piperidine, wherein all other variables shown in Formula I are defined as in Embodiment 1.

Also within the first embodiment, the invention encompasses a twenty-third embodiment ("Embodiment 23") of compounds of Formula I wherein p is 2, wherein all other variables shown in Formula I are defined as in Embodiment 1.

Also within the first embodiment, the invention encompasses a twenty-fourth embodiment ("Embodiment 24") of compounds of Formula I wherein R$^6$ is

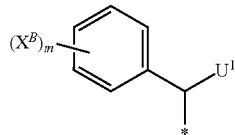

wherein U$^1$ is selected from cyclopropyl, cyclobutyl, cyclopentyl or cyclohexyl, wherein each of the aforementioned rings is optionally substituted with 1 to 4 substituents independently selected from halogen, C$_{1-4}$alkyl, C$_{1-4}$haloalkyl, hydroxy and C$_{1-4}$alkoxy.

The present invention includes any of the Examples 1-148, 150-160, 162-369 described herein, and pharmaceutically acceptable salts thereof.

The invention also encompasses pharmaceutical compositions comprising an effective amount of a compound of the invention or a pharmaceutically acceptable salt thereof, and a pharmaceutically acceptable carrier.

The invention also encompasses methods for the treatment or prophylaxis of infection by HIV or for the treatment, prophylaxis, or delay in the onset of AIDS in a subject in need thereof, which comprises administering to the subject an effective amount of a compound of the invention or a pharmaceutically acceptable salt thereof.

The invention also encompasses a compound of the invention, or a pharmaceutically acceptable salt thereof, for use in the preparation of a medicament for the inhibition of HIV protease, for the treatment or prophylaxis of infection by HIV, or for the treatment, prophylaxis, or delay in the onset of AIDS in a subject in need thereof.

The invention also encompasses a pharmaceutical composition comprising an effective amount of a compound of the invention, or a pharmaceutically acceptable salt thereof, and a pharmaceutically acceptable carrier and further comprising an effective amount of an anti-HIV agent selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

Compounds of Formula Ia, Ib and Ic form a subset of the compounds included in Formula I. Any description which follows that refers to a compound of Formula I also applies to a compound of Formula Ia, Ib and Ic.

Another embodiment of the present invention is a compound of Formula I, or a pharmaceutically acceptable salt thereof, as originally defined or as defined in any of the foregoing embodiments, aspects, classes, or subclasses, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. The compounds of the invention have two or more asymmetric centers and can occur as mixtures of stereoisomers. It is understood that a substantially pure compound can be either a substantially pure mixture of stereoisomers or a substantially pure individual diastereomer or enantiomer.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof.

(k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof.

(n) The method of (m), wherein the compound is administered in combination with an effective amount of at least one other HIV antiviral, selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c) or (d) or the combination of (e) or (f).

(q) A method for the prophylaxis or treatment of infection by HIV (e.g., HIV-1) in a subject in need thereof which comprises administering to the subject the pharmaceutical composition of (a), (b), (c), (d) or (e).

(r) A method for the prophylaxis, treatment, or delay in the onset or progression of AIDS in a subject in need thereof which comprises administering to the subject the pharmaceutical composition of (a), (b), (c), (d) or (e).

The present invention also includes a compound of Formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, aspects, classes or subclasses described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

The term "aryl" refers to phenyl and naphthyl. The aryl of particular interest is phenyl.

Suitable 5- and 6-membered heteroaromatic rings within the definition of HetA include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, oxazolyl, isooxazolyl, oxadiazolyl, oxatriazolyl, thiazolyl, isothiazolyl, and thiadiazolyl.

Examples of 4- to 7-membered, saturated heterocyclic rings within the scope of this invention (see HetB) include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention (see HetB) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aromatic or heteroaromatic ring described as optionally substituted with "from 1 to 4 substituents" is intended to include as aspects thereof, an aromatic or heteroaromatic ring substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $X^A$ or $X^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring provided such ring substitution is chemically allowed and results in a stable compound. When any of $W^1$ to $W^5$ is CH, that hydrogen shown on the carbon atom may be replaced by $X^C$, provided such ring substitution results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

The methods of the present invention involve the use of compounds of the present invention in the inhibition of HIV protease (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts.

The term "administration" and variants thereof (e.g., "administering" a compound) in reference to a compound of Formula I mean providing the compound to the individual in need of treatment or prophylaxis. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for reduced likelihood of the symptoms of the disease or condition being prevented. The term also includes herein the amount of active compound sufficient to inhibit HIV protease (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the methods of the present invention (e.g., inhibiting HIV protease, treating or prophylaxis of HIV infection or treating, prophylaxis of, or delaying the onset or progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following routes: orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase, protease, or another enzyme required for HIV replication or infection, the inhibition of HIV replication, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), or the 59$^{th}$ edition (2005). The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be used for these purposes.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Abbreviations employed herein include the following: Bn=benzyl; BOC (or Boc)=t-butyloxycarbonyl; Boc$_2$O=di-t-butyl carbonate; BOP=benzotriazol-1-yloxytris-(dimethylamino)phosphonium; BSA=bovine serum albumin; CBS=Corey, Bakshi, Shibata chiral oxazaborolidine mediated ketone reduction; Cbz=benzyloxycarbonyl; DBU=1,8-diazabicyclo[5.4.0]undec-7-one; DCAD=di-(4-chlorobenzyl) azodicarboxylate; DCE=1,2-dichloroethane; DCM=dichloromethane; DEAD=diethyl azodicarboxylate; DIAD=diisopropylazodicarboxylate; Dibal-H=diisobutylaluminum hydride; DMAP=4-dimethylaminopyridine; DMF=dimethylformamide; DMSO=dimethyl sulfoxide; EDC=1-ethyl-3-(3-dimethylaminopropyl)carbodiimide; Et=ethyl; EtOAc=ethyl acetate; EtOH=ethanol; G-2G=Grubbs catalyst, 2$^{nd}$ generation; HOAt=1-hydroxy-7-azabenzotriazole; HPLC=high performance liquid chromatography; HSU=hydroxysuccinimide; i-PrOH=isopropanol; LAH=lithium aluminum hydride; LC-MS=liquid chromatography-mass spectroscopy; Me=methyl; MeOH=methanol; MOC=methoxycarbonyl; Ms=mesyl or methanesulfonyl; NMR=nuclear magnetic resonance; Ph=phenyl; RCM=ring closing metathesis; Piv=pivaloyl; PPTS=pyridinium p-toluene sulfonate; PyBrOP=bromo-tris-pyrrolidinophosphonium hexafluorophosphate; SCX=strong cation exchange resin; STP=standard temperature and pressure (i.e., 25° C. & 1 atmosphere); TBS=tert-butyldimethylsilyl; TBDPS=tert-butyl(diphenyl)silyl; TBDPSCl=tert-butyl(dimethyl)silyl chloride; TEA=triethylamine; TFA=trifluoroacetic acid; THF=tetrahydrofuran; TLC=thin layer chromatography; TMAF=tetramethyl ammonium fluoride; TMSCHN$_2$=trimethylsilyl diazomethane; TPAP=tetrapropylammonium perruthenate; TPP=triphenylphosphine.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The term "Ar" appears in several of the schemes and refers to phenyl optionally substituted with one or more $X^A$. In the examples that follow, when a nitrogen atom is depicted without the necessary hydrogen atoms to complete the valence, it is assumed those nitrogen atoms are present unless specifically depicted to the contrary.

Intermediate 1

(S)-2-((tert-butoxycarbonyl)amino)-3,3-bis(4-fluorophenyl)propanoic acid

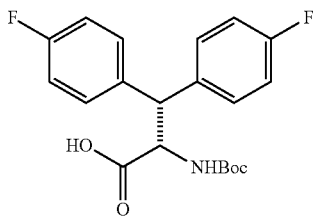

[Patterson, D. E., et al. *Org. Proc. Res. Dev.* 2009, 13, 900-906.] MS: m/z=378 (M+H$^+$).

Intermediate 2

(3S)-3-(3,5-Difluorophenyl)-3-(4-fluorophenyl)propanoic acid

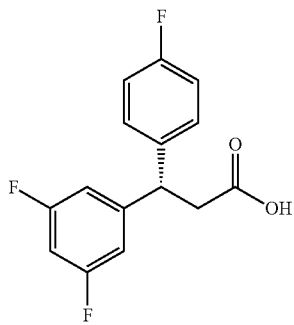 [SMILES: O=C(O)C[C@@H](c1ccc(F)cc1)c1cc(F)cc(F)c1]

Step 1. (4R)-3-[(2E)-3-(3,5-Difluorophenyl)prop-2-enoyl]-4-phenyl-1,3-oxazolidin-2-one

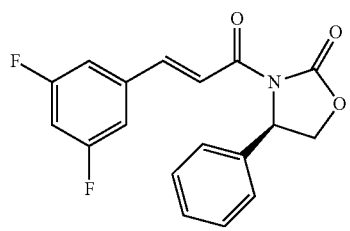 [SMILES: O=C(/C=C/c1cc(F)cc(F)c1)N1C(=O)OC[C@H]1c1ccccc1]

To a slurry of 3,5-difluorocinammic acid (6.3 g, 34 mmol) in CH$_2$Cl$_2$ (130 mL) was added thionyl chloride (6.2 mL, 85 mmol). The mixture was heated to reflux under a nitrogen atmosphere for 5 h, at which time all solids had dissolved. The solvents were removed in vacuo to give the acid chloride as a solid. A solution of (4R)-4-phenyl-1,3-oxazolidin-2-one (5.6 g, 34 mmol) in THF (100 mL) under an atmosphere of nitrogen was cooled to −10° C. in an ice-acetone bath. To the stirred solution was added nBuLi (13.6 mL of a 2.5 M solution in hexane, 34 mmol) dropwise over a period of 10 min. To this solution was added a solution of the acid chloride in 40 mL of THF dropwise over 10 min. The resulting solution was stirred at 0° C. in an ice-water bath for 1 h. The reaction was quenched with the addition of aqueous NaHCO$_3$, and the mixture was extracted three times with EtOAc. The combined organic extracts were washed with water and brine, then dried (MgSO4), filtered, and the solvent was removed in vacuo. The residue was chromatographed on a 330 g SiO2 column using a gradient elution of 0-50% EtOAc:A, where A=1:1 hexanes:CHCl3. Fractions containing product were combined and the solvents were removed in vacuo to give a solid.

Step 2. (4R)-3-[(3S)-3-(3,5-Difluorophenyl)-3-(4-fluorophenyl)propanoyl]-4-phenyl-1,3-oxazolidin-2-one

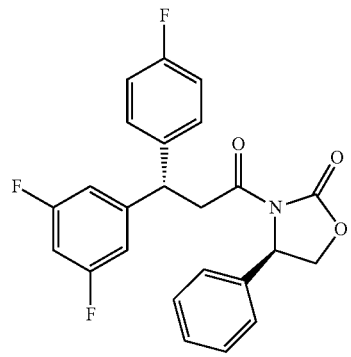 [SMILES: O=C(C[C@@H](c1ccc(F)cc1)c1cc(F)cc(F)c1)N1C(=O)OC[C@H]1c1ccccc1]

A solution of 4-fluorophenylmagnesium bromide (29 mL of a 2.0 M solution in THF, 58 mmol) and copper(I) bromide-dimethylsulfide complex (12 g, 59 mmol) in THF (100 mL) under an atmosphere of nitrogen was cooled to −40° C. in a dry ice-acetonitrile bath. To the stirred solution was added a solution of (4R)-3-[(2E)-3-(3,5-difluorophenyl)prop-2-enoyl]-4-phenyl-1,3-oxazolidin-2-one (7.7 g, 23 mmol) in 100 mL of THF dropwise over 15 min. The resulting mixture was stirred at −40° C. for 1.5 h, then the cooling bath was removed and the stirred mixture was allowed to warm to ambient temperature. The reaction was quenched by the addition of aqueous NH4Cl solution. The resulting mixture was stirred for 15 min then extracted with two portions of EtOAc. The combined organic phases were washed with water and brine, then dried (MgSO4), filtered, and the solvents were removed in vacuo. The residue was chromatographed on a 330 g SiO2 column using a gradient elution of 0-50% EtOAc:A, where A=1:1 hexanes:CHCl$_3$. Fractions containing product were combined and the solvents were removed in vacuo to give a solid.

Step 3. (3S)-3-(3,5-Difluorophenyl)-3-(4-fluorophenyl)propanoic acid

A solution of (4R)-3-[(3S)-3-(3,5-difluorophenyl)-3-(4-fluorophenyl)propanoyl]-4-phenyl-1,3-oxazolidin-2-one (7.3 g, 17 mmol) in 90 mL of THF and 30 mL of water was cooled to 0° C. in an ice-water bath. To the solution was added hydrogen peroxide (7.0 mL of a 30% solution in water, 69 mmol) and LiOH (0.83 g g, 35 mmol). After 45 min, a solution of sodium sulfite (8.7 g, 69 mmol) in 30 mL of water was added, followed by 170 mL of a 0.5 M solution of aqueous NaHCO3 (86 mmol). The stirred mixture was warmed to ambient temperature and most of the THF was removed in vacuo. The aqueous mixture was extracted with two portions of $CH_2Cl_2$ to remove the chiral auxiliary. The aqueous phase was then acidified to pH 1 with the addition of 6 N HCl and extracted with two portions of EtOAc. The combined EtOAc layers were dried (MgSO4), filtered, and the solvent was removed in vacuo to give a solid.

Intermediate 3

(2S,3S)-2-Azido-3-(3,5-difluorophenyl)-3-(4-fluorophenyl)propanoic acid

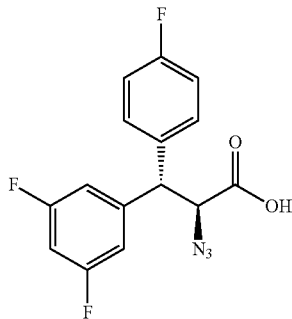 [SMILES: [N-]=[N+]=N[C@H](C(=O)O)[C@@H](c1ccc(F)cc1)c1cc(F)cc(F)c1]

Step 1. (4S)-3-[(3S)-3-(3,5-Difluorophenyl)-3-(4-fluorophenyl)propanoyl]-4-phenyl-1,3-oxazolidin-2-one

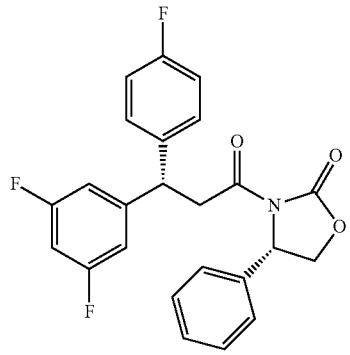 [SMILES: O=C(C[C@@H](c1ccc(F)cc1)c1cc(F)cc(F)c1)N1C(=O)OC[C@@H]1c1ccccc1]

To a solution of (3S)-3-(3,5-difluorophenyl)-3-(4-fluorophenyl)propanoic acid (Intermediate 2, step 3) (3.0 g, 11 mmol) in $CH_2Cl_2$ (70 mL) was added thionyl chloride (2.0 mL, 27 mmol). The mixture was heated to reflux under a nitrogen atmosphere for 1 h. The solvents were removed in vacuo to give the acid chloride as a gum. A solution of (4S)-4-phenyl-1,3-oxazolidin-2-one (1.7 g, 11 mmol) in THF (60 mL) under an atmosphere of nitrogen was cooled to −10° C. in an ice-acetone bath. To the stirred solution was added nBuLi (4.3 mL of a 2.5 M solution in hexane, 11 mmol) dropwise over a period of 5 min. To this solution was added a solution of the acid chloride in 20 mL of THF dropwise over 5 min. The resulting solution was stirred at 0° C. in an ice-water bath for 1 h. The reaction was quenched with the addition of aqueous NaHCO3, and the mixture was extracted three times with EtOAc. The combined organic extracts were washed with water and brine, then dried (MgSO4), filtered, and the solvent was removed in vacuo. The residue was chromatographed on a 120 g SiO2 column using a gradient elution of 0-50% EtOAc:A, where A=1:1 hexanes:CHCl3. Fractions containing product were combined and the solvents were removed in vacuo to give a solid.

Step 2. (4S)-3-[(2S,3S)-2-Azido-3-(3,5-difluorophenyl)-3-(4-fluorophenyl)propanoyl]-4-phenyl-1,3-oxazolidin-2-one

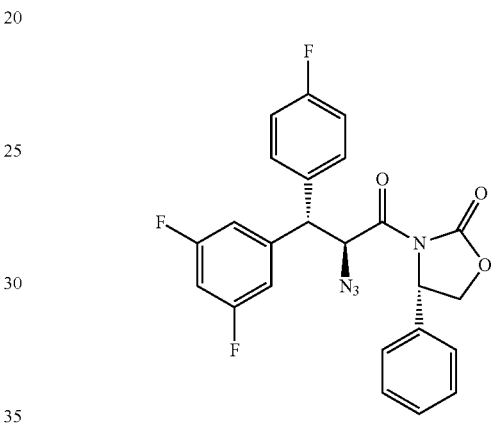

10 mL of THF under an atmosphere of nitrogen was cooled to −78° C. in a dry ice-acetone bath and to the stirred solution was added sodium hexamethyldisilazide (9.1 mL of a 1.0 M solution in THF, 9.1 mmol). A solution of (4S)-3-[(3S)-3-(3,5-difluorophenyl)-3-(4-fluorophenyl)propanoyl]-4-phenyl-1,3-oxazolidin-2-one (3.5 g, 8.2 mmol) in 20 mL of THF under nitrogen atmosphere was cooled to −78° C. in a dry ice-acetone bath and added via cannula to the cold sodium hexamethyldisilazide solution. The resulting mixture was stirred at −78° C. for 30 min when trisyl azide (3.3 g, 11 mmol) was added as a solid. The solids dissolved and the cold solution was stirred for 2 min. To the cold solution was added HOAc (2.8 mL, 49 mmol) and solid tetramethylammonium acetate (4.4 g, 33 mmol). The cooling bath was removed and the mixture was stirred at ambient temperature for 4 h. The reaction was diluted with EtOAc and washed with brine. The aqueous phase was extracted with EtOAc, and the combined EtOAc layers were washed with aqueous Na HCO3 and brine, then dried (MgSO4), filtered, and the solvents were removed in vacuo. The residue was chromatographed on a 120 g SiO2 column using a gradient elution of 0-40% EtOAc in hexanes. Fractions containing product were combined and the solvents were removed in vacuo to give a solid.

Step 3. (2S,3S)-2-Azido-3-(3,5-difluorophenyl)-3-(4-fluorophenyl)propanoic acid

A solution of (4S)-3-[(2S,3S)-2-azido-3-(3,5-difluorophenyl)-3-(4-fluorophenyl)propanoyl]-4-phenyl-1,3-oxazolidin-2-one (3.1 g, 6.7 mmol) in 45 mL of THF and 15 mL of water was cooled to 0° C. in an ice-water bath. To the stirred solution was added hydrogen peroxide (2.7 mL of a 30% solution in water, 27 mmol) and LiOH (0.32 g, 13 mmol), and the mixture was stirred at 0° C. for 45 min. The reaction was quenched by the addition of a solution of sodium sulfite (3.4 g, 27 mmol) in 20 mL of water, followed by 67 mL of a 0.5 M solution of aqueous NaHCO3 (33 mmol). The stirred mixture was warmed to ambient temperature and most of the THF was removed in vacuo. The aqueous mixture was extracted with two portions of $CH_2Cl_2$ to remove the chiral auxiliary. The aqueous phase was then acidified to pH 1 with the addition of 6 N HCl and extracted with two portions of EtOAc. The combined EtOAc layers were dried (MgSO4), filtered, and the solvent was removed in vacuo to give a gum.

Intermediate 4

(2S,3R)-2-azido-3-(3-fluorophenyl)-3-(4-fluorophenyl)propanoic acid

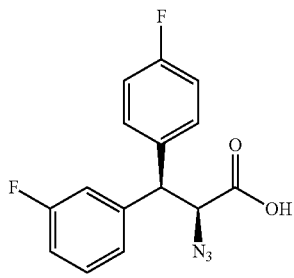 [SMILES: [N-]=[N+]=N[C@H](C(=O)O)[C@H](c1ccc(F)cc1)c1cccc(F)c1]

Step 1. ((4S)-3-[(2E)-3-(3-fluorophenyl)prop-2-enoyl]-4-phenyl-1,3-oxazolidin-2-one

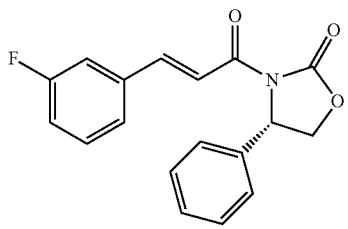 [SMILES: O=C(/C=C/c1cccc(F)c1)N1C(=O)OC[C@@H]1c1ccccc1]

To a slurry of 3-fluorocinammic acid (2.0 g, 12 mmol) in dichloromethane (25 mL) was added thionyl chloride (1.8 mL, 24 mmol). The mixture was heated to reflux under a nitrogen atmosphere for 6 h. The solvents were removed in vacuo to give the acid chloride as a solid. A solution of (4S)-4-phenyl-1,3-oxazolidin-2-one (2.0 g, 12 mmol) in THF (20 mL) under an atmosphere of nitrogen was cooled to −10° C. in an ice-acetone bath. To the stirred solution was added nBuLi (4.8 mL of a 2.5 M solution in hexane, 12 mmol) dropwise over a period of 10 min. To this cold solution was added a solution of the acid chloride in 15 mL of THF dropwise over 10 min. The resulting solution was stirred at 0° C. in an ice-water bath for 1 h. The reaction was quenched with the addition of aqueous NaHCO3, and the mixture was extracted three times with EtOAc. The combined organic extracts were washed with water and brine, then dried (MgSO4), filtered, and the solvent was removed in vacuo. The residue was chromatographed on a 80 g silica gel column using a gradient elution of 0-50% EtOAc:A, where A=1:1 hexanes:$CHCl_3$. Fractions containing product were combined and the solvents were removed in vacuo to give the title compound as a solid.

Step 2. (4S)-3-[(3R)-3-(3-fluorophenyl)-3-(4-fluorophenyl)propanoyl]-4-phenyl-1,3-oxazolidin-2-one

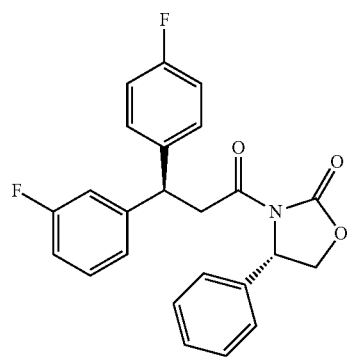 [SMILES: O=C(C[C@H](c1ccc(F)cc1)c1cccc(F)c1)N1C(=O)OC[C@@H]1c1ccccc1]

A solution of 4-fluorophenylmagnesium bromide (12 mL of a 1.0 M solution in THF, 12 mmol) and copper(I) bromide-dimethylsulfide complex (2.4 g, 59 mmol) in THF (20 mL) under an atmosphere of nitrogen was cooled to −40° C. in a dry ice-acetonitrile bath. To the stirred cold solution was added a solution of the product from step 1 (1.5 g, 4.8 mmol) in 10 mL of THF dropwise over 10 min. The resulting mixture was stirred at −40° C. for 1.5 h, then the cooling bath was removed and the stirred mixture was allowed to warm to ambient temperature over 1 h. The reaction was quenched by the addition of aqueous NH4Cl solution. The resulting mixture was stirred for 15 min then extracted with two portions of EtOAc. The combined EtOAc extracts were washed with water and brine, then dried (MgSO4), filtered, and the solvents were removed in vacuo. The residue was chromatographed on an 80 g silica gel column using a gradient elution of 0-50% EtOAc:hexanes. Fractions containing product were combined and the solvents were removed in vacuo to give the title compound as a solid.

Step 3. (4S)-3-[(2S,3R)-2-azido-3-(3-fluorophenyl)-3-(4-fluorophenyl)propanoyl]-4-phenyl-1,3-oxazolidin-2-one

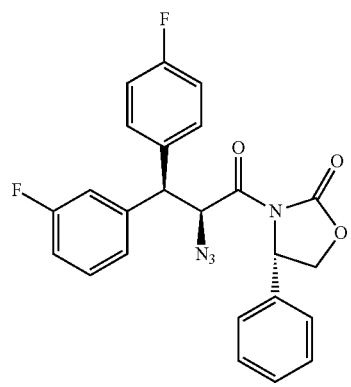 [SMILES: [N-]=[N+]=N[C@H](C(=O)N1C(=O)OC[C@@H]1c1ccccc1)[C@H](c1ccc(F)cc1)c1cccc(F)c1]

5 mL of THF under an atmosphere of nitrogen was cooled to −78° C. in a dry ice-acetone bath and to the stirred solution was added sodium hexamethyldisilazide (5.5 mL of a 1.0 M solution in THF, 5.5 mmol). A solution of the product from step 2 (1.5 g, 3.7 mmol) in 8 mL of THF under nitrogen atmosphere was cooled to −78° C. in a dry ice-acetone bath and added via cannula to the cold sodium hexamethyldisilazide solution. The resulting mixture was stirred at −78° C. for 30 min when trisyl azide (1.5 g, 4.8 mmol) was added as a solid. The solids dissolved and the cold solution was stirred for 2 min. To the cold solution was added HOAc (1.3 mL, 22 mmol) and solid tetramethylammonium acetate (2.0 g, 15 mmol). The cooling bath was removed and the mixture was stirred at ambient temperature for 4 h. The reaction was diluted with EtOAc and washed with brine. The aqueous phase was extracted with EtOAc, and the combined EtOAc layers were washed with aqueous NaHCO₃ and brine, then dried (MgSO₄), filtered, and the solvents were removed in vacuo. The residue was chromatographed on an 80 g silica gel column using a gradient elution of 0-50% EtOAc in hexanes. Fractions containing product were combined and the solvents were removed in vacuo to give the title compound as a solid.

Step 4. (2S,3R)-2-azido-3-(3-fluorophenyl)-3-(4-fluorophenyl)propanoic acid

A solution of the product from step 3 (0.7 g, 1.6 mmol) in 15 mL of THF and 5 mL of water was cooled to 0° C. in an ice-water bath. To the stirred solution was added hydrogen peroxide (0.7 mL of a 30% solution in water, 7 mmol) and LiOH (75 mg, 3.1 mmol), and the mixture was stirred at 0° C. for 45 min. The reaction was quenched by the addition of a solution of sodium sulfite (0.8 g, 7 mmol) in 5 mL of water, followed by a 0.5 M solution of aqueous NaHCO₃ (16 mL, 8 mmol). The stirred mixture was warmed to ambient temperature and most of the THF was removed in vacuo. The aqueous mixture was extracted with two portions of dichloromethane to remove the chiral auxiliary. The aqueous phase was acidified to pH 1 with the addition of 6 N HCl and extracted with two portions of EtOAc. The combined EtOAc layers were dried (MgSO₄), filtered, and the solvent was removed in vacuo to give the title compound as a gum. MS: m/z=276 (M+—N₂+H⁺).

Intermediate 5

(2S,3R)-2-Azido-3-(benzo[d][1,3]dioxol-5-yl)-3-(4-chlorophenyl)propanoic acid

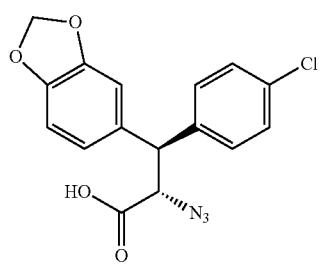 [SMILES: [N-]=[N+]=N[C@H](C(=O)O)[C@H](c1ccc(Cl)cc1)c1ccc2c(c1)OCO2]

Step 1. (R)-3-(2-Bromoacetyl)-4-phenyloxazolidin-2-one

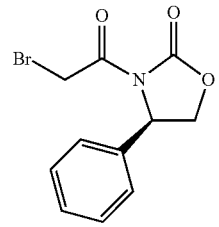 [SMILES: O=C(CBr)N1C(=O)OC[C@H]1c1ccccc1]

A solution of (4R)-4-phenyl-1,3-oxazolidin-2-one (100 g, 613 mmol) in THF (2 L) under a nitrogen atmosphere was cooled to −78° C. in dry ice-acetone bath. To the stirred solution was added n-BuLi (337 mL, 2 M solution in cyclohexane, 675 mmol) dropwise over a period of 30 min, followed by the addition of 2-bromoacetyl bromide (123.7 g, 613 mmol) over 15 min. The resulting solution was stirred at 25° C. for 2 h. The reaction was quenched with aqueous NH₄Cl (500 mL), and the mixture was extracted three times with EtOAc (3×1 L). The combined organic extracts were washed with water (500 mL) and brine (500 mL), dried (MgSO₄), filtered, and the solvent was removed under reduced pressure to give the title compound as a brown solid. The crude product was used directly in the next step.

Step 2. (R)-Dimethyl [2-oxo-2-(2-oxo-4-phenyloxazolidin-3-yl)ethyl]phosphonate

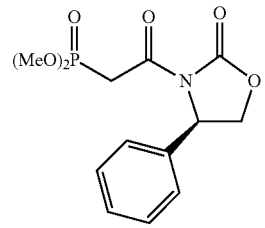

A solution of (R)-3-(2-bromoacetyl)-4-phenyloxazolidin-2-one (175 g, 616 mmol) and trimethyl phosphite (83.3 g, 671 mmol) in toluene (870 mL) was heated to reflux for 16 h. The reaction mixture was cooled to ambient temperature and the solvent was concentrated under reduced pressure to give a brown colored gum, which was triturated with 1:1 CH₂Cl₂ and hexanes (250 mL) to provide a brown solid. The solid was collected by filtration under reduced pressure and washed with CH₂Cl₂ (50 mL) to provide the product (98.8 g) as light brown solid.

Step 3. (R,E)-3-(3-(4-chlorophenyl)acryloyl)-4-phenyloxazolidin-2-one

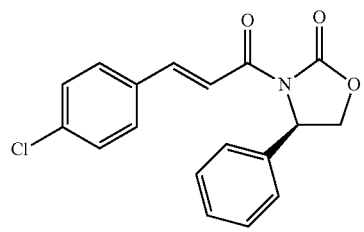 [SMILES: O=C(/C=C/c1ccc(Cl)cc1)N1C(=O)OC[C@H]1c1ccccc1]

A solution of (R)-dimethyl 2-oxo-2-(2-oxo-4-phenyloxazolidin-3-yl)ethylphosphonate (60.7 g, 177.8 mmol) in dry THF (275 ml) under an atmosphere of N₂ was cooled to 0° C. in an ice-water bath. Potassium tert-butoxide (23.9 g, 213.4 mmol, 1.0 M solution in THF) was added over a period of 45 min in a dropwise manner and the reaction mixture stirred at 0° C. for 30 min. A solution of 4-chlorobenzaldehyde (25.0 g, 177.84 mmol) in dry THF (100 ml) was added over a period of 20 min and the reaction mixture was stirred at ambient temperature for 16 h. The reaction mixture was cooled to 0° C. and quenched with saturated solution of ammonium chloride (250 mL) and diluted with EtOAc (1.5 L). The biphasic system was stirred at ambient temperature for 10 min and the layers were separated. The organic layer was washed with brine (250 mL), dried (Na₂SO₄), filtered and concentrated under reduced pressure. The residue was purified by SiO₂ column using a gradient elution of 0-25% EtOAc in hexanes. Fractions containing product were combined and the solvents were removed in vacuo to provide the product (43.0 g, 74%) as a pale yellow solid.

Step 4. (2S,3R)-2-Azido-3-(benzo[d][1,3]dioxol-5-yl)-3-(4-chlorophenyl)propanoic acid The title compound was prepared from the product of step 3 and 1,3-benzodioxol-5-ylmagnesium bromide using the procedures given in steps 2 and 3 of Intermediate 2 and steps 1-3 of Intermediate 3.

Intermediate 6

(2S,3S)-2-Azido-3-(4-chlorophenyl)-3-(3,5-difluorophenyl)propanoic acid

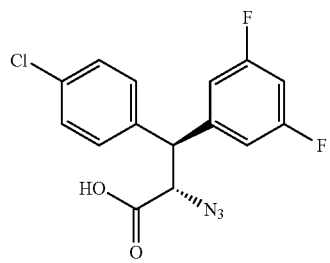 [SMILES: [N-]=[N+]=N[C@H](C(=O)O)[C@@H](c1ccc(Cl)cc1)c1cc(F)cc(F)c1]

The title compound was prepared from 4-chlorobenzaldehyde and 3,5-difluorophenylmagnesium bromide using the procedures given for Intermediate 12.

Intermediate 7

(2S,3S)-2-Azido-3-(4-chlorophenyl)-3-(3-(trifluoromethoxy)phenyl)propanoic acid

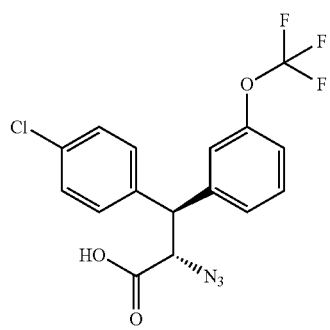 [SMILES: [N-]=[N+]=N[C@H](C(=O)O)[C@@H](c1ccc(Cl)cc1)c1cccc(OC(F)(F)F)c1]

The title compound was prepared from 4-chlorobenzaldehyde and 3-trifluoromethoxyphenylmagnesium bromide using the procedures given for Intermediate 12.

Intermediate 8

(2S,3R)-2-Azido-3-(4-chloro-3-fluorophenyl)-3-(tetrahydro-2H-pyran-4-yl)propanoic acid

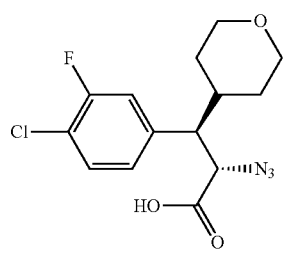 [SMILES: [N-]=[N+]=N[C@H](C(=O)O)[C@@H](c1ccc(Cl)c(F)c1)C1CCOCC1]

The title compound was prepared from tetrahydropyran-4-carboxaldehyde and 4-chloro-3-fluorophenylmagnesium bromide using the procedures given for Intermediate 11.

Intermediate 9

(2S,3S)-2-Azido-3-(4-chlorophenyl)-3-(5-fluoropyridin-3-yl)propanoic acid

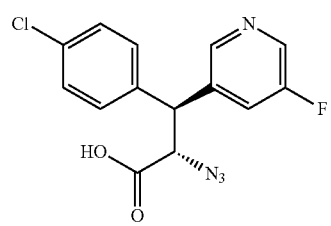 [SMILES: [N-]=[N+]=N[C@H](C(=O)O)[C@@H](c1ccc(Cl)cc1)c1cncc(F)c1]

The title compound was prepared from 3-fluoropyridine-5-carboxaldehyde and 4-chlorophenylmagnesium bromide using the procedures given for Intermediate 10. MS: m/z=321 (M+H⁺).

Intermediate 10

(2S,3S)-2-azido-3-(4-chlorophenyl)-3-(6-methoxypyridin-3-yl)propanoic acid

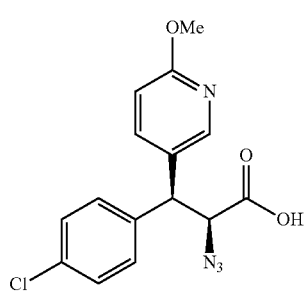 [SMILES: COc1ccc([C@H](c2ccc(Cl)cc2)[C@H](N=[N+]=[N-])C(=O)O)cn1]

Step 1. (R,E)-3-(3-(6-Methoxypyridin-3-yl)acryloyl)-4-phenyloxazolidin-2-one

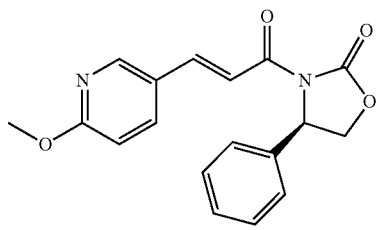 [SMILES: COc1ccc(/C=C/C(=O)N2C(=O)OC[C@H]2c2ccccc2)cn1]

To a solution of dimethyl (2-oxo-2-((4R)-2-oxo-4-phenyltetrahydrofuran-3-yl)ethyl)phosphonate (17.4 g, 52.5 mmol) in THF (70.0 mL) was added t-BuOK (1M solution in THF, 65.6 mL, 65.6 mmol) and stirred at room temperature for 1 h. A solution of 6-methoxynicitinaldehyde (6.00 g, 43.4 mmol) in THF (30.0 mL) was added drop-wise and continued stirring at room temperature for 1 h. The reaction mixture was quenched with saturated solution of $NH_4Cl$ (75.0 mL) and extracted with EtOAc (2×200 mL). The combined EtOAc extracts were washed with water (100 mL), brine (50.0 mL), dried ($Na_2SO_4$), filtered and concentrated under reduced pressure to provide the product (5.70 g, 60%) as light yellow solid.

MS: m/z=325 (M+H$^+$).

Step 2. (R)-3-(4-Chlorophenyl)-3-(6-methoxypyridin-3yl)propanoyl)-4-phenyloxazolidi-2-one

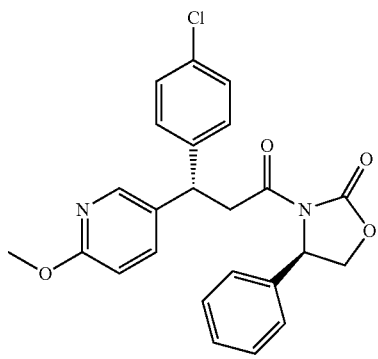 [SMILES: COc1ccc([C@@H](CC(=O)N2C(=O)OC[C@H]2c2ccccc2)c2ccc(Cl)cc2)cn1]

To a precooled (−40° C.) solution of copper (I) bromide methylsulfide complex (5.40 g, 26.4 mmol) in anhydrous THF (30.0 mL) was added dimethylsulfide (15.0 mL), followed by the slow addition of 4-chlorophenylmagnesiumbromide (1M solution in THF, 8.83 mmol). The reaction mixture was allowed to warm to −20° C. and stirred for 20 min. A solution of (R,E)-3-(3-(6-methoxypyridin-3-yl)acryloyl)-4-phenyloxazolidin-2-one (5.70 g, 17.6 mmol) in THF (25.0 mL) was added drop wise over 20 min. The resulting solution was stirred at −20° C. for 1 h and continued stirring at room temperature for 16 h. The reaction mixture was quenched with saturated solution of $NH_4Cl$ (250 mL) and extracted with EtOAc (2×200 mL). The combined EtOAc extracts were washed with brine (200 mL), dried ($Na_2SO_4$), filtered and concentrated under reduced pressure. The residue was purified on 40 g $SiO_2$ column using a gradient elution of 0-20% EtOAc in hexanes. Fractions containing the product were combined and concentrated in vacuo to provide product (5.50 g, 71%) as off-white solid. MS: m/z=437 (M+H$^+$).

Step 3. (S)-3-(4-Chlorophenyl)-3-(6-methoxypyidin-3-yl)propanoic acid

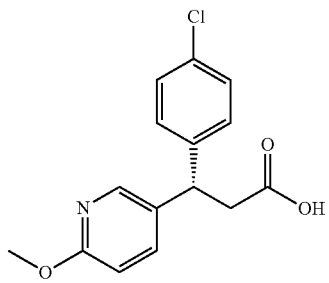 [SMILES: COc1ccc([C@@H](CC(=O)O)c2ccc(Cl)cc2)cn1]

To a precooled (0° C.) solution of (R)-3-(4-chlorophenyl)-3-(6-methoxypyridin-3yl)propanoyl)-4-phenyloxazolidi-2-one (5.50 g, 12.6 mmol) in THF (25.0 mL) and water (5 mL) was added 30% hydrogen peroxide (8.50 mL) drop-wise and stirred for 10 min. A solution of LiOH (906 mg, 37.8 mmol) in water (3.00 mL) was added at 0° C. and reaction mixture was stirred at 0° C. for 2 h. The reaction mixture was quenched with saturated solution of sodium sulphite (100 mL), water (500 mL) and extracted with EtOAc (2×100 mL). The aqueous phase was acidified to pH 3 and extracted with EtOAc (2×150 mL). The combined EtOAc extracts were washed with brine (100 mL), dried ($Na_2SO_4$), filtered and concentrated under reduced pressure to provide product (3.30 g, 89%) as a white solid. MS: m/z=292 (M+H$^+$).

Step 4. (S)-3-((S)-3-(4-Chlorophenyl)-3-(6-methoxypyridin-3-yl)propanoyl)-4-phenyloxazolidin-2-one

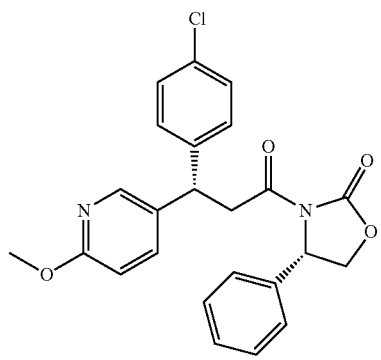 [SMILES: COc1ccc([C@@H](CC(=O)N2C(=O)OC[C@@H]2c2ccccc2)c2ccc(Cl)cc2)cn1]

To a precooled (0° C.) solution of (S)-3-(4-chlorophenyl)-3-(6-methoxypyidin-3-yl)propanoic acid (3.30 g, 11.3 mmol) in THF (30.0 mL) was added pivolyl chloride (1.39 mL, 11.3 mmol), DMAP (cat) and triethylamine (3.15 mL, 22.6 mmol) drop-wise and stirred for 1 h. In another precooled (−78° C.) suspension of (S)-4-phenyloxazolidin-2-one (2.03 g, 12.4 mmol) in THF (10.0 mL) was added n-BuLi (2.50 M solution in hexanes, 9.30 mL, 14.9 mmol) drop-wise and stirred at −20° C. for 1 h. The solution of the above mixed anhydride was added slowly and stirred for additional 3 h. The reaction mixture was quenched with saturated solution of NH₄Cl (250 mL) and extracted with EtOAc (2×200 mL). The combined EtOAc extracts were washed with brine (200 mL), dried (Na₂SO₄), filtered and concentrated under reduced pressure. The residue was purified on 40 g SiO₂ column using a gradient elution of 0-40% EtOAc in hexanes. Fractions containing the product were combined and concentrated under reduced pressure to provide the product (3.20 g, 65%) as white solid. MS: m/z=437 (M+H⁺).

Step 5. (S)-3-((2S,3S)-2-Azido-3-(4-chlorophenyl)-3-(6-methoxypyridin-3-yl)propanoyl)-4-phenyloxazolidin-2-one

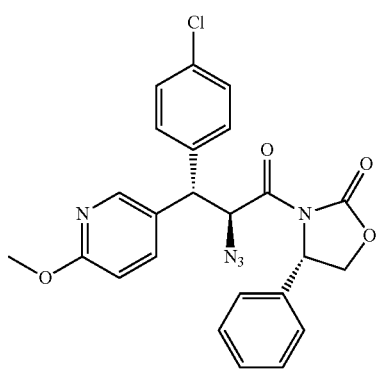 [SMILES: COc1ccc([C@H](c2ccc(Cl)cc2)[C@H](N=[N+]=[N-])C(=O)N2C(=O)OC[C@@H]2c2ccccc2)cn1]

To a precooled (−78° C.) solution of (S)-3-((S)-3-(4-chlorophenyl)-3-(6-methoxypyridin-3-yl)propanoyl)-4-phenyloxazolidin-2-one (2.10 g, 4.81 mmol) in dry THF (30.0 mL) was added NaHMDS (1M solution in THF, 7.20 mL, 7.20 mmol) at −78° C. slowly stirred for 1 h, when trisyl azide (1.93 g, 6.25 mmol) was added as a solid. To the cold solution was added tetramethyl ammonium acetate (1.28 g, 9.61 mmol) and acetic acid (1.73 mL, 28.8 mmol). The cooling bath was removed and stirred at room temperature for 1 h. The reaction mixture was diluted with water (80.0 mL) and extracted with EtOAc (2×100 mL). The combined organic extracts were washed with brine (100 mL), dried (Na₂SO₄), filtered and concentrated under reduced pressure. The residue was purified on 24 g SiO₂ column using a gradient elution of 0-60% EtOAc in hexanes. Fractions containing the product were combined and concentrated under reduced pressure to provide the product (1.23 g, 53%) as a white solid.

MS: m/z=478 (M+H⁺).

Step 6. (2S,3R)-2-Azido-3-(4-chlorophenyl)-3-(6-methoxypyridin-3-yl)propanoic acid To a precooled (0° C.) solution of (S)-3-((2S,3S)-2-azido-3-(4-chlorophenyl)-3-(6-methoxypyridin-3-yl)propanoyl)-4-phenyloxazolidin-2-one (1.64 g, 3.42 mmol) in THF (15.0 mL) and water (3.00 mL) was added 30% hydrogen peroxide (1.10 mL) drop wise and stirred for 10 min. A solution of LiOH (245 mg, 10.2 mmol) in water (4.00 mL) was added dropwise at 0° C. and stirred for 2 h. The reaction mixture was quenched with saturated solution of sodium sulphite (10.0 mL), water (40.0 mL) and extracted with EtOAc (2×50.0 mL). The aqueous phase was acidified to pH 3 with 6 N HCl and extracted with EtOAc (2×150 mL). The combined EtOAc extracts were washed with brine (100 mL), dried (Na₂SO₄), filtered and concentrated under reduced pressure to provide the product (0.95 g, 84%) as a white solid. MS: m/z=292 (M+H⁺).

Intermediate 11

(2S,3R)-2-azido-3-(4-fluorophenyl)-3-(tetrahydro-2H-pyran-4-yl)propanoic acid

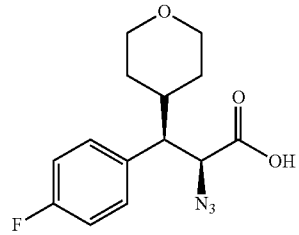 [SMILES: [N-]=[N+]=N[C@H](C(=O)O)[C@@H](c1ccc(F)cc1)C1CCOCC1]

Step 1. (R,E)-4-Phenyl-3-(3-(tetrahydro-2H-pyran-4-yl)acryloyl)oxazolidin-2-one

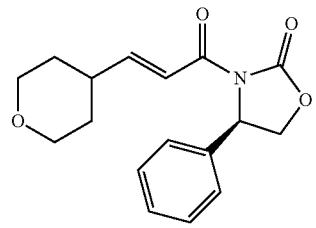 [SMILES: O=C(/C=C/C1CCOCC1)N1C(=O)OC[C@H]1c1ccccc1]

To a solution of dimethyl (2-oxo-2-((4R)-2-oxo-4-phenyltetrahydrofuran-3-yl)ethyl)phosphonate (31.8 g, 98.0 mmol) in THF (140 mL) was added t-BuOK (1M solution in THF (96.0 mL, 96.0 mmol) and stirred at room temperature for 1 h. A solution of 4-tetrahydropyran carboxaldehyde (10.0 g, 87.0 mmol) in THF (70.0 mL) was added drop wise and continued stirring at room temperature for 1 h. The reaction mixture was quenched with saturated solution of NH₄Cl (150 mL) and extracted with EtOAc (2×500 mL). The combined EtOAc extracts were washed with water (250 mL), brine (100 mL), dried (Na₂SO₄), filtered and concentrated under reduced pressure to provide the product (15.0 g, 63%) as an off-white solid.

Step 2. (R)-3-((R)-3-(4-Fluorophenyl)-3-(tetrahydro-2H-pyran-4-yl)propanoyl)-4-phenyloxazolidin-2-one

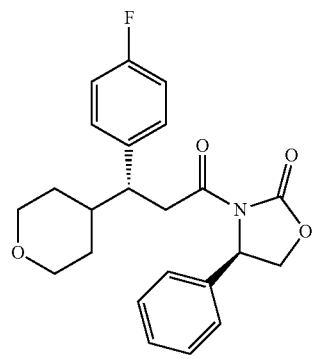 [SMILES: O=C(C[C@@H](c1ccc(F)cc1)C1CCOCC1)N1C(=O)OC[C@H]1c1ccccc1]

To a precooled (−40° C.) solution of copper (I) bromide methylsulfide complex (17.7 g, 82.5 mmol) in anhydrous THF (100 mL) was added dimethylsulfide (82.5 mL), followed by the slow addition of 4-fluorophenylmagnesium-bromide (1M solution in THF, 82.5 mL, 82.5 mmol). The reaction mixture was allowed to warm to −20° C. and stirred for 20 min. A solution of (R,E)-4-phenyl-3-(3-(tetrahydro-2H-pyran-4-yl)acryloyl)oxazolidin-2-one (15.0 g, 55.0 mmol) in THF (100 mL) was added drop wise over 20 min. The resulting solution was stirred at −20° C. for 1 h and continued stirring at room temperature for 16 h. The reaction mixture was quenched with saturated solution of NH$_4$Cl (250 mL) and extracted with EtOAc (2×500 mL). The combined EtOAc extracts were washed with brine (250 mL), dried (Na$_2$SO$_4$), filtered and concentrated under reduced pressure. The residue was purified on 80 g SiO$_2$ column using a gradient elution of 0-20% EtOAc in hexanes. Fractions containing the compound were combined and concentrated in vacuo to provide product (16.5 g, 81%) as off-white solid. MS: m/z=370 (M+H$^+$).

Step 3. (R)-3-(4-Fluorophenyl)-3-(tetrahydro-2H-pyran-4-yl)propanoic acid

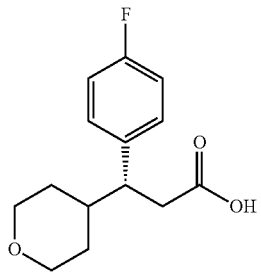 [SMILES: O=C(O)C[C@@H](c1ccc(F)cc1)C1CCOCC1]

To a precooled (0° C.) solution of (R)-3-((R)-3-(4-fluorophenyl)-3-(tetrahydro-2H-pyran-4-yl)propanoyl)-4-phenyloxazolidin-2-one (16.5 g, 45.0 mmol) in THF (100 mL) and water (20 mL) was added 30% hydrogen peroxide (30.0 mL) drop wise and stirred for 10 min. A solution of LiOH (4.16 g, 99.0 mmol) in water (30.0 mL) was added at 0° C. and reaction mixture was stirred at 0° C. for 2 h. The reaction mixture was quenched with saturated solution of sodium sulphite (100 mL), water (500 mL) and extracted with EtOAc (2×250 mL). The aqueous phase was acidified to pH 3 with 6 N HCl extracted with EtOAc (2×300 mL). The combined EtOAc extracts were washed with brine (200 mL), dried (Na$_2$SO$_4$), filtered and concentrated under reduced pressure to provide product (10.1 g, 90%) as a white solid. MS: m/z=251 (M+H$^+$).

Step 4. (S)-3-((R)-3-(4-Fluorophenyl)-3-(tetrahydro-2H-pyran-4-yl)propanoyl)-4-phenyloxazolidin-2-one

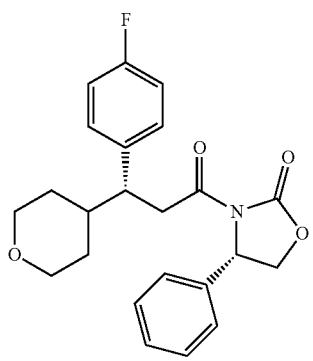 [SMILES: O=C(C[C@@H](c1ccc(F)cc1)C1CCOCC1)N1C(=O)OC[C@@H]1c1ccccc1]

To a precooled (0° C.) solution of (R)-3-(4-fluorophenyl)-3-(tetrahydro-2H-pyran-4-yl)propanoic acid (10.1 g, 40.4 mmol) in THF (30.0 mL) was added thionyl chloride (14.7 mL, 202 mmol) and the reaction mixture was heated at reflux for 1 h. In another precooled (0° C.) suspension of 60% NaH (1.45 g, 60.6 mmol) in THF (20.0 mL), was added a solution of (S)-4-phenyloxazolidin-2-one (6.50 g, 40.4 mmol) in THF (10.0 mL) dropwise and stirred at 0° C. for 1 h. A solution of the above acid chloride in THF (10.0 mL) was added and stirred for additional 5 h. The reaction mixture was quenched with water (30.0 mL) and extracted with EtOAc (2×300 mL). The combined EtOAc extracts were washed with brine (150 mL), dried (Na$_2$SO$_4$), filtered, and concentrated under reduced pressure. The residue was purified on using a gradient elution of 0-20% EtOAc in hexanes. Fractions containing the product were combined and concentrated under reduced pressure to provide the product (7.50 g, 47%) as a white solid. MS: m/z=352 (M+H$^+$).

Step 5. (S)-3-((2S,3R)-2-Azido-3-(4-fluorophenyl)-3-(tetrahydro-2H-pyran-4-yl)propanoyl)-4-phenyloxazolidin-2-one

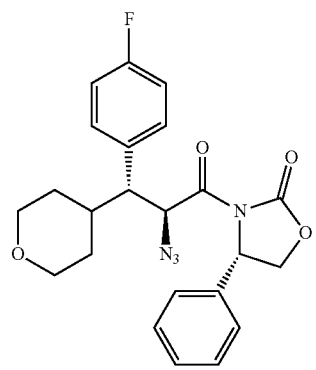 [SMILES: [N-]=[N+]=N[C@H](C(=O)N1C(=O)OC[C@@H]1c1ccccc1)[C@@H](c1ccc(F)cc1)C1CCOCC1]

To a precooled (−78° C.) solution of (S)-3-((R)-3-(4-fluorophenyl)-3-(tetrahydro-2H-pyran-4-yl)propanoyl)-4-phenyloxazolidin-2-one (5.60 g, 15.6 mmol) in dry THF (100 mL) was added NaHMDS (1M solution in THF, 23.9 mL, 23.9 mmol) slowly and stirred for 1 h at −78° C. when trisyl azide (6.42 g, 20.7 mmol) was added as a solid. To the cold solution was added tetramethyl ammonium acetate (4.22 g, 31.9 mmol) and acetic acid (5.47 mL, 95.7 mmol). The cooling bath was removed and stirred at room temperature for 1 h. The reaction mixture was diluted with water (200 mL) and extracted with EtOAc (2×500 mL). The combined EtOAc extracts were washed with brine (300 mL), dried (Na$_2$SO$_4$), filtered and concentrated under reduced pressure. The residue was purified on 40 g SiO$_2$ column using a gradient elution of 0-60% EtOAc in hexanes. Fractions containing the product were combined and concentrated under reduced pressure to provide the product (3.90 g, 63%) as a white solid. MS: m/z=393 (M+H$^+$).

Step 6. (2S,3S)-2-Azido-3-(4-fluorophenyl)-3-(tetrahydro-2H-pyran-4-yl)propanoic acid To a precooled (0° C.) solution of (S)-3-((2S,3R)-2-azido-3-(4-fluorophenyl)-3-(tetrahydro-2H-pyran-4-yl)propanoyl)-4-phenyloxazolidin-2-one (3.90 g, 9.95 mmol) in THF (45.0 mL) and water (9.00 mL) was added 30% hydrogen peroxide (6.76 mL) drop wise and stirred for 10 min. A solution of LiOH (919 mg, 21.9 mmol) in water (12.0 mL) was added dropwise at 0° C. and stirred for 2 h. The reaction mixture was quenched with saturated solution of sodium sulfite (200 mL), water (400 mL) and extracted with EtOAc (2×300 mL). The aqueous phase was acidified to pH 3 and extracted with EtOAc (2×300 mL). The combined EtOAc extracts were washed with brine (200 mL), dried (Na$_2$SO$_4$), filtered and concentrated under reduced pressure to provide the product (2.30 g, 88%) as a white solid. MS: m/z=262 (M+H$^+$).

Intermediate 12

(2S,3R)-2-Azido-3-(4-chlorophenyl)-4-methylpentanoic acid

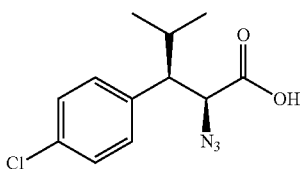 [SMILES: CC(C)[C@H](c1ccc(Cl)cc1)[C@H](N=[N+]=[N-])C(=O)O]

Step 1. (S,E)-3-(3-(4-Chlorophenyl)acryloyl)-4-phenyloxazolidin-2-one

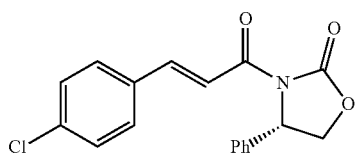 [SMILES: O=C(/C=C/c1ccc(Cl)cc1)N1C(=O)OC[C@@H]1c1ccccc1]

To a stirred solution of (S)-dimethyl 2-oxo-2-(2-oxo-4-phenyloxazolidin-3-yl)ethylphosphonate (20.0 g, 63.8 mmol) in dry THF (100 mL) was added potassium tert-butoxide (76.6 mL, 76.6 mmol, 1.0 M solution in THF) under an atmosphere of N$_2$ at 0° C. over a period of 10 min and the reaction mixture stirred at 0° C. for 30 min. A solution of 4-chloro benzaldehyde (8.98 g, 63.8 mmol) in dry THF (50.0 ml) was added over a period of 20 min and the reaction mixture was stirred at room temperature for 2 h. The reaction mixture was quenched with saturated solution of NH$_4$Cl (250 mL) and diluted with EtOAc (500 mL). The biphasic system was stirred at room temperature for 10 min and the layers were separated. The organic layer was washed with brine (250 mL), dried (Na$_2$SO$_4$), filtered and concentrated under reduced pressure. The residue was purified by recrystallization from MTBE/Hexanes to give the product (11.6 g, 56%) as a pale yellow solid.

Step 2. (S)-3-((R)-3-(4-Chlorophenyl)-4-methylpentanoyl)-4-phenyloxazolidin-2-one

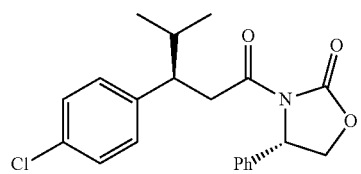 [SMILES: CC(C)[C@@H](CC(=O)N1C(=O)OC[C@@H]1c1ccccc1)c1ccc(Cl)cc1]

To a precooled (−40° C.) solution of copper (I) bromide methylsulfide complex (3.76 g, 18.3 mmol), in dry THF (120 mL), was added dimethyl sulfide (20.0 mL), followed by a solution of isopropyl magnesium bromide (9.20 mL, 2.90M solution) and stirred for 1 h. A solution of (S,E)-3-(3-(4-chlorophenyl)acryloyl)-4-phenyloxazolidin-2-one (4.00 g, 12.2 mmol) in dry THF (40.0 mL) was added slowly at −45° C. and stirred for 3 h. Quenched the reaction mixture with saturated solution of NH$_4$Cl (150 mL) and extracted with EtOAc (200 mL). The EtOAc extract was washed with brine (200 mL), dried (Na$_2$SO$_4$), filtered and concentrated under reduced pressure. The residue was purified by 120 g SiO$_2$ column using a gradient elution of 0-20% EtOAc in hexanes. Fractions containing product were combined and the solvents were removed in vacuo to provide the product (3.00 g, 66%) pale yellow solid. MS: m/z=372 (M+H$^+$).

Step 3. (S)-3-((2S,3R)-2-Azido-3-(4-chlorophenyl)-4-methylpentanoyl)-4-phenyloxazolidin-2-one

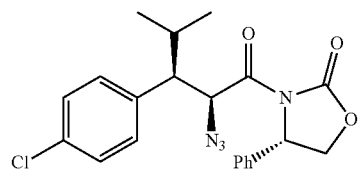 [SMILES: CC(C)[C@H](c1ccc(Cl)cc1)[C@H](N=[N+]=[N-])C(=O)N1C(=O)OC[C@@H]1c1ccccc1]

To a precooled (−78° C.) solution of (S)-3-((R)-3-(4-chlorophenyl)-4-methylpentanoyloxazolidin-2-one (3.00 g, 8.0 mmol) in dry THF (120 mL) was added NaHMDS (16.9 mL, 1M solution in THF) slowly and the resulting solution was stirred for 1 h at −75° C. when trisyl azide (3.30 g, 10.5 mmol) was added as a solid. To the cold solution was added tetramethyl ammonium acetate (2.15 g, 16.7 mmol) and acetic acid (2.77 mL, 48.5 mmol). The cooling bath was removed and the reaction mixture was stirred at room temperature for an additional for 1 h. Diluted the reaction mixture with water (150 mL) and extracted with EtOAc (200 mL). The organic layer was washed with brine (200 mL), dried (Na$_2$SO$_4$), filtered and concentrated under reduced pressure. The residue was purified by 80 g SiO$_2$ column using a gradient elution of 0-20% EtOAc in hexanes. Fractions containing product were combined and the solvents were removed in vacuo to provide the product (2.05 g, 62%) pale yellow solid.

Step 4. (2S,3R)-2-Azido-3-(4-chlorophenyl)-4-methylpentanoic acid

To a precooled (0° C.) solution of (S)-3-((2S,3R)-2-azido-3-(4-chlorophenyl)-4-methylpentanoyl)-4-phenyloxazolidin-2-one (4.1 g, 9.9 mmol) in a mixture of THF (160 mL), and water (120 mL) added 30% hydrogen peroxide solution (6.76 mL) and stirred for 10 min. A solution of LiOH (525 mg, 21.8 mmol) in water (2.00 mL) was added at 0° C. and stirred for 3 h. The reaction mixture was quenched with saturated solution of sodium sulfite (40.0 mL) and stirred for at room temperature for additional 20 min. The reaction mixture was acidified to pH 3 using 6N HCl and extracted with EtOAc (250 mL). The organic layer was dried (Na$_2$SO$_4$), filtered and concentrated under reduced pressure. The residue was purified by 80 g SiO$_2$ column using a gradient elution of 0-20% EtOAc in hexanes. Fractions containing product were combined and the solvents were removed in vacuo to provide the product (2.6 g, 98%) pale yellow gum. MS: m/z=266 (M−H$^+$).

Intermediate 13

(2S,3S)-2-Azido-3-(4-chlorophenyl)-3-(3-fluorophenyl)propanoic acid

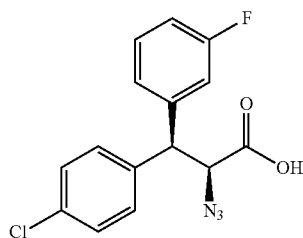 [SMILES: [N-]=[N+]=N[C@H](C(=O)O)[C@@H](c1ccc(Cl)cc1)c1cccc(F)c1]

Step 1. (S)-3-((S)-3-(4-Chlorophenyl)-3-(3-fluorophenyl)propanoyl)-4-phenyloxazolidin-2-one

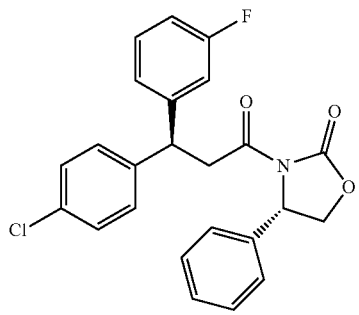 [SMILES: O=C(C[C@@H](c1ccc(Cl)cc1)c1cccc(F)c1)N1C(=O)OC[C@@H]1c1ccccc1]

To a precooled (−40° C.) solution of copper (I) bromide methylsulfide complex (1.88 g, 9.17 mmol) in anhydrous THF (40.0 mL) was added dimethylsulfide (4.00 mL), followed by the slow addition of 3-flurophenylmagnesiumbromide (12.5 mL of 1M solution in THF, 12.2 mmol). The mixture was allowed to warm to −20° C. over 15 to 20 min and a solution of (S,E)-3-(3-(4-chlorophenyl)acryloyl)-4-phenyloxazolidin-2-one (2.00 g, 6.11 mmol) (Step 1 of Intermediate 12) in THF (20.0 mL) was added drop wise over 30 min. The resulting solution was stirred at −20° C. for 1 h, allowed to come to room temperature and stirred for 2 h. The reaction mixture was quenched with saturated solution of ammonium chloride (100 mL) and extracted with EtOAc (2×100 mL). The combined organic extracts were washed with brine (100 mL), dried (Na$_2$SO$_4$), filtered, and concentrated under reduced pressure. The residue was purified on 24 g SiO$_2$ column using a gradient elution of 0-20% EtOAc in hexanes. Fractions containing the product were concentrated under reduced pressure to give product (2.10 g, 84%) as a pale yellow solid.

Step 2. (S)-3-((2S,3S)-2-Azido-3-(4-chlorophenyl)-3-(3-fluorophenyl)propanoyl)-4-phenyloxazolidin-2-one

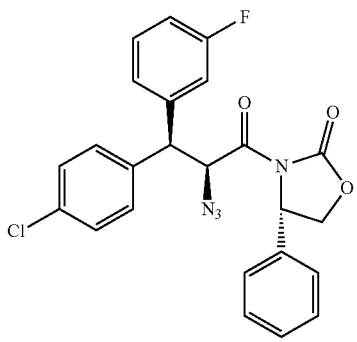 [SMILES: [N-]=[N+]=N[C@H](C(=O)N1C(=O)OC[C@@H]1c1ccccc1)[C@@H](c1ccc(Cl)cc1)c1cccc(F)c1]

To a precooled (−78° C.) solution of (S)-3-((S)-3-(4-chlorophenyl)-3-(3-fluorophenyl)propanoyl)-4-phenyloxazolidin-2-one (2.00 g, 4.72 mmol) in dry THF (30.0 mL) was added NaHMDS (9.50 mL of a 1M solution in THF, 9.50 mmol) slowly and stirred for 1 h at −78° C. when trisyl azide (1.92 g, 6.13 mmol) as solid. To the cold solution was added tetramethyl ammonium acetate (1.25 g, 9.44 mmol) and acetic acid (1.60 mL, 28.3 mmol). The reaction mixture was stirred at room temperature for 1 h. The reaction mixture was diluted with water (50.0 mL) and extracted with EtOAc (2×50.0 mL). The EtOAc extract was washed with brine (50.0 mL), dried (Na$_2$SO$_4$), filtered and concentrated under reduced pressure. The residue was purified by 80 g SiO$_2$ column using a gradient elution of 0-50% EtOAc in hexanes. Fractions containing product were combined and the solvents were removed in vacuo to provide the product (1.43 g, 63%) pale yellow gum.

Step 3. (2S,3S)-2-Azido-3-(4-chlorophenyl)-3-(3-fluorophenyl)propanoic acid

To a precooled (0° C.) solution of (S)-3-((2S,3S)-2-azido-3-(4-chlorophenyl)-3-(3-fluorophenyl)propanoyl)-4-phenyloxazolidin-2-one (1.40 g, 3.01 mmol) in a mixture of THF (15.0 mL), and water (15.0 mL) added 30% hydrogen peroxide solution (2.00 mL) and stirred for 10 min. A solution of lithium hydroxide (150 mg, 6.63 mmol) in water (2.00 mL) was added at 0° C. and stirred for 2 h. The reaction mixture was quenched with a solution of saturated sodium sulfite (20.0 mL) and stirred at room temperature 20 min. The reaction mixture was acidified to pH 3 using 6N HCl and extracted with EtOAc (2×50.0 mL). The organic layer was dried (Na$_2$SO$_4$), filtered and concentrated under reduced pressure. The residue was purified by 24 g SiO$_2$ column using a gradient elution of 0-100% EtOAc in hexanes. Fractions containing product were combined and the solvents were removed in vacuo to provide the product (815 mg, 56%) as pale yellow solid.

Intermediate 14

(2S,3S)-2-Azido-3-(4-chlorophenyl)-3-(5-(trifluoromethyl)pyridine-3-yl)propanoic acid

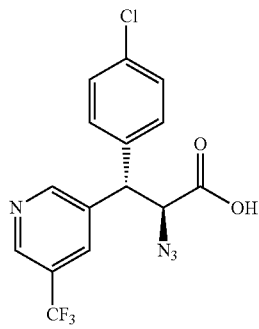 [SMILES: [N-]=[N+]=N[C@H](C(=O)O)[C@@H](c1ccc(Cl)cc1)c1cncc(C(F)(F)F)c1]

Step 1. (R,E)-4-Phenyl-3-(3-(5-(trifluoromethyl)pyridine-3-yl)acryloyl)oxazolidin-2-one

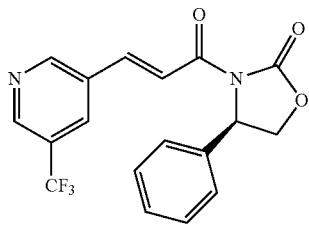 [SMILES: O=C(/C=C/c1cncc(C(F)(F)F)c1)N1C(=O)OC[C@H]1c1ccccc1]

To a solution of 3-bromo-5-(trifluoromethyl)pyridine (6.20 g, 27.5 mmol) in triethyl amine (45.0 mL) was added (R)-3-acryloyl-4-phenyloxazolidin-2-one (6.00 g, 27.6 mmol) followed by DMF (5.00 mL) and purged with argon gas for 10 min. Added palladium acetate (386 mg, 1.72 mmol) and tri-(O-tolyl)phosphine (1.65 g, 5.42 mmol) and the reaction mixture was heated at 110° C. 1 h. The reaction mixture was diluted with EtOAc (200 mL) and washed with water (100 mL), brine (50.0 mL), dried ($Na_2SO_4$), filtered, and concentrated under reduced pressure. The residue was purified on 40 g $SiO_2$ column using a gradient elution of 0-25% EtOAc in hexanes. Fractions containing the product were concentrated under reduced pressure to provide product (4.50 g, 46%) as a white solid. MS: m/z=363 (M+H$^+$).

Step 2. (R)-3-((S)-3-(4-Chlorophenyl)-3-(5-(trifluoromethyl)pyridin-3-yl)propanoyl)-4-phenyloxazolidin-2-one

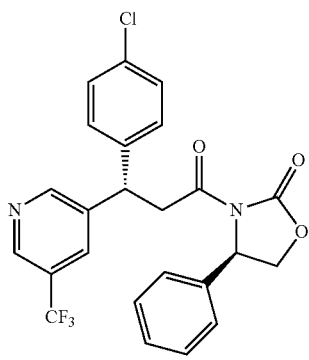 [SMILES: O=C(C[C@@H](c1ccc(Cl)cc1)c1cncc(C(F)(F)F)c1)N1C(=O)OC[C@H]1c1ccccc1]

To a precooled (−40° C.) solution of copper (I) bromide methylsulfide complex (1.36 g, 6.60 mmol) in anhydrous THF (10.0 mL) was added dimethylsulfide (8.00 mL), followed by 4-chlorophenylmagnesiumbromide (1M solution in THF, 8.83 mL, 8.83 mmol) in a drop-wise manner. The mixture was allowed to warm to −20° C. over 20 min and a solution of (R,E)-4-phenyl-3-(3-(5-(trifluoromethyl)pyridine-3-yl)acryloyl)oxazolidin-2-one (1.60 g, 4.41 mmol) in THF (10.0 mL) was added drop wise over 30 min. The resulting solution was stirred at −20° C. for 1 h and stirred room temperature for 16 h. The reaction mixture was quenched with saturated solution of $NH_4Cl$ (100 mL) and extracted with EtOAc (2×100 mL). The combined organic extracts were washed with brine (100 mL), dried ($Na_2SO_4$), filtered, and concentrated under reduced pressure. The residue was purified on 24 g $SiO_2$ column using a gradient elution of 0-20% EtOAc in hexanes. Fractions containing the product were combined and concentrated under reduced pressure to provide the product (1.50 g, 79%) as a white solid. MS: m/z=475 (M+H$^+$).

Step 3. (S)-3-(4-Chlorophenyl)-3-(5-(trifluoromethyl)pyridin-3-yl)acrylic acid

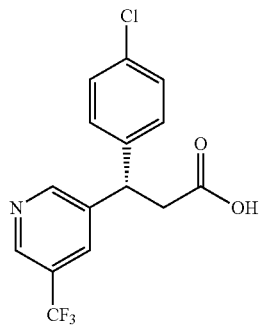 [SMILES: O=C(O)C[C@@H](c1ccc(Cl)cc1)c1cncc(C(F)(F)F)c1]

To a precooled (0° C.) solution of (R)-3-((S)-3-(4-chlorophenyl)-3-(5-(trifluoromethyl)pyridin-3-yl)propanoyl)-4-phenyloxazolidin-2-one (1.50 g, 3.15 mmol) in THF (15.0 mL) and water (5.00 mL) was added 30% hydrogen peroxide (3.20 mL) drop-wise and stirred for 10 min. Added a solution of LiOH (167 mg, 6.97 mmol) in water (3.00 mL) at 0° C. and stirred for 2 h. The reaction mixture was quenched with saturated solution of sodium sulfite (100 mL) and extracted with EtOAc (2×100 mL). The combined EtOAc extracts were washed with brine (100 mL), dried ($Na_2SO_4$), filtered, and concentrated under reduced pressure. The residue was purified on 12 g $SiO_2$ using a gradient elution of 0-100% EtOAc in hexanes. Fractions containing the product were combined and concentrated under reduced pressure to provide the product (679 mg, 70%) as a white solid. MS: m/z=330 (M+H$^+$).

Step 4. (S)-3-((S)-3-(4-Chlorophenyl)-3-(5-(trifluoromethyl)pyridin-3-yl)propanoyl)-4-phenyloxazolidin-2-one

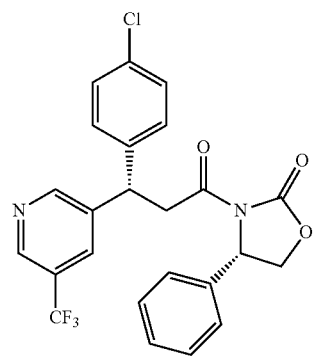 [SMILES: O=C(C[C@@H](c1ccc(Cl)cc1)c1cncc(C(F)(F)F)c1)N1C(=O)OC[C@@H]1c1ccccc1]

To a precooled (0° C.) solution of (S)-3-(4-chlorophenyl)-3-(5-(trifluoromethyl)pyridin-3-yl)acrylic acid (1.30 g, 3.94 mmol) in THF (10.0 mL) was added pivolyl chloride (570 mg, 4.73 mmol), DMAP (cat), followed by triethylamine (796 mg, 7.88 mmol) and stirred for 1 h. In another precooled (0° C.) suspension of 60% NaH (7.88 mmol) in THF, was added (S)-4-phenyloxazolidin-2-one (772 mg, 4.73 mmol) in THF (10.0 mL) drop-wise and stirred at 0° C. for 1 h. The mixed anhydride was added to the reaction mixture and stirred for another 5 h. The reaction mixture was quenched with water (20.0 mL) and extracted with EtOAc (2×100 mL). The combined EtOAc extracts were washed with brine (100 mL), dried (Na₂SO₄), filtered, and concentrated under reduced pressure. The residue was purified on 12 g SiO₂ using a gradient elution of 0-20% EtOAc in hexanes. Fractions containing the product were combined and concentrated under reduced pressure to provide the product (1.40 g, 76%) as a white solid. MS: m/z=475 (M+H⁺).

Step 5. (S)-3-((2S,3S)-2-Azido-3-(4-chlorophenyl)-3-(5-(trifluoromethyl)pyridin-3-yl)acryloyl)-4-phenyloxazolidin-2-one

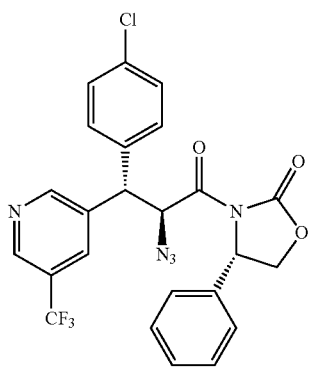 [SMILES: [N-]=[N+]=N[C@H](C(=O)N1C(=O)OC[C@@H]1c1ccccc1)[C@@H](c1ccc(Cl)cc1)c1cncc(C(F)(F)F)c1]

To a precooled (−78° C.) solution of (S)-3-((S)-3-(4-chlorophenyl)-3-(5-(trifluoromethyl)pyridin-3-yl)propanoyl)-4-phenyloxazolidin-2-one (655 mg, 1.38 mmol) in dry THF (10.0 mL) was added NaHMDS (2.00 mL, 1M solution in THF) slowly and stirred for 1 h at −78° C. when trisyl azide (555 mg, 1.79 mmol) was added as a solid. To the cold solution was added tetramethyl ammonium acetate (368 mg, 2.76 mmol) and acetic acid (0.45 mL, 8.28 mmol). The cooling bath was removed and stirred the reaction mixture at room temperature for 1 h. Added water (20.0 mL) and extracted with EtOAc (50.0 mL). The organic layer was washed with brine (50.0 mL), dried (Na₂SO₄), filtered and concentrated under reduced pressure. The residue was purified on 12 g SiO₂ column using a gradient elution of 0-60% EtOAc in hexanes. Fractions containing the product were combined and concentrated under reduced pressure to provide the product (507 mg, 71%) as a white solid. MS: m/z=516 (M+H⁺).

Step 6. (2S,3S)-2-Azido-3-(4-chlorophenyl)-3-(5-(trifluoromethyl)pyridin-3-yl)propanoic acid To a precooled (0° C.) solution of (S)-3-((2S,3S)-2-azido-3-(4-chlorophenyl)-3-(5-(trifluoromethyl)pyridin-3-yl)acryloyl)-4-phenyloxazolidin-2-one (507 mg, 0.98 mmol) in THF (10.0 mL) and water (3.00 mL) was added 30% hydrogen peroxide (1.10 mL) drop-wise and stirred for 10 min. Added a solution of LiOH (52 mg, 2.16 mmol) in water (2.00 mL) at 0° C. and the reaction mixture was stirred for 2 h. The reaction mixture was quenched with saturated solution of sodium sulphite (6.00 mL) and extracted with EtOAc (2×20.0 mL). The combined EtOAc extracts were washed with brine (10.0 mL), dried (Na₂SO₄), filtered, and concentrated under reduced pressure. The residue was purified on 12 g SiO₂ column using a gradient elution of 0-75% EtOAc in hexanes. Fractions containing the product were combined and concentrated under reduced pressure to provide the product (273 mg, 75%) as a white solid. MS: m/z=371 (M+H⁺).

Intermediate 15

(S)-2-azido-3,3-bis(3-fluorophenyl)propanoic acid

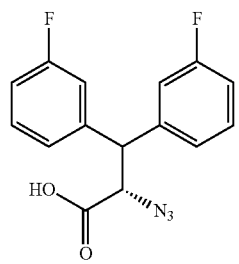 [SMILES: [N-]=[N+]=N[C@H](C(=O)O)C(c1cccc(F)c1)c1cccc(F)c1]

The title compound was prepared from 3-fluorobenzaldehyde and 3-fluorophenylmagnesium bromide using the procedures given for Intermediate 12.

Intermediate 16

(2S,3R)-2-azido-3-(4-chlorophenyl)-3-(tetrahydro-2H-pyran-4-yl)propanoic acid

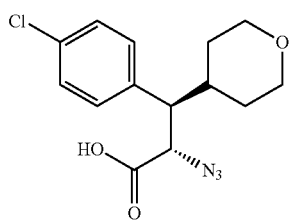

The title compound was prepared from tetrahydropyran-4-carboxaldehyde and 4-chlorophenylmagnesium bromide using the procedures given for Intermediate 11.

Intermediate 17

(S)-2-azido-3,3-bis(3,5-difluorophenyl)propanoic acid

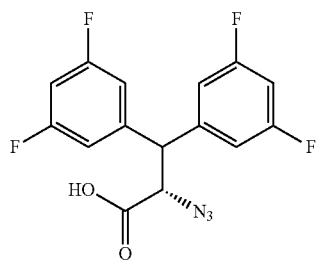 [SMILES: [N-]=[N+]=N[C@H](C(=O)O)C(c1cc(F)cc(F)c1)c1cc(F)cc(F)c1]

The title compound was prepared from 3,5-difluorobenzaldehyde and 3,5-difluorophenylmagnesium bromide using the procedures given for Intermediate 12.

Intermediate 18

(2S,3R)-2-azido-3-(4-chlorophenyl)-3-(1,1-dioxido-tetrahydro-2H-thiopyran-4-yl)propanoic acid

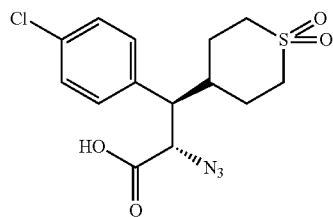 [SMILES: [N-]=[N+]=N[C@H](C(=O)O)[C@@H](c1ccc(Cl)cc1)C1CCS(=O)(=O)CC1]

Intermediate 18 was prepared using similar procedure for Intermediate 22, using (4-(hydroxymethyl)tetrahydro-2H-thiopyran 1,1-dioxide as starting material.

Intermediate 19

(S)-2-azido-2-(4-(4-chlorophenyl)tetrahydro-2H-pyran-4-yl)acetic acid

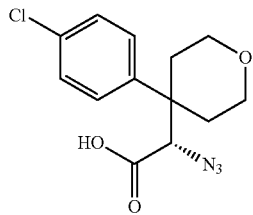 [SMILES: [N-]=[N+]=N[C@H](C(=O)O)C1(c2ccc(Cl)cc2)CCOCC1]

Step 1. ethyl 2-cyano-2-(dihydro-2H-pyran-4(3H)-ylidene)acetate

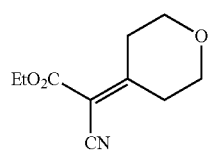

Dihydro-2H-pyran-4(3H)-one (5.0 g, 50 mmol) was dissolved in toluene (50 mL) and ethyl 2-cyanoacetate (5.65 g, 50 mmol), ammonium acetate (0.77 g, 10 mmol), and acetic acid (2.4 mL, 40 mmol) were added. Piperidine (3 drops) was then added and the stirred mixture was heated to reflux for 3.5 hrs. The mixture was cooled to ambient temperature and the solvent was removed in vacuo to give an oil. The oil was dissolved in EtOAc and extracted with water, saturated aqueous NaHCO3, and brine. The organic phase was dried over MgSO4 and the solvent was removed in vacuo to give a solid. The crude product was chromatographed on a 120 g SiO2 column using 0-40% EtOAc:hexane over 30 min at 85 mL/min. Pure fractions were combined and the solvents were removed in vacuo to give a solid.

Step 2. Ethyl 2-(4-(4-chlorophenyl)tetrahydro-2H-pyran-4-yl)-2-cyanoacetate

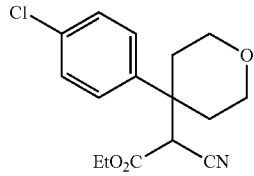 [SMILES: CCOC(=O)C(C#N)C1(c2ccc(Cl)cc2)CCOCC1]

Ethyl 2-cyano-2-(dihydro-2H-pyran-4(3H)-ylidene)acetate (5.8 g, 30 mmol) was dissolved in 120 mL of dry ether and to the stirred solution was added 4-chlorophenylmagnesium bromide (37 mL of a 1.0 M solution in THF, 37 mmol) dropwise over a period of 10 min. A thick suspension formed and the mixture was heated to reflux for 2.5 hrs. The mixture was then cooled in an ice bath and quenched with the addition of 25 mL 1M HCl. The reaction was diluted with water and extract with ether. The organic phase was dried over MgSO4 and the solvents were removed under reduced pressure to give a yellow oil. The crude product was chromatographed on a 120 g SiO2 column using 0-50% EtOAc:hexane over 30 min at 85 mL/min. Pure fractions were combined and the solvents were removed in vacuo to give an oil.

Step 3. 2-(4-(4-chlorophenyl)tetrahydro-2H-pyran-4-yl)acetic acid

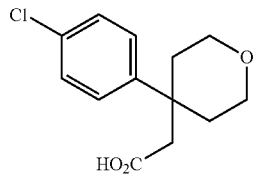 [SMILES: O=C(O)CC1(c2ccc(Cl)cc2)CCOCC1]

Ethyl 2-(4-(4-chlorophenyl)tetrahydro-2H-pyran-4-yl)-2-cyanoacetate (5.9 g, 19 mmol) was dissolved in 100 mL of ethylene glycol and to the stirred solution was added a solution of KOH (9.1 g, 160 mmol) in 20 mL water. The mixture was heated to reflux for 18 h. The mixture was cooled to ambient temperature and the solvents were removed in vacuo. The residue was dissolved in water and the solution was extracted with ether. The aqueous phase was acidified to pH 1 with conc. HCl and extracted with three portions of ether. The combined organic phases were washed with brine, died over MgSO4, and the solvent was removed under reduced pressure to give a solid.

Step 4. 2-(4-(4-chlorophenyl)tetrahydro-2H-pyran-4-yl)acetyl chloride

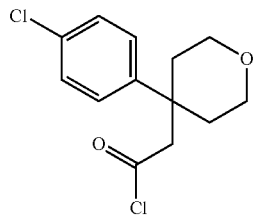 [SMILES: O=C(Cl)CC1(c2ccc(Cl)cc2)CCOCC1]

2-(4-(4-Chlorophenyl)tetrahydro-2H-pyran-4-yl)acetic acid (390 mg, 1.5 mmol) was dissolved in 15 mL of DCM and to the solution was added thionyl chloride (0.54 g, 4.6 mmol). The stirred solution was heated to reflux for 4 hrs. The reaction was cooled to ambient temperature and the solvent was removed in vacuo to give a dense gum.

Step 5. (S)-3-(2-(4-(4-chlorophenyl)tetrahydro-2H-pyran-4-yl)acetyl)-4-phenyloxazolidin-2-one

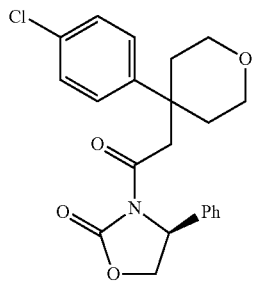 [SMILES: O=C(CC1(c2ccc(Cl)cc2)CCOCC1)N1C(=O)OC[C@@H]1c1ccccc1]

(S)-4-Phenyloxazolidin-2-one (250 mg, 1.5 mmol) was dissolved in 15 mL of dry THF and cooled to −10° C. under an atmosphere of nitrogen. To the stirred solution was added n-BuLi (1.5 mL of a 1.0 M solution in hexanes, 1.5 mmol) dropwise and the resulting solution was stirred for 10 min. 2-(4-(4-Chlorophenyl)tetrahydro-2H-pyran-4-yl)acetyl chloride (420 mg, 1.5 mmol) was dissolved in 6 mL of dry THF and added dropwise to oxazolidinone anion solution. The reaction mixture was stirred at 0° C. for 1 h, then quenched with 20% NH4Cl and extracted with EtOAc. The organic phase was washed with water, saturated aqueous NaHCO3, and brine, then dried over MgSO4. The solvents were removed in vacuo to give a solid. The crude product was chromatograph on a 12 g SiO2 column using 0-70% hexane:EtOAc over 15 min at 30 mL/min. Pure fractions were combined and the solvents were removed in vacuo to give a solid.

Step 6. (S)-3-((S)-2-azido-2-(4-(4-chlorophenyl)tetrahydro-2H-pyran-4-yl)acetyl)-4-phenyloxazolidin-2-one

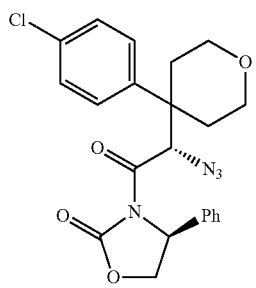 [SMILES: [N-]=[N+]=N[C@H](C(=O)N1C(=O)OC[C@@H]1c1ccccc1)C1(c2ccc(Cl)cc2)CCOCC1]

NaHMDS (13.7 mL of a 1.0 M solution in THF, 13.8 mmol) was added to 14 mL of dry THF under nitrogen atmosphere and cooled to −78° C. (S)-3-(2-(4-(4-chlorophenyl)tetrahydro-2H-pyran-4-yl)acetyl)-4-phenyloxazolidin-2-one (5.0 g, 12.5 mmol) was dissolved in 60 mL of dry THF under nitrogen atmosphere, the solution was cooled to −78° C. and transferred by cannula into the stirred solution of NaHMDS. The resulting solution was stirred at −78° C. for 45 min. Trisyl azide (5.0 g, 16 mmol) was added as a solid and the mixture was stirred for 15 min at −78° C. Acetic acid (4.5 mL, 75 mmol) and solid Me4NOAc (6.7 g, 50 mmol) were then added to the mixture. The cooling bath was removed and the mixture was stirred at ambient temperature overnight. The reaction was diluted with EtOAc and brine. The layers were separated and the aqueous phase was extracted with EtOAc. The combined organic extracts were washed with saturated aqueous NaHCO3 and brine, then dried over MgSO4 and the solvents were removed in vacuo to give an oil. The crude product was chromatographed on a 120 g SiO2 column using 0-40% EtOAc:hexane over 30 min at 85 mL/min. Pure fractions were combined and the solvents were removed in vacuo to give a dense gum, LCMS: m/z=400.3 (M+H).

Step 7. (S)-2-azido-2-(4-(4-chlorophenyl)tetrahydro-2H-pyran-4-yl)acetic acid (S)-3-((S)-2-Azido-2-(4-(4-chlorophenyl)tetrahydro-2H-pyran-4-yl)acetyl)-4-phenyloxazolidin-2-one (265 mg, 0.60 mmol) was dissolved in 4.5 mL THF and 1.5 mL water and cooled in an ice-water bath. To the solution was added 30% aqeuous hydrogen peroxide (0.21 mL, 2.4 mmol) and solid LiOH (29 mg, 1.2 mmol). The mixture was stirred for 45 min. Sodium sulfite (300 mg, 2.4 mmol) in 3 mL of water and NaHCO3 solution (6 mL of a 0.5 M solution, 3 mmol) were added and the reaction mixture was stirred for 5 min. Most of the THF was removed under reduced pressure and the resulting solution was diluted with water. The solution was washed with two portions of DCM to remove the chiral auxiliary. The aqueous phase was then acidified with 6N aqueous HCl to pH 2 and extracted with two portions of EtOAc. The EtOAc phases were combined, dried over MgSO4, and the solvent was removed in vacuo to give a dense gum, LCMS m/z=296.2 (M+H).

Intermediate 20

2-(1-(tert-butoxycarbonyl)-3-phenylpiperidin-3-yl)acetic acid

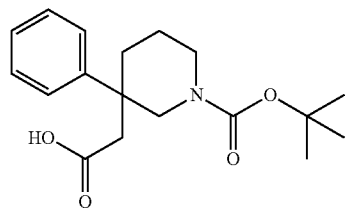 [SMILES: CC(C)(C)OC(=O)N1CCCC(CC(=O)O)(c2ccccc2)C1]

Piperidine and pyrrolidine analogs are commercially available.

Intermediate 21

(2S,3R)-2-azido-3-(4-chloro-3-fluorophenyl)-5-(tetrahydro-2H-pyran-4-yl)pentanoic acid

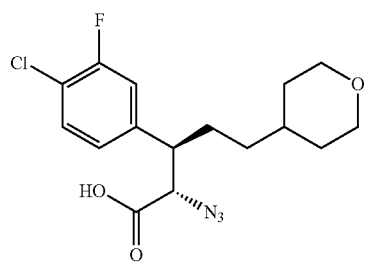 [SMILES: [N-]=[N+]=N[C@H](C(=O)O)[C@H](CCC1CCOCC1)c1ccc(Cl)c(F)c1]

The title compound was prepared from 3-(tetrahydropyran-4-yl)propanal and 4-chloro-3-fluorophenylmagnesium bromide using the procedures given in Intermediate 11.

Intermediate 22

(2S,3R)-2-azido-3-(4-chlorophenyl)-3-((S)-2,2-dimethyltetrahydro-2H-pyran-4-yl)propanoic acid

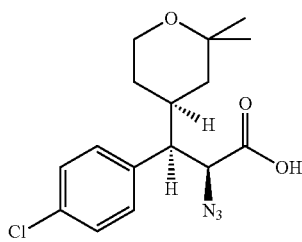 [SMILES: CC1(C)C[C@@H]([C@H](c2ccc(Cl)cc2)[C@H](N=[N+]=[N-])C(=O)O)CCO1]

Step 1.
2,2-dimethyltetrahydro-2H-pyran-4-carbaldehyde

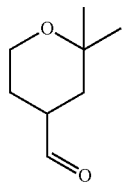

To a solution of (2,2-dimethyltetrahydro-2H-pyran-4-yl)methanol (8 g, 55.5 mmol) in 260 mL DCM cooled to 0° C. via ice/water bath was added Dess-Martin Periodinane (29.4 g, 69.3 mmol) in portions over 3 minute and the resulting mixture was stirred for 1 h at 0° C. The mixture was quenched with solid calcium hydroxide (excess) and stirred vigorously for 45 minutes. The solids were filtered off and washed with DCM (2×100 mL). The organics were concentrated to dryness under reduced pressure and the aldehyde was used as is for the next reaction sequence (7.11 g, 90%). $^1$HNMR (CD$_3$OD) δ: 9.56 (s, 1H); 4.16 (dd, J=3.3 and 16.1 Hz, 1H); 3.80-3.62 (m, 2H); 2.76-2.66 (m, 1H); 1.90-1.85 (m, 1H); 1.72-1.64 (m, 1H); 1.62-1.52 (m, 1H); 1.24 (s, 3H); 1.22 (s, 3H).

Step 2. (E)-tert-butyl 3-(2,2-dimethyltetrahydro-2H-pyran-4-yl)acrylate

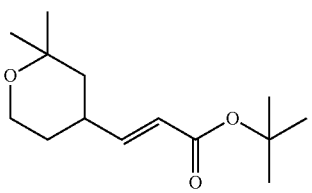 [SMILES: CC(C)(C)OC(=O)/C=C/C1CCOC(C)(C)C1]

To a solution of 2,2-dimethyltetrahydro-2H-pyran-4-carbaldehyde (7.11 g, 50.0 mmol) in anhydrous DCM (500 mL) under nitrogen atmosphere was added solid tert-butyl 2-(triphenylphosphoranylidene)acetate (19.39 g, 51.5 mmol) and the resulting solution stirred overnight at room temperature. The solution was concentrated to dryness and the residue purified by Biotage (RediSep 220 gram silica gel column) eluting with a gradient of 0-100% ethyl acetate in hexane) The tubes containing the product were collected and the solvent removed in vacuo to afford the product as a clear oil (11.6 g, 97%). MS: m/z=241 (M+H$^+$).

Step 3. (E)-3-(2,2-dimethyltetrahydro-2H-pyran-4-yl)acrylic acid

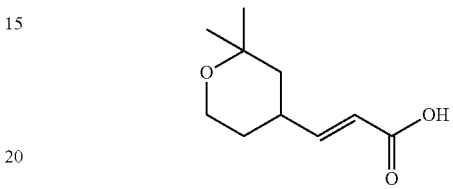

To a solution of (E)-tert-butyl 3-(2,2-dimethyltetrahydro-2H-pyran-4-yl)acrylate (11.6 g, 48.3 mmol) in DCM (150 mL) cooled to 0° C. via ice/water bath was added TFA (45 mL) and the cooling bath removed after 5 minutes. The resulting mixture was stirred at room temperature for 2 hours and then the solvent removed under reduced pressure. The residue was then taken up in 50 mL DCM and 50 mL of toluene was added. This solution was concentrated to dryness under reduced pressure to afford the product, as a white solid, (9 g, 100%) which was used without further purification for the next reaction. $^1$HNMR (CD$_3$OD) δ: 6.85 (dd, J=6.6 and 16.3 Hz, 1H); 5.80 (dd, J=1.5 and 16.3 Hz, 1H); 3.80-3.71 (m, 2H); 2.68-2.60 (m, 1H); 1.70-1.62 (m, 2H); 1.42-1.32 (m, 1H); 1.26 (s, 3H); 1.22 (s, 3H).

Step 4. (R,E)-4-Phenyl-3-(3-(2,2-dimethyltetrahydro-2H-pyran-4-yl)acryloyl)oxazolidin-2-one

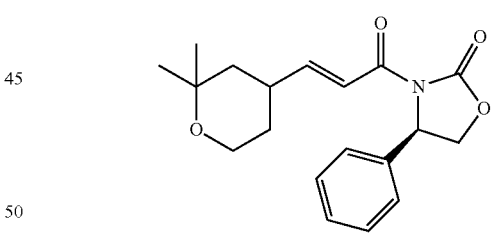

To the solution of (E)-3-(2,2-dimethyltetrahydro-2H-pyran-4-yl)acrylic acid (9 g, 48.9 mmol) in 350 ml of THF was added TEA (7.49 mL, 53.7 mmol) and the resulting solution was stirred under N$_2$ atmosphere and cooled to −10° C. (ice/salt water bath). Piv-Cl (6.37 mL, 51.8 mmol) was then added dropwise via syringe over 5 minutes, a thick precipitate formed, this resulting suspension (A) was stirred at −10° C. for 15 min then cooled to −78° C. (R)-4-phenyloxazolidin-2-one (9.01 g, 55.2 mmol) was charged to a separate 500 mL round bottom flask and was dissolved in THF (150 mL) and the resulting solution was stirred and cooled to −78° C. under N$_2$ atmosphere. n-BuLi (20.52 mL of a 2.5 M solution in hexane) was then added dropwise via syringe over 5 minutes, to which a precipitate formed and this resulting suspension (B) was stirred at −78° C. for 10 min. Then solution A (cooled at −78° C.) was then added to solution B via cannula over about 5 minutes. The resulting mixture was then stirred at −78° C. for 10 minutes and then the cooling bath was removed and the mixture was stirred for 1.5 h while it gradually warmed up to room temperature. The reaction mixture was poured into a 1000 mL Erlenmeyer flask and was diluted with EtOAc (400 mL). This solution was then extracted with water (2×300 mL) and washed by brine (300 mL), then dried over sodium sulfate, filtered, and stripped in vacuo to give a clear oil. The oil was taken up in DCM and purified via Biotage (RediSep 220 g silica gel) eluting with a gradient of 0-60% ethyl acetate in hexane. The tubes containing the product were collected and the solvent removed under reduced pressure to afford the product as a white solid (10.12 g, 62.9%). MS: m/z=330 (M+H$^+$).

Step 5

(R)-3-((R)-3-(4-chlorophenyl)-3-((R)-2,2-dimethyl-tetrahydro-2H-pyran-4-yl)propanoyl)-4-phenyloxazolidin-2-one and (R)-3-((R)-3-(4-chlorophenyl)-3-((S)-2,2-dimethyltetrahydro-2H-pyran-4-yl)propanoyl)-4-phenyloxazolidin-2-one peak A

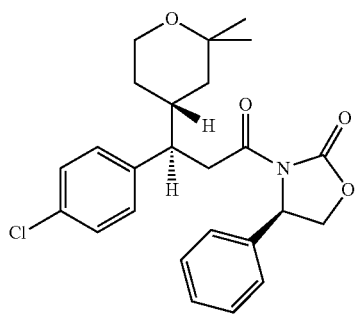

peak B

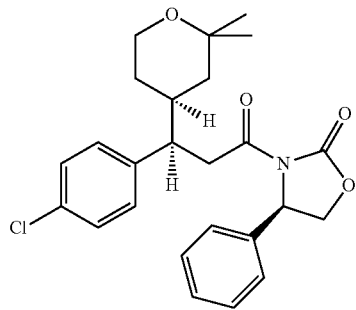

CuBr/DMS complex (4.31 g, 21.35 mmol) was suspended in 200 mL anhydrous THF under N2 atmosphere and the stirred suspension was cooled to −78° C. After stirring for 20 mins, (4-chlorophenyl)magnesium bromide (21.3 mL of a 1.0M solution in THF, 21.3 mmol) was added over 3 min and the resulting solution stirred 10 min at −78° C. and 10 min without cold bath, then the dry-ice/acetone cold bath was put back. After 5 additional minutes, a pre-made solution of (R,E)-4-phenyl-3-(3-(2,2-dimethyltetrahydro-2H-pyran-4-yl)acryloyl)oxazolidin-2-one (7 g, 21.25 mmol) in 35 ml of THF (cooled to ~0° C.) was then transferred to this Cu/grignard solution at −78° C. via cannula over 3 min; to which the resulting mixture turned dark. After 10 minutes, the cold bath was removed and the reaction mixture was stirred for 3 hrs at rt (the solution turned tan color). The reaction was then quenched by the addition of sat'd NH4Cl aq. solution (150 ml) and water (150 ml), extracted with EtOAc (2×150 ml). The aqueous phase was removed. The organic phase was washed with brine, dried (NaSO4), fil-tered, and stripped in vacuo to give a white solid. The residue was purified by the Biotage system using a silica gel column (RediSep 220 g), which was eluted with 20-80% ethyl acetate in hexane over 12 column volumes (CV). Two spots were isolated from this reaction that had the same desired mass spectrum. The fractions containing the two products were combined and the solvent removed to afford 3.11 grams (33.1% of total) of isomer 1 (faster eluting, Peak A) and 3.00 g (31.9% of total) of isomer 2 (slower eluting, Peak B). The second more polar isomer was used in the next reaction. MS of isomer 1 and isomer 2: m/z=442 (M+H$^+$).

Step 6. (R)-3-(4-chlorophenyl)-3-((S)-2,2-dimethyl-tetrahydro-2H-pyran-4-yl)propanoic acid

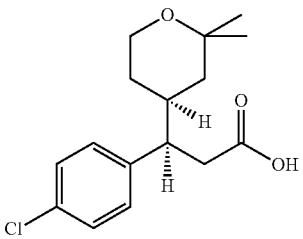 [SMILES: CC1(C)C[C@@H]([C@@H](CC(=O)O)c2ccc(Cl)cc2)CCO1]

To a solution of and (R)-3-((R)-3-(4-chlorophenyl)-3-((S)-2,2-dimethyltetrahydro-2H-pyran-4-yl)propanoyl)-4-phenyloxazolidin-2-one (second eluting isomer, 3.0 g, 6.79 mmol) in THF/water (75 mL/25 mL) cooled to 0° C. via ice/water bath was added hydrogen peroxide (2.38 mL, 27.2 mmol) followed by solid LiOH (325 mg, 13.58 mmol) and the resulting solution stirred for 1 h at 0° C. A solution of sodium sulfite (3.42 g) in 10 mL of water was added to the reaction and the resulting mixture was stirred for 30 minutes allowing to warm to room temperature. Sat'd sodium bicarbonate solution was then added and the mixture stirred for 10 minutes. The solvent was removed under reduced pressure and the aqueous was diluted with water (100 mL). The aqueous was washed with DCM (100 mL) to remove the auxiliary by-product and then the aqueous layer was acidify to pH~4 with addition of 6N HCl solution. The acidic solution was extracted with ethyl acetate (2×150 mL). The organics were combined, dried over sodium sulfate, filtered, and the filtrate concentrated under reduced pressure to afford the crude product. (1.65 g, 82%). MS: m/z=297 (M+H$^+$).

Step 7. (S)-3-((R)-3-(4-chlorophenyl)-3-((S)-2,2-dimethyltetrahydro-2H-pyran-4-yl)propanoyl)-4-phenyloxazolidin-2-one

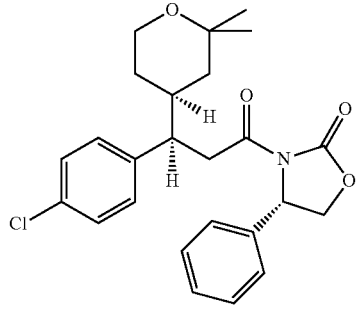 [SMILES: CC1(C)C[C@@H]([C@@H](CC(=O)N2C(=O)OC[C@@H]2c2ccccc2)c2ccc(Cl)cc2)CCO1]

To the solution of (3R)-3-(4-chlorophenyl)-3-((S)-2,2-dimethyltetrahydro-2H-pyran-4-yl)propanoic acid (1.62 g, 5.46 mmol) in 30 ml of THF was added TEA (0.84 mL, 6.0 mmol) and the resulting solution was stirred under N₂ atmosphere and cooled to −10° C. (ice/salt water bath). Piv-Cl (0.71 mL, 5.79 mmol) was then added dropwise via syringe over 2 minutes, a thick precipitate formed, this resulting suspension (A) was stirred at −10° C. for 15 min then cooled to −78° C. (S)-4-phenyloxazolidin-2-one (1.01 g, 6.17 mmol) was charged to a separate 500 mL round bottom flask and was dissolved in THF (10 mL) and the resulting solution was stirred and cooled to −78° C. under N₂ atmosphere. n-BuLi (2.29 mL of a 2.5 M solution in hexane) was then added dropwise via syringe over 2 minutes, to which a precipitate formed and this resulting suspension (B) was stirred at −78° C. for 10 min. Then solution A (cooled at −78° C.) was then added to solution B via cannula over about 2 minutes. The resulting mixture was then stirred at −78° C. for 10 minutes and then the cooling bath was removed and the mixture was stirred for 1.5 h while it gradually warmed up to room temperature. The reaction mixture was poured into a 500 mL Erlenmeyer flask and was diluted with EtOAc (100 mL). This solution was then extracted with water (2×100 mL) and washed by brine (100 mL), then dried over sodium sulfate, filtered, and stripped in vacuo to give a clear oil. The oil was taken up in DCM and purified via Biotage (RediSep 220 g silica gel) eluting with a gradient of 0-60% ethyl acetate in hexane. The tubes containing the product were collected and the solvent removed under reduced pressure to afford the product as a white solid (2.13 g, 88%). MS: m/z=442 (M+H⁺).

Step 8. (4S)-3-((2S,3R)-2-azido-3-(4-chlorophenyl)-3-((S)-2,2-dimethyltetrahydro-2H-pyran-4-yl)propanoyl)-4-phenyloxazolidin-2-one

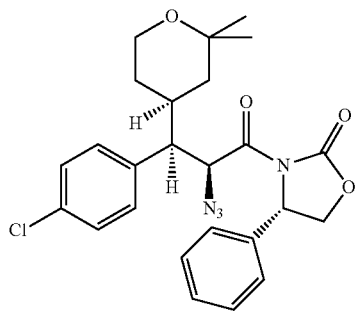 [SMILES: CC1(C)C[C@@H]([C@H](c2ccc(Cl)cc2)[C@H](N=[N+]=[N-])C(=O)N2C(=O)OC[C@@H]2c2ccccc2)CCO1]

To the pre-cooled (−78° C.) solution of (S)-3-((R)-3-(4-chlorophenyl)-3-((S)-2,2-dimethyltetrahydro-2H-pyran-4-yl)propanoyl)-4-phenyloxazolidin-2-one (2.10 g, 4.75 mmol) in 20 ml of anhydrous THF, under N₂ atmosphere, was added NaHMDS (1.0M soln in THF, 6.0 ml, 6.0 mmol) and the resulting solution was stirred at −78° C. for 25 min. Solid trisyl azide (1.55 g, 6.32 mmol) was then added in one portion. After 30 minutes stirring, a mixture of tetramethyl ammonium acetate (633 mg, 4.75 mmol) in HOAc (0.343 mL) was then added and the resulting mixture was removed from the cooling bath and left stirring for 3 hrs. The mixture was diluted with EtOAc (25 mL) and extracted twice with sat'd aq. NaHCO₃ solution (15 mL) and washed by brine (15 mL). The combined aqueous layers were back extracted with EtOAc (25 mL). The EtOAc layers were combined and dried over sodium sulfate, filtered, and stripped to give a foam. The residue was purified via Biotage using a SNAP 80 g, silica gel column, eluting with a gradient of 0-70% ethyl acetate in hexane over 12 column volumes. The tubes containing the product were collected and concentrated to dryness under reduced pressure to afford the product as a white foam (1.21 g, 52.7%). MS: m/z=455 (M-N₂+H)⁺ and m/z 505 (M+Na)⁺.

Step 9. (2S,3R)-2-azido-3-(4-chlorophenyl)-3-((S)-2,2-dimethyltetrahydro-2H-pyran-4-yl)propanoic acid To a precooled (0° C.) solution of (4S)-3-((2S,3R)-2-azido-3-(4-chlorophenyl)-3-((S)-2,2-dimethyltetrahydro-2H-pyran-4-yl)propanoyl)-4-phenyloxazolidin-2-one (1.1 g, 2.28 mmol) in THF (25.0 mL) and water (8.3.00 mL) was added 30% hydrogen peroxide (0.8 mL, 9.11 mmol) drop wise and stirred for 10 min. A solution of LiOH (109 mg, 4.56 mmol) in water (1.0 mL) was then added dropwise at 0° C. and stirred for 2 h. The reaction mixture was quenched with a solution of sodium sulfite (1.15 g) in 5 mL of water and the resulting mixture was stirred for 30 minutes allowing to warm to room temperature. Sat'd sodium bicarbonate solution (15 mL) was then added and the mixture stirred for 10 minutes. The solvent was removed under reduced pressure and the aqueous was diluted with water (15 mL). The aqueous was washed with DCM (2×25 mL) to remove the auxiliary by-product and then the aqueous layer was acidify to pH~4 with addition of 6N HCl solution. The acidic solution was extracted with ethyl acetate (2×100 mL). The organics were combined, dried over sodium sulfate, filtered, and the filtrate concentrated under reduced pressure to afford the crude product. (602 mg, 78%) The material did not need further purification. MS: m/z=310 (M-N₂+H)⁺ and m/z 338 (M+H)⁺.

Intermediate 23

(2S,3R)-2-azido-3-(4-chlorophenyl)-3-(2,2,6,6-tetramethyltetrahydro-2H-pyran-4-yl)propanoic acid

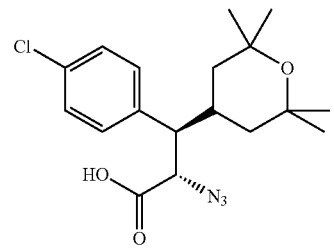 [SMILES: CC1(C)CC([C@H](c2ccc(Cl)cc2)[C@H](N=[N+]=[N-])C(=O)O)CC(C)(C)O1]

Intermediate 23 was prepared using similar procedure for Intermediate 22, using (2,2,6,6-tetramethyltetrahydro-2H-pyran-4-yl)methanol as starting material.

Intermediate 24

(2S,3S)-2-azido-3-(4-chlorophenyl)-4-(4-fluorophenyl)butanoic acid

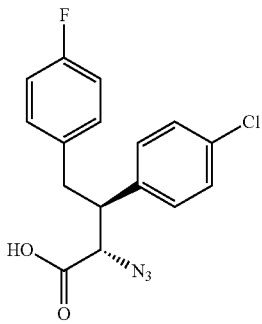 [SMILES: [N-]=[N+]=N[C@H](C(=O)O)[C@@H](Cc1ccc(F)cc1)c1ccc(Cl)cc1]

Step 1. (S,E)-3-(4-(4-fluorophenyl)but-2-enoyl)-4-phenyloxazolidin-2-one

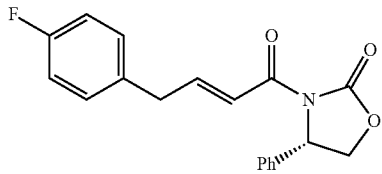 [SMILES: O=C(/C=C/Cc1ccc(F)cc1)N1C(=O)OC[C@@H]1c1ccccc1]

To a stirred solution of (S)-dimethyl 2-oxo-2-(2-oxo-4-phenyloxazolidin-3-yl)ethylphosphonate (1.01 g, 3.07 mmol) in dry THF (20 mL) was added potassium tert-butoxide (3.07 mL, 3.07 mmol, 1.0 M solution in THF) under an atmosphere of $N_2$ at 0° C. over a period of 10 min and the reaction mixture stirred at 0° C. for 30 min. A solution of 2-(4-fluorophenyl)acetaldehyde (1.0 g, 3.07 mmol) in dry THF (10 mL) was added over a period of 5 min and the reaction mixture was stirred at room temperature for 2 h. The reaction mixture was quenched with saturated solution of $NH_4Cl$ (250 mL) and diluted with EtOAc (500 mL). The biphasic system was stirred at room temperature for 10 min and the layers were separated. The organic layer was washed with brine (250 mL), dried ($Na_2SO_4$), filtered and concentrated under reduced pressure. The residue was purified by flash chromatography to give the product (1.1 g, 47%) as a pale yellow solid. MS: m/z=325 (M+H$^+$).

Step 2. (S)-3-((R)-3-(4-chlorophenyl)-4-(4-fluorophenyl)butanoyl)-4-phenyloxazolidin-2-one

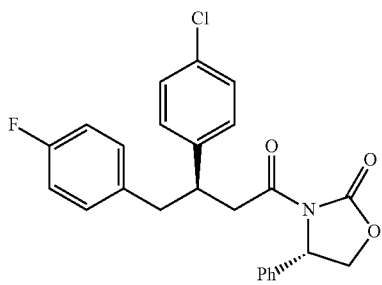 [SMILES: O=C(C[C@@H](Cc1ccc(F)cc1)c1ccc(Cl)cc1)N1C(=O)OC[C@@H]1c1ccccc1]

To a precooled (−40° C.) solution of copper (I) bromide methylsulfide complex (1.04 g, 5.076 mmol), in dry THF (120 mL), was added dimethyl sulfide (5 mL), followed by a solution of 4-chlorophenyl magnesium bromide (13.5 mL, 0.5M solution) and stirred for 1 h. A solution of (S,E)-3-(4-(4-fluorophenyl)but-2-enoyl)-4-phenyloxazolidin-2-one (1.1 g, 3.38 mmol) in dry THF (40.0 mL) was added slowly at −45° C. and stirred for 3 h. Quenched the reaction mixture with saturated solution of $NH_4Cl$ (150 mL) and extracted with EtOAc (200 mL). The EtOAc extract was washed with brine (100 mL), dried ($Na_2SO_4$), filtered and concentrated under reduced pressure. The residue was purified by 120 g $SiO_2$ column using a gradient elution of 0-20% EtOAc in hexanes. Fractions containing product were combined and the solvents were removed in vacuo to provide the product (0.89 g, 60%) pale yellow solid. MS: m/z=438 (M+H$^+$).

Step 3. (S)-3-((2R,3R)-2-azido-3-(4-chlorophenyl)-4-(4-fluorophenyl)butanoyl)-4-phenyloxazolidin-2-one

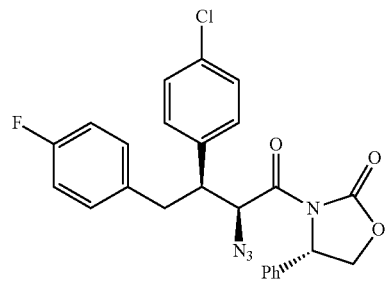 [SMILES: [N-]=[N+]=N[C@H](C(=O)N1C(=O)OC[C@@H]1c1ccccc1)[C@@H](Cc1ccc(F)cc1)c1ccc(Cl)cc1]

To a precooled (−78° C.) solution (S)-3-((R)-3-(4-chlorophenyl)-4-(4-fluorophenyl)butanoyl)-4-phenyloxazolidin-2-one (0.89 g, 1.85 mmol) in dry THF (15 mL) was added NaHMDS (2.87 mL, 1M solution in THF) slowly and the resulting solution was stirred for 1 h at −75° C. when trisyl azide (0.69 g, 2.23 mmol) was added as a solid. To the cold solution was added tetramethyl ammonium acetate (4.95 g, 3.71 mmol) and acetic acid (0.67 g, 11.15 mmol). The cooling bath was removed and the reaction mixture was stirred at room temperature for an additional for 1 h. Diluted the reaction mixture with water (15 mL) and extracted with EtOAc (50 mL). The organic layer was washed with brine (20 mL), dried ($Na_2SO_4$), filtered and concentrated under reduced pressure. The residue was purified by 80 g $SiO_2$ column using a gradient elution of 0-20% EtOAc in hexanes. Fractions containing product were combined and the solvents were removed in vacuo to provide the product (0.69 g, 71%) pale yellow solid. MS: m/z=479 (M+H$^+$).

Step 4. (2R,3R)-2-Azido-3-(4-chlorophenyl)-4-(4-fluorophenyl)butatanoic acid

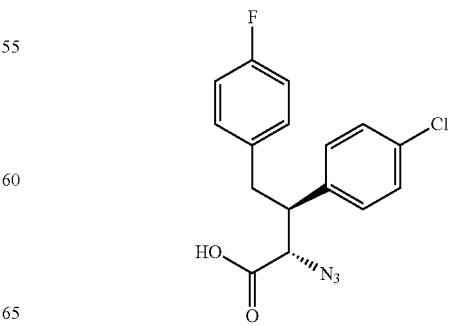

To a precooled (0° C.) solution of (S)-3-((2R,3R)-2-azido-3-(4-chlorophenyl)-4-(4-fluorophenyl)butanoyl)-4-phenyloxazolidin-2-one (0.69 g, 1.45 mmol) in a mixture of THF (15 mL), and water (10 mL) added 30% hydrogen peroxide solution (0.5 mL) and stirred for 5 min. A solution of LiOH (104 mg, 4.35 mmol) in water (0.5 mL) was added at 0° C. and stirred for 3 h. The reaction mixture was quenched with saturated solution of sodium sulfite (10.0 mL) and stirred for at room temperature for additional 20 min. The reaction mixture was acidified to pH 3 using 6N HCl and extracted with EtOAc (50 mL). The organic layer was dried (Na$_2$SO$_4$), filtered and concentrated under reduced pressure. The residue was purified by 12 g SiO$_2$ column using a gradient elution of 0-20% EtOAc in hexanes. Fractions containing product were combined and the solvents were removed in vacuo to provide the product (320 mg, 66%) pale yellow gum. MS: m/z=334 (M−H$^+$).

Intermediate 25

(2S,3S)-2-azido-3-(3-chlorophenyl)-3-(5-fluoropyridin-3-yl)propanoic acid

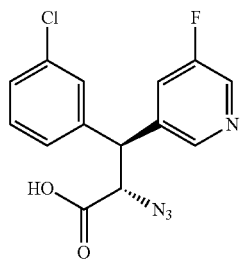 [SMILES: [N-]=[N+]=N[C@H](C(=O)O)[C@H](c1cncc(F)c1)c1cccc(Cl)c1]

The title compound was prepared using the procedures given for Intermediate 10 using 5-fluoronicontinaldehyde in place of 6-methoxyniconinaldehyde in step 1 and 3-chlorophenylmagnesium bromide in place of 4-chlorophenylmagnesium bromide in step 2.

Intermediate 26

(S)-2-azido-2-(4-(3,5-difluorophenyl)tetrahydro-2H-pyran-4-yl)acetic acid

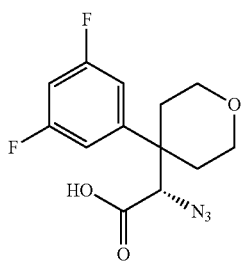

The title compound was prepared using the procedures given for Intermediate 19 using 3,5-difluorophenylmagnesium bromide in place of 4-chlorophenylmagnesium bromide.

Intermediate 27

(2S,3R)-2-azido-3-(3,5-difluorophenyl)-3-(tetrahydro-2H-pyran-4-yl)propanoic acid

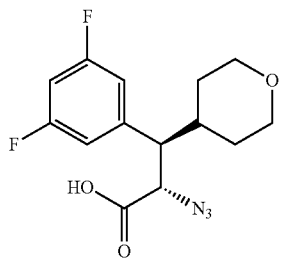 [SMILES: [N-]=[N+]=N[C@H](C(=O)O)[C@@H](c1cc(F)cc(F)c1)C1CCOCC1]

The title compound was prepared from tetrahydropyran-4-carboxaldehyde and 3,5-difluorophenylmagnesium bromide using the procedures given for Intermediate 11.

Intermediate 28

(2S,3R)-2-azido-3-(3,4-difluorophenyl)-3-(tetrahydro-2H-pyran-4-yl)propanoic acid

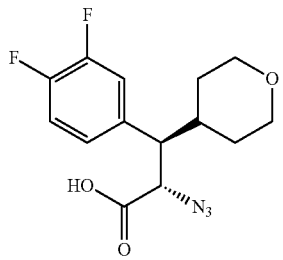 [SMILES: [N-]=[N+]=N[C@H](C(=O)O)[C@@H](c1ccc(F)c(F)c1)C1CCOCC1]

The title compound was prepared from tetrahydropyran-4-carboxaldehyde and 3,4-difluorophenylmagnesium bromide using the procedures given for Intermediate 11.

Intermediate 29

(S)-2-azido-2-(4-(3,4-difluorophenyl)tetrahydro-2H-pyran-4-yl)acetic acid

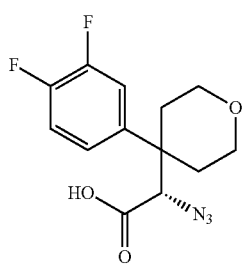 [SMILES: [N-]=[N+]=N[C@H](C(=O)O)C1(c2ccc(F)c(F)c2)CCOCC1]

The title compound was prepared using the procedures given for Intermediate 19 using 3,4-difluorophenylmagnesium bromide in place of 4-chlorophenylmagnesium bromide.

Intermediate 30

(S)-2-azido-2-((2R,4r,6S)-4-(4-chlorophenyl)-2,6-dimethyltetrahydro-2H-pyran-4-yl)acetic acid

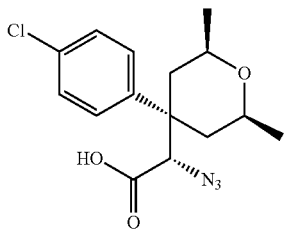 [SMILES: C[C@@H]1C[C@](c2ccc(Cl)cc2)([C@H](N=[N+]=[N-])C(=O)O)C[C@H](C)O1]

Step 1. (2R,6S)-4-(4-chlorophenyl)-2,6-dimethyltetrahydro-2H-pyran-4-ol

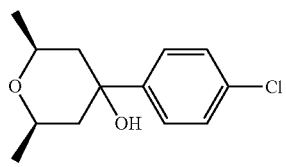 [SMILES: C[C@@H]1CC(O)(c2ccc(Cl)cc2)C[C@H](C)O1]

n-BuLi (30 ml, 75 mmol) was dropwise added to a solution of 4-chlorobromobenzene (14.24 g, 75 mmol) in THF (200 ml) at −78 C and then stirred for 30 min. (2R,6S)-2,6-Dimethyldihydro-2H-pyran-4(3H)-one (8 g, 62.5 mmol) was added dropwise to the solution and then stirred additional 1 h. The reaction mixture was quenched with saturated NH$_4$Cl, and extracted with EtOAc three times, the combined organic extracts were washed with brine, dried over Na$_2$SO$_4$, concentrated in vacuo. The residual was purified by chromatography on silica gel (PE:EA=20:1) to afford the title compound (4.5 g).

Step 2. (2R,4s,6S)-4-allyl-4-(4-chlorophenyl)-2,6-dimethyltetrahydro-2H-pyran

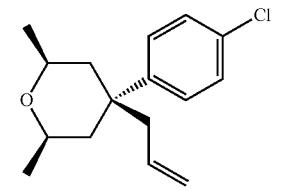 [SMILES: C=CC[C@@]1(c2ccc(Cl)cc2)C[C@@H](C)O[C@@H](C)C1]

To an ice-cooled solution of (2R,6S)-4-(4-chlorophenyl)-2,6-dimethyltetrahydro-2H-pyran-4-ol (4.5 g, 18.75 mmol) and allyltrimethylsilane (3.75 ml, 22.5 mmol) in DCM (50 ml) was added BF$_3$.OEt$_2$ (3 ml, 22.5 mmol). The resulting mixture was stirred at room temperature for 15 h. Then the reaction mixture was concentrated in vacuo and partitioned between H$_2$O and EtOAc, the organic layers were washed successively with saturated sodium bicarbonate solution and brine, dried over Na$_2$SO$_4$ and evaporated in vacuo. The residual was purified by pre-HPLC to afford the title compound (2.8 g). MS (ESI) m/z (M+H)$^+$: 265.

Step 3. 2-((2R,4s,6S)-4-(4-chlorophenyl)-2,6-dimethyltetrahydro-2H-pyran-4-yl)acetic acid

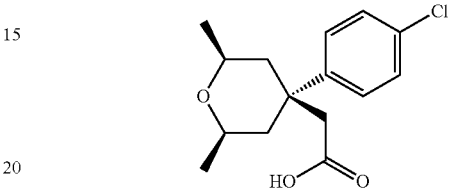

To a solution of (2R,4s,6S)-4-allyl-4-(4-chlorophenyl)-2,6-dimethyltetrahydro-2H-pyran (2.5 g, 9.47 mmol) in acetone (50 ml) was added a solution of KMnO$_4$ (838 mg, 5.303 mmol) and NaIO$_4$ (7.17 g, 33.523 mmol) in water (50 ml) at room temperature and the mixture was stirred for 2 h at room temperature. The precipitate was removed by filtration and the acetone was removed under reduced pressure. The residue was basified to PH 13 by addition of 1M aqueous sodium hydroxide, and then extracted with ether. The aqueous phase was acidified to PH 1 by addition of aqueous 1M HCl and then extracted with EtOAc. The combined organic layers were washed with brine, dried over Na$_2$SO$_4$ and then concentrated in vacuo to afford the title compound. $^1$H NMR (400 MHz, CDCl$_3$) 7.34-7.27 (m, 2H), 7.25-7.18 (m, 2H), 3.59-3.35 (m, 2H), 2.47 (s, 4H), 1.58-1.38 (m, 2H), 1.17 (d, J=6.3 Hz, 6H).

Step 4. (S)-3-(2-((2R,4s,6S)-4-(4-chlorophenyl)-2,6-dimethyltetrahydro-2H-pyran-4-yl)acetyl)-4-phenyloxazolidin-2-one

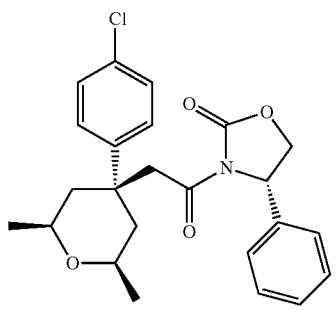 [SMILES: C[C@@H]1C[C@@](CC(=O)N2C(=O)OC[C@@H]2c2ccccc2)(c2ccc(Cl)cc2)C[C@H](C)O1]

To a solution of 2-((2R,4s,6S)-4-(4-chlorophenyl)-2,6-dimethyltetrahydro-2H-pyran-4-yl)acetic acid (1.8 g, 6.383 mmol) in DCM (20 ml) was added DMF (0.5 ml) at 0 C under N$_2$. After 5 minutes, oxalyl chloride (973 mg, 7.66 mmol) was added to the mixture, after 2 h, the mixture was concentrated and used directly. A solution of chiral control groups in dry THF (20 ml) was cooled to −10° C. Then nBuLi (3.06 ml, 7.65 mmol) was added dropwise thereto, and stirred for 30 min. A solution of acyl chloride (1.914 g, 6.38 mmol) in THF (10 ml) was added dropwise to anion. The resulting mixture was stirred for 1 hr at 0° C. The reaction was quenched with 20% NH$_4$Cl and extracted with EtOAc. The combined organics were washed with water, aqueous NaHCO$_3$ and brine. It was dried over anhydrous Na$_2$SO$_4$ and concentrated in vaccuo to give a solid. The solid was purified by column chromatograph on silicon to afford the title compound (2.4 g). MS (ESI) m/z (M+H)$^+$: 428.

Step 5. (S)-3-((S)-2-azido-2-((2R,4r,6S)-4-(4-chlorophenyl)-2,6-dimethyltetrahydro-2H-pyran-4-yl) acetyl)-4-phenyloxazolidin-2-one

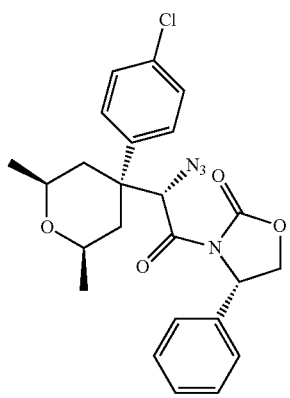 [SMILES: C[C@@H]1C[C@](c2ccc(Cl)cc2)([C@H](N=[N+]=[N-])C(=O)N2C(=O)OC[C@@H]2c2ccccc2)C[C@H](C)O1]

A solution of NaHMDS in 10 mL dry THF was cooled to −78° C. Then it was added dropwise to a solution of (S)-3-(2-((2R,4s,6S)-4-(4-chlorophenyl)-2,6-dimethyltetrahydro-2H-pyran-4-yl)acetyl)-4-phenyloxazolidin-2-one (2.4 g, 5.621 mmol) in 40 ml dry THF at −78° C. Then the resulting mixture was stirred for 45 min at this temperature. TosN$_3$ was added thereto. The resulting mixture was stirred for 15 min. Then HOAc and Bu$_4$NOAc were added. The bath was removed and stirred overnight. It was partitioned between EtOAc and brine. The organic layer was washed with saturated NaHCO$_3$ and brine. The organics was dried over Na$_2$SO$_4$ and concentrated in vaccuo to give an oil. Then it was purified by column chromatography on silicon (PE: EA=10:1) to afford the title compound (0.78 g).

Step 6. (S)-2-azido-2-((2R,4r,6S)-4-(4-chlorophenyl)-2,6-dimethyltetrahydro-2H-pyran-4-yl)acetic acid A solution of (S)-3-((S)-2-azido-2-((2R,4r,6S)-4-(4-chlorophenyl)-2,6-dimethyltetrahydro-2H-pyran-4-yl)acetyl)-4-phenyloxazolidin-2-one (780 mg, 1.667 mmol) in 15 ml THF and 5 ml water was cooled in an ice bath. Add hydrogen peroxide, then solid LiOH. Stir cold for 40 min. Dissolve sodium sulfite in water and add to reaction. Then add NaHCO$_3$ solution and stir for 5 min. Rotovap off THF and dilute with water. Wash with DCM to remove the chiral auxiliary. Acidify aqueous with 6N HCl and extracted with EtOAc. Dry combined organics over Na$_2$SO$_4$ and rotovap off solvent to afford the title compound (350 mg). $^1$H NMR (400 MHz, CDCl$_3$) 7.31-7.25 (m, 2H), 7.19-7.10 (m, 2H), 3.95-3.84 (m, 1H), 3.45-3.24 (m, 2H), 2.49-2.29 (m, 2H), 1.66-1.41 (m, 2H), 1.13 (d, J=5.9 Hz, 6H)

Intermediate A (S)-tert-Butyl 3-(2-amino-6-fluorophenethyl)-4-(phenylsulfonyl)piperazine-1-carboxylate

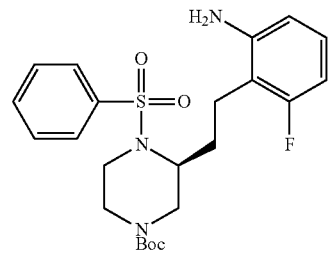 [SMILES: CC(C)(C)OC(=O)N1CCN(S(=O)(=O)c2ccccc2)[C@@H](CCc2c(N)cccc2F)C1]

Step 1. tert-Butyl 3-(hydroxymethyl)-4-(phenylsulfonyl)piperazine-1-carboxylate

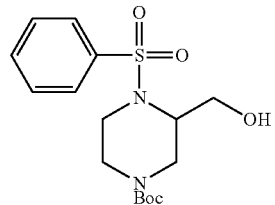 [SMILES: CC(C)(C)OC(=O)N1CCN(S(=O)(=O)c2ccccc2)C(CO)C1]

To a solution of tert-butyl 3-(hydroxymethyl)piperazine-1-carboxylate (16.0 g, 73.9 mmol) in THF/H$_2$O (80/25 mL) was added MgO (14.0 g, 369.8 mmol) and the mixture was stirred for 30 min. Benzene sulfonyl chloride (19.5 g, 110.8 mmol) was added in dropwise manner over a period of 20 min and the reaction mixture was stirred at room temperature for 16 h. The reaction mixture was diluted with EtOAc and filtered through a pad of celite and washed with EtOAc (500 mL). The filtrate was concentrated under reduced pressure to give the product (24.0 g, 94%) as colorless oil. MS: m/z=357 (M+H$^+$).

Step 2. tert-Butyl 3-formyl-4-(phenylsulfonyl)piperazine-1-carboxylate

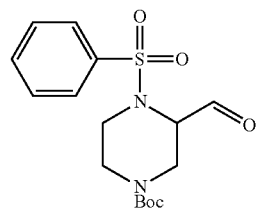 [SMILES: CC(C)(C)OC(=O)N1CCN(S(=O)(=O)c2ccccc2)C(C=O)C1]

To a solution of tert-butyl 3-(hydroxymethyl)-4-(phenylsulfonyl)piperazine-1-carboxylate (24.0 g, 66.8 mmol) in CH$_2$Cl$_2$ (200 mL) at 0° C. was added Dess-Martin periodinane (42.4 g, 100 mmol) in portion-wise over a period of 10 min, and the reaction mixture was stirred at 0° C. for 1 h. The reaction mixture was quenched with a saturated solution of NaHCO₃ (50 mL) and filtered through a pad of celite. The filtrate was extracted with CH₂Cl₂ (2×500 mL) and the combined extracts were dried (Na₂SO₄), filtered and concentrated under reduced pressure. The residue was purified by 330 g SiO₂ column using a gradient elution of 0-10% EtOAc in hexanes. Fractions containing the product were combined and concentrated under reduced pressure to provide the product (15.0 g, 86%) as colorless oil. MS: m/z=355 (M+H⁺).

Step 3. Synthesis of (2-fluoro-6-nitrobenzyl)triphenylphosphonium bromide salt

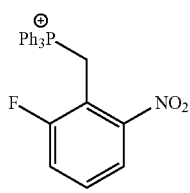

To a solution of 2-(bromomethyl)-1-fluoro-3-nitrobenzene (14.0 g, 60.3 mmol) in acetonitrile (150 mL) was added triphenyl phosphine (27.0 g, 102 mmol) and heated at 85° C. for 6 h. The reaction mixture was cooled to room temperature and concentrated under reduced pressure. The residue was diluted with tert-butyl methyl ether and stirred for 30 min. The precipitated solids were collected by filtration using Buchner funnel under reduced pressure and dried under vacuum to provide the product (32.0 g) as a yellow solid.

Step 4. (E)-tert-Butyl 3-(2-fluoro-6-nitrostyryl)-4-(phenylsulfonyl)piperazine-1-carboxylate

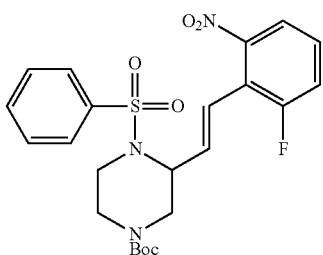 [SMILES: CC(C)(C)OC(=O)N1CCN(S(=O)(=O)c2ccccc2)C(/C=C/c2c(F)cccc2[N+](=O)[O-])C1]

To a solution of (2-fluoro-6-nitrobenzyl)triphenylphosphonium bromide salt (21.2 g, 42.8 mmol) in 1,2-dimetoxyethane/acetonitrile (300/80 mL) was added 18-crown-6 (1.10 g, 4.20 mmol) followed by potassium carbonate (11.6 g, 84.0 mmol) and stirred for 30 min. A solution of ten-butyl 3-formyl-4-(phenylsulfonyl)piperazine-1-carboxylate (15.0 g, 42.0 mmol) in 40 mL DME was added slowly and reaction mixture was stirred at room temperature for 16 h. The reaction mixture was filtered through a pad of celite and the pad was washed with EtOAc (1 L). The filtrate was concentrated under reduced pressure. The residue was purified by 120 g SiO₂ column using a gradient elution of 10-20% EtOAc in hexanes. Fractions containing the compound were combined and concentrated under reduced pressure to provide the product (7.00 g, 94%) as a racemic mixture. The product was carried into next step without purification.

Step 5. (S)-tert-Butyl 3-(2-amino-6-fluorophenethyl)-4-(phenylsulfonyl)piperazine-1-carboxylate

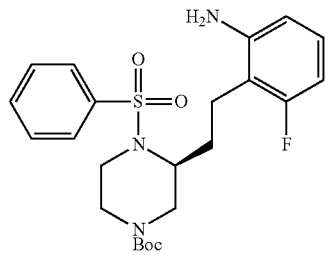 [SMILES: CC(C)(C)OC(=O)N1CCN(S(=O)(=O)c2ccccc2)[C@@H](CCc2c(N)cccc2F)C1]

A solution of (E)-tert-butyl 3-(2-fluoro-6-nitrostyryl)-4-(phenylsulfonyl)piperazine-1-carboxylate (7.00 g, 14.2 mmol) in EtOAc (60 mL) was de-gassed with N₂ (g) for 10 min, and palladium hydroxide on carbon (3.00 g) was added and the reaction mixture was hydrogenated at 1 atm pressure at room temperature for 24 h. The reaction mixture was diluted with EtOAc and filtered through a pad of celite and the pad was washed with EtOAc (500 mL). The filtrate was concentrated under reduced pressure and the residue was purified by 120 g SiO₂ column using a gradient elution of 20-50% EtOAc in hexanes. Fractions containing the product were combined and concentrated under reduced pressure to provide the product (5.00 g, 75%) as a racemic mixture. The racemic mixture was purified by chiral column (AD), 30% IPA-heptane as eluent. Fractions containing the pure compounds were combined and concentrated under reduced pressure to obtain (2.00 g) of the desired (S)-enantiomer as an off-white solid and (2.30 g) of the undesired (R)-enantiomer as a pale yellow solid.

Intermediate B (S)-tert-Butyl 3-(2-amino-6-fluoropyridin-4-yl)ethyl)-4-(phenylsulfonyl)piperazine-1-carboxylate

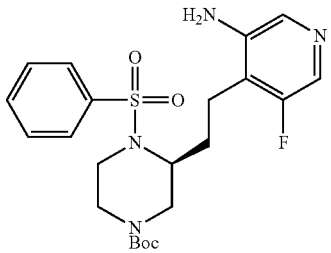 [SMILES: CC(C)(C)OC(=O)N1CCN(S(=O)(=O)c2ccccc2)[C@@H](CCc2c(N)cncc2F)C1]

Step 1. tert-Butyl 3-(2,2-dibromovinyl)-4-(phenylsulfonyl)piperizine-1-carboxylate

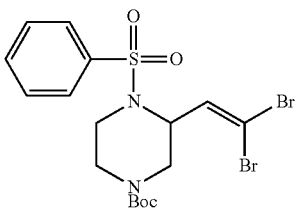 [SMILES: CC(C)(C)OC(=O)N1CCN(S(=O)(=O)c2ccccc2)C(C=C(Br)Br)C1]

To a solution of the product from Step 2 of Intermediate A (8.5 g, 24.01 mmol) in CH₂Cl₂ (200 mL) was added CBr₄

(15.9 g, 48.02 mmol), PPh₃ (25.0 g, 96.04 mmol) and stirred for 1 h at room temperature. The reaction mixture was quenched with H₂O and extracted with CH₂Cl₂ (2×200 mL). The combined extracts were dried (Na₂SO₄), filtered, and concentrated under reduced pressure. The residue was purified by 80 g SiO₂ column using a gradient elution of 0-30% EtOAc in hexanes. Fractions containing product were combined and the solvents were removed in vacuo to provide the product (8.1 g, 70%) as a pale yellow solid.

Step 2. (S)-tert-Butyl 3-ethynyl-4-(phenylsulfonyl)piperazine-1-carboxylate

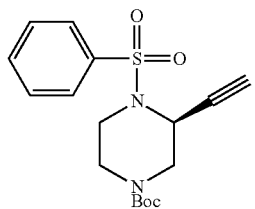 [SMILES: C#C[C@H]1CN(C(=O)OC(C)(C)C)CCN1S(=O)(=O)c1ccccc1]

To a solution of tert-butyl 3-(2,2-dibromovinyl)-4-(phenylsulfonyl)piperizine-1-carboxylate (7.00 g, 15.88 mmol) in DMSO (150 mL) was added K₂CO₃ and stirred for 16 h at 120° C. The reaction mixture was diluted with brine solution (100 mL) and extracted with EtOAc (2×200 mL). The combined extracts were dried (Na₂SO₄), filtered and concentrated under reduced pressure. The residue was purified by 40 g SiO₂ column using a gradient elution of 0-40% EtOAc in hexanes. Fractions containing product were combined and the solvents were removed in vacuo to provide the product (0.75 g, 15%) as colorless oil. MS: m/z=351 (M+H⁺).

Step 3. (S)-tert-Butyl 3 ((3-amino-5-fluoropyridin-4-yl)ethynyl)-4-(phenylsulfonyl)piperizine-1-carboxylate

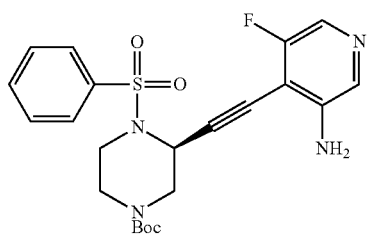 [SMILES: CC(C)(C)OC(=O)N1CCN(S(=O)(=O)c2ccccc2)[C@@H](C#Cc2c(N)cncc2F)C1]

To a solution of (S)-tert-butyl 3-ethynyl-4-(phenylsulfonyl)piperazine-1-carboxylate
(0.75 g, 2.14 mmol) in CH₃CN (15 mL) was added 5-fluoro-4-iodopyridin-3-amine (0.56 g, 2.354 mmol) and Et₃N (1.49 mL, 2.14 mmol). Then the reaction mixture was purged with N₂ for 15 min and added CuI (40 mg, 0.214 mmol), PdCl₂(PPh₃)₂ (105 mg, 0.149 mmol) and stirred at 70° C. for 3 h. The reaction mixture was cooled to room temperature and diluted with EtOAc (50 mL), washed with brine (50 mL), dried (Na₂SO₄), filtered and concentrated under reduced pressure. The residue was purified by 24 g SiO₂ column using a gradient elution of 0-70% EtOAC in hexanes. Fractions containing product were combined and the solvents were removed in vacuo to provide the product (0.65 g, 66%) as tan oil. MS: m/z=461 (M+H⁺).

Step 4. (S)-tert-Butyl 3((3-amino-5-fluoropyridin-4-yl)ethyl)-4-(phenylsulfonyl)piperizine-1-carboxylate

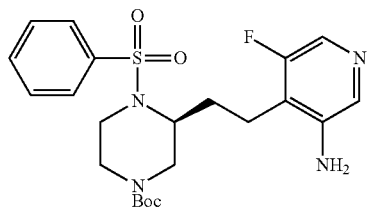 [SMILES: CC(C)(C)OC(=O)N1CCN(S(=O)(=O)c2ccccc2)[C@@H](CCc2c(N)cncc2F)C1]

A solution of (S)-tert-butyl 3 ((3-amino-5-fluoropyridin-4-yl)ethynyl)-4-(phenylsulfonyl)piperizine-1-carboxylate (0.65 g, 14.2 mmol) in EtOAc (25 mL) was de-gassed with N₂ (g) for 10 min, and palladium hydroxide on carbon (3.00 g) was added and the reaction mixture was hydrogenated at 1 atm pressure at room temperature for 24 h. The reaction mixture was diluted with EtOAc (50 mL) and filtered through a pad of celite and the pad was washed with EtOAc (200 mL). The filtrate was concentrated under reduced pressure and the residue was purified by 12 g SiO₂ column using a gradient elution of 20-80% EtOAc in hexane. Fractions containing product were combined and the solvents were removed in vacuo to provide the product (0.64 g, 97%) as an off-white solid (racemic mixture). MS: m/z=465 (M+H⁺).

Intermediate C (S)-tert-butyl 4-(2-amino-6-fluorophenethyl)-2,2-dimethyloxazolidine-3-carboxylate

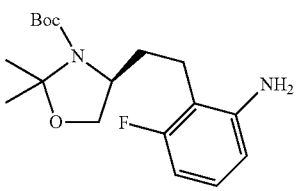 [SMILES: CC(C)(C)OC(=O)N1[C@@H](CCc2c(N)cccc2F)COC1(C)C]

Step 1: (S,Z)-tert-butyl 4-(2-fluoro-6-nitrostyryl)-2,2-dimethyloxazolidine-3-carboxylate

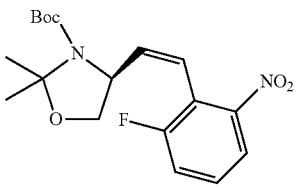 [SMILES: CC(C)(C)OC(=O)N1[C@@H](/C=C\c2c(F)cccc2[N+](=O)[O-])COC1(C)C]

To a stirred solution of (2-fluoro-6-nitrobenzyl)triphenyl phosphonium bromide (10.2 g, 20.5 mmol) in DME (80 mL) and acetonitrile (140 mL) was added K₂CO₃ (2.37 g, 17.1 mmol), 18-crown-6 (0.45 g, 1.71 mmol) and the reaction mixture was stirred for 40 min at room temperature. A solution of (R)-tert-butyl 4-formyl-2,2-dimethyloxazolidine-3-carboxylate (3.21 g, 17.1 mmol) in acetonitrile (10 mL) was added and the reaction mixture was stirred at room temperature for 16 h. The reaction mixture was concentrated under reduced pressure and the residue was triturated with toluene (120 mL). The precipitate was filtered and washed with additional amounts of toluene (60 mL), and the filtrate was concentrated under reduced pressure. The residue obtained was diluted with EtOAc (200 mL), washed with saturated solution of sodium metabisulfite solution (200 mL), brine (100 mL), dried (Na₂SO₄), filtered and concentrated under reduced pressure. The residue was purified by 120 g SiO₂ column using a gradient elution of 0-20% EtOAc in hexanes. Fractions containing product were combined and the solvents were removed in vacuo to provide the product (3.7 g, 72%) as a yellow viscous liquid. MS: m/z=367 (M+H⁺)

Step 2: (S)-tert-butyl 4-(2-amino-6-fluorophenethyl)-2,2-dimethyloxazolidine-3-carboxylate

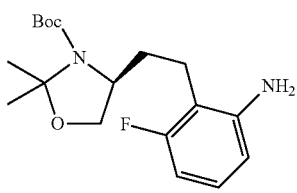 [SMILES: CC(C)(C)OC(=O)N1[C@@H](CCc2c(N)cccc2F)COC1(C)C]

To a stirred solution of (S,Z)-tert-butyl 4-(2-fluoro-6-nitrostyryl)-2,2dimethyloxazolidine-3-carboxylate (3.7 g, 10.1 mmol) in EtOAc (37 mL) was added 20% palladium hydroxide on carbon (0.37 g) and the mixture was hydrogenated at 1 atm pressure for 36 h. The reaction mixture was filtered through a celite pad and the celite pad was washed with EtOAc (50 mL). The filtrate was concentrated under reduced pressure and the residue was purified by 80 g SiO₂ column using a gradient elution of 0-30% EtOAc in hexanes. Fractions containing product were combined and the solvents were removed in vacuo to provide the product (3.0 g, 88%) as a yellow gum. MS: m/z=339 (M+H⁺)

Intermediate D (S)-tert-butyl 3-(2-(3-amino-5-fluoropyridin-4-yl)ethyl)-4-(cyclopropylsulfonyl)piperazine-1-carboxylate

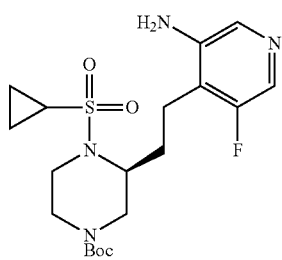 [SMILES: CC(C)(C)OC(=O)N1CCN(S(=O)(=O)C2CC2)[C@@H](CCc2c(N)cncc2F)C1]

Intermediate D was prepared using the procedure for Intermediate B, using cyclopropylsulfonyl chloride.

Intermediate E (S)-tert-butyl 3-(2-(3-amino-5-fluoropyridin-4-yl)ethyl)-4-(pyrrolidin-1-ylsulfonyl)piperazine-1-carboxylate

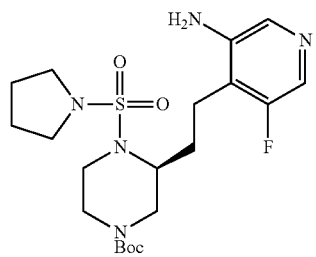 [SMILES: CC(C)(C)OC(=O)N1CCN(S(=O)(=O)N2CCCC2)[C@@H](CCc2c(N)cncc2F)C1]

Intermediate E was prepared using the procedure for Intermediate B, using pyrrolidine-1-sulfonyl chloride.

Intermediate F (S)-tert-butyl 4-(2-(3-amino-5-fluoropyridin-4-yl)ethyl)-2,2-dimethyloxazolidine-3-carboxylate

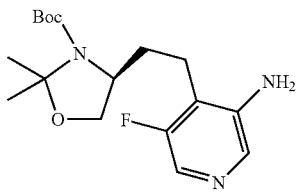 [SMILES: CC(C)(C)OC(=O)N1[C@@H](CCc2c(N)cncc2F)COC1(C)C]

Step 1. (S)-tert-butyl 4-ethynyl-2,2-dimethyloxazolidine-3-carboxylate

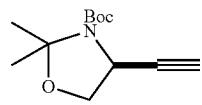

Prepared according to the procedure in *Tetrahedron*, 2011, 67, 6547.

Step 2. (S)-tert-butyl 4-((3-amino-5-fluoropyridin-4-yl)ethynyl)-2,2-dimethyloxazolidine-3-carboxylate

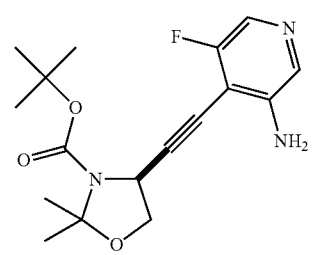 [SMILES: CC(C)(C)OC(=O)N1[C@@H](C#Cc2c(N)cncc2F)COC1(C)C]

Bis(triphenylphosphine)palladium(II) chloride (1.389 g, 1.979 mmol) and Copper (I) Iodide (0.539 g, 2.83 mmol) were added to a solution of (S)-tert-butyl 4-ethynyl-2,2-dimethyloxazolidine-3-carboxylate (6.37 g, 28.3 mmol), 5-fluoro-4-iodopyridin-3-amine (6.73 g, 28.3 mmol), and TEA (118 ml, 848 mmol) in Acetonitrile (141 ml). The reaction was heated at 70° C. for 2 hours. The reaction was quenched with aqueous potassium phosphate monobasic (saturated) and the mixture was extracted with ethyl acetate (×3). The combined organic fractions were dried (MgSO4), filtered and the solvent was evaporated under reduced pressure. Purification on silica (750 g) 0-100% EtOAc/hexanes afford (5)-tert-butyl 4-((3-amino-5-fluoropyridin-4-yl)ethynyl)-2,2-dimethyloxazolidine-3-carboxylate (7.44 g, 22.18 mmol, 78% yield) as a viscous oil, LCMS shows 78% pure. MS: m/z=279 (M-$^t$Bu).

Step 3. (S)-tert-butyl 4-(2-(3-amino-5-fluoropyridin-4-yl)ethyl)-2,2-dimethyloxazolidine-3-carboxylate Platinum(IV) Oxide (2.52 g, 11.09 mmol) and Pearlman's Catalyst (2.337 g, 3.33 mmol) were added to a nitrogen degassed solution of (S)-tert-butyl 4-((3-amino-5-fluoropyridin-4-yl)ethynyl)-2,2-dimethyloxazolidine-3-carboxylate (7.44 g, 22.18 mmol) in Trifluoroethanol (111 ml). The reaction was shaken at 50 psi hydrogen on the Parr for 48 hrs. The reaction was purged with nitrogen then filtered through a pad of celite and concentrated in vacuo. Purification on silica (330 g) eluting with a gradient of 0-100% EtOAc/hexanes afford (S)-tert-butyl 4-(2-(3-amino-5-fluoropyridin-4-yl)ethyl)-2,2-dimethyloxazolidine-3-carboxylate (5.09 g, 15.00 mmol, 67.6% yield) as a tan solid, LCMS shows the compound is 100% pure. MS: m/z=340 (M+H$^+$). Analysis by Chiral HPLC on an OJ-H column 20% IPA/hexanes shows ~25:1 in favour of expected stereochemistry rt 6.92 min=desired, rt 9.06 min=undesired.

Intermediate G (S)-tert-butyl 3-(2-(3-((S)-3-(3,5-difluorophenyl)-3-(4-fluorophenyl)propanamido)-5-fluoropyridin-4-yl)ethyl)piperazine-1-carboxylate

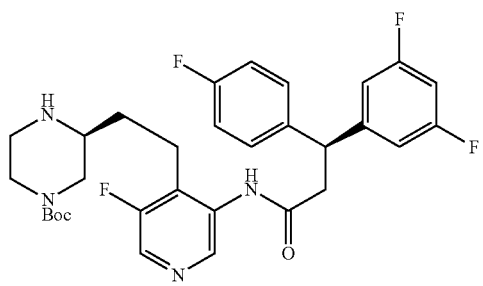 [SMILES: CC(C)(C)OC(=O)N1CCN[C@@H](CCc2c(F)cncc2NC(=O)C[C@@H](c2ccc(F)cc2)c2cc(F)cc(F)c2)C1]

Step 1. (R)-1-benzyl 4-tert-butyl 2-(hydroxymethyl)piperazine-1,4-dicarboxylate

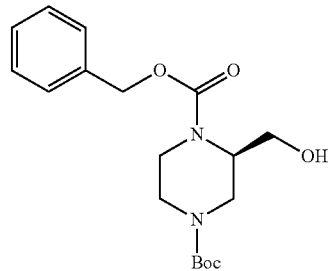 [SMILES: CC(C)(C)OC(=O)N1CCN(C(=O)OCc2ccccc2)[C@@H](CO)C1]

R)-1-Boc-3-(Hydroxymethyl)piperazine (10 g, 46.2 mmol) was dissolved in a mixture of DCM (180 ml) and sat. NaHCO3 (180 ml). CBZ—Cl (6.60 ml, 46.2 mmol) was dissolved in DCM (15 ml) and added dropwise with vigorous stirring. The mixture was stirred for 2.5 hours. The layers were separated and the aqueous phase was extracted with DCM. The combined organic phases were washed with brine, dried over Na2SO4 and the solvent was removed in vacuo to give an oil which was used in the next step without purification.

Step 2. (R)-1-benzyl 4-tert-butyl 2-formylpiperazine-1,4-dicarboxylate

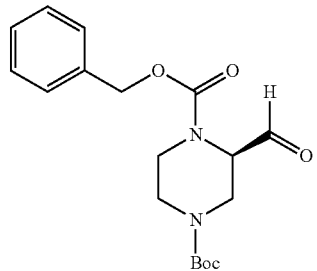 [SMILES: CC(C)(C)OC(=O)N1CCN(C(=O)OCc2ccccc2)[C@@H](C=O)C1]

Dess-Martin Periodinane (23.53 g, 55.5 mmol) was added to a 0° C. solution of (R)-1-benzyl 4-tert-butyl 2-(hydroxymethyl)piperazine-1,4-dicarboxylate (16.2 g, 46.2 mmol) in DCM (460 ml). The reaction was stirred at 0° C. for 3 h, then filtered through a fine scintered glass funnel to remove the white solids. The filtrate was diluted with water and the layers were separated. The aqeuous layer was extracted with DCM. The combined organic extracts were washed with brine then dried over Na2SO4, filtered and the solvents were removed in vacuo. The crude product was purified on a 330 g silica column running a 0-50% EtOAc/hexane gradient over 70 min. Fractions containing product were combined and the solvents were removed in vacuo to give a colorless oil.

Step 3. (S)-1-benzyl 4-tert-butyl 2-(2,2-dibromovinyl)piperazine-1,4-dicarboxylate

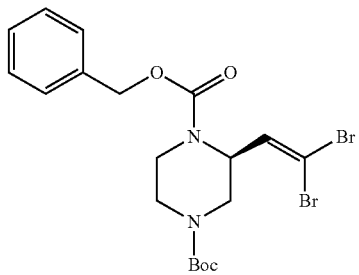 [SMILES: CC(C)(C)OC(=O)N1CCN(C(=O)OCc2ccccc2)[C@@H](C=C(Br)Br)C1]

Triphenylphosphine (29.2 g, 111 mmol) and carbon tetrabromide (18.47 g, 55.7 mmol) were added to a 0° C. solution of (R)-1-benzyl 4-tert-butyl 2-formylpiperazine-1,4-dicarboxylate (9.7 g, 27.8 mmol) in DCM (200 ml). The reaction was stirred for 1 hour at 0° C. and then the cooling bath was removed and the progress of the reaction was monitored by TLC. When the aldehyde was consumed, water (100 mL) was added and the layers were separated. The aqueous phase was extracted with DCM. The combined organic extracts were dried over Na2SO4, filtered and the solvent was removed in vacuo. The crude product was purified on a 120 g silica column running a 0-50% EtOAc/hexane gradient over 40 min. Fractions containing product were combined and the solvents were removed in vacuo to give a colorless oil. LCMS: m/z=449.2 (M+H-tert-butyl).

Step 4. (S)-1-benzyl 4-tert-butyl 2-ethynylpiperazine-1,4-dicarboxylate

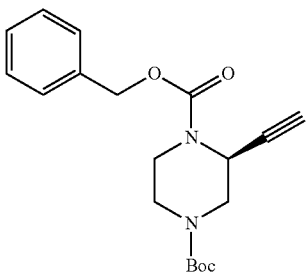 [SMILES: C#C[C@H]1CN(C(=O)OC(C)(C)C)CCN1C(=O)OCc1ccccc1]

Potassium carbonate (8.20 g, 59.3 mmol) was added to a solution of (S)-1-benzyl 4-tert-butyl 2-(2,2-dibromovinyl)piperazine-1,4-dicarboxylate (11.96 g, 23.72 mmol) dissolved in DMSO (237 ml), and the stirred mixture was heated in an oil bath at 115° C. for 18 h then cooled to ambient temperature. TLC the analysis indicated remaining dibromide (25% EtOAc/hexane, ninhydrin stain & heat). The reaction was filtered and a new batch of K2CO3 (8.20 g, 59.3 mmol) was added. The reaction was heated in an oil bath at 120° C. for 18 h. The reaction was cooled to ambient temperature and partitioned between water/brine (1:1) and ethyl acetate. The layers were separated and the aqueous phase was extracted with two portions of ethyl acetate. The combined organic extracts were dried over Na2SO4, filtered and the solvents were removed in vacuo. The crude product was purified on a 120 g silica column running a 0-50% EtOAc/hexane gradient over 45 min. Fractions containing product were combined and the solvents were removed in vacuo to give a colorless oil. LCMS: m/z=289.3 (M+H-tert-butyl).

Step 5. (S)-1-benzyl 4-tert-butyl 2-((3-amino-5-fluoropyridin-4-yl)ethynyl)piperazine-1,4-dicarboxylate

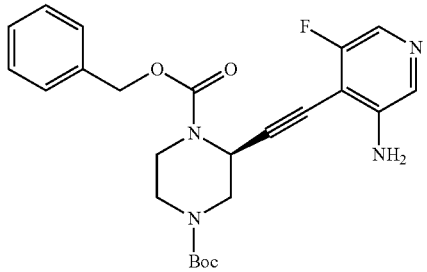 [SMILES: CC(C)(C)OC(=O)N1CCN(C(=O)OCc2ccccc2)[C@@H](C#Cc2c(N)cncc2F)C1]

(S)-1-benzyl 4-tert-butyl 2-ethynylpiperazine-1,4-dicarboxylate (4 g, 11.61 mmol), 5-fluoro-4-iodopyridin-3-amine (2.76 g, 11.61 mmol), and TEA (16.19 ml, 116 mmol) were combined in acetonitrile (58.1 ml) and the solution was purged with nitrogen gas for 5 minutes. Copper(1) iodide (0.310 g, 1.626 mmol) and bis(triphenylphosphine)palladium(II) chloride (0.326 g, 0.465 mmol) were added to the solution and the mixture was heated in an oil bath at 85° C. for 1 h. The solvent was removed in vacuo and the residue was partitioned between water and ethyl acetate. The layers were separated and the aqueous phase was extracted with two portions of EtOAc. The combined organic extracts were dried over Na2SO4, filtered and the solvents were removed in vacuo. The crude product was purified on a 40 g silica column running a 30-100% EtOAc/hexane gradient over 25 min. Fractions containing product were combined and the solvents were removed in vacuo to give a pale yellow oil. Analysis on a chiral column showed a 1:4 mixture with the major peak being the desired S-isomer. The material was separated on ChiralCel AD column, 10×50 cm, 150 mL/min, 100% EtOH. Fractions containing the second peak were combined and the solvent was removed in vacuo to give a colorless gum. LCMS: m/z=455.5 (M+H)

Step 6. (S)-1-benzyl 4-tert-butyl 2-((3-((S)-3-(3,5-difluorophenyl)-3-(4-fluorophenyl)propanamido)-5-fluoropyridin-4-yl)ethynyl)piperazine-1,4-dicarboxylate

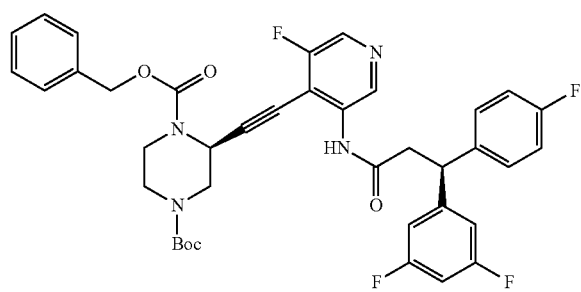 [SMILES: CC(C)(C)OC(=O)N1CCN(C(=O)OCc2ccccc2)[C@@H](C#Cc2c(F)cncc2NC(=O)C[C@@H](c2ccc(F)cc2)c2cc(F)cc(F)c2)C1]

POCl3 (0.492 ml, 5.28 mmol) was added to a mixture of (S)-1-benzyl 4-tert-butyl 2-((3-amino-5-fluoropyridin-4-yl)

ethynyl)piperazine-1,4-dicarboxylate (2.0 g, 4.40 mmol) and (3S)-3-(3,5-Difluorophenyl)-3-(4-fluorophenyl)propanoic acid (Intermediate 2; 1.295 g, 4.62 mmol) in dry pyridine (14.67 ml) at −10° C. (acetone/ice bath). After 45 min, saturated aqueous NaHCO3 solution was added slowly to quench the reaction and the mixture was diluted with ethyl acetate. The layers were separated and the aqueous phase was extracted with two more portions of EtOAc. The combined organic extracts were dried over Na2SO4, filtered and the solvents were removed in vacuo. The crude product was purified on a 40 g silica column running a 10-60% EtOAc/hexane gradient over 25 min. Fractions containing product were combined and the solvents were removed in vacuo to give a yellow gum. LCMS: m/z=717.6 (M+H)

Step 7. (S)-tert-butyl 3-(2-(3-(((S)-3-(3,5-difluorophenyl)-3-(4-fluorophenyl)propanamido)-5-fluoropyridin-4-yl)ethyl)piperazine-1-carboxylate (S)-1-benzyl 4-tert-butyl 2-((3-(((S)-3-(3,5-difluorophenyl)-3-(4-fluorophenyl)propanamido)-5-fluoropyridin-4-yl)ethynyl)piperazine-1,4-dicarboxylate (2.68 g, 3.74 mmol) was dissolved in ethanol (75 ml) in a large Parr vessel and the solution was degassed with nitrogen. Platinum(IV) oxide (600 mg, 2.64 mmol) and palladium hydroxide on carbon (600 mg, 0.427 mmol) were added to the solution and the mixture was shaken on Parr apparatus under 50 psi of hydrogen at ambient temperature for 18 h. The reaction was purged with nitrogen and then filtered through a thin pack of celite, washing with ethanol. The solvent was removed in vacuo and the crude product was purified on a 12 g silica column running a 0-10% MeOH/CH2Cl2 gradient over 20 min. Fractions containing product were combined and the solvents were removed in vacuo to give a pale yellow gum. LCMS: m/z=587.5 (M+H).

Intermediate H

Benzyl ((1S,2R)-2-vinylcyclopentyl)carbamate

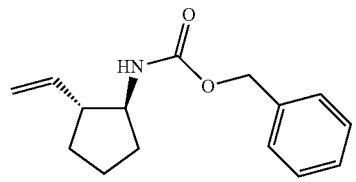 [SMILES: C=C[C@H]1CCC[C@@H]1NC(=O)OCc1ccccc1]

Step 1. tert-butyl ((1S,2S)-2-(hydroxymethyl)cyclopentyl)carbamate

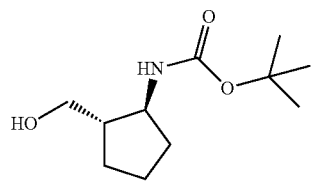

To a solution of (1S,2S)-2-((tert-butoxycarbonyl)amino)cyclopentanecarboxylic acid (4 g, 17.45 mmol) in anhydrous THF (20 mL) under nitrogen atmosphere cooled to 0° C. via ice/water bath was added dropwise, via syringe, 1.0M BH3-THF (19.2 mL, 19.2 mmol) and the resulting mixture stirred for 1 h at 0° C. To the mixture was then added via syringe another 19.2 mL of 1.0M BH3-THF. The mixture was then stirred for an additional 2 h allowing to warm to room temperature by removal of the ice/water bath. After the 2 h, the mixture was SLOWLY quenched with 15 mL of methanol. The resulting solution was stirred at room temperature overnight. The reaction was concentrated under reduced pressure and the residue was purified via Biotage (RediSep 80 g silica gel column) eluting with a gradient of 0-100% ethyl acetate in hexane over 12 CV. The tubes containing the product were collected and the solvent removed under reduce pressure to afford the desired compound (3.16 g, 83%) as a clear oil. After drying overnight, the oil crystallized to a nice white solid. MS: m/z=216 (M+H+).

Step 2. tert-butyl ((1S,2S)-2-formylcyclopentyl)carbamate

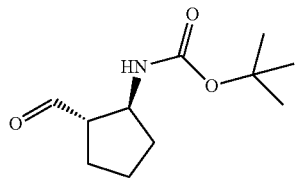

To a mixture of tert-butyl ((1S,2S)-2-(hydroxymethyl)cyclopentyl)carbamate (reagent 1, 3.16 g, 14.7 mmol) in DCM (100 mL) under nitrogen atmosphere, cooled to 0° C. via ice/water bath, was added Dess-Martin Periodinane (7.47 g. 17.6 mmol) in three portions over 3 minutes. The resulting mixture was stirred for 3 h at 0° C. and a small aliquot was worked up and analyzed via LC-MS. LC-MS proved that all starting material was consumed. Solid calcium hydroxide (20 g) was added in excess and the suspension stirred vigorously for 30 minutes (50 mL DCM was added because the suspension became to thick to stir). The solids were filtered off through celite and washed with DCM (2×100 mL). The combined organics were concentrated to dryness to afford the crude aldehyde (2.90 g, ~88%). MS: m/z=214 (M+H+).

Step 3. tert-butyl ((1S,2R)-2-vinylcyclopentyl)carbamate

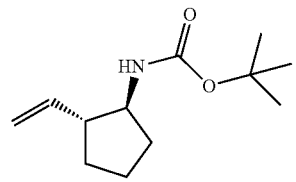

To a solution of methyltriphenylphosphonium bromide (7.77 g, 21.76 mmol) in 55 mL THF at rt was added a 0.5 M solution of KHMDS (43.5 mL, 21.76 mmol) dropwise via syringe to afford a yellow solution. The mixture was stirred for 45 minutes at rt and then was cooled to −78° C. via dry ice/acetone bath. To the cooled solution was then added tert-butyl ((1S,2S)-2-formylcyclopentyl)carbamate (2.9 g, 13.6 mmol) in 20 mL THF via syringe dropwise over 10 minutes. The resulting solution stirred at −78° C. for 30 minutes and then allowed to warm to room temperature overnight. TLC analysis revealed consumption of sm so the mixture was quenched with methanol (~20 mL) and stirred for 15 min. Sat. aq. Rochelle's salt (35 mL) was added followed by ethyl ether (100 mL) and the mixture stirred an additional 15 minutes. The mixture was transferred to a separatory funnel and the layers separated. The organic layer was washed with brine (25 mL), dried over sodium sulfate, filtered and the filtrate concentrated under reduced pressure. The crude material was purified via ISCO system using a 120 g silica gel column and eluting with a gradient of 0-60% ethyl acetate in hexane over 13 CV. The tubes containing the product were combined and concentrated to dryness under reduced pressure to afford the product as a white solid. (2.18 g, 80%). MS: m/z=212 (M+H$^+$).

Step 4. (1S,2R)-2-vinylcyclopentanamine 2,2,2-trifluoroacetate

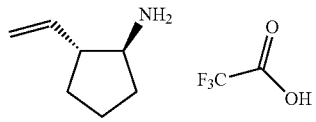

To a solution of tert-butyl ((1S,2R)-2-vinylcyclopentyl) carbamate (2.18 g, 10.32 mmol) in DCM (45 mL) under nitrogen atmosphere was added dropwise via syringe TFA (12 mL, 156 mmol) and the resulting solution stirred for 2 hours at room temperature. LC-MS proved that all starting material was consumed. The mixture was concentrated to dryness under reduced pressure and then was azeotroped with toluene (2×10 mL) to remove excess TFA. No further purification was needed and the material was used crude for the next reaction. (yellow oil, 2.20 g). $^1$HNMR (CD$_3$OD) δ: 5.70 (ddd, J=8.6, 10.2 and 17.1 Hz, 1H); 5.16 (dd, J=10.2, 17.0 Hz, 1H); 3.34-3.26 (m, 1H); 2.54 (p, J=8.6 Hz, 1H); 2.22-2.14 (m, 1H); 2.09-2.01 (m, 1H); 1.92-1.70 (m, 3H); 1.60-1.51 (m, 1H).

Step 5. benzyl ((1S,2R)-2-vinylcyclopentyl)carbamate

To a mixture of (1S,2R)-2-vinylcyclopentanamine 2,2,2-trifluoroacetate (2.10 g, 9.36 mmol) in DCM (50 mL) under nitrogen atmosphere cooled to 0° C. via ice/water bath was added TEA (3.28 mL, 23.44 mmol) followed by benzyl chloroformate (1.60 mL, 11.24 mmol) and the resulting mixture stirred overnight allowing to warm to room temperature. The mixture was quenched with sat. aq. sodium bicarbonate (25 mL) and the solution transferred to a separatory funnel. The layers were separated and the aqueous was extracted with DCM (2×50 mL). The organics were combined and washed with brine (75 mL), dried over sodium sulfate, filtered, and the filtrate concentrated to dryness under reduced pressure. The material was taken up in DCM and loaded unto the a 120 g silica gel column on the ISCO system and eluted with a gradient of 0-60% ethyl acetate in hexane over 13 CV. The tubes containing product were collected and the solvent removed under reduce pressure to afford the product as a white solid (1.51 g, 65.4%). MS: m/z=246 (M+H$^+$).

Intermediate I

Benzyl ((1R,2S)-2-vinylcyclopentyl)carbamate

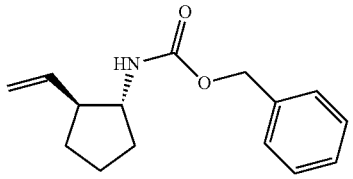 [SMILES: C=C[C@@H]1CCC[C@H]1NC(=O)OCc1ccccc1]

Intermediate I was prepared using similar procedure for Intermediate H, using (1R,2R)-2-((tert-butoxycarbonyl) amino)cyclopentanecarboxylic acid as starting material.

Intermediate J

Benzyl ((1S,2S)-2-vinylcyclopentyl)carbamate

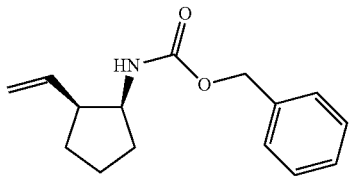 [SMILES: C=C[C@@H]1CCC[C@@H]1NC(=O)OCc1ccccc1]

Intermediate J was prepared using similar procedure for Intermediate H, using (1S,2R)-2-((tert-butoxycarbonyl) amino)cyclopentanecarboxylic acid as starting material.

Intermediate K

Benzyl ((1R,2R)-2-vinylcyclopentyl)carbamate

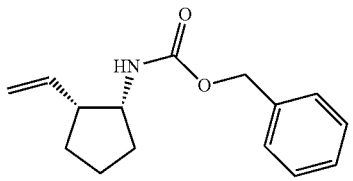 [SMILES: C=C[C@H]1CCC[C@H]1NC(=O)OCc1ccccc1]

Intermediate K was prepared using similar procedure for Intermediate H, using (1R,2S)-2-((tert-butoxycarbonyl) amino)cyclopentanecarboxylic acid as starting material.

Intermediate L

Benzyl ((1R,2S)-2-vinylcyclohexyl)carbamate

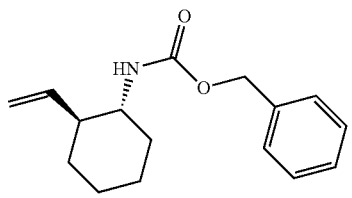 [SMILES: C=C[C@@H]1CCCC[C@H]1NC(=O)OCc1ccccc1]

Intermediate L was prepared using similar procedure for Intermediate H, using (1S,2S)-2-((tert-butoxycarbonyl) amino)cyclohexylcarboxylic acid as starting material.

Intermediate M

Benzyl ((1S,2R)-2-vinylcyclohexyl)carbamate

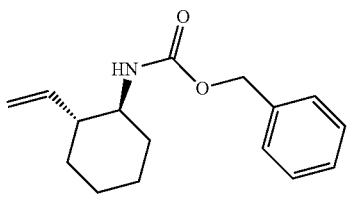 [SMILES: C=C[C@H]1CCCC[C@@H]1NC(=O)OCc1ccccc1]

Intermediate M was prepared using similar procedure for Intermediate H, using (1R,2R)-2-((tert-butoxycarbonyl)amino)cyclohexylcarboxylic acid as starting material.

EXAMPLE 1 AND EXAMPLE 2

2S-Amino-3,3-di-(4-fluorophenyl)-N-(5-fluoro-4-(2-(1-methylsulfonylpiperazin-2-yl)ethyl)pyridin-3-yl)propanamide Example 1

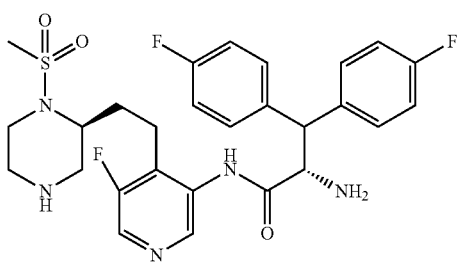

Example 2

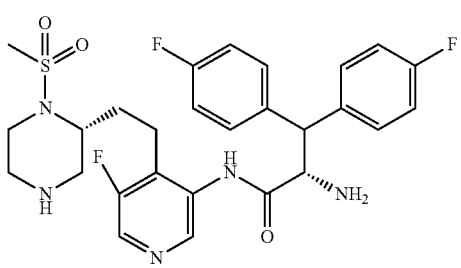

Step 1. 1-Benzyloxycarbonyl-4-(tert-butyloxycarbonyl)-2-hydroxymethylpiperazine

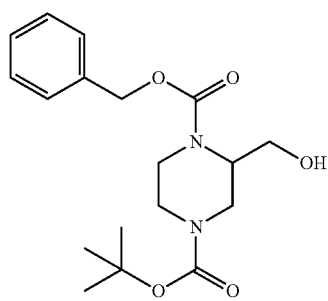 [SMILES: CC(C)(C)OC(=O)N1CCN(C(=O)OCc2ccccc2)C(CO)C1]

4-tert-Butyloxycarbonyl-2-hydroxymethylpiperazine (4.5 g, 21 mmol) was dissolved in 50 mL of THF and to the stirred solution was added an equal volume of saturated aqueous NaHCO3 solution. To the rapidly stirred biphasic mixture was added benzyl chloroformate (3.9 g, 23 mmol) dropwise over a period of 20 min. The mixture was stirred at room temp for 1.5 h, diluted with water and EtOAc, stirred for 10 min, then the aqueous phase was removed. The organic phase was washed with aqueous NaHCO3, brine, then dried (MgSO4), filtered, and stripped in vacuo to give a dense gum. The crude product was chromatographed on a 120 g SiO2 column eluting with 0-100% EtOAc-hexanes. The broad peak eluting between 45-80% EtOAc was collected to give a colorless gum. LCMS (4 min gradient, 215 nm): 2.03 min, m/z=351.4.

Step 2. 1-Benzyloxycarbonyl-4-(tert-butyloxycarbonyl)piperazine-2-carboxaldehyde

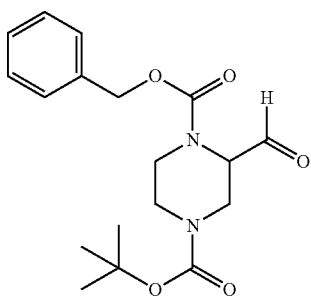 [SMILES: CC(C)(C)OC(=O)N1CCN(C(=O)OCc2ccccc2)C(C=O)C1]

1-Benzyloxycarbonyl-4-(tert-butyloxycarbonyl)-2-hydroxymethylpiperazine (2.2 g, 6.4 mmol) was dissolved in 60 mL of $CH_2Cl_2$ and the solution was cooled to 0° C. in an ice-water bath. To the stirred solution was added 1,1,1-triacetoxy-1,1-dihydro-1,2-benziodoxol-3(1H)-one (3.3 g, 7.6 mmol). The mixture was stirred at 0° C. for 1 h, then the cooling bath was removed and the mixture was stirred at ambient temp for 1 h. The solids were removed by filtration through a pad of MgSO4. The filtrate was washed with aq NaHCO3 two times, and the organic layer was dried (MgSO4), filtered, and the solvent was removed in vacuo. The crude product was dissolved in $CH_2Cl_2$ and chromatographed on an 80 g SiO2 column eluting with 0-80% EtOAc over 30 min. The broad peak eluting between 40-65% EtOAc was collected to give the product as a colorless gum. LCMS (4 min gradient, 215 nm): 1.9-2.3 min (irregular peak shape), m/z=349.4.

Step 3. 1-Benzyloxycarbonyl-4-(tert-butyloxycarbonyl)-2-ethynylpiperazine

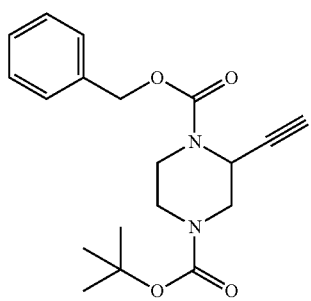 [SMILES: C#CC1CN(C(=O)OC(C)(C)C)CCN1C(=O)OCc1ccccc1]

1-Benzyloxycarbonyl-4-(tert-butyloxycarbonyl)piperazine-2-carboxaldehyde (1.9 g, 5.5 mmol) and dimethyl-1-diazo-2-oxopropylphosphonate (1.4 g, 7.1 mmol) were dissolved in 30 mL of MeOH and to the stirred solution was added K2CO3 (0.83 g, 6.0 mmol). The mixture was stirred at ambient temperature under an atmosphere of nitrogen for 4 h. The reaction was quenched by the addition of EtOAc and water. The layers were separated and the organic phase was washed with water and brine. The organic phase was dried (MgSO4), filtered and the solvents were removed in vacuo to give a colorless oil. The crude product was chromatographed on a 40 g SiO2 column using a gradient elution of 0-80% EtOAc in hexanes. The component eluting at 30-40% EtOAc was collected to give the product as an oil. LCMS (4 min gradient, 215 nm): 2.46 min, m/z=345.4.

Step 4. 2S-(tert-butyloxycarbonylamino)-3,3-di-(4-fluorophenyl)-N-(5-fluoro-4-iodopyridin-3-yl)propanamide

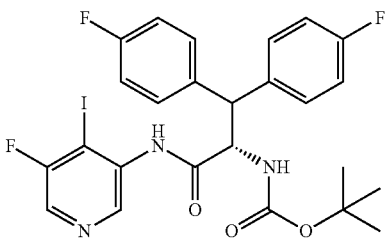 [SMILES: CC(C)(C)OC(=O)N[C@H](C(=O)Nc1cncc(F)c1I)C(c1ccc(F)cc1)c1ccc(F)cc1]

3-Amino-5-fluoro-4-iodopyridine (1.0 g, 4.2 mmol) and (S)-2-((tert-butoxycarbonyl)amino)-3,3-bis(4-fluorophenyl)propanoic acid (Intermediate 1) (1.6 g, 4.2 mmol) were dissolved in pyridine (10 mL). The solution was cooled to −20° C. in an ice-acetone bath. To the stirred solution was added POCl3 (0.71 g, 4.6 mmol) dropwise over a period of 15 min. The mixture was stirred at −20° C. for 30 min then quenched by the addition of aqueous NaHCO3 solution. The mixture was warmed to ambient temperature and extracted twice with DCM. The DCM extracts were combined, washed with brine, dried over Na2SO4, and filtered. The solvents were removed in vacuo and the residue was chromatographed on an 80 g SiO$_2$ column using a gradient elution of 0-50% EtOAc in hexanes. Fractions containing product were combined and the solvents were removed in vacuo to give a dense gum. LCMS (2 min gradient, 215 nm) 1.39 min, m/z=599.4.

Step 5. 2S-(tert-Butyloxycarbonylamino)-3,3-di-(4-fluorophenyl)-N-(5-fluoro-4-(2-(1-benzyloxycarbonyl-4-(tert-butyloxycarbonyl)piperazin-2-yl)ethynyl)pyridin-3-yl)propanamide

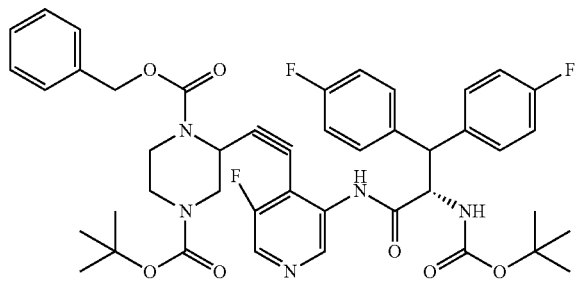 [SMILES: CC(C)(C)OC(=O)N[C@H](C(=O)Nc1cncc(F)c1C#CC1CN(C(=O)OC(C)(C)C)CCN1C(=O)OCc1ccccc1)C(c1ccc(F)cc1)c1ccc(F)cc1]

1-Benzyloxycarbonyl-4-(tert-butyloxycarbonyl)-2-ethynylpiperazine (250 mg, 0.73 mmol), 2S-(tert-butyloxycarbonylamino)-3,3-di-(4-fluorophenyl)-N-(5-fluoro-4-iodopyridin-3-yl)propanamide (430 mg, 0.73 mmol), and triethylamine (2 mL) were dissolved in acetonitrile (4 mL). The stirred solution was purged with nitrogen gas for 1 min, then CuI (14 mg, 0.073 mmol) and bis(triphenylphosphine)palladium(II) chloride (36 mg, 0.051 mmol) were added. The mixture was heated to 70° C. with stirring under an atmosphere of nitrogen for 1 h. The mixture was cooled to ambient temperature and diluted with EtOAc. The solution was washed with water and brine, then dried over MgSO4, filtered, and the solvents were removed in vacuo. The residue was chromatographed on a 24 g SiO2 column using a gradient elution of 0-60% EtOAc in hexanes. Fractions containing product were combined and the solvents were removed in vacuo to give a dense gum. LCMS (2 min gradient, 215 nm) 1.72 and 1.73 min, m/z=814.9.

Step 6. 2S-(tert-Butyloxycarbonylamino)-3,3-di-(4-fluorophenyl)-N-(5-fluoro-4-(2-(4-(tert-butyloxycarbonyl)piperazin-2-yl)ethyl)pyridin-3-yl)propanamide

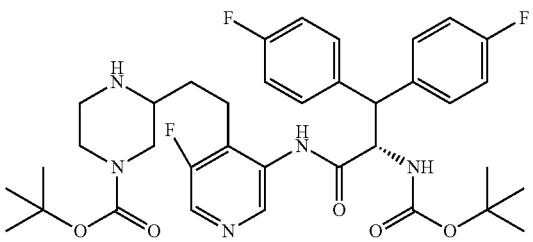 [SMILES: CC(C)(C)OC(=O)N[C@H](C(=O)Nc1cncc(F)c1CCC1CN(C(=O)OC(C)(C)C)CCN1)C(c1ccc(F)cc1)c1ccc(F)cc1]

2S-(tert-Butyloxycarbonylamino)-3,3-di-(4-fluorophenyl)-N-(5-fluoro-4-(2-(1-benzyloxycarbonyl-4-(tert-butyloxycarbonyl)piperazin-2-yl)ethynyl)pyridin-3-yl)propanamide (450 mg, 0.55 mmol) was dissolved in 15 mL of trifluoroethanol and the solution was purged with nitrogen gas for 2 min. To the solution was added platinum oxide (50 mg) and palladium hydroxide on carbon (100 mg). The mixture was shaken on a Parr apparatus at ambient temperature under an atmosphere of hydrogen gas at 50 psi for 48 h. The catalysts were removed by filtration and the filtrate solvent was removed under reduced pressure to give a dense gum. LCMS analysis of this material indicated removal of the benzyl carbamate protecting group and reduction of the triple bond to a double bond. The dense gum was dissolved in 15 mL of MeOH and the solution was purged with nitrogen gas for 2 min. To the solution was added palladium hydroxide on carbon (100 mg). The mixture was shaken on a Parr apparatus at ambient temperature under an atmosphere of hydrogen gas at 50 psi for 24 h. The catalyst was removed by filtration and the filtrate solvent was removed under reduced pressure to give a dense gum which was used without further purification. LCMS (2 min gradient, 215 nm) 1.22 min, m/z=684.7.

Step 7. 2S-(tert-Butyloxycarbonylamino)-3,3-di-(4-fluorophenyl)-N-(5-fluoro-4-(2-(4-(tert-butyloxycarbonyl)-1-methylsulfonylpiperazin-2-yl)ethyl)pyridin-3-yl)propanamide

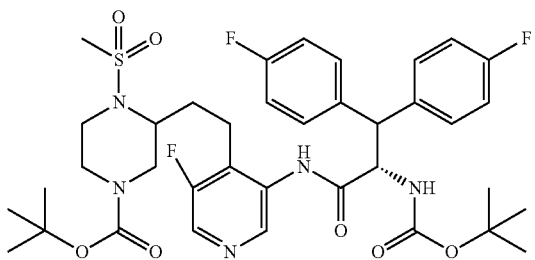 [SMILES: CC(C)(C)OC(=O)N[C@H](C(=O)Nc1cncc(F)c1CCC1CN(C(=O)OC(C)(C)C)CCN1S(C)(=O)=O)C(c1ccc(F)cc1)c1ccc(F)cc1]

2S-(tert-Butyloxycarbonylamino)-3,3-di-(4-fluorophenyl)-N-(5-fluoro-4-(2-(4-(tert-butyloxycarbonyl)piperazin-2-yl)ethyl)pyridin-3-yl)propanamide (100 mg, 0.15 mmol) and triethylamine (0.061 mL, 0.44 mmol) were dissolved in $CH_2Cl_2$ (3 mL). The solution was stirred with cooling in an ice-water bath. Methanesulfonyl chloride (0.017 mL, 0.22 mmol) was added and the solution was stirred at 0° C. for 1 h. The solution was diluted with $CH_2Cl_2$ and washed with water and brine. The organic phase was dried over MgSO4, filtered, and the solvent was removed in vacuo. The residue was chromatographed on a 12 g SiO2 column using a gradient elution of 0-100% EtOAc in hexanes. Fractions containing product were combined and the solvents were removed in vacuo to give a dense gum. LCMS (2 min gradient, 215 nm) 1.43 min, m/z=762.7.

Step 8. 2S-Amino-3,3-di-(4-fluorophenyl)-N-(5-fluoro-4-(2-(1-methylsulfonylpiperazin-2-yl)ethyl)pyridin-3-yl)propanamide To a solution of 2S-(tert-butyloxycarbonylamino)-3,3-di-(4-fluorophenyl)-N-(5-fluoro-4-(2-(4-(tert-butyloxycarbonyl)-1-methylsulfonylpiperazin-2-yl)ethyl)pyridin-3-yl)propanamide (69 mg, 0.091 mmol) in 4M HCl in dioxane (1 mL). The solution was stirred at ambient temperature for 1 h and the solvent was removed in vacuo. The residue was purified by preparative HPLC on a C18 column using a gradient elution of 5-70% CH3CN in water containing 0.1% TFA. Two diastereomeric product peaks were collected, each was lyophilized to give a product TFA salt as a white solid. Example 1: 1H NMR (DMSO-d6): 10.43 ppm, s, 1H; 8.57 ppm, br s, 4H; 8.37 ppm, s, 1H; 7.89 ppm, s, 1H; 7.56-7.58 ppm, m, 4H; 7.26 ppm, t, 2H, J=8.7 Hz; 7.18 ppm, t, 2H, J=8.7 Hz; 5.06-5.14 ppm, m, 1H; 4.47 ppm, d, 1H, J=11.3 Hz; 3.97-4.02 ppm, m, 1H; 3.54-3.91 ppm, m, 5H; 3.24-3.38 ppm, m, 2H; 3.12-3.38 ppm, m, 1H; 2.98-3.09 ppm, m, 1H; 2.48-2.58 ppm, m, 1H; 2.34-2.48 ppm, m, 1H; 1.91-2.05 ppm, m, 1H; 1.45-1.54 ppm, m, 1H. High Resolution MS: Calc: M+H=562.2094, Meas: M+H=562.2085. Example 2: 10.48 ppm, s, 1H; 9.38 ppm, br s, 1H; 8.60 ppm, br s, 4H; 8.38 ppm, s, 1H; 7.89 ppm, s, 1H; 7.49-7.60 ppm, m, 4H; 7.27 ppm, t, 2H, J=8.7 Hz; 7.18 ppm, t, 2H, J=8.7 Hz; 5.06 ppm, br d, 1H, J=10.2 Hz; 4.45 ppm, d, 1H, J=11.3 Hz; 3.97-4.02 ppm, m, 1H; 3.83-3.90 ppm, m, 1H; 3.44-3.78 ppm, m, 5H; 3.24-3.38 ppm, m, 2H; 3.12-3.38 ppm, m, 1H; 2.98-3.09 ppm, m, 1H; 2.39-2.48 ppm, m, 1H; 2.21-2.30 ppm, m, 1H; 1.97-2.09 ppm, m, 1H; 1.60-1.70 ppm, m, 1H; High Resolution MS: Calc: M+H=562.2094, Meas: M+H=562.2079.

EXAMPLE 3

Methyl ((S)-1-((3-fluoro-2-(2-((S)-1-(phenylsulfonyl)piperazin-2-yl)ethyl)phenyl)amino)-3,3-bis(3-fluorophenyl)-1-oxopropan-2-yl)carbamate

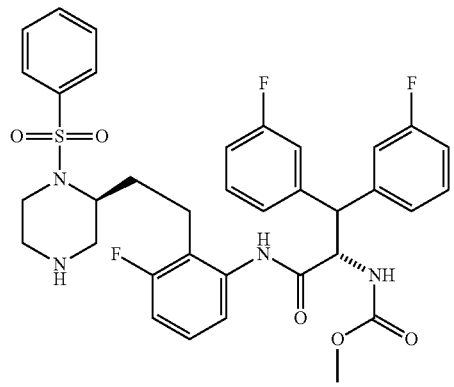 [SMILES: COC(=O)N[C@H](C(=O)Nc1cccc(F)c1CC[C@H]1CNCCN1S(=O)(=O)c1ccccc1)C(c1cccc(F)c1)c1cccc(F)c1]

Step 1. (S)-tert-butyl 3-(2-((S)-2-azido-3,3-bis(3-fluorophenyl)propanamido)-6-fluorophenethyl)-4-(phenylsulfonyl)piperazine-1-carboxylate

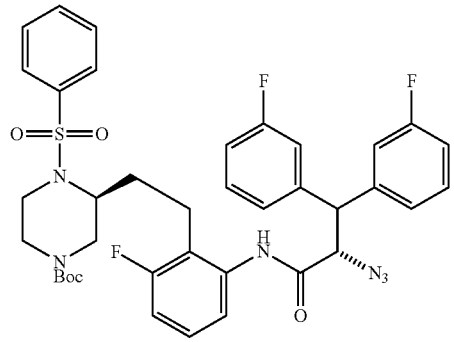 [SMILES: CC(C)(C)OC(=O)N1CCN(S(=O)(=O)c2ccccc2)[C@@H](CCc2c(F)cccc2NC(=O)[C@@H](N=[N+]=[N-])C(c2cccc(F)c2)c2cccc(F)c2)C1]

To a stirred solution of (S)-tert-butyl 3-(2-amino-6-fluorophenethyl)-4(phenylsulfonyl)piperazine-1-carboxylate (Intermediate A) (160 mg, 0.345 mmol) and (S)-2-azido-3,3-bis(3-fluorophenyl)propanoic acid (Intermediate 15) (115 mg, 0.38 mmol) in pyridine (5 mL) at −20° C. was added POCl3 (40 μL, 0.44 mmol) dropwise and the reaction solution was allowed to reach 0° C. over a period of 2 h. The reaction mixture was quenched with saturated solution of $KH_2PO_4$ (1 mL), extracted with EtOAc (3×20 mL) and the combined organic extracts were washed with brine (20 mL), dried ($Na_2SO_4$), filtered and concentrated under reduced pressure. The residue was purified by 24 g $SiO_2$ column using a gradient elution of 0-100% EtOAc in hexanes Fractions containing product were combined and the solvents were removed in vacuo to provide the product (215 mg, 83%) as a pale pink semi-solid.

Step 2. (S)-tert-butyl 3-(2-((S)-2-amino-3,3-bis(3-fluorophenyl)propanamido)-6-fluorophenethyl)-4-(phenylsulfonyl)piperazine-1-carboxylate

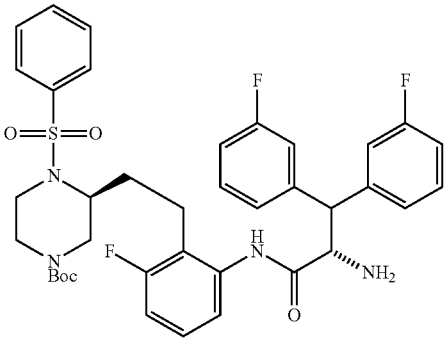 [SMILES: CC(C)(C)OC(=O)N1CCN(S(=O)(=O)c2ccccc2)[C@@H](CCc2c(F)cccc2NC(=O)[C@@H](N)C(c2cccc(F)c2)c2cccc(F)c2)C1]

To a stirred solution of (S)-tert-butyl 3-(2-((S)-2-azido-3,3-bis(3-fluorophenyl)propanamido)-6-fluorophenethyl)-4-(phenylsulfonyl)piperazine-1-carboxylate (210 mg, 0.28 mmol) in a mixture of EtOAc (5 mL), water (1 mL), added trimethylphosphine (0.42 mL, 1M solution in THF, 0.42 mmol) and stirred at room temperature for 16 h. Water (10 mL) was added and extracted with EtOAc (2×30 mL). The organic layer was washed with brine (20 mL), dried (Na$_2$SO$_4$), filtered and concentrated under reduced pressure. The crude product (240 mg) was taken to the next step without any further purification.

Step 3. (S)-tert-butyl 3-(2-((S)-3,3-bis(3-fluorophenyl)-2((methoxycarbonyl)amino)propanamido)-6-fluorophenethyl)-4-(phenylsulfonyl)piperazine-1-carboxylate

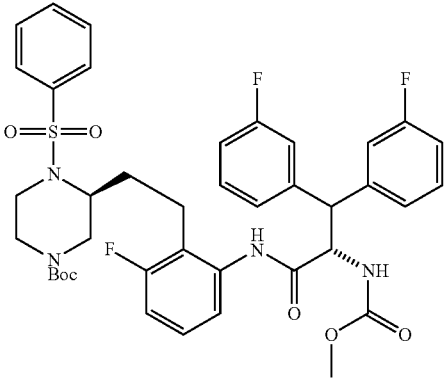 [SMILES: COC(=O)N[C@H](C(=O)Nc1cccc(F)c1CC[C@H]1CN(C(=O)OC(C)(C)C)CCN1S(=O)(=O)c1ccccc1)C(c1cccc(F)c1)c1cccc(F)c1]

To a stirred solution of (S)-tert-butyl 3-(2-((S)-2-amino-3,3-bis(3-fluorophenyl)propanamido)-6-fluorophenethyl)-4-(phenylsulfonyl)piperazine-1-carboxylate (120 mg, 0.16 mmol) in dichloromethane (3 mL) was added diisopropylethylamine (58 µL, 0.32 mmol), methylchloroformate (14 µL, 0.176 mmol) at 0° C. and stirred for 15 min. Water (5 mL) was added and extracted with dichloromethane (2×20 mL). The organic layer was washed with brine (10 mL), dried (Na$_2$SO$_4$), filtered and concentrated under reduced pressure. The residue was purified by 12 g SiO$_2$ column using a gradient elution of 0-100% EtOAc in hexanes. Fractions containing product were combined and the solvents were removed in vacuo to provide the product (105 mg, 81%) as an off-white solid.

Step 4. Methyl ((S)-1-((3-fluoro-2-(2-((S)-1-(phenylsulfonyl)piperazin-2-yl)ethyl)phenyl)amino)-3,3-bis(3-fluorophenyl)-1-oxopropan-2-yl)carbamate To a stirred solution of (S)-tert-butyl 3-(2-((S)-3,3-bis(3-fluorophenyl)-2((methoxycarbonyl)amino)propanamido)-6-fluorophenethyl)-4-(phenylsulfonyl)piperazine-1-carboxylate (100 mg, 0.128 mmol) in dichloromethane (2.0 mL), added trifluoroacetic acid (1.0 mL) and stirred at room temperature for 2 h. The reaction mixture was concentrated to dryness under reduced pressure and azeotroped with dichloromethane (5 mL). The residue was purified by 30 g C18 column using a gradient elution of 0-100% acetonitrile in water. Fractions containing product were combined and the solvents were removed in vacuo to provide the product (45 mg, 44%) as an amorphous white solid. MS: m/z 681.2 (M+H$^+$).

EXAMPLE 4

(S)-2-Amino-N-(5-fluoro-4-(2-((S)-1-(phenylsulfonyl)piperazin-2-yl)ethyl)pyridine-3-yl)-3,3-bis(3-fluorophenyl)propanamide

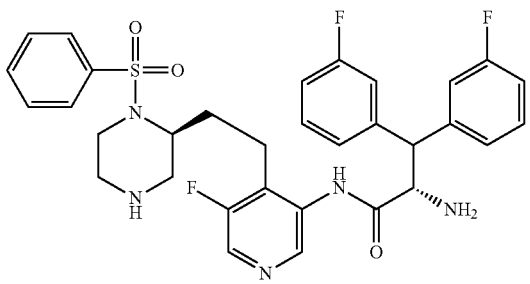 [SMILES: N[C@H](C(=O)Nc1cncc(F)c1CC[C@H]1CNCCN1S(=O)(=O)c1ccccc1)C(c1cccc(F)c1)c1cccc(F)c1]

Step 1. (S)-tert-butyl 3-(2-((S)-2-azido-3,3-bis(3-fluorophenyl)propanamido)-5-fluoropyridin-4-yl)ethyl)-4-(phenylsulfonyl)piperizine-1-carboxylate

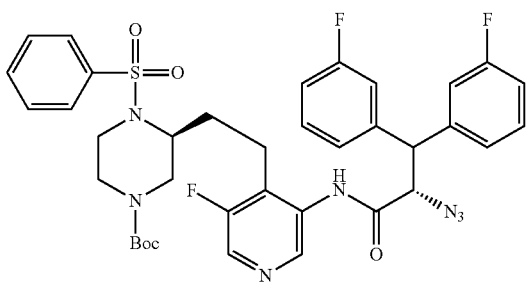 [SMILES: CC(C)(C)OC(=O)N1CCN(S(=O)(=O)c2ccccc2)[C@@H](CCc2c(F)cncc2NC(=O)[C@@H](N=[N+]=[N-])C(c2cccc(F)c2)c2cccc(F)c2)C1]

To a solution of (S)-tert-butyl 3((3-amino-5-fluoropyridin-4-yl)ethyl)-4-(phenylsulfonyl)piperizine-1-carboxylate (Intermediate B) (180 mg, 0.387 mmol) and (S)-2-azido-3,3-bis(3-fluorophenyl)propanoic acid (Intermediate 15) (129 mg, 0.426 mmol) in pyridine (5 mL) was added POCl$_3$ (5.3 µL, 0.581 mmol) at 0° C. and the mixture was stirred for 2 h. The reaction mixture was quenched with saturated solution of KH$_2$PO$_4$ (2 mL), extracted with EtOAc (2×25 mL) and the combined organic layers were concentrated under reduced pressure. The residue was purified by 12 g SiO$_2$ column using a gradient elution of 0-60% EtOAc in hexanes. Fractions containing product were combined and the sol-

83 vents were removed in vacuo to provide the product (112 mg, 38%) as a light pink solid. MS: m/z=750 (M+H⁺)

Step 2. (S)-tert-butyl 3-(2-((S)-2-amino-3,3-bis(3-fluorophenyl)propanamido)-5-fluoropyridin-4-yl)ethyl)-4-(phenylsulfonyl)piperizine-1-carboxylate

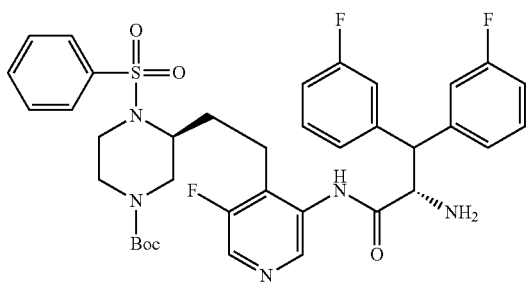 [SMILES: CC(C)(C)OC(=O)N1CCN(S(=O)(=O)c2ccccc2)[C@@H](CCc2c(F)cncc2NC(=O)[C@@H](N)C(c2cccc(F)c2)c2cccc(F)c2)C1]

To a solution of (S)-tert-butyl 3-(2-((S)-2-azido-3,3-bis(3-fluorophenyl)propanamido)-5-fluoropyridin-4-yl)ethyl)-4-(phenylsulfonyl)piperizine-1-carboxylate (112 mg, 0.149 mmol) in THF/H₂O (12 mL) was added trimethyl phosphine (0.22 mL, 0.224 mmol) and the mixture was stirred for 16 h at room temperature. Following the addition of water (20 mL), the reaction mixture was extracted with EtOAc (2×25 mL) and the combined organic phases were concentrated under reduced pressure. The residue was purified by 12 g SiO₂ column using a gradient elution of 0-90% EtOAc in hexanes. Fractions containing product were combined and the solvents were removed in vacuo to provide the product (105 mg, 97%) as a white solid. MS: m/z=724 (M+H⁺)

Step 3. (S)-2amino-N-(5-fluoro-4-(2-((S)-1-(phenylsulfonyl)piperazin-2-yl)ethyl)pyridine-3-yl)-3,3-bis(3-fluorophenyl)propanamide To a solution of (S)-tert-butyl 3-(2-((S)-2-amino-3,3-bis(3-fluorophenyl)propanamido)-5-fluoropyridin-4-yl)ethyl)-4-(phenylsulfonyl)piperizine-1-carboxylate (45 mg, 0.062 mmol) in CH₂Cl₂ (1 mL) was added TFA (0.3 mL) and the mixture was stirred for 1 h at room temperature before being concentrated. The residue was purified by semi preparative HPLC. Fractions containing product were combined and the solvents were removed in vacuo to provide the product (9 mg, 15%) as a white solid. MS: m/z=624 (M+H⁺)

EXAMPLE 5

Methyl ((1S,2S)-1-(4-chlorophenyl)-3-((3-fluoro-2-(2((S)-1-(phenylsulfonyl)piperizin-2-yl)ethyl)phenyl)amino)-1-(6-methoxypyridin-3-yl)-3-oxopropan-2-yl)carbamate

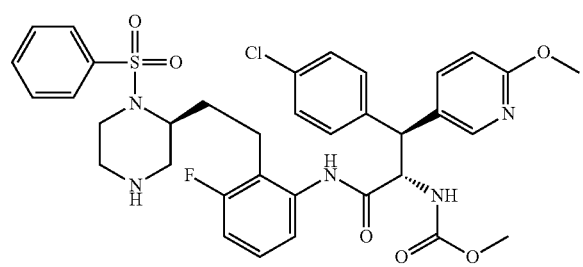 [SMILES: COC(=O)N[C@H](C(=O)Nc1cccc(F)c1CC[C@H]1CNCCN1S(=O)(=O)c1ccccc1)[C@@H](c1ccc(Cl)cc1)c1ccc(OC)nc1]

84

Step 1. (3S)-tert-butyl 3-(2-((2S,3S)-2-azido-3-(4-chloorophenyl)-3-(6-methoxypyridin-3-yl)propanamido)-6-fluorophenethyl)-4-(phenylsulfonyl)piperizine-1-carboxylate

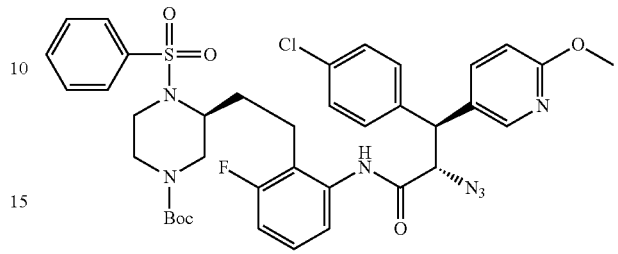

To a solution of (S)-tert-butyl 3-(2-amino-6-fluorophenethyl)-4-(phenylsulfonyl)piperizine-1-carboxylate (Intermediate A) (208 mg, 0.450 mmol) and (2S,3S)-2-azido-3-(4-chlorophenyl)-3-(6-methoxypyridin-3-yl)propanoic acid (Intermediate 10) (150 mg, 0.450 mmol) in pyridine (8 mL) was added POCl₃ (61.0 µL, 0.675 mmol) at 0° C. and the mixture was stirred for 2 h. The reaction mixture was quenched with KH₂PO₄ (saturated solution, 3 mL), extracted with EtOAc (2×25 mL) and the combined organic layers were concentrated under reduced pressure. The residue was purified by 12 g SiO₂ column using a gradient elution of 0-60% EtOAc in hexanes. Fractions containing product were combined and the solvents were removed in vacuo to provide the product (201 mg, 63%) as a white solid. MS: m/z=778 (M+H⁺)

Step 2. (3S)-tert-butyl 3-(2-((2S,3S)-2-amino-3-(4-chlorophenyl)-3-(6-methoxypyridin-3-yl)propanamido)-6-fluorophenethyl)-4-(phenylsulfonyl)piperizine-1-carboxylate

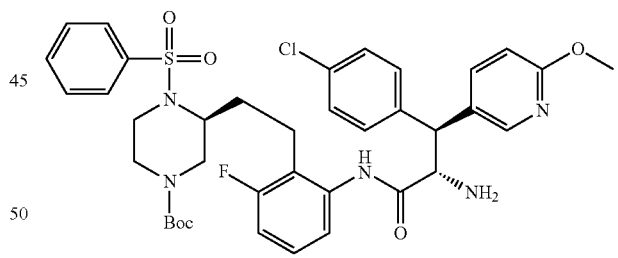

To a solution of (3S)-tert-butyl 3-(2-((2S,3S)-2-azido-3-(4-chlorophenyl)-3-(6-methoxypyridin-3-yl)propanamido)-6-fluorophenethyl)-4-(phenylsulfonyl)piperizine-1-carboxylate (200 mg, 0.252 mmol) in THF/H₂O (15 mL) was added trimethyl phosphine (0.38 mL, 0.385 mmol) and the mixture was stirred for 16 h at room temperature. Diluted the reaction mixture with water (20 mL) and extracted with EtOAc (2×25 mL). The combined organic extracts were dried (Na₂SO₄), filtered, and concentrated under reduced pressure. The residue was purified by 12 g SiO₂ column using a gradient elution of 0-60% EtOAc in hexanes. Fractions containing product were combined and the solvents were removed in vacuo to provide the product (165 mg, 85%) as an off-white solid. MS: m/z=752 (M+H⁺)

Step 3. (3S)-tert-butyl 3-(2-((2S,3S)-3-(4-chlorophenyl)-2-((methoxycarbonyl)amino)-3-(6-methoxypyridin-3-yl)propanamido)-6-fluorophenethyl)-4-(phenylsulfonyl)piperizine-1-carboxylate

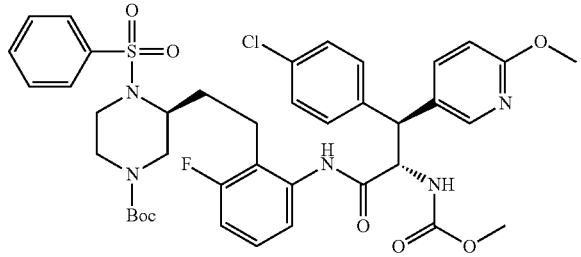 [SMILES: COC(=O)N[C@H](C(=O)Nc1cccc(F)c1CC[C@H]1CN(C(=O)OC(C)(C)C)CCN1S(=O)(=O)c1ccccc1)[C@@H](c1ccc(Cl)cc1)c1ccc(OC)nc1]

To a stirred solution of (3S)-tert-butyl 3-(2-((2S,3S)-2-amino-3-(4-chlorophenyl)-3-(6-methoxypyridin-3-yl)propanamido)-6-fluorophenethyl)-4-(phenylsulfonyl)piperizine-1-carboxylate (100 mg, 0.132 mmol) in dichloromethane (10 mL) at 0° C. was added diisopropylethylamine (46 μL, 0.165 mmol) followed by slow addition of methylchloroformate (15 μL, 0.124 mmol) and stirred for 1 h. The reaction was quenched with water (10 mL) and extracted with dichloromethane (2×20 mL). The combined organic extracts were dried (Na$_2$SO$_4$), filtered, and concentrated under reduced pressure. The residue was purified by 12 g SiO$_2$ column using a gradient elution of 0-60% EtOAc in hexanes. Fractions containing product were combined and the solvents were removed in vacuo to provide the product (82 mg, 76%) as an off-white solid. MS: m/z=810 (M+H$^+$)

Step 4. Methyl ((1S,2S)-1-(4-chlorophenyl)-3-((3-fluoro-2-(2((S)-1-(phenylsulfonyl)piperizin-2-yl)ethyl)phenyl)amino)-1-(6-methoxypyridin-3-yl)-3-oxopropan-2-yl)carbamate To a solution of (3S)-tert-butyl 3-(2-((2S,3S)-3-(4-chlorophenyl)-2-((methoxycarbonyl)amino)-3-(6-methoxypyridin-3-yl)propanamido)-6-fluorophenethyl)-4-(phenylsulfonyl)piperizine-1-carboxylate (82 mg, 0.101 mmol) in CH$_2$Cl$_2$ (2 mL) was added TFA (0.3 mL) and the mixture was stirred at room temperature for 1 h. The reaction mixture was concentrated under reduced pressure and the residue was triturated with diethyl ether to obtain a solid. The solid was collected by filtration in vacuo and washed with diethyl ether (15 mL) to provide the product (56 mg, 59%) as an off-white solid. MS: m/z=710 (M+H$^+$).

EXAMPLE 6

(2S,3S)-2-amino-3-(4-chlorophenyl)-N-(3-fluoro-2-(2-((S)-1-(phenylsulfonyl)piperazin-2-yl)ethyl)phenyl)-3-(5-(trifluoromethyl)pyridine-3-yl)propanamide

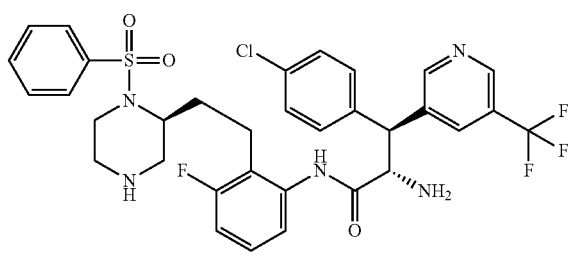 [SMILES: N[C@H](C(=O)Nc1cccc(F)c1CC[C@H]1CNCCN1S(=O)(=O)c1ccccc1)[C@@H](c1ccc(Cl)cc1)c1cncc(C(F)(F)F)c1]

Step 1. (S)-tert-Butyl 3-(2-((2S,3S))-2-azido-3,(4-chlorophenyl)-3-(5-trifluoromethyl)pyridine-3-yl)propanamido)-6-fluorophenethyl)-4-(phenylsulfonyl)piperazine-1-carboxylate

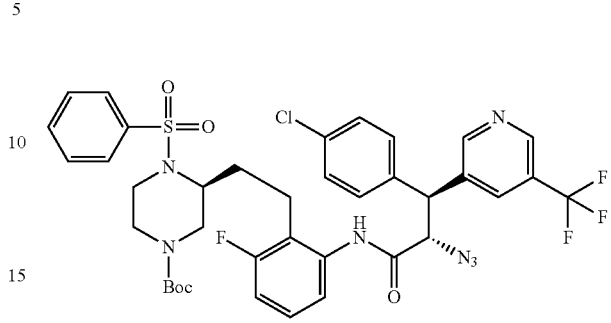

To a solution of (S)-tert-butyl 3-(2-amino-6-fluorophenethyl)-4-(phenylsulfonyl)piperizine-1-carboxylate (Intermediate A) (150 mg, 0.324 mmol) and (2S,3S)-2-azido-3-(4-chlorophenyl)-3-(5-trifluoromethyl)pyridine-3-yl)propanoic acid (Intermediate 14) (120 mg, 0.324 mmol) in pyridine (5 mL) was added POCl$_3$ (33 μL, 0.356 mmol) at 0° C. and the mixture was stirred for 2 h. The reaction mixture was quenched with saturated solution of KH$_2$PO$_4$ (1 mL), extracted with EtOAc (2×25 mL). The combined organic extracts were dried (Na$_2$SO$_4$), filtered and concentrated under reduced pressure. The residue was purified by 12 g SiO$_2$ column using a gradient elution of 0-60% EtOAc in hexanes. Fractions containing product were combined and the solvents were removed in vacuo to provide the product (222 mg, 84%).

MS: m/z=816 (M+H$^+$)

Step 2. (S)-tert-butyl 3-(2-((2S,3S))-2-amino-3,(4-chlorophenyl)-3-(5-trifluoromethyl)pyridine-3-yl)propanamido)-6-fluorophenethyl)-4-(phenylsulfonyl)piperazine-1-carboxylate

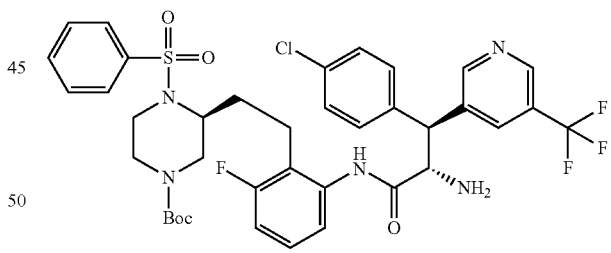

To a solution of (S)-tert-butyl 3-(2-((2S,3S))-2-azido-3,(4-chlorophenyl)-3-(5-trifluoromethyl)pyridine-3-yl)propanamido)-6-fluorophenethyl)-4-(phenylsulfonyl)piperazine-1-carboxylate (222 mg, 0.272 mmol) in Ethyl acetate/H$_2$O (6 mL) was added trimethyl phosphine (0.8 mL, 0.817 mmol) and the mixture was stirred at room temperature for 16 h. Diluted the reaction mixture with water (20 mL), and extracted with EtOAc (2×25 mL). The combined organic extracts were dried (Na$_2$SO$_4$), filtered and concentrated under reduced pressure. The residue was purified by 12 g SiO$_2$ column using a gradient elution of 0-90% EtOAc in hexanes. Fractions containing product were combined and the solvents were removed in vacuo to provide the product (110 mg, 51%) as a white solid. MS: m/z=790 (M+H$^+$)

Step 3. (2S,3S)-2-amino-3-(4-chlorophenyl)-N-(3-fluoro-2-(2-((S)-1-(phenylsulfonyl)piperazin-2-yl)ethyl)phenyl)-3-(5-(trifluoromethyl)pyridin-3-yl)propanamide To a solution of (S)-tert-butyl 3-(2-((2S,3S))-2-amino-3,(4-chlorophenyl)-3-(5-trifluoromethyl)pyridine-3-yl)propanamido)-6-fluorophenethyl)-4-(phenylsulfonyl)piperazine-1-carboxylate (30 mg, 0.038 mmol) in CH₂Cl₂ (1 mL) was added TFA (0.3 mL) and the mixture was stirred at room temperature for 1 h. The reaction mixture was concentrated under reduced pressure and the residue was purified by semi preparative HPLC. Fractions containing product were combined and the solvents were removed in vacuo to provide the product (25 mg, 67%).

MS: m/z=690 (M+H⁺)

EXAMPLE 7

Methyl ((2S,3R)-1-((3-fluoro-2-(2-((2S,6S)-6-methyl-1-(phenylsulfonyl)piperazin-2-yl)ethyl)phenyl)amino)-3-(4-fluorophenyl)-1-oxo-3-(tetrahydro-2H-pyran-4-yl)propan-2-yl)carbamate

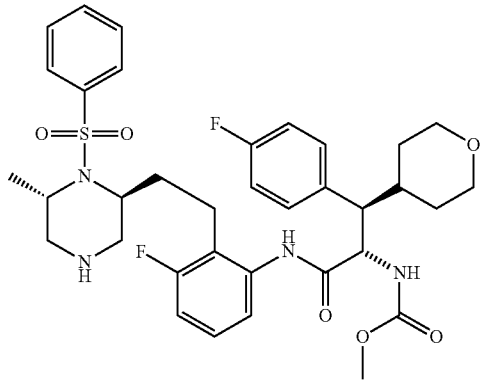 [SMILES: COC(=O)N[C@H](C(=O)Nc1cccc(F)c1CC[C@H]1CNC[C@H](C)N1S(=O)(=O)c1ccccc1)[C@@H](c1ccc(F)cc1)C1CCOCC1]

Step 1. (S)-tert-Butyl 4-(2-((2S,3R)-2-azido-3-(4-fluorophenyl)-3-(tetrahydro-2H-pyran-4-yl)propanamido)-6-fluorophenethyl)-2,2-dimethyloxazolidine-3-carboxylate

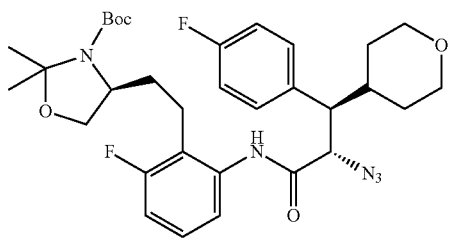 [SMILES: CC(C)(C)OC(=O)N1[C@@H](CCc2c(F)cccc2NC(=O)[C@@H](N=[N+]=[N-])[C@@H](c2ccc(F)cc2)C2CCOCC2)COC1(C)C]

To a stirred solution of (S)-tert-butyl 4-(2-amino-6-fluorophenethyl)-2,2-dimethyloxazolidine-3-carboxylate (Intermediate C) (1.50 g, 4.43 mmol) and (2S,3R)-2-azido-3-(4-fluorophenyl)-3-(tetrahydro-2H-pyran-4-yl)propanoic acid (Intermediate 11) (1.30 g, 4.43 mmol) in pyridine (15 mL) at −20° C. was added slowly POCl₃ (0.50 mL, 5.32 mmol) and the reaction mixture was allowed to reach 0° C. and stirred for 3 h. The reaction was quenched with a saturated solution of KH₂PO₄ (50 mL) and extracted with EtOAc (200 mL). The organic layer was washed with brine (200 mL), dried (Na₂SO₄), filtered and concentrated under reduced pressure. The residue was purified by 80 g SiO₂ column using a gradient elution of 0-30% EtOAc in hexanes. Fractions containing product were combined and the solvents were removed in vacuo to provide the product (2.20 g, 81%) as a pale yellow solid.

Step 2. (2S,3R)—N-(2-((S)-3-amino-4-hydroxybutyl)-3-fluorophenyl)-2-azido-3-(4-fluorophenyl)-3-(tetrahydro-2H-pyran-4-yl)propanamide

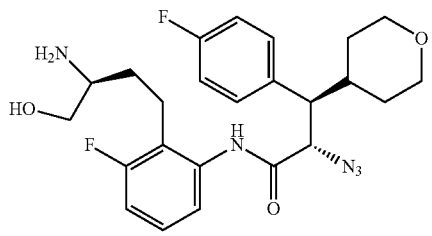 [SMILES: [N-]=[N+]=N[C@H](C(=O)Nc1cccc(F)c1CC[C@H](N)CO)[C@@H](c1ccc(F)cc1)C1CCOCC1]

To a stirred solution of (S)-tert-butyl 4-(2-((2S,3R)-2-azido-3-(4-fluorophenyl)-3-(tetrahydro-2H-pyran-4-yl)propanamido)-6-fluorophenethyl)-2,2-dimethyloxazolidine-3-carboxylate (2.20 g, 3.58 mmol) in dichloromethane (30 mL) was added trifluoroacetic acid (14 mL) and water (4 mL) and the solution was stirred at room temperature for 16 h. Concentrated the solvents under reduced pressure and the residue was diluted with EtOAc (250 mL) and saturated solution of sodium bicarbonate (100 mL) and the biphasic solution was stirred for 10 min. The organic layer was separated and washed with brine (100 mL), dried (Na₂SO₄), filtered and concentrated under reduced pressure. The pale yellow solid (1.40 g, quantitative) obtained was carried into next step without further purification.

Step 3. (2S,3R)-2-Azido-N-(3-fluoro-2-(2-((S)-1-(phenylsulfonyl)aziridin-2-yl)ethyl)phenyl)-3-(4-fluorophenyl)-3-(tetrahydro-2H-pyran-4-yl)propanamide

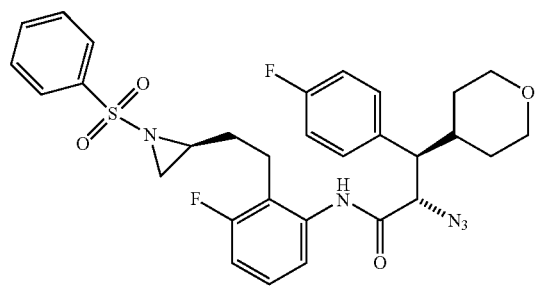 [SMILES: [N-]=[N+]=N[C@H](C(=O)Nc1cccc(F)c1CC[C@H]1CN1S(=O)(=O)c1ccccc1)[C@@H](c1ccc(F)cc1)C1CCOCC1]

To a stirred solution of (2S,3R)—N-(2-((S)-3-amino-4-hydroxybutyl)-3-fluorophenyl)-2-azido-3-(4-fluorophenyl)-3-(tetrahydro-2H-pyran-4-yl)propanamide (1.80 g, 3.80 mmol) in dichloromethane at −20° C. was added triethylamine (2.60 mL, 19.0 mmol), DMAP (40 mg, 0.38 mmol) and benzene sulfonylchloride (0.58 mL, 4.56 mmol) and the reaction mixture was stirred 1.5 h. This was followed by the addition of methane sulfonylchloride (0.35 mL, 4.56 mmol) and stirring was continued for 30 min, and stirred the reaction mixture at 0° C. The reaction mixture was quenched with saturated solution of sodium bicarbonate (10 mL) and stirred for an additional 30 minutes. Diluted with water (20 mL) and extracted with dichloromethane (2×50 mL). The combined organic extracts were washed with brine (10 mL), dried (Na$_2$SO$_4$), filtered and concentrated under reduced pressure. The residue obtained was purified by 80 g SiO$_2$ column using a gradient elution of 0-30% EtOAc in hexanes. Fractions containing product were combined and the solvents were removed in vacuo to provide the product (1.10 g, 63%) as a pale yellow solid.

Step 4. (2S,3R)-2-Azido-N-(3-fluoro-2-((S)-4-(((R)-2-hydroxypropyl)amino)-3-(phenylsulfonamido)butyl)phenyl)-3-(4-fluorophenyl)-3-(tetrahydro-2H-pyran-4-yl)propanamide

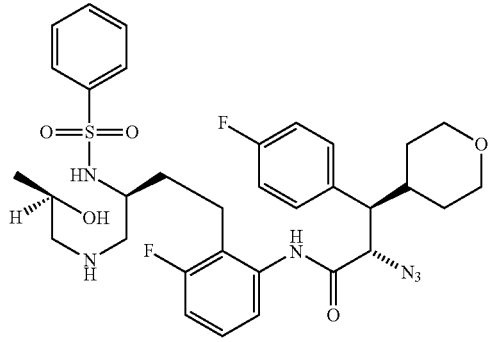 [SMILES: C[C@@H](O)CNC[C@H](CCc1c(F)cccc1NC(=O)[C@@H](N=[N+]=[N-])[C@@H](c1ccc(F)cc1)C1CCOCC1)NS(=O)(=O)c1ccccc1]

To a stirred solution of (2S,3R)-2-azido-N-(3-fluoro-2-(2-((S)-1-(phenylsulfonyl)aziridin-2-yl)ethyl)phenyl)-3-(4-fluorophenyl)-3-(tetrahydro-2H-pyran-4-yl)propanamide (0.40 g, 0.67 mmol) in 1,2-dichloroethane (3 mL) was added (R)-1-amino 2-propanol (0.353 g, 4.70 mmol) and the solution was heated to 50° C. for 1.5 h. The reaction mixture was cooled to room temperature and diluted with water (50 mL) and extracted with EtOAc (100 mL). The organic layer was washed with water (50 mL), brine (50 mL), dried (Na$_2$SO$_4$), filtered and concentrated under reduced pressure. The yellow gum (0.48 g, quantitative) obtained was taken forward to the next step without further purification.

Step 5. tert-Butyl ((S)-4-(2-((2S,3R)-2-azido-3-(4-fluorophenyl)-3-(tetrahydro-2H-pyran-4-yl)propanamido)-6-fluorophenyl)-2-(phenylsulfonamido)butyl)((R)-2-hydroxypropyl)carbamate To a stirred solution of (2S,3R)-2-azido-N-(3-fluoro-2-((S)-4-(((R)-2-hydroxypropyl)amino)-3-(phenylsulfonamido)butyl)phenyl)-3-(4-fluorophenyl)-3-(tetrahydro-2H-pyran-4-yl)propanamide (0.47 g, 0.70 mmol) in dichloromethane (10 mL) was added di-tert-butyl dicarbonate (0.32 mL, 1.40 mmol) and triethylamine (0.19 mL, 1.40 mmol) and the reaction mixture was stirred at room temperature for 16 h. Diluted the reaction mixture with water (50 mL) and EtOAc (100 mL), the layers were separated and the organic layer was washed with brine (50 mL), dried (Na$_2$SO$_4$), filtered and concentrated under reduced pressure. The residue was purified by 24 g SiO$_2$ column using a gradient elution of 0-35% EtOAc in hexanes. Fractions containing product were combined and the solvents were removed in vacuo to provide the product (0.40 g, 77% over two steps) as a pale yellow gum.

Step 6. (3S,5S)-tert-Butyl 3-(2-((2S,3R)-2-azido-3-(4-fluorophenyl)-3-(tetrahydro-2H-pyran-4-yl)propanamido)-6-fluorophenethyl)-5-methyl-4-(phenylsulfonyl)piperazine-1-carboxylate

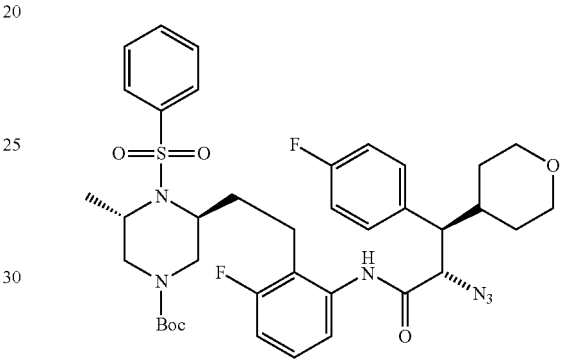

To a stirred solution of tert-butyl ((S)-4-(2-((2S,3R)-2-azido-3-(4-fluorophenyl)-3-(tetrahydro-2H-pyran-4-yl)propanamido)-6-fluorophenyl)-2-(phenylsulfonamido)butyl)((R)-2-hydroxypropyl)carbamate (0.40 g, 0.51 mmol) in dry THF was added DIAD (0.315 g, 1.55 mmol) and triphenyl phosphine (0.408 g, 1.55 mmol) and the reaction mixture was stirred at room temperature for 20 min. Added silica-gel and concentrated under reduced pressure. The compound was purified by 12 g SiO$_2$ column using a gradient elution of 0-30% EtOAc in hexanes. Fractions containing product were combined and the solvents were removed in vacuo to provide the product (0.38 g, 97%) as a pale yellow gum.

Step 7. (3S,5S)-tert-Butyl 3-(2-((2S,3R)-2-amino-3-(4-fluorophenyl)-3-(tetrahydro-2H-pyran-4-yl)propanamido)-6-fluorophenethyl)-5-methyl-4-(phenylsulfonyl)piperazine-1-carboxylate

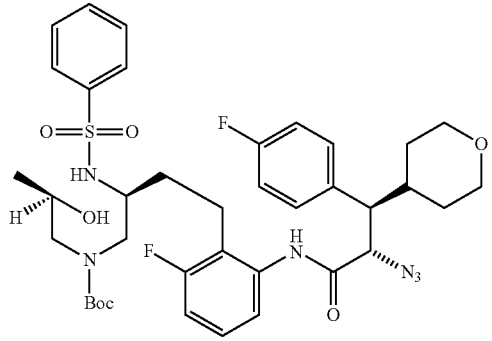 [SMILES: C[C@@H](O)CN(C[C@H](CCc1c(F)cccc1NC(=O)[C@@H](N=[N+]=[N-])[C@@H](c1ccc(F)cc1)C1CCOCC1)NS(=O)(=O)c1ccccc1)C(=O)OC(C)(C)C]

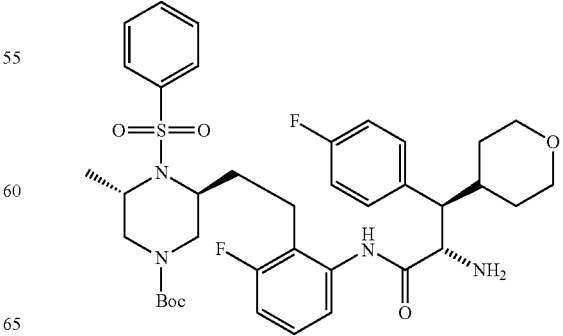

To a stirred solution of (3S,5S)-tert-butyl 3-(2-((2S,3R)-2-azido-3-(4-fluorophenyl)-3-(tetrahydro-2H-pyran-4-yl)propanamido)-6-fluorophenethyl)-5-methyl-4-(phenylsulfonyl)piperazine-1-carboxylate (0.38 g, 0.50 mmol) in a mixture of EtOAc (20 mL), water (5 mL) was added trimethyl phosphine (2.50 mL, 2.52 mmol, 1M solution in THF) and the reaction mixture was stirred at room temperature for 16 h. Diluted the reaction mixture with water (50 mL) and EtOAc (75 mL) the layers were separated. The organic layer was washed with brine (30 mL), dried (Na$_2$SO$_4$), filtered and concentrated under reduced pressure. The residue was purified by 12 g SiO$_2$ column using a gradient elution of 0-5% MeOH in dichloromethane. Fractions containing product were combined and the solvents were removed in vacuo to provide the product (0.25 g, 68%) as a pale yellow gum.

Step 8. (3S,5S)-tert-Butyl 3-(2-fluoro-6-((2S,3R)-3-(4-fluorophenyl)-2-((methoxycarbonyl)amino)-3-(tetrahydro-2H-pyran-4-yl)propanamido)phenethyl)-5-methyl-4-(phenylsulfonyl)piperazine-1-carboxylate

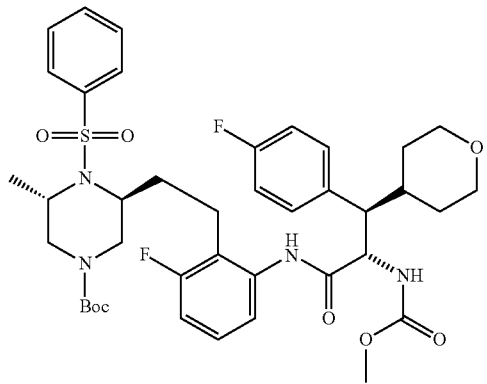 [SMILES: COC(=O)N[C@H](C(=O)Nc1cccc(F)c1CC[C@H]1CN(C(=O)OC(C)(C)C)C[C@H](C)N1S(=O)(=O)c1ccccc1)[C@@H](c1ccc(F)cc1)C1CCOCC1]

To a stirred solution of (3S,5S)-tert-butyl 3-(2-((2S,3R)-2-amino-3-(4-chlorophenyl)-3-(tetrahydro-2H-pyran-4-yl)propanamido)-6-fluorophenethyl)-5-methyl-4-(phenylsulfonyl)piperazine-1-carboxylate (0.10 mg, 0.13 mmol) in dichloromethane at 0° C. was added diisopropylethylamine (0.048 ml, 0.27 mmol) and methylchloroformate (0.013 mL, 0.16 mmol) and the reaction mixture was stirred for 30 min. Diluted the reaction mixture with water (50 mL) and EtOAc (50 mL) the layers were separated. The organic layer was washed with brine (30 mL), dried (Na$_2$SO$_4$), filtered and concentrated under reduced pressure. The residue was purified by 12 g SiO$_2$ column using a gradient elution of 0-5% MeOH in dichloromethane. Fractions containing product were combined and the solvents were removed in vacuo to provide the product (93 mg, 86%) as a pale yellow gum.

Step 9. Methyl ((2S,3R)-1-((3-fluoro-2-(2-((2S,6S)-6-methyl-1-(phenylsulfonyl)piperazin-2-yl)ethyl)phenyl)amino)-3-(4-fluorophenyl)-1-oxo-3-(tetrahydro-2H-pyran-4-yl)propan-2-yl)carbamate To a stirred solution of (3S,5S)-tert-butyl 3-(2-fluoro-6-((2S,3R)-3-(4-fluorophenyl)-2-((methoxycarbonyl)amino)-3-(tetrahydro-2H-pyran-4-yl)propanamido)phenethyl)-5-methyl-4-(phenylsulfonyl)piperazine-1-carboxylate (90 mg, 0.11 mmol) in dichloromethane was added trifluoroacetic acid (0.2 mL) and the reaction mixture was stirred at room temperature for 2 h. Concentrated the reaction mixture and lyophilized over 1 day to provide the product (85 mg, 93%) as an off-white solid. MS: m/z=685 (M+H$^+$).

EXAMPLE 8

Methyl ((2S,3R)-3-(4-chlorophenyl)-1-((5-fluoro-4-(2-((2S,6S)-6-methyl-1-(phenylsulfonyl)piperzin-2-yl)ethyl)pyridin-3-yl)amino)-4-methyl-1-oxopentan-2-yl)carbamate

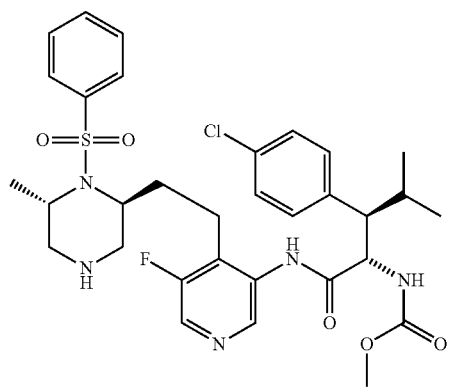 [SMILES: COC(=O)N[C@H](C(=O)Nc1cncc(F)c1CC[C@H]1CNC[C@H](C)N1S(=O)(=O)c1ccccc1)[C@@H](c1ccc(Cl)cc1)C(C)C]

Step 1. (S)-tert-butyl 4-(2-(3-((2S,3R)-2-azido-3-(4-chlorophenyl)-4-methylpentanamido)-5-fluoropyridin-4-yl)ethyl)-2,2-dimethyloxazolidine-3-carboxylate

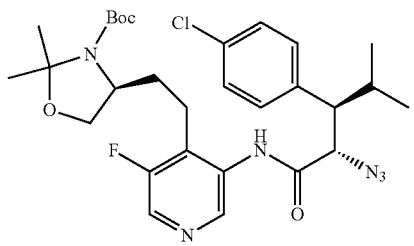 [SMILES: CC(C)[C@H](c1ccc(Cl)cc1)[C@H](N=[N+]=[N-])C(=O)Nc1cncc(F)c1CC[C@H]1COC(C)(C)N1C(=O)OC(C)(C)C]

To a stirred solution of (S)-tert-butyl 4-(2-(3-amino-5-fluoropyridin-4-yl)ethyl)-2,2dimethyloxazolidine-3-carboxylate (1.90 g, 5.61 mmol) and (2S,3R)-2-azido-3-(4-chlorophenyl)-4-methylpenatnoic acid (Intermediate 12) (1.50 g, 5.61 mmol) in pyridine (15 mL) at −20° C. was slowly added POCl$_3$ (0.63 mL, 6.74 mmol) and the reaction mixture was allowed to reach 0° C. and stirred for 3 h. The reaction was quenched with a saturated solution of KH$_2$PO$_4$ (50 mL) and extracted with EtOAc (200 mL). The organic layer was washed with brine (200 mL), dried (Na$_2$SO$_4$), filtered and concentrated under reduced pressure. The residue was purified by 80 g SiO$_2$ column using a gradient elution of 0-50% EtOAc in hexanes. Fractions containing product were combined and the solvents were removed in vacuo to provide the product (3.0 g, 90%) as a pale yellow solid. MS: m/z=589 (M+H$^+$)

Step 2. (2S,3R)—N-(4-((S)-3-amino-4-hydroxybutyl)-5-fluoropyridin-3-yl)-2-azido-3-(4-chlorophenyl)-4-methylpentanamide

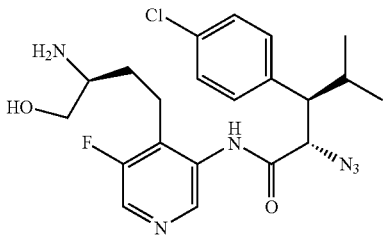 [SMILES: CC(C)[C@H](c1ccc(Cl)cc1)[C@H](N=[N+]=[N-])C(=O)Nc1cncc(F)c1CC[C@H](N)CO]

To a stirred solution of (S)-tert-butyl 4-(2-(3-((2S,3R)-2-azido-3-(4-chlorophenyl)-4-methylpentanamido)-5-fluoropyridin-4-yl)ethyl)-2,2-dimethyloxazolidine-3-carboxylate (3.0 g, 5.10 mmol) in dichloromethane (60 mL) was added trifluoroacetic acid (20 mL), water (6 mL) and the reaction mixture was stirred at room temperature for 16 h. Concentrated the solvents and the residue obtained was diluted with EtOAc (250 mL) and saturated solution of sodium bicarbonate (100 mL) and the biphasic solution was stirred for 10 min. The organic layer was separated and washed with brine (100 mL), dried (Na$_2$SO$_4$), filtered and concentrated under reduced pressure. The pale yellow solid (2.3 g, quantitative) obtained was carried into next step without further purification. MS: m/z=449 (M+H$^+$)

Step 3. (2S,3R)-2-Azido-3-(4-chlorophenyl)-N-(5-fluoro-4-(2-((S)-1-(phenylsulfonyl)aziridin-2-yl)ethyl)pyridine-3-yl)-4-methylpentanamide

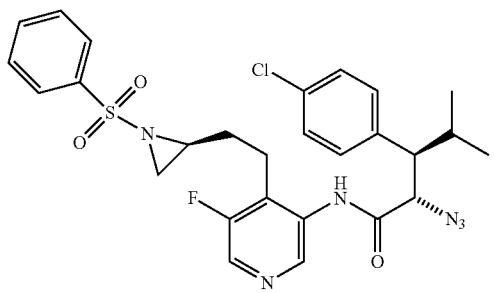 [SMILES: CC(C)[C@H](c1ccc(Cl)cc1)[C@H](N=[N+]=[N-])C(=O)Nc1cncc(F)c1CC[C@H]1CN1S(=O)(=O)c1ccccc1]

To a stirred solution of (2S,3R)—N-(4-((S)-3-amino-4-hydroxybutyl)-5-fluoropyridin-3-yl)-2-azido-3-(4-chlorophenyl)-4-methylpentanamide (0.68 g, 1.51 mmol) in dichloromethane kept at −20° C. was added triethylamine (1.05 mL, 7.55 mmol), DMAP (18.50 mg, 0.15 mmol) and benzene sulfonyl chloride (0.23 mL, 1.81 mmol) and the reaction mixture was stirred at −20° C. for 1.5 h. This was followed by the addition of methane sulfonyl chloride (0.14 mL, 1.81 mmol) and stirring was continued for 30 min., while allowing the temperature to rise to 0° C. The reaction was quenched with saturated solution of NaHCO$_3$ (10 mL) and stirred for additional 30 min. Diluted with water (50 mL) and extracted with dichloromethane (3×50 mL). The combined organic layers were washed with brine (100 mL), dried (Na$_2$SO$_4$), filtered and concentrated under reduced pressure. The residue was purified by 40 g SiO$_2$ column using a gradient elution of 0-50% EtOAc in hexanes. Fractions containing product were combined and the solvents were removed in vacuo to provide the product (0.68 g, 79%) as a pale yellow solid.

MS: m/z=571 (M+H$^+$)

Step 4. (2S,3R)-2-Azido-3-(4-chlorophenyl)-N-(5-fluoro-4-((S)-4-(((R)-2-hydroxypropyl)amino)-3-(phenylsulfonamido)butyl)pyridin-3-yl)-4-methylpentanamide

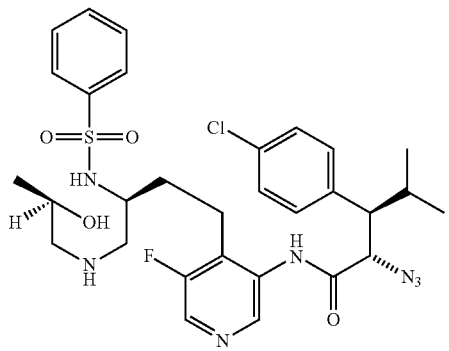 [SMILES: CC(C)[C@H](c1ccc(Cl)cc1)[C@H](N=[N+]=[N-])C(=O)Nc1cncc(F)c1CC[C@@H](CNC[C@@H](C)O)NS(=O)(=O)c1ccccc1]

To a stirred solution of (2S,3R)-2-azido-3-(4-chlorophenyl)-N-(5-fluoro-4-(2-((S)-1-(phenylsulfonyl)aziridin-2-yl)ethyl)pyridine-3-yl)-4-methylpentanamide (0.24 g, 0.42 mmol) in 1,2-dichloroethane (10 mL) was added (R)-1-amino 2-propanol (0.221 g, 2.94 mmol) and the solution was heated to 60° C. for 1.5 h. Cooled the reaction mixture to room temperature, and diluted with water (50 mL) and extracted with EtOAc (100 mL). The organic layer was washed with water (50 mL), brine (50 mL), dried (Na$_2$SO$_4$), filtered and concentrated under reduced pressure. The yellow gum (0.31 g, quantitative) obtained was taken forward to the next step without further purification.

MS: m/z=646 (M+H$^+$)

Step 5. tert-Butyl((S)-4-(3-((2S,3R)-2-azido-3-(4-chlorophenyl)-4-methylpentanamido)-5-fluoropyridin-4-yl)-2-(phenylfulfanamido)butyl)((R)-2-hydroxypropyl)carbamate

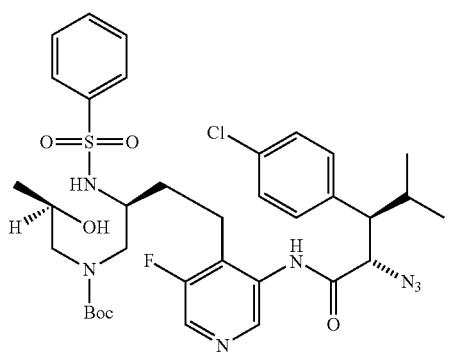 [SMILES: CC(C)[C@H](c1ccc(Cl)cc1)[C@H](N=[N+]=[N-])C(=O)Nc1cncc(F)c1CC[C@@H](CN(C[C@@H](C)O)C(=O)OC(C)(C)C)NS(=O)(=O)c1ccccc1]

To a stirred solution of (2S,3R)-2-azido-3-(4-chlorophenyl)-N-(5-fluoro-4-((S)-4-(((R)-2-hydroxypropyl)amino)-3-(phenylsulfonamido)butyl)pyridin-3-yl)-4-methylpentanamide (0.31 g, 0.47 mmol) in dichloromethane (10 mL) was added di-tert-butyl dicarbonate (0.21 mL, 0.95 mmol) and triethylamine (0.13 mL, 0.95 mmol) and the reaction mixture was stirred at room temperature for 16 h. Diluted the reaction mixture with water (50 mL) and EtOAc (100 mL) the layers were separated and the organic layer was washed with brine (50 mL), dried (Na$_2$SO$_4$), filtered and concentrated under reduced pressure. The residue was purified by 24 g SiO$_2$ column using a gradient elution of 0-80% EtOAc in hexanes. Fractions containing product were combined and the solvents were removed in vacuo to provide the product (0.15 g, 48% over two steps) as a pale yellow gum. MS: m/z=746 (M+H$^+$)

Step 6. (3S,5S)-tert-Butyl 3-(2-(3-((2S,3R)-2-azido-3-(4-chlorophenyl)-4-methylpentanamido)-5-fluoropyridin-4-yl)ethyl)-5-methyl-4-(phenylsulfonyl)piperazine-1-carboxylate

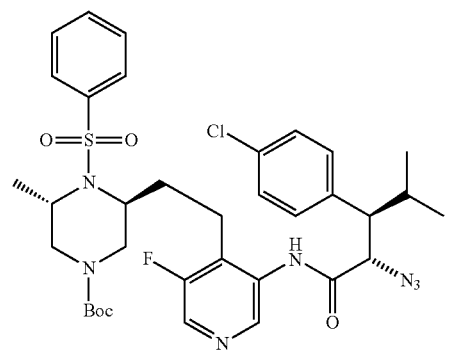 [SMILES: CC(C)[C@H](c1ccc(Cl)cc1)[C@H](N=[N+]=[N-])C(=O)Nc1cncc(F)c1CC[C@H]1CN(C(=O)OC(C)(C)C)C[C@H](C)N1S(=O)(=O)c1ccccc1]

To a stirred solution of tert-butyl((S)-4-(3-((2S,3R)-2-azido-3-(4-chlorophenyl)-4-methylpentanamido)-5-fluoropyridin-4-yl)-2-(phenylfulfanamido)butyl)((R)-2-hydroxypropyl)carbamate (0.15 g, 0.20 mmol) in dry THF was added DIAD (0.122 g, 0.60 mmol) and triphenyl phosphine (0.158 g, 0.60 mmol) and the reaction mixture was stirred at room temperature for 20 min. Added silica-gel and concentrated under reduced pressure. The product was purified by 12 g SiO$_2$ column using a gradient elution of 0-80% EtOAc in hexanes. Fractions containing product were combined and the solvents were removed in vacuo to provide the product (0.12 g, 82%) as a pale yellow gum. MS: m/z=728 (M+H$^+$)

Step 7. (3S,5S)-tert-butyl 3-(2-(3-((2S,3R)-2-amino-3-(4-chlorophenyl)-4-methylpentanamido)-5-fluoropyridin-4-yl)ethyl)-5-methyl-4-(phenylsulfonyl)piperazine-1-carboxylate

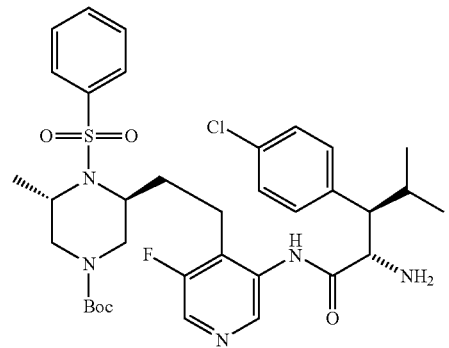 [SMILES: CC(C)[C@H](c1ccc(Cl)cc1)[C@H](N)C(=O)Nc1cncc(F)c1CC[C@H]1CN(C(=O)OC(C)(C)C)C[C@H](C)N1S(=O)(=O)c1ccccc1]

To a stirred solution of (3S,5S)-tert-butyl 3-(2-(3-((2S,3R)-2-azido-3-(4-chlorophenyl)-4-methylpentanamido)-5-fluoropyridin-4-yl)ethyl)-5-methyl-4-(phenylsulfonyl)piperazine-1-carboxylate (0.12 g, 0.16 mmol) in a mixture of EtOAc (20 mL) and water (5 mL) was added trimethyl phosphine (0.32 mL, 1M solution in THF) and the reaction mixture was stirred at room temperature for 16 h. Diluted with water (50 mL) and EtOAc (75 mL) the layers were separated and the organic layer was washed with brine (30 mL), dried (Na$_2$SO$_4$), filtered and concentrated under reduced pressure. The residue was purified by 12 g SiO$_2$ column using a gradient elution of 0-5% MeOH in dichloromethane. Fractions containing product were combined and the solvents were removed in vacuo to provide the product (0.045 g, 39%) as a pale yellow gum. MS: m/z=702 (M+H$^+$)

Step 8. (3S,5S)-tert-butyl 3-(2-(3-((2S,3R)-3-(4-chlorophenyl)-2-((methoxycarbonyl)amino)-4-methylpentanamido)-5-fluoropyridin-4-yl)ethyl)-5-methyl-4-(phenylsulfonyl)piperazine-1-carboxylate

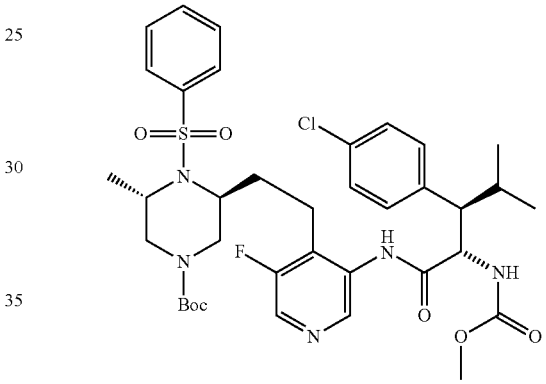

To a stirred solution of (3S,5S)-tert-butyl 3-(2-(3-((2S,3R)-2-amino-3-(4-chlorophenyl)-4-methylpentanamido)-5-fluoropyridin-4-yl)ethyl)-5-methyl-4-(phenylsulfonyl)piperazine-1-carboxylate (25 mg, 0.035 mmol) in dichloromethane kept at 0° C. was added diisopropylethylamine (0.012 ml, 0.071 mmol) and methylchloroformate (0.003 mL, 0.042 mmol) and the reaction mixture was stirred for 30 min. After addition of water and EtOAc (50 mL) the layers were separated and the organic layer was washed with brine (30 mL), dried (Na$_2$SO$_4$), filtered and concentrated under reduced pressure. The residue was purified by 12 g SiO$_2$ column using a gradient elution of 0-80% EtOAc in hexanes. Fractions containing product were combined and the solvents were removed in vacuo to provide the product (15 mg, 56%) as a pale yellow gum. MS: m/z=760 (M+H$^+$)

Step 9. Methyl ((2S,3R)-3-(4-chlorophenyl)-1-((5-fluoro-4-(2-((2S,6S)-6-methyl-1-(phenylsulfonyl)piperazin-2-yl)ethyl)pyridin-3-yl)amino)-4-methyl-1-oxopentan-2-yl)carbamate To a stirred solution of (3S,5S)-tert-butyl 3-(2-(3-((2S,3R)-3-(4-chlorophenyl)-2-((methoxycarbonyl)amino)-4-methylpentanamido)-5-fluoropyridin-4-yl)ethyl)-5-methyl-4-(phenylsulfonyl)piperazine-1-carboxylate (15 mg, 0.02 mmol) in dichloromethane was added trifluoroacetic acid (0.2 mL) and the reaction mixture was stirred at room temperature for 2 h. Concentration of the reaction mixture followed by trituration with diethyl ether (0.5 mL) and n-hexanes (2.0 mL) and subsequent lyophilisation provided the product (9.1 mg, 52%) as an off-white solid. MS: m/z=660 (M+H⁺)

EXAMPLE 9

(2S,3R)-2-Amino-3-(4-chlorophenyl)-N-(5-fluoro-4-(2-((2S,6S)-1-((4-methoxyphenyl)sulfonyl)-6-methylpiperazin-2-yl)ethyl)pyridin-3-yl)-3-(tetrahydro-2H-pyran-4-yl)propanamide

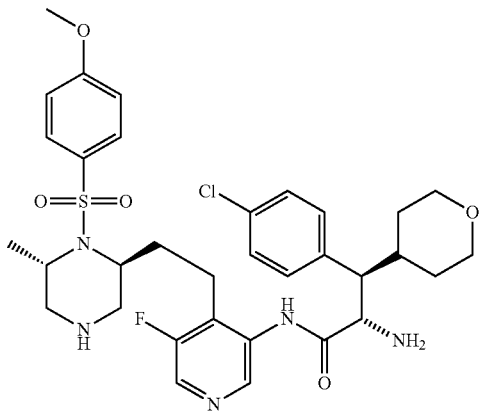 [SMILES: COc1ccc(S(=O)(=O)N2[C@@H](CCc3c(F)cncc3NC(=O)[C@@H](N)[C@@H](c3ccc(Cl)cc3)C3CCOCC3)CNC[C@@H]2C)cc1]

Step 1. (S)-tert-Butyl 4-(2-(3-((2S,3R)-2-azido-3-(4-chlorophenyl)-3-(tetrahydro-2H-pyran-4-yl)propanamido)-5-fluoropyridin-4-yl)ethyl)-2,2-dimethyloxazolidine-3-carboxylate

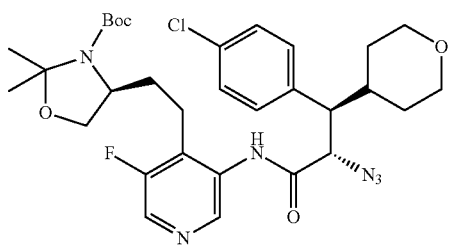 [SMILES: CC(C)(C)OC(=O)N1[C@@H](CCc2c(F)cncc2NC(=O)[C@@H](N=[N+]=[N-])[C@@H](c2ccc(Cl)cc2)C2CCOCC2)COC1(C)C]

To a stirred solution of (S)-tert-butyl 4-(2-(3-amino-5-fluoropyridin-4-yl)ethyl)-2,2dimethyloxazolidine-3-carboxylate (0.90 g, 2.61 mmol) and (2S,3R)-2-azido-3-(4-chlorophenyl)-3-(tetrahydro-2H-pyran-4-yl)propanoic acid (Intermediate 16) (0.90 g, 2.90 mmol) in pyridine (10 mL) kept at −20° C. was slowly added POCl₃ (0.32 mL, 3.5 mmol) and the reaction mixture was allowed to reach 0° C. and stirred for 3 h. The reaction was quenched saturated solution of KH₂PO₄ solution (30 mL) and extracted with EtOAc (100 mL). The organic layer was washed with brine (100 mL), dried (Na₂SO₄), filtered and concentrated under reduced pressure. The residue was purified by 40 g SiO₂ column using a gradient elution of 0-50% EtOAc in hexanes. Fractions containing product were combined and the solvents were removed in vacuo to provide the product (1.37 g, 82%) as a pale yellow solid. MS: m/z=631 (M+H⁺).

Step 2. (2S,3R)—N-(4-((S)-3-Amino-4-hydroxybutyl)-5-fluoropyridin-3-yl)-2-azido-3-(4-chlorophenyl)-3-(tetrahydro-2H-pyran-4-yl)propanamide

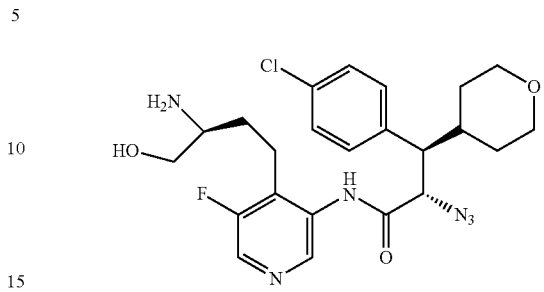

To a stirred solution of (S)-tert-butyl 4-(2-(3-((2S,3R)-2-azido-3-(4-chlorophenyl)-3-(tetrahydro-2H-pyran-4-yl)propanamido)-5-fluoropyridin-4-yl)ethyl)-2,2-dimethyloxazolidine-3-carboxylate (1.37 g, 2.10 mmol) in dichloromethane (15 mL) was added trifluoroacetic acid (7 mL) and water (1.5 mL) and the reaction mixture was stirred at room temperature for 16 h. Concentrated the solvents and the residue obtained was diluted with EtOAc (250 mL) and saturated solution of sodium bicarbonate (100 mL) and the biphasic solution was stirred for 10 min. The organic layer was separated and washed with brine (100 mL), dried (Na₂SO₄), filtered and concentrated under reduced pressure. The residue was purified by 40 g SiO₂ column using a gradient elution of 0-100 EtOAc in hexanes. Fractions containing product were combined and the solvents were removed under reduced pressure to provide the product (0.90 g, 90%) as a pale yellow solid. MS: m/z=491 (M+H⁺).

Step 3. (2S,3R)-2-Azido-3-(4-chlorophenyl)-N-(5-fluoro-4-(2-((S)-1-((4-methoxyphenyl)sulfonyl)aziridin-2-yl)ethyl)pyridin-3-yl)-3-(tetrahydro-2H-pyran-4-yl)propanamide

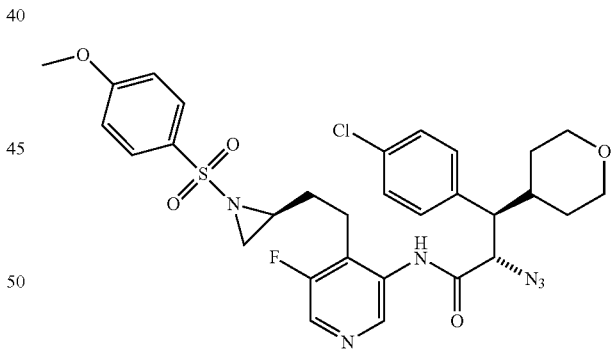

To a stirred solution of (2S,3R)—N-(4-((S)-3-amino-4-hydroxybutyl)-5-fluoropyridin-3-yl)-2-azido-3-(4-chlorophenyl)-3-(tetrahydro-2H-pyran-4-yl)propanamide (0.46 g, 0.93 mmol) in dichloromethane kept at −20° C. was added triethylamine (0.65 mL, 4.70 mmol), DMAP (0.011 g, 0.09 mmol) and 4-methoxybenzene sulfonyl chloride (0.23 g, 1.12 mmol) and the reaction was stirred at −20° C. for 1.5 h. This was followed by the addition of methane sulfonyl chloride (0.09 mL, 1.12 mmol), the reaction was allowed to warm up to room temperature and stirring was continued for 16 h. The reaction was quenched with saturated solution of sodium bicarbonate (10 mL) and stirred for additional 30 min. The reaction mixture was diluted with water (50 mL) and extracted with dichloromethane. The organic layer was washed with brine (10 mL), dried (Na₂SO₄), filtered and concentrated under reduced pressure. The residue was purified by 40 g SiO₂ column using a gradient elution of 0-55% EtOAc in hexanes. Fractions containing product were combined and the solvents were removed under reduced pressure to provide the product (0.36 g, 60%) as a pale yellow solid. MS: m/z=643 (M+H⁺).

Step 4. (2S,3R)-2-Azido-3-(4-chlorophenyl)-N-(5-fluoro-4-((S)-4-(((R)-2-hydroxypropyl)amino)-3-(4-methoxyphenylsulfonamido)butyl)pyridin-3-yl)-3-(tetrahydro-2H-pyran-4-yl)propanamide

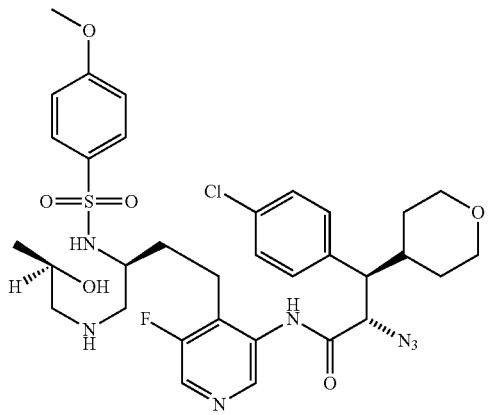 [SMILES: COc1ccc(S(=O)(=O)N[C@@H](CCc2c(F)cncc2NC(=O)[C@@H](N=[N+]=[N-])[C@@H](c2ccc(Cl)cc2)C2CCOCC2)CNC[C@@H](C)O)cc1]

To a stirred solution of (2S,3R)-2-azido-3-(4-chlorophenyl)-N-(5-fluoro-4-(2-((S)-1-((4-methoxyphenyl)sulfonyl)aziridin-2-yl)ethyl)pyridin-3-yl)-3-(tetrahydro-2H-pyran-4-yl)propanamide (0.36 g, 0.56 mmol) in 1,2 dichloroethane (5 mL) was added (R)-1-amino 2-propanol (0.294 g, 3.91 mmol) and the solution was heated to 55° C. for 2.5 h. Cooled the reaction mixture to room temperature, and diluted with water (50 mL) and extracted with EtOAc (100 mL). The organic layer was washed with water (50 mL), brine (50 mL), dried (Na₂SO₄), filtered and concentrated under reduced pressure. The yellow gum (0.34 g, crude) obtained was taken forward to the next step without further purification. MS: m/z=718 (M+H⁺).

Step 5. tert-Butyl ((S)-4-(3-((2S,3R)-2-azido-3-(4-chlorophenyl)-3-(tetrahydro-2H-pyran-4-yl)propanamido)-5-fluoropyridin-4-yl)-2-(4-methoxyphenylsulfonamido)butyl)((R)-2-hydroxypropyl)carbamate

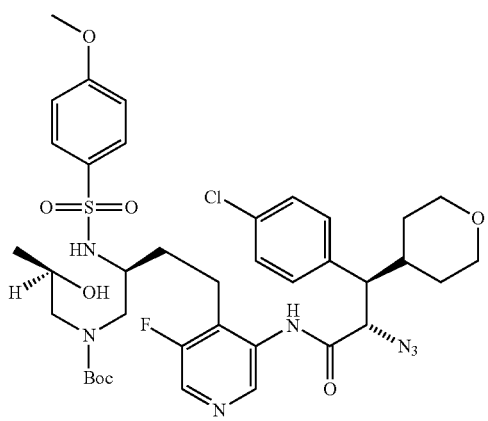 [SMILES: COc1ccc(S(=O)(=O)N[C@@H](CCc2c(F)cncc2NC(=O)[C@@H](N=[N+]=[N-])[C@@H](c2ccc(Cl)cc2)C2CCOCC2)CN(C[C@@H](C)O)C(=O)OC(C)(C)C)cc1]

To a stirred solution of (2S,3R)-2-azido-3-(4-chlorophenyl)-N-(5-fluoro-4-((S)-4-(((R)-2-hydroxypropyl)amino)-3-(4-methoxyphenylsulfonamido)butyl)pyridin-3-yl)-3-(tetrahydro-2H-pyran-4-yl)propanamide (0.34 g, crude) in dichloromethane (10 mL), was added di-tert-butyl dicarbonate (0.26 mL, 1.12 mmol) and triethylamine (0.16 mL, 1.12 mmol) and the reaction mixture was stirred for 16 h at room temperature. Diluted the reaction mixture with water (50 mL) and EtOAc (100 mL) the layers were separated and the organic layer was washed with brine (50 mL), dried (Na₂SO₄), filtered and concentrated under reduced pressure. The residue was purified by 24 g SiO₂ column using a gradient elution of 0-75% EtOAc in hexanes. Fractions containing product were combined and the solvents were removed in vacuo to provide the product (0.285 g) as a pale yellow gum. MS: m/z=818 (M+H⁺).

Step 6. (3S,5S)-tert-Butyl 3-(2-(3-((2S,3R)-2-azido-3-(4-chlorophenyl)-3-(tetrahydro-2H-pyran-4-yl)propanamido)-5-fluoropyridin-4-yl)ethyl)-4-((4-methoxyphenyl)sulfonyl)-5-methylpiperazine-1-carboxylate

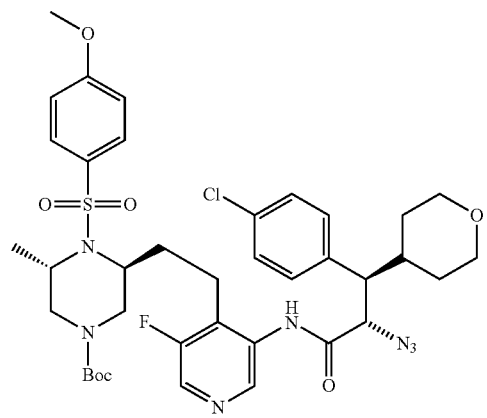 [SMILES: COc1ccc(S(=O)(=O)N2[C@@H](CCc3c(F)cncc3NC(=O)[C@@H](N=[N+]=[N-])[C@@H](c3ccc(Cl)cc3)C3CCOCC3)CN(C(=O)OC(C)(C)C)C[C@@H]2C)cc1]

To a stirred solution of tert-butyl ((S)-4-(3-((2S,3R)-2-azido-3-(4-chlorophenyl)-3-(tetrahydro-2H-pyran-4-yl)propanamido)-5-fluoropyridin-4-yl)-2-(4-methoxyphenylsulfonamido)butyl)((R)-2-hydroxypropyl)carbamate (0.285 g, 0.34 mmol) in dry THF (~4 mL) was added DIAD (0.212 g, 1.04 mmol) and triphenyl phosphine (0.274 g, 1.04 mmol) and the reaction mixture was stirred at room temperature for 2 h. Added silica-gel and concentrated under reduced pressure. The product was purified by 12 g SiO₂ column using a gradient elution of 0-80% EtOAc in hexanes. Fractions containing product were combined and the solvents were removed in vacuo to provide the product (0.30 g, contaminated with impurity) as a pale yellow gum. This material was directly used in the next step. MS: m/z=800 (M+H⁺).

Step 7. (3S,5S)-tert-Butyl 3-(2-(3-(((2S,3R)-2-amino-3-(4-chlorophenyl)-3-(tetrahydro-2H-pyran-4-yl)propanamido)-5-fluoropyridin-4-yl)ethyl)-4-((4 methoxyphenyl)sulfonyl)-5-methylpiperazine-1-carboxylate

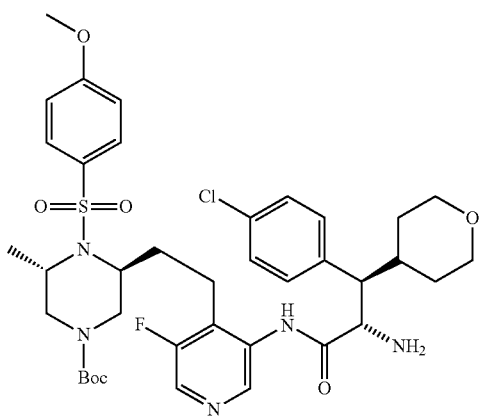 [SMILES: COc1ccc(S(=O)(=O)N2[C@@H](CCc3c(F)cncc3NC(=O)[C@@H](N)[C@@H](c3ccc(Cl)cc3)C3CCOCC3)CN(C(=O)OC(C)(C)C)C[C@@H]2C)cc1]

To a stirred solution of (3S,5S)-tert-butyl 3-(2-(3-(((2S,3R)-2-azido-3-(4-chlorophenyl)-3-(tetrahydro-2H-pyran-4-yl)propanamido)-5-fluoropyridin-4-yl)ethyl)-4-((4-methoxyphenyl)sulfonyl)-5-methylpiperazine-1-carboxylate (0.30 g, crude) in a mixture of EtOAc (12 mL) and water (3 mL) was added trimethyl phosphine (0.51 mL, 1 M solution in THF) and the reaction mixture was stirred at room temperature for 16 h. Diluted the reaction mixture with water (50 mL) and EtOAc (75 mL) the layers were separated. The organic layer was washed with brine (30 mL), dried ($Na_2SO_4$), filtered and concentrated under reduced pressure. The residue was purified by 12 g $SiO_2$ column using a gradient elution of 0-90% EtOAc in hexanes. Fractions containing product were combined and the solvents were removed in vacuo to provide the product (0.14 g, 52%, over 2-steps) as a pale yellow gum. MS: m/z=774 (M+H$^+$).

Step 8. (2S,3R)-2-Amino-3-(4-chlorophenyl)-N-(5-fluoro-4-(2-((2S,6S)-1-((4-methoxyphenyl)sulfonyl)-6-methylpiperazin-2-yl)ethyl)pyridin-3-yl)-3-(tetrahydro-2H-pyran-4-yl)propanamide To a stirred solution of (3S,5S)-tert-butyl 3-(2-(3-(((2S,3R)-2-amino-3-(4-chlorophenyl)-3-(tetrahydro-2H-pyran-4-yl)propanamido)-5-fluoropyridin-4-yl)ethyl)-4-((4 methoxyphenyl)sulfonyl)-5-methylpiperazine-1-carboxylate (60 mg, 0.077 mmol) in dichloromethane was added trifluoroacetic acid (0.85 mL) and the reaction mixture was stirred at room temperature for 1 h. Concentrated the reaction mixture and lyophilized over 1 day to provide the product (62.1 mg, 79%) as a white solid. MS: m/z=674 (M+H$^+$).

EXAMPLE 10

(S)-2-Amino-N-(3-fluoro-2-(2-((2S,6S)-6-methyl-1-(phenylsulfonyl)piperazin-2-yl)ethyl)phenyl)-3,3-bis(3-fluorophenyl)propanamide

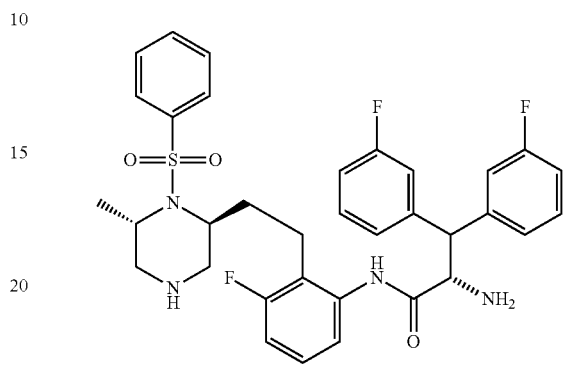

Step 1. (S)-tert-Butyl 4-(2-((S)-2-azido-3,3-bis(3-fluorophenyl)propanamido)-6-fluorophenethyl)-2,2-dimethyloxazolidine-3-carboxylate To a stirred solution of (S)-tert-butyl 4-(2-amino-6-fluorophenethyl)-2,2-dimethyloxazolidine-3-carboxylate (Intermediate C) (750 mg, 2.20 mmol) and (S)-2-azido-3,3-bis(3-fluorophenyl)propanoic acid (Intermediate 15) (700 mg, 2.30 mmol) in pyridine (16 mL) at −20° C. was slowly added POCl$_3$ (0.25 mL, 2.66 mmol) and the reaction mixture was allowed to reach 0° C. and stirred for 3 h. The reaction was quenched with a saturated solution of KH$_2$PO$_4$ (50 mL) and extracted with EtOAc (200 mL). The organic layer was washed with brine (200 mL), dried (Na$_2$SO$_4$), filtered and concentrated under reduced pressure. The residue was purified by 80 g SiO$_2$ column using a gradient elution of 0-30% EtOAc in hexanes. Fractions containing product were combined and the solvents were removed in vacuo to provide the product (740 g, 57%) as a pale yellow solid. MS: m/z=624 (M+H$^+$).

Step 2. ((S)—N-(2-((S)-3-Amino-4-hydroxybutyl)-3-fluorophenyl)-2-azido-3,3-bis(3-fluorophenyl)propanamide

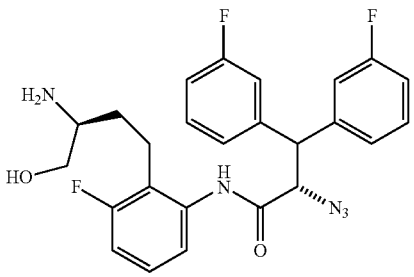 [SMILES: [N-]=[N+]=N[C@H](C(=O)Nc1cccc(F)c1CC[C@H](N)CO)C(c1cccc(F)c1)c1cccc(F)c1]

To a stirred solution of (S)-tert-butyl 4-(2-((S)-2-azido-3,3-bis(3-fluorophenyl)propanamido)-6-fluorophenethyl)-2,2-dimethyloxazolidine-3-carboxylate (740 mg, 1.18 mmol) in dichloromethane (25 mL) was added trifluoroacetic acid (3.50 mL) and water (1 mL) and the reaction mixture was stirred at room temperature for 16 h. Concentrated the solvents and the residue was diluted with EtOAc (250 mL) and saturated solution of NaHCO₃ (100 mL) and the biphasic solution was stirred for 10 min. The organic layer was separated and washed with brine (100 mL), dried (Na₂SO₄), filtered and concentrated under reduced pressure. The pale yellow solid (400 mg, crude) obtained was taken into next step without further purification. MS: m/z=484 (M+H⁺).

Step 3. (S)-2-Azido-N-(3-fluoro-2-(2-((S)-1-(phenylsulfonyl)aziridin-2-yl)ethyl)phenyl)-3,3-bis(3-fluorophenyl)propanamide

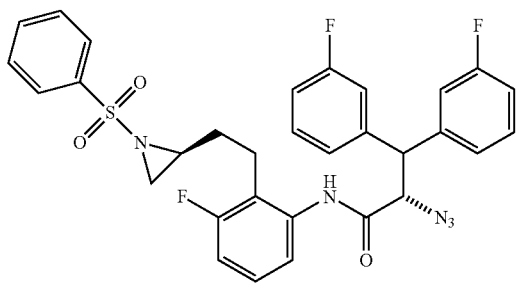 [SMILES: [N-]=[N+]=N[C@H](C(=O)Nc1cccc(F)c1CC[C@H]1CN1S(=O)(=O)c1ccccc1)C(c1cccc(F)c1)c1cccc(F)c1]

To a stirred solution of ((S)—N-(2-((S)-3-amino-4-hydroxybutyl)-3-fluorophenyl)-2-azido-3,3-bis(3-fluorophenyl)propanamide (400 mg, 0.82 mmol) in dichloromethane kept at −20° C. was added triethylamine (0.6 mL, 4.10 mmol), DMAP (10 mg, 0.08 mmol) and phenyl sulfonyl chloride (0.13 mL, 0.99 mmol) and the reaction mixture was warmed to 0° C. and stirred for 1.5 h. This was followed by the addition of methane sulfonyl chloride (0.08 mL, 0.99 mmol) and stirred at 0° C. for 30 min. The reaction was quenched with a saturated solution of NaHCO₃ (10 mL) and stirred for additional 30 min. The reaction was diluted with water (30 mL) and extracted with CH₂Cl₂ (2×50 mL). The combined organic extracts were washed with brine (50 mL), dried (Na₂SO₄), filtered and concentrated under reduced pressure. The residue was purified by 80 g SiO₂ column using a gradient elution of 0-30% EtOAc in hexanes. Fractions containing product were combined and the solvents were removed in vacuo to provide the product (260 mg, 50%) as a pale yellow solid. MS: m/z=606 (M+H⁺).

Step 4. (S)-2-Azido-N-(3-fluoro-2-((S)-4-((R)-2-hydroxypropylamino)-3-(phenylsulfonamido)butyl)phenyl)-3,3-bis(3-fluorophenyl)propanamide

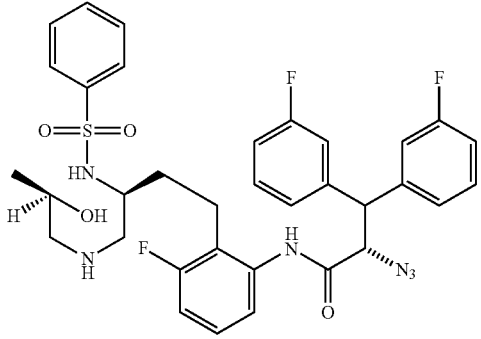 [SMILES: C[C@@H](O)CNC[C@H](CCc1c(F)cccc1NC(=O)[C@@H](N=[N+]=[N-])C(c1cccc(F)c1)c1cccc(F)c1)NS(=O)(=O)c1ccccc1]

To a stirred solution of (S)-2-azido-N-(3-fluoro-2-(2-((S)-1-(phenylsulfonyl)aziridin-2-yl)ethyl)phenyl)-3,3-bis(3-fluorophenyl)propanamide (0.26 g, 0.43 mmol) in 1,2-dichloroethane (10 mL) was added (R)-1-amino 2-propanol (0.220 g, 3.00 mmol) and the solution was heated to 60° C. for 16 h. The reaction mixture was cooled to room temperature and diluted with water (50 mL) and extracted with EtOAc (100 mL). The organic layer was washed with water (50 mL), brine (50 mL), dried (Na₂SO₄), filtered and concentrated under reduced pressure. The yellow gum (292 mg, crude) obtained was taken forward to the next step without further purification. MS: m/z=681 (M+H⁺).

Step 5. tert-Butyl (S)-4-(2-((S)-2-azido-3,3-bis(3-fluorophenyl)propanamido)-6-fluorophenyl)-2-(phenylsulfonamido)butyl((R)-2-hydroxypropyl)carbamate

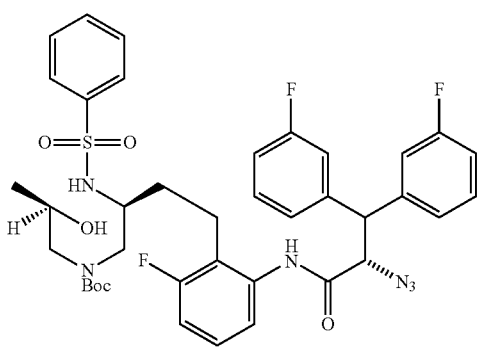 [SMILES: C[C@@H](O)CN(C[C@H](CCc1c(F)cccc1NC(=O)[C@@H](N=[N+]=[N-])C(c1cccc(F)c1)c1cccc(F)c1)NS(=O)(=O)c1ccccc1)C(=O)OC(C)(C)C]

To a stirred solution of (S)-2-azido-N-(3-fluoro-2-((S)-4-((R)-2-hydroxypropylamino)-3-(phenylsulfonamido)butyl)phenyl)-3,3-bis(3-fluorophenyl)propanamide (292 mg, 0.42 mmol) in dichloromethane (10 mL) was added di-tert-butyl dicarbonate (0.20 mL, 0.85 mmol) and triethyl amine (0.10 mL, 0.85 mmol) and the reaction mixture was stirred for 16 h at room temperature. The reaction mixture was diluted with water (50 mL) and EtOAc (100 mL) the layers were separated. The organic layer was washed with brine (50 mL), dried (Na$_2$SO$_4$), filtered and concentrated under reduced pressure. The residue was purified by 24 g SiO$_2$ column using a gradient elution of 0-80% EtOAc in hexanes. Fractions containing product were combined and the solvents were removed in vacuo to provide the product (260 mg, 90% over two steps) as a pale yellow gum. MS: m/z=781 (M+H$^+$).

Step 6. (3S,5S)-tert-Butyl 3-(2-((S)-2-azido-3,3-bis(3-fluorophenyl)propanamido)-6-fluorophenethyl)-5-methyl-4-(phenylsulfonyl)piperazine-1-carboxylate

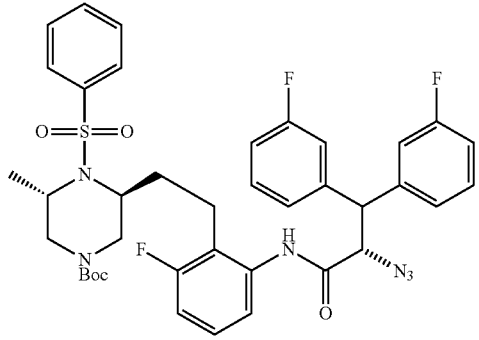

To a stirred solution of tert-butyl (S)-4-(2-((S)-2-azido-3,3-bis(3-fluorophenyl)propanamido)-6-fluorophenyl)-2-(phenylsulfonamido)butyl((R)-2-hydroxypropyl)carbamate (260 mg, 0.33 mmol) in dry THF (2.50 mL) was added DIAD (200 mg, 0.99 mmol) and triphenyl phosphine (260 mg, 0.99 mmol) and the reaction mixture was stirred at room temperature for 20 min. Concentrated solvents in vacuo and dried in vacuo to provide the product (300 mg, crude) as a pale yellow gum. The crude product was used in the next step without purification.

Step 7. (3S,5S)-tert-Butyl 3-(2-((S)-2-amino-3,3-bis(3-fluorophenyl)propanamido)-6-fluorophenethyl)-5-methyl-4-(phenylsulfonyl)piperazine-1-carboxylate

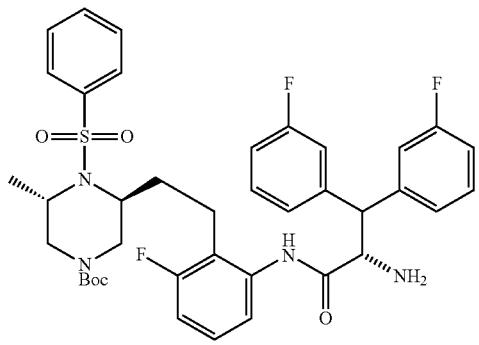

To a stirred solution of (3S,5S)-tert-butyl 3-(2-((S)-2-azido-3,3-bis(3-fluorophenyl)propanamido)-6-fluorophenethyl)-5-methyl-4-(phenylsulfonyl)piperazine-1-carboxylate (300 mg, crude) in a mixture of EtOAc (20 mL) and water (5 mL) was added trimethyl phosphine (3.9 mL, 1M solution in THF) and the reaction mixture was stirred at room temperature for 16 h. The reaction mixture was diluted with water (50 mL) and EtOAc (75 mL) the layers were separated. The organic layer was washed with brine (30 mL), dried (Na$_2$SO$_4$), filtered and concentrated under reduced pressure. The yellow gum (300 mg, crude) obtained was taken forward to the next step without further purification. MS: m/z=762 (M+H$^+$).

Step 8. (S)-2-Amino-N-(3-fluoro-2-(2-((2S,6S)-6-methyl-1-(phenylsulfonyl)piperazin-2-yl)ethyl)phenyl)-3,3-bis(3-fluorophenyl)propanamide To a stirred solution of (3S,5S)-tert-butyl 3-(2-((S)-2-amino-3,3-bis(3-fluorophenyl)propanamido)-6-fluorophenethyl)-5-methyl-4-(phenylsulfonyl)piperazine-1-carboxylate (100 mg, crude) in dichloromethane was added trifluoroacetic acid (0.5 mL) and the reaction mixture was stirred at room temperature for 2 h. The reaction mixture was concentrated and the residue was purified by semi prep HPLC. Fractions containing product were combined and the solvents were removed in vacuo and the residue lyophilized to provide the product (50 mg, 50%) as a white solid. MS: m/z=636 (M+H$^+$).

EXAMPLE 11

Methyl ((1S,2S)-1-(4-chlorophenyl)-3-((4-(2-((2S,6S)-1-(cyclopropylsulfonyl)-6-methylpiperazin-2-yl)ethyl)-5-fluoropyridin-3-yl)amino)-1-(3-fluorophenyl)-3-oxopropan-2-yl)carbamate

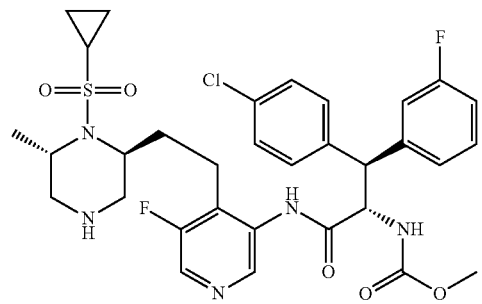

Step 1. (S)-tert-Butyl 4-(2-(3-((2S,3S)-2-azido-3-(4-chlorophenyl)-3-(3-fluorophenyl)propanamido)-5-fluoropyridin-4-yl)ethyl)-2,2-dimethyloxazolidine-3-carboxylate

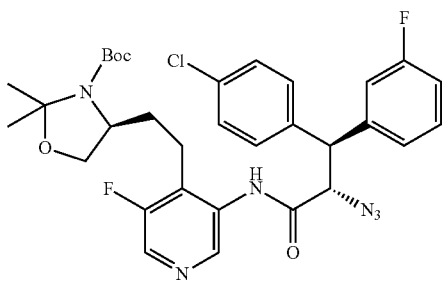 [SMILES: CC(C)(C)OC(=O)N1[C@@H](CCc2c(F)cncc2NC(=O)[C@@H](N=[N+]=[N-])[C@@H](c2ccc(Cl)cc2)c2cccc(F)c2)COC1(C)C]

To a stirred solution of (S)-tert-butyl 4-(2-(3-amino-5-fluoropyridin-4-yl)ethyl)-2,2dimethyloxazolidine-3-carboxylate (2.64 g, 7.8 mmol) and (2S,3S)-2-azido-3-(4-chlorophenyl)-3-(3-fluorophenyl)propanoic acid (Intermediate 13) (2.50 g, 7.8 mmol) in pyridine (25 mL) kept at −20° C. was slowly added POCl$_3$ (0.80 mL, 8.50 mmol) and the reaction mixture was allowed to reach 0° C. and stirred for 3 hours. The reaction was quenched with saturated solution of KH$_2$PO$_4$ (50 mL) and extracted with EtOAc (200 mL). The organic layer was washed with brine (200 mL), dried (Na$_2$SO$_4$), filtered and concentrated under reduced pressure.

The residue was purified by 80 g SiO$_2$ column using a gradient elution of 0-50% EtOAc in hexanes. Fractions containing product were combined and the solvents were removed in vacuo to provide the product (3.5 g, 70%) as a pale yellow solid. MS (APCI+) m/z 613 (M-29).

Step 2. (2S,3S)—N-(4-((S)-3-Amino-4-hydroxybutyl)-5-fluoropyridin-3-yl)-2-azido-3-(4-chlorophenyl)-3-(3-fluorophenyl)propanamide

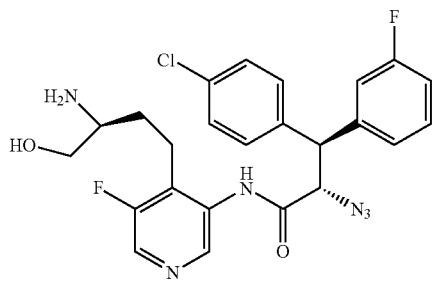 [SMILES: [N-]=[N+]=N[C@H](C(=O)Nc1cncc(F)c1CC[C@H](N)CO)[C@@H](c1ccc(Cl)cc1)c1cccc(F)c1]

To a stirred solution of (S)-tert-Butyl 4-(2-(3-((2S,3S)-2-azido-3-(4-chlorophenyl)-3-(3-fluorophenyl)propanamido)-5-fluoropyridin-4-yl)ethyl)-2,2-dimethyloxazolidine-3-carboxylate (3.4 g, 5.30 mmol) in dichloromethane (60 mL) was added trifluoroacetic acid (20 mL) and water (6 mL) and the reaction mixture was stirred at room temperature for 16 h. Concentrated the solvents and the residue was diluted with EtOAc (250 mL) and saturated solution of NaHCO$_3$ (100 mL) and the biphasic solution was stirred for 10 min. The organic layer was washed with brine (100 mL), dried (Na$_2$SO$_4$), filtered and concentrated under reduced pressure. The pale yellow solid (3.0 g, crude) obtained was taken for next step without further purification. MS (APCI+) m/z 501 (M+H).

Step 3. (2S,3S)-2-Azido-3-(4-chlorophenyl)-N-(4-(2-((S)-1-(cyclopropylsulfonyl)aziridin-2-yl)ethyl)-5-fluoropyridin-3-yl)-3-(3-fluorophenyl)propanamide

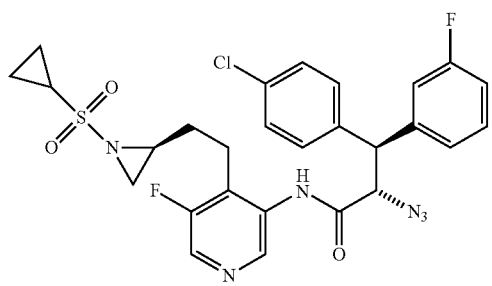 [SMILES: [N-]=[N+]=N[C@H](C(=O)Nc1cncc(F)c1CC[C@H]1CN1S(=O)(=O)C1CC1)[C@@H](c1ccc(Cl)cc1)c1cccc(F)c1]

To a stirred solution of (2S,3S)—N-(4-((S)-3-Amino-4-hydroxybutyl)-5-fluoropyridin-3-yl)-2-azido-3-(4-chlorophenyl)-3-(3-fluorophenyl)propanamide (2.00 g, 3.99 mmol) in dichloromethane kept at −20° C. was added triethylamine (2.68 mL, 19.95 mmol), DMAP (40 mg, 0.39 mmol) and cyclopropyl sulfonyl chloride (0.67 g, 4.78 mmol) and the reaction mixture was stirred for 1.5 h at −20° C. This was followed by the addition of methane sulfonyl chloride (0.55 g, 4.78 mmol) and the reaction mixture was stirred for 30 min., while allowing the temperature to rise to 0° C. The reaction was quenched with a saturated solution of NaHCO$_3$ (10 mL) and stirred for additional 30 min. The reaction was diluted with water (30 mL) and extracted with CH$_2$Cl$_2$ (2×50 mL). The combined organic extracts were washed with brine (50 mL), dried (Na$_2$SO$_4$), filtered and concentrated under reduced pressure. The residue was purified by 24 g SiO$_2$ column using a gradient elution of 0-50% EtOAc in hexanes. Fractions containing product were combined and the solvents were removed in vacuo to provide the product (0.5 g, 22%) as a pale yellow solid. MS (APCI+) m/z 559 (M-29).

Step 4. (2S,3S)-2-Azido-3-(4-chlorophenyl)-N-(4-((S)-3-(cyclopropanesulfonamido)-4-((R)-2-hydroxypropyl)amino)butyl)-5-fluoropyridin-3-yl)-3-(3-fluorophenyl)propanamide

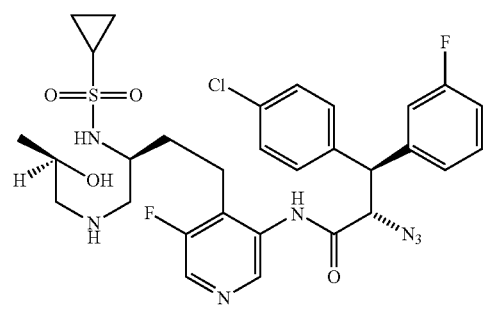 [SMILES: C[C@@H](O)CNC[C@H](CCc1c(F)cncc1NC(=O)[C@@H](N=[N+]=[N-])[C@@H](c1ccc(Cl)cc1)c1cccc(F)c1)NS(=O)(=O)C1CC1]

To a stirred solution of (2S,3S)-2-Azido-3-(4-chlorophenyl)-N-(4-(2-((S)-1-(cyclopropylsulfonyl)aziridin-2-yl)ethyl)-5-fluoropyridin-3-yl)-3-(3-fluorophenyl)propanamide (0.50 g, 0.85 mmol) in 1,2-dichloroethane (20 mL) was added (R)-1-amino 2-propanol (0.43 g, 5.95 mmol) and the solution was heated to 60° C. for 16 h. The reaction mixture was cooled to room temperature and diluted with water (50 mL) and extracted with EtOAc (100 mL). The organic layer was washed with water (50 mL), brine (50 mL), dried (Na$_2$SO$_4$), filtered and concentrated under reduced pressure. The yellow gum (0.57 g, crude) obtained was taken forward to the next step without further purification. MS (APCI+) m/z 662 (M+H).

Step 5. tert-Butyl ((S)-4-(3-((2S,3S)-2-azido-3-(4-chlorophenyl)-3-(3-fluorophenyl)propanamido)-5-fluoropyridin-4-yl)-2-(cyclopropanesulfonamido) butyl)((R)-2-hydroxypropyl)carbamate

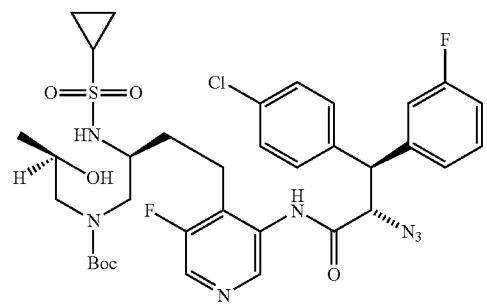 [SMILES: C[C@@H](O)CN(C[C@H](CCc1c(F)cncc1NC(=O)[C@@H](N=[N+]=[N-])[C@@H](c1ccc(Cl)cc1)c1cccc(F)c1)NS(=O)(=O)C1CC1)C(=O)OC(C)(C)C]

To a stirred solution of (2S,3S)-2-Azido-3-(4-chlorophenyl)-N-(4-(((S)-3-(cyclopropanesulfonamido)-4-(((R)-2-hydroxypropyl)amino)butyl)-5-fluoropyridin-3-yl)-3-(3-fluorophenyl)propanamide (0.57 g, 0.86 mmol) in dichloromethane (20 mL) was added di-tert-butyl dicarbonate (0.24 g, 1.12 mmol) and triethylamine (0.24 mL, 1.72 mmol) and the reaction mixture was stirred at room temperature for 16 h. The reaction mixture was diluted with water (50 mL) and EtOAc (100 mL) the layers were separated. The organic layer was washed with brine (50 mL), dried (Na$_2$SO$_4$), filtered and concentrated under reduced pressure. The residue was purified by 12 g SiO$_2$ column using a gradient elution of 0-90% EtOAc in hexanes. Fractions containing product were combined and the solvents were removed in vacuo to provide the product (0.65 g, crude) as a pale yellow solid. MS (APCI−) m/z 732 (M-29).

Step 6. (3S,5S)-tert-Butyl 3-(2-(3-((2S,3S)-2-azido-3-(4-chlorophenyl)-3-(3-fluorophenyl)propanamido)-5-fluoropyridin-4-yl)ethyl)-4-(cyclopropylsulfonyl)-5-methylpiperazine-1-carboxylate

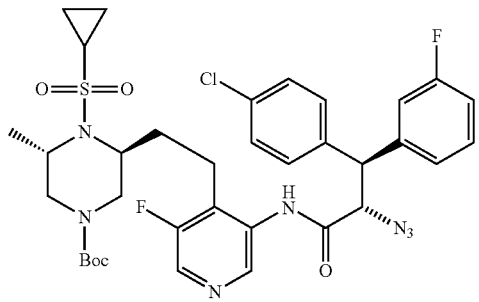 [SMILES: C[C@H]1CN(C(=O)OC(C)(C)C)C[C@H](CCc2c(F)cncc2NC(=O)[C@@H](N=[N+]=[N-])[C@@H](c2ccc(Cl)cc2)c2cccc(F)c2)N1S(=O)(=O)C1CC1]

To a stirred solution of tert-Butyl ((S)-4-(3-((2S,3S)-2-azido-3-(4-chlorophenyl)-3-(3-fluorophenyl)propanamido)-5-fluoropyridin-4-yl)-2-(cyclopropanesulfonamido)butyl)((R)-2-hydroxypropyl)carbamate (0.65 g, 0.85 mmol) in dry THF was added DIAD (0.49 mL, 2.56 mmol) and triphenyl phosphine (0.67 g, 2.56 mmol) and the reaction mixture was stirred at room temperature for 20 min. Concentrated on silica and purified by 12 g SiO$_2$ column using a gradient elution of 0-80% EtOAc in hexanes. Fractions containing product were combined and the solvents were removed in vacuo to provide the product (0.28 g, 43% over three steps) as a pale yellow solid. MS (APCI−) m/z 714 (M-29).

Step 7. (3S,5S)-tert-Butyl 3-(2-(3-((2S,3S)-2-amino-3-(4-chlorophenyl)-3-(3-fluorophenyl)propanamido)-5-fluoropyridin-4-yl)ethyl)-4-(cyclopropylsulfonyl)-5-methylpiperazine-1-carboxylate

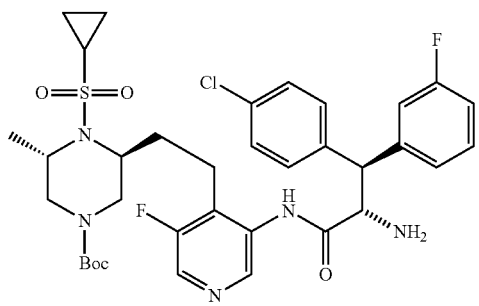 [SMILES: C[C@H]1CN(C(=O)OC(C)(C)C)C[C@H](CCc2c(F)cncc2NC(=O)[C@@H](N)[C@@H](c2ccc(Cl)cc2)c2cccc(F)c2)N1S(=O)(=O)C1CC1]

To a stirred solution of (3S,5S)-tert-Butyl 3-(2-(3-((2S,3S)-2-azido-3-(4-chlorophenyl)-3-(3-fluorophenyl)propanamido)-5-fluoropyridin-4-yl)ethyl)-4-(cyclopropylsulfonyl)-5-methylpiperazine-1-carboxylate (0.28 g, 0.39 mmol) in a mixture of EtOAc (20 mL) and water (5 mL) was added trimethyl phosphine (0.59 mL, 1M solution in THF) and the reaction mixture was stirred at room temperature for 16 h. The reaction mixture was diluted with water (50 mL) and EtOAc (75 mL) the layers were separated. The organic layer was washed with brine (30 mL), dried (Na$_2$SO$_4$), filtered and concentrated under reduced pressure. The residue was purified by 4 g SiO$_2$ column using a gradient elution of 0-5% MeOH in dichloromethane. Fractions containing product were combined and the solvents were removed in vacuo to provide the product (0.14 g, 52%) as a pale yellow gum. MS (APCI+) m/z 718 (M+H).

Step 8. (3S,5S)-tert-Butyl 3-(2-(3-((2S,3S)-3-(4-chlorophenyl)-3-(3-fluorophenyl)-2-((methoxycarbonyl)amino)propanamido)-5-fluoropyridin-4-yl)ethyl)-4-(cyclopropylsulfonyl)-5-methylpiperazine-1-carboxylate

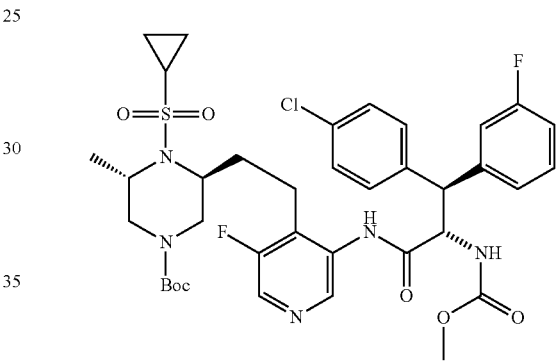

To a stirred solution of (3S,5S)-tert-Butyl 3-(2-(3-((2S,3S)-2-amino-3-(4-chlorophenyl)-3-(3-fluorophenyl)propanamido)-5-fluoropyridin-4-yl)ethyl)-4-(cyclopropylsulfonyl)-5-methylpiperazine-1-carboxylate (70 mg, 0.097 mmol) in dichloromethane kept at 0° C. was added diisopropylethylamine (0.03 ml, 0.195 mmol) and methylchloroformate (0.009 mL, 0.117 mmol) and the reaction mixture was stirred for 30 min. Diluted the reaction mixture with water (50 mL) and EtOAc (50 mL) the layers were separated and the organic layer was washed with brine (30 mL), dried (Na$_2$SO$_4$), filtered and concentrated under reduced pressure. The residue was purified by 12 g SiO$_2$ column using a gradient elution of 0-80% EtOAc in hexanes. Fractions containing product were combined and the solvents were removed in vacuo to provide the product (15 mg, 56%) as a colorless gum. MS (APCI+) m/z 776 (M+H).

Step 9. Methyl ((1S,2S)-1-(4-chlorophenyl)-3-((4-(2-((2S,6S)-1-(cyclopropylsulfonyl)-6-methylpiperazin-2-yl)ethyl)-5-fluoropyridin-3-yl)amino)-1-(3-fluorophenyl)-3-oxopropan-2-yl)carbamate To a stirred solution of (3S,5S)-tert-Butyl 3-(2-(3-((2S,3S)-3-(4-chlorophenyl)-3-(3-fluorophenyl)-2-((methoxycarbonyl)amino)propanamido)-5-fluoropyridin-4-yl)ethyl)-4-(cyclopropylsulfonyl)-5-methylpiperazine-1-carboxylate (50 mg, 0.064 mmol) in dichloromethane was added trifluoroacetic acid (0.5 mL) and the reaction mixture was stirred at room temperature for 1 h. Concentrated the reaction mixture and the residue was purified by trituration with diethyl ether (0.5 mL) and n-hexanes (2.0 mL). The solid obtained was lyophilized to obtain the product (23 mg, 40%) as an off-white solid.

MS (APCI+) m/z 676 (M+H).

EXAMPLE 12

Methyl (1R,2S)-1-(4-chlorophenyl)-3-(2-(2-((2S, 6S)-1-(cyclopropylsulfonyl)-6-methylpiperazin-2-yl) ethyl)-3-fluorophenylamino)-3-oxo-1-(tetrahydro-2H-pyran-4-yl)propan-2-ylcarbamate

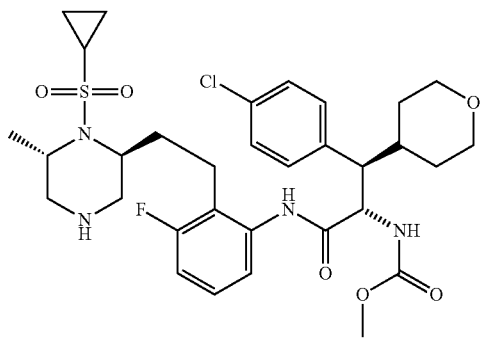 [SMILES: COC(=O)N[C@H](C(=O)Nc1cccc(F)c1CC[C@H]1CNC[C@H](C)N1S(=O)(=O)C1CC1)[C@@H](c1ccc(Cl)cc1)C1CCOCC1]

Step 1. (S)-tert-Butyl 4-(2-((2S,3R)-2-azido-3-(4-chlorophenyl)-3-(tetrahydro-2H-pyran-4-yl)propanamido)-6-fluorophenethyl)-2,2-dimethyloxazolidine-3-carboxylate

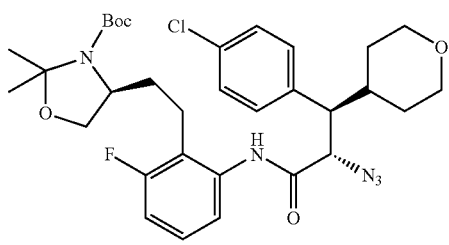 [SMILES: CC(C)(C)OC(=O)N1[C@@H](CCc2c(F)cccc2NC(=O)[C@@H](N=[N+]=[N-])[C@@H](c2ccc(Cl)cc2)C2CCOCC2)COC1(C)C]

To a stirred solution of (S)-tert-butyl 4-(2-amino-6-fluorophenethyl)-2,2-dimethyloxazolidine-3-carboxylate (Intermediate C) (1.60 g, 4.73 mmol) and (2S,3R)-2-azido-3-(4-chlorophenyl)-3-(tetrahydro-2H-pyran-4-yl)propanoic acid (1.61 g, 5.20 mmol) in pyridine (16 mL) at −20° C. was slowly added POCl$_3$ (0.50 mL, 5.20 mmol) and the reaction mixture was allowed to reach 0° C. and stirred for 3 h. The reaction was quenched with saturated solution of KH$_2$PO$_4$ (50 mL) and extracted with EtOAc (200 mL). The organic layer was washed with brine (200 mL), dried (Na$_2$SO$_4$), filtered and concentrated under reduced pressure. The residue was purified by 80 g SiO$_2$ column using a gradient elution of 0-30% EtOAc in hexanes. Fractions containing product were combined and the solvents were removed in vacuo to provide the product (2.50 g, 76%) as a pale yellow solid.

Step 2. (2S,3R)—N-(2-((S)-3-amino-4-hydroxybutyl)-3-fluorophenyl)-2-azido-3-(4-chlorophenyl)-3-(tetrahydro-2H-pyran-4-yl)propanamide

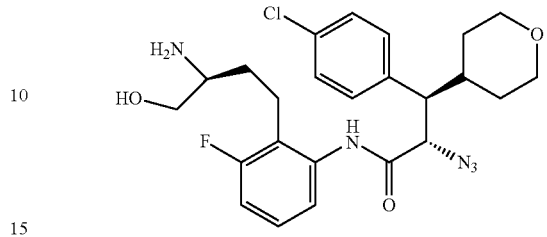

To a stirred solution of (S)-tert-butyl 4-(2-((2S,3R)-2-azido-3-(4-chlorophenyl)-3-(tetrahydro-2H-pyran-4-yl)propanamido)-6-fluorophenethyl)-2,2-dimethyloxazolidine-3-carboxylate (2.50 g, 3.96 mmol) in dichloromethane (25 mL) was added trifluoroacetic acid (13.47 mL) and water (3 mL) and the reaction mixture was stirred at room temperature for 16 h. Concentrated the solvents and the residue was diluted with EtOAc (250 mL) and saturated solution of NaHCO$_3$ (100 mL) and the biphasic solution was stirred for 10 min. The organic layer was washed with brine (100 mL), dried (Na$_2$SO$_4$), filtered and concentrated under reduced pressure. The pale yellow solid (1.80 g, crude) obtained was taken forward to the next step without further purification.

Step 3. (2S,3R)-2-azido-3-(4-chlorophenyl)-N-(2-(2-((S)-1-(cyclopropylsulfonyl)aziridin-2-yl)ethyl)-3-fluorophenyl)-3-(tetrahydro-2H-pyran-4-yl)propanamide

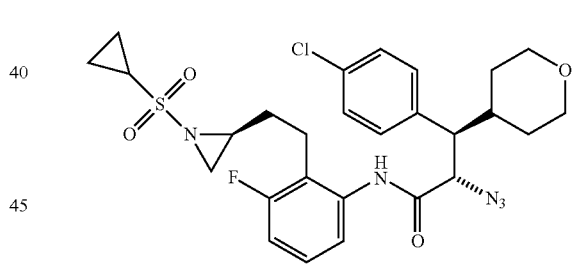

To a stirred solution of (2S,3R)—N-(2-((S)-3-amino-4-hydroxybutyl)-3-fluorophenyl)-2-azido-3-(4-chlorophenyl)-3-(tetrahydro-2H-pyran-4-yl)propanamide (800 mg, 1.64 mmol) in dichloromethane kept at −20° C. was added triethylamine (1.14 mL, 8.20 mmol), DMAP (19 mg, 0.164 mmol) and cyclopropane sulfonyl chloride (0.21 mL, 1.97 mmol) and the reaction mixture was stirred for 1.5 h at −20° C. This was followed by the addition of methane sulfonyl chloride (0.15 mL, 1.97 mmol) and the reaction mixture was stirred for 30 min, while allowing the temperature to rise to 0° C. The reaction was quenched with a saturated solution of NaHCO$_3$ (10 mL) and stirred for additional 30 min. The reaction was diluted with water (30 mL) and extracted with CH$_2$Cl$_2$ (2×50 mL). The combined organic extracts were washed with brine (50 mL), dried (Na$_2$SO$_4$), filtered and concentrated under reduced pressure. The residue was purified by 80 g SiO$_2$ column using a gradient elution of 0-30% EtOAc in hexanes. Fractions containing product were combined and the solvents were removed in vacuo to provide the product (300 mg, 38%) as a pale yellow solid.

Step 4. (2S,3R)-2-azido-3-(4-chlorophenyl)-N-(2-((S)-3-(cyclopropanesulfonamido)-4-((R)-2-hydroxypropylamino)butyl)-3-fluorophenyl)-3-(tetrahydro-2H-pyran-4-yl)propanamide

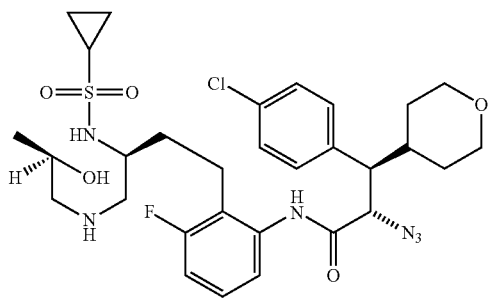 [SMILES: C[C@@H](O)CNC[C@H](CCc1c(F)cccc1NC(=O)[C@@H](N=[N+]=[N-])[C@@H](c1ccc(Cl)cc1)C1CCOCC1)NS(=O)(=O)C1CC1]

To a stirred solution of (2S,3R)-2-azido-3-(4-chlorophenyl)-N-(2-(2-((S)-1-(cyclopropylsulfonyl)aziridin-2-yl)ethyl)-3-fluorophenyl)-3-(tetrahydro-2H-pyran-4-yl)propanamide (0.3 g, 0.53 mmol) in 1,2-dichloroethane (10 mL) was added (R)-1-amino 2-propanol (0.278 g, 3.7 mmol) and the solution was heated to 60° C. for 16 h. The reaction mixture was cooled to room temperature and diluted with water (50 mL) and extracted with EtOAc (100 mL). The organic layer was washed with water (50 mL), brine (50 mL), dried (Na$_2$SO$_4$), filtered and concentrated under reduced pressure. The yellow gum (0.35 g, crude) obtained was taken forward to the next step without further purification.

Step 5. tert-Butyl (S)-4-(2-((2S,3R)-2-azido-3-(4-chlorophenyl)-3-(tetrahydro-2H-pyran-4-yl)propanamido)-6-fluorophenyl)-2-(cyclopropanesulfonamido)butyl((R)-2-hydroxypropyl)carbamate

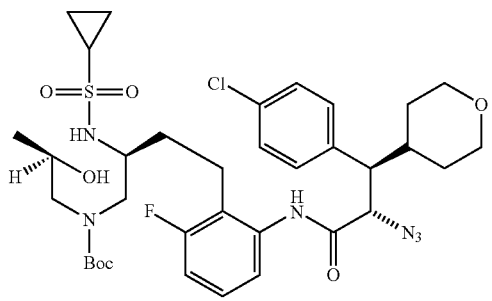 [SMILES: C[C@@H](O)CN(C[C@H](CCc1c(F)cccc1NC(=O)[C@@H](N=[N+]=[N-])[C@@H](c1ccc(Cl)cc1)C1CCOCC1)NS(=O)(=O)C1CC1)C(=O)OC(C)(C)C]

To a stirred solution of (2S,3R)-2-azido-3-(4-chlorophenyl)-N-(2-((S)-3-(cyclopropanesulfonamido)-4-((R)-2-hydroxypropylamino)butyl)-3-fluorophenyl)-3-(tetrahydro-2H-pyran-4-yl)propanamide (0.35 g, 0.537 mmol) in dichloromethane (10 mL) was added di-tert-butyl dicarbonate (0.23 mL, 1.07 mmol) and triethylamine (0.15 mL, 1.07 mmol) and the reaction mixture was stirred for 16 h at room temperature. The reaction mixture was diluted with water (50 mL) and EtOAc (100 mL) the layers were separated. The organic layer was washed with brine (50 mL), dried (Na$_2$SO$_4$), filtered and concentrated under reduced pressure.

The residue was purified by 24 g SiO$_2$ column using a gradient elution of 0-50% EtOAc in hexanes. Fractions containing product were combined and the solvents were removed in vacuo to provide the product (0.28 g, 72% over two steps) as a pale white gum.

Step 6. (3S,5S)-tert-Butyl 3-(2-((2S,3R)-2-azido-3-(4-chlorophenyl)-3-(tetrahydro-2H-pyran-4-yl)propanamido)-6-fluorophenethyl)-4-(cyclopropylsulfonyl)-5-methylpiperazine-1-carboxylate

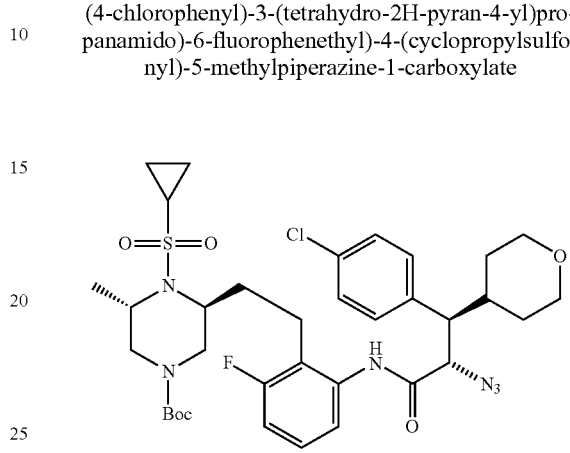

To a stirred solution of tert-butyl (S)-4-(2-((2S,3R)-2-azido-3-(4-chlorophenyl)-3-(tetrahydro-2H-pyran-4-yl)propanamido)-6-fluorophenyl)-2-(cyclopropanesulfonamido)butyl((R)-2-hydroxypropyl)carbamate (0.28 g, 0.37 mmol) in dry THF was added DIAD (0.244 g, 1.11 mmol) and triphenyl phosphine (0.291 g, 1.11 mmol) and the reaction mixture was stirred for 20 min at room temperature. Added silica-gel and concentrated under reduced pressure. The product was purified by 12 g SiO$_2$ column using a gradient elution of 0-50% EtOAc in hexanes. Fractions containing product were combined and the solvents were removed in vacuo to provide the product (0.20 g, 72%) as a white gum.

Step 7. (3S,5S)-tert-Butyl 3-(2-((2S,3R)-2-amino-3-(4-chlorophenyl)-3-(tetrahydro-2H-pyran-4-yl)propanamido)-6-fluorophenethyl)-4-(cyclopropylsulfonyl)-5-methylpiperazine-1-carboxylate

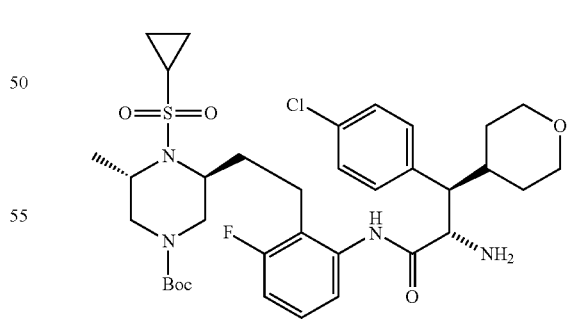

To a stirred solution of (3S,5S)-tert-butyl 3-(2-((2S,3R)-2-azido-3-(4-chlorophenyl)-3-(tetrahydro-2H-pyran-4-yl)propanamido)-6-fluorophenethyl)-4-(cyclopropylsulfonyl)-5-methylpiperazine-1-carboxylate (0.20 g, 0.27 mmol) in a mixture of EtOAc (6 mL) and water (4 mL) was added trimethyl phosphine (1.35 mL, 1M solution in THF) and the reaction mixture was stirred at room temperature for 16 h.

The reaction mixture was diluted with water (50 mL) and EtOAc (75 mL) the layers were separated. The organic layer was washed with brine (30 mL), dried (Na$_2$SO$_4$), filtered and concentrated under reduced pressure. The residue was purified by 12 g SiO$_2$ column using a gradient elution of 0-5% MeOH in dichloromethane. Fractions containing product were combined and the solvents were removed in vacuo to provide the product (0.20 g, 95%) as a pale yellow gum.

Step 8. (3S,5S)-tert-Butyl 3-(2-((2S,3R)-3-(4-chlorophenyl)-2-(methoxycarbonylamino)-3-(tetrahydro-2H-pyran-4-yl)propanamido)-6-fluorophenethyl)-4-(cyclopropylsulfonyl)-5-methylpiperazine-1-carboxylate

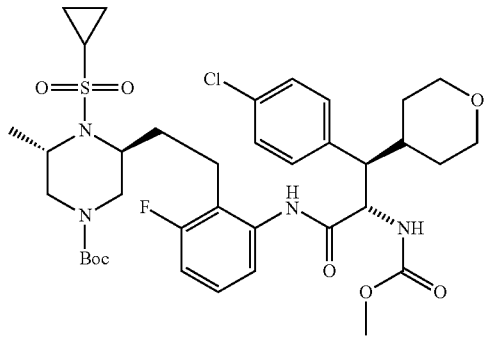 [SMILES: COC(=O)N[C@H](C(=O)Nc1cccc(F)c1CC[C@H]1CN(C(=O)OC(C)(C)C)C[C@H](C)N1S(=O)(=O)C1CC1)[C@@H](c1ccc(Cl)cc1)C1CCOCC1]

To a stirred solution of (3S,5S)-tert-butyl 3-(2-((2S,3R)-2-amino-3-(4-chlorophenyl)-3-(tetrahydro-2H-pyran-4-yl)propanamido)-6-fluorophenethyl)-4-(cyclopropylsulfonyl)-5-methylpiperazine-1-carboxylate (100 mg, 0.14 mmol) in dichloromethane kept at 0° C. was added diisopropylethylamine (36 mg, 2.8 mmol) and methylchloroformate (0.013 mL, 0.154 mmol) and the reaction mixture was stirred for 30 min. Diluted the reaction mixture with water (50 mL) and EtOAc (50 mL) the layers were separated and the organic layer was washed with brine (30 mL), dried (Na$_2$SO$_4$), filtered and concentrated under reduced pressure. The residue was purified by 12 g SiO$_2$ column using a gradient elution of 0-80% EtOAc in hexanes. Fractions containing product were combined and the solvents were removed in vacuo to provide the product (100 mg, 93%) as a white gum.

Step 9. Methyl (1R,2S)-1-(4-chlorophenyl)-3-(2-(2-((2S,6S)-1-(cyclopropylsulfonyl)-6-methylpiperazin-2-yl)ethyl)-3-fluorophenylamino)-3-oxo-1-(tetrahydro-2H-pyran-4-yl)propan-2-ylcarbamate To a stirred solution of (3S,5S)-tert-butyl 3-(2-((2S,3R)-3-(4-chlorophenyl)-2-(methoxycarbonylamino)-3-(tetrahydro-2H-pyran-4-yl)propanamido)-6-fluorophenethyl)-4-(cyclopropylsulfonyl)-5-methylpiperazine-1-carboxylate (100 mg) in dichloromethane was added trifluoroacetic acid (0.2 mL) and the reaction mixture was stirred at room temperature for 2 h. After concentration of the reaction solution, the residue was purified by trituration with diethyl ether and n-hexanes. The solid obtained was lyophilized to provide the product (40.0 mg, 52%) as an off-white solid.

EXAMPLE 13

(βS)-β-(3,5-difluorophenyl)-4-fluoro-N-(5-fluoro-4-{2-[(2S,6R)-6-methyl-1-(phenylsulfonyl)piperazin-2-yl]ethyl}pyridin-3-yl)-L-phenylalaninamide

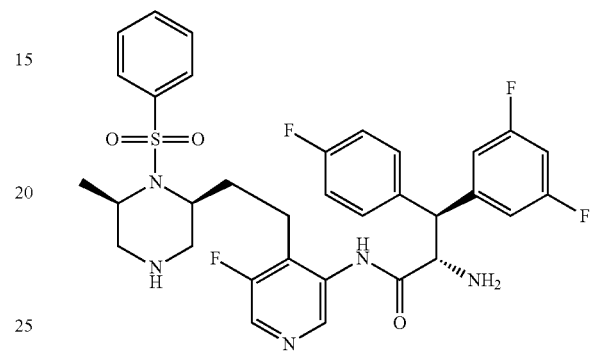

Step 1. (S)-tert-butyl 4-(2-(3-((2S,3S)-2-azido-3-(3,5-difluorophenyl)-3-(4-fluorophenyl)propanamido)-5-fluoropyridin-4-yl)ethyl)-2,2-dimethyl oxazolidine-3-carboxylate

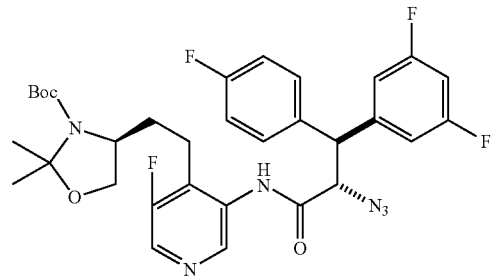

POCl$_3$ (131 μl, 1.40 mmol) was added to a solution of (S)-tert-butyl 4-(2-(3-amino-5-fluoropyridin-4-yl)ethyl)-2,2-dimethyloxazolidine-3-carboxylate (433 mg, 1.28 mmol) and (2S,3S)-2-azido-3-(3,5-difluorophenyl)-3-(4-fluorophenyl)propanoic acid (410 mg, 1.28 mmol) in Pyridine (6.38 ml) at −15° C. (external temperature) and the reaction stirred for 30 minutes then warmed to 0° C. and stirred for 10 mins. LC/MS shows that no starting material remained at this time, so the reaction was quenched with a solution of saturated aqueous KH$_2$PO$_4$ (25 mL) and the mixture was extracted with ethyl acetate (3×30 mL). The combined organic fractions were dried (MgSO$_4$), filtered and the solvent was evaporated under reduced pressure. Purification on silica gel (80 g) eluting 0-100% EtOAc in hexanes over 30 minutes afforded (S)-tert-butyl 4-(2-(3-((2S,3S)-2-azido-3-(3,5-difluorophenyl)-3-(4-fluorophenyl)propanamido)-5-fluoropyridin-4-yl)ethyl)-2,2-dimethyloxazolidine-3-carboxylate (723 mg, 1.13 mmol, 88% yield) as a pink foam. LC/MS shows 100% pure. MS: m/z=643.5 (M+1).

Step 2. (2S,3S)—N-(4-((S)-3-amino-4-hydroxybutyl)-5-fluoropyridin-3-yl)-2-azido-3-(3,5-difluorophenyl)-3-(4-fluorophenyl)propanamide

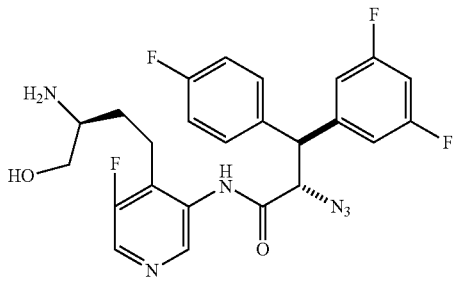

To a solution of (S)-tert-butyl 4-(2-(3-((2S,3S)-2-azido-3-(3,5-difluorophenyl)-3-(4-fluorophenyl)propanamido)-5-fluoropyridin-4-yl)ethyl)-2,2-dimethyloxazolidine-3-carboxylate (723 mg, 1.13 mmol) in DCM (5.63 ml) is added TFA (3467 μl, 45.0 mmol) followed by water (811 μl, 45.0 mmol) with stirring at room temperature. LC/MS shows reaction is about 90% after two hours, but sluggish after this point. Stirring is continued overnight and LC/MS shows complete the next morning. The material is diluted with MeOH (5 mL) and the product is passed through a 10 g SCX cartridge (1CV MeOH equilibration, material load, 2 CVs MeOH wash and 2 CVs NH3 in MeOH) to afford (2S,3S)—N-(4-((S)-3-amino-4-hydroxybutyl)-5-fluoropyridin-3-yl)-2-azido-3-(3,5-difluorophenyl)-3-(4-fluorophenyl)propanamid as a white solid. The material was taken on as/is, without further purification. LC/MS shows 100% pure. MS: m/z=503.3 (M+1).

Step 3. (2S,3S)-2-azido-3-(3,5-difluorophenyl)-N-(5-fluoro-4-((S)-4-hydroxy-3-(phenylsulfonamido)butyl)pyridin-3-yl)-3-(4-fluorophenyl)propanamide

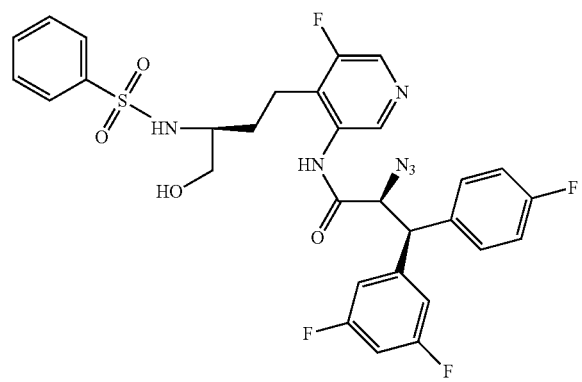 [SMILES: [N-]=[N+]=N[C@H](C(=O)Nc1cncc(F)c1CC[C@@H](CO)NS(=O)(=O)c1ccccc1)[C@@H](c1ccc(F)cc1)c1cc(F)cc(F)c1]

A solution of (2S,3S)—N-(4-((S)-3-amino-4-hydroxybutyl)-5-fluoropyridin-3-yl)-2-azido-3-(3,5-difluorophenyl)-3-(4-fluorophenyl)propanamide (340 mg, 0.68 mmol) and TEA (189 μl, 1.35 mmol) in DMF (6.77 ml) was cooled to 0° C. Then, benzenesulfonlyl chloride (92 μl, 0.71 mmol) was added dropwise. The mixture was allowed to stir for 20 minutes, at which point, LC/MS indicates completion. The contents were quenched with water and then partitioned between EtOAc (3×20 mL) and saturated aqueous sodium bicarbonate. The organics were dried over mag. sulf., filtered and concentrated to afford (2S,3S)-2-azido-3-(3,5-difluorophenyl)-N-(5-fluoro-4-((S)-4-hydroxy-3-(phenylsulfonamido)butyl)pyridin-3-yl)-3-(4-fluorophenyl)propanamide as an orange semi-solid. The material was taken on crude to the next step. LC/MS shows 88% pure. MS: m/z=643.4 (M+1).

Step 4. (2S,3S)-2-azido-3-(3,5-difluorophenyl)-N-(5-fluoro-4-(2-((S)-1-(phenylsulfonyl)aziridin-2-yl)ethyl)pyridin-3-yl)-3-(4-fluorophenyl)propanamide

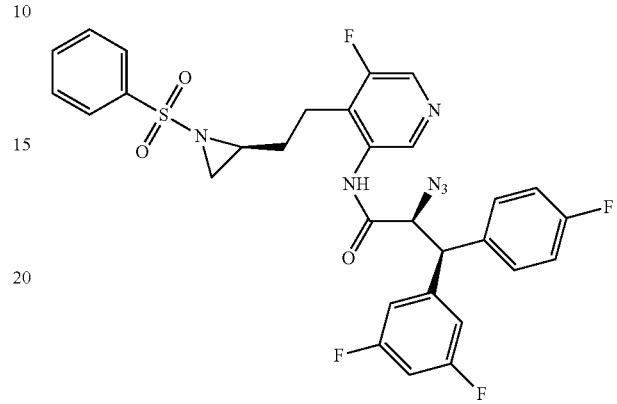

(2S,3S)-2-azido-3-(3,5-difluorophenyl)-N-(5-fluoro-4-((S)-4-hydroxy-3-(phenylsulfonamido)butyl)pyridin-3-yl)-3-(4-fluorophenyl)propanamide (243 mg, 0.38 mmol) was dissolved in THF (3.78 ml) and then cooled to 0° C. Then, diisopropyl azodicarboxylate (110 μl, 0.57 mmol), followed by triphenylphosphine (149 mg, 0.57 mmol) were added and the contents stirred for 30 minutes. LC/MS shows reaction is complete at this time. The contents were quenched with water and then extracted with EtOAc (3×30 mL). The organics were dried over MgSO4, filtered and concentrated. Purification on silica gel (24 g), eluting 30-100% EtOAc in hexanes over 18 minutes afforded (2S,3S)-2-azido-3-(3,5-difluorophenyl)-N-(5-fluoro-4-(2-((S)-1-(phenylsulfonyl)aziridin-2-yl)ethyl)pyridin-3-yl)-3-(4-fluorophenyl)propanamide (133 mg, 0.213 mmol, 56% yield) as a white foam. LC/MS shows 100% pure. MS: m/z=625.2 (M+1). The compound was stored in the refrigerator due to instability of the aziridine ring.

Step 5. (2S,3S)-2-azido-3-(3,5-difluorophenyl)-N-(5-fluoro-4-((R)-4-((S)-2-hydroxypropyl)amino)-3-(phenylsulfonamido)butyl)pyridin-3-yl)-3-(4-fluorophenyl)propanamide

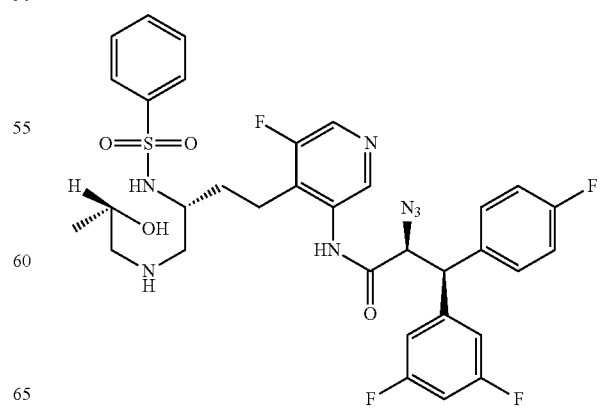

To a solution of (2S,3S)-2-azido-3-(3,5-difluorophenyl)-N-(5-fluoro-4-(2-((S)-1-(phenylsulfonyl)aziridin-2-yl)ethyl)pyridin-3-yl)-3-(4-fluorophenyl)propanamide (39.5 mg, 0.063 mmol) in DCE (632 µl) is added (S)-1-aminopropan-2-ol (33.2 mg, 0.44 mmol) while stirring at room temperature. Then, the mixture is heated at 40° C. until complete by LC/MS (1 hour). The solvent was then evaporated under reduced pressure and the residual mass is partitioned between water and EtOAc (3×20 mL). The organics were dried over MgSO$_4$, filtered and concentrated. Purification on silica gel (4 g), eluting 30-100% [70:20:10] {CHCl3:EtOAc:MeOH} in CHCl3 over 20 minutes afforded (2S,3S)-2-azido-3-(3,5-difluorophenyl)-N-(5-fluoro-4-((R)-4-(((S)-2-hydroxypropyl)amino)-3-(phenylsulfonamido)butyl)pyridin-3-yl)-3-(4-fluorophenyl)propanamide (13.5 mg, 0.019 mmol, 30% yield) as a yellow oil. LC/MS shows 100% pure. MS: m/z=700.4 (M+1).

Step 6. tert-butyl ((S)-4-(3-((2S,3S)-2-azido-3-(3,5-difluorophenyl)-3-(4-fluorophenyl)propanamido)-5-fluoropyridin-4-yl)-2-(phenylsulfonamido)butyl)((S)-2-hydroxypropyl)carbamate

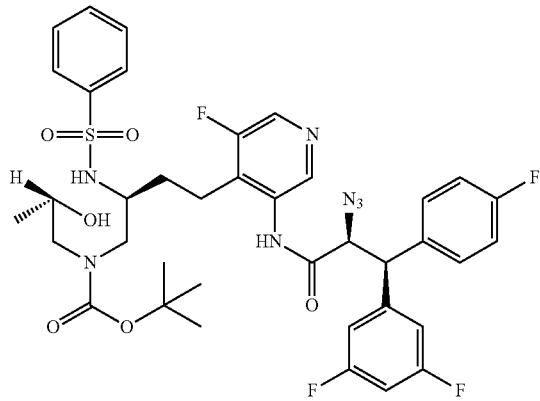 [SMILES: C[C@H](O)CN(C[C@H](CCc1c(F)cncc1NC(=O)[C@@H](N=[N+]=[N-])[C@@H](c1ccc(F)cc1)c1cc(F)cc(F)c1)NS(=O)(=O)c1ccccc1)C(=O)OC(C)(C)C]

(2S,3S)-2-azido-3-(3,5-difluorophenyl)-N-(5-fluoro-4-((R)-4-(((S)-2-hydroxypropyl)amino)-3-(phenylsulfonamido)butyl)pyridin-3-yl)-3-(4-fluorophenyl)propanamide (13.5 mg, 0.019 mmol) was dissolved in Acetonitrile (193 µl) and then, BOC$_2$O (11.20 µl, 0.048 mmol) and TEA (6.72 µl, 0.048 mmol) were added to the solution at room temperature. LC/MS shows complete after 3 hours of stirring. The contents were partitioned between saturated aqueous sodium bicarbonate solution and EtOAc (3×10 mL). The organics were dried over MgSO$_4$, filtered and concentrated to afford tert-butyl ((S)-4-(3-((2S,3S)-2-azido-3-(3,5-difluorophenyl)-3-(4-fluorophenyl)propanamido)-5-fluoropyridin-4-yl)-2-(phenylsulfonamido)butyl)((S)-2-hydroxypropyl)carbamate as a yellow oil. The material was taken on crude to the next step. LC/MS shows 100% pure. MS: m/z=800.5 (M+1).

Step 7. (3S,5R)-tert-butyl 3-(2-(3-((2S,3S)-2-azido-3-(3,5-difluorophenyl)-3-(4-fluorophenyl)propanamido)-5-fluoropyridin-4-yl)ethyl)-5-methyl-4-(phenylsulfonyl)piperazine-1-carboxylate

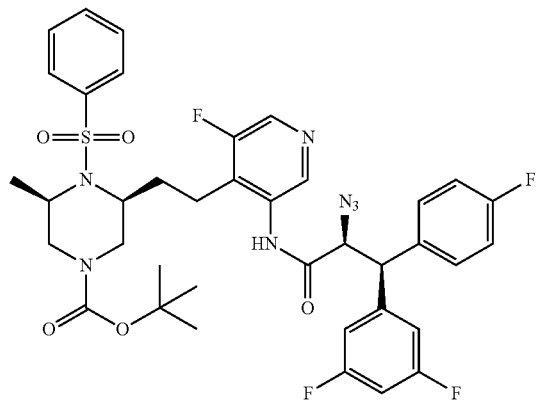 [SMILES: C[C@@H]1CN(C(=O)OC(C)(C)C)C[C@H](CCc2c(F)cncc2NC(=O)[C@@H](N=[N+]=[N-])[C@@H](c2ccc(F)cc2)c2cc(F)cc(F)c2)N1S(=O)(=O)c1ccccc1]

To a solution of tert-butyl ((S)-4-(3-((2S,3S)-2-azido-3-(3,5-difluorophenyl)-3-(4-fluorophenyl)propanamido)-5-fluoropyridin-4-yl)-2-(phenylsulfonamido)butyl)((S)-2-hydroxypropyl)carbamate (15 mg, 0.019 mmol) in dry THF (375 µl) is added triphenylphosphine (14.76 mg, 0.056 mmol), followed by DIAD (10.94 µl, 0.056 mmol) with stirring at room temperature. LC/MS after 30 minutes shows reaction is complete. Partitioned contents between water and EtOAc (3×15 mL). Dried organics over MgSO$_4$, filtered and concentrated. Purification on a silica gel (4 g), eluting 20-100% EtOAc in hexanes over 18 minutes afforded (3S,5R)-tert-butyl 3-(2-(3-((2S,3S)-2-azido-3-(3,5-difluorophenyl)-3-(4-fluorophenyl)propanamido)-5-fluoropyridin-4-yl)ethyl)-5-methyl-4-(phenylsulfonyl)piperazine-1-carboxylate (14 mg, 0.017 mmol, 91% yield) as a clear gum. LC/MS shows 95% pure. MS: m/z=782.5 (M+1).

Step 8. (3S,5R)-tert-butyl 3-(2-(3-((2S,3S)-2-amino-3-(3,5-difluorophenyl)-3-(4-fluorophenyl)propanamido)-5-fluoropyridin-4-yl)ethyl)-5-methyl-4-(phenylsulfonyl)piperazine-1-carboxylate

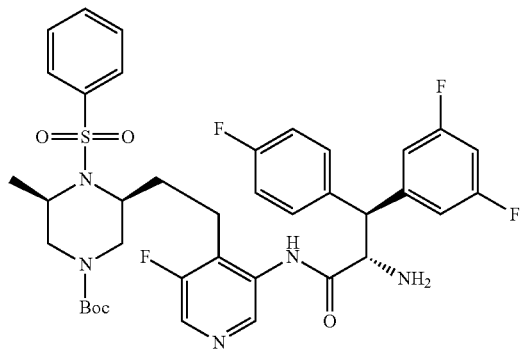 [SMILES: C[C@@H]1CN(C(=O)OC(C)(C)C)C[C@H](CCc2c(F)cncc2NC(=O)[C@@H](N)[C@@H](c2ccc(F)cc2)c2cc(F)cc(F)c2)N1S(=O)(=O)c1ccccc1]

Dissolved (3S,5R)-tert-butyl 3-(2-(3-((2S,3S)-2-azido-3-(3,5-difluorophenyl)-3-(4-fluorophenyl)propanamido)-5-fluoropyridin-4-yl)ethyl)-5-methyl-4-(phenylsulfonyl)piperazine-1-carboxylate (14 mg, 0.018 mmol) in Ethyl acetate (358 μl) and to this solution, 10% Pd/C (5.72 mg, 5.37 μmol) was carefully added. A hydrogen balloon was attached and the contents were evacuated and backfilled with H$_2$ several times. Allowed mixture to stir at room temperature until complete (6 hours). Filtered off solids through a syringe filter and concentrated. Purification on silica gel (4 g), eluting 30-100% [70:20:10] {CHCl3:EtOAc:MeOH} in CHCl3 over 20 minutes afforded (3S,5R)-tert-butyl 3-(2-(3-((2S,3S)-2-amino-3-(3,5-difluorophenyl)-3-(4-fluorophenyl)propanamido)-5-fluoropyridin-4-yl)ethyl)-5-methyl-4-(phenylsulfonyl)piperazine-1-carboxylate (9 mg, 0.012 mmol, 66% yield) as a clear oil. LC/MS shows 95% pure. MS: m/z=756.5 (M+1).

Step 9. (βS)-β-(3,5-difluorophenyl)-4-fluoro-N-(5-fluoro-4-{2-[(2S,6R)-6-methyl-1-(phenylsulfonyl)piperazin-2-yl]ethyl}pyridin-3-yl)-L-phenylalaninamide (3S,5R)-tert-butyl 3-(2-(3-((2S,3S)-2-amino-3-(3,5-difluorophenyl)-3-(4-fluorophenyl)propanamido)-5-fluoropyridin-4-yl)ethyl)-5-methyl-4-(phenylsulfonyl)piperazine-1-carboxylate (9 mg, 0.012 mmol) was dissolved in 2-MeTHF (119 μl) at room temperature, and to this solution, HCl (30 μl, 0.12 mmol) (4N in dioxane) was added. The contents were stirred at room temperature until complete (4 hrs). The material was concentrated in vacuo and then taken up in 1 mL of MeOH and passed through a 1 g SCX cartridge (1CV MeOH equilibration, material load, 2 CVs MeOH wash and 2 CVs NH3 in MeOH) to afford (βS)-β-(3,5-difluorophenyl)-4-fluoro-N-(5-fluoro-4-{2-[(2S,6R)-6-methyl-1-(phenylsulfonyl)piperazin-2-yl]ethyl}pyridin-3-yl)-L-phenylalaninamide (3.5 mg, 5.34 μmol, 45% yield) as a white solid. LC/MS shows 100% pure. MS: m/z=656.5 (M+1).

EXAMPLE 14

(βS)-4-chloro-N-(3-fluoro-2-{2-[(2S,6R)-6-methyl-1-(phenylsulfonyl)piperazin-2-yl]ethyl}phenyl)-β-(6-methoxypyridin-3-yl)-L-phenylalaninamide

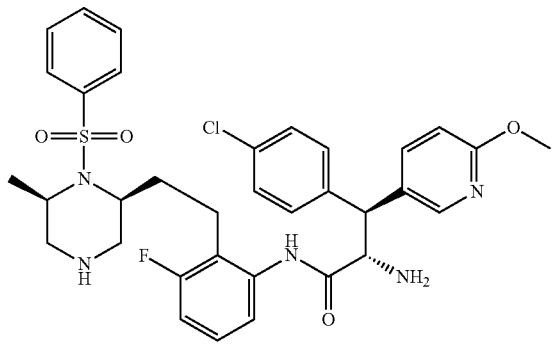

Step 1. (2S,3S)-2-Azido-N-(3-fluoro-2-(2-((S)-1-(phenylsulfonyl)aziridin-2-yl)ethyl)phenyl)-3-(4-fluorophenyl)-3-(6-methoxypyridin-3-yl)propanamide

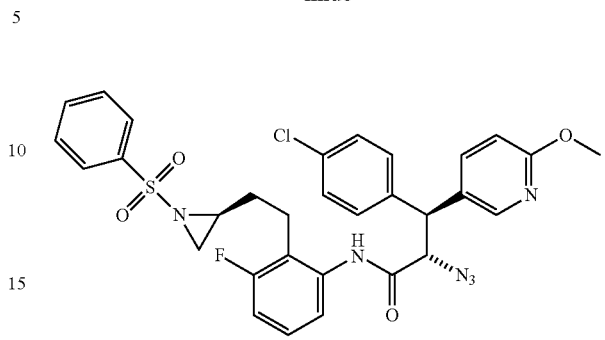

To a stirred solution of (2S,3S)—N-(2-((S)-3-amino-4-hydroxybutyl)-3-fluorophenyl)-2-azido-3-(4-fluorophenyl)-3-(6-methoxypyridin-3-yl)propanamide (Example 19, step 3) (0.75 g, 1.46 mmol) in dichloromethane at −20° C. was added triethylamine (1.4 mL, 7.32 mmol), DMAP (16 mg, 0.14 mmol) and benzene sulfonylchloride (0.22 mL, 1.757 mmol) and the reaction mixture was stirred 1.5 h. This was followed by the addition of methane sulfonylchloride (0.13 mL, 1.757 mmol) and stirring was continued for 30 min, and stirred the reaction mixture at 0° C. The reaction mixture was quenched with saturated solution of sodium bicarbonate (10 mL) and stirred for an additional 30 minutes. Diluted with water (20 mL) and extracted with dichloromethane (2×50 mL). The combined organic extracts were washed with brine (10 mL), dried (Na$_2$SO$_4$), filtered and concentrated under reduced pressure. The residue obtained was purified by 80 g SiO$_2$ column using a gradient elution of 0-35% EtOAc in hexanes. Fractions containing product were combined and the solvents were removed in vacuo to provide the product (0.59 g, 63%) as a pale yellow solid. MS: m/z=619 (M+H$^+$).

Step 2. (2S,3S)-2-Azido-3-(4-chlorophenyl)-N-(3-fluoro-2-((S)-4-(((R)-2-hydroxypropyl)amino)-3-(phenylsulfonamido)butyl)phenyl)-3-(6-methoxypyridin-3-yl)propanamide

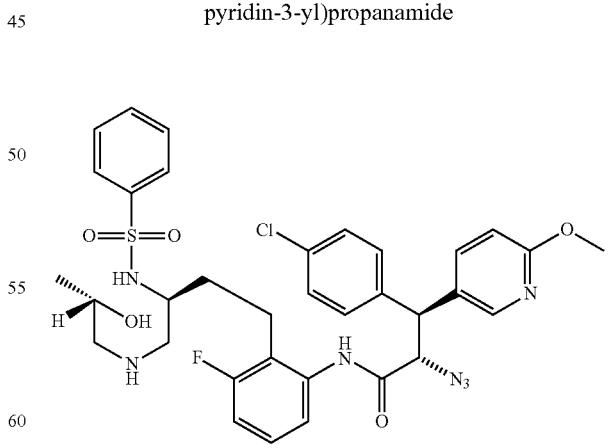

To a stirred solution of (2S,3S)-2-azido-3-(4-chlorophenyl)-N-(3-fluoro-2-(2-((S)-1-(phenylsulfonyl)aziridin-2-yl)ethyl)phenyl-3-(6-methoxypyridin-3-yl)propanamide (0.2 g, 0.314 mmol) in 1,2-dichloroethane (3 mL) was added (S)-1-amino 2-propanol (0.165 g, 2.20 mmol) and the solution was heated to 50° C. for 1.5 h. The reaction mixture was cooled to room temperature and diluted with water (50 mL) and extracted with EtOAc (100 mL). The organic layer was washed with water (50 mL), brine (50 mL), dried (Na$_2$SO$_4$), filtered and concentrated under reduced pressure. The yellow gum (0.15 g, 66%) obtained was taken forward to the next step without further purification. MS: m/z=710 (M+H$^+$).

Step 3. tert-Butyl ((S)-4-(2-((2S,3S)-2-azido-3-(4-chlorophenyl)-3-(6-methoxypyridin-3-yl)propanamido)-6-fluorophenyl)-2-(phenylsulfonamido)butyl)((S)-2-hydroxypropyl)carbamate

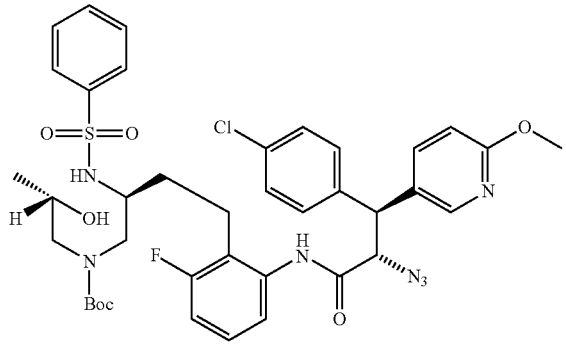 [SMILES: COc1ccc([C@H](c2ccc(Cl)cc2)[C@H](N=[N+]=[N-])C(=O)Nc2cccc(F)c2CC[C@@H](CN(C[C@H](C)O)C(=O)OC(C)(C)C)NS(=O)(=O)c2ccccc2)cn1]

To a stirred solution of (2S,3S)-2-azido-N-(3-fluoro-2-((S)-4-(((R)-2-hydroxypropyl)amino)-3-(phenylsulfonamido)butyl)phenyl)-3-(6-methoxypyridin-3-yl)propanamide (0.15 g, 0.70 mmol) in dichloromethane (10 mL) was added di-tert-butyl dicarbonate (0.32 mL, 0.208 mmol) and triethylamine (0.06 mL, 0.41 mmol) and the reaction mixture was stirred at room temperature for 16 h. Diluted the reaction mixture with water (50 mL) and EtOAc (100 mL), the layers were separated and the organic layer was washed with brine (50 mL), dried (Na$_2$SO$_4$), filtered and concentrated under reduced pressure. The residue was purified by 24 g SiO$_2$ column using a gradient elution of 0-35% EtOAc in hexanes. Fractions containing product were combined and the solvents were removed in vacuo to provide the product (0.15 g, 90% over two steps) as a pale yellow gum. MS: m/z=810 (M+H$^+$).

Step 4. (S)-tert-Butyl 3-(2-((2S,3S)-2-azido-3-(4-chlorophenyl)-3-(6-methoxypyridin-3-yl)propanamido)-6-fluorophenethyl)-4-(phenylsulfonyl)piperazine-1-carboxylate

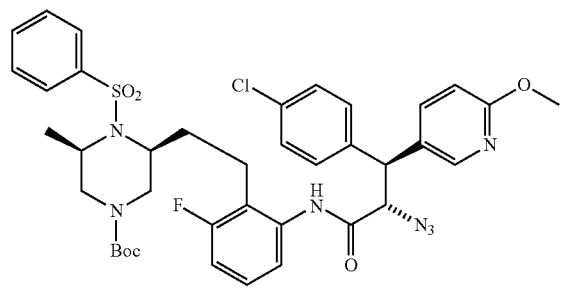 [SMILES: COc1ccc([C@H](c2ccc(Cl)cc2)[C@H](N=[N+]=[N-])C(=O)Nc2cccc(F)c2CC[C@H]2CN(C(=O)OC(C)(C)C)C[C@@H](C)N2S(=O)(=O)c2ccccc2)cn1]

To a stirred solution of tert-Butyl ((S)-4-(2-((2S,3S)-2-azido-3-(4-chlorophenyl)-3-(6-methoxypyridin-3-yl)propanamido)-6-fluorophenyl)-2-(phenylsulfonamido)butyl)((S)-2-hydroxypropyl)carbamate (0.15 g, 0.187 mmol) in dry THF was added DIAD (0.11 g, 0.562 mmol) and triphenyl phosphine (0.147 g, 0.562 mmol) and the reaction mixture was stirred at room temperature for 20 min. Added silica-gel and concentrated under reduced pressure. The compound was purified by 12 g SiO$_2$ column using a gradient elution of 0-30% EtOAc in hexanes. Fractions containing product were combined and the solvents were removed in vacuo to provide the product (0.130 g, 87%) as a pale yellow gum. MS: m/z=792 (M+H$^+$).

Step 5. (S)-tert-Butyl 3-(2-((2S,3S)-2-amino-3-(4-chlorophenyl)-3-(6-methoxypyridin-3-yl)propanamido)-6-fluorophenethyl)-4-(phenylsulfonyl)piperazine-1-carboxylate

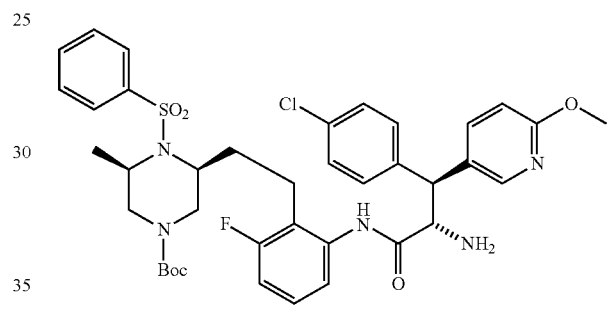

To a stirred solution of (S)-tert-butyl 3-(2-((2S,3S)-2-azido-3-(4-chlorophenyl)-3-(6-methoxypyridin-3-yl)propanamido)-6-fluorophenethyl)-4-(phenylsulfonyl)piperazine-1-carboxylate (0.13 g, 0.164 mmol) in a mixture of EtOAc (20 mL), water (5 mL) was added trimethyl phosphine (0.24 mL, 0.246 mmol, 1M solution in THF) and the reaction mixture was stirred at room temperature for 16 h. Diluted the reaction mixture with water (50 mL) and EtOAc (75 mL) the layers were separated. The organic layer was washed with brine (30 mL), dried (Na$_2$SO$_4$), filtered and concentrated under reduced pressure. The residue was purified by 12 g SiO$_2$ column using a gradient elution of 0-5% MeOH in dichloromethane. Fractions containing product were combined and the solvents were removed in vacuo to provide the product (55 mg, 44%) as a pale yellow gum. MS: m/z=766 (M+H$^+$).

Step 6. (βS)-4-chloro-N-(3-fluoro-2-{2-[(2S,6R)-6-methyl-1-(phenylsulfonyl)piperazin-2-yl]ethyl}phenyl)-β-(6-methoxypyridin-3-yl)-L-phenylalaninamide To a solution of (S)-tert-butyl 3-(2-((2S,3S)-2-amino-3-(4-chlorophenyl)-3-(6-methoxypyridin-3-yl)propanamido)-6-fluorophenethyl)-4-(phenylsulfonyl)piperazine-1-carboxylate (25 mg, 0.032 mmol) in CH$_2$Cl$_2$ (2 mL) was added TFA (0.6 mL) and the mixture was stirred at room temperature for 1 h. The reaction mixture was concentrated under reduced pressure and the product was crystallized from ether (0.5 mL) and hexanes (2 mL) to provide the product (18.5 mg, 56%). MS: m/z=666 (M+H$^+$).

EXAMPLE 15

(βS)—N-(4-{2-[(2S,6R)-1-(cyclopropylsulfonyl)-6-methylpiperazin-2-yl]ethyl}-5-fluoropyridin-3-yl)-β-(3,5-difluorophenyl)-4-fluoro-L-phenylalaninamide

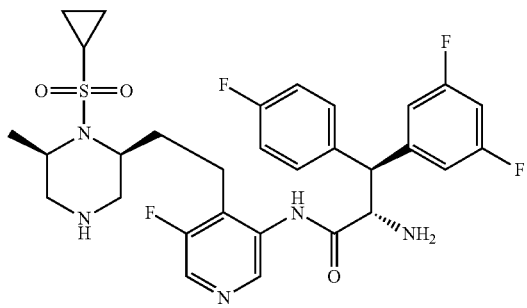 [SMILES: C[C@@H]1CNC[C@H](CCc2c(F)cncc2NC(=O)[C@@H](N)[C@@H](c2ccc(F)cc2)c2cc(F)cc(F)c2)N1S(=O)(=O)C1CC1]

Step 1. (S)-tert-Butyl 4-(2-(3-((2S,3S)-2-azido-3-(3,5-difluorophenyl)-3-(-4-fluorophenyl)propanamido)-5-fluoropyridin-4-yl)ethyl)-2,2-dimethyloxazolidine-3-carboxylate

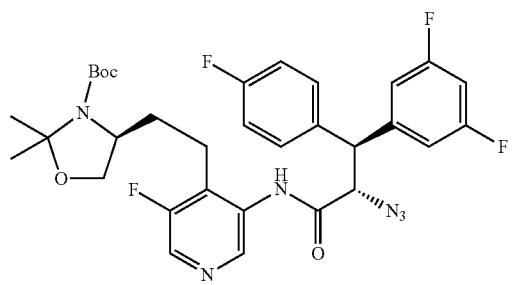 [SMILES: CC(C)(C)OC(=O)N1[C@@H](CCc2c(F)cncc2NC(=O)[C@@H](N=[N+]=[N-])[C@@H](c2ccc(F)cc2)c2cc(F)cc(F)c2)COC1(C)C]

To a stirred solution of (S)-tert-butyl 4-(2-(3-amino-5-fluoropyridin-4-yl)ethyl)-2,2-dimethyloxazolidine-3-carboxylate (Intermediate F) (2.64 g, 7.78 mmol) and (2S,3S)-2-azido-3-(3,5-difluorophenyl)-3-(4-fluorophenyl) propanoic acid (Intermediate 3) (2.50 g, 7.78 mmol) in pyridine (25 mL) at −20° C. was added slowly POCl$_3$ (0.87 mL, 9.34 mmol) and the reaction mixture was allowed to reach 0° C. and stirred for 3 h. The reaction was quenched with a saturated solution of KH$_2$PO$_4$ (50 mL) and extracted with EtOAc (200 mL). The organic layer was washed with brine (200 mL), dried (Na$_2$SO$_4$), filtered and concentrated under reduced pressure. The residue was purified by 80 g SiO$_2$ column using a gradient elution of 0-50% EtOAc in hexanes. Fractions containing product were combined and the solvents were removed in vacuo to provide the product (4.10 g, 82%) as a pale yellow solid. MS: m/z=643 (M+H$^+$).

Step 2. (2S,3S)—N-(4-((S)-3-amino-4-hydroxybutyl)-5-fluoropyridin-3-yl)-2-azido-3-(3,5-difluorophenyl)-3-(4-fluorophenyl)propanamide

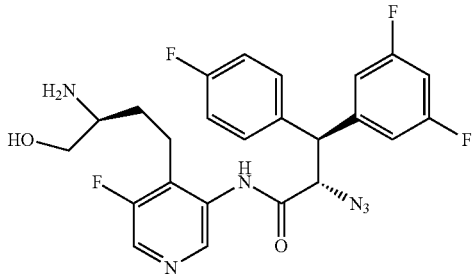 [SMILES: [N-]=[N+]=N[C@H](C(=O)Nc1cncc(F)c1CC[C@H](N)CO)[C@@H](c1ccc(F)cc1)c1cc(F)cc(F)c1]

To a stirred solution of (S)-tert-butyl 4-(2-(3-((2S,3S)-2-azido-3-(3,5-difluorophenyl)-3-(-4-fluorophenyl)propanamido)-5-fluoropyridin-4-yl)ethyl)-2,2-dimethyloxazolidine-3-carboxylate (4.10 g, 6.38 mmol) in dichloromethane (80 mL) was added trifluoroacetic acid (30 mL) and water (8 mL) and the solution was stirred at room temperature for 16 h. Concentrated the solvents under reduced pressure and the residue was diluted with EtOAc (250 mL) and saturated solution of sodium bicarbonate (100 mL) and the biphasic solution was stirred for 10 min. The organic layer was separated and washed with brine (100 mL), dried (Na$_2$SO$_4$), filtered and concentrated under reduced pressure. The pale yellow solid (3.2 g, quantitative) obtained was carried into next step without further purification. MS: m/z=503 (M+H$^+$).

Step 3. (2S,3S)-2-azido-N-(4-(2-((S)-1-(cyclopropylsulfonyl)aziridin-2-yl)ethyl)-5-fluoropyridin-3-yl)-3-(3,5-difluorophenyl)-3-(4-fluorophenyl)propanamide

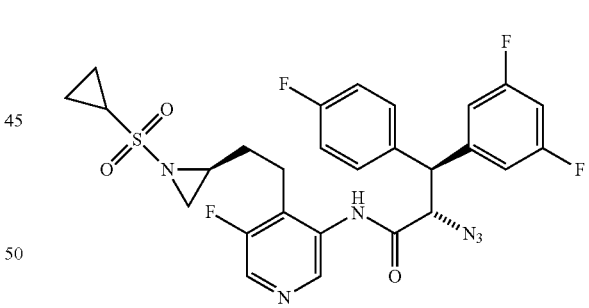

To a stirred solution of (2S,3S)—N-(4-((S)-3-amino-4-hydroxybutyl)-5-fluoropyridin-3-yl)-2-azido-3-(3,5-difluorophenyl)-3-(4-fluorophenyl)propanamide (1.00 g, 1.99 mmol) in dichloromethane at −20° C. was added triethylamine (1.38 mL, 9.96 mmol), DMAP (22 mg, 0.19 mmol) and cyclopropyl sulfonylchloride (0.24 mL, 2.39 mmol) and the reaction mixture was stirred 1.5 h. This was followed by the addition of methane sulfonylchloride (0.19 mL, 2.39 mmol) and stirring was continued for 30 min, and stirred the reaction mixture at 0° C. The reaction mixture was quenched with saturated solution of sodium bicarbonate (10 mL) and stirred for an additional 30 minutes. Diluted with water (20 mL) and extracted with dichloromethane (2×50 mL). The combined organic extracts were washed with brine (10 mL), dried (Na$_2$SO$_4$), filtered and concentrated under reduced pressure. The residue obtained was purified by 80 g SiO$_2$ column using a gradient elution of 0-50% EtOAc in hexanes. Fractions containing product were combined and the solvents were removed in vacuo to provide the product (0.90 g, 76%) as a pale yellow solid. MS: m/z=589 (M+H$^+$).

Step 4. (2S,3S)-2-azido-N-(4-((S)-3-(cyclopropanesulfonamido)-4-(((S)-2-hydroxypropyl)amino)butyl)-5-fluoropyridin-3-yl)-3-(3,5-difluorophenyl)-3-(4-fluorophenyl)propanamide

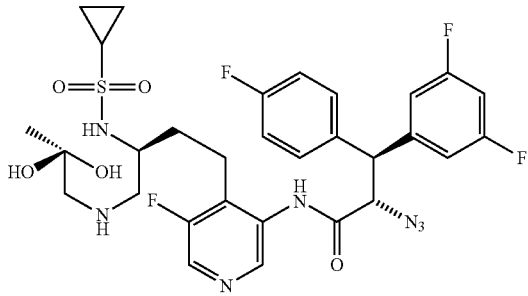

To a stirred solution of ((2S,3S)-2-azido-N-(4-(2-((S)-1-(cyclopropylsulfonyl)aziridin-2-yl)ethyl)-5-fluoropyridin-3-yl)-3-(3,5-difluorophenyl)-3-(4-fluorophenyl)propanamide (0.45 g, 0.76 mmol) in 1,2-dichloroethane (20 mL) was added (S)-1-amino 2-propanol (0.402 g, 5.35 mmol) and the solution was heated to 50° C. for 1.5 h. The reaction mixture was cooled to room temperature and diluted with water (50 mL) and extracted with EtOAc (100 mL). The organic layer was washed with water (50 mL), brine (50 mL), dried (Na$_2$SO$_4$), filtered and concentrated under reduced pressure. The yellow gum (0.50 g, quantitative) obtained was taken forward to the next step without further purification. MS: m/z=664 (M+H$^+$).

Step 5. tert-butyl ((S)-4-(3-((2S,3S)-2-azido-3-(3,5-diflurophenyl)-3-(4-fluorophenyl)propanamido)-5-fluoropyridin-4-yl)-2-(cyclopropanesulfonamido) butyl)((S)-2-hydroxypropyl)carbamate

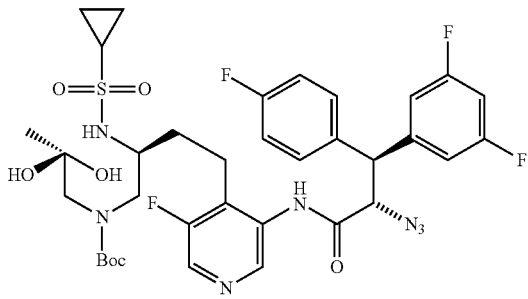

To a stirred solution of (2S,3S)-2-azido-N-(4-((S)-3-(cyclopropanesulfonamido)-4-(((S)-2-hydroxypropyl)amino) butyl)-5-fluoropyridin-3-yl)-3-(3,5-difluorophenyl)-3-(4-fluorophenyl)propanamide (0.50 g, 0.75 mmol) in dichloromethane (20 mL) was added di-tert-butyl dicarbonate (0.22 mL, 0.98 mmol) and triethylamine (0.21 mL, 1.51 mmol) and the reaction mixture was stirred at room temperature for 2 h. Diluted the reaction mixture with water (50 mL) and dichloromethane (100 mL), the layers were separated and the organic layer was washed with brine (50 mL), dried (Na$_2$SO$_4$), filtered and concentrated under reduced pressure. The residue was purified by 24 g SiO$_2$ column using a gradient elution of 0-50% EtOAc in hexanes. Fractions containing product were combined and the solvents were removed in vacuo to provide the product (0.46 g, 80% over two steps) as a pale yellow gum. MS: m/z=764 (M+H$^+$).

Step 6. (3S,5R)-tert-butyl 3-(2-(3-((2S,3S)-2-azido-3-(3,5-difluorophenyl)-3-(4-fluorophenyl)propanamido)-5-fluoropyridin-4-yl)ethyl)-4-(cyclopropylsulfonyl)-5-methylpiperazine-1-carboxylate

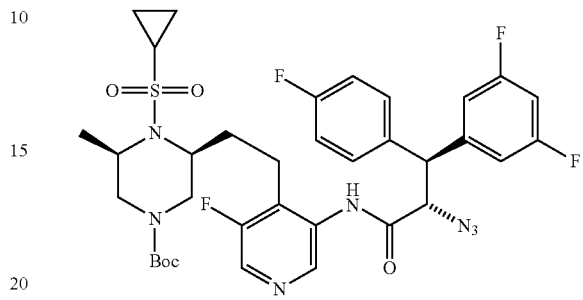

To a stirred solution of tert-butyl ((S)-4-(3-((2S,3S)-2-azido-3-(3,5difluorophenyl)-3-(4-fluorophenyl)propanamido)-5-fluoropyridin-4-yl)-2(cyclopropanesulfonamido) butyl)((S)-2-hydroxypropyl)carbamate (0.46 g, 0.60 mmol) in dry THF was added DIAD (0.365 g, 1.81 mmol) and triphenyl phosphine (0.474 g, 1.81 mmol) and the reaction mixture was stirred at room temperature for 20 min. Added silica-gel and concentrated under reduced pressure. The compound was purified by 12 g SiO$_2$ column using a gradient elution of 0-50% EtOAc in hexanes. Fractions containing product were combined and the solvents were removed in vacuo to provide the product (0.30 g, 66%) as a pale yellow gum. MS: m/z=746 (M+H$^+$).

Step 7. (3S,5R)-tert-butyl 3-(2-(3-((2S,3S)-2-amino-3-(3,5-difluorophenyl)-3-(4-fluorophenyl)propanamido)-5-fluoropyridin-4-yl)ethyl)-4-(cyclopropylsulfonyl)-5-methylpiperazine-1-carboxylate

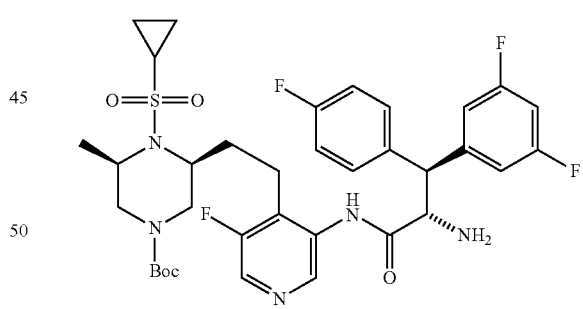

To a stirred solution of (3S,5R)-tert-butyl 3-(2-(3-((2S,3S)-2-azido-3-(3,5-difluorophenyl)-3-(4-fluorophenyl)propanamido)-5-fluoropyridin-4-yl)ethyl)-4-(cyclopropylsulfonyl)-5-methylpiperazine-1-carboxylate (0.30 g, 0.40 mmol) in a mixture of EtOAc (20 mL), water (4 mL) was added trimethyl phosphine (0.80 mL, 0.80 mmol, 1M solution in THF) and the reaction mixture was stirred at room temperature for 16 h. Diluted the reaction mixture with water (50 mL) and EtOAc (75 mL) the layers were separated. The organic layer was washed with brine (30 mL), dried (Na$_2$SO$_4$), filtered and concentrated under reduced pressure. The residue was purified by 12 g SiO$_2$ column using a gradient elution of 0-5% MeOH in dichloromethane. Fractions containing product were combined and the solvents were removed in vacuo to provide the product (0.22 g, 76%) as a pale yellow gum.

Step 8. (βS)—N-(4-{2-[(2S,6R)-1-(cyclopropylsulfonyl)-6-methylpiperazin-2-yl]ethyl}-5-fluoropyridin-3-yl)-β-(3,5-difluorophenyl)-4-fluoro-L-phenylalaninamide To a solution of (3S,5R)-tert-butyl 3-(2-(3-((2S,3S)-2-amino-3-(3,5-difluorophenyl)-3-(4-fluorophenyl)propanamido)-5-fluoropyridin-4-yl)ethyl)-4-(cyclopropylsulfonyl)-5-methylpiperazine-1-carboxylate (60 mg, 0.083 mmol) in CH$_2$Cl$_2$ (2 mL) was added TFA (0.6 mL) and the mixture was stirred at room temperature for 1 h. The reaction mixture was concentrated under reduced pressure and the product was crystallized from ether (0.5 mL) and hexanes (2 mL) to provide the product (73 mg, 91%). MS: m/z=620 (M+H$^+$).

EXAMPLE 16

(βS)-β-(3,5-difluorophenyl)-4-fluoro-N-[3-fluoro-2-(2-{(2S,6R)-1-[(4-methoxyphenyl)sulfonyl]-6-methylpiperazin-2-yl}ethyl)phenyl]-L-phenylalaninamide

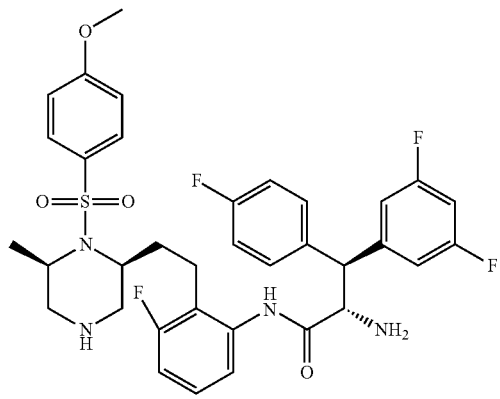 [SMILES: COc1ccc(S(=O)(=O)N2[C@@H](CCc3c(F)cccc3NC(=O)[C@@H](N)[C@@H](c3ccc(F)cc3)c3cc(F)cc(F)c3)CNC[C@H]2C)cc1]

Step 1. (S)-tert-Butyl 4-(2-((2S,3S)-2-azido-3-(3,5-difluorophenyl)-3-(4-fluorophenyl)propanamido)-6-fluorophenethyl)-2,2-dimethyloxazolidine-3-carboxylate

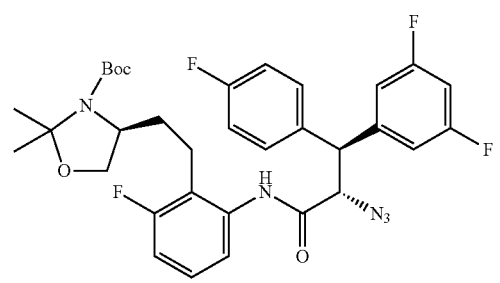 [SMILES: CC(C)(C)OC(=O)N1[C@@H](CCc2c(F)cccc2NC(=O)[C@@H](N=[N+]=[N-])[C@@H](c2ccc(F)cc2)c2cc(F)cc(F)c2)COC1(C)C]

To a stirred solution of (S)-tert-butyl 4-(2-amino-6-fluorophenethyl)-2,2-dimethyloxazolidine-3-carboxylate (Intermediate C) (3.38 g, 10.0 mmol) and (2S,3S)-2-azido-3-(3,5-difluorophenyl)-3-(4-fluorophenyl)propanoic acid (Intermediate 3) (3.21 g, 10.0 mmol) in pyridine (20 mL) at −20° C. was added slowly POCl$_3$ (1.02 mL, 10.66 mmol) and the reaction mixture was allowed to reach 0° C. and stirred for 3 h. The reaction was quenched with a saturated solution of KH$_2$PO$_4$ (50 mL) and extracted with EtOAc (200 mL). The organic layer was washed with brine (200 mL), dried (Na$_2$SO$_4$), filtered and concentrated under reduced pressure. The residue was purified by 80 g SiO$_2$ column using a gradient elution of 0-30% EtOAc in hexanes. Fractions containing product were combined and the solvents were removed in vacuo to provide the product (5.80 g, 88%) as a pale yellow solid. MS: m/z=642 (M+H$^+$).

Step 2. (2S,3S)—N-(2-((S)-3-amino-4-hydroxybutyl)-3-fluorophenyl)-2-azido-3-(3,5-difluorophenyl)-3-(4-fluorophenyl)propanamide

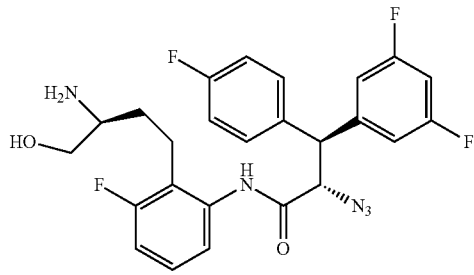 [SMILES: [N-]=[N+]=N[C@H](C(=O)Nc1cccc(F)c1CC[C@H](N)CO)[C@@H](c1ccc(F)cc1)c1cc(F)cc(F)c1]

To a stirred solution of (S)-tert-butyl 4-(2-((2S,3S)-2-azido-3-(3,5-difluorophenyl)-3-(4-fluorophenyl)propanamido)-6-fluorophenethyl)-2,2-dimethyloxazolidine-3-carboxylate (2.85 g, 4.40 mmol) in dichloromethane (30 mL) was added trifluoroacetic acid (14 mL) and water (4 mL) and the solution was stirred at room temperature for 16 h. Concentrated the solvents under reduced pressure and the residue was diluted with EtOAc (250 mL) and saturated solution of sodium bicarbonate (100 mL) and the biphasic solution was stirred for 10 min. The organic layer was separated and washed with brine (100 mL), dried (Na$_2$SO$_4$), filtered and concentrated under reduced pressure. The pale yellow solid (1.60 g, quantitative) obtained was carried into next step without further purification. MS: m/z=502 (M+H$^+$).

Step 3. (2S,3S)-2-Azido-3-(3,5-difluorophenyl)-N-(3-fluoro-2-(2-((S)-1-((4-methoxyphenyl)sulfonyl)aziridin-2-yl)ethyl)phenyl)-3-(4-fluorophenyl)propanamide

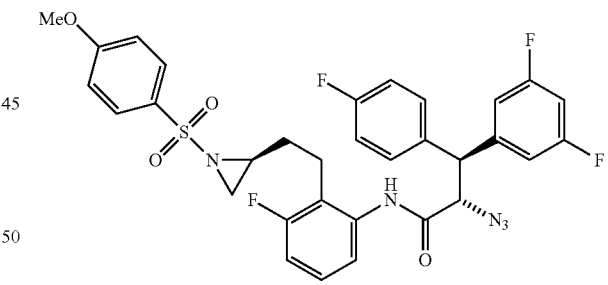

To a stirred solution of (2S,3S)—N-(2-((S)-3-amino-4-hydroxybutyl)-3-fluorophenyl)-2-azido-3-(3,5-difluorophenyl)-3-(4-fluorophenyl)propanamide (0.40 g, 0.79 mmol) in dichloromethane at −20° C. was added triethylamine (0.35 mL, 3.99 mmol), DMAP (9 mg, 0.07 mmol) and benzene sulfonylchloride (0.49 mL, 2.39 mmol) and the reaction mixture was stirred at 1.5 h. The reaction mixture was quenched with saturated solution of sodium bicarbonate (10 mL) and stirred for an additional 30 minutes. Diluted with water (20 mL) and extracted with dichloromethane (2×50 mL). The combined organic extracts were washed with brine (10 mL), dried (Na$_2$SO$_4$), filtered and concentrated under reduced pressure. The residue obtained was purified by 12 g SiO$_2$ column using a gradient elution of 0-30% EtOAc in hexanes. Fractions containing product were combined and the solvents were removed in vacuo to provide the product (0.38 g, 73%) as a pale yellow solid. MS: m/z=654 (M+H⁺).

Step 4. (2S,3S)-2-Azido-3-(3,5-difluorophenyl)-N-(3-fluoro-2-((S)-4-(((S)-2-hydroxypropyl)amino)-3-(4-methoxyphenylsulfonamido)butyl)phenyl)-3-(4-fluorophenyl)propanamide

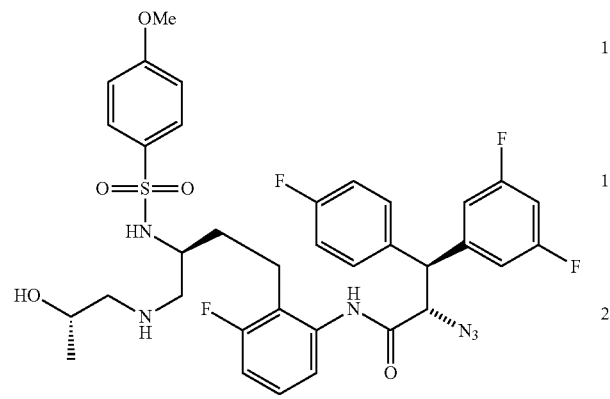

To a stirred solution of (2S,3S)-2-azido-3-(3,5-difluorophenyl)-N-(3-fluoro-2-(2-((S)-1-((4-methoxyphenyl)sulfonyl)aziridin-2-yl)ethyl)phenyl)-3-(4-fluorophenyl)propanamide (0.15 g, 0.22 mmol) in 1,2-dichloroethane (3 mL) was added (R)-1-amino 2-propanol (0.12 g, 1.60 mmol) and the solution was heated to 50° C. for 1.5 h. The reaction mixture was cooled to room temperature and diluted with water (10 mL) and extracted with EtOAc (20 mL). The organic layer was washed with water (5 mL), brine (5 mL), dried (Na₂SO₄), filtered and concentrated under reduced pressure. The yellow gum (0.48 g, quantitative) obtained was taken forward to the next step without further purification. MS: m/z=729 (M+H⁺).

Step 5. tert-Butyl ((S)-4-(2-((2S,3S)-2-azido-3-(3,5-difluorophenyl)-3-(4-fluorophenyl)propanamido)-6-fluorophenyl)-2-(4-methoxyphenylsulfonamido)butyl((S)-2-hydroxypropyl)carbamate

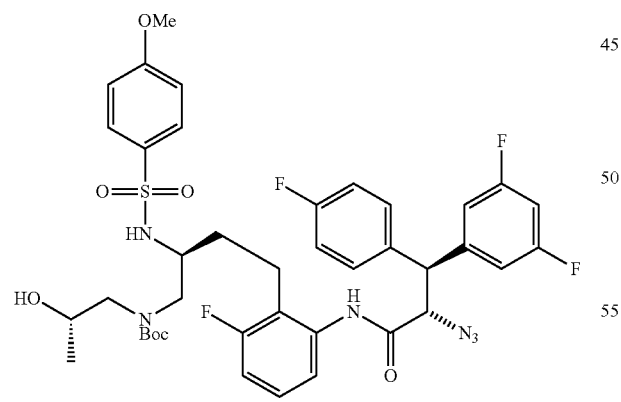

To a stirred solution of (2S,3S)-2-azido-3-(3,5-difluorophenyl)-N-(3-fluoro-2-((S)-4-(((S)-2-hydroxypropyl)amino)-3-(4-methoxyphenylsulfonamido)butyl)phenyl)-3-(4-fluorophenyl)propanamide (0.20 g, 0.27 mmol) in dichloromethane (3 mL) was added di-tert-butyl dicarbonate (0.09 mL, 0.41 mmol) and triethylamine (0.07 mL, 0.54 mmol) and the reaction mixture was stirred at room temperature for 16 h. Diluted the reaction mixture with water (10 mL) and EtOAc (20 mL), the layers were separated and the organic layer was washed with brine (5 mL), dried (Na₂SO₄), filtered and concentrated under reduced pressure. The residue was purified by 12 g SiO₂ column using a gradient elution of 0-35% EtOAc in hexanes. Fractions containing product were combined and the solvents were removed in vacuo to provide the product (0.11 g, 52% over two steps). MS: m/z=829 (M+H⁺).

Step 6. (3S,5R)-tert-butyl 3-(2-((2S,3S)-2-azido-3-(3,5-difluorophenyl)-3-(4-fluorophenyl)propanamido)-6-fluorophenethyl)-4-((4-methoxyphenyl)sulfonyl)-5-methylpiperazine-1-carboxylate

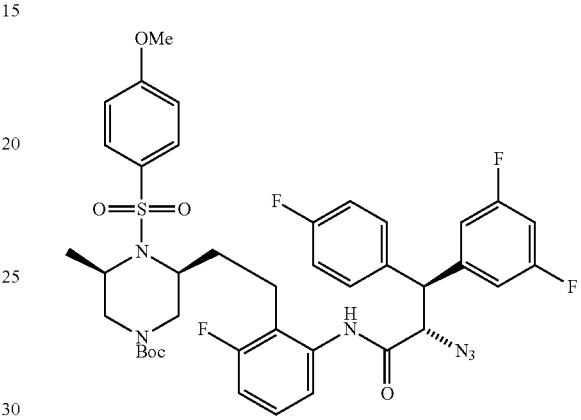

To a stirred solution of tert-butyl tert-butyl ((S)-4-(2-((2S,3S)-2-azido-3-(3,5-difluorophenyl)-3-(4-fluorophenyl)propanamido)-6-fluorophenyl)-2-(4 methoxyphenylsulfonamido)butyl)((S)-2-hydroxypropyl)carbamate (0.11 g, 0.13 mmol) in dry THF was added DIAD (0.08 g, 0.39 mmol) and triphenyl phosphine (0.104 g, 0.39 mmol) and the reaction mixture was stirred at room temperature for 20 min. Added silica-gel and concentrated under reduced pressure. The compound was purified by 12 g SiO₂ column using a gradient elution of 0-30% EtOAc in hexanes. Fractions containing product were combined and the solvents were removed in vacuo to provide the product (0.09 g, 84%).

Step 7. (3S,5R)-tert-Butyl 3-(2-((2S,3S)-2-amino-3-(3,5-difluorophenyl)-3-(4-fluorophenyl)propanamido)-6-fluorophenethyl)-4-((4-methoxyphenyl)sulfonyl)-5-methylpiperazine-1-carboxylate

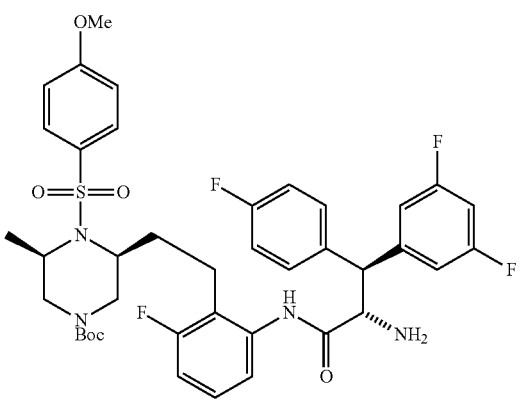 [SMILES: COc1ccc(S(=O)(=O)N2[C@@H](CCc3c(F)cccc3NC(=O)[C@@H](N)[C@@H](c3ccc(F)cc3)c3cc(F)cc(F)c3)CN(C(=O)OC(C)(C)C)C[C@H]2C)cc1]

To a stirred solution of (3S,5R)-tert-butyl 3-(2-((2S,3S)-2-azido-3-(3,5-difluorophenyl)-3-(4-fluorophenyl)propanamido)-6-fluorophenethyl)-4-((4-methoxyphenyl)sulfonyl)-5-methylpiperazine-1-carboxylate (0.09 g, 0.11 mmol) in a mixture of EtOAc (2 mL), water (1 mL) was added trimethyl phosphine (0.55 mL, 0.55 mmol, 1M solution in THF) and the reaction mixture was stirred at room temperature for 16 h. Diluted the reaction mixture with water (10 mL) and EtOAc (25 mL) the layers were separated. The organic layer was washed with brine (5 mL), dried ($Na_2SO_4$), filtered and concentrated under reduced pressure. The residue was purified by 12 g $SiO_2$ column using a gradient elution of 0-5% MeOH in dichloromethane. Fractions containing product were combined and the solvents were removed in vacuo to provide the product (0.05 g, 57%).

Step 8. (βS)-β-(3,5-difluorophenyl)-4-fluoro-N-[3-fluoro-2-(2-{(2S,6R)-1-[(4-methoxyphenyl)sulfonyl]-6-methylpiperazin-2-yl}ethyl)phenyl]-L-phenylalaninamide To a solution of ((3S,5R)-tert-butyl 3-(2-((2S,3S)-2-amino-3-(3,5-difluorophenyl)-3-(4-fluorophenyl)propanamido)-6-fluorophenethyl)-4-((4-methoxyphenyl)sulfonyl)-5-methylpiperazine-1-carboxylate (20 mg, 0.025 mmol) in $CH_2Cl_2$ (1 mL) was added TFA (0.3 mL) and the mixture was stirred at room temperature for 1 h. The reaction mixture was concentrated under reduced pressure and the residue was purified by semi preparative HPLC. Fractions containing product were combined and the solvents were removed in vacuo to provide the product (6 mg, 30%). MS: m/z=685 (M+H$^+$).

EXAMPLE 17

(βR)-4-chloro-N-(5-fluoro-4-{2-[(2S,6R)-6-methyl-1-(phenylsulfonyl)piperazin-2-yl]ethyl}pyridin-3-yl)-Nα-(methoxycarbonyl)-β-(1-methylethyl)-L-phenylalaninamide

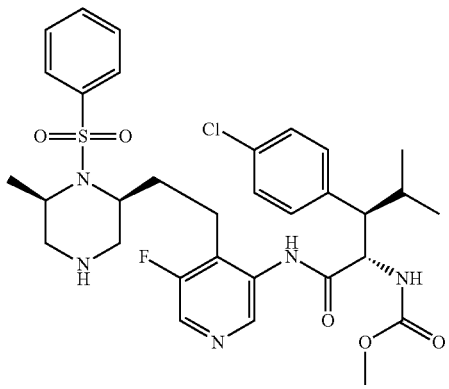 [SMILES: COC(=O)N[C@H](C(=O)Nc1cncc(F)c1CC[C@H]1CNC[C@@H](C)N1S(=O)(=O)c1ccccc1)[C@@H](c1ccc(Cl)cc1)C(C)C]

The title compound was prepared using the procedures given for Example 8 using (S)-1-amino-2-propanol in place of (R)-1-amino-2-propanol in step 4.

EXAMPLE 18

Methyl ((1R,2S)-1-(4-chlorophenyl)-3-((3-fluoro-2-(2-((2S,6R)-1-((4-fluorophenyl)sulfonyl)-6-methylpiperazin-2-yl)ethyl)phenyl)amino)-3-oxo-1-(tetrahydro-2H-pyran-4-yl)propan-2-yl)carbamate

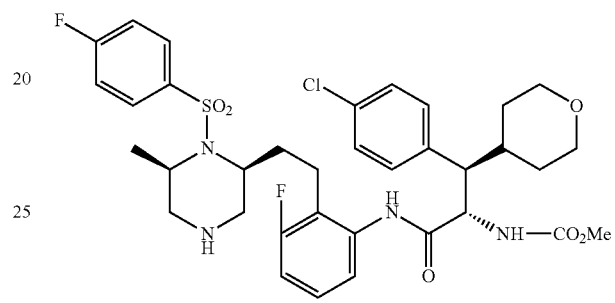

Step 1. (2S,3R)-2-ASzido-3-(4-chlorophenyl)-N-(3-fluoro-2-((S)-3-(4-fluorophenylsulfonamido)-4-hydroxybutyl)phenyl)-3-(tetrahydro-2H-pyran-4-yl)propanamide

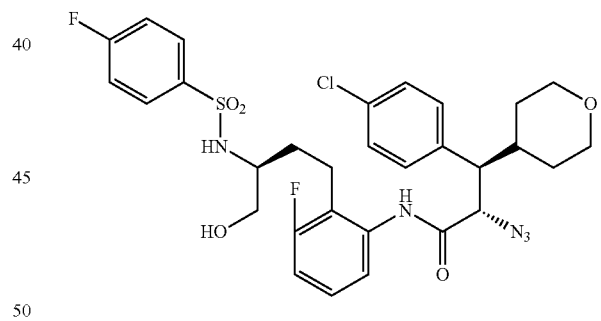

A solution of (2S,3R)—N-(2-((S)-3-amino-4-hydroxybutyl)-3-fluorophenyl)-2-azido-3-(4-chlorophenyl)-3-(tetrahydro-2H-pyran-4-yl)propanamide from Step 2 of Example 12 (582 mg, 1.19 mmol) and TEA (331 μL, 2.38 mmol) in DMF (6 mL) was cooled to 0° C. 4-fluorobenzenesulfonyl chloride (243 mg, 1.25 mmol) was added dropwise. The mixture was stirred for 20 minutes, at which point LCMS indicated completion. The reaction was quenched with aqueous sodium hydrogen carbonate (saturated) and the mixture was extracted three times with ethyl acetate. The combined organic fractions were dried (Na2SO4), filtered, and the solvent was evaporated under reduced pressure to afford the desired product as a vicsous oil (LCMS m/z=648.3).

Step 2. (2S,3R)-2-Azido-3-(4-chlorophenyl)-N-(3-fluoro-2-(2-((S)-1-((4-fluorophenyl)sulfonyl)aziridin-2-yl)ethyl)phenyl)-3-(tetrahydro-2H-pyran-4-yl)propanamide

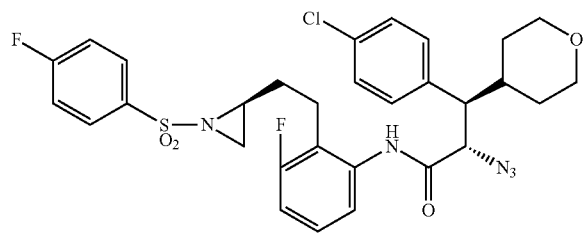 [SMILES: [N-]=[N+]=N[C@H](C(=O)Nc1cccc(F)c1CC[C@H]1CN1S(=O)(=O)c1ccc(F)cc1)[C@@H](c1ccc(Cl)cc1)C1CCOCC1]

Triphenylphosphine (436 mg, 1.66 mmol), followed by DIAD (0.323 mL, 1.66 mmol), was added to a 0° C. solution of (2S,3R)-2-azido-3-(4-chlorophenyl)-N-(3-fluoro-2-((S)-3-(4-fluorophenylsulfonamido)-4-hydroxybutyl)phenyl)-3-(tetrahydro-2H-pyran-4-yl)propanamide (770 mg, 1.19 mmol) in dry THF (12 mL). After 2 hours the solvent was removed in vacuo and the residue was partitioned between water and ethyl acetate. The layers were separated and the aqueous layer was extracted twice more with ethyl acetate. The combined organic extracts were dried over Na2SO4, filtered, and concentrated under reduced pressure. The crude product was purified by flash chromatography (12 g SiO2 column) running a 10-70% EtOAc/hexane gradient over 15 minutes to afford the product as a white foam (LCMS m/z=630.3).

Step 3. (2S,3R)-2-Azido-3-(4-chlorophenyl)-N-(3-fluoro-2-((S)-3-(4-fluorophenylsulfonamido)-4-(((S)-2-hydroxypropyl)amino)butyl)phenyl)-3-(tetrahydro-2H-pyran-4-yl)propanamide

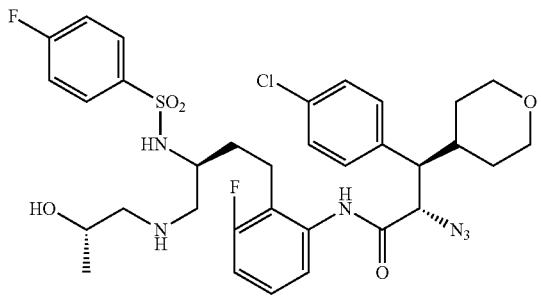 [SMILES: C[C@H](O)CNC[C@H](CCc1c(F)cccc1NC(=O)[C@@H](N=[N+]=[N-])[C@@H](c1ccc(Cl)cc1)C1CCOCC1)NS(=O)(=O)c1ccc(F)cc1]

(S)-1-aminopropan-2-ol (577 mg, 7.68 mmol) was added to a solution of (2S,3R)-2-azido-3-(4-chlorophenyl)-N-(3-fluoro-2-(2-((S)-1-((4-fluorophenyl)sulfonyl)aziridin-2-yl)ethyl)phenyl)-3-(tetrahydro-2H-pyran-4-yl)propanamide (484 mg, 0.768 mmol) in THF (7.5 mL) and the mixture was heated overnight at 45° C. The solvent was removed in vacuo and the residue was partitioned between water (with a little brine) and ethyl acetate. The layers were separated and the aqueous layer was extracted twice more with ethyl acetate. The combined organic extracts were washed once with brine, dried over Na2SO4, filtered and concentrated in vacuo to give a white foam (LCMS m/z=705.4).

Step 4. tert-butyl ((S)-4-(2-((2S,3R)-2-azido-3-(4-chlorophenyl)-3-(tetrahydro-2H-pyran-4-yl)propanamido)-6-fluorophenyl)-2-(4-fluorophenylsulfonamido)butyl)((S)-2-hydroxypropyl)carbamate

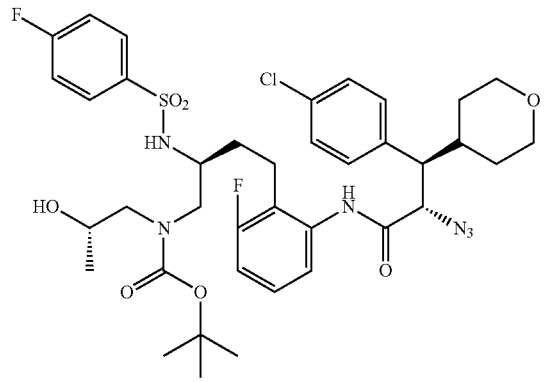 [SMILES: C[C@H](O)CN(C[C@H](CCc1c(F)cccc1NC(=O)[C@@H](N=[N+]=[N-])[C@@H](c1ccc(Cl)cc1)C1CCOCC1)NS(=O)(=O)c1ccc(F)cc1)C(=O)OC(C)(C)C]

Di-tert-butyldicarbonate (432 µl, 1.86 mmol) was added to a 0° C. solution of (2S,3R)-2-azido-3-(4-chlorophenyl)-N-(3-fluoro-2-((S)-3-(4-fluorophenylsulfonamido)-4-(((S)-2-hydroxypropyl)amino)butyl)phenyl)-3-(tetrahydro-2H-pyran-4-yl)propanamide (525 mg, 0.744 mmol) and TEA (259 µL, 1.86 mmol) in dichloromethane (7.5 mL). The mixture was stirred overnight at ambient temperature. The reaction was partitioned between water and dichloromethane. The layers were separated and the aqueous layer was extracted twice more with dichloromethane. The combined organic extracts were dried over Na2SO4, filtered, and concentrated in vacuo. The crude product was purified by flash chromatography (12 g SiO2 column) running a 10-60% EtOAc/hexane gradient over 15 minutes to afford the product as a white foam (LCMS m/z=805.5).

Step 5. (3S,5R)-tert-butyl 3-(2-((2S,3R)-2-azido-3-(4-chlorophenyl)-3-(tetrahydro-2H-pyran-4-yl)propanamido)-6-fluorophenethyl)-4-((4-fluorophenyl)sulfonyl)-5-methylpiperazine-1-carboxylate

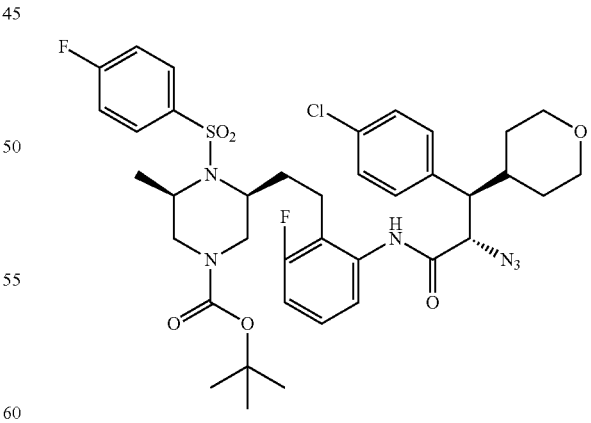

Triphenylphosphine (292 mg, 1.11 mmol), followed by DIAD (217 µL, 1.11 mmol), was added to a solution of tert-butyl ((S)-4-(2-((2S,3R)-2-azido-3-(4-chlorophenyl)-3-(tetrahydro-2H-pyran-4-yl)propanamido)-6-fluorophenyl)-2-(4-fluorophenylsulfonamido)butyl)((S)-2-hydroxypropyl)carbamate (299 mg, 0.371 mmol) in dry THF (7.5 mL) under nitrogen. The reaction was stirred at ambient temperature overnight. The solvent was removed in vacuo and the residue was purified by flash chromatography (12 g SiO2 column) running a 10-60% EtOAc/hexane gradient over 15 minutes to afford the product as a white foam (LCMS m/z=787.3).

Step 6. (3S,5R)-tert-butyl 3-(2-((2S,3R)-2-amino-3-(4-chlorophenyl)-3-(tetrahydro-2H-pyran-4-yl)propanamido)-6-fluorophenethyl)-4-((4-fluorophenyl)sulfonyl)-5-methylpiperazine-1-carboxylate

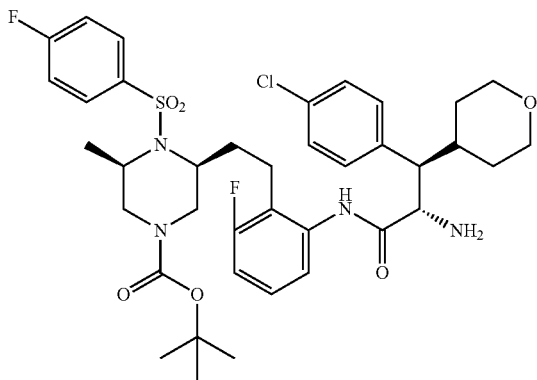 [SMILES: C[C@@H]1CN(C(=O)OC(C)(C)C)C[C@H](CCc2c(F)cccc2NC(=O)[C@@H](N)[C@@H](c2ccc(Cl)cc2)C2CCOCC2)N1S(=O)(=O)c1ccc(F)cc1]

Triphenylphosphine (64.6 mg, 0.246 mmol) was added to a solution of (3S,5R)-tert-butyl 3-(2-((2S,3R)-2-azido-3-(4-chlorophenyl)-3-(tetrahydro-2H-pyran-4-yl)propanamido)-6-fluorophenethyl)-4-((4-fluorophenyl)sulfonyl)-5-methylpiperazine-1-carboxylate (194 mg, 0.246 mmol) dissolved in THF (2 mL) and water (0.4 mL). The reaction was heated to reflux for 18 h. The material was purified by preparative reverse phase HPLC (C18 column) eluting with 80-10% water (0.1% TFA)/acetonitrile gradient to afford the product as a gum (LCMS m/z=761.3).

Step 7. (3S,5R)-tert-butyl 3-(2-((2S,3R)-3-(4-chlorophenyl)-2-((methoxycarbonyl)amino)-3-(tetrahydro-2H-pyran-4-yl)propanamido)-6-fluorophenethyl)-4-((4-fluorophenyl)sulfonyl)-5-methylpiperazine-1-carboxylate

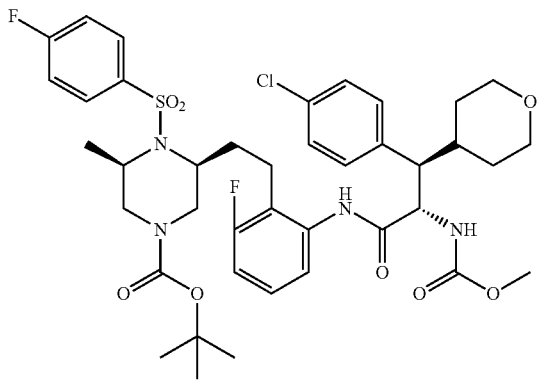 [SMILES: COC(=O)N[C@H](C(=O)Nc1cccc(F)c1CC[C@H]1CN(C(=O)OC(C)(C)C)C[C@@H](C)N1S(=O)(=O)c1ccc(F)cc1)[C@@H](c1ccc(Cl)cc1)C1CCOCC1]

(3S,5R)-tert-butyl 3-(2-((2S,3R)-2-amino-3-(4-chlorophenyl)-3-(tetrahydro-2H-pyran-4-yl)propanamido)-6-fluorophenethyl)-4-((4-fluorophenyl)sulfonyl)-5-methylpipera-zine-1-carboxylate (78 mg, 0.10 mmol) and 2,5-dioxopyrrolidin-1-yl methyl carbonate (7.30 mg, 0.042 mmol) were stirred together in dichloromethane (0.35 mL) overnight at ambient temperature. The reaction was purified by flash chromatography (4 g SiO2 column) running a 20-80% EtOAc/hexane gradient over 15 minutes to afford the product as a white solid (LCMS m/z=819.3).

Step 8. Methyl ((1R,2S)-1-(4-chlorophenyl)-3-((3-fluoro-2-(2-((2S,6R)-1-((4-fluorophenyl)sulfonyl)-6-methylpiperazin-2-yl)ethyl)phenyl)amino)-3-oxo-1-(tetrahydro-2H-pyran-4-yl)propan-2-yl)carbamate (3S,5R)-tert-butyl 3-(2-((2S,3R)-3-(4-chlorophenyl)-2-((methoxycarbonyl)amino)-3-(tetrahydro-2H-pyran-4-yl)propanamido)-6-fluorophenethyl)-4-((4-fluorophenyl)sulfonyl)-5-methylpiperazine-1-carboxylate (67 mg, 0.082 mmol) was stirred in 4M HCl in dioxane (0.3 mL, 1.2 mmol) at ambient temperature overnight. The solvent was removed in vacuo and the residue was purified by preparative HPLC (C18 column) eluting with 90-25% water (0.1% TFA)/acetonitrile gradient. Product containing fractions were combined and lyophilized to give the TFA salt of the title compound as a white solid (LCMS m/z=719.3).

EXAMPLE 19

Methyl ((1S,2S)-1-(4-chlorophenyl)-3-((3-fluoro-2-(2-((S)-5-phenylsulfonyl)-5,8-diazaspiro[2.6]nonan-6-yl)ethyl)phenylamino)-1-(6-methoxypyridin-3-yl)-3-oxopropan-2-yl)carbamate 2,2,2-trifluoroacetate

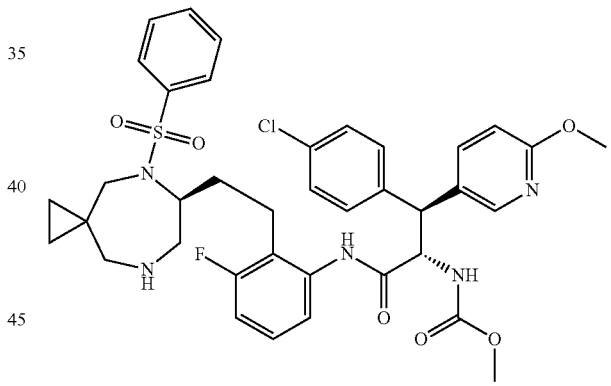

Step 1. (S)-tert-Butyl 4-(2-(3-((2S,3S)-2-azido-3-(4-chlorophenyl)-3-(6-methoxypyridin-3-yl)propanamido)-6-fluorophenyl)-2,2-dimethyloxazolidine-3-carboxylate

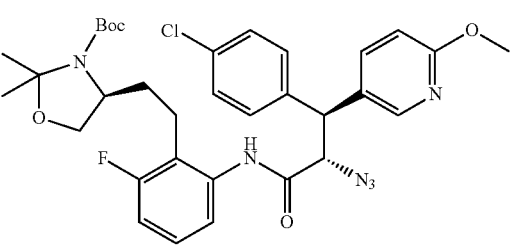

To a stirred solution of (S)-tert-butyl 4-(2-amino-6-fluorophenrthyl)-2,2-dimethyloxazolidine-3-carboxylate (Intermediate C) (0.75 g, 2.218 mmol) and (2S,3S)-2-azido-3-(4-chlorophenyl)-3-(6-methoxypyridin-3-yl)propanoic acid (Intermediate 10) (0.812 g, 2.440 mmol) in pyridine (20 mL) kept at −20° C. was slowly added POCl₃ (0.31 mL, 3.33 mmol) and the reaction mixture was allowed to reach 0° C. and stirred for 3 h. The reaction was quenched with saturated solution of KH₂PO₄ (50 mL) and extracted with EtOAc (2×200 mL). The organic layer was washed with brine (200 mL), dried (Na₂SO₄), filtered and concentrated under reduced pressure. The residue was purified by 24 g SiO₂ column using a gradient elution of 0-30% EtOAc in hexanes. Fractions containing product were combined and the solvents were removed in vacuo to provide the product (1.01 g, 72%) as an off-white solid. LC MS: M+H=653.

Step 2. (2S,3S)—N-(2-((S)-3-Amino-4-hydroxybutyl)-3-fluorophenyl)-3-(6-methoxypyridin-3-yl)propanamide

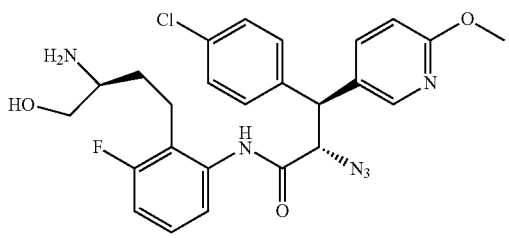 [SMILES: COc1ccc([C@H](c2ccc(Cl)cc2)[C@H](N=[N+]=[N-])C(=O)Nc2cccc(F)c2CC[C@H](N)CO)cn1]

To a stirred solution of (S)-tert-butyl 4-(2-(3-((2S,3S)-2-azido-3-(4-chlorophenyl)-3-(6-methoxypyridin-3-yl)propanamido)-6-fluorophenyl)-2,2-dimethyloxazolidine-3-carboxylate (1.01 g, 1.546 mmol) in dichloromethane (10 mL) was added trifluoroacetic acid (15 mL) and water (4 mL) and the reaction mixture was stirred at room temperature for 16 h. Concentrated the solvents and the residue was diluted with EtOAc (250 mL) and saturated solution of NaHCO₃ (100 mL) and the biphasic solution was stirred for 10 min. The organic layer was washed with brine (100 mL), dried (Na₂SO₄), filtered and concentrated under reduced pressure to provide the product (0.75 g, crude) as a pale yellow solid. LC MS: M+H=513

Step 3. (2S,3S)-2-Azido-3-(4-chlorophenyl)-N-(3-fluoro-2-(2-((S)-1-(phenylsulfonyl)aziridin-2-yl)ethyl)phenyl)-3-(6-methoxypyridin-3-yl)propanamide

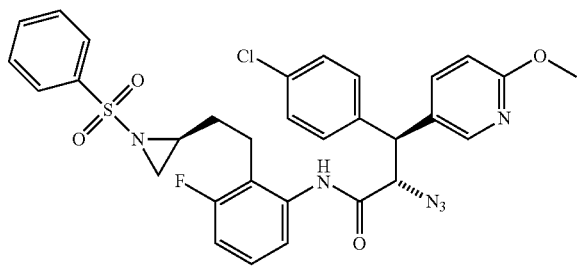 [SMILES: COc1ccc([C@H](c2ccc(Cl)cc2)[C@H](N=[N+]=[N-])C(=O)Nc2cccc(F)c2CC[C@H]2CN2S(=O)(=O)c2ccccc2)cn1]

To a stirred solution of (2S,3S)—N-(2-((S)-3-amino-4-hydroxybutyl)-3-fluorophenyl)-3-(6-methoxypyridin-3-yl)propanamide (0.75 g, 1.464 mmol) in dichloromethane kept at −20° C. was added triethylamine (1.4 mL, 7.324 mmol), DMAP (16.4 mg, 0.146 mmol) and benzene sulfonyl chloride (0.22 mL, 1.757 mmol) and the reaction mixture was stirred for 1.5 h at −20° C. This was followed by the addition of methane sulfonyl chloride (0.13 mL, 0.757 mmol) and the reaction mixture was stirred for 30 min., while allowing the temperature to rise to 0° C. The reaction was quenched with a saturated solution of NaHCO₃ (10 mL) and stirred for additional 30 min. The reaction was diluted with water (30 mL) and extracted with CH₂Cl₂ (2×50 mL). The combined organic extracts were washed with brine (50 mL), dried (Na₂SO₄), filtered and concentrated under reduced pressure. The residue was purified by 24 g SiO₂ column using a gradient elution of 0-35% EtOAc in hexanes. Fractions containing product were combined and the solvents were removed in vacuo to provide the product (0.59 g, 63%) as an off-white solid. LC MS: M+H=635.

Step 4. (2S,3S)-2-Azido-3-(4-chlorophenyl)-N-(3-fluoro-2-((S)-4-(((1-hydroxymethyl)cyclopropyl)methyl)amino)-3-(phenylsulfonamido)butyl)phenyl)-3-(6-methoxypyridin-3-yl)propanamide

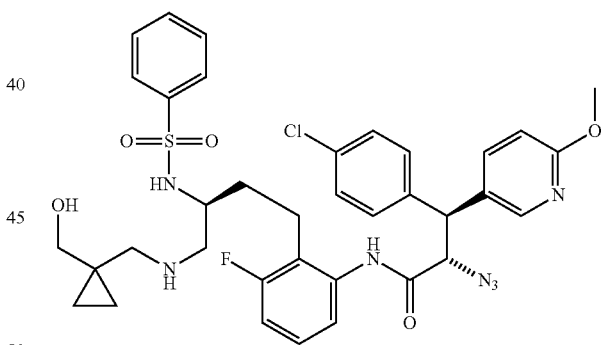

To a stirred solution of (2S,3S)-2-azido-3-(4-chlorophenyl)-N-(3-fluoro-2-(2-((S)-1-(phenylsulfonyl)aziridin-2-yl)ethyl)phenyl)-3-(6-methoxypyridin-3-yl)propanamide (0.200 g, 0.314 mmol) in 1,2-dichloroethane (8 mL) was added (1-(aminomethyl)cyclopropyl)methanol (0.222 g, 2.204 mmol) and the solution was heated to 60° C. for 16 h. The reaction mixture was cooled to room temperature and diluted with water (50 mL) and extracted with EtOAc (100 mL). The organic layer was washed with water (50 mL), brine (50 mL), dried (Na₂SO₄), filtered and concentrated under reduced pressure. The yellow gum (0.192 g, crude) obtained was taken forward to the next step without purification. LC MS: M+H=736.

Step 5. tert-Butyl((S)-4-(2-((2S, S)-2-azido-3-(4-chlorophenyl)-3-(6-methoxypyridin-3-yl)propanamido)-6-fluorophenyl)-2-(phenylsulfonamido)butyl)butyl)((1-(hydroxymethyl)cyclopropyl)methyl) carbamate

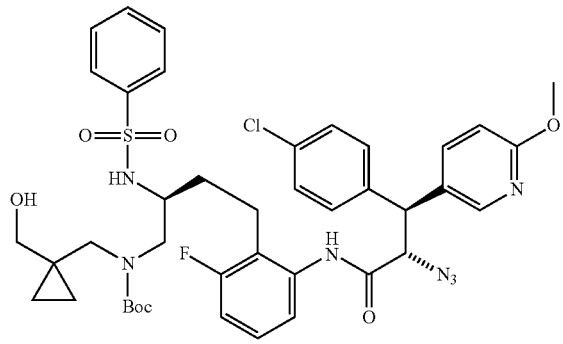 [SMILES: COc1ccc([C@H](c2ccc(Cl)cc2)[C@H](N=[N+]=[N-])C(=O)Nc2cccc(F)c2CC[C@@H](CN(CC2(CO)CC2)C(=O)OC(C)(C)C)NS(=O)(=O)c2ccccc2)cn1]

To a stirred solution of (2S,3S)-2-azido-3-(4-chlorophenyl)-N-(3-fluoro-2-((S)-4-(((1-hydroxymethyl)cyclopropyl)methyl)amino)-3-(phenylsulfonamido)butyl)phenyl)-3-(6-methoxypyridin-3-yl)propanamide (0.19 g, 0.258 mmol) in dichloromethane (10 mL) was added di-tert-butyl dicarbonate (0.11 mL, 0.516 mmol) and triethylamine (0.07 mL, 0.516 mmol) and the reaction mixture was stirred for 16 h at room temperature. The reaction mixture was diluted with water (50 mL) and EtOAc (100 mL) the layers were separated. The organic layer was washed with brine (50 mL), dried (Na$_2$SO$_4$), filtered and concentrated under reduced pressure. The colorless gum (0.205 g, crude) obtained was taken forward to the next step without purification. LC MS: M+H=836.

Step 6. (S)-tert-Butyl 7-(2-((2S,3S)-2-azido-3-(4-chlorophenyl)-3-(6-methoxypyridin-3-yl)propanamido)-6-fluorophenethyl)-8-(phenylsulfonyl)-5,8-diazaspiro[2.6]nonane-5-carboxylate

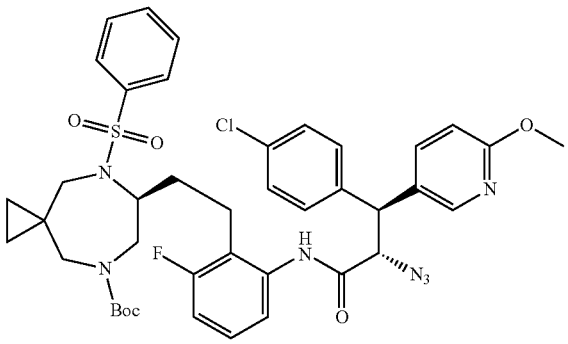 [SMILES: COc1ccc([C@H](c2ccc(Cl)cc2)[C@H](N=[N+]=[N-])C(=O)Nc2cccc(F)c2CC[C@H]2CN(C(=O)OC(C)(C)C)CC3(CC3)CN2S(=O)(=O)c2ccccc2)cn1]

To a stirred solution of tert-butyl((S)-4-(2-((2S,S)-2-azido-3-(4-chlorophenyl)-3-(6-methoxypyridin-3-yl)propanamido)-6-fluorophenyl)-2-(phenylsulfonamido)butyl)butyl)((1-(hydroxymethyl)cyclopropyl)methyl)carbamate (0.205 g, 0.245 mmol) in dry THF was added DIAD (0.14 g, 0.735 mmol) and triphenyl phosphine (0.192 g, 0.735 mmol) and the reaction mixture was stirred for 20 min at room temperature. Added silica-gel and concentrated under reduced pressure. The product was purified by 12 g SiO$_2$ column using a gradient elution of 0-80% EtOAc in hexanes. Fractions containing product were combined and the solvents were removed in vacuo to provide the product (0.185 g, 72% over 3 steps) as a white solid. LC MS: M+H=818

Step 7. (S)-tert-Butyl 7-(2-((2S,3S)-2-amino-3-(4-chlorophenyl)-3-(6-methoxypyridin-3-yl)propanamido)-6-fluorophenethyl)-8-(phenylsulfonyl)-5,8-diazaspiro[2.6]nonane-5-carboxylate

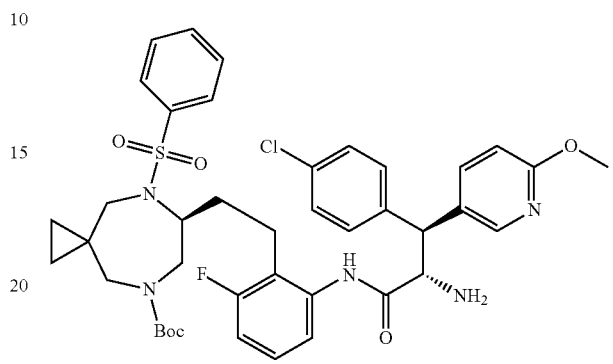

To a stirred solution (S)-tert-butyl 7-(2-((2S,3S)-2-azido-3-(4-chlorophenyl)-3-(6-methoxypyridin-3-yl)propanamido)-6-fluorophenethyl)-8-(phenylsulfonyl)-5,8-diazaspiro[2.6]nonane-5-carboxylate (0.185 g, 0.226 mmol) in a mixture of EtOAc (20 mL) and water (5 mL) was added trimethyl phosphine (0.34 mL, 0.339 mmol, 1M solution in THF) and the reaction mixture was stirred at room temperature for 16 h. The reaction mixture was diluted with water (50 mL) and EtOAc (75 mL) the layers were separated. The organic layer was washed with brine (30 mL), dried (Na$_2$SO$_4$), filtered and concentrated under reduced pressure. The residue was purified by 12 g SiO$_2$ column using a gradient elution of 0-100% EtOAc in hexanes. Fractions containing product were combined and the solvents were removed in vacuo to provide the product (0.102 g, 57%) as a white solid. LC MS: M+H=792.

Step 8. (S)-tert-Butyl 7-(2-((2S,3S)-3-(4-chlorophenyl)-2-((methoxycarbonyl)amino)-3-(6-methoxypyridin-3-yl)propanamido)-6-fluorophenethyl)-8-(phenylsulfonyl)-5,8-diazaspiro[2.6]nonane-5-carboxylate

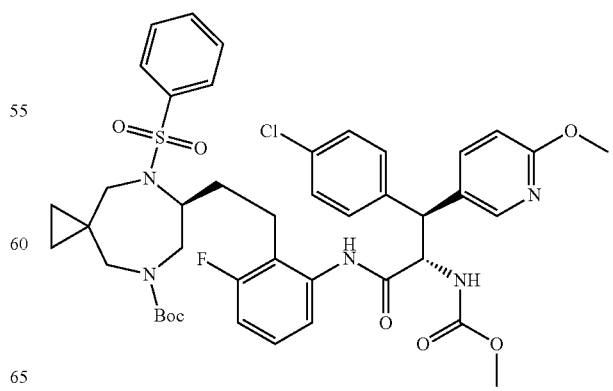

To a stirred solution of (S)-tert-butyl 7-(2-((2S,3S)-2-amino-3-(4-chlorophenyl)-3-(6-methoxypyridin-3-yl)propanamido)-6-fluorophenethyl)-8-(phenylsulfonyl)-5,8-diazaspiro[2.6]nonane-5-carboxylate (60 mg, 0.075 mmol) in dichloromethane (10 mL) kept at 0° C. was added diisopropylethylamine (0.013 ml, 0.078 mmol) and methylchloroformate (0.005 mL, 0.0587 mmol) and the reaction mixture was stirred for 30 min. Diluted the reaction mixture with water (50 mL) and EtOAc (50 mL) the layers were separated and the organic layer was washed with brine (30 mL), dried (Na$_2$SO$_4$), filtered and concentrated under reduced pressure. The residue was purified by 12 g SiO$_2$ column using a gradient elution of 0-80% EtOAc in hexanes. Fractions containing product were combined and the solvents were removed in vacuo to provide the product (51 mg, 79%) as a white solid. LC MS: M+H=850.

Step 9. Methyl ((1S,2S)-1-(4-chlorophenyl)-3-((3-fluoro-2-(2-((S)-5-phenylsulfonyl)-5,8-diazaspiro[2.6]nonan-6-yl)ethyl)phenyl0amino)-1-(6-methoxypyridin-3-yl)-3-oxopropan-2-yl)carbamate 2,2,2-trifluoroacetate To a stirred solution of (S)-tert-butyl 7-(2-((2S,3S)-3-(4-chlorophenyl)-2-((methoxycarbonyl)amino)-3-(6-methoxypyridin-3-yl)propanamido)-6-fluorophenethyl)-8-(phenylsulfonyl)-5,8-diazaspiro[2.6]nonane-5-carboxylate (50 mg, 0.058 mmol) in dichloromethane (1 mL) was added trifluoroacetic acid (0.2 mL) and the reaction mixture was stirred at room temperature for 2 h. Concentrated the reaction mixture and the residue was purified by trituration with diethyl ether and n-hexanes. The solid obtained was lyophilized to provide the product (31 mg, 49%) as an off-white solid.

EXAMPLE 20

Methyl ((2S,3R)-1-((3-fluoro-2-(2-((S)-5-(phenylsulfonyl)-5,8-diazaspiro[2.6]nonan-6-yl)ethyl)phenyl)amino)-3-(4-fluorophenyl)-1-oxo-3-(tetrahydro-2H-pyran-4-yl)propan-2-yl)carbamate

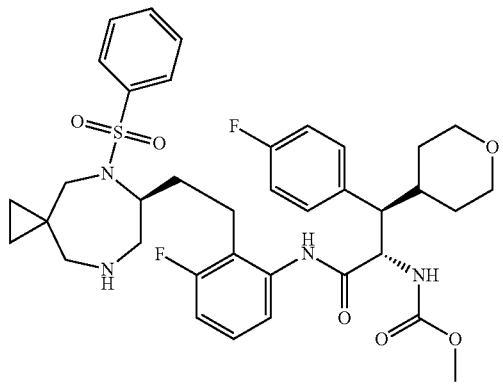 [SMILES: COC(=O)N[C@H](C(=O)Nc1cccc(F)c1CC[C@H]1CNCC2(CC2)CN1S(=O)(=O)c1ccccc1)[C@@H](c1ccc(F)cc1)C1CCOCC1]

Step 1. (2S,3R)-2-azido-N-(3-fluoro-2-((S)-4-(((1-(hydroxymethyl)cyclopropyl)methyl)amino)-3-(phenylsulfonamido)butyl)phenyl)-3-(4-fluorophenyl)-3-(tetrahydro-2H-pyran-4-yl)propanamide

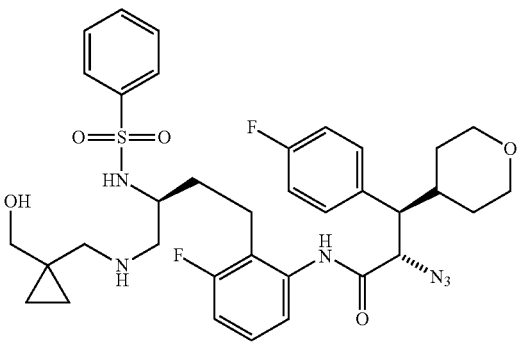 [SMILES: [N-]=[N+]=N[C@H](C(=O)Nc1cccc(F)c1CC[C@@H](CNCC1(CO)CC1)NS(=O)(=O)c1ccccc1)[C@@H](c1ccc(F)cc1)C1CCOCC1]

To a stirred solution of (2S,3R)-2-Azido-N-(3-fluoro-2-(2-((S)-1-(phenylsulfonyl)aziridin-2-yl)ethyl)phenyl)-3-(4-fluorophenyl)-3-(tetrahydro-2H-pyran-4-yl)propanamide (Step 3, Example 7) (0.25 g, 0.35 mmol) in 1,2-dichloroethane (4 mL) was added (1-(aminomethyl)cyclopropyl)methanol (2.47 g, 2.204 mmol) and the solution was heated to 60° C. for 16 h. The reaction mixture was cooled to room temperature and diluted with water (50 mL) and extracted with EtOAc (100 mL). The organic layer was washed with water (50 mL), brine (50 mL), dried (Na$_2$SO$_4$), filtered and concentrated under reduced pressure. The yellow gum (0.30 g, crude) obtained was taken forward to the next step without further purification.

Step 2. tert-Butyl ((S)-4-(2-((2S,3R)-2-azido-3-(4-fluorophenyl)-3-(tetrahydro-2H-pyran-4-yl)propanamido)-6-fluorophenyl)-2-(phenylsulfonamido)butyl)((1-(hydroxymethyl)cyclopropyl)methyl)carbamate

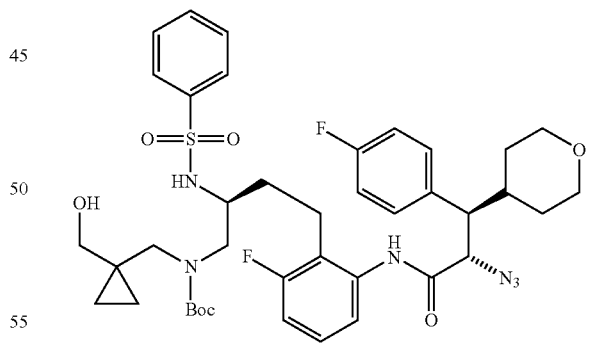

To a stirred solution of (2S,3R)-2-azido-N-(3-fluoro-2-((S)-4-(((1-(hydroxymethyl)cyclopropyl)methyl)amino)-3-(phenylsulfonamido)butyl)phenyl)-3-(4-fluorophenyl)-3-(tetrahydro-2H-pyran-4-yl)propanamide (0.30 g, 0.43 mmol) in dichloromethane (10 mL) was added di-tert-butyl dicarbonate (0.2 mL, 0.86 mmol), triethylamine (0.12 mL, 0.86 mmol) and the reaction mixture was stirred for 16 h at room temperature. The reaction mixture was diluted with water (50 mL) and EtOAc (100 mL) the layers were separated. The organic layer was washed with brine (50 mL), dried (Na$_2$SO$_4$), filtered and concentrated under reduced pressure. The residue was purified by 12 g SiO$_2$ column using a gradient elution of 0-30% EtOAc in hexanes. Fractions containing product were combined and the solvents were removed in vacuo to provide the product (0.33 g, 98%) as a pale yellow solid.

Step 3. (S)-tert-butyl 7-(2-((2S,3R)-2-azido-3-(4-fluorophenyl)-3-(tetrahydro-2H-pyran-4-yl)propanamido)-6-fluorophenethyl)-8-(phenylsulfonyl)-5,8-diazaspiro[2.6]nonane-5-carboxylate

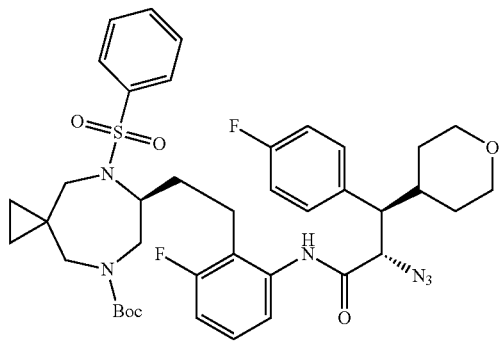 [SMILES: CC(C)(C)OC(=O)N1C[C@H](CCc2c(F)cccc2NC(=O)[C@@H](N=[N+]=[N-])[C@@H](c2ccc(F)cc2)C2CCOCC2)N(S(=O)(=O)c2ccccc2)CC2(CC2)C1]

To a stirred solution of tert-butyl ((S)-4-(2-((2S,3R)-2-azido-3-(4-fluorophenyl)-3-(tetrahydro-2H-pyran-4-yl)propanamido)-6-fluorophenyl)-2-(phenylsulfonamido)butyl)((1-(hydroxymethyl)cyclopropyl)methyl)carbamate (0.33 g, 0.47 mmol) in dry THF was added DIAD (0.289 g, 1.43 mmol) and triphenyl phosphine (0.375 g, 1.43 mmol) and the reaction mixture was stirred for 20 min at room temperature Added silica-gel and concentrated under reduced pressure. The product was purified by 12 g SiO$_2$ column using a gradient elution of 0-80% EtOAc in hexanes. Fractions containing product were combined and the solvents were removed in vacuo to provide the product (0.30 g, 93%) as a white solid.

Step 4. (5)-tert-Butyl 7-(2-((2S,3R)-2-amino-3-(4-fluorophenyl)-3-(tetrahydro-2H-pyran-4-yl)propanamido)-6-fluorophenethyl)-8-(phenylsulfonyl)-5,8-diazaspiro[2.6]nonane-5-carboxylate

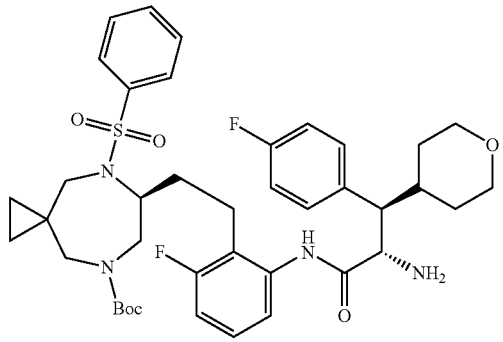 [SMILES: CC(C)(C)OC(=O)N1C[C@H](CCc2c(F)cccc2NC(=O)[C@@H](N)[C@@H](c2ccc(F)cc2)C2CCOCC2)N(S(=O)(=O)c2ccccc2)CC2(CC2)C1]

To a stirred solution (S)-tert-butyl 7-(2-((2S,3R)-2-azido-3-(4-fluorophenyl)-3-(tetrahydro-2H-pyran-4-yl)propanamido)-6-fluorophenethyl)-8-(phenylsulfonyl)-5,8-diazaspiro[2.6]nonane-5-carboxylate (0.30 g, 0.38 mmol) in a mixture of EtOAc (20 mL) and water (5 mL) was added trimethyl phosphine (1.90 mL, 1.92 mmol, 1M solution in THF) and the reaction mixture was stirred at room temperature for 16 h The reaction mixture was diluted with water (50 mL) and EtOAc (75 mL) the layers were separated. The organic layer was washed with brine (30 mL), dried (Na$_2$SO$_4$), filtered and concentrated under reduced pressure. The residue was purified by 12 g SiO$_2$ column using a gradient elution of 0-10% MeOH in DCM. Fractions containing product were combined and the solvents were removed in vacuo to provide the product (0.23 g, 79%) as a white solid.

Step 5. (S)-tert-Butyl 7-(2-fluoro-6-((2S,3R)-3-(4-fluorophenyl)-2-((methoxycarbonyl)amino)-3-(tetrahydro-2H-pyran-4-yl)propanamido)phenethyl)-8-(phenylsulfonyl)-5,8-diazaspiro[2.6]nonane-5-carboxylate

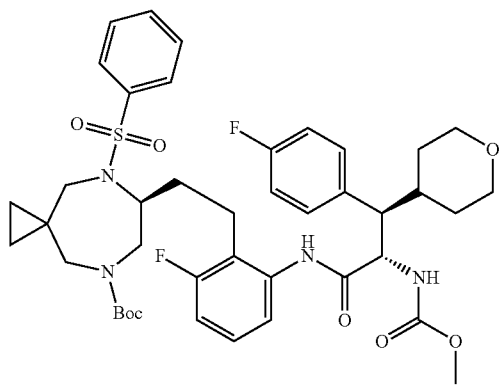 [SMILES: COC(=O)N[C@H](C(=O)Nc1cccc(F)c1CC[C@H]1CN(C(=O)OC(C)(C)C)CC2(CC2)CN1S(=O)(=O)c1ccccc1)[C@@H](c1ccc(F)cc1)C1CCOCC1]

To a stirred solution (S)-tert-butyl 7-(2-((2S,3R)-2-amino-3-(4-fluorophenyl)-3-(tetrahydro-2H-pyran-4-yl)propanamido)-6-fluorophenethyl)-8-(phenylsulfonyl)-5,8-diazaspiro[2.6]nonane-5-carboxylate (75 mg, 0.099 mmol) in dichloromethane (10 m L) kept at 0° C. was added diisopropylethylamine (0.04 ml, 0.199 mmol), and methylchloroformate (0.009 mL, 0.119 mmol) and the reaction mixture was stirred for 30 min. Diluted the reaction mixture with water (50 mL) and EtOAc (50 mL) the layers were separated and the organic layer was washed with brine (30 mL), dried (Na$_2$SO$_4$), filtered and concentrated under reduced pressure. The residue was purified by 12 g SiO$_2$ column using a gradient elution of 0-10% MeOH in DCM. Fractions containing product were combined and the solvents were removed in vacuo to provide the product (55 mg, 68%) as a white solid.

Step 6. Methyl ((2S,3R)-1-((3-fluoro-2-(2-((S)-5-(phenylsulfonyl)-5,8-diazaspiro[2.6]nonan-6-yl)ethyl)phenyl)amino)-3-(4-fluorophenyl)-1-oxo-3-(tetrahydro-2H-pyran-4-yl)propan-2-yl)carbamate To a stirred solution of (S)-tert-butyl 7-(2-fluoro-6-((2S, 3R)-3-(4-fluorophenyl)-2-((methoxycarbonyl)amino)-3-(tetrahydro-2H-pyran-4-yl)propanamido)phenethyl)-8-(phenylsulfonyl)-5,8-diazaspiro[2.6]nonane-5-carboxylate (54 mg, 0.066 mmol) in dichloromethane (1 mL) was added trifluoro acetic acid (0.2 mL) and the reaction mixture was stirred at room temperature for 2 h. Concentrated the solvents and the azeotroped the residue with CH$_3$CN (×3 times) and diluted with CH$_3$CN:H$_2$O (4 mL:1 mL) and lyophilized to provide the product (57 mg, 93%) as an off-white solid. MS: m/z=711 (M+H$^+$).

The Compounds shown in Tables 1 through 4 were made by following procedures analagous to Example 1 to 20.

TABLE 1

| Ex # | Structure | IUPAC Name | Exact Mass [M + H]+ |
|---|---|---|---|
| 21 | 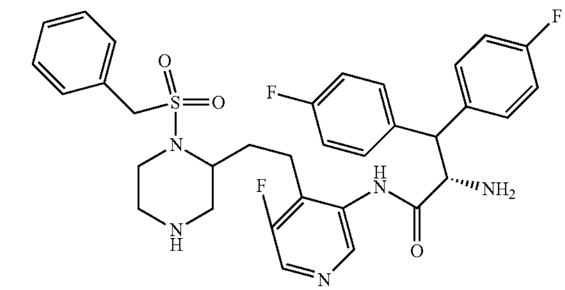 [SMILES: N[C@H](C(=O)Nc1cncc(F)c1CCC1CNCCN1S(=O)(=O)Cc1ccccc1)C(c1ccc(F)cc1)c1ccc(F)cc1] | N-(4-{2-[1-(benzylsulfonyl)piperazin-2-yl]ethyl}-5-fluoropyridin-3-yl)-4-fluoro-β-(4-fluorophenyl)-L-phenylalaninamide | 638.2 |
| 22 | 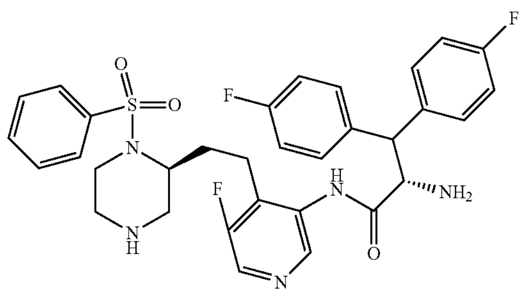 [SMILES: N[C@H](C(=O)Nc1cncc(F)c1CC[C@H]1CNCCN1S(=O)(=O)c1ccccc1)C(c1ccc(F)cc1)c1ccc(F)cc1] | (S)-2-amino-N-(5-fluoro-4-(2-((S)-1-(phenylsulfonyl)piperazin-2-yl)ethyl)pyridin-3-yl)-3,3-bis(4-fluorophenyl)propanamide | 624.2 |
| 23 | 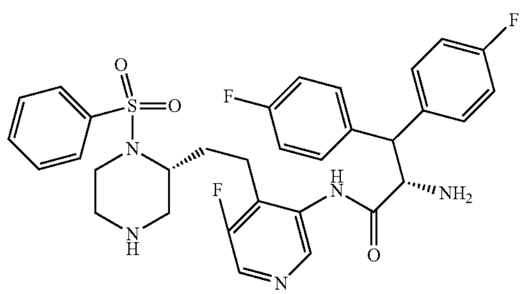 [SMILES: N[C@H](C(=O)Nc1cncc(F)c1CC[C@@H]1CNCCN1S(=O)(=O)c1ccccc1)C(c1ccc(F)cc1)c1ccc(F)cc1] | (S)-2-amino-N-(5-fluoro-4-(2-((R)-1-(phenylsulfonyl)piperazin-2-yl)ethyl)pyridin-3-yl)-3,3-bis(4-fluorophenyl)propanamide | 624.2 |
| 24 | 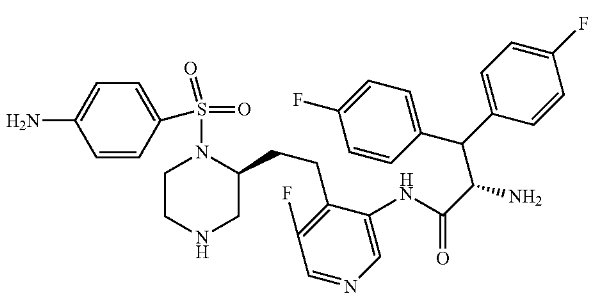 [SMILES: Nc1ccc(S(=O)(=O)N2CCNC[C@@H]2CCc2c(F)cncc2NC(=O)[C@@H](N)C(c2ccc(F)cc2)c2ccc(F)cc2)cc1] | (S)-2-amino-N-(4-(2-((S)-1-((4-aminophenyl)sulfonyl)piperazin-2-yl)ethyl)-5-fluoropyridin-3-yl)-3,3-bis(4-fluorophenyl)propanamide | 639.2 |
| 25 | 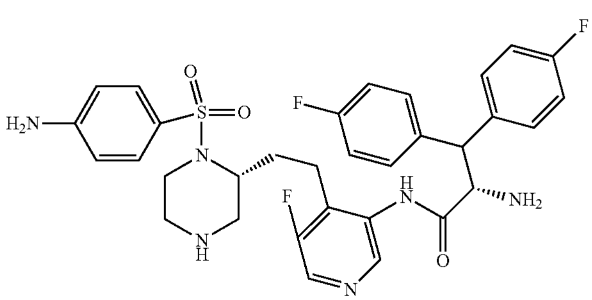 [SMILES: Nc1ccc(S(=O)(=O)N2CCNC[C@H]2CCc2c(F)cncc2NC(=O)[C@@H](N)C(c2ccc(F)cc2)c2ccc(F)cc2)cc1] | (S)-2-amino-N-(4-(2-((R)-1-((4-aminophenyl)sulfonyl)piperazin-2-yl)ethyl)-5-fluoropyridin-3-yl)-3,3-bis(4-fluorophenyl)propanamide | 639.2 |

TABLE 1-continued

| Ex # | Structure | IUPAC Name | Exact Mass [M + H]+ |
|---|---|---|---|
| 26 | 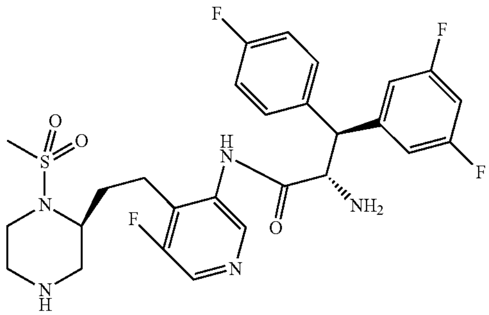 [SMILES: CS(=O)(=O)N1CCNC[C@@H]1CCc1c(F)cncc1NC(=O)[C@@H](N)[C@@H](c1ccc(F)cc1)c1cc(F)cc(F)c1] | (2S,3S)-2-amino-3-(3,5-difluorophenyl)-N-(5-fluoro-4-(2-((S)-1-(methylsulfonyl)piperazin-2-yl)ethyl)pyridin-3-yl)-3-(4-fluorophenyl)propanamide | 580.2 |
| 27 | 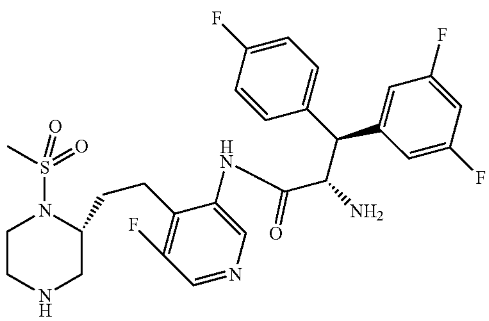 [SMILES: CS(=O)(=O)N1CCNC[C@H]1CCc1c(F)cncc1NC(=O)[C@@H](N)[C@@H](c1ccc(F)cc1)c1cc(F)cc(F)c1] | (2S,3S)-2-amino-3-(3,5-difluorophenyl)-N-(5-fluoro-4-(2-((R)-1-(methylsulfonyl)piperazin-2-yl)ethyl)pyridin-3-yl)-3-(4-fluorophenyl)propanamide | 580.2 |
| 28 | 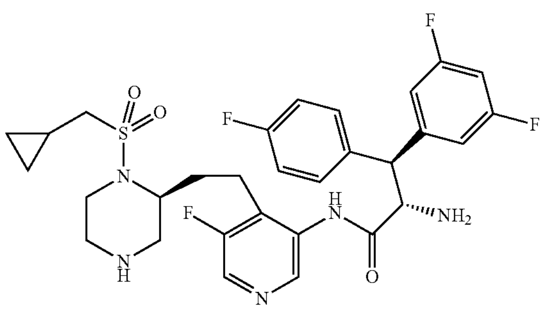 [SMILES: N[C@H](C(=O)Nc1cncc(F)c1CC[C@H]1CNCCN1S(=O)(=O)CC1CC1)[C@@H](c1ccc(F)cc1)c1cc(F)cc(F)c1] | (βS)-N-[4-(2-{(2S)-1-[(cyclopropylmethyl)sulfonyl]piperazin-2-yl}ethyl)-5-fluoropyridin-3-yl]-3,5-difluoro-β-(4-fluorophenyl)-L-phenylalaninamide | 620.2 |
| 29 | 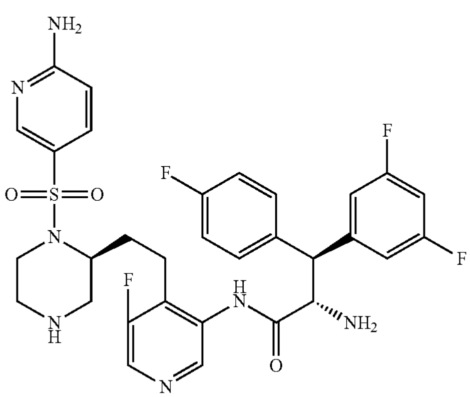 [SMILES: Nc1ccc(S(=O)(=O)N2CCNC[C@@H]2CCc2c(F)cncc2NC(=O)[C@@H](N)[C@@H](c2ccc(F)cc2)c2cc(F)cc(F)c2)cn1] | (βS)-N-[4-(2-{(2S)-1-[(6-aminopyridin-3-yl)sulfonyl]piperazin-2-yl}ethyl)-5-fluoropyridin-3-yl]-3,5-difluoro-β-(4-fluorophenyl)-L-phenylalaninamide | 658.2 |

TABLE 1-continued

| Ex # | Structure | IUPAC Name | Exact Mass [M + H]+ |
|---|---|---|---|
| 30 | 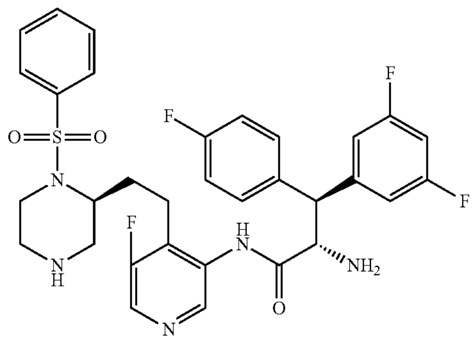 [SMILES: N[C@H](C(=O)Nc1cncc(F)c1CC[C@H]1CNCCN1S(=O)(=O)c1ccccc1)[C@@H](c1ccc(F)cc1)c1cc(F)cc(F)c1] | (βS)-β-(3,5-difluorophenyl)-4-fluoro-N-(5-fluoro-4-{2-[(2S)-1-(phenylsulfonyl)piperazin-2-yl]ethyl}pyridin-3-yl)-L-phenylalaninamide | 642.2 |
| 21 | 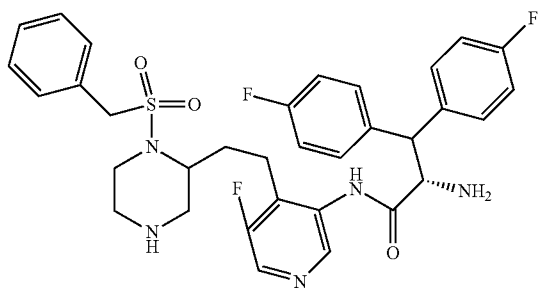 [SMILES: N[C@H](C(=O)Nc1cncc(F)c1CCC1CNCCN1S(=O)(=O)Cc1ccccc1)C(c1ccc(F)cc1)c1ccc(F)cc1] | N-(4-{2-[1-(benzylsulfonyl)piperazin-2-yl]ethyl}-5-fluoropyridin-3-yl)-4-fluoro-β-(4-fluorophenyl)-L-phenylalaninamide | 638.2 |
| 22 | 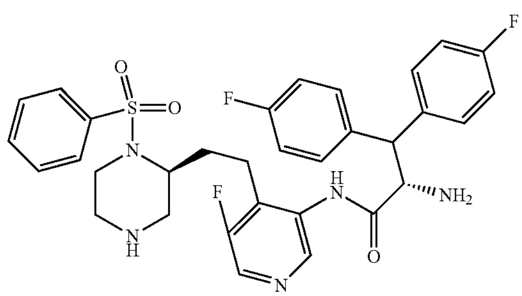 [SMILES: N[C@H](C(=O)Nc1cncc(F)c1CC[C@H]1CNCCN1S(=O)(=O)c1ccccc1)C(c1ccc(F)cc1)c1ccc(F)cc1] | (S)-2-amino-N-(5-fluoro-4-(2-((S)-1-(phenylsulfonyl)piperazin-2-yl)ethyl)pyridin-3-yl)-3,3-bis(4-fluorophenyl)propanamide | 624.2 |
| 23 | 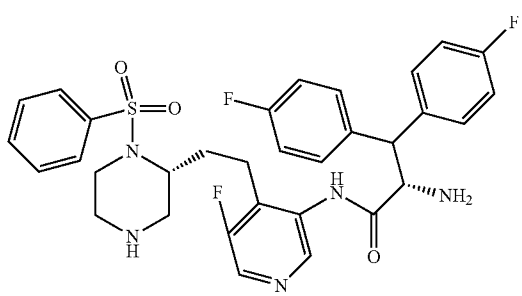 [SMILES: N[C@H](C(=O)Nc1cncc(F)c1CC[C@@H]1CNCCN1S(=O)(=O)c1ccccc1)C(c1ccc(F)cc1)c1ccc(F)cc1] | (S)-2-amino-N-(5-fluoro-4-(2-((R)-1-(phenylsulfonyl)piperazin-2-yl)ethyl)pyridin-3-yl)-3,3-bis(4-fluorophenyl)propanamide | 624.2 |
| 24 | 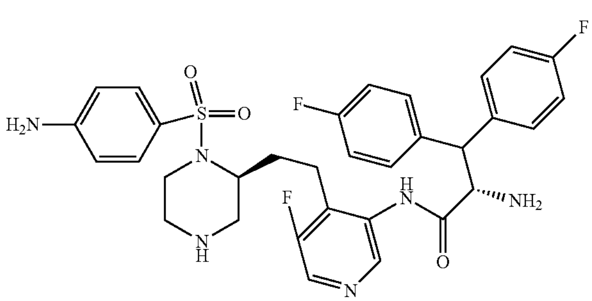 [SMILES: Nc1ccc(S(=O)(=O)N2CCNC[C@@H]2CCc2c(F)cncc2NC(=O)[C@@H](N)C(c2ccc(F)cc2)c2ccc(F)cc2)cc1] | (S)-2-amino-N-(4-(2-((S)-1-((4-aminophenyl)sulfonyl)piperazin-2-yl)ethyl)-5-fluoropyridin-3-yl)-3,3-bis(4-fluorophenyl)propanamide | 639.2 |

TABLE 1-continued

| Ex # | Structure | IUPAC Name | Exact Mass [M + H]+ |
|---|---|---|---|
| 25 | 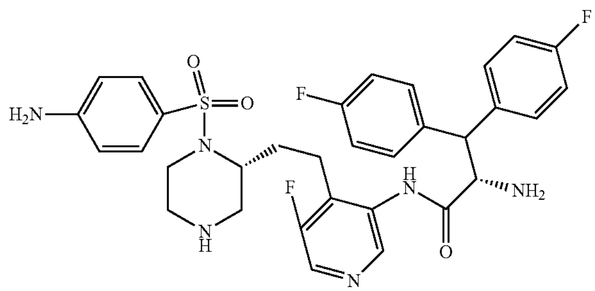 [SMILES: Nc1ccc(S(=O)(=O)N2CCNC[C@H]2CCc2c(F)cncc2NC(=O)[C@@H](N)C(c2ccc(F)cc2)c2ccc(F)cc2)cc1] | (S)-2-amino-N-(4-(2-((R)-1-((4-aminophenyl)sulfonyl)piperazin-2-yl)ethyl)-5-fluoropyridin-3-yl)-3,3-bis(4-fluorophenyl)propanamide | 639.2 |
| 26 | 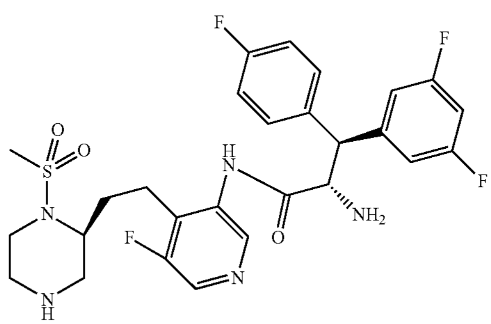 [SMILES: CS(=O)(=O)N1CCNC[C@@H]1CCc1c(F)cncc1NC(=O)[C@@H](N)[C@@H](c1ccc(F)cc1)c1cc(F)cc(F)c1] | (2S,3S)-2-amino-3-(3,5-difluorophenyl)-N-(5-fluoro-4-(2-((S)-1-(methylsulfonyl)piperazin-2-yl)ethyl)pyridin-3-yl)-3-(4-fluorophenyl)propanamide | 580.2 |
| 27 | 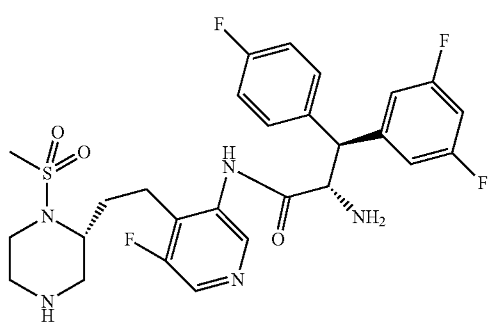 [SMILES: CS(=O)(=O)N1CCNC[C@H]1CCc1c(F)cncc1NC(=O)[C@@H](N)[C@@H](c1ccc(F)cc1)c1cc(F)cc(F)c1] | (2S,3S)-2-amino-3-(3,5-difluorophenyl)-N-(5-fluoro-4-(2-((R)-1-(methylsulfonyl)piperazin-2-yl)ethyl)pyridin-3-yl)-3-(4-fluorophenyl)propanamide | 580.2 |
| 28 | 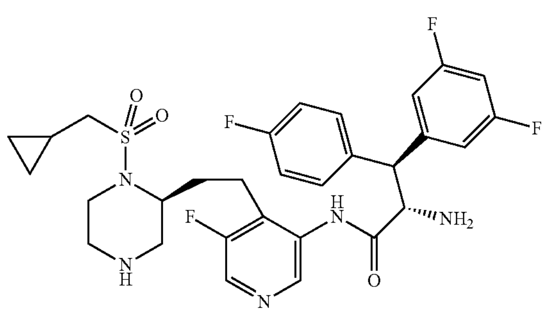 [SMILES: N[C@H](C(=O)Nc1cncc(F)c1CC[C@H]1CNCCN1S(=O)(=O)CC1CC1)[C@@H](c1ccc(F)cc1)c1cc(F)cc(F)c1] | (βS)-N-[4-(2-{(2S)-1-[(cyclopropylmethyl)sulfonyl]piperazin-2-yl}ethyl)-5-fluoropyridin-3-yl]-3,5-difluoro-β-(4-fluorophenyl)-L-phenylalaninamide | 620.2 |

TABLE 1-continued

| Ex # | Structure | IUPAC Name | Exact Mass [M + H]+ |
|---|---|---|---|
| 29 | 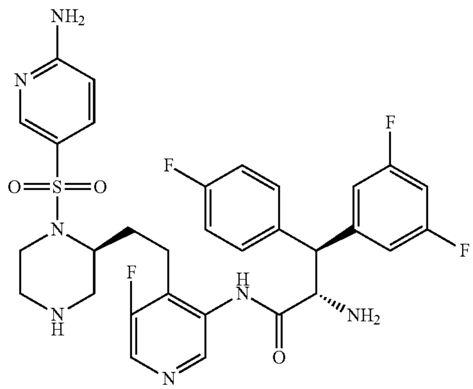 [SMILES: Nc1ccc(S(=O)(=O)N2CCNC[C@@H]2CCc2c(F)cncc2NC(=O)[C@@H](N)[C@@H](c2ccc(F)cc2)c2cc(F)cc(F)c2)cn1] | (βS)-N-[4-(2-{(2S)-1-[(6-aminopyridin-3-yl)sulfonyl]piperazin-2-yl}ethyl)-5-fluoropyridin-3-yl]-3,5-difluoro-β-(4-fluorophenyl)-L-phenylalaninamide | 658.2 |
| 30 | 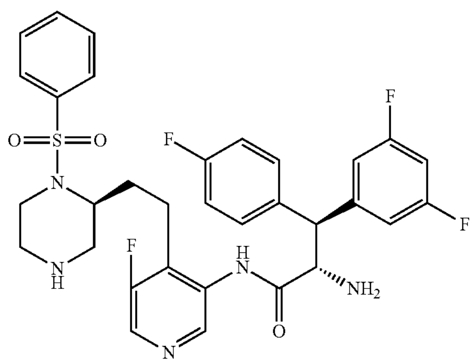 [SMILES: N[C@H](C(=O)Nc1cncc(F)c1CC[C@H]1CNCCN1S(=O)(=O)c1ccccc1)[C@@H](c1ccc(F)cc1)c1cc(F)cc(F)c1] | (βS)-β-(3,5-difluorophenyl)-4-fluoro-N-(5-fluoro-4-{2-[(2S)-1-(phenylsulfonyl)piperazin-2-yl]ethyl}pyridin-3-yl)-L-phenylalaninamide | 642.2 |
| 31 | 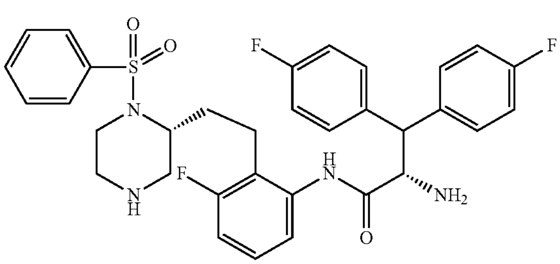 [SMILES: N[C@H](C(=O)Nc1cccc(F)c1CC[C@@H]1CNCCN1S(=O)(=O)c1ccccc1)C(c1ccc(F)cc1)c1ccc(F)cc1] | (S)-2-amino-N-(3-fluoro-2-(2-((R)-1-(phenylsulfonyl)piperazin-2-yl)ethyl)phenyl)-3,3-bis(4-fluorophenyl)propanamide | 623.2 |
| 32 | 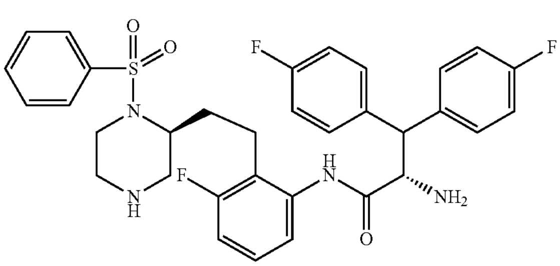 [SMILES: N[C@H](C(=O)Nc1cccc(F)c1CC[C@H]1CNCCN1S(=O)(=O)c1ccccc1)C(c1ccc(F)cc1)c1ccc(F)cc1] | (S)-2-amino-N-(3-fluoro-2-(2-((S)-1-(phenylsulfonyl)piperazin-2-yl)ethyl)phenyl)-3,3-bis(4-fluorophenyl)propanamide | 623.2 |

TABLE 1-continued

| Ex # | Structure | IUPAC Name | Exact Mass [M + H]+ |
|---|---|---|---|
| 33 | 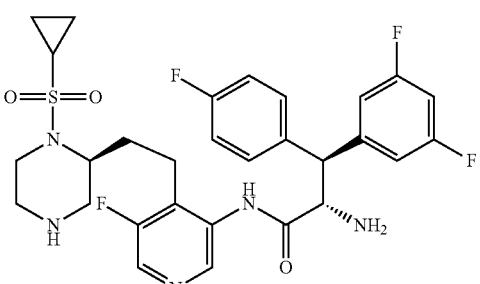 | (βS)-N-(4-{2-[(2S)-1-(cyclopropylsulfonyl)piperazin-2-yl]ethyl}-5-fluoropyridin-3-yl)-3,5-difluoro-β-(4-fluorophenyl)-L-phenylalaninamide | 606.2 |
| 34 | 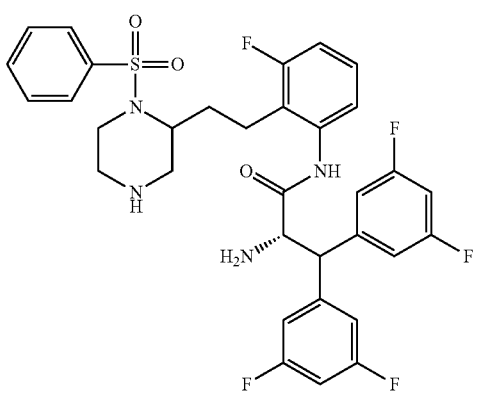 [SMILES: N[C@H](C(=O)Nc1cccc(F)c1CCC1CNCCN1S(=O)(=O)c1ccccc1)C(c1cc(F)cc(F)c1)c1cc(F)cc(F)c1] | β-(3,5-difluorophenyl)-3,5-difluoro-N-(3-fluoro-2-{2-[1-(phenylsulfonyl)piperazin-2-yl]ethyl}phenyl)-L-phenylalaninamide | 659.2 |
| 35 | 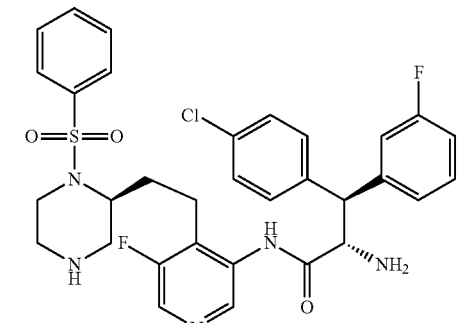 | (βS)-4-chloro-β-(3-fluorophenyl)-N-(5-fluoro-4-{2-[(2S)-1-(phenylsulfonyl)piperazin-2-yl]ethyl}pyridin-3-yl)-L-phenylalaninamide | 640.2 |
| 36 | 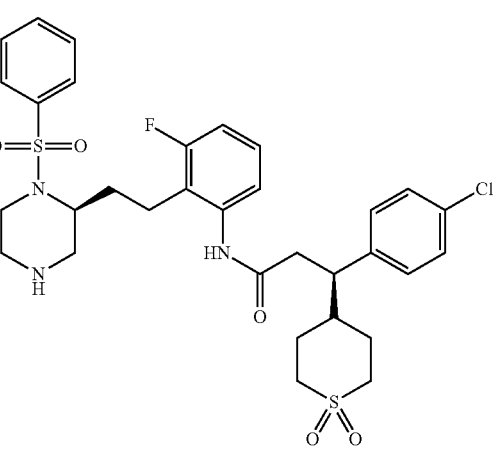 | (3R)-3-(4-chlorophenyl)-3-(1,1-dioxidotetrahydro-2H-thiopyran-4-yl)-N-(3-fluoro-2-{2-[(2S)-1-(phenylsulfonyl)piperazin-2-yl]ethyl}phenyl)propanamide | 662.2 |

TABLE 1-continued

| Ex # | Structure | IUPAC Name | Exact Mass [M + H]+ |
|---|---|---|---|
| 37 | 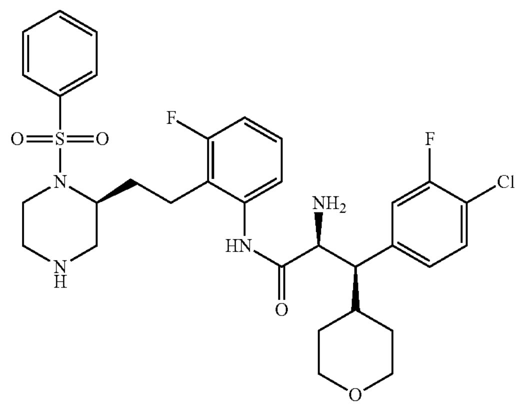 [SMILES: N[C@H](C(=O)Nc1cccc(F)c1CC[C@H]1CNCCN1S(=O)(=O)c1ccccc1)[C@@H](c1ccc(Cl)c(F)c1)C1CCOCC1] | (βR)-4-chloro-3-fluoro-N-(3-fluoro-2-{2-[(2S)-1-(phenylsulfonyl)piperazin-2-yl]ethyl}phenyl)-β-(tetrahydro-2H-pyran-4-yl)-L-phenylalaninamide | 647.2 |
| 38 | 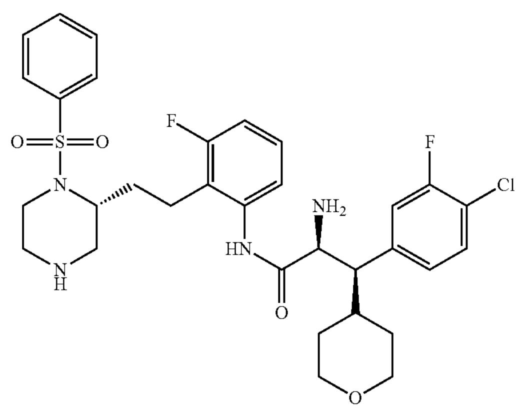 [SMILES: N[C@H](C(=O)Nc1cccc(F)c1CC[C@@H]1CNCCN1S(=O)(=O)c1ccccc1)[C@@H](c1ccc(Cl)c(F)c1)C1CCOCC1] | (βR)-4-chloro-3-fluoro-N-(3-fluoro-2-{2-[(2R)-1-(phenylsulfonyl)piperazin-2-yl]ethyl}phenyl)-β-(tetrahydro-2H-pyran-4-yl)-L-phenylalaninamide | 647.2 |
| 39 | 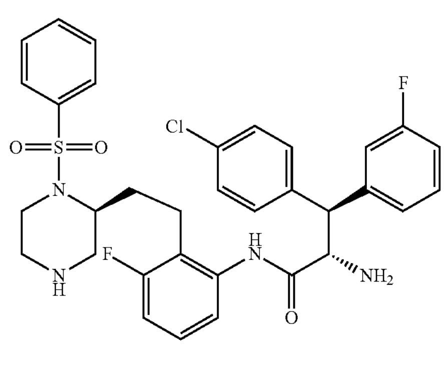 [SMILES: N[C@H](C(=O)Nc1cccc(F)c1CC[C@H]1CNCCN1S(=O)(=O)c1ccccc1)[C@@H](c1ccc(Cl)cc1)c1cccc(F)c1] | (βS)-4-chloro-β-(3-fluorophenyl)-N-(3-fluoro-2-{2-[(2S)-1-(phenylsulfonyl)piperazin-2-yl]ethyl}phenyl)-L-phenylalaninamide | 639.2 |
| 40 | 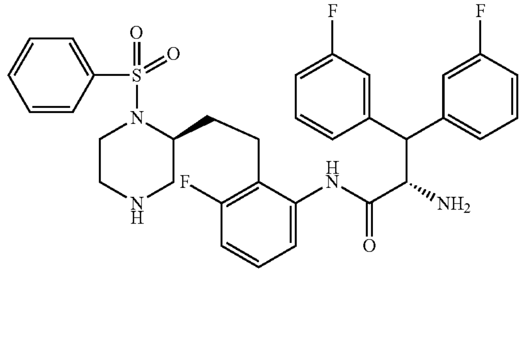 [SMILES: N[C@H](C(=O)Nc1cccc(F)c1CC[C@H]1CNCCN1S(=O)(=O)c1ccccc1)C(c1cccc(F)c1)c1cccc(F)c1] | 3-fluoro-β-(3-fluorophenyl)-N-(3-fluoro-2-{2-[(2S)-1-(phenylsulfonyl)piperazin-2-yl]ethyl}phenyl)-L-phenylalaninamide | 623.2 |

TABLE 1-continued

| Ex # | Structure | IUPAC Name | Exact Mass [M + H]+ |
|---|---|---|---|
| 41 | 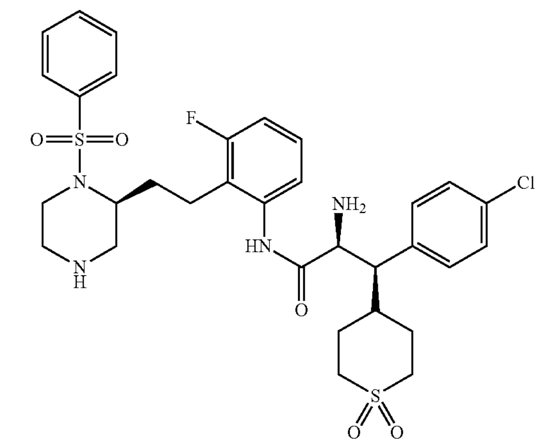 [SMILES: N[C@H](C(=O)Nc1cccc(F)c1CC[C@H]1CNCCN1S(=O)(=O)c1ccccc1)[C@@H](c1ccc(Cl)cc1)C1CCS(=O)(=O)CC1] | (βR)-4-chloro-β-(1,1-dioxidotetrahydro-2H-thiopyran-4-yl)-N-(3-fluoro-2-{2-[(2S)-1-(phenylsulfonyl)piperazin-2-yl]ethyl}phenyl)-L-phenylalaninamide | 677.2 |
| 42 | 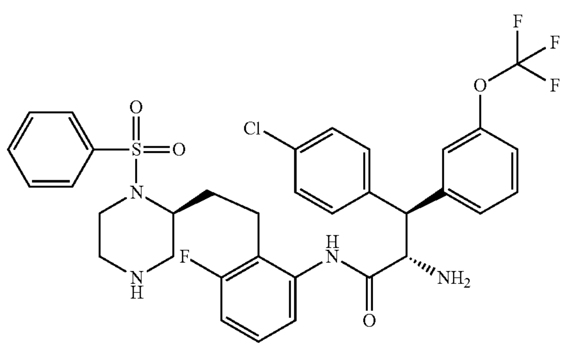 [SMILES: N[C@H](C(=O)Nc1cccc(F)c1CC[C@H]1CNCCN1S(=O)(=O)c1ccccc1)[C@@H](c1ccc(Cl)cc1)c1cccc(OC(F)(F)F)c1] | (βS)-4-chloro-N-(3-fluoro-2-{2-[(2S)-1-(phenylsulfonyl)piperazin-2-yl]ethyl}phenyl)-β-[3-(trifluoromethoxy)phenyl]-L-phenylalaninamide | 705.2 |
| 43 | 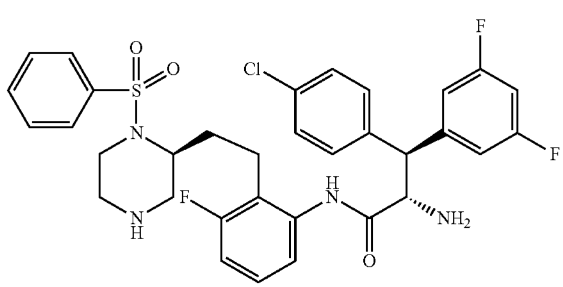 [SMILES: N[C@H](C(=O)Nc1cccc(F)c1CC[C@H]1CNCCN1S(=O)(=O)c1ccccc1)[C@@H](c1ccc(Cl)cc1)c1cc(F)cc(F)c1] | (βS)-4-chloro-β-(3,5-difluorophenyl)-N-(3-fluoro-2-{2-[(2S)-1-(phenylsulfonyl)piperazin-2-yl]ethyl}phenyl)-L-phenylalaninamide | 657.2 |
| 44 | 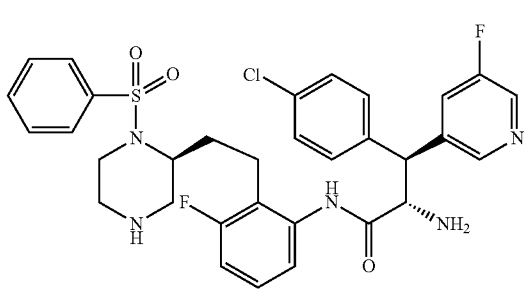 [SMILES: N[C@H](C(=O)Nc1cccc(F)c1CC[C@H]1CNCCN1S(=O)(=O)c1ccccc1)[C@@H](c1ccc(Cl)cc1)c1cncc(F)c1] | (βS)-4-chloro-N-(3-fluoro-2-{2-[(2S)-1-(phenylsulfonyl)piperazin-2-yl]ethyl}phenyl)-β-(5-fluoropyridin-3-yl)-L-phenylalaninamide | 640.2 |

TABLE 1-continued

| Ex # | Structure | IUPAC Name | Exact Mass [M + H]+ |
|---|---|---|---|
| 45 | 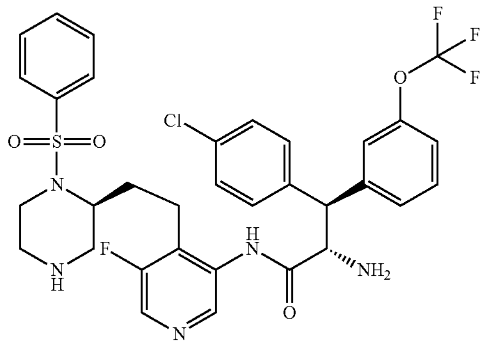 [SMILES: N[C@H](C(=O)Nc1cncc(F)c1CC[C@H]1CNCCN1S(=O)(=O)c1ccccc1)[C@@H](c1ccc(Cl)cc1)c1cccc(OC(F)(F)F)c1] | (βS)-4-chloro-N-(5-fluoro-4-{2-[(2S)-1-(phenylsulfonyl)piperazin-2-yl]ethyl}pyridin-3-yl)-β-[3-(trifluoromethoxy)phenyl]-L-phenylalaninamide | 706.2 |
| 46 | 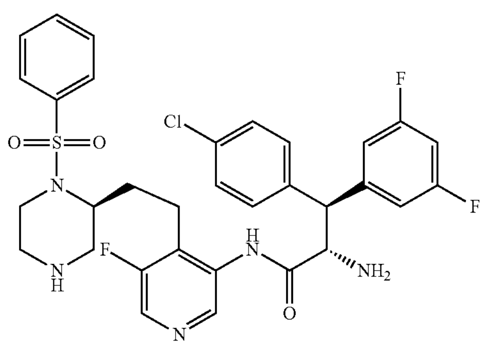 [SMILES: N[C@H](C(=O)Nc1cncc(F)c1CC[C@H]1CNCCN1S(=O)(=O)c1ccccc1)[C@@H](c1ccc(Cl)cc1)c1cc(F)cc(F)c1] | (βS)-4-chloro-β-(3,5-difluorophenyl)-N-(5-fluoro-4-{2-[(2S)-1-(phenylsulfonyl)piperazin-2-yl]ethyl}pyridin-3-yl)-L-phenylalaninamide | 658.2 |
| 47 | 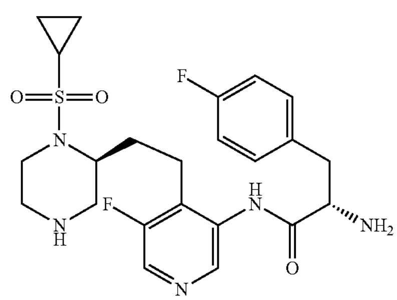 [SMILES: N[C@@H](Cc1ccc(F)cc1)C(=O)Nc1cncc(F)c1CC[C@H]1CNCCN1S(=O)(=O)C1CC1] | N-(4-{2-[(2S)-1-(cyclopropylsulfonyl)piperazin-2-yl]ethyl}-5-fluoropyridin-3-yl)-4-fluoro-L-phenylalaninamide | 494.2 |
| 48 | 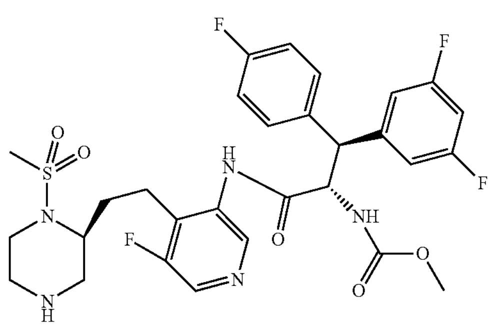 [SMILES: COC(=O)N[C@H](C(=O)Nc1cncc(F)c1CC[C@H]1CNCCN1S(C)(=O)=O)[C@@H](c1ccc(F)cc1)c1cc(F)cc(F)c1] | methyl ((1S,2S)-1-(3,5-difluorophenyl)-3-((5-fluoro-4-(2-((S)-1-(methylsulfonyl)piperazin-2-yl)ethyl)pyridin-3-yl)amino)-1-(4-fluorophenyl)-3-oxopropan-2-yl)carbamate | 638.2 |

TABLE 1-continued

| Ex # | Structure | IUPAC Name | Exact Mass [M + H]+ |
|---|---|---|---|
| 49 | 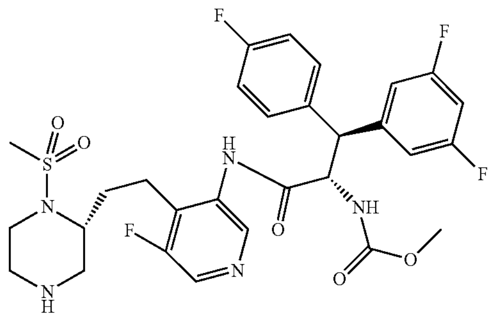 [SMILES: COC(=O)N[C@H](C(=O)Nc1cncc(F)c1CC[C@@H]1CNCCN1S(C)(=O)=O)[C@@H](c1ccc(F)cc1)c1cc(F)cc(F)c1] | methyl ((1S,2S)-1-(3,5-difluorophenyl)-3-((5-fluoro-4-(2-((R)-1-(methylsulfonyl)piperazin-2-yl)ethyl)pyridin-3-yl)amino)-1-(4-fluorophenyl)-3-oxopropan-2-yl)carbamate | 638.2 |
| 50 | 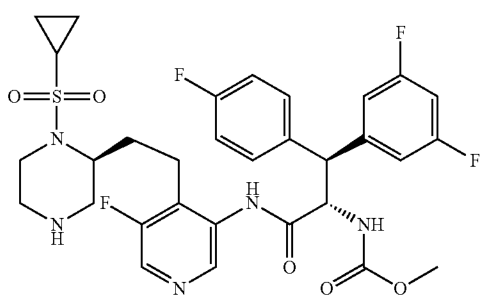 [SMILES: COC(=O)N[C@H](C(=O)Nc1cncc(F)c1CC[C@H]1CNCCN1S(=O)(=O)C1CC1)[C@@H](c1ccc(F)cc1)c1cc(F)cc(F)c1] | (βS)-N-(4-{2-[(2S)-1-(cyclopropylsulfonyl)piperazin-2-yl]ethyl}-5-fluoropyridin-3-yl)-3,5-difluoro-β-(4-fluorophenyl)-Nα-(methoxycarbonyl)-L-phenylalaninamide | 664.2 |
| 51 | 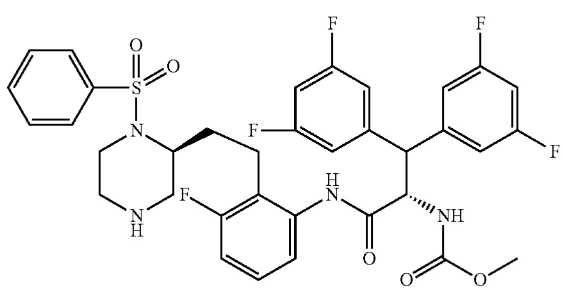 [SMILES: COC(=O)N[C@H](C(=O)Nc1cccc(F)c1CC[C@H]1CNCCN1S(=O)(=O)c1ccccc1)C(c1cc(F)cc(F)c1)c1cc(F)cc(F)c1] | β-(3,5-difluorophenyl)-3,5-difluoro-N-(3-fluoro-2-{2-[(2S)-1-(phenylsulfonyl)piperazin-2yl]ethyl}phenyl)-Nα-(methoxycarbonyl)-L-phenylalaninamide | 717.2 |
| 52 | 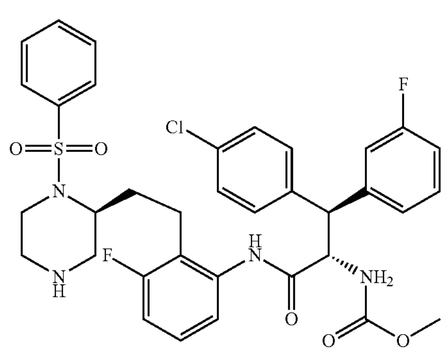 [SMILES: COC(=O)N[C@H](C(=O)Nc1cccc(F)c1CC[C@H]1CNCCN1S(=O)(=O)c1ccccc1)[C@@H](c1ccc(Cl)cc1)c1cccc(F)c1] | (βS)-4-chloro-β-(3-fluorophenyl)-N-(3-fluoro-2-{2-[(2S)-1-(phenylsulfonyl)piperazin-2-yl]ethyl}phenyl)-Nα-(methoxycarbonyl)-L-phenylalaninamide | 697.2 |

TABLE 1-continued

| Ex # | Structure | IUPAC Name | Exact Mass [M + H]+ |
|---|---|---|---|
| 53 | 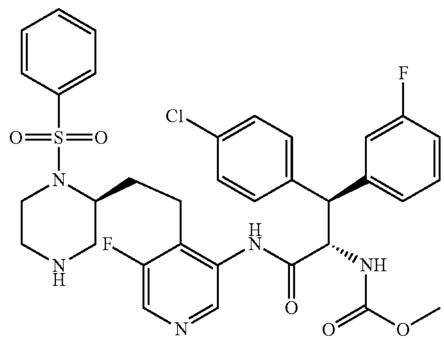 [SMILES: COC(=O)N[C@H](C(=O)Nc1cncc(F)c1CC[C@H]1CNCCN1S(=O)(=O)c1ccccc1)[C@@H](c1ccc(Cl)cc1)c1cccc(F)c1] | (βS)-4-chloro-β-(3-fluorophenyl)-N-(5-fluoro-4-{2-[(2S)-1-(phenylsulfonyl)piperazin-2-yl]ethyl}pyridin-3-yl)-Nα-(methoxycarbonyl)-L-phenylalaninamide | 698.2 |
| 54 | 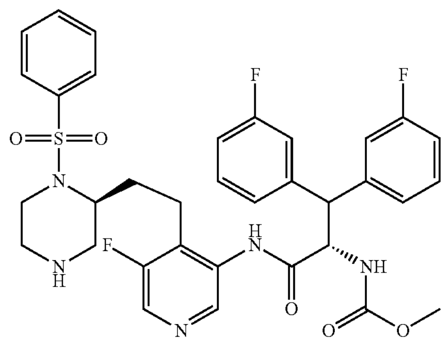 [SMILES: COC(=O)N[C@H](C(=O)Nc1cncc(F)c1CC[C@H]1CNCCN1S(=O)(=O)c1ccccc1)C(c1cccc(F)c1)c1cccc(F)c1] | 3-fluoro-β-(3-fluorophenyl)-N-(5-fluoro-4-{2-[(2S)-1-(phenylsulfonyl)piperazin-2-yl]ethyl}pyridin-3-yl)-Nα-(methoxycarbonyl)-L-phenylalaninamide | 682.2 |
| 55 | 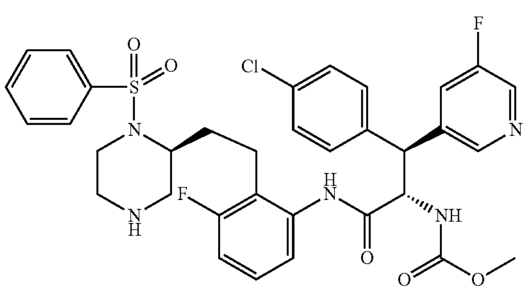 [SMILES: COC(=O)N[C@H](C(=O)Nc1cccc(F)c1CC[C@H]1CNCCN1S(=O)(=O)c1ccccc1)[C@@H](c1ccc(Cl)cc1)c1cncc(F)c1] | (βS)-4-chloro-N-(3-fluoro-2-{2-[(2S)-1-(phenylsulfonyl)piperazin-2-yl]ethyl}phenyl)-β-(5-fluoropyridin-3-yl)-Nα-(methoxycarbonyl)-L-phenylalaninamide | 698.2 |
| 56 | 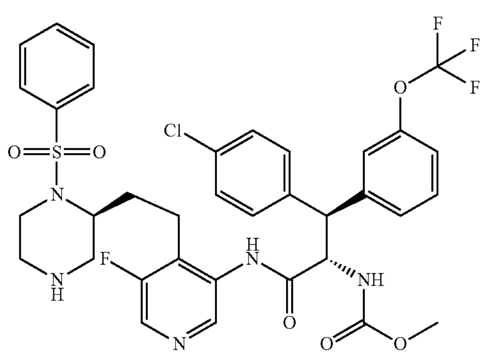 [SMILES: COC(=O)N[C@H](C(=O)Nc1cncc(F)c1CC[C@H]1CNCCN1S(=O)(=O)c1ccccc1)[C@@H](c1ccc(Cl)cc1)c1cccc(OC(F)(F)F)c1] | (βS)-4-chloro-N-(5-fluoro-4-{2-[(2S)-1-(phenylsulfonyl)piperazin-2-yl]ethyl}pyridin-3-yl)-Nα-(methoxycarbonyl)-β-[3-(trifluoromethoxy)phenyl]-L-phenylalaninamide | 764.2 |

TABLE 1-continued

| Ex # | Structure | IUPAC Name | Exact Mass [M + H]+ |
|---|---|---|---|
| 57 | 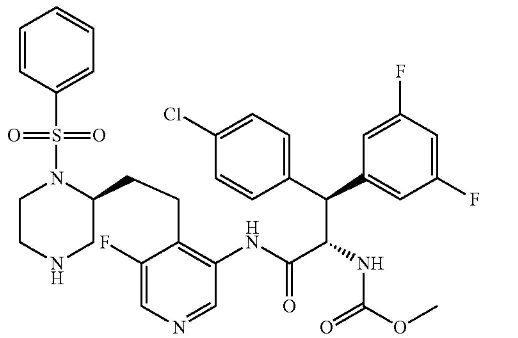 [SMILES: COC(=O)N[C@H](C(=O)Nc1cncc(F)c1CC[C@H]1CNCCN1S(=O)(=O)c1ccccc1)[C@@H](c1ccc(Cl)cc1)c1cc(F)cc(F)c1] | (βS)-4-chloro-β-(3,5-difluorophenyl)-N-(5-fluoro-4-{2-[(2S)-1-(phenylsulfonyl)piperazin-2-yl]ethyl}pyridin-3-yl)-Nα-(methoxycarbonyl)-L-phenylalaninamide | 716.2 |
| 58 | 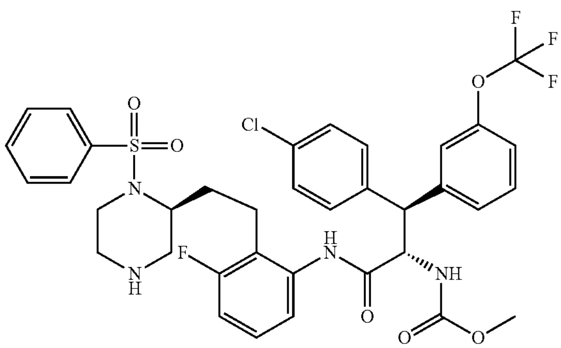 [SMILES: COC(=O)N[C@H](C(=O)Nc1cccc(F)c1CC[C@H]1CNCCN1S(=O)(=O)c1ccccc1)[C@@H](c1ccc(Cl)cc1)c1cccc(OC(F)(F)F)c1] | (βS)-4-chloro-N-(3-fluoro-2-{2-[(2S)-1-(phenylsulfonyl)piperazin-2-yl]ethyl}phenyl)-Nα-(methoxycarbonyl)-β-[3-(trifluoromethoxy)phenyl]-L-phenylalaninamide | 763.2 |
| 59 | 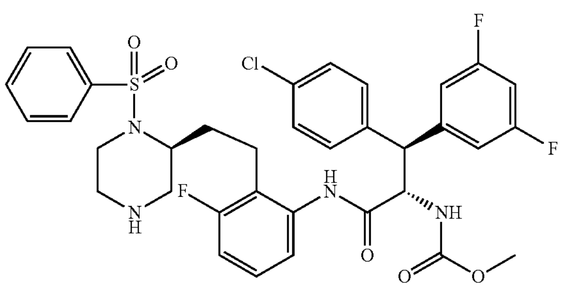 [SMILES: COC(=O)N[C@H](C(=O)Nc1cccc(F)c1CC[C@H]1CNCCN1S(=O)(=O)c1ccccc1)[C@@H](c1ccc(Cl)cc1)c1cc(F)cc(F)c1] | (βS)-4-chloro-β-(3,5-difluorophenyl)-N-(3-fluoro-2-{2-[(2S)-1-(phenylsulfonyl)piperazin-2-yl]ethyl}phenyl)-Nα-(methoxycarbonyl)-L-phenylalaninamide | 715.2 |
| 60 | 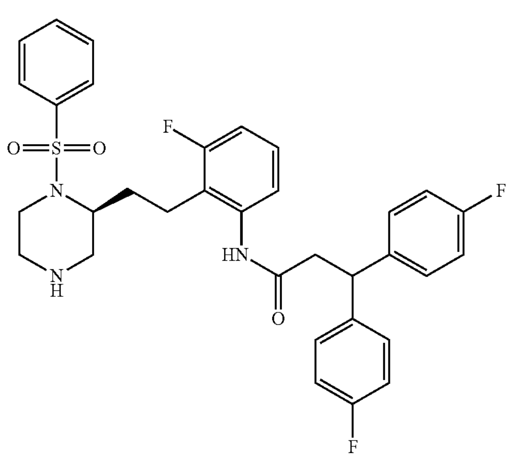 [SMILES: O=C(CC(c1ccc(F)cc1)c1ccc(F)cc1)Nc1cccc(F)c1CC[C@H]1CNCCN1S(=O)(=O)c1ccccc1] | 3,3-bis(4-fluorophenyl)-N-(3-fluoro-2-{2-[(2S)-1-(phenylsulfonyl)piperazin-2-yl]ethyl}phenyl)propanamide | 608.2 |

TABLE 1-continued

| Ex # | Structure | IUPAC Name | Exact Mass [M + H]+ |
|---|---|---|---|
| 61 | 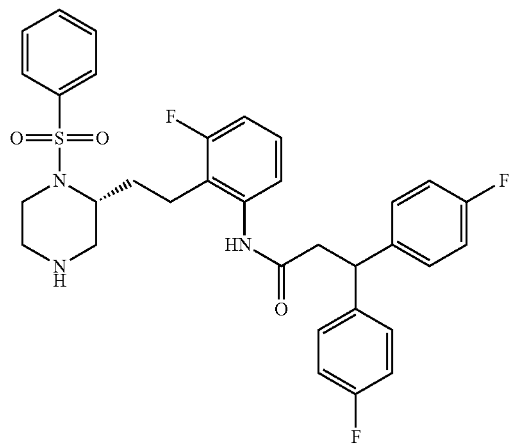 [SMILES: O=C(CC(c1ccc(F)cc1)c1ccc(F)cc1)Nc1cccc(F)c1CC[C@@H]1CNCCN1S(=O)(=O)c1ccccc1] | 3,3-bis(4-fluorophenyl)-N-(3-fluoro-2-{2-[(2R)-1-(phenylsulfonyl)piperazin-2-yl]ethyl}phenyl)propanamide | 608.2 |
| 62 | 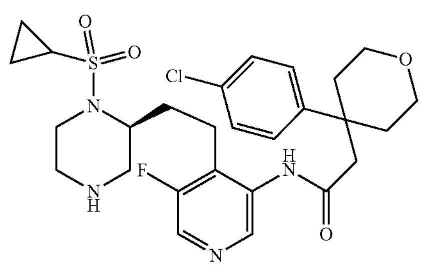 [SMILES: O=C(CC1(c2ccc(Cl)cc2)CCOCC1)Nc1cncc(F)c1CC[C@H]1CNCCN1S(=O)(=O)C1CC1] | 2-[4-(4-chlorophenyl)tetrahydro-2H-pyran-4-yl]-N-(4-{2-[(2S)-1-(cyclopropylsulfonyl)piperazin-2-yl]ethyl}-5-fluoropyridin-3-yl)acetamide | 565.2 |
| 63 | 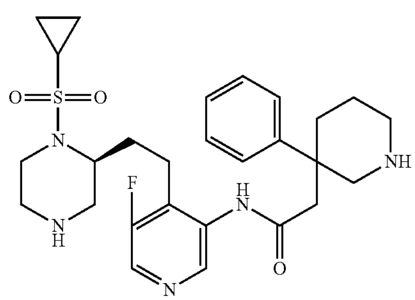 [SMILES: O=C(CC1(c2ccccc2)CCCNC1)Nc1cncc(F)c1CC[C@H]1CNCCN1S(=O)(=O)C1CC1] | N-(4-{2-[(2S)-1-(cyclopropylsulfonyl)piperazin-2-yl]ethyl}-5-fluoropyridin-3-yl)-2-(3-phenylpiperidin-3-yl)acetamide | 530.3 |
| 64 | 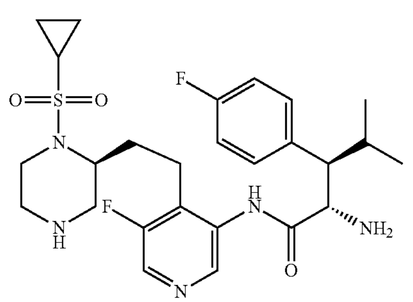 [SMILES: CC(C)[C@H](c1ccc(F)cc1)[C@H](N)C(=O)Nc1cncc(F)c1CC[C@H]1CNCCN1S(=O)(=O)C1CC1] | (βR)-N-(4-{2-[(2S)-1-(cyclopropylsulfonyl)piperazin-2-yl]ethyl}-5-fluoropyridin-3-yl)-4-fluoro-β-(1-methylethyl)-L-phenylalaninamide | 536.3 |

TABLE 1-continued

| Ex # | Structure | IUPAC Name | Exact Mass [M + H]+ |
|---|---|---|---|
| 65 | 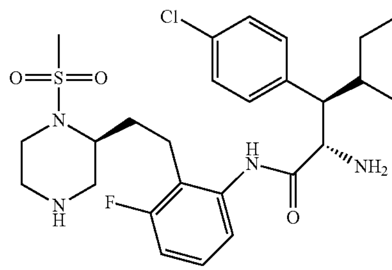 | (βR)-4-chloro-N-(3-fluoro-2-{2-[(2S)-1-(methylsulfonyl)piperazin-2-yl]ethyl}phenyl)-β-(tetrahydro-2H-pyran-4-yl)-L-phenylalaninamide | 567.2 |
| 66 | 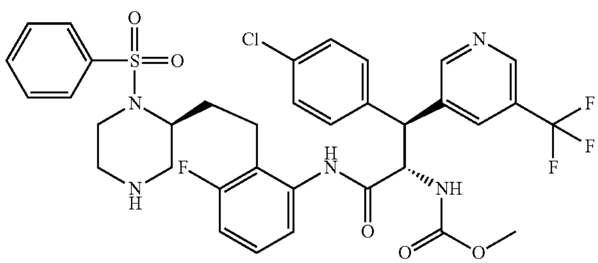 [SMILES: COC(=O)N[C@H](C(=O)Nc1cccc(F)c1CC[C@H]1CNCCN1S(=O)(=O)c1ccccc1)[C@@H](c1ccc(Cl)cc1)c1cncc(C(F)(F)F)c1] | (βS)-4-chloro-N-(3-fluoro-2-{2-[(2S)-1-(phenylsulfonyl)piperazin-2-yl]ethyl}phenyl)-Nα-(methoxycarbonyl)-β-[5-(trifluoromethyl)pyridin-3-yl]-L-phenylalaninamide | 748.2 |
| 67 | 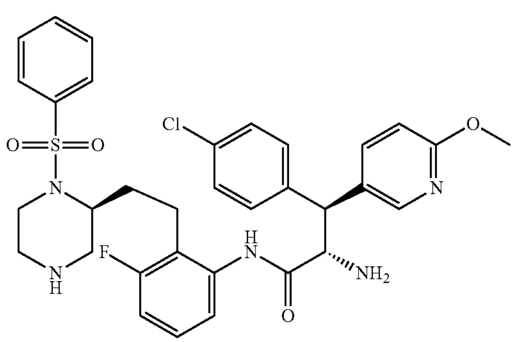 [SMILES: COc1ccc([C@H](c2ccc(Cl)cc2)[C@H](N)C(=O)Nc2cccc(F)c2CC[C@H]2CNCCN2S(=O)(=O)c2ccccc2)cn1] | (βS)-4-chloro-N-(3-fluoro-2-{2-[(2S)-1-(phenylsulfonyl)piperazin-2-yl]ethyl}phenyl)-β-(6-methoxypridin-3-yl)-L-phenylalaninamide | 652.2 |
| 68 | 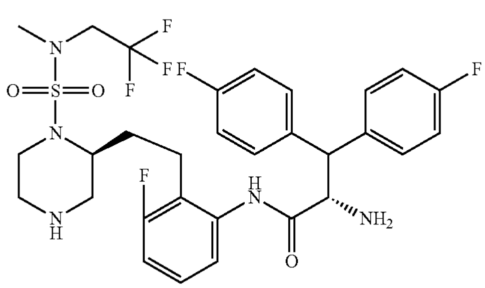 [SMILES: CN(CC(F)(F)F)S(=O)(=O)N1CCNC[C@@H]1CCc1c(F)cccc1NC(=O)[C@@H](N)C(c1ccc(F)cc1)c1ccc(F)cc1] | 4-fluoro-N-[3-fluoro-2-(2-{(2S)-1-[methyl(2,2,2-trifluoroethyl)sulfamoyl]piperazin-2-yl}ethyl)phenyl]-β-(4-fluorophenyl)-L-phenylalaninamide | 658.2 |
| 69 | 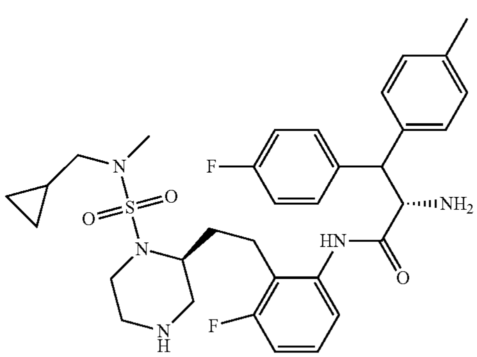 [SMILES: Cc1ccc(C(c2ccc(F)cc2)[C@H](N)C(=O)Nc2cccc(F)c2CC[C@H]2CNCCN2S(=O)(=O)N(C)CC2CC2)cc1] | N-[2-(2-{(2S)-1-[(cyclopropylmethyl)methyl)sulfamoyl]piperazin-2-yl}ethyl)-3-fluorophenyl]-4-fluoro-β-(4-fluorophenyl)-L-phenylalaninamide | 630.3 |

TABLE 1-continued

| Ex # | Structure | IUPAC Name | Exact Mass [M + H]+ |
|---|---|---|---|
| 70 | 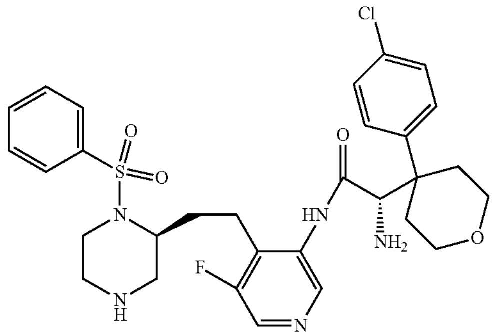 [SMILES: N[C@H](C(=O)Nc1cncc(F)c1CC[C@H]1CNCCN1S(=O)(=O)c1ccccc1)C1(c2ccc(Cl)cc2)CCOCC1] | (2S)-2-amino-2-[4-(4-chlorophenyl)tetrahydro-2H-pyran-4-yl]-N-(5-fluoro-4-{2-[(2S)-1-(phenylsulfonyl)piperazin-2-yl]ethyl}pyridin-3-yl)ethanamide | 616.2 |
| 71 | 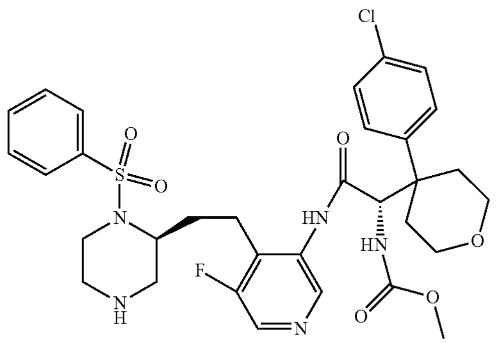 [SMILES: COC(=O)N[C@H](C(=O)Nc1cncc(F)c1CC[C@H]1CNCCN1S(=O)(=O)c1ccccc1)C1(c2ccc(Cl)cc2)CCOCC1] | methyl {(1S)-1-[4-(4-chlorophenyl)tetrahydro-2H-pyran-4-yl]-2-[(5-fluoro-4-{2-[(2S)-1-(phenylsulfonyl)piperazin-2-yl]ethyl}pyridin-3-yl)amino]-2-oxoethyl}carbamate | 674.2 |
| 72 | 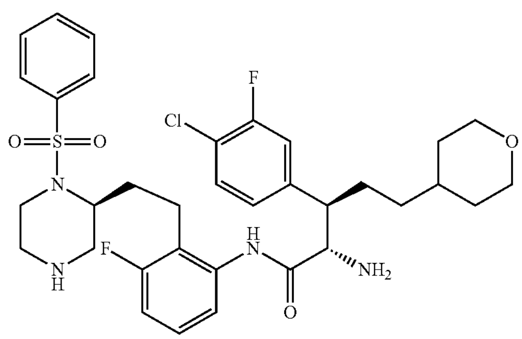 [SMILES: N[C@H](C(=O)Nc1cccc(F)c1CC[C@H]1CNCCN1S(=O)(=O)c1ccccc1)[C@H](CCC1CCOCC1)c1ccc(Cl)c(F)c1] | (βR)-4-chloro-3-fluoro-N-(3-fluoro-2-{2-[(2S)-1-(phenylsulfonyl)piperazin-2-yl]ethyl}phenyl)-β-[2-(tetrahydro-2H-pyran-4-yl)ethyl]-L-phenylalaninamide | 675.3 |
| 73 | 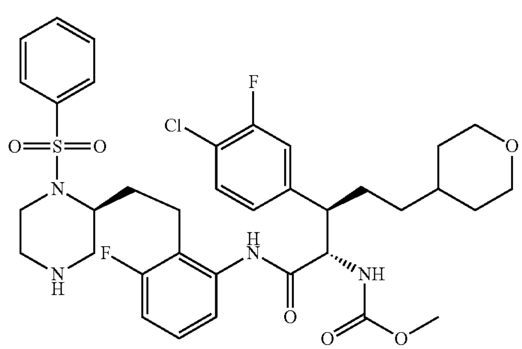 [SMILES: COC(=O)N[C@H](C(=O)Nc1cccc(F)c1CC[C@H]1CNCCN1S(=O)(=O)c1ccccc1)[C@H](CCC1CCOCC1)c1ccc(Cl)c(F)c1] | (βR)-4-chloro-3-fluoro-N-(3-fluoro-2-{2-[(2S)-1-(phenylsulfonyl)piperazin-2-yl]ethyl}phenyl)-Nα-(methoxycarbonyl)-β-[2-(tetrahydro-2H-pyran-4-yl)ethyl]-L-phenylalaninamide | 733.3 |

TABLE 1-continued

| Ex # | Structure | IUPAC Name | Exact Mass [M + H]+ |
|---|---|---|---|
| 74 | 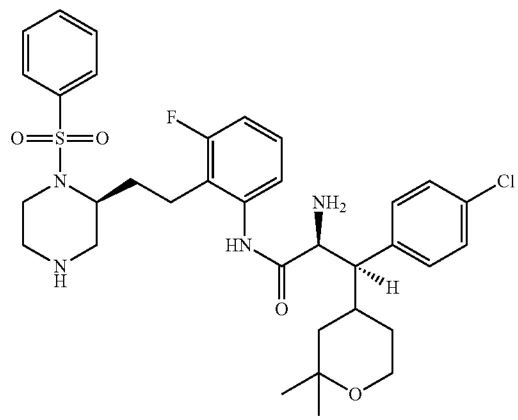 [SMILES: CC1(C)CC([C@H](c2ccc(Cl)cc2)[C@H](N)C(=O)Nc2cccc(F)c2CC[C@H]2CNCCN2S(=O)(=O)c2ccccc2)CCO1] | (βR)-4-chloro-β-(2,2-dimethyltetrahydro-2H-pyran-4-yl)-N-(3-fluoro-2-{2-[(2S)-1-(phenylsulfonyl)piperazin-2-yl]ethyl}phenyl)-L-phenylalaninamide | 657.3 |
| 75 | 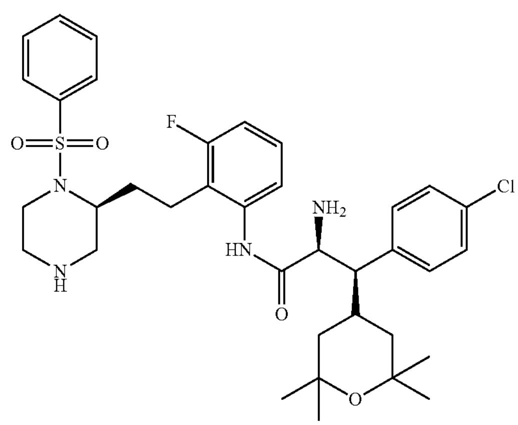 [SMILES: CC1(C)CC([C@H](c2ccc(Cl)cc2)[C@H](N)C(=O)Nc2cccc(F)c2CC[C@H]2CNCCN2S(=O)(=O)c2ccccc2)CC(C)(C)O1] | (βR)-4-chloro-N-(3-fluoro-2-{2-[(2S)-1-(phenylsulfonyl)piperazin-2-yl]ethyl}phenyl)-β-(2,2,6,6-tetramethyltetrahydro-2H-pyran-4-yl)-L-phenylalaninamide | 685.3 |
| 76 | 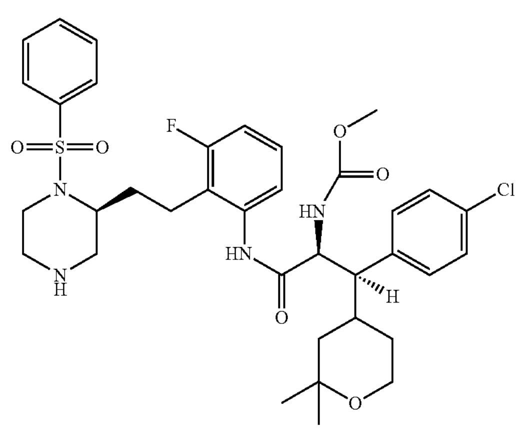 [SMILES: COC(=O)N[C@H](C(=O)Nc1cccc(F)c1CC[C@H]1CNCCN1S(=O)(=O)c1ccccc1)[C@@H](c1ccc(Cl)cc1)C1CCOC(C)(C)C1] | (βR)-4-chloro-β-(2,2-dimethyltetrahydro-2H-pyran-4-yl)-N-(3-fluoro-2-{2-[(2S)-1-(phenylsulfonyl)piperazin-2-yl]ethyl}phenyl)-Nα-(methoxycarbonyl)-L-phenylalaninamide | 715.3 |

TABLE 1-continued

| Ex # | Structure | IUPAC Name | Exact Mass [M + H]+ |
|---|---|---|---|
| 77 | 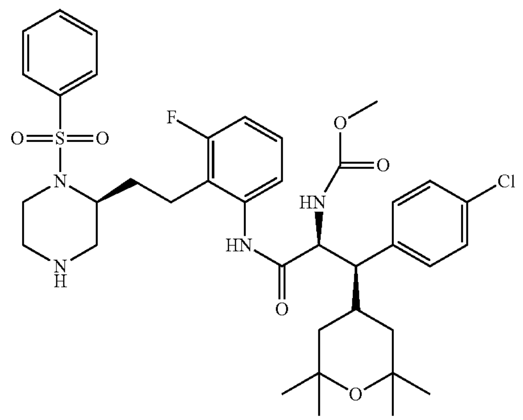 [SMILES: COC(=O)N[C@H](C(=O)Nc1cccc(F)c1CC[C@H]1CNCCN1S(=O)(=O)c1ccccc1)[C@@H](c1ccc(Cl)cc1)C1CC(C)(C)OC(C)(C)C1] | (βR)-4-chloro-N-(3-fluoro-2-{2-[(2S)-1-(phenylsulfonyl)piperazin-2-yl]ethyl}phenyl)-Nα-(methoxycarbonyl)-β-(2,2,6,6-tetramethyltetrahydro-2H-pyran-4-yl)-L-phenylalaninamide | 743.3 |
| 78 | 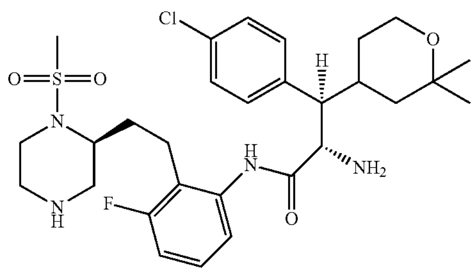 [SMILES: CC1(C)CC([C@H](c2ccc(Cl)cc2)[C@H](N)C(=O)Nc2cccc(F)c2CC[C@H]2CNCCN2S(C)(=O)=O)CCO1] | (βR)-4-chloro-β-(2,2-dimethyltetrahydro-2H-pyran-4-yl)-N-(3-fluoro-2-{2-[(2S)-1-(methylsulfonyl)piperazin-2-yl]ethyl}phenyl)-L-phenylalaninamide | 595.3 |
| 79 | 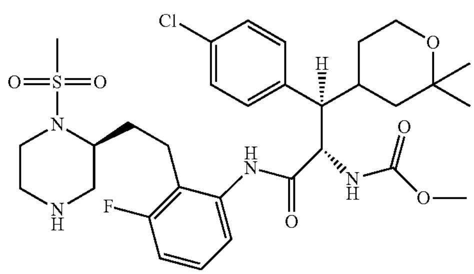 [SMILES: COC(=O)N[C@H](C(=O)Nc1cccc(F)c1CC[C@H]1CNCCN1S(C)(=O)=O)[C@@H](c1ccc(Cl)cc1)C1CCOC(C)(C)C1] | (βR)-4-chloro-β-(2,2-dimethyltetrahydro-2H-pyran-4-yl)-N-(3-fluoro-2-{2-[(2S)-1-(methylsulfonyl)piperazin-2-yl]ethyl}phenyl)-Nα-(methoxycarbonyl)-L-phenylalaninamide | 653.3 |

TABLE 2

| Ex # | Structure | IUPAC Name | Exact Mass [M + H]+ |
|---|---|---|---|
| 80 | 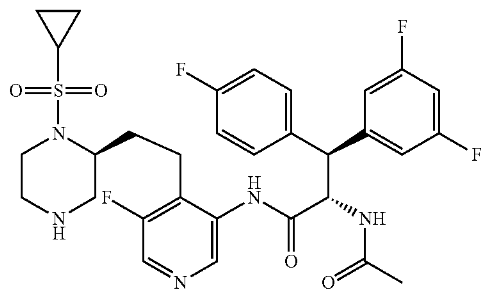 [SMILES: CC(=O)N[C@H](C(=O)Nc1cncc(F)c1CC[C@H]1CNCCN1S(=O)(=O)C1CC1)[C@@H](c1ccc(F)cc1)c1cc(F)cc(F)c1] | (βS)-Nα-acetyl-N-(4-{2-[(2S)-1-(cyclopropylsulfonyl)piperazin-2-yl]ethyl}-5-fluoropyridin-3-yl)-3,5-difluoro-β-(4-fluorophenyl)-L-phenylalaninamide | 648.2 |

TABLE 2-continued

| Ex # | Structure | IUPAC Name | Exact Mass [M + H]+ |
|---|---|---|---|
| 81 | 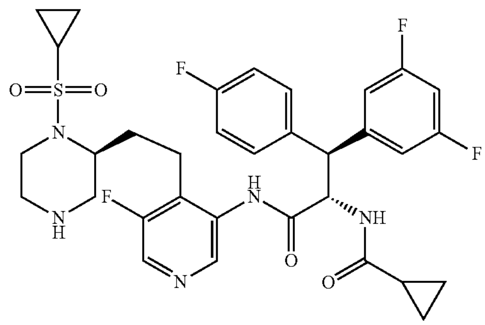 [SMILES: O=C(N[C@H](C(=O)Nc1cncc(F)c1CC[C@H]1CNCCN1S(=O)(=O)C1CC1)[C@@H](c1ccc(F)cc1)c1cc(F)cc(F)c1)C1CC1] | (βS)-Nα-(cyclopropylcarbonyl)-N-(4-{2-[(2S)-1-(cyclopropylsulfonyl)piperazin-2-yl]ethyl}-5-fluoropyridin-3-yl)-3,5-difluoro-β-(4-fluorophenyl)-L-phenylalaninamide | 674.2 |
| 82 | 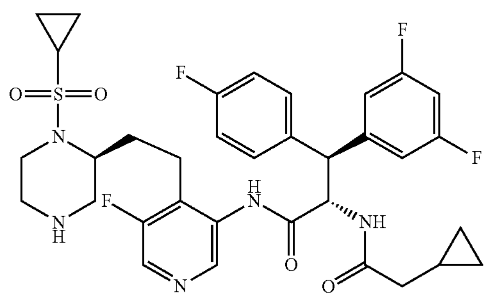 [SMILES: O=C(CC1CC1)N[C@H](C(=O)Nc1cncc(F)c1CC[C@H]1CNCCN1S(=O)(=O)C1CC1)[C@@H](c1ccc(F)cc1)c1cc(F)cc(F)c1] | (βS)-Nα-(cyclopropylacetyl)-N-(4-{2-[(2S)-1-(cyclopropylsulfonyl)piperazin-2-yl]ethyl}-5-fluoropyridin-3-yl)-3,5-difluoro-β-(4-fluorophenyl)-L-phenylalaninamide | 688.3 |
| 83 | 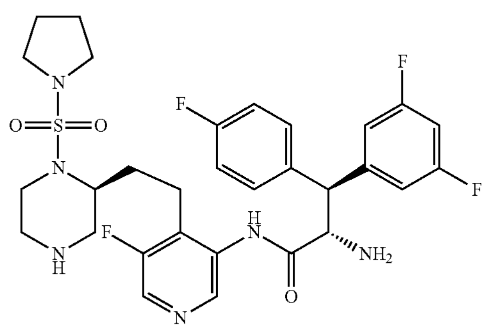 [SMILES: N[C@H](C(=O)Nc1cncc(F)c1CC[C@H]1CNCCN1S(=O)(=O)N1CCCC1)[C@@H](c1ccc(F)cc1)c1cc(F)cc(F)c1] | (βS)-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-L-phenylalaninamide | 635.2 |
| 84 | 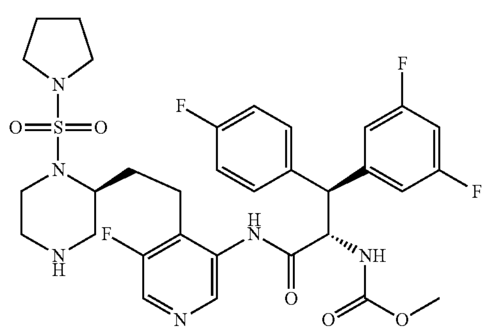 [SMILES: COC(=O)N[C@H](C(=O)Nc1cncc(F)c1CC[C@H]1CNCCN1S(=O)(=O)N1CCCC1)[C@@H](c1ccc(F)cc1)c1cc(F)cc(F)c1] | (βS)-3,5-difluoro-β-(4-fluorophenyl)-N-(5-fluoro-4-{2-[(2S)-1-(pyrroldin-1-ylsulfonyl)piperazin-2-yl]ethyl}pyridin-3-yl)-Nα-(methoxycarbonyl)-L-phenylalaninamide | 693.2 |

TABLE 2-continued

| Ex # | Structure | IUPAC Name | Exact Mass [M + H]+ |
|---|---|---|---|
| 85 | 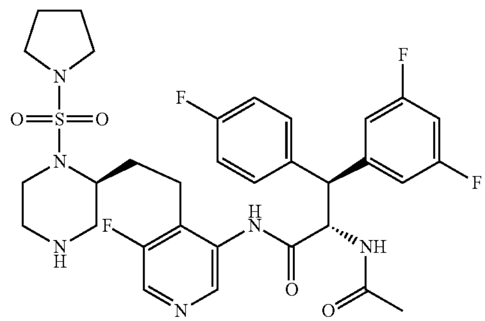 [SMILES: CC(=O)N[C@H](C(=O)Nc1cncc(F)c1CC[C@H]1CNCCN1S(=O)(=O)N1CCCC1)[C@@H](c1ccc(F)cc1)c1cc(F)cc(F)c1] | (βS)-Nα-acetyl-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-L-phenylalaninamide | 677.3 |
| 86 | 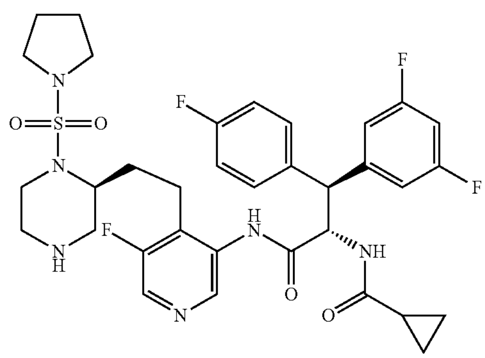 [SMILES: O=C(N[C@H](C(=O)Nc1cncc(F)c1CC[C@H]1CNCCN1S(=O)(=O)N1CCCC1)[C@@H](c1ccc(F)cc1)c1cc(F)cc(F)c1)C1CC1] | (βS)-Nα-(cyclopropylcarbonyl)-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-L-phenylalaninamide | 703.3 |
| 87 | 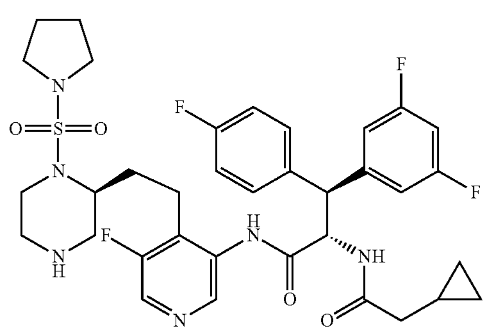 [SMILES: O=C(CC1CC1)N[C@H](C(=O)Nc1cncc(F)c1CC[C@H]1CNCCN1S(=O)(=O)N1CCCC1)[C@@H](c1ccc(F)cc1)c1cc(F)cc(F)c1] | (βS)-Nα-(cyclopropylacetyl)-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-L-phenylalaninamide | 717.3 |

TABLE 3

| Ex # | Structure | IUPAC Name | Exact Mass [M + H]+ |
|---|---|---|---|
| 88 | 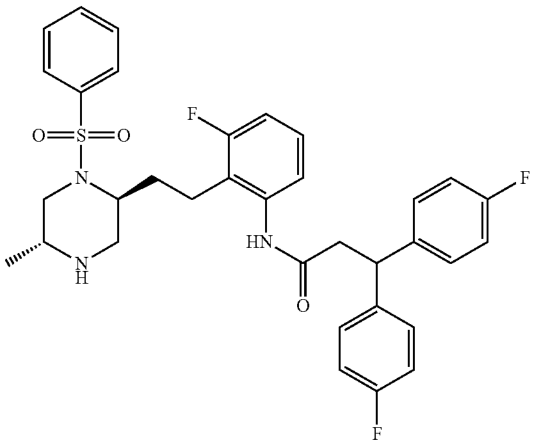 [SMILES: C[C@@H]1CN(S(=O)(=O)c2ccccc2)[C@@H](CCc2c(F)cccc2NC(=O)CC(c2ccc(F)cc2)c2ccc(F)cc2)CN1] | N-(3-fluoro-2-{2-[(2S,5R)-5-methyl-1-(phenylsulfonyl)piperazin-2-yl]ethyl}phenyl)-3,3-bis(4-fluorophenyl)propanamide | 622.2 |
| 89 | 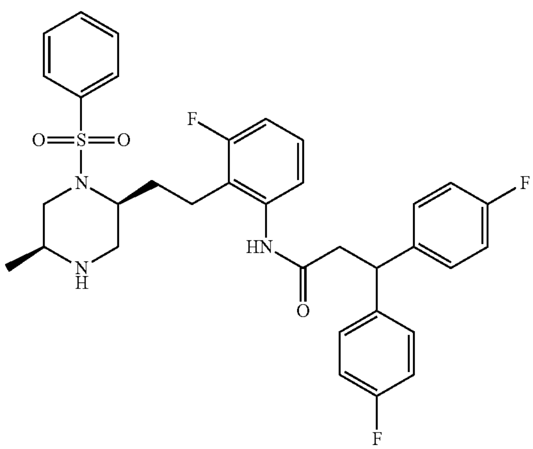 [SMILES: C[C@H]1CN(S(=O)(=O)c2ccccc2)[C@@H](CCc2c(F)cccc2NC(=O)CC(c2ccc(F)cc2)c2ccc(F)cc2)CN1] | N-(3-fluoro-2-{2-[(2S,5S)-5-methyl-1-(phenylsulfonyl)piperazin-2-yl]ethyl}phenyl)-3,3-bis(4-fluorophenyl)propanamide | 622.2 |
| 90 | 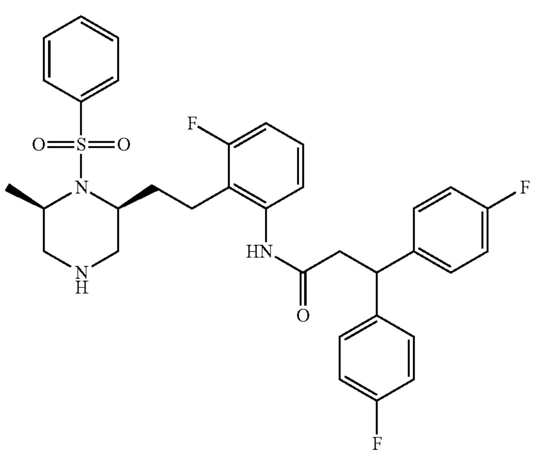 [SMILES: C[C@@H]1CNC[C@H](CCc2c(F)cccc2NC(=O)CC(c2ccc(F)cc2)c2ccc(F)cc2)N1S(=O)(=O)c1ccccc1] | N-(3-fluoro-2-{2-[(2S,6R)-6-methyl-1-(phenylsulfonyl)piperazin-2-yl]ethyl}phenyl)-3,3-bis(4-fluorophenyl)propanamide | 622.2 |

TABLE 3-continued

| Ex # | Structure | IUPAC Name | Exact Mass [M + H]+ |
|---|---|---|---|
| 91 | 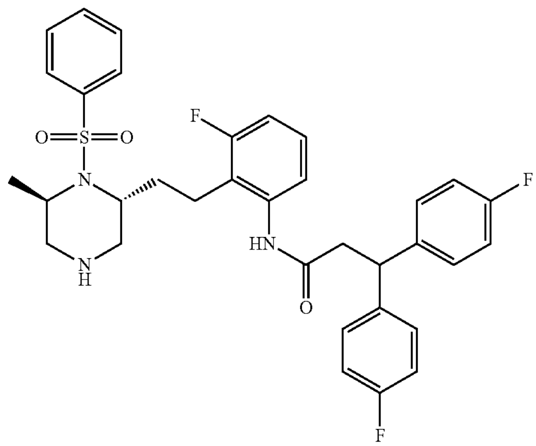 [SMILES: C[C@@H]1CNC[C@@H](CCc2c(F)cccc2NC(=O)CC(c2ccc(F)cc2)c2ccc(F)cc2)N1S(=O)(=O)c1ccccc1] | N-(3-fluoro-2-{2-[(2R,6R)-6-methyl-1-(phenylsulfonyl)piperazin-2-yl]ethyl}phenyl)-3,3-bis(4-fluorophenyl)propanamide | 622.2 |
| 92 | 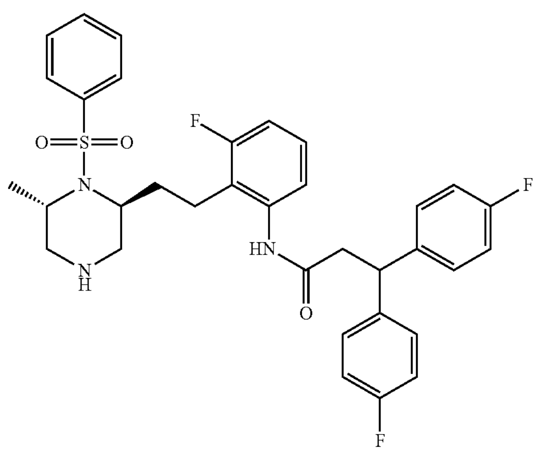 [SMILES: C[C@H]1CNC[C@H](CCc2c(F)cccc2NC(=O)CC(c2ccc(F)cc2)c2ccc(F)cc2)N1S(=O)(=O)c1ccccc1] | N-(3-fluoro-2-{2-[(2S,6S)-6-methyl-1-(phenylsulfonyl)piperazin-2-yl]ethyl}phenyl)-3,3-bis(4-fluorophenyl)propanamide | 622.2 |
| 93 | 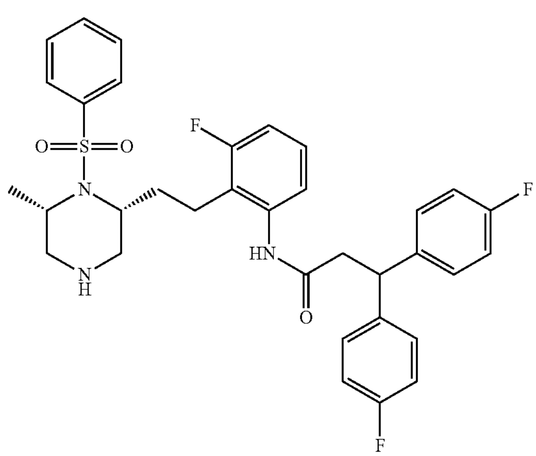 [SMILES: C[C@H]1CNC[C@@H](CCc2c(F)cccc2NC(=O)CC(c2ccc(F)cc2)c2ccc(F)cc2)N1S(=O)(=O)c1ccccc1] | N-(3-fluoro-2-{2-[(2R,6S)-6-methyl-1-(phenylsulfonyl)piperazin-2-yl]ethyl}phenyl)-3,3-bis(4-fluorophenyl)propanamide | 622.2 |

TABLE 3-continued

| Ex # | Structure | IUPAC Name | Exact Mass [M + H]+ |
|---|---|---|---|
| 94 | 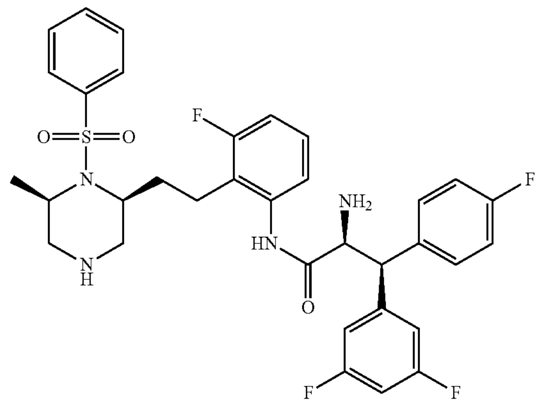 [SMILES: C[C@@H]1CNC[C@H](CCc2c(F)cccc2NC(=O)[C@@H](N)[C@@H](c2ccc(F)cc2)c2cc(F)cc(F)c2)N1S(=O)(=O)c1ccccc1] | (βS)-β-(3,5-difluorophenyl)-4-fluoro-N-(3-fluoro-2-{2-[(2S,6R)-6-methyl-1-(phenylsulfonyl)piperazin-2-yl]ethyl}phenyl)-L-phenylalaninamide | 655.2 |
| 95 | 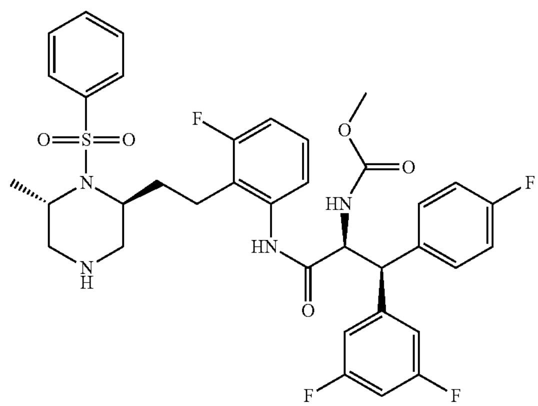 [SMILES: COC(=O)N[C@H](C(=O)Nc1cccc(F)c1CC[C@H]1CNC[C@H](C)N1S(=O)(=O)c1ccccc1)[C@@H](c1ccc(F)cc1)c1cc(F)cc(F)c1] | (βS)-β-(3,5-difluorophenyl)-4-fluoro-N-(3-fluoro-2-{2-[(2S,6S)-6-methyl-1-(phenylsulfonyl)piperazin-2-yl]ethyl}phenyl)-Nα-(methoxycarbonyl)-L-phenylalaninamide | 713.2 |
| 96 | 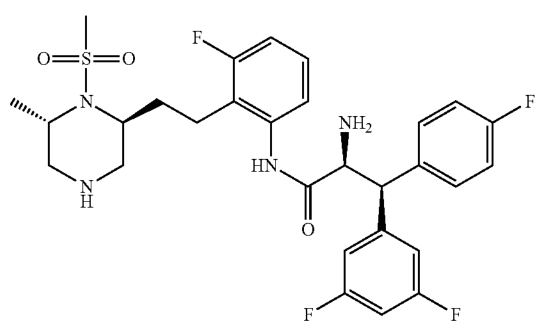 [SMILES: C[C@H]1CNC[C@H](CCc2c(F)cccc2NC(=O)[C@@H](N)[C@@H](c2ccc(F)cc2)c2cc(F)cc(F)c2)N1S(C)(=O)=O] | (βS)-β-(3,5-difluorophenyl)-4-fluoro-N-(3-fluoro-2-{2-[(2S,6S)-6-methyl-1-(methylsulfonyl)piperazin-2-yl]ethyl}phenyl)-L-phenylalaninamide | 593.2 |
| 97 | 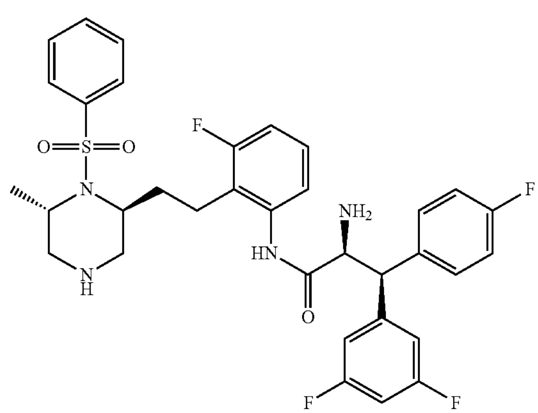 [SMILES: C[C@H]1CNC[C@H](CCc2c(F)cccc2NC(=O)[C@@H](N)[C@@H](c2ccc(F)cc2)c2cc(F)cc(F)c2)N1S(=O)(=O)c1ccccc1] | (βS)-β-(3,5-difluorophenyl)-4-fluoro-N-(3-fluoro-2-{2-[(2S,6S)-6-methyl-1-(phenylsulfonyl)piperazin-2-yl]ethyl}phenyl)-L-phenylalaninamide | 655.2 |

TABLE 3-continued

| Ex # | Structure | IUPAC Name | Exact Mass [M + H]+ |
|---|---|---|---|
| 98 | 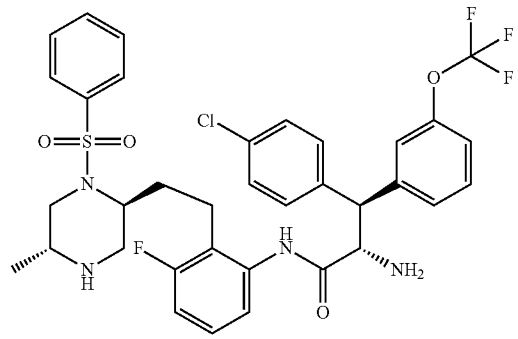 [SMILES: C[C@@H]1CN(S(=O)(=O)c2ccccc2)[C@@H](CCc2c(F)cccc2NC(=O)[C@@H](N)[C@@H](c2ccc(Cl)cc2)c2cccc(OC(F)(F)F)c2)CN1] | (βS)-4-chloro-N-(3-fluoro-2-{2-[(2S,5R)-5-methyl-1-(phenylsulfonyl)piperazin-2-yl]ethyl}phenyl)-β-[3-(trifluoromethoxy)phenyl]-L-phenylalaninamide | 719.2 |
| 99 | 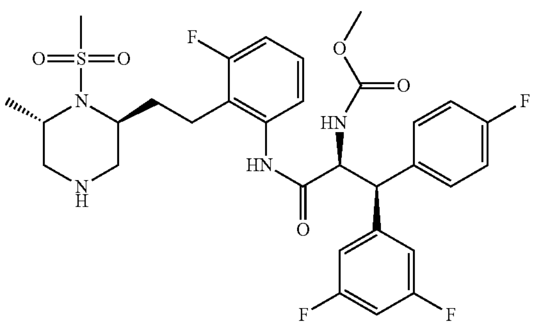 [SMILES: COC(=O)N[C@H](C(=O)Nc1cccc(F)c1CC[C@H]1CNC[C@H](C)N1S(C)(=O)=O)[C@@H](c1ccc(F)cc1)c1cc(F)cc(F)c1] | (βS)-β-(3,5-difluorophenyl)-4-fluoro-N-(3-fluoro-2-{2-[(2S,6S)-6-methyl-1-(methylsulfonyl)piperazin-2-yl]ethyl}phenyl)-Nα-(methoxycarbonyl)-L-phenylalaninamide | 651.2 |
| 100 | 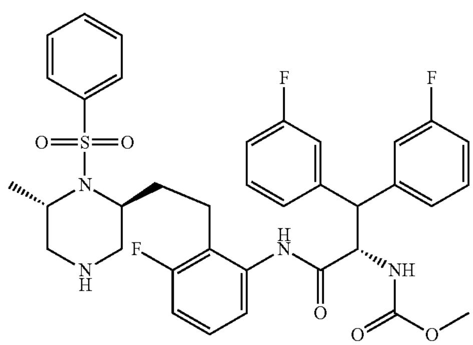 | 3-fluoro-N-(3-fluoro-2-{2-[(2S,6S)-6-methyl-1-(phenylsulfonyl)piperazin-2-yl]ethyl}phenyl)-β-(3-fluorophenyl)-Nα-(methoxycarbonyl)-L-phenylalaninamide | 695.3 |
| 101 | 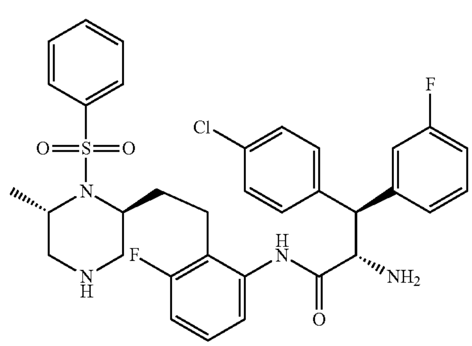 [SMILES: C[C@H]1CNC[C@H](CCc2c(F)cccc2NC(=O)[C@@H](N)[C@@H](c2ccc(Cl)cc2)c2cccc(F)c2)N1S(=O)(=O)c1ccccc1] | (βS)-4-chloro-N-(3-fluoro-2-{2-[(2S,6S)-6-methyl-1-(phenylsulfonyl)piperazin-2-yl]ethyl}phenyl)-β-(3-fluorophenyl)-L-phenylalaninamide | 653.2 |

TABLE 3-continued

| Ex # | Structure | IUPAC Name | Exact Mass [M + H]+ |
|---|---|---|---|
| 102 | 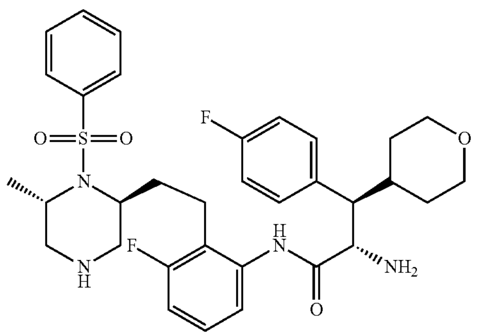 [SMILES: C[C@H]1CNC[C@H](CCc2c(F)cccc2NC(=O)[C@@H](N)[C@@H](c2ccc(F)cc2)C2CCOCC2)N1S(=O)(=O)c1ccccc1] | (βR)-4-fluoro-N-(3-fluoro-2-{2-[(2S,6S)-6-methyl-1-(phenylsulfonyl)piperazin-2-yl]ethyl}phenyl)-β-(tetrahydro-2H-pyran-4-yl)-L-phenylalaninamide | 627.3 |
| 103 | 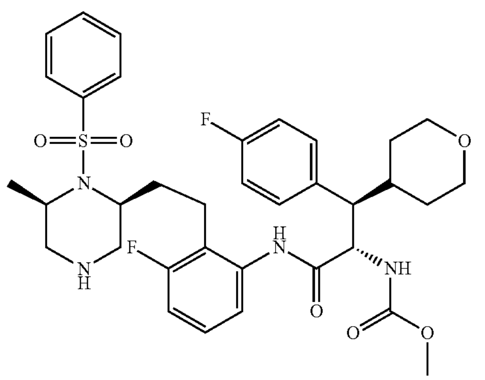 [SMILES: COC(=O)N[C@H](C(=O)Nc1cccc(F)c1CC[C@H]1CNC[C@@H](C)N1S(=O)(=O)c1ccccc1)[C@@H](c1ccc(F)cc1)C1CCOCC1] | (βR)-4-fluoro-N-(3-fluoro-2-{2-[(2S,6R)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide | 685.3 |
| 104 | 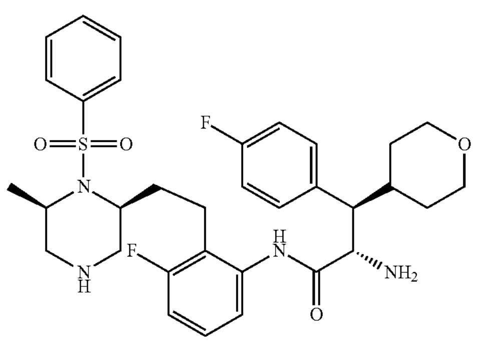 [SMILES: C[C@@H]1CNC[C@H](CCc2c(F)cccc2NC(=O)[C@@H](N)[C@@H](c2ccc(F)cc2)C2CCOCC2)N1S(=O)(=O)c1ccccc1] | (βR)-4-fluoro-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide | 627.3 |
| 105 | 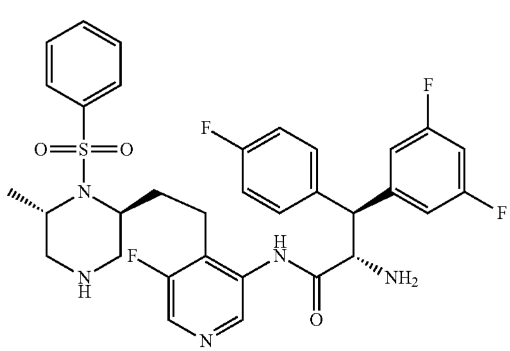 [SMILES: C[C@H]1CNC[C@H](CCc2c(F)cncc2NC(=O)[C@@H](N)[C@@H](c2ccc(F)cc2)c2cc(F)cc(F)c2)N1S(=O)(=O)c1ccccc1] | (βS)-β-(3,5-difluorophenyl)-4-fluoro-N-(5-fluoro-4-{2-[(2S,6S)-6-methyl-1-(phenylsulfonyl)piperazin-2-yl]ethyl}pyridin-3-yl)-L-phenylalaninamide | 656.2 |

TABLE 3-continued

| Ex # | Structure | IUPAC Name | Exact Mass [M + H]+ |
|---|---|---|---|
| 106 | 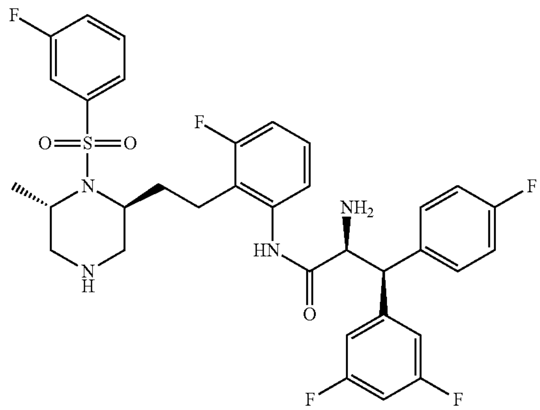 [SMILES: C[C@H]1CNC[C@H](CCc2c(F)cccc2NC(=O)[C@@H](N)[C@@H](c2ccc(F)cc2)c2cc(F)cc(F)c2)N1S(=O)(=O)c1cccc(F)c1] | (βS)-β-(3,5-difluorophenyl)-4-fluoro-N-[3-fluoro-2-(2-{(2S,6S)-1-[(3-fluorophenyl)sulfonyl]-6-methylpiperazin-2-yl}ethyl)phenyl]-L-phenylalaninamide | 673.2 |
| 107 | 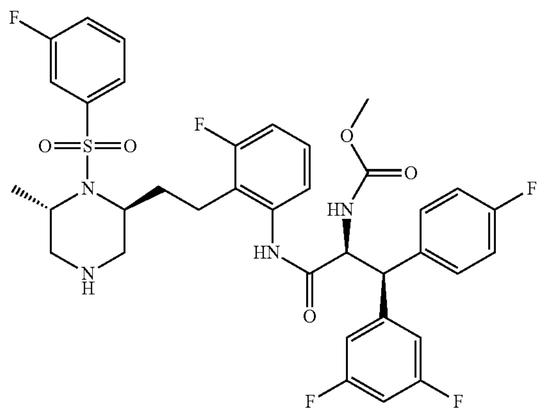 [SMILES: COC(=O)N[C@H](C(=O)Nc1cccc(F)c1CC[C@H]1CNC[C@H](C)N1S(=O)(=O)c1cccc(F)c1)[C@@H](c1ccc(F)cc1)c1cc(F)cc(F)c1] | (βS)-β-(3,5-difluorophenyl)-4-fluoro-N-[3-fluoro-2-(2-{(2S,6S)-1-[(3-fluorophenyl)sulfonyl]-6-methylpiperazin-2-yl}ethyl)phenyl]-Nα-(methoxycarbonyl)-L-phenylalaninamide | 731.2 |
| 108 | 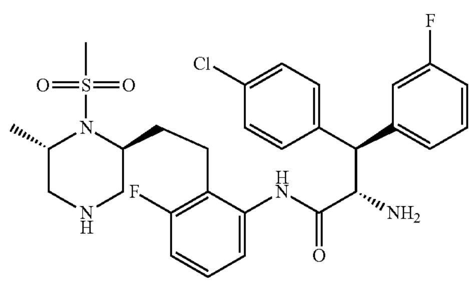 [SMILES: C[C@H]1CNC[C@H](CCc2c(F)cccc2NC(=O)[C@@H](N)[C@@H](c2ccc(Cl)cc2)c2cccc(F)c2)N1S(C)(=O)=O] | (βS)-4-chloro-N-(3-fluoro-2-{2-[(2S,6S)-6-methyl-1-(methylsulfonyl)piperazin-2-yl]ethyl}phenyl)-β-(3-fluorophenyl)-L-phenylalaninamide | 591.2 |
| 109 | 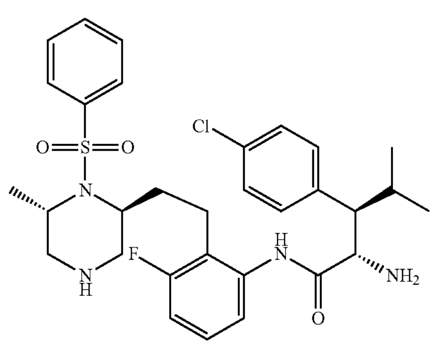 [SMILES: CC(C)[C@H](c1ccc(Cl)cc1)[C@H](N)C(=O)Nc1cccc(F)c1CC[C@H]1CNC[C@H](C)N1S(=O)(=O)c1ccccc1] | (βR)-4-chloro-N-(3-fluoro-2-{2-[(2S,6S)-6-methyl-1-(phenylsulfonyl)piperazin-2-yl]ethyl}phenyl)-β-(1-methylethyl)-L-phenylalaninamide | 601.2 |

TABLE 3-continued

| Ex # | Structure | IUPAC Name | Exact Mass [M + H]+ |
|---|---|---|---|
| 110 | 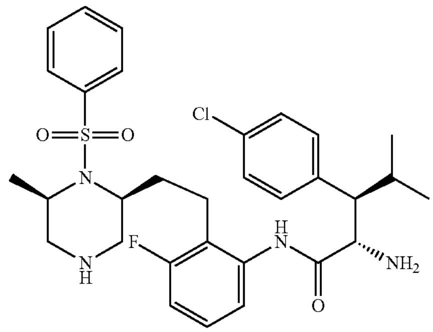 [SMILES: CC(C)[C@H](c1ccc(Cl)cc1)[C@H](N)C(=O)Nc1cccc(F)c1CC[C@H]1CNC[C@@H](C)N1S(=O)(=O)c1ccccc1] | (βR)-4-chloro-N-(3-fluoro-2-{2-[(2S,6R)-6-methyl-1-(phenylsulfonyl)piperazin-2-yl]ethyl}phenyl)-β-(1-methylethyl)-L-phenylalaninamide | 601.2 |
| 111 | 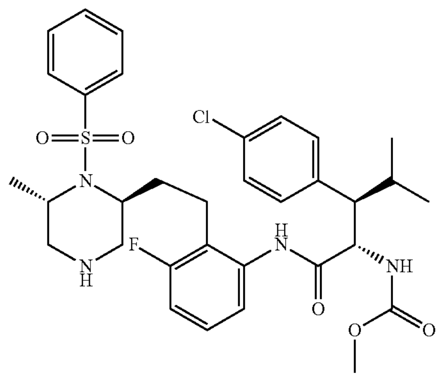 [SMILES: COC(=O)N[C@H](C(=O)Nc1cccc(F)c1CC[C@H]1CNC[C@H](C)N1S(=O)(=O)c1ccccc1)[C@@H](c1ccc(Cl)cc1)C(C)C] | (βR)-4-chloro-N-(3-fluoro-2-{2-[(2S,6S)-6-methyl-1-(phenylsulfonyl)piperazin-2-yl]ethyl}phenyl)-Nα-(methoxycarbonyl)-β-(1-methylethyl)-L-phenylalaninamide | 659.2 |
| 112 | 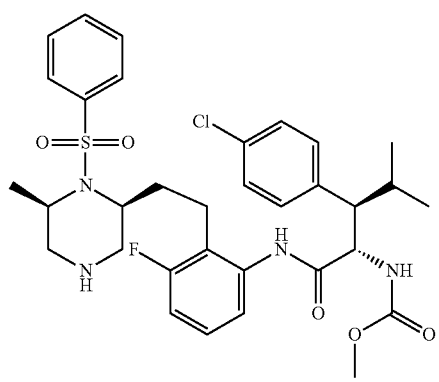 [SMILES: COC(=O)N[C@H](C(=O)Nc1cccc(F)c1CC[C@H]1CNC[C@@H](C)N1S(=O)(=O)c1ccccc1)[C@@H](c1ccc(Cl)cc1)C(C)C] | (βR)-4-chloro-N-(3-fluoro-2-{2-[(2S,6R)-6-methyl-1-(phenylsulfonyl)piperazin-2-yl]ethyl}phenyl)-Nα-(methoxycarbonyl)-β-(1-methylethyl)-L-phenylalaninamide | 659.2 |
| 113 | 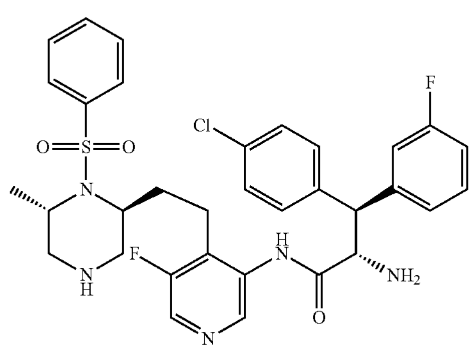 [SMILES: C[C@H]1CNC[C@H](CCc2c(F)cncc2NC(=O)[C@@H](N)[C@@H](c2ccc(Cl)cc2)c2cccc(F)c2)N1S(=O)(=O)c1ccccc1] | (βS)-β-(4-chlorophenyl)-3-fluoro-N-(5-fluoro-4-{2-[(2S,6S)-6-methyl-1-(phenylsulfonyl)piperazin-2-yl]ethyl}pyridin-3-yl)-L-phenylalaninamide | 654.2 |

TABLE 3-continued

| Ex # | Structure | IUPAC Name | Exact Mass [M + H]+ |
|---|---|---|---|
| 114 | 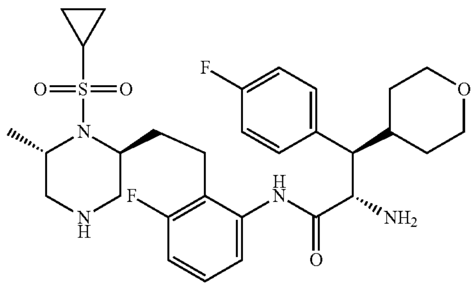 [SMILES: C[C@H]1CNC[C@H](CCc2c(F)cccc2NC(=O)[C@@H](N)[C@@H](c2ccc(F)cc2)C2CCOCC2)N1S(=O)(=O)C1CC1] | (βR)-N-(2-{2-[(2S,6S)-1-(cyclopropylsulfonyl)-6-methylpiperazin-2-yl]ethyl}-3-fluorophenyl)-4-fluoro-β-(tetrahydro-2H-pyran-4-yl)-L-phenylalaninamide | 591.3 |
| 115 | 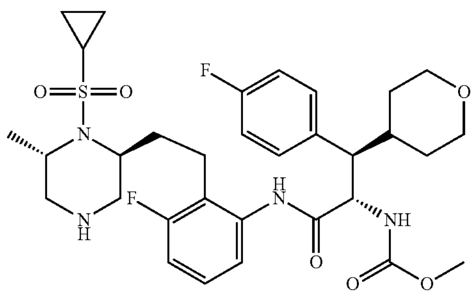 | (βR)-N-(2-{2-[(2S,6S)-1-(cyclopropylsulfonyl)-6-methylpiperazin-2-yl]ethyl}-3-fluorophenyl)-4-fluoro-Nα-(methoxycarbonyl)-β-(tetrahydro-2H-pyran-4-yl)-L-phenylalaninamide | 649.3 |
| 116 | 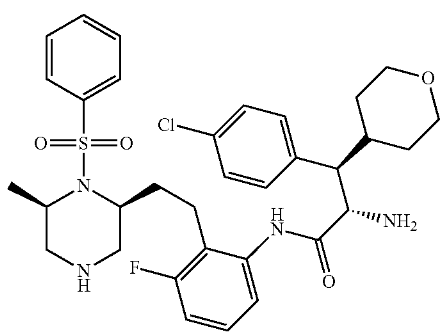 [SMILES: C[C@@H]1CNC[C@H](CCc2c(F)cccc2NC(=O)[C@@H](N)[C@@H](c2ccc(Cl)cc2)C2CCOCC2)N1S(=O)(=O)c1ccccc1] | (βR)-4-chloro-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide | 643.3 |
| 117 | 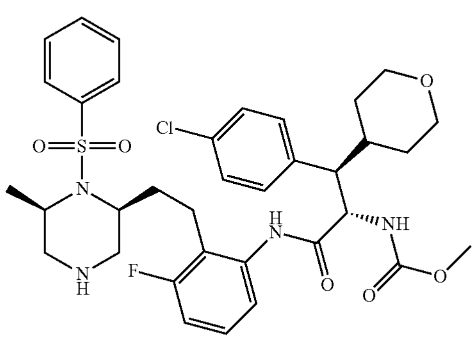 | (βR)-4-chloro-N-(3-fluoro-2-{2-[(2S,6R)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide | 701.3 |

TABLE 3-continued

| Ex # | Structure | IUPAC Name | Exact Mass [M + H]+ |
|---|---|---|---|
| 118 | 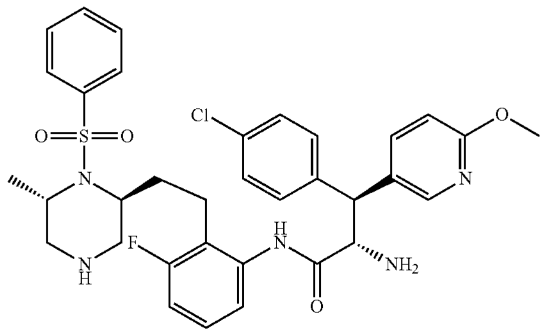 | (βS)-4-chloro-N-(3-fluoro-2-{2-[(2S,6S)-6-methyl-1-(phenylsulfonyl)piperazin-2-yl]ethyl}phenyl)-β-(6-methoxypyridin-3-yl)-L-phenylalaninamide | 666.2 |
| 119 | 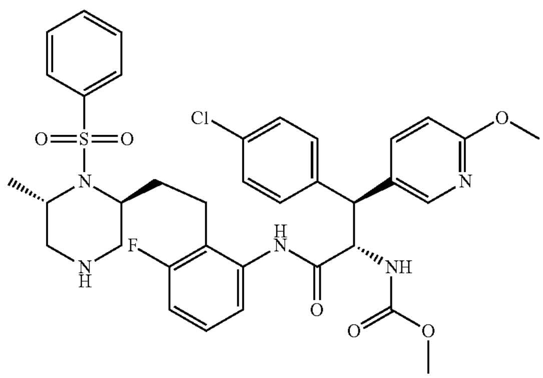 | (βS)-4-chloro-N-(3-fluoro-2-{2-[(2S,6S)-6-methyl-1-(phenylsulfonyl)piperazin-2-yl]ethyl}phenyl)-Nα-(methoxycarbonyl)-β-(6-methoxypyridin-3-yl)-L-phenylalaninamide | 724.2 |
| 120 | 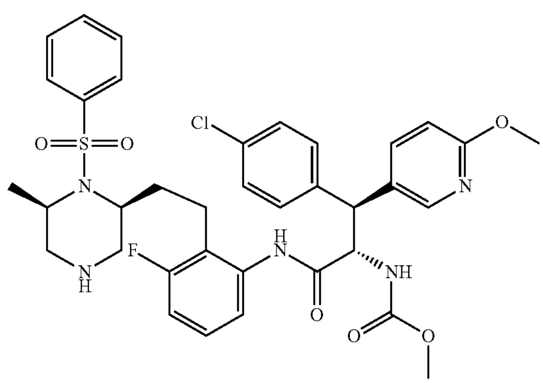 | (βS)-4-chloro-N-(3-fluoro-2-{2-[(2S,6R)-6-methyl-1-(phenylsulfonyl)piperazin-2-yl]ethyl}phenyl)-Nα-(methoxycarbonyl)-β-(6-methoxypyridin-3-yl)-L-phenylalaninamide | 724.2 |
| 121 | 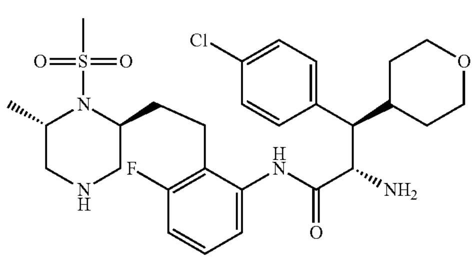 [SMILES: C[C@H]1CNC[C@H](CCc2c(F)cccc2NC(=O)[C@@H](N)[C@@H](c2ccc(Cl)cc2)C2CCOCC2)N1S(C)(=O)=O] | (βR)-4-chloro-N-(3-fluoro-2-{2-[(2S,6S)-6-methyl-1-(methylsulfonyl)piperazin-2-yl]ethyl}phenyl)-β-(tetrahydro-2H-pyran-4-yl)-L-phenylalaninamide | 581.2 |

TABLE 3-continued

| Ex # | Structure | IUPAC Name | Exact Mass [M + H]+ |
|---|---|---|---|
| 122 | 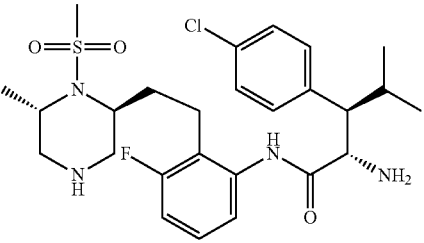 [SMILES: CC(C)[C@H](c1ccc(Cl)cc1)[C@H](N)C(=O)Nc1cccc(F)c1CC[C@H]1CNC[C@H](C)N1S(C)(=O)=O] | (βR)-4-chloro-N-(3-fluoro-2-{2-[(2S,6S)-6-methyl-1-(methylsulfonyl)piperazin-2-yl]ethyl}phenyl)-β-(1-methylethyl)-L-phenylalaninamide | 539.2 |
| 123 | 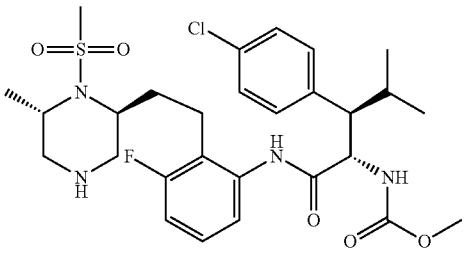 | (βR)-4-chloro-N-(3-fluoro-2-{2-[(2S,6S)-6-methyl-1-(methylsulfonyl)piperazin-2-yl]ethyl}phenyl)-Nα-(methoxycarbonyl)-β-(1-methylethyl)-L-phenylalaninamide | 597.2 |
| 124 | 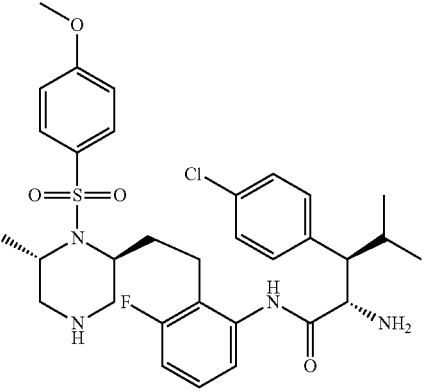 [SMILES: COc1ccc(S(=O)(=O)N2[C@@H](CCc3c(F)cccc3NC(=O)[C@@H](N)[C@@H](c3ccc(Cl)cc3)C(C)C)CNC[C@@H]2C)cc1] | (βR)-4-chloro-N-[3-fluoro-2-(2-{(2S,6S)-1-[(4-methoxyphenyl)sulfonyl]-6-methylpiperazin-2-yl}ethyl)phenyl]-β-(1-methylethyl)-L-phenylalaninamide | 631.3 |
| 125 | 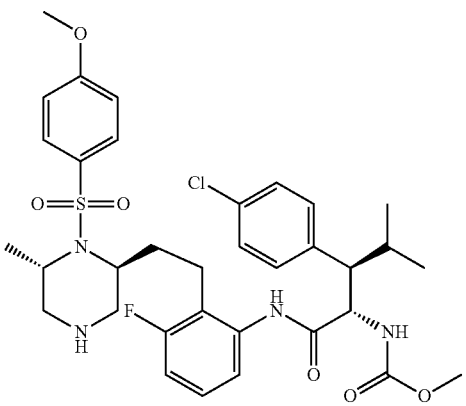 | (βR)-4-chloro-N-[3-fluoro-2-(2-{(2S,6S)-1-[(4-methoxyphenyl)sulfonyl]-6-methylpiperazin-2-yl}ethyl)phenyl]-Nα-(methoxycarbonyl)-β-(1-methylethyl)-L-phenylalaninamide | 689.3 |

TABLE 3-continued

| Ex # | Structure | IUPAC Name | Exact Mass [M + H]+ |
|---|---|---|---|
| 126 | 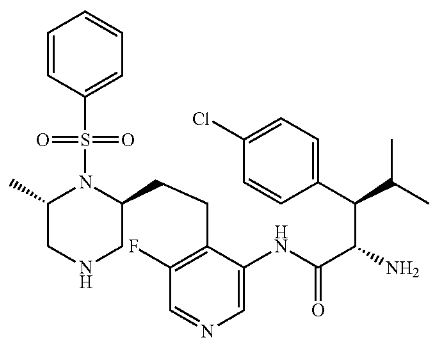 [SMILES: CC(C)[C@H](c1ccc(Cl)cc1)[C@H](N)C(=O)Nc1cncc(F)c1CC[C@H]1CNC[C@H](C)N1S(=O)(=O)c1ccccc1] | (βR)-4-chloro-N-(5-fluoro-4-{2-[(2S,6S)-6-methyl-1-(phenylsulfonyl)piperazin-2-yl]ethyl}pyridin-3-yl)-β-(1-methylethyl)-L-phenylalaninamide | 602.2 |
| 127 | 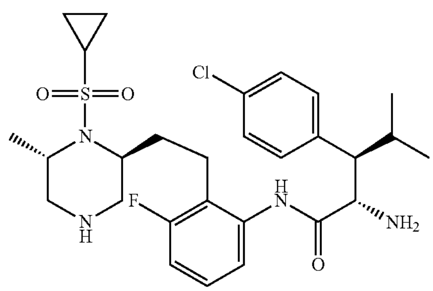 [SMILES: CC(C)[C@H](c1ccc(Cl)cc1)[C@H](N)C(=O)Nc1cccc(F)c1CC[C@H]1CNC[C@H](C)N1S(=O)(=O)C1CC1] | (βR)-4-chloro-N-(2-{2-[(2S,6S)-1-(cyclopropylsulfonyl)-6-methylpiperazin-2-yl]ethyl}-3-fluorophenyl)-β-(1-methylethyl)-L-phenylalaninamide | 565.2 |
| 128 | 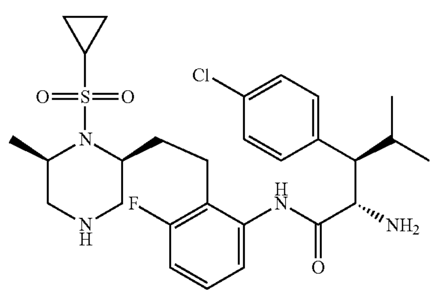 [SMILES: CC(C)[C@H](c1ccc(Cl)cc1)[C@H](N)C(=O)Nc1cccc(F)c1CC[C@H]1CNC[C@@H](C)N1S(=O)(=O)C1CC1] | (βR)-4-chloro-N-(2-{2-[(2S,6R)-1-(cyclopropylsulfonyl)-6-methylpiperazin-2-yl]ethyl}-3-fluorophenyl)-β-(1-methylethyl)-L-phenylalaninamide | 565.2 |
| 129 | 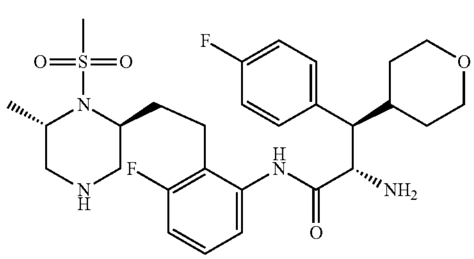 [SMILES: C[C@H]1CNC[C@H](CCc2c(F)cccc2NC(=O)[C@@H](N)[C@@H](c2ccc(F)cc2)C2CCOCC2)N1S(C)(=O)=O] | (βR)-4-fluoro-N-(3-fluoro-2-{2-[(2S,6S)-6-methyl-1-(methylsulfonyl)piperazin-2-yl]ethyl}phenyl)-β-(tetrahydro-2H-pyran-4-yl)-L-phenylalaninamide | 565.3 |
| 130 | 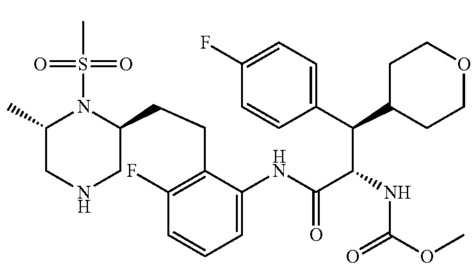 | (βR)-4-fluoro-N-(3-fluoro-2-{2-[(2S,6S)-6-methyl-1-(methylsulfonyl)piperazin-2-yl]ethyl}phenyl)-Nα-(methoxycarbonyl)-β-(tetrahydro-2H-pyran-4-yl)-L-phenylalaninamide | 623.3 |

TABLE 3-continued

| Ex # | Structure | IUPAC Name | Exact Mass [M + H]+ |
|---|---|---|---|
| 131 | 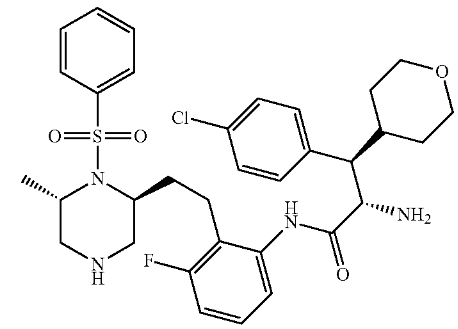 [SMILES: C[C@H]1CNC[C@H](CCc2c(F)cccc2NC(=O)[C@@H](N)[C@@H](c2ccc(Cl)cc2)C2CCOCC2)N1S(=O)(=O)c1ccccc1] | (βR)-4-chloro-N-(3-fluoro-2-{2-[(2S,6S)-6-methyl-1-(phenylsulfonyl)piperazin-2-yl]ethyl}phenyl)-β-(tetrahydro-2H-pyran-4-yl)-L-phenylalaninamide | 643.3 |
| 132 | 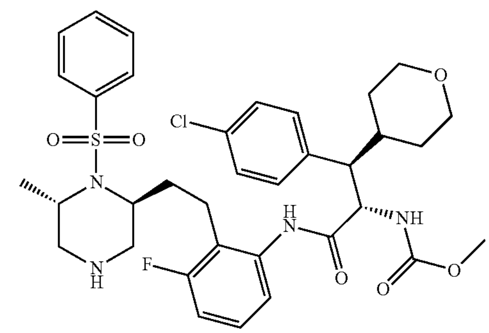 | (βR)-4-chloro-N-(3-fluoro-2-{2-[(2S,6S)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide | 701.3 |
| 133 | 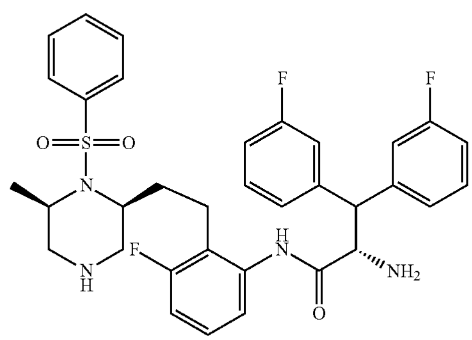 [SMILES: C[C@@H]1CNC[C@H](CCc2c(F)cccc2NC(=O)[C@@H](N)C(c2cccc(F)c2)c2cccc(F)c2)N1S(=O)(=O)c1ccccc1] | 3-fluoro-N-(3-fluoro-2-{2-[(2S,6R)-6-methyl-1-(phenylsulfonyl)piperazin-2-yl]ethyl}phenyl)-β-(3-fluorophenyl)-L-phenylalaninamide | 637.2 |
| 134 | 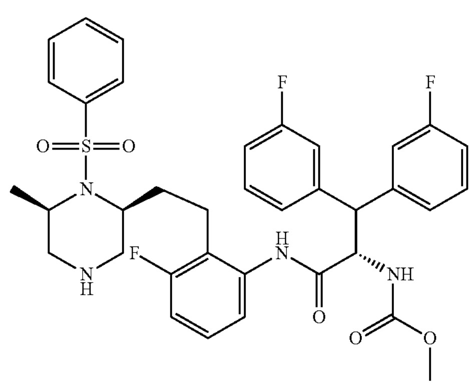 [SMILES: COC(=O)N[C@H](C(=O)Nc1cccc(F)c1CC[C@H]1CNC[C@@H](C)N1S(=O)(=O)c1ccccc1)C(c1cccc(F)c1)c1cccc(F)c1] | 3-fluoro-N-(3-fluoro-2-{2-[(2S,6R)-6-methyl-1-(phenylsulfonyl)piperazin-2-yl]ethyl}phenyl)-β-(3-fluorophenyl)-Nα-(methoxycarbonyl)-L-phenylalaninamide | 695.3 |

TABLE 3-continued

| Ex # | Structure | IUPAC Name | Exact Mass [M + H]+ |
|---|---|---|---|
| 135 | 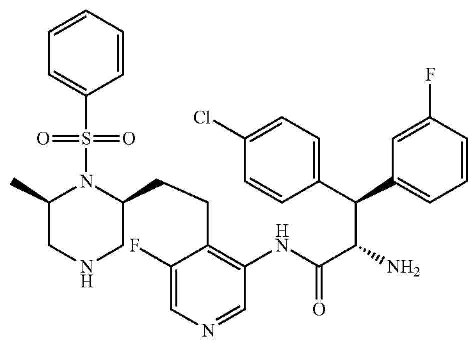 [SMILES: C[C@@H]1CNC[C@H](CCc2c(F)cncc2NC(=O)[C@@H](N)[C@@H](c2ccc(Cl)cc2)c2cccc(F)c2)N1S(=O)(=O)c1ccccc1] | (βS)-4-chloro-N-(5-fluoro-4-{2-[(2S,6R)-6-methyl-1-(phenylsulfonyl)piperazin-2-yl]ethyl}pyridin-3-yl)-β-(3-fluorophenyl)-L-phenylalaninamide | 654.2 |
| 136 | 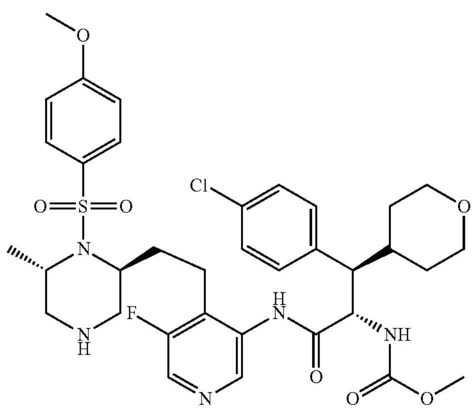 | (βR)-4-chloro-N-[5-fluoro-4-(2-{(2S,6S)-1-[(4-methoxyphenyl)sulfonyl]-6-methylpiperazin-2-yl}ethyl)pyridin-3-yl]-Nα-(methoxycarbonyl)-β-(tetrahydro-2H-pyran-4-yl)-L-phenylalaninamide | 732.3 |
| 137 | 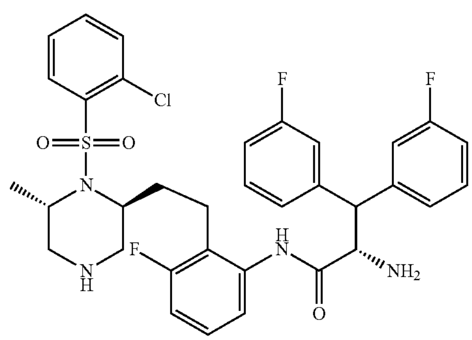 [SMILES: C[C@H]1CNC[C@H](CCc2c(F)cccc2NC(=O)[C@@H](N)C(c2cccc(F)c2)c2cccc(F)c2)N1S(=O)(=O)c1ccccc1Cl] | N-[2-(2-{(2S,6S)-1-[(2-chlorophenyl)sulfonyl]-6-methylpiperazin-2-yl}ethyl)-3-fluorophenyl]-3-fluoro-β-(3-fluorophenyl)-L-phenylalaninamide | 671.2 |
| 138 | 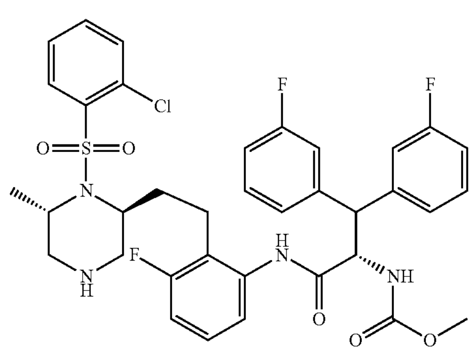 | N-[2-(2-{(2S,6S)-1-[(2-chlorophenyl)sulfonyl]-6-methylpiperazin-2-yl}ethyl)-3-fluorophenyl]-3-fluoro-β-(3-fluorophenyl)-Nα-(methoxycarbonyl)-L-phenylalaninamide | 729.2 |

TABLE 3-continued

| Ex # | Structure | IUPAC Name | Exact Mass [M + H]+ |
|---|---|---|---|
| 139 | 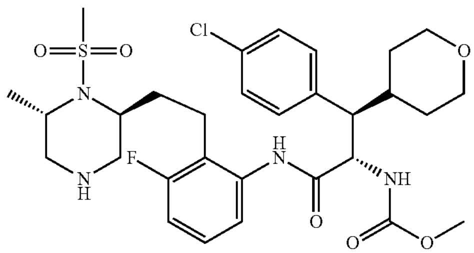 | (βR)-4-chloro-N-(3-fluoro-2-{2-[(2S,6S)-6-methyl-1-(methylsulfonyl)piperazin-2-yl]ethyl}phenyl)-Nα-(methoxycarbonyl)-β-(tetrahydro-2H-pyran-4-yl)-L-phenylalaninamide | 639.2 |
| 140 | 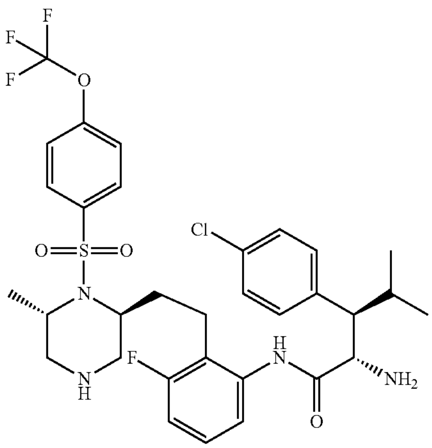 [SMILES: CC(C)[C@H](c1ccc(Cl)cc1)[C@H](N)C(=O)Nc1cccc(F)c1CC[C@H]1CNC[C@H](C)N1S(=O)(=O)c1ccc(OC(F)(F)F)cc1] | (βR)-4-chloro-N-(3-fluoro-2-{2-[(2S,6S)-6-methyl-1-{[4-(trifluoromethoxy)phenyl]sulfonyl}piperazin-2-yl]ethyl}phenyl)-β-(1-methylethyl)-L-phenylalaninamide | 685.2 |
| 141 | 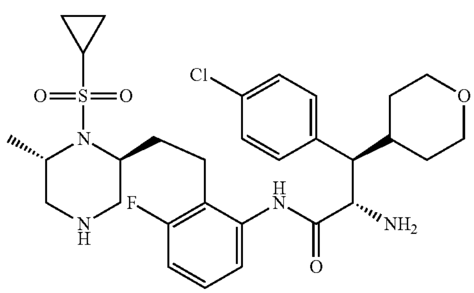 [SMILES: C[C@H]1CNC[C@H](CCc2c(F)cccc2NC(=O)[C@@H](N)[C@@H](c2ccc(Cl)cc2)C2CCOCC2)N1S(=O)(=O)C1CC1] | (βR)-4-chloro-N-(2-{2-[(2S,6S)-1-(cyclopropylsulfonyl)-6-methylpiperazin-2-yl]ethyl}-3-fluorophenyl)-β-(tetrahydro-2H-pyran-4-yl)-L-phenylalaninamide | 607.3 |
| 142 | 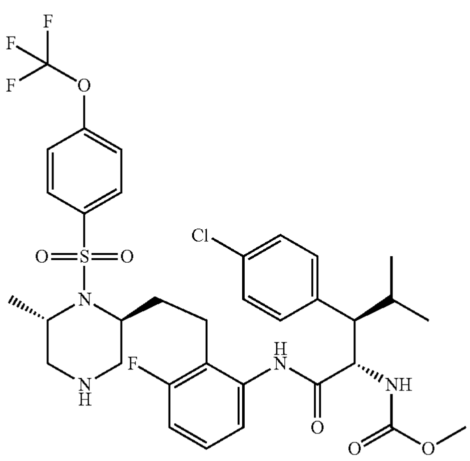 | (βR)-4-chloro-N-(3-fluoro-2-{2-[(2S,6S)-6-methyl-1-{[4-(trifluoromethoxy)phenyl]sulfonyl}piperazin-2-yl]ethyl}phenyl)-Nα-(methoxycarbonyl)-β-(1-methylethyl)-L-phenylalaninamide | 743.2 |

TABLE 3-continued

| Ex # | Structure | IUPAC Name | Exact Mass [M + H]+ |
|---|---|---|---|
| 143 | 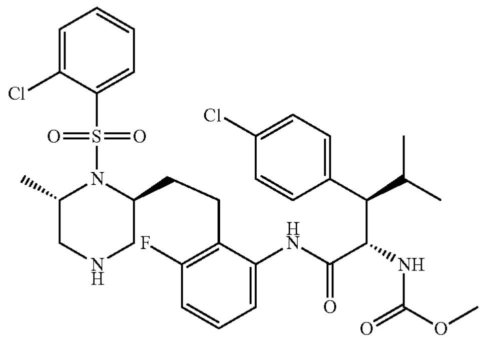 | (βR)-4-chloro-N-[2-(2-{(2S,6S)-1-[(2-chlorophenyl)sulfonyl]-6-methylpiperazin-2-yl}ethyl)-3-fluorophenyl]-Nα-(methoxycarbonyl)-β-(1-methylethyl)-L-phenylalaninamide | 693.2 |
| 144 | 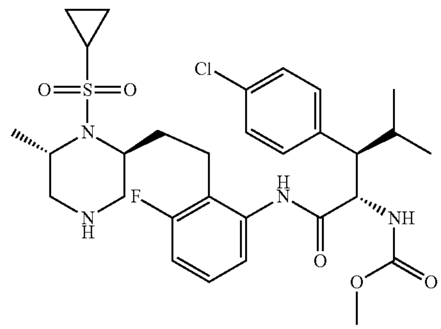 [SMILES: COC(=O)N[C@H](C(=O)Nc1cccc(F)c1CC[C@H]1CNC[C@H](C)N1S(=O)(=O)C1CC1)[C@@H](c1ccc(Cl)cc1)C(C)C] | (βR)-4-chloro-N-(2-{2-[(2S,6S)-1-(cyclopropylsulfonyl)-6-methylpiperazin-2-yl]ethyl}-3-fluorophenyl)-Nα-(methoxycarbonyl)-β-(1-methylethyl)-L-phenylalaninamide | 623.2 |
| 145 | 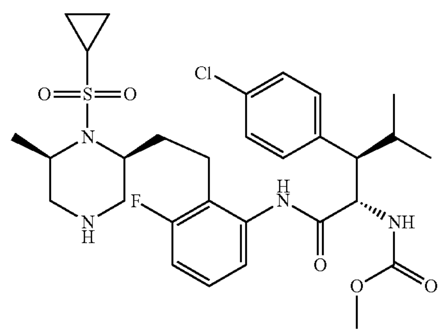 [SMILES: COC(=O)N[C@H](C(=O)Nc1cccc(F)c1CC[C@H]1CNC[C@@H](C)N1S(=O)(=O)C1CC1)[C@@H](c1ccc(Cl)cc1)C(C)C] | (βR)-4-chloro-N-(2-{2-[(2S,6R)-1-(cyclopropylsulfonyl)-6-methylpiperazin-2-yl]ethyl}-3-fluorophenyl)-Nα-(methoxycarbonyl)-β-(1-methylethyl)-L-phenylalaninamide | 623.2 |
| 146 | 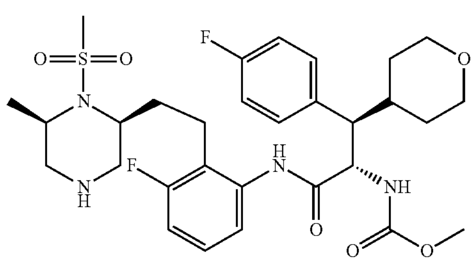 | (βR)-4-fluoro-N-(3-fluoro-2-{2-[(2S,6R)-6-methyl-1-(methylsulfonyl)piperazin-2-yl]ethyl}phenyl)-Nα-(methoxycarbonyl)-β-(tetrahydro-2H-pyran-4-yl)-L-phenylalaninamide | 623.3 |
| 147 | 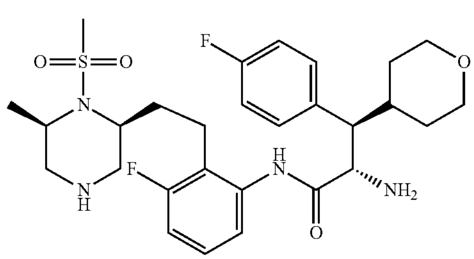 [SMILES: C[C@@H]1CNC[C@H](CCc2c(F)cccc2NC(=O)[C@@H](N)[C@@H](c2ccc(F)cc2)C2CCOCC2)N1S(C)(=O)=O] | (βR)-4-fluoro-N-(3-fluoro-2-{2-[(2S,6R)-6-methyl-1-(methylsulfonyl)piperazin-2-yl]ethyl}phenyl)-β-(tetrahydro-2H-pyran-4-yl)-L-phenylalaninamide | 565.3 |

TABLE 3-continued

| Ex # | Structure | IUPAC Name | Exact Mass [M + H]+ |
|---|---|---|---|
| 148 | 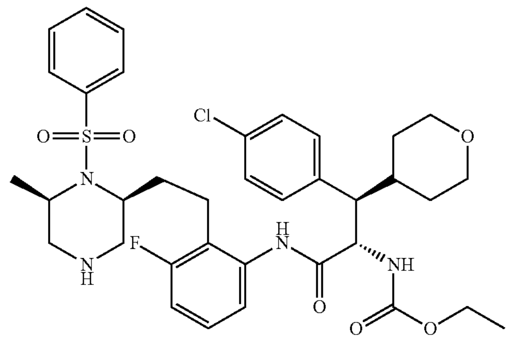 [SMILES: CCOC(=O)N[C@H](C(=O)Nc1cccc(F)c1CC[C@H]1CNC[C@@H](C)N1S(=O)(=O)c1ccccc1)[C@@H](c1ccc(Cl)cc1)C1CCOCC1] | (βR)-4-chloro-Nα-(ethoxycarbonyl)-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide | 715.3 |
| 150 | 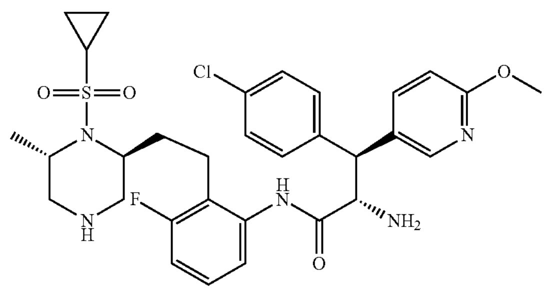 | (βS)-4-chloro-N-(2-{2-[(2S,6S)-1-(cyclopropylsulfonyl)-6-methylpiperazin-2-yl]ethyl}-3-fluorophenyl)-β-(6-methoxypyridin-3-yl)-L-phenylalaninamide | 630.2 |
| 151 | 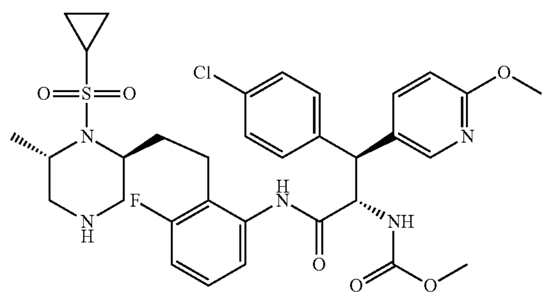 | (βS)-4-chloro-N-(2-{2-[(2S,6S)-1-(cyclopropylsulfonyl)-6-methylpiperazin-2-yl]ethyl}-3-fluorophenyl)-Nα-(methoxycarbonyl)-β-(6-methoxypyridin-3-yl)-L-phenylalaninamide | 688.2 |
| 152 | 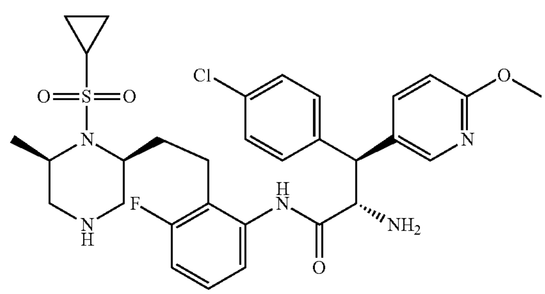 | (βS)-4-chloro-N-(2-{2-[(2S,6S)-1-(cyclopropylsulfonyl)-6-methylpiperazin-2-yl]ethyl}-3-fluorophenyl)-β-(6-methoxypyridin-3-yl)-L-phenylalaninamide | 630.2 |
| 153 | 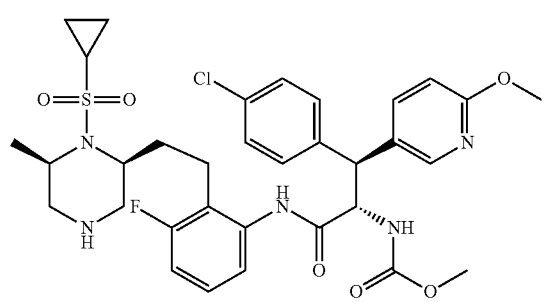 | (βS)-4-chloro-N-(2-{2-[(2S,6R)-1-(cyclopropylsulfonyl)-6-methylpiperazin-2-yl]ethyl}-3-fluorophenyl)-Nα-(methoxycarbonyl)-β-(6-methoxypyridin-3-yl)-L-phenylalaninamide | 688.2 |

TABLE 3-continued

| Ex # | Structure | IUPAC Name | Exact Mass [M + H]+ |
|---|---|---|---|
| 154 | 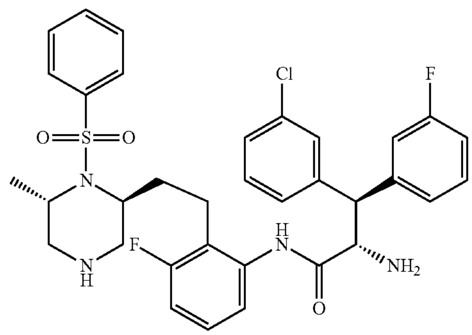 [SMILES: C[C@H]1CNC[C@H](CCc2c(F)cccc2NC(=O)[C@@H](N)[C@H](c2cccc(F)c2)c2cccc(Cl)c2)N1S(=O)(=O)c1ccccc1] | (βR)-3-chloro-N-(3-fluoro-2-{2-[(2S,6S)-6-methyl-1-(phenylsulfonyl)piperazin-2-yl]ethyl}phenyl)-β-(3-fluorophenyl)-L-phenylalaninamide | 653.2 |
| 155 | 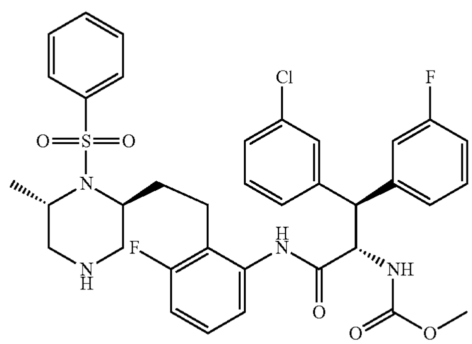 | (βR)-3-chloro-N-(3-fluoro-2-{2-[(2S,6S)-6-methyl-1-(phenylsulfonyl)piperazin-2-yl]ethyl}phenyl)-β-(3-fluorophenyl)-Nα-(methoxycarbonyl)-L-phenylalaninamide | 711.2 |
| 156 | 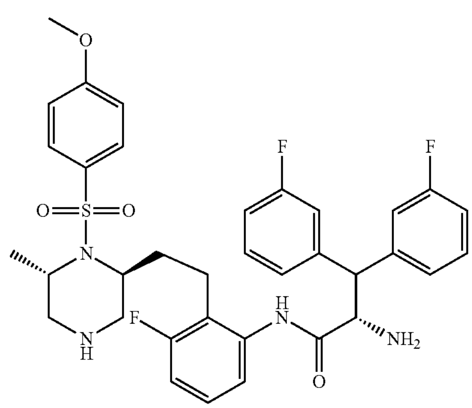 [SMILES: COc1ccc(S(=O)(=O)N2[C@@H](CCc3c(F)cccc3NC(=O)[C@@H](N)C(c3cccc(F)c3)c3cccc(F)c3)CNC[C@@H]2C)cc1] | 3-fluoro-N-[3-fluoro-2-(2-{(2S,6S)-1-[(4-methoxyphenyl)sulfonyl]-6-methylpiperazin-2-yl}ethyl)phenyl]-β-(3-fluorophenyl)-L-phenylalaninamide | 667.3 |
| 157 | 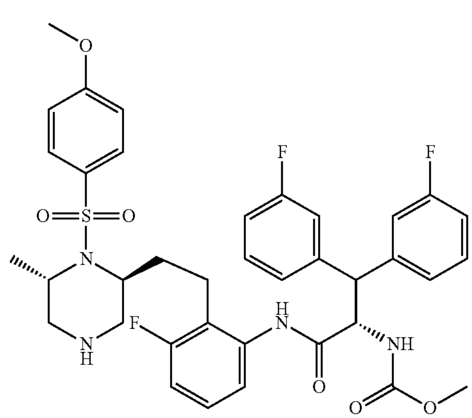 | 3-fluoro-N-[3-fluoro-2-(2-{(2S,6S)-1-[(4-methoxyphenyl)sulfonyl]-6-methylpiperazin-2-yl}ethyl)phenyl]-β-(3-fluorophenyl)-Nα-(methoxycarbonyl)-L-phenylalaninamide | 725.3 |

| Ex # | Structure | IUPAC Name | Exact Mass [M + H]+ |
|---|---|---|---|
| 158 | 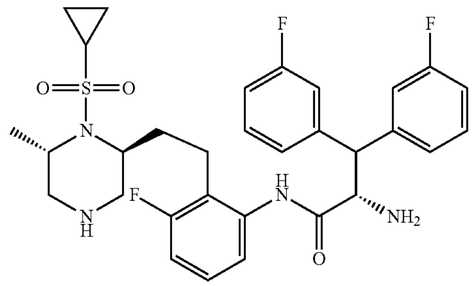 [SMILES: C[C@H]1CNC[C@H](CCc2c(F)cccc2NC(=O)[C@@H](N)C(c2cccc(F)c2)c2cccc(F)c2)N1S(=O)(=O)C1CC1] | N-(2-{2-[(2S,6S)-1-(cyclopropylsulfonyl)-6-methylpiperazin-2-yl]ethyl}-3-fluorophenyl)-3-fluoro-β-(3-fluorophenyl)-L-phenylalaninamide | 601.2 |
| 159 | 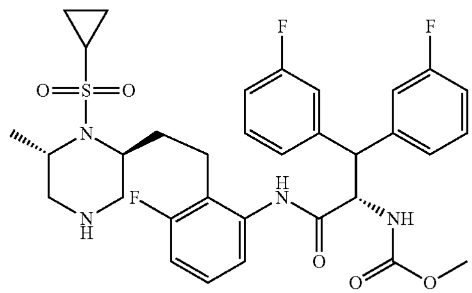 | N-(2-{2-[(2S,6S)-1-(cyclopropylsulfonyl)-6-methylpiperazin-2-yl]ethyl}-3-fluorophenyl)-3-fluoro-β-(3-fluorophenyl)-Nα-(methoxycarbonyl)-L-phenylalaninamide | 659.3 |
| 160 | 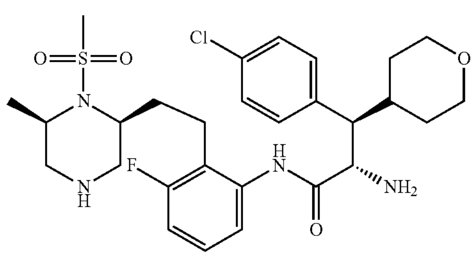 [SMILES: C[C@@H]1CNC[C@H](CCc2c(F)cccc2NC(=O)[C@@H](N)[C@@H](c2ccc(Cl)cc2)C2CCOCC2)N1S(C)(=O)=O] | (βR)-4-chloro-N-(3-fluoro-2-{2-[(2S,6R)-6-methyl-1-(methylsulfonyl)piperazin-2-yl]ethyl}phenyl)-β-(tetrahydro-2H-pyran-4-yl)-L-phenylalaninamide | 581.2 |
| 162 | 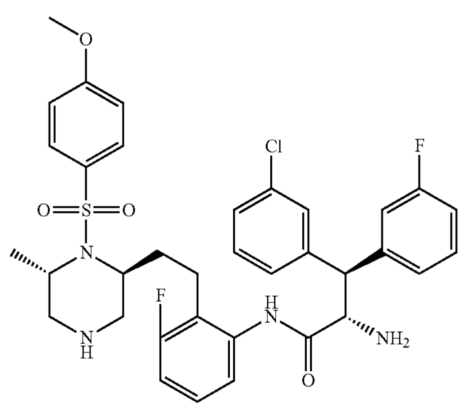 [SMILES: COc1ccc(S(=O)(=O)N2[C@@H](CCc3c(F)cccc3NC(=O)[C@@H](N)[C@H](c3cccc(F)c3)c3cccc(Cl)c3)CNC[C@@H]2C)cc1] | (βR)-3-chloro-N-[3-fluoro-2-(2-{(2S,6S)-1-[(4-methoxyphenyl)sulfonyl]-6-methylpiperazin-2-yl}ethyl)phenyl]-β-(3-fluorophenyl)-L-phenylalaninamide | 683.2 |

TABLE 3-continued

| Ex # | Structure | IUPAC Name | Exact Mass [M + H]+ |
|---|---|---|---|
| 163 | 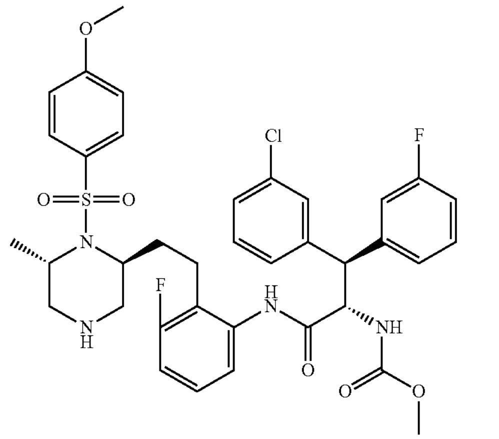 [SMILES: COC(=O)N[C@H](C(=O)Nc1cccc(F)c1CC[C@H]1CNC[C@H](C)N1S(=O)(=O)c1ccc(OC)cc1)[C@H](c1cccc(F)c1)c1cccc(Cl)c1] | (βR)-3-chloro-N-[3-fluoro-2-(2-{(2S,6S)-1-[(4-methoxyphenyl)sulfonyl]-6-methylpiperazin-2-yl}ethyl)phenyl]-β-(3-fluorophenyl)-Nα-(methoxycarbonyl)-L-phenylalaninamide | 741.2 |
| 164 | 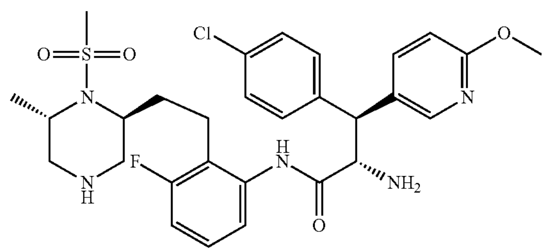 | (βS)-4-chloro-N-(3-fluoro-2-{2-[(2S,6S)-6-methyl-1-(methylsulfonyl)piperazin-2-yl]ethyl}phenyl)-β-(6-methoxypyridin-3-yl)-L-phenylalaninamide | 604.2 |
| 165 | 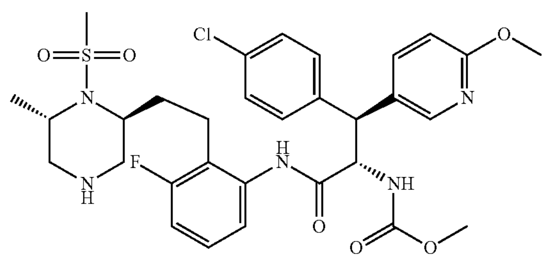 | (βS)-4-chloro-N-(3-fluoro-2-{2-[(2S,6S)-6-methyl-1-(methylsulfonyl)piperazin-2-yl]ethyl}phenyl)-Nα-(methoxycarbonyl)-β-(6-methoxypyridin-3-yl)-L-phenylalaninamide | 662.2 |
| 166 | 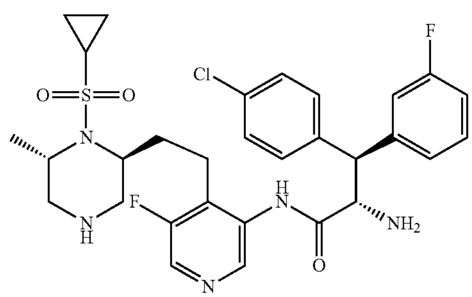 [SMILES: C[C@H]1CNC[C@H](CCc2c(F)cncc2NC(=O)[C@@H](N)[C@@H](c2ccc(Cl)cc2)c2cccc(F)c2)N1S(=O)(=O)C1CC1] | (βS)-4-chloro-N-(4-{2-[(2S,6S)-1-(cyclopropylsulfonyl)-6-methylpiperazin-2-yl]ethyl}-5-fluoropyridin-3-yl)-β-(3-fluorophenyl)-L-phenylalaninamide | 618.2 |
| 167 | 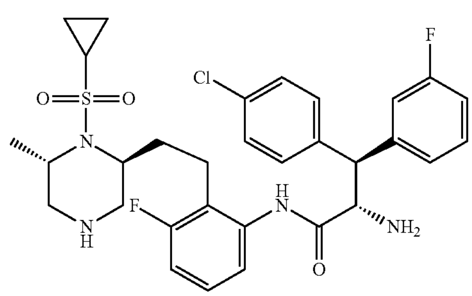 [SMILES: C[C@H]1CNC[C@H](CCc2c(F)cccc2NC(=O)[C@@H](N)[C@@H](c2ccc(Cl)cc2)c2cccc(F)c2)N1S(=O)(=O)C1CC1] | (βS)-4-chloro-N-(2-{2-[(2S,6S)-1-(cyclopropylsulfonyl)-6-methylpiperazin-2-yl]ethyl}-3-fluorophenyl)-β-(3-fluorophenyl)-L-phenylalaninamide | 617.2 |

TABLE 3-continued

| Ex # | Structure | IUPAC Name | Exact Mass [M + H]+ |
|---|---|---|---|
| 168 | 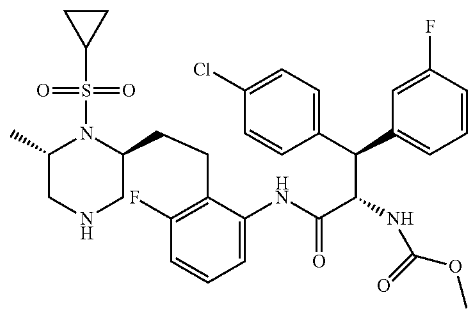 [SMILES: COC(=O)N[C@H](C(=O)Nc1cccc(F)c1CC[C@H]1CNC[C@H](C)N1S(=O)(=O)C1CC1)[C@@H](c1ccc(Cl)cc1)c1cccc(F)c1] | (βS)-4-chloro-N-(2-{2-[(2S,6S)-1-(cyclopropylsulfonyl)-6-methylpiperazin-2-yl]ethyl}-3-fluorophenyl)-β-(3-fluorophenyl)-Nα-(methoxycarbonyl)-L-phenylalaninamide | 675.2 |
| 169 | 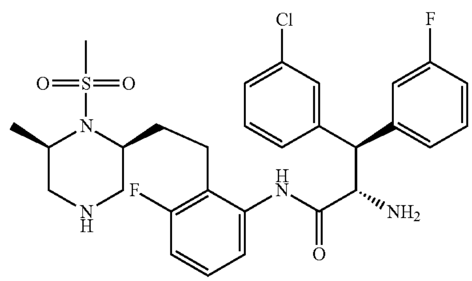 [SMILES: C[C@@H]1CNC[C@H](CCc2c(F)cccc2NC(=O)[C@@H](N)[C@H](c2cccc(F)c2)c2cccc(Cl)c2)N1S(C)(=O)=O] | (βR)-3-chloro-N-(3-fluoro-2-{2-[(2S,6R)-6-methyl-1-(methylsulfonyl)piperazin-2-yl]ethyl}phenyl)-β-(3-fluorophenyl)-L phenylalaninamide | 591.2 |
| 170 | 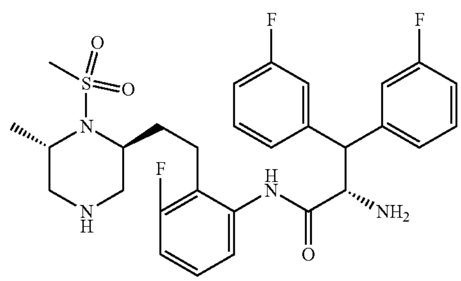 [SMILES: C[C@H]1CNC[C@H](CCc2c(F)cccc2NC(=O)[C@@H](N)C(c2cccc(F)c2)c2cccc(F)c2)N1S(C)(=O)=O] | 3-fluoro-N-(3-fluoro-2-{2-[(2S,6S)-6-methyl-1-(methylsulfonyl)piperazin-2-yl]ethyl}phenyl)-β-(3-fluorophenyl)-L-phenylalaninamide | 575.2 |
| 171 | 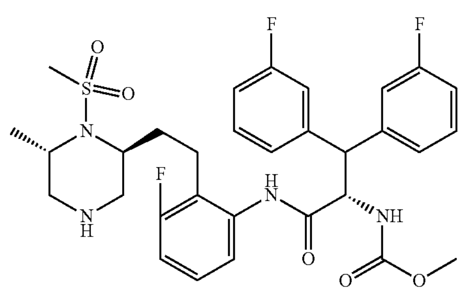 | 3-fluoro-N-(3-fluoro-2-{2-[(2S,6S)-6-methyl-1-(methylsulfonyl)piperazin-2-yl]ethyl}phenyl)-β-(3-fluorophenyl)-Nα-(methoxycarbonyl)-L-phenylalaninamide | 633.2 |
| 172 | 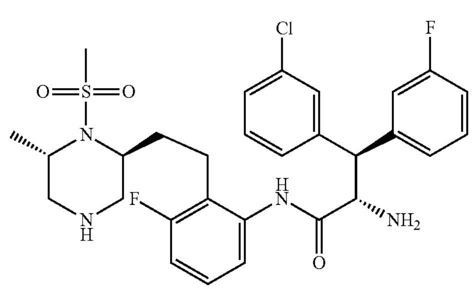 [SMILES: C[C@H]1CNC[C@H](CCc2c(F)cccc2NC(=O)[C@@H](N)[C@H](c2cccc(F)c2)c2cccc(Cl)c2)N1S(C)(=O)=O] | (βR)-3-chloro-N-(3-fluoro-2-{2-[(2S,6S)-6-methyl-1-(methylsulfonyl)piperazin-2-yl]ethyl}phenyl)-β-(3-fluorophenyl)-L-phenylalaninamide | 591.2 |

TABLE 3-continued

| Ex # | Structure | IUPAC Name | Exact Mass [M + H]+ |
|---|---|---|---|
| 173 | 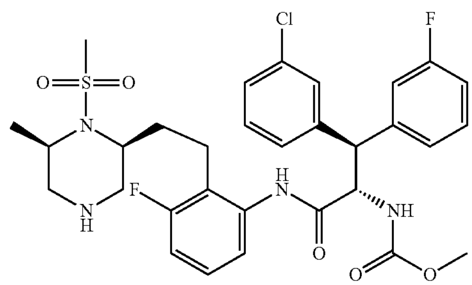 | (βR)-3-chloro-N-(3-fluoro-2-{2-[(2S,6R)-6-methyl-1-(methylsulfonyl)piperazin-2-yl]ethyl}phenyl)-β-(3-fluorophenyl)-Nα-(methoxycarbonyl)-L-phenylalaninamide | 649.2 |
| 174 | 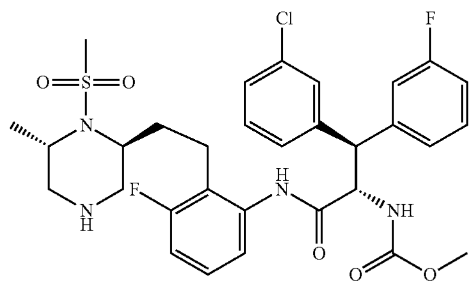 | (βR)-3-chloro-N-(3-fluoro-2-{2-[(2S,6S)-6-methyl-1-(methylsulfonyl)piperazin-2-yl]ethyl}phenyl)-β-(3-fluorophenyl)-Nα-(methoxycarbonyl)-L-phenylalaninamide | 649.2 |
| 175 | 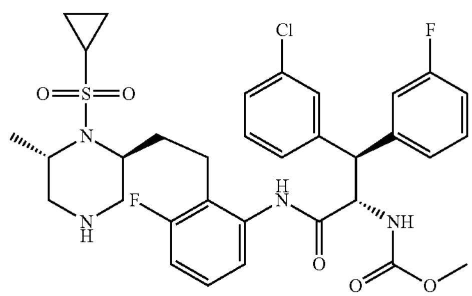 | (βR)-3-chloro-N-(2-{2-[(2S,6S)-1-(cyclopropylsulfonyl)-6-methylpiperazin-2-yl]ethyl}-3-fluorophenyl)-β-(3-fluorophenyl)-Nα-(methoxycarbonyl)-L-phenylalaninamide | 675.2 |
| 176 | 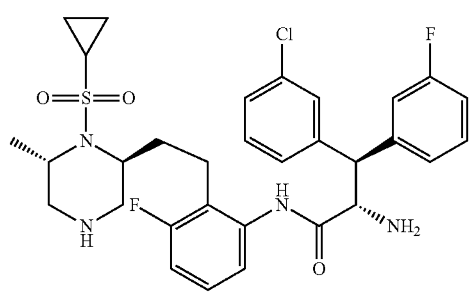 [SMILES: C[C@H]1CNC[C@H](CCc2c(F)cccc2NC(=O)[C@@H](N)[C@H](c2cccc(F)c2)c2cccc(Cl)c2)N1S(=O)(=O)C1CC1] | (βR)-3-chloro-N-(2-{2-[(2S,6S)-1-(cyclopropylsulfonyl)-6-methylpiperazin-2-yl]ethyl}-3-fluorophenyl)-β-(3-fluorophenyl)-L-phenylalaninamide | 617.2 |
| 177 | 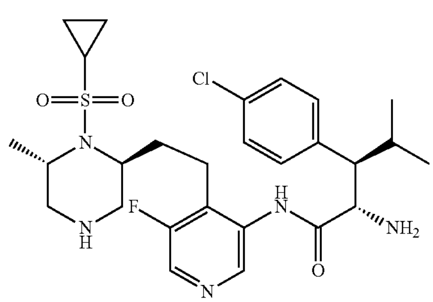 [SMILES: CC(C)[C@H](c1ccc(Cl)cc1)[C@H](N)C(=O)Nc1cncc(F)c1CC[C@H]1CNC[C@H](C)N1S(=O)(=O)C1CC1] | (βR)-4-chloro-N-(4-{2-[(2S,6S)-1-(cyclopropylsulfonyl)-6-methylpiperazin-2-yl]ethyl}-5-fluoropyridin-3-yl)-β-(1-methylethyl)-L-phenylalaninamide | 566.2 |

TABLE 3-continued

| Ex # | Structure | IUPAC Name | Exact Mass [M + H]+ |
|---|---|---|---|
| 178 | 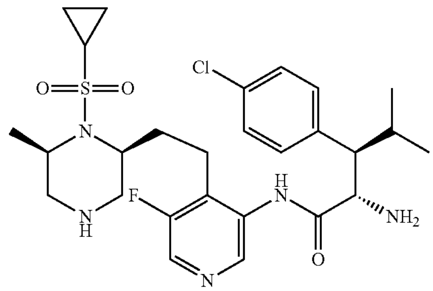 [SMILES: CC(C)[C@H](c1ccc(Cl)cc1)[C@H](N)C(=O)Nc1cncc(F)c1CC[C@H]1CNC[C@@H](C)N1S(=O)(=O)C1CC1] | (βR)-4-chloro-N-(4-{2-[(2S,6R)-1-(cyclopropylsulfonyl)-6-methylpiperazin-2-yl]ethyl}-5-fluoropyridin-3-yl)-β-(1-methylethyl)-L-phenylalaninamide | 566.2 |
| 179 | 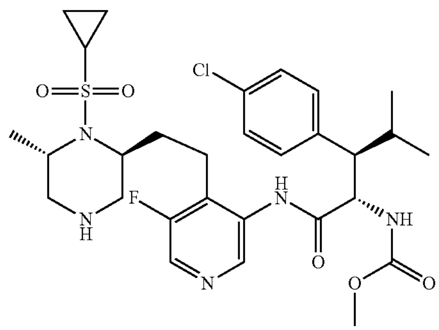 [SMILES: COC(=O)N[C@H](C(=O)Nc1cncc(F)c1CC[C@H]1CNC[C@H](C)N1S(=O)(=O)C1CC1)[C@@H](c1ccc(Cl)cc1)C(C)C] | (βR)-4-chloro-N-(4-{2-[(2S,6S)-1-(cyclopropylsulfonyl)-6-methylpiperazin-2-yl]ethyl}-5-fluoropyridin-3-yl)-Nα-(methoxycarbonyl)-β-(1-methylethyl)-L-phenylalaninamide | 624.2 |
| 180 | 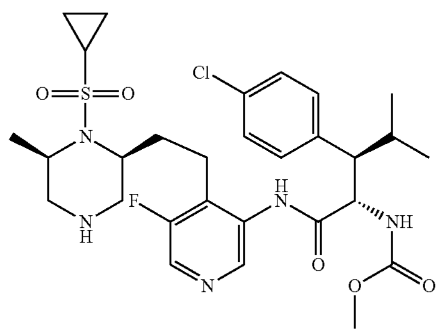 | (βR)-4-chloro-N-(4-{2-[(2S,6R)-1-(cyclopropylsulfonyl)-6-methylpiperazin-2-yl]ethyl}-5-fluoropyridin-3-yl)-Nα-(methoxycarbonyl)-β-(1-methylethyl)-L-phenylalaninamide | 624.2 |
| 181 | 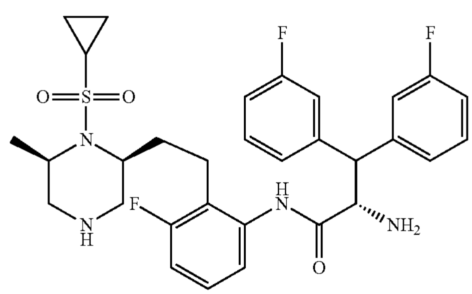 [SMILES: C[C@@H]1CNC[C@H](CCc2c(F)cccc2NC(=O)[C@@H](N)C(c2cccc(F)c2)c2cccc(F)c2)N1S(=O)(=O)C1CC1] | N-(2-{2-[(2S,6R)-1-(cyclopropylsulfonyl)-6-methylpiperazin-2-yl]ethyl}-3-fluorophenyl)-3-fluoro-β-(3-fluorophenyl)-L-phenylalaninamide | 601.2 |
| 182 | 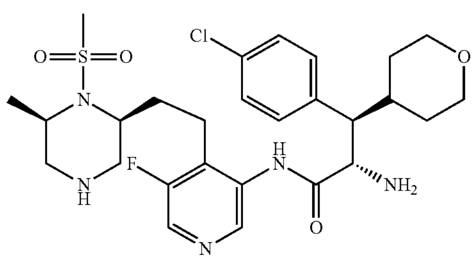 [SMILES: C[C@@H]1CNC[C@H](CCc2c(F)cncc2NC(=O)[C@@H](N)[C@@H](c2ccc(Cl)cc2)C2CCOCC2)N1S(C)(=O)=O] | (βR)-4-chloro-N-(5-fluoro-4-{2-[(2S,6R)-6-methyl-1-(methylsulfonyl)piperazin-2-yl]ethyl}pyridin-3-yl)-β-(tetrahydro-2H-pyran-4-yl)-L-phenylalaninamide | 582.2 |

| Ex # | Structure | IUPAC Name | Exact Mass [M + H]+ |
|---|---|---|---|
| 183 | 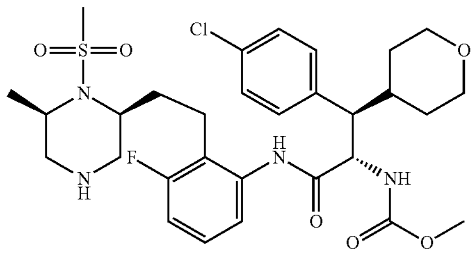 | (βR)-4-chloro-N-(3-fluoro-2-{2-[(2S,6R)-6-methyl-1-(methylsulfonyl)piperazin-2-yl]ethyl}phenyl)-Nα-(methoxycarbonyl)-β-(tetrahydro-2H-pyran-4-yl)-L-phenylalaninamide | 639.2 |
| 184 | 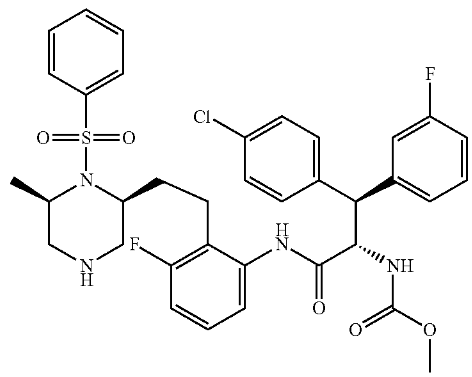 [SMILES: COC(=O)N[C@H](C(=O)Nc1cccc(F)c1CC[C@H]1CNC[C@@H](C)N1S(=O)(=O)c1ccccc1)[C@@H](c1ccc(Cl)cc1)c1cccc(F)c1] | (βS)-4-chloro-N-(3-fluoro-2-{2-[(2S,6R)-6-methyl-1-(phenylsulfonyl)piperazin-2-yl]ethyl}phenyl)-β-(3-fluorophenyl)-Nα-(methoxycarbonyl)-L-phenylalaninamide | 711.2 |
| 185 | 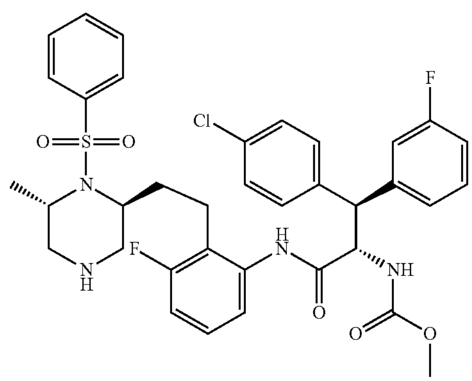 [SMILES: COC(=O)N[C@H](C(=O)Nc1cccc(F)c1CC[C@H]1CNC[C@H](C)N1S(=O)(=O)c1ccccc1)[C@@H](c1ccc(Cl)cc1)c1cccc(F)c1] | (βS)-4-chloro-N-(3-fluoro-2-{2-[(2S,6S)-6-methyl-1-(phenylsulfonyl)piperazin-2-yl]ethyl}phenyl)-β-(3-fluorophenyl)-Nα-(methoxycarbonyl)-L-phenylalaninamide | 711.2 |
| 186 | 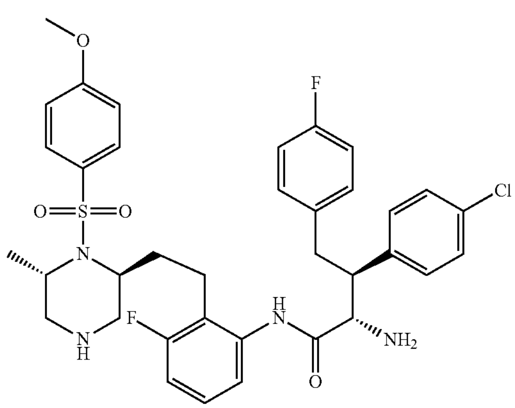 [SMILES: COc1ccc(S(=O)(=O)N2[C@@H](CCc3c(F)cccc3NC(=O)[C@@H](N)[C@@H](Cc3ccc(F)cc3)c3ccc(Cl)cc3)CNC[C@@H]2C)cc1] | (βS)-4-chloro-β-(4-fluorobenzyl)-N-[3-fluoro-2-(2-{(2S,6S)-1-[(4-methoxyphenyl)sulfonyl]-6-methylpiperazin-2-yl}ethyl)phenyl]-L-phenylalaninamide | 697.2 |

TABLE 3-continued

| Ex # | Structure | IUPAC Name | Exact Mass [M + H]+ |
|---|---|---|---|
| 187 | 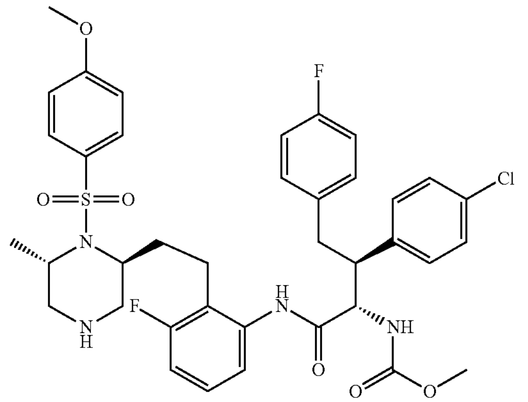 [SMILES: COC(=O)N[C@H](C(=O)Nc1cccc(F)c1CC[C@H]1CNC[C@H](C)N1S(=O)(=O)c1ccc(OC)cc1)[C@@H](Cc1ccc(F)cc1)c1ccc(Cl)cc1] | (βS)-4-chloro-β-(4-fluorobenzyl)-N-[3-fluoro-2-(2-{(2S,6S)-1-[(4-methoxyphenyl)sulfonyl]-6-methylpiperazin-2-yl}ethyl)phenyl]-Nα-(methoxycarbonyl)-L-phenylalaninamide | 755.2 |
| 188 | 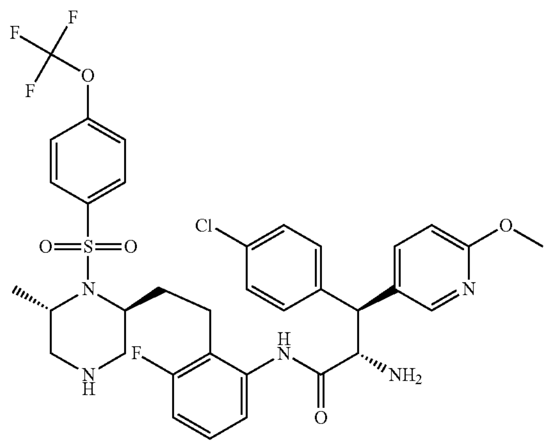 | (βS)-4-chloro-N-(3-fluoro-2-{2-[(2S,6S)-6-methyl-1-{[4-(trifluoromethoxy)phenyl]sulfonyl}piperazin-2-yl]ethyl}phenyl)-β-(6-methoxypyridin-3-yl)-L-phenylalaninamide | 750.2 |
| 189 | 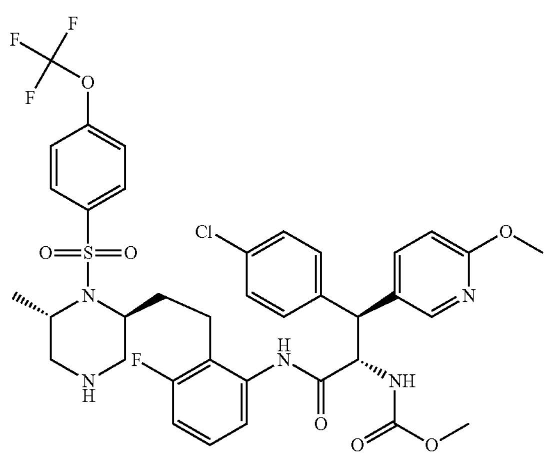 | (βS)-4-chloro-N-(3-fluoro-2-{2-[(2S,6S)-6-methyl-1-{[4-(trifluoromethoxy)phenyl]sulfonyl}piperazin-2-yl]ethyl}phenyl)-Nα-(methoxycarbonyl)-β-(6-methoxypyridin-3-yl)-L-phenylalaninamide | 808.2 |

TABLE 3-continued

| Ex # | Structure | IUPAC Name | Exact Mass [M + H]+ |
|---|---|---|---|
| 190 | 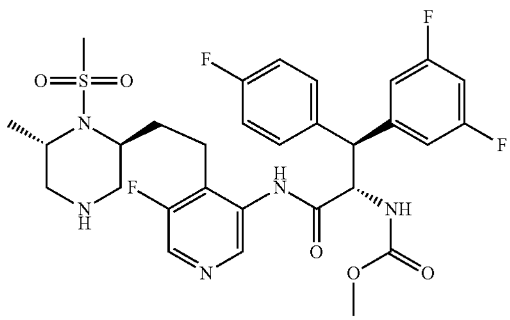 [SMILES: COC(=O)N[C@H](C(=O)Nc1cncc(F)c1CC[C@H]1CNC[C@H](C)N1S(C)(=O)=O)[C@@H](c1ccc(F)cc1)c1cc(F)cc(F)c1] | (βS)-β-(3,5-difluorophenyl)-4-fluoro-N-(5-fluoro-4-{2-[(2S,6S)-6-methyl-1-(methylsulfonyl)piperazin-2-yl]ethyl}pyridin-3-yl)-Nα-(methoxycarbonyl)-L-phenylalaninamide | 652.2 |
| 191 | 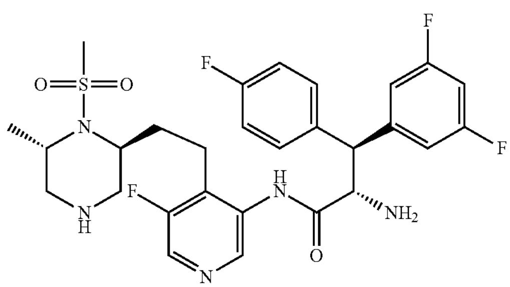 [SMILES: C[C@H]1CNC[C@H](CCc2c(F)cncc2NC(=O)[C@@H](N)[C@@H](c2ccc(F)cc2)c2cc(F)cc(F)c2)N1S(C)(=O)=O] | (βS)-β-(3,5-difluorophenyl)-4-fluoro-N-(5-fluoro-4-{2-[(2S,6S)-6-methyl-1-(methylsulfonyl)piperazin-2-yl]ethyl}pyridin-3-yl)-L-phenylalaninamide | 594.2 |
| 192 | 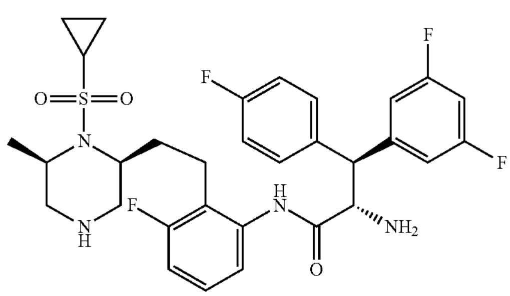 [SMILES: C[C@@H]1CNC[C@H](CCc2c(F)cccc2NC(=O)[C@@H](N)[C@@H](c2ccc(F)cc2)c2cc(F)cc(F)c2)N1S(=O)(=O)C1CC1] | (βS)-N-(2-{2-[(2S,6R)-1-(cyclopropylsulfonyl)-6-methylpiperazin-2-yl]ethyl}-3-fluorophenyl)-β-(3,5-difluorophenyl)-4-fluoro-L-phenylalaninamide | 619.2 |
| 193 | 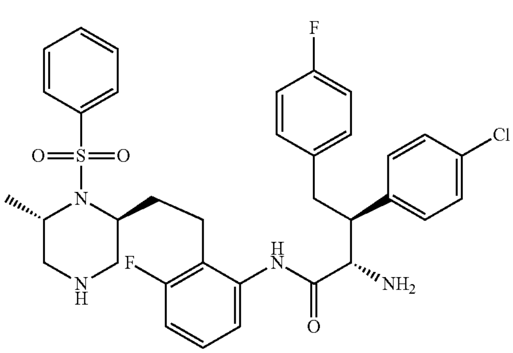 [SMILES: C[C@H]1CNC[C@H](CCc2c(F)cccc2NC(=O)[C@@H](N)[C@@H](Cc2ccc(F)cc2)c2ccc(Cl)cc2)N1S(=O)(=O)c1ccccc1] | (βS)-4-chloro-β-(4-fluorobenzyl)-N-(3-fluoro-2-{2-[(2S,6S)-6-methyl-1-(phenylsulfonyl)piperazin-2-yl]ethyl}phenyl)-L-phenylalaninamide | 667.2 |

TABLE 3-continued

| Ex # | Structure | IUPAC Name | Exact Mass [M + H]+ |
|---|---|---|---|
| 194 | 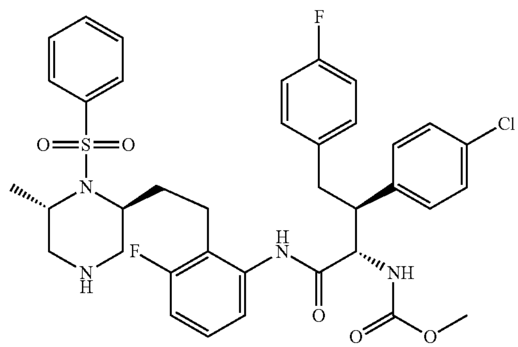 [SMILES: COC(=O)N[C@H](C(=O)Nc1cccc(F)c1CC[C@H]1CNC[C@H](C)N1S(=O)(=O)c1ccccc1)[C@@H](Cc1ccc(F)cc1)c1ccc(Cl)cc1] | (βS)-4-chloro-β-(4-fluorobenzyl)-N-(3-fluoro-2-{2-[(2S,6S)-6-methyl-1-(phenylsulfonyl)piperazin-2-yl]ethyl}phenyl)-Nα-(methoxycarbonyl)-L-phenylalaninamide | 725.2 |
| 195 | 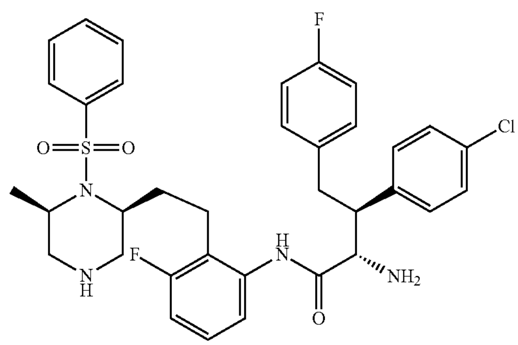 [SMILES: C[C@@H]1CNC[C@H](CCc2c(F)cccc2NC(=O)[C@@H](N)[C@@H](Cc2ccc(F)cc2)c2ccc(Cl)cc2)N1S(=O)(=O)c1ccccc1] | (βS)-4-chloro-β-(4-fluorobenzyl)-N-(3-fluoro-2-{2-[(2S,6R)-6-methyl-1-(phenylsulfonyl)piperazin-2-yl]ethyl}phenyl)-L-phenylalaninamide | 667.2 |
| 196 | 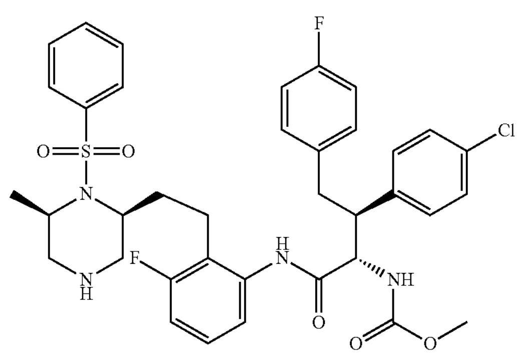 [SMILES: COC(=O)N[C@H](C(=O)Nc1cccc(F)c1CC[C@H]1CNC[C@@H](C)N1S(=O)(=O)c1ccccc1)[C@@H](Cc1ccc(F)cc1)c1ccc(Cl)cc1] | (βS)-4-chloro-β-(4-fluorobenzyl)-N-(3-fluoro-2-{2-[(2S,6R)-6-methyl-1-(phenylsulfonyl)piperazin-2-yl]ethyl}phenyl)-Nα-(methoxycarbonyl)-L-phenylalaninamide | 725.2 |
| 197 | 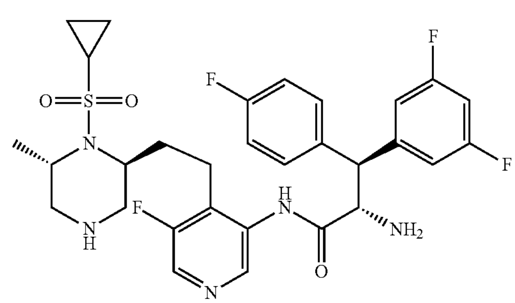 [SMILES: C[C@H]1CNC[C@H](CCc2c(F)cncc2NC(=O)[C@@H](N)[C@@H](c2ccc(F)cc2)c2cc(F)cc(F)c2)N1S(=O)(=O)C1CC1] | (BS)-N-(4-{2-[(2S,6S)-1-(cyclopropylsulfonyl)-6-methylpiperazin-2-yl]ethyl}-5-fluoropyridin-3-yl)-β-(3,5-difluorophenyl)-4-fluoro-L-phenylalaninamide | 620.2 |

TABLE 3-continued

| Ex # | Structure | IUPAC Name | Exact Mass [M + H]+ |
|---|---|---|---|
| 198 | 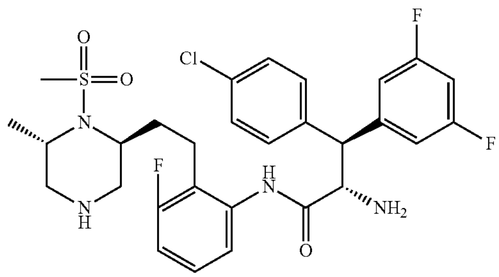 [SMILES: C[C@H]1CNC[C@H](CCc2c(F)cccc2NC(=O)[C@@H](N)[C@@H](c2ccc(Cl)cc2)c2cc(F)cc(F)c2)N1S(C)(=O)=O] | (βS)-4-chloro-β-(3,5-difluorophenyl)-N-(3-fluoro-2-{2-[(2S,6S)-6-methyl-1-(methylsulfonyl)piperazin-2-yl]ethyl}phenyl)-L-phenylalaninamide | 609.2 |
| 199 | 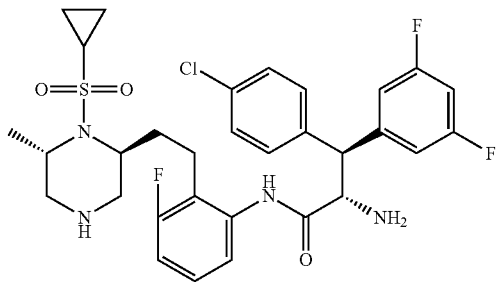 [SMILES: C[C@H]1CNC[C@H](CCc2c(F)cccc2NC(=O)[C@@H](N)[C@@H](c2ccc(Cl)cc2)c2cc(F)cc(F)c2)N1S(=O)(=O)C1CC1] | (βS)-4-chloro-N-(2-{2-[(2S,6S)-1-(cyclopropylsulfonyl)-6-methylpiperazin-2-yl]ethyl}-3-fluorophenyl)-β-(3,5-difluorophenyl)-L-phenylalaninamide | 635.2 |
| 200 | 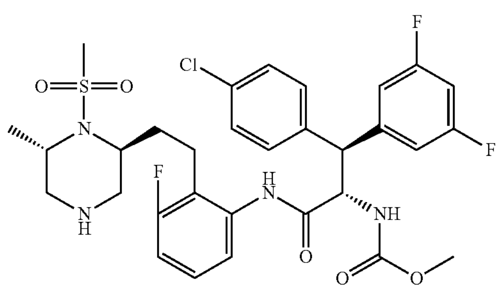 [SMILES: COC(=O)N[C@H](C(=O)Nc1cccc(F)c1CC[C@H]1CNC[C@H](C)N1S(C)(=O)=O)[C@@H](c1ccc(Cl)cc1)c1cc(F)cc(F)c1] | (βS)-4-chloro-β-(3,5-difluorophenyl)-N-(3-fluoro-2-{2-[(2S,6S)-6-methyl-1-(methylsulfonyl)piperazin-2-yl]ethyl}phenyl)-Nα-(methoxycarbonyl)-L-phenylalaninamide | 667.2 |
| 201 | 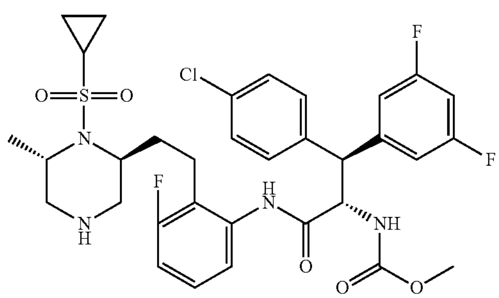 [SMILES: COC(=O)N[C@H](C(=O)Nc1cccc(F)c1CC[C@H]1CNC[C@H](C)N1S(=O)(=O)C1CC1)[C@@H](c1ccc(Cl)cc1)c1cc(F)cc(F)c1] | (βS)-4-chloro-N-(2-{2-[(2S,6S)-1-(cyclopropylsulfonyl)-6-methylpiperazin-2-yl]ethyl}-3-fluorophenyl)-β-(3,5-difluorophenyl)-Nα-(methoxycarbonyl)-L-phenylalaninamide | 693.2 |
| 202 | 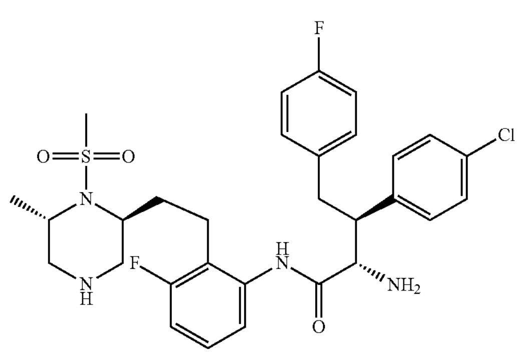 [SMILES: C[C@H]1CNC[C@H](CCc2c(F)cccc2NC(=O)[C@@H](N)[C@@H](Cc2ccc(F)cc2)c2ccc(Cl)cc2)N1S(C)(=O)=O] | (βS)-4-chloro-β-(4-fluorobenzyl)-N-(3-fluoro-2-{2-[(2S,6S)-6-methyl-1-(methylsulfonyl)piperazin-2-yl]ethyl}phenyl)-L-phenylalaninamide | 605.2 |

TABLE 3-continued

| Ex # | Structure | IUPAC Name | Exact Mass [M + H]+ |
|---|---|---|---|
| 203 | 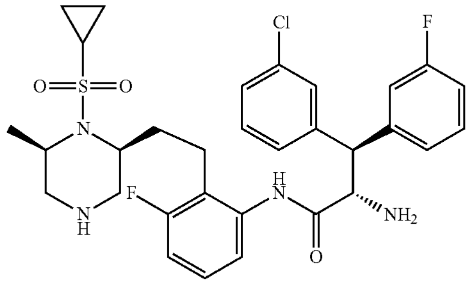 [SMILES: C[C@@H]1CNC[C@H](CCc2c(F)cccc2NC(=O)[C@@H](N)[C@H](c2cccc(F)c2)c2cccc(Cl)c2)N1S(=O)(=O)C1CC1] | (βR)-3-chloro-N-(2-{2-[(2S,6R)-1-(cyclopropylsulfonyl)-6-methylpiperazin-2-yl]ethyl}-3-fluorophenyl)-β-(3-fluorophenyl)-L-phenylalaninamide | 617.2 |
| 204 | 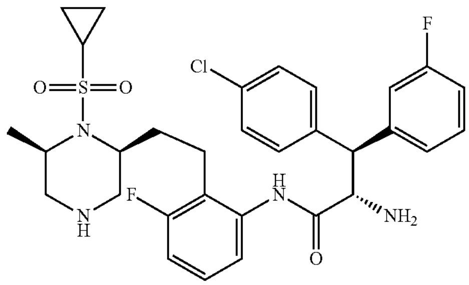 [SMILES: C[C@@H]1CNC[C@H](CCc2c(F)cccc2NC(=O)[C@@H](N)[C@@H](c2ccc(Cl)cc2)c2cccc(F)c2)N1S(=O)(=O)C1CC1] | (βS)-4-chloro-N-(2-{2-[(2S,6R)-1-(cyclopropylsulfonyl)-6-methylpiperazin-2-yl]ethyl}-3-fluorophenyl)-β-(3-fluorophenyl)-L-phenylalaninamide | 617.2 |
| 205 | 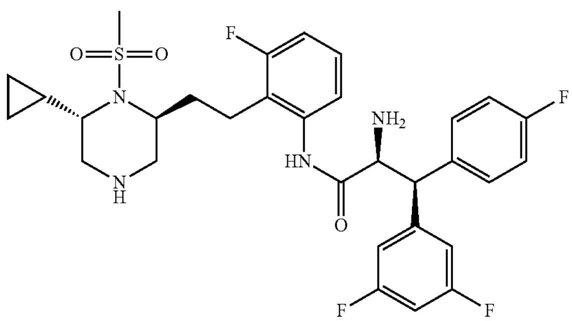 [SMILES: CS(=O)(=O)N1[C@@H](CCc2c(F)cccc2NC(=O)[C@@H](N)[C@@H](c2ccc(F)cc2)c2cc(F)cc(F)c2)CNC[C@@H]1C1CC1] | (βS)-N-(2-{2-[(2S,6S)-6-cyclopropyl-1-(methylsulfonyl)piperazin-2-yl]ethyl}-3-fluorophenyl)-β-(3,5-difluorophenyl)-4-fluoro-L-phenylalaninamide | 619.2 |
| 206 | 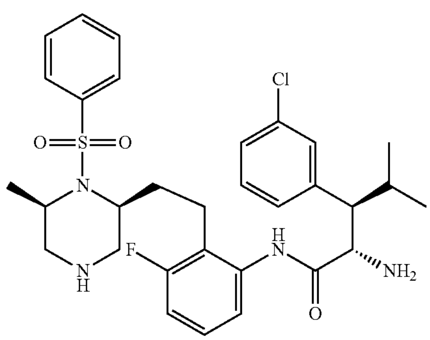 [SMILES: CC(C)[C@H](c1cccc(Cl)c1)[C@H](N)C(=O)Nc1cccc(F)c1CC[C@H]1CNC[C@@H](C)N1S(=O)(=O)c1ccccc1] | (βR)-3-chloro-N-(3-fluoro-2-{2-[(2S,6R)-6-methyl-1-(phenylsulfonyl)piperazin-2-yl]ethyl}phenyl)-β-(1-methylethyl)-L-phenylalaninamide | 601.2 |
| 207 | 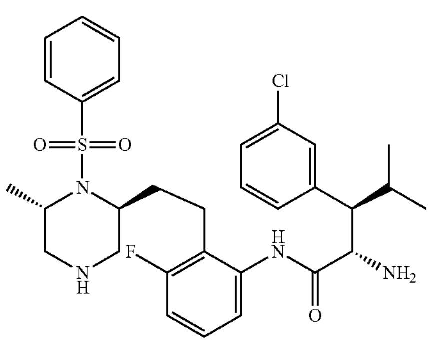 [SMILES: CC(C)[C@H](c1cccc(Cl)c1)[C@H](N)C(=O)Nc1cccc(F)c1CC[C@H]1CNC[C@H](C)N1S(=O)(=O)c1ccccc1] | (βR)-3-chloro-N-(3-fluoro-2-{2-[(2S,6S)-6-methyl-1-(phenylsulfonyl)piperazin-2-yl]ethyl}phenyl)-β-(1-methylethyl)-L-phenylalaninamide | 601.2 |

TABLE 3-continued

| Ex # | Structure | IUPAC Name | Exact Mass [M + H]+ |
|---|---|---|---|
| 208 | 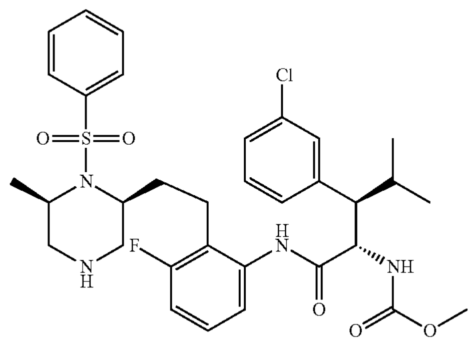 | (βR)-3-chloro-N-(3-fluoro-2-{2-[(2S,6R)-6-methyl-1-(phenylsulfonyl)piperazin-2-yl]ethyl}phenyl)-Nα-(methoxycarbonyl)-β-(1-methylethyl)-L-phenylalaninamide | 659.2 |
| 209 | 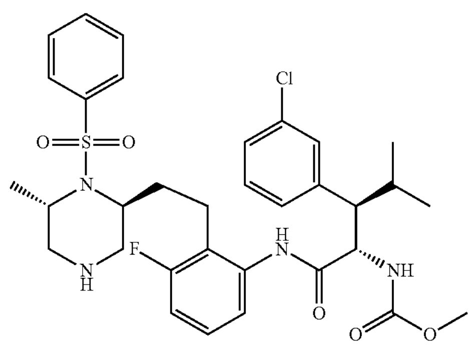 | (βR)-3-chloro-N-(3-fluoro-2-{2-[(2S,6S)-6-methyl-1-(phenylsulfonyl)piperazin-2-yl]ethyl}phenyl)-Nα-(methoxycarbonyl)-β-(1-methylethyl)-L-phenylalaninamide | 659.2 |
| 210 | 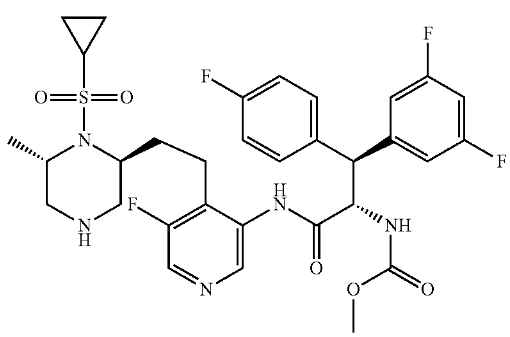 [SMILES: COC(=O)N[C@H](C(=O)Nc1cncc(F)c1CC[C@H]1CNC[C@H](C)N1S(=O)(=O)C1CC1)[C@@H](c1ccc(F)cc1)c1cc(F)cc(F)c1] | (βS)-N-(4-{2-[(2S,6S)-1-(cyclopropylsulfonyl)-6-methylpiperazin-2-yl]ethyl}-5-fluoropyridin-3-yl)-β-(3,5-difluorophenyl)-4-fluoro-Nα-(methoxycarbonyl)-L-phenylalaninamide | 678.2 |
| 211 | 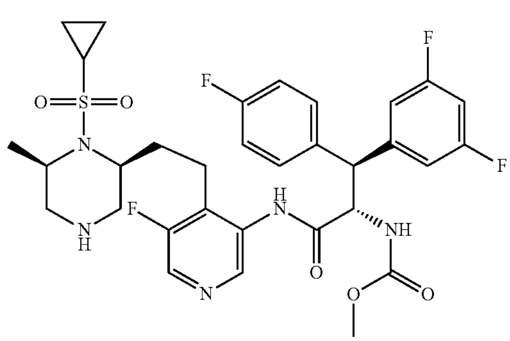 [SMILES: COC(=O)N[C@H](C(=O)Nc1cncc(F)c1CC[C@H]1CNC[C@@H](C)N1S(=O)(=O)C1CC1)[C@@H](c1ccc(F)cc1)c1cc(F)cc(F)c1] | (βS)-N-(4-{2-[(2S,6R)-1-(cyclopropylsulfonyl)-6-methylpiperazin-2-yl]ethyl}-5-fluoropyridin-3-yl)-β-(3,5-difluorophenyl)-4-fluoro-Nα-(methoxycarbonyl)-L-phenylalaninamide | 678.2 |

TABLE 3-continued

| Ex # | Structure | IUPAC Name | Exact Mass [M + H]+ |
|---|---|---|---|
| 212 | 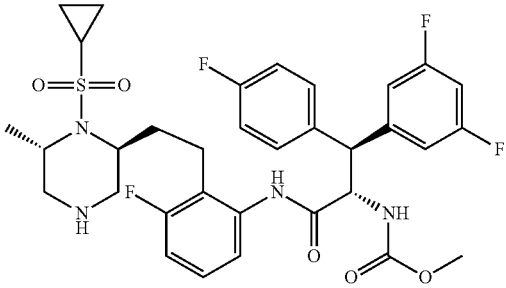 [SMILES: COC(=O)N[C@H](C(=O)Nc1cccc(F)c1CC[C@H]1CNC[C@H](C)N1S(=O)(=O)C1CC1)[C@@H](c1ccc(F)cc1)c1cc(F)cc(F)c1] | (βS)-N-(2-{2-[(2S,6S)-1-(cyclopropylsulfonyl)-6-methylpiperazin-2-yl]ethyl}-3-fluorophenyl)-β-(3,5-difluorophenyl)-4-fluoro-Nα-(methoxycarbonyl)-L-phenylalaninamide | 677.2 |
| 213 | 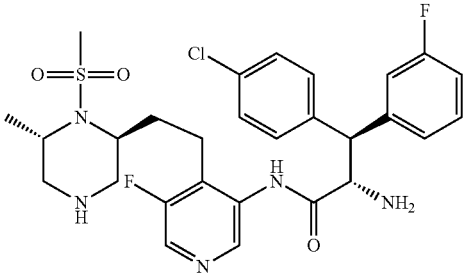 [SMILES: C[C@H]1CNC[C@H](CCc2c(F)cncc2NC(=O)[C@@H](N)[C@@H](c2ccc(Cl)cc2)c2cccc(F)c2)N1S(C)(=O)=O] | (βS)-4-chloro-N-(5-fluoro-4-{2-[(2S,6S)-6-methyl-1-(methylsulfonyl)piperazin-2-yl]ethyl}pyridin-3-yl)-β-(3-fluorophenyl)-L-phenylalaninamide | 592.2 |
| 214 | 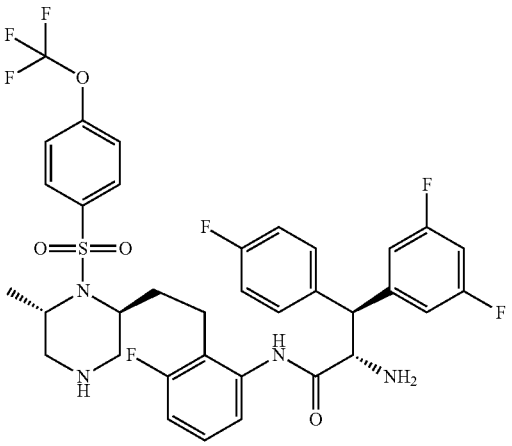 [SMILES: C[C@H]1CNC[C@H](CCc2c(F)cccc2NC(=O)[C@@H](N)[C@@H](c2ccc(F)cc2)c2cc(F)cc(F)c2)N1S(=O)(=O)c1ccc(OC(F)(F)F)cc1] | (βS)-β-(3,5-difluorophenyl)-4-fluoro-N-(3-fluoro-2-{2-[(2S,6S)-6-methyl-1-{[4-(trifluoromethoxy)phenyl]sulfonyl}piperazin-2-yl]ethyl}phenyl)-L-phenylalaninamide | 739.2 |
| 215 | 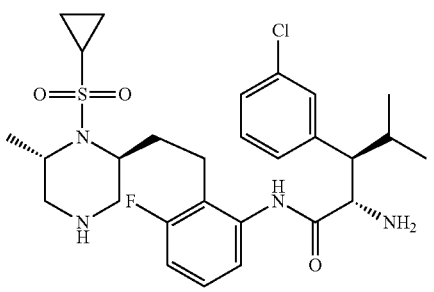 [SMILES: CC(C)[C@H](c1cccc(Cl)c1)[C@H](N)C(=O)Nc1cccc(F)c1CC[C@H]1CNC[C@H](C)N1S(=O)(=O)C1CC1] | (βR)-3-chloro-N-(2-{2-[(2S,6S)-1-(cyclopropylsulfonyl)-6-methylpiperazin-2-yl]ethyl}-3-fluorophenyl)-β-(1-methylethyl)-L-phenylalaninamide | 565.2 |

TABLE 3-continued

| Ex # | Structure | IUPAC Name | Exact Mass [M + H]+ |
|---|---|---|---|
| 216 | 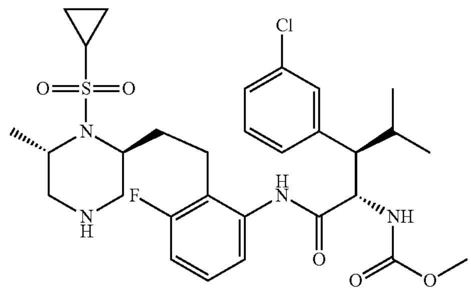 | (βR)-3-chloro-N-(2-{2-[(2S,6S)-1-(cyclopropylsulfonyl)-6-methylpiperazin-2-yl]ethyl}-3-fluorophenyl)-Nα-(methoxycarbonyl)-β-(1-methylethyl)-L-phenylalaninamide | 623.2 |
| 217 | 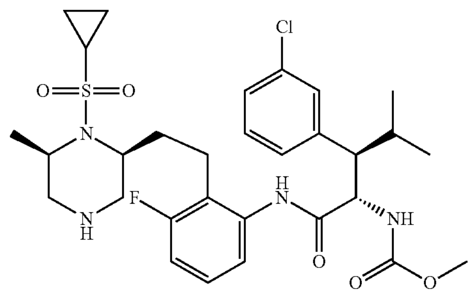 | (βR)-3-chloro-N-(2-{2-[(2S,6R)-1-(cyclopropylsulfonyl)-6-methylpiperazin-2-yl]ethyl}-3-fluorophenyl)-Nα-(methoxycarbonyl)-β-(1-methylethyl)-L-phenylalaninamide | 623.2 |
| 218 | 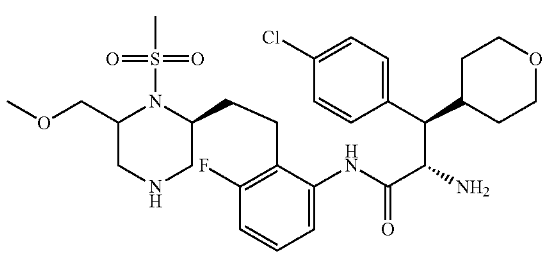 [SMILES: COCC1CNC[C@H](CCc2c(F)cccc2NC(=O)[C@@H](N)[C@@H](c2ccc(Cl)cc2)C2CCOCC2)N1S(C)(=O)=O] | (βR)-4-chloro-N-(3-fluoro-2-{2-[(2S)-6-(methoxymethyl)-1-(methylsulfonyl)piperazin-2-yl]ethyl}phenyl)-β-(tetrahydro-2H-pyran-4-yl)-L-phenylalaninamide | 611.2 |
| 219 | 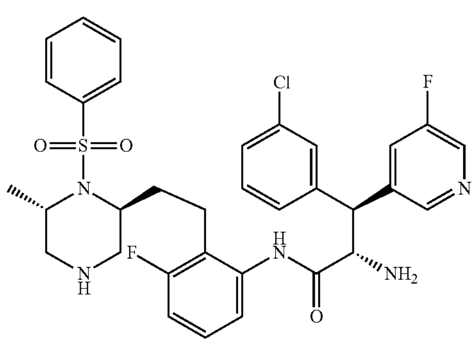 [SMILES: C[C@H]1CNC[C@H](CCc2c(F)cccc2NC(=O)[C@@H](N)[C@H](c2cncc(F)c2)c2cccc(Cl)c2)N1S(=O)(=O)c1ccccc1] | (βS)-3-chloro-N-(3-fluoro-2-{2-[(2S,6S)-6-methyl-1-(phenylsulfonyl)piperazin-2-yl]ethyl}phenyl)-β-(5-fluoropyridin-3-yl)-L-phenylalaninamide | 654.2 |

TABLE 3-continued

| Ex # | Structure | IUPAC Name | Exact Mass [M + H]+ |
|---|---|---|---|
| 220 | 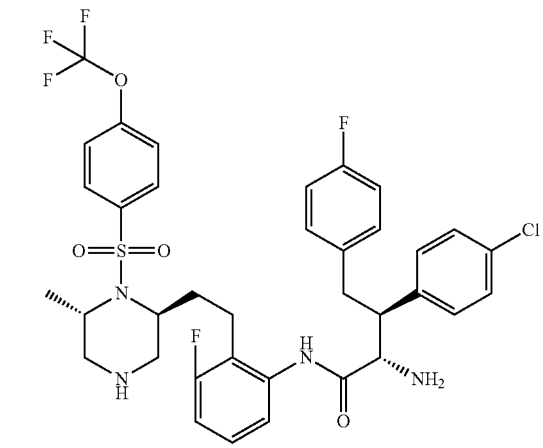 [SMILES: C[C@H]1CNC[C@H](CCc2c(F)cccc2NC(=O)[C@@H](N)[C@@H](Cc2ccc(F)cc2)c2ccc(Cl)cc2)N1S(=O)(=O)c1ccc(OC(F)(F)F)cc1] | (βS)-4-chloro-β-(4-fluorobenzyl)-N-(3-fluoro-2-{2-[(2S,6S)-6-methyl-1-{[4-(trifluoromethoxy)phenyl]sulfonyl}piperazin-2-yl]ethyl}phenyl)-L-phenylalaninamide | 751.2 |
| 221 | 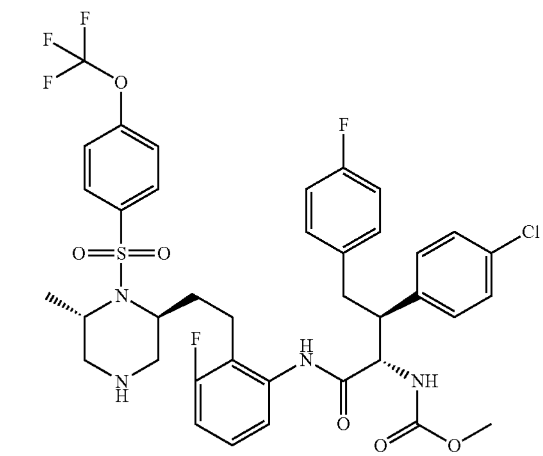 [SMILES: COC(=O)N[C@H](C(=O)Nc1cccc(F)c1CC[C@H]1CNC[C@H](C)N1S(=O)(=O)c1ccc(OC(F)(F)F)cc1)[C@@H](Cc1ccc(F)cc1)c1ccc(Cl)cc1] | (βS)-4-chloro-β-(4-fluorobenzyl)-N-(3-fluoro-2-{2-[(2S,6S)-6-methyl-1-{[4-(trifluoromethoxy)phenyl]sulfonyl}piperazin-2-yl]ethyl}phenyl)-Nα-(methoxycarbonyl)-L-phenylalaninamide | 809.2 |
| 222 | 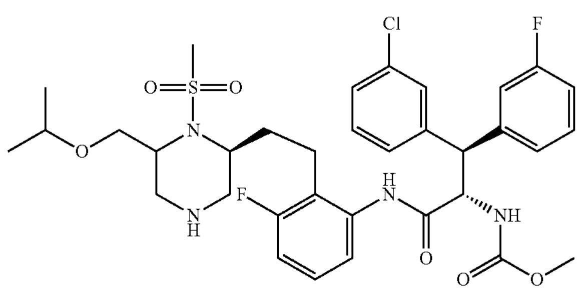 [SMILES: COC(=O)N[C@H](C(=O)Nc1cccc(F)c1CC[C@H]1CNCC(COC(C)C)N1S(C)(=O)=O)[C@H](c1cccc(F)c1)c1cccc(Cl)c1] | (βR)-β-(3-chlorophenyl)-3-fluoro-N-(3-fluoro-2-{2-[(2S)-6-[(1-methylethoxy)methyl]-1-(methylsulfonyl)piperazin-2-yl]ethyl}phenyl)-Nα-(methoxycarbonyl)-L-phenylalaninamide | 707.2 |
| 223 | 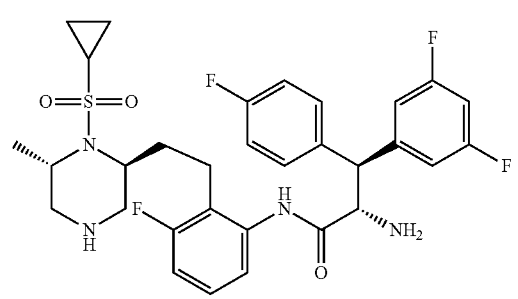 [SMILES: C[C@H]1CNC[C@H](CCc2c(F)cccc2NC(=O)[C@@H](N)[C@@H](c2ccc(F)cc2)c2cc(F)cc(F)c2)N1S(=O)(=O)C1CC1] | (βS)-N-(2-{2-[(2S,6S)-1-(cyclopropylsulfonyl)-6-methylpiperazin-2-yl]ethyl}-3-fluorophenyl)-β-(3,5-difluorophenyl)-4-fluoro-L-phenylalaninamide | 619.2 |

TABLE 3-continued

| Ex # | Structure | IUPAC Name | Exact Mass [M + H]+ |
|---|---|---|---|
| 224 | 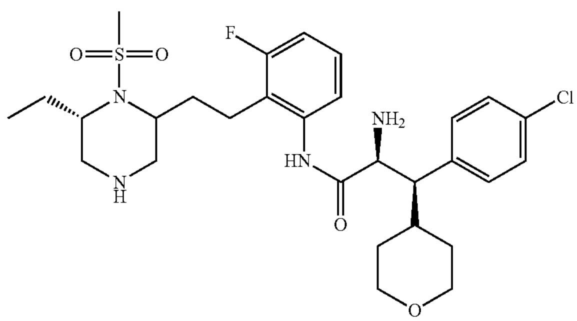 [SMILES: CC[C@H]1CNCC(CCc2c(F)cccc2NC(=O)[C@@H](N)[C@@H](c2ccc(Cl)cc2)C2CCOCC2)N1S(C)(=O)=O] | (βR)-4-chloro-N-(2-{2-[(2S,6S)-6-ethyl-1-(methylsulfonyl)piperazin-2-yl]ethyl}-3-fluorophenyl)-β-(tetrahydro-2H-pyran-4-yl)-L-phenylalaninamide | 595.3 |
| 225 | 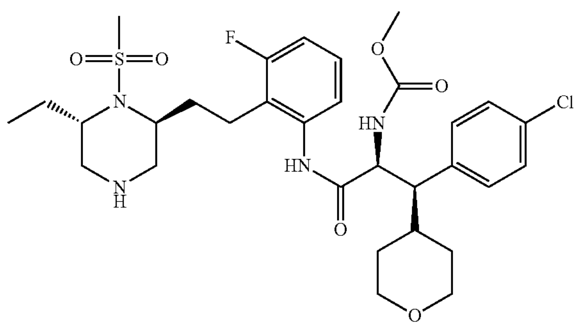 [SMILES: CC[C@H]1CNC[C@H](CCc2c(F)cccc2NC(=O)[C@@H](NC(=O)OC)[C@@H](c2ccc(Cl)cc2)C2CCOCC2)N1S(C)(=O)=O] | (βR)-4-chloro-N-(2-{2-[(2S,6S)-6-ethyl-1-(methylsulfonyl)piperazin-2-yl]ethyl}-3-fluorophenyl)-Nα-(methoxycarbonyl)-β-(tetrahydro-2H-pyran-4-yl)-L-phenylalaninamide | 653.3 |
| 226 | 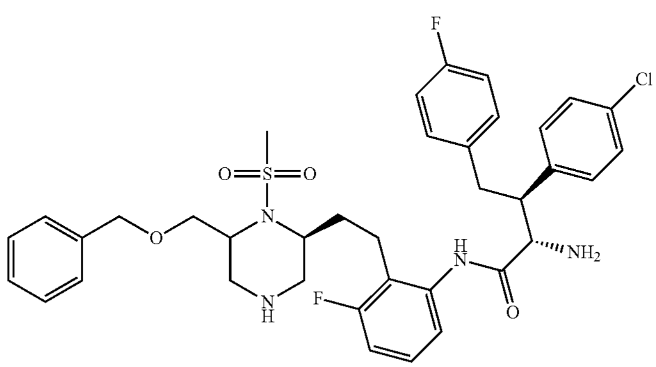 [SMILES: CS(=O)(=O)N1C(COCc2ccccc2)CNC[C@@H]1CCc1c(F)cccc1NC(=O)[C@@H](N)[C@@H](Cc1ccc(F)cc1)c1ccc(Cl)cc1] | (βS)-N-(2-{2-[(2S)-6-[(benzyloxy)methyl]-1-(methylsulfonyl)piperazin-2-yl]ethyl}-3-fluorophenyl)-4-chloro-β-(4-fluorobenzyl)-L-phenylalaninamide | 711.3 |
| 227 | 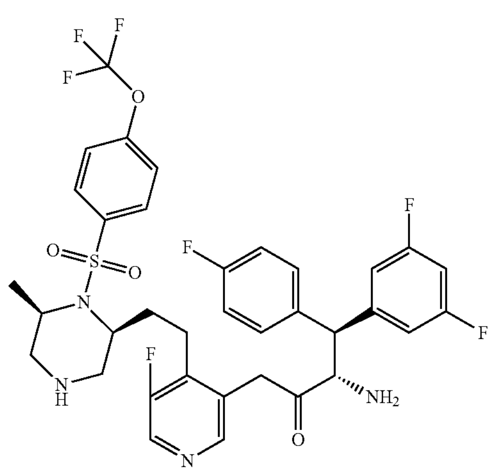 [SMILES: C[C@@H]1CNC[C@H](CCc2c(F)cncc2CC(=O)[C@@H](N)[C@@H](c2ccc(F)cc2)c2cc(F)cc(F)c2)N1S(=O)(=O)c1ccc(OC(F)(F)F)cc1] | (βS)-β-(3,5-difluorophenyl)-4-fluoro-N-(5-fluoro-4-{2-[(2S,6R)-6-methyl-1-{[4-(trifluoromethoxy)phenyl]sulfonyl}piperazin-2-yl]ethyl}pyridin-3-yl)-L-phenylalaninamide | 740.2 |

| Ex # | Structure | IUPAC Name | Exact Mass [M + H]+ |
|---|---|---|---|
| 228 | 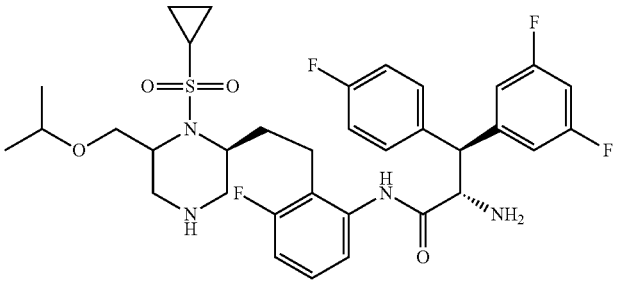 [SMILES: CC(C)OCC1CNC[C@H](CCc2c(F)cccc2NC(=O)[C@@H](N)[C@@H](c2ccc(F)cc2)c2cc(F)cc(F)c2)N1S(=O)(=O)C1CC1] | (βS)-N-[2-(2-{(2S)-1-(cyclopropylsulfonyl)-6-[(1-methylethoxy)methyl]piperazin-2-yl}ethyl)-3-fluorophenyl]-β-(3,5-difluorophenyl)-4-fluoro-L-phenylalaninamide | 677.3 |
| 229 | 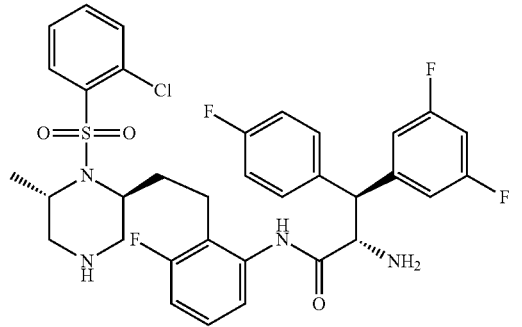 [SMILES: C[C@H]1CNC[C@H](CCc2c(F)cccc2NC(=O)[C@@H](N)[C@@H](c2ccc(F)cc2)c2cc(F)cc(F)c2)N1S(=O)(=O)c1ccccc1Cl] | (βS)-N-[2-(2-{(2S,6S)-1-[(2-chlorophenyl)sulfonyl]-6-methylpiperazin-2-yl}ethyl)-3-fluorophenyl]-β-(3,5-difluorophenyl)-4-fluoro-L-phenylalaninamide | 689.2 |
| 230 | 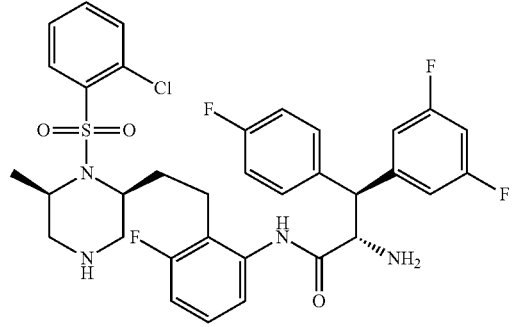 [SMILES: C[C@@H]1CNC[C@H](CCc2c(F)cccc2NC(=O)[C@@H](N)[C@@H](c2ccc(F)cc2)c2cc(F)cc(F)c2)N1S(=O)(=O)c1ccccc1Cl] | (βS)-N-[2-(2-{(2S,6R)-1-[(2-chlorophenyl)sulfonyl]-6-methylpiperazin-2-yl}ethyl)-3-fluorophenyl]-β-(3,5-difluorophenyl)-4-fluoro-L-phenylalaninamide | 689.2 |
| 231 | 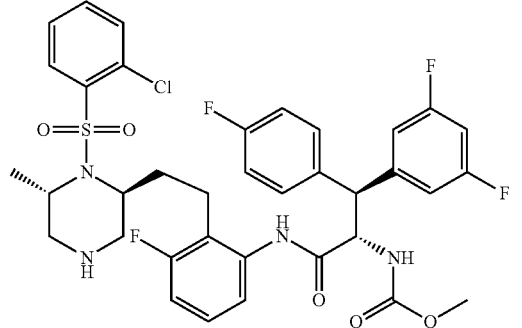 [SMILES: COC(=O)N[C@H](C(=O)Nc1cccc(F)c1CC[C@H]1CNC[C@H](C)N1S(=O)(=O)c1ccccc1Cl)[C@@H](c1ccc(F)cc1)c1cc(F)cc(F)c1] | (βS)-N-[2-(2-{(2S,6S)-1-[(2-chlorophenyl)sulfonyl]-6-methylpiperazin-2-yl}ethyl)-3-fluorophenyl]-β-(3,5-difluorophenyl)-4-fluoro-Nα-(methoxycarbonyl)-L-phenylalaninamide | 747.2 |

TABLE 3-continued

| Ex # | Structure | IUPAC Name | Exact Mass [M + H]+ |
|---|---|---|---|
| 232 | 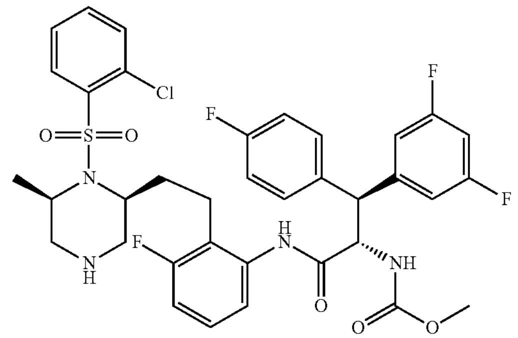 [SMILES: COC(=O)N[C@H](C(=O)Nc1cccc(F)c1CC[C@H]1CNC[C@@H](C)N1S(=O)(=O)c1ccccc1Cl)[C@@H](c1ccc(F)cc1)c1cc(F)cc(F)c1] | (βS)-N-[2-(2-{(2S,6R)-1-[(2-chlorophenyl)sulfonyl]-6-methylpiperazin-2-yl}ethyl)-3-fluorophenyl]-β-(3,5-difluorophenyl)-4-fluoro-Nα-(methoxycarbonyl)-L-phenylalaninamide | 747.2 |
| 233 | 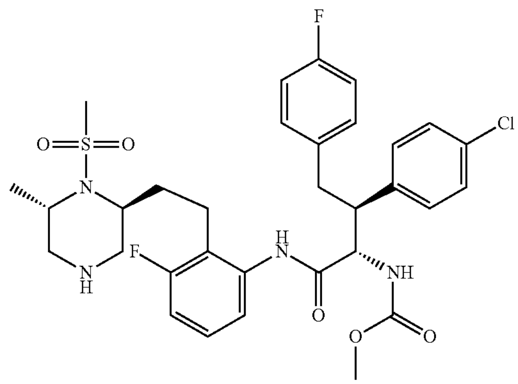 [SMILES: COC(=O)N[C@H](C(=O)Nc1cccc(F)c1CC[C@H]1CNC[C@H](C)N1S(C)(=O)=O)[C@@H](Cc1ccc(F)cc1)c1ccc(Cl)cc1] | (βS)-4-chloro-β-(4-fluorobenzyl)-N-(3-fluoro-2-{2-[(2S,6S)-6-methyl-1-(methylsulfonyl)piperazin-2-yl]ethyl}phenyl)-Nα-(methoxycarbonyl)-L-phenylalaninamide | 663.2 |
| 234 | 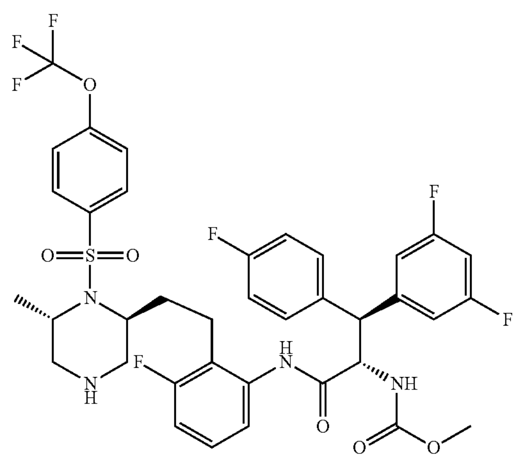 [SMILES: COC(=O)N[C@H](C(=O)Nc1cccc(F)c1CC[C@H]1CNC[C@H](C)N1S(=O)(=O)c1ccc(OC(F)(F)F)cc1)[C@@H](c1ccc(F)cc1)c1cc(F)cc(F)c1] | (βS)-β-(3,5-difluorophenyl)-4-fluoro-N-(3-fluoro-2-{2-[(2S,6S)-6-methyl-1-{[4-(trifluoromethoxy)phenyl]sulfonyl}piperazin-2-yl]ethyl}phenyl)-Nα-(methoxycarbonyl)-L-phenylalaninamide | 797.2 |
| 235 | 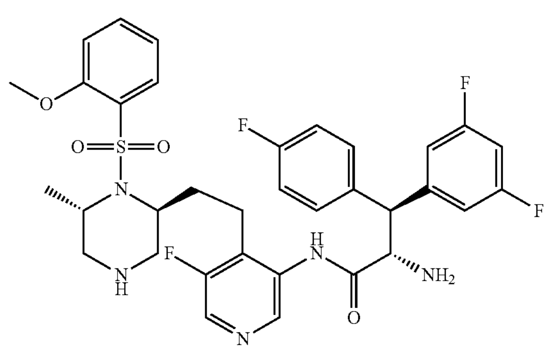 [SMILES: COc1ccccc1S(=O)(=O)N1[C@@H](CCc2c(F)cncc2NC(=O)[C@@H](N)[C@@H](c2ccc(F)cc2)c2cc(F)cc(F)c2)CNC[C@@H]1C] | (βS)-β-(3,5-difluorophenyl)-4-fluoro-N-[5-fluoro-4-(2-{(2S,6S)-1-[(2-methoxyphenyl)sulfonyl]-6-methylpiperazin-2-yl}ethyl)pyridin-3-yl]-L-phenylalaninamide | 686.2 |

TABLE 3-continued

| Ex # | Structure | IUPAC Name | Exact Mass [M + H]+ |
|---|---|---|---|
| 236 | 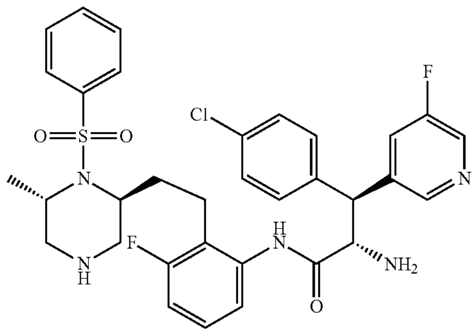 [SMILES: C[C@H]1CNC[C@H](CCc2c(F)cccc2NC(=O)[C@@H](N)[C@@H](c2ccc(Cl)cc2)c2cncc(F)c2)N1S(=O)(=O)c1ccccc1] | (βS)-4-chloro-N-(3-fluoro-2-{2-[(2S,6S)-6-methyl-1-(phenylsulfonyl)piperazin-2-yl]ethyl}phenyl)-β-(5-fluoropyridin-3-yl)-L-phenylalaninamide | 654.2 |
| 237 | 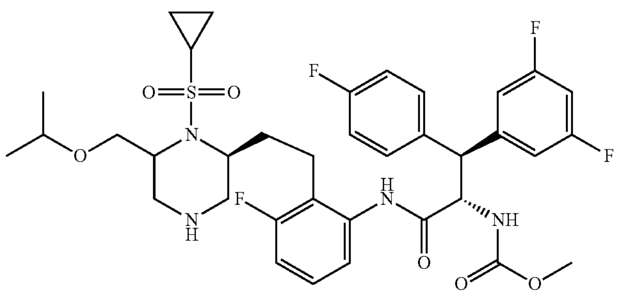 [SMILES: COC(=O)N[C@H](C(=O)Nc1cccc(F)c1CC[C@H]1CNCC(COC(C)C)N1S(=O)(=O)C1CC1)[C@@H](c1ccc(F)cc1)c1cc(F)cc(F)c1] | (βS)-N-[2-(2-{(2S)-1-(cyclopropylsulfonyl)-6-[(1-methylethoxy)methyl]piperazin-2-yl}ethyl)-3-fluorophenyl]-β-(3,5-difluorophenyl)-4-fluoro-Nα-(methoxycarbonyl)-L-phenylalaninamide | 735.3 |
| 238 | 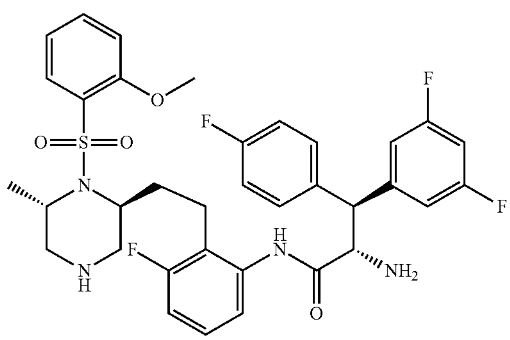 [SMILES: COc1ccccc1S(=O)(=O)N1[C@@H](CCc2c(F)cccc2NC(=O)[C@@H](N)[C@@H](c2ccc(F)cc2)c2cc(F)cc(F)c2)CNC[C@@H]1C] | (βS)-β-(3,5-difluorophenyl)-4-fluoro-N-[3-fluoro-2-(2-{(2S,6S)-1-[(2-methoxyphenyl)sulfonyl]-6-methylpiperazin-2-yl}ethyl)phenyl]-L-phenylalaninamide | 685.2 |
| 239 | 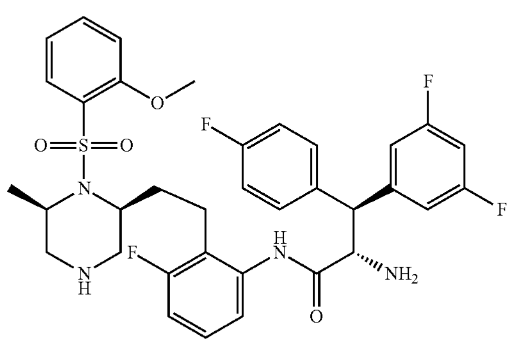 [SMILES: COc1ccccc1S(=O)(=O)N1[C@@H](CCc2c(F)cccc2NC(=O)[C@@H](N)[C@@H](c2ccc(F)cc2)c2cc(F)cc(F)c2)CNC[C@H]1C] | (βS)-β-(3,5-difluorophenyl)-4-fluoro-N-[3-fluoro-2-(2-{(2S,6R)-1-[(2-methoxyphenyl)sulfonyl]-6-methylpiperazin-2-yl}ethyl)phenyl]-L-phenylalaninamide | 685.2 |

TABLE 3-continued

| Ex # | Structure | IUPAC Name | Exact Mass [M + H]+ |
|---|---|---|---|
| 240 | 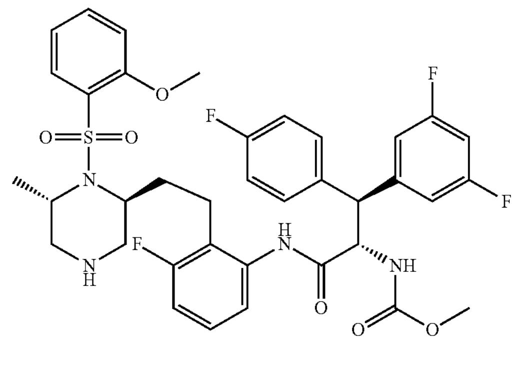 [SMILES: COC(=O)N[C@H](C(=O)Nc1cccc(F)c1CC[C@H]1CNC[C@H](C)N1S(=O)(=O)c1ccccc1OC)[C@@H](c1ccc(F)cc1)c1cc(F)cc(F)c1] | (βS)-β-(3,5-difluorophenyl)-4-fluoro-N-[3-fluoro-2-(2-{(2S,6S)-1-[(2-methoxyphenyl)sulfonyl]-6-methylpiperazin-2-yl}ethyl)phenyl]-Nα-(methoxycarbonyl)-L-phenylalaninamide | 743.3 |
| 241 | 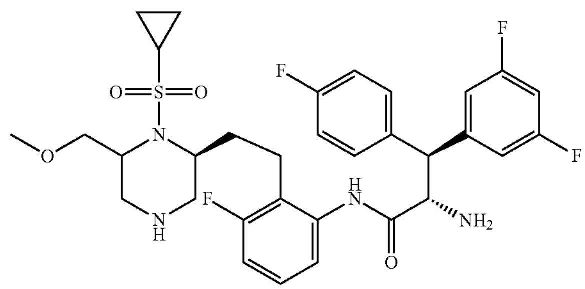 [SMILES: COCC1CNC[C@H](CCc2c(F)cccc2NC(=O)[C@@H](N)[C@@H](c2ccc(F)cc2)c2cc(F)cc(F)c2)N1S(=O)(=O)C1CC1] | (βS)-N-(2-{2-[(2S)-1-(cyclopropylsulfonyl)-6-(methoxymethyl)piperazin-2-yl]ethyl}-3-fluorophenyl)-β-(3,5-difluorophenyl)-4-fluoro-L-phenylalaninamide | 649.2 |
| 242 | 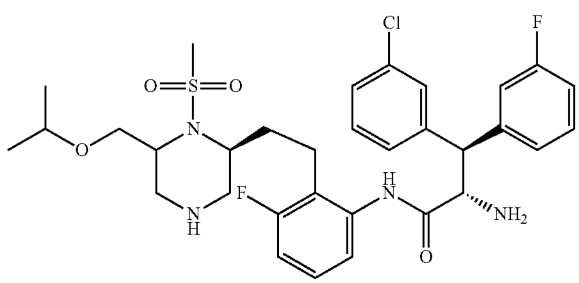 [SMILES: CC(C)OCC1CNC[C@H](CCc2c(F)cccc2NC(=O)[C@@H](N)[C@H](c2cccc(F)c2)c2cccc(Cl)c2)N1S(C)(=O)=O] | (βR)-β-(3-chlorophenyl)-3-fluoro-N-(3-fluoro-2-{2-[(2S)-6-[(1-methylethoxy)methyl]-1-(methylsulfonyl)piperazin-2-yl]ethyl}phenyl)-L-phenylalaninamide | 649.2 |
| 243 | 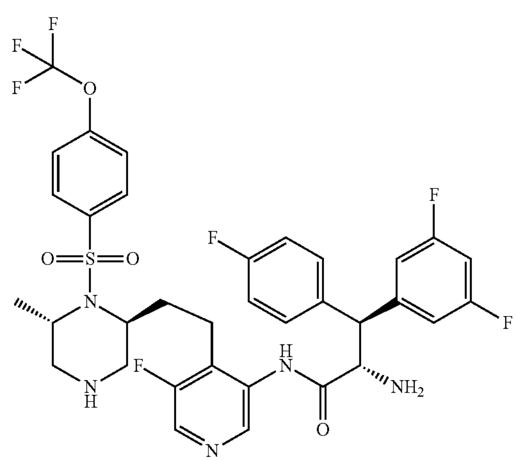 [SMILES: C[C@H]1CNC[C@H](CCc2c(F)cncc2NC(=O)[C@@H](N)[C@@H](c2ccc(F)cc2)c2cc(F)cc(F)c2)N1S(=O)(=O)c1ccc(OC(F)(F)F)cc1] | (βS)-β-(3,5-difluorophenyl)-4-fluoro-N-(5-fluoro-4-{2-[(2S,6S)-6-methyl-1-{[4-(trifluoromethoxy)phenyl]sulfonyl}piperazin-2-yl]ethyl}pyridin-3-yl)-L-phenylalaninamide | 740.2 |

| Ex # | Structure | IUPAC Name | Exact Mass [M + H]+ |
|---|---|---|---|
| 244 | 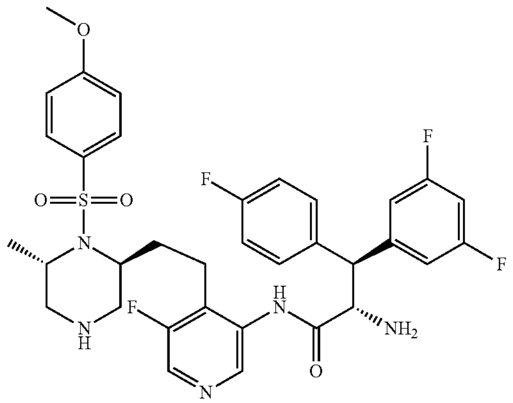 [SMILES: COc1ccc(S(=O)(=O)N2[C@@H](CCc3c(F)cncc3NC(=O)[C@@H](N)[C@@H](c3ccc(F)cc3)c3cc(F)cc(F)c3)CNC[C@@H]2C)cc1] | (βS)-β-(3,5-difluorophenyl)-4-fluoro-N-[5-fluoro-4-(2-{(2S,6S)-1-[(4-methoxyphenyl)sulfonyl]-6-methylpiperazin-2-yl}ethyl)pyridin-3-yl]-L-phenylalaninamide | 686.2 |
| 245 | 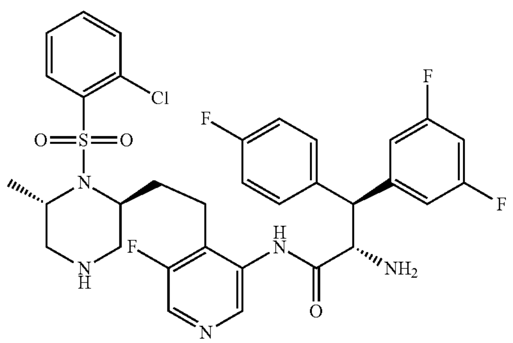 [SMILES: C[C@H]1CNC[C@H](CCc2c(F)cncc2NC(=O)[C@@H](N)[C@@H](c2ccc(F)cc2)c2cc(F)cc(F)c2)N1S(=O)(=O)c1ccccc1Cl] | (βS)-N-[4-(2-{(2S,6S)-1-[(2-chlorophenyl)sulfonyl]-6-methylpiperazin-2-yl}ethyl)-5-fluoropyridin-3-yl]-β-(3,5-difluorophenyl)-4-fluoro-L-phenylalaninamide | 690.2 |
| 246 | 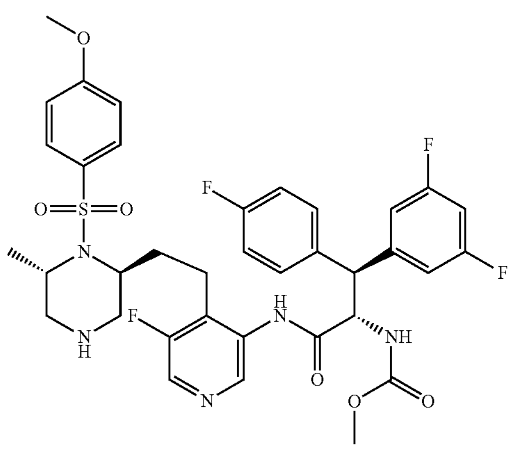 [SMILES: COC(=O)N[C@H](C(=O)Nc1cncc(F)c1CC[C@H]1CNC[C@H](C)N1S(=O)(=O)c1ccc(OC)cc1)[C@@H](c1ccc(F)cc1)c1cc(F)cc(F)c1] | (βS)-β-(3,5-difluorophenyl)-4-fluoro-N-[5-fluoro-4-(2-{(2S,6S)-1-[(4-methoxyphenyl)sulfonyl]-6-methylpiperazin-2-yl}ethyl)pyridin-3-yl]-Nα-(methoxycarbonyl)-L-phenylalaninamide | 744.2 |

TABLE 3-continued

| Ex # | Structure | IUPAC Name | Exact Mass [M + H]+ |
|---|---|---|---|
| 247 | 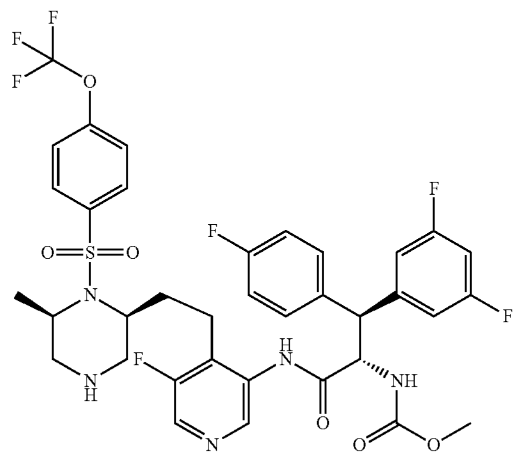 | (βS)-β-(3,5-difluorophenyl)-4-fluoro-N-(5-fluoro-4-{2-[(2S,6R)-6-methyl-1-{[4-(trifluoromethoxy)phenyl]sulfonyl}piperazin-2-yl]ethyl}pyridin-3-yl)-Nα-(methoxycarbonyl)-L-phenylalaninamide | 798.2 |
| 248 | 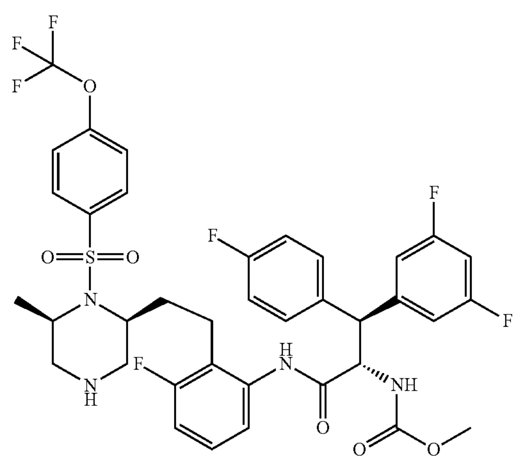 [SMILES: COC(=O)N[C@H](C(=O)Nc1cccc(F)c1CC[C@H]1CNC[C@@H](C)N1S(=O)(=O)c1ccc(OC(F)(F)F)cc1)[C@@H](c1ccc(F)cc1)c1cc(F)cc(F)c1] | (βS)-β-(3,5-difluorophenyl)-4-fluoro-N-(3-fluoro-2-{2-[(2S,6R)-6-methyl-1-{[4-(trifluoromethoxy)phenyl]sulfonyl}piperazin-2-yl]ethyl}phenyl)-Nα-(methoxycarbonyl)-L-phenylalaninamide | 797.2 |
| 249 | 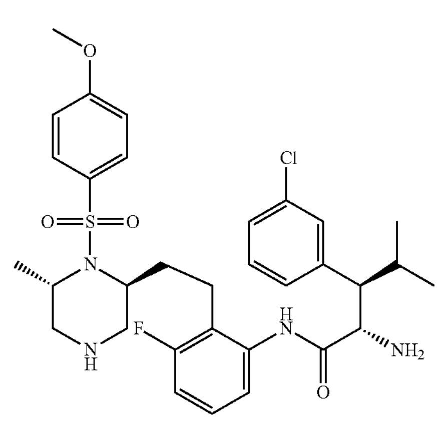 [SMILES: COc1ccc(S(=O)(=O)N2[C@@H](CCc3c(F)cccc3NC(=O)[C@@H](N)[C@@H](c3cccc(Cl)c3)C(C)C)CNC[C@@H]2C)cc1] | (βR)-3-chloro-N-[3-fluoro-2-(2-{(2S,6S)-1-[(4-methoxyphenyl)sulfonyl]-6-methylpiperazin-2-yl}ethyl)phenyl]-β-(1-methylethyl)-L-phenylalaninamide | 631.3 |

TABLE 3-continued

| Ex # | Structure | IUPAC Name | Exact Mass [M + H]+ |
|---|---|---|---|
| 250 | 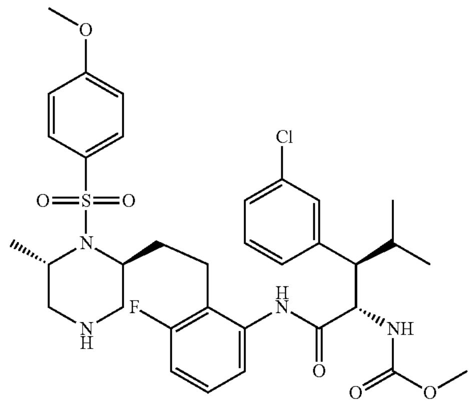 | (βR)-3-chloro-N-[3-fluoro-2-(2-{(2S,6S)-1-[(4-methoxyphenyl)sulfonyl]-6-methylpiperazin-2-yl}ethyl)phenyl]-Nα-(methoxycarbonyl)-β-(1-methylethyl)-L-phenylalaninamide | 689.3 |
| 251 | 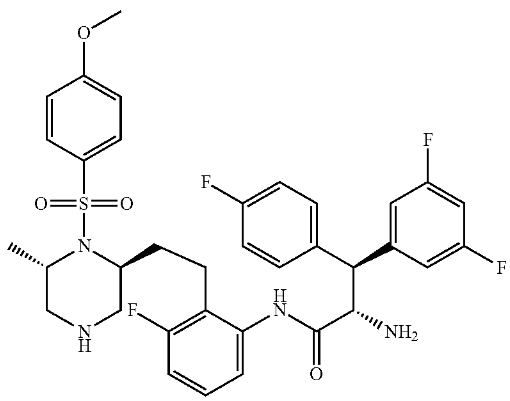 [SMILES: COc1ccc(S(=O)(=O)N2[C@@H](CCc3c(F)cccc3NC(=O)[C@@H](N)[C@@H](c3ccc(F)cc3)c3cc(F)cc(F)c3)CNC[C@@H]2C)cc1] | (βS)-β-(3,5-difluorophenyl)-4-fluoro-N-[3-fluoro-2-(2-{(2S,6S)-1-[(4-methoxyphenyl)sulfonyl]-6-methylpiperazin-2-yl}ethyl)phenyl]-L-phenylalaninamide | 685.2 |
| 252 | 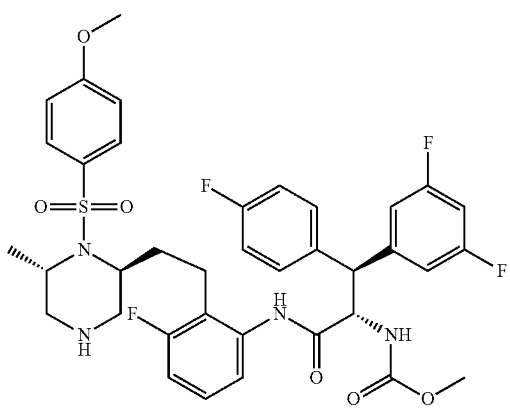 [SMILES: COC(=O)N[C@H](C(=O)Nc1cccc(F)c1CC[C@H]1CNC[C@H](C)N1S(=O)(=O)c1ccc(OC)cc1)[C@@H](c1ccc(F)cc1)c1cc(F)cc(F)c1] | (βS)-β-(3,5-difluorophenyl)-4-fluoro-N-[3-fluoro-2-(2-{(2S,6S)-1-[(4-methoxyphenyl)sulfonyl]-6-methylpiperazin-2-yl}ethyl)phenyl]-Nα-(methoxycarbonyl)-L-phenylalaninamide | 743.3 |
| 253 | 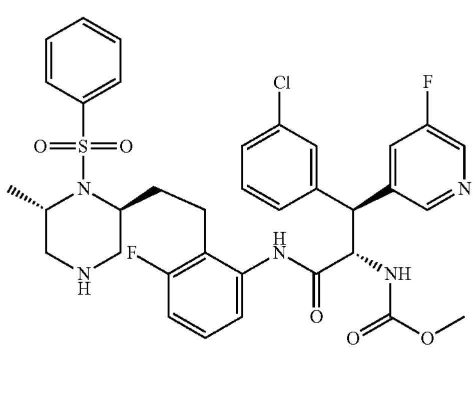 | (βS)-3-chloro-N-(3-fluoro-2-{2-[(2S,6S)-6-methyl-1-(phenylsulfonyl)piperazin-2-yl]ethyl}phenyl)-β-(5-fluoropyridin-3-yl)-Nα-(methoxycarbonyl)-L-phenylalaninamide | 712.2 |

TABLE 3-continued

| Ex # | Structure | IUPAC Name | Exact Mass [M + H]+ |
|---|---|---|---|
| 254 | 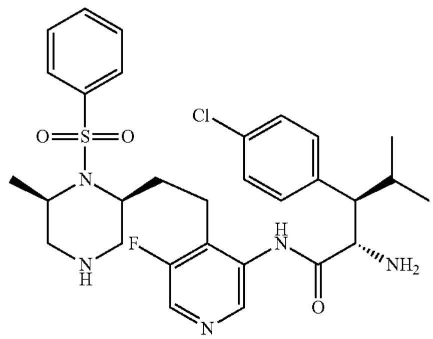 [SMILES: CC(C)[C@H](c1ccc(Cl)cc1)[C@H](N)C(=O)Nc1cncc(F)c1CC[C@H]1CNC[C@@H](C)N1S(=O)(=O)c1ccccc1] | (βR)-4-chloro-N-(5-fluoro-4-{2-[(2S,6R)-6-methyl-1-(phenylsulfonyl)piperazin-2-yl]ethyl}pyridin-3-yl)-β-(1-methylethyl)-L-phenylalaninamide | 602.2 |
| 255 | 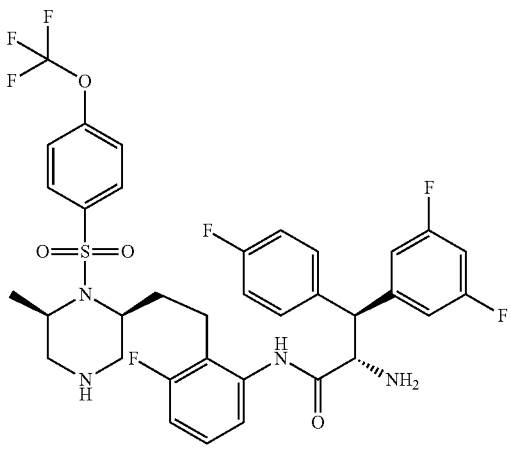 [SMILES: C[C@@H]1CNC[C@H](CCc2c(F)cccc2NC(=O)[C@@H](N)[C@@H](c2ccc(F)cc2)c2cc(F)cc(F)c2)N1S(=O)(=O)c1ccc(OC(F)(F)F)cc1] | (βS)-β-(3,5-difluorophenyl)-4-fluoro-N-(3-fluoro-2-{2-[(2S,6R)-6-methyl-1-{[4-(trifluoromethoxy)phenyl]sulfonyl}piperazin-2-yl]ethyl}phenyl)-L-phenylalaninamide | 739.2 |
| 256 | 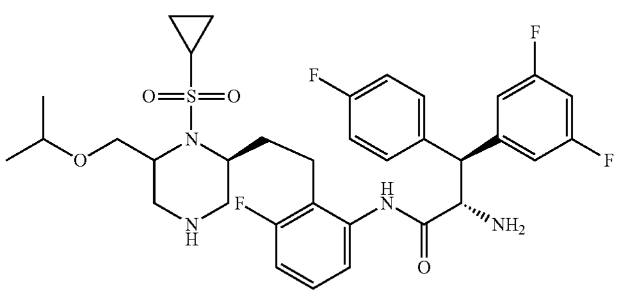 [SMILES: CC(C)OCC1CNC[C@H](CCc2c(F)cccc2NC(=O)[C@@H](N)[C@@H](c2ccc(F)cc2)c2cc(F)cc(F)c2)N1S(=O)(=O)C1CC1] | (βS)-N-[2-(2-{(2S)-1-(cyclopropylsulfonyl)-6-[(1-methylethoxy)methyl]piperazin-2-yl}ethyl)-3-fluorophenyl]-β-(3,5-difluorophenyl)-4-fluoro-L-phenylalaninamide | 677.3 |
| 257 | 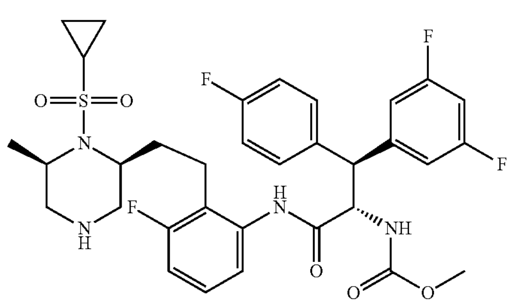 | (βS)-N-(2-{2-[(2S,6R)-1-(cyclopropylsulfonyl)-6-methylpiperazin-2-yl]ethyl}-3-fluorophenyl)-β-(3,5-difluorophenyl)-4-fluoro-Nα-(methoxycarbonyl)-L-phenylalaninamide | 677.2 |

TABLE 3-continued

| Ex # | Structure | IUPAC Name | Exact Mass [M + H]+ |
|---|---|---|---|
| 258 | 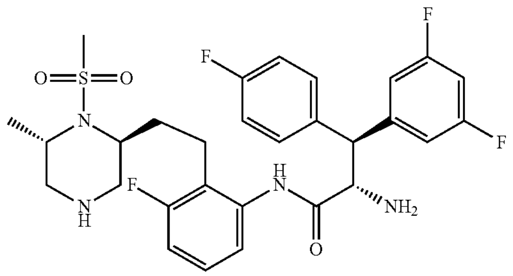 [SMILES: C[C@H]1CNC[C@H](CCc2c(F)cccc2NC(=O)[C@@H](N)[C@@H](c2ccc(F)cc2)c2cc(F)cc(F)c2)N1S(C)(=O)=O] | (βS)-β-(3,5-difluorophenyl)-4-fluoro-N-(3-fluoro-2-{2-[(2S,6S)-6-methyl-1-(methylsulfonyl)piperazin-2-yl]ethyl}phenyl)-L-phenylalaninamide | 593.2 |
| 259 | 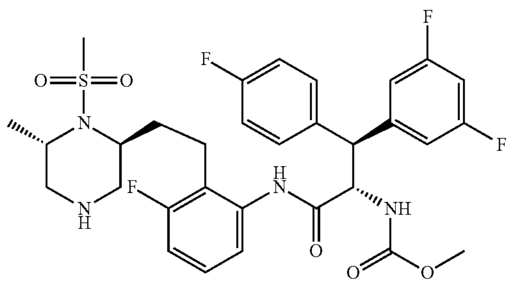 [SMILES: COC(=O)N[C@H](C(=O)Nc1cccc(F)c1CC[C@H]1CNC[C@H](C)N1S(C)(=O)=O)[C@@H](c1ccc(F)cc1)c1cc(F)cc(F)c1] | (βS)-β-(3,5-difluorophenyl)-4-fluoro-N-(3-fluoro-2-{2-[(2S,6S)-6-methyl-1-(methylsulfonyl)piperazin-2-yl]ethyl}phenyl)-Nα-(methoxycarbonyl)-L-phenylalaninamide | 651.2 |
| 260 | 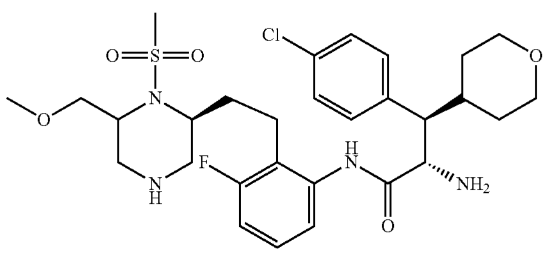 [SMILES: COCC1CNC[C@H](CCc2c(F)cccc2NC(=O)[C@@H](N)[C@@H](c2ccc(Cl)cc2)C2CCOCC2)N1S(C)(=O)=O] | (βR)-4-chloro-N-(3-fluoro-2-{2-[(2S)-6-(methoxymethyl)-1-(methylsulfonyl)piperazin-2-yl]ethyl}phenyl)-β-(tetrahydro-2H-pyran-4-yl)-L-phenylalaninamide | 611.2 |
| 261 | 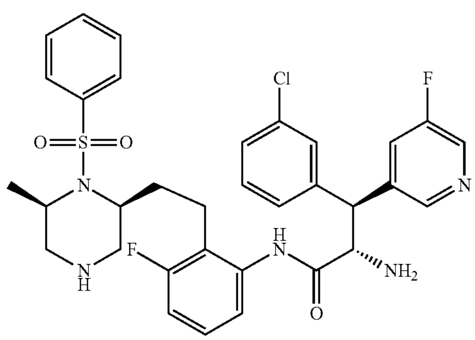 [SMILES: C[C@@H]1CNC[C@H](CCc2c(F)cccc2NC(=O)[C@@H](N)[C@H](c2cncc(F)c2)c2cccc(Cl)c2)N1S(=O)(=O)c1ccccc1] | (βS)-3-chloro-N-(3-fluoro-2-{2-[(2S,6R)-6-methyl-1-(phenylsulfonyl)piperazin-2-yl]ethyl}phenyl)-β-(5-fluoropyridin-3-yl)-L-phenylalaninamide | 654.2 |
| 262 | 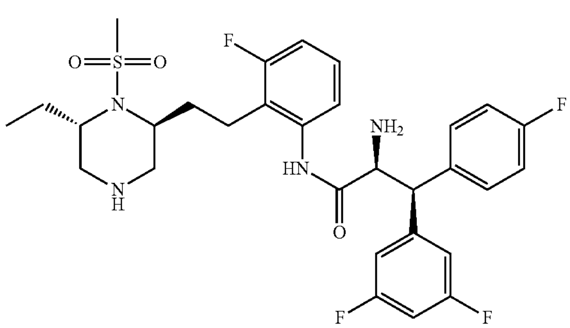 [SMILES: CC[C@H]1CNC[C@H](CCc2c(F)cccc2NC(=O)[C@@H](N)[C@@H](c2ccc(F)cc2)c2cc(F)cc(F)c2)N1S(C)(=O)=O] | (βS)-β-(3,5-difluorophenyl)-N-(2-{2-[(2S,6S)-6-ethyl-1-(methylsulfonyl)piperazin-2-yl]ethyl}-3-fluorophenyl)-4-fluoro-L-phenylalaninamide | 607.2 |

TABLE 3-continued

| Ex # | Structure | IUPAC Name | Exact Mass [M + H]+ |
|---|---|---|---|
| 263 | 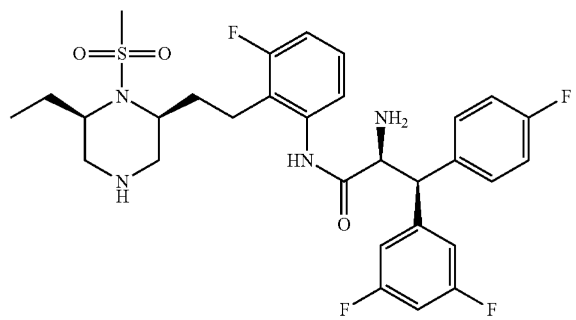 [SMILES: CC[C@@H]1CNC[C@H](CCc2c(F)cccc2NC(=O)[C@@H](N)[C@@H](c2ccc(F)cc2)c2cc(F)cc(F)c2)N1S(C)(=O)=O] | (βS)-β-(3,5-difluorophenyl)-N-(2-{2-[(2S,6R)-6-ethyl-1-(methylsulfonyl)piperazin-2-yl]ethyl}-3-fluorophenyl)-4-fluoro-L-phenylalaninamide | 607.2 |
| 264 | 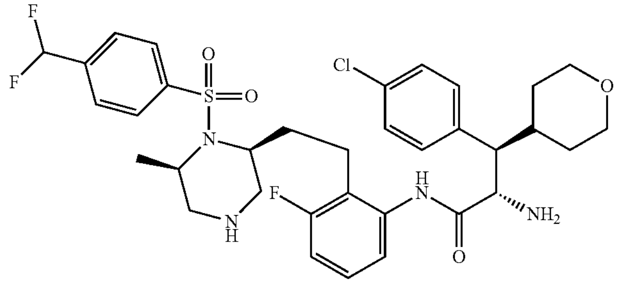 [SMILES: C[C@@H]1CNC[C@H](CCc2c(F)cccc2NC(=O)[C@@H](N)[C@@H](c2ccc(Cl)cc2)C2CCOCC2)N1S(=O)(=O)c1ccc(C(F)F)cc1] | (βR)-4-chloro-N-(2-{2-[(2S,6R)-1-{[4-(difluoromethyl)phenyl]sulfonyl}-6-methylpiperazin-2-yl]ethyl}-3-fluorophenyl)-β-(tetrahydro-2H-pyran-4-yl)-L-phenylalaninamide | 693.2 |
| 265 | 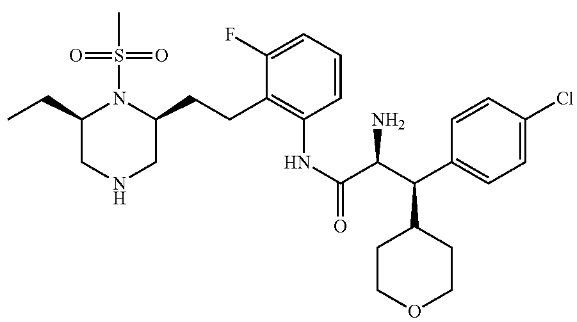 [SMILES: CC[C@@H]1CNC[C@H](CCc2c(F)cccc2NC(=O)[C@@H](N)[C@@H](c2ccc(Cl)cc2)C2CCOCC2)N1S(C)(=O)=O] | (βR)-4-chloro-N-(2-{2-[(2S,6R)-6-ethyl-1-(methylsulfonyl)piperazin-2-yl]ethyl}-3-fluorophenyl)-β-(tetrahydro-2H-pyran-4-yl)-L-phenylalaninamide | 595.3 |
| 266 | 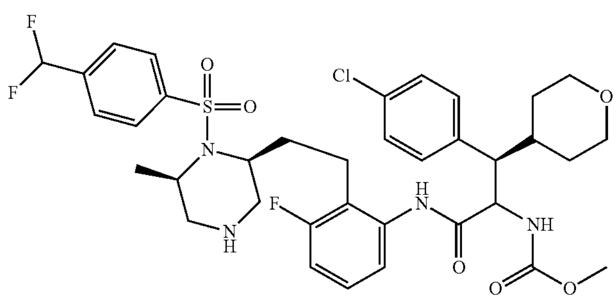 [SMILES: COC(=O)NC(C(=O)Nc1cccc(F)c1CC[C@H]1CNC[C@@H](C)N1S(=O)(=O)c1ccc(C(F)F)cc1)[C@@H](c1ccc(Cl)cc1)C1CCOCC1] | (βR)-4-chloro-N-(2-{2-[(2S,6R)-1-{[4-(difluoromethyl)phenyl]sulfonyl}-6-methylpiperazin-2-yl]ethyl}-3-fluorophenyl)-Nα-(methoxycarbonyl)-β-(tetrahydro)-2H-pyran-4-yl)-L-phenylalaninamide | 751.3 |
| 267 | 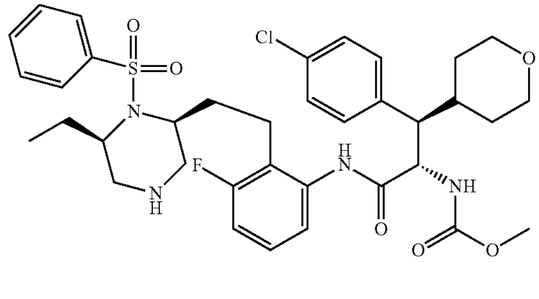 [SMILES: CC[C@@H]1CNC[C@H](CCc2c(F)cccc2NC(=O)[C@@H](NC(=O)OC)[C@@H](c2ccc(Cl)cc2)C2CCOCC2)N1S(=O)(=O)c1ccccc1] | methyl ((1R,2S)-1-(4-chlorophenyl)-3-((2-(2-((2S,6R)-6-ethyl-1-(phenylsulfonyl)piperazin-2-yl)ethyl)-3-fluorophenyl)amino)-3-oxo-1-(tetrahydro-2H-pyran-4-yl)propan-2-yl)carbamate | 715.3 |

TABLE 3-continued

| Ex # | Structure | IUPAC Name | Exact Mass [M + H]+ |
|---|---|---|---|
| 268 | 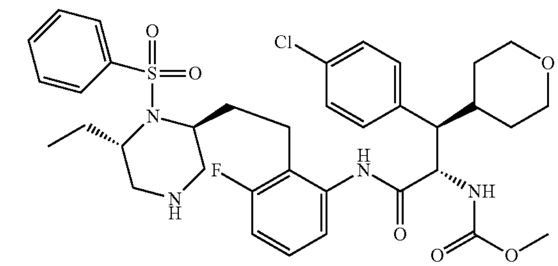 [SMILES: CC[C@H]1CNC[C@H](CCc2c(F)cccc2NC(=O)[C@@H](NC(=O)OC)[C@@H](c2ccc(Cl)cc2)C2CCOCC2)N1S(=O)(=O)c1ccccc1] | methyl ((1R,2S)-1-(4-chlorophenyl)-3-((2-(2-((2S,6S)-6-ethyl-1-(phenylsulfonyl)piperazin-2-yl)ethyl)-3-fluorophenyl) amino)-3-oxo-1-(tetrahydro-2H-pyran-4-yl)propan-2-yl) carbamate | 715.3 |
| 269 | 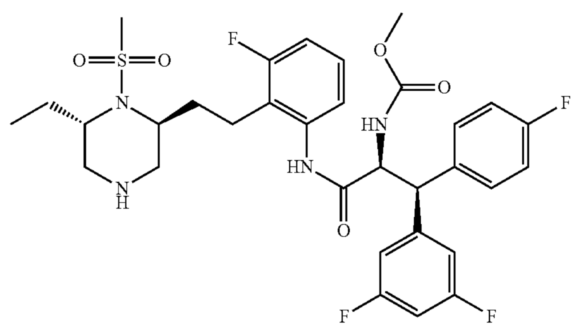 [SMILES: CC[C@H]1CNC[C@H](CCc2c(F)cccc2NC(=O)[C@@H](NC(=O)OC)[C@@H](c2ccc(F)cc2)c2cc(F)cc(F)c2)N1S(C)(=O)=O] | (βS)-β-(3,5-difluorophenyl)-N-(2-{2-[(2S,6S)-6-ethyl-1-(methylsulfonyl)piperazin-2-yl]ethyl}-3-fluorophenyl)-4-fluoro-Nα-(methoxycarbonyl)-L-phenylalaninamide | 665.2 |
| 270 | 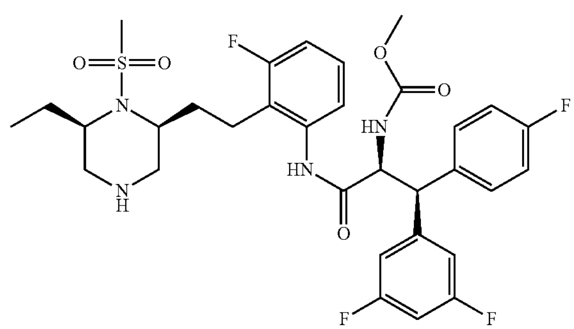 [SMILES: CC[C@@H]1CNC[C@H](CCc2c(F)cccc2NC(=O)[C@@H](NC(=O)OC)[C@@H](c2ccc(F)cc2)c2cc(F)cc(F)c2)N1S(C)(=O)=O] | (βS)-β-(3,5-difluorophenyl)-N-(2-{2-[(2S,6R)-6-ethyl-1-(methylsulfonyl)piperazin-2-yl]ethyl}-3-fluorophenyl)-4-fluoro-Nα-(methoxycarbonyl)-L-phenylalaninamide | 665.2 |
| 271 | 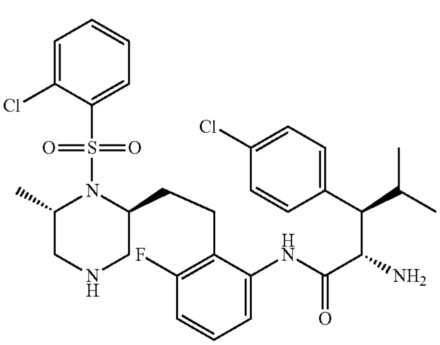 [SMILES: CC(C)[C@H](c1ccc(Cl)cc1)[C@H](N)C(=O)Nc1cccc(F)c1CC[C@H]1CNC[C@H](C)N1S(=O)(=O)c1ccccc1Cl] | (βR)-4-chloro-N-[2-(2-{(2S,6S)-1-[(2-chlorophenyl)sulfonyl]-6-methylpiperazin-2-yl}ethyl)-3-fluorophenyl]-β-(1-methylethyl)-L-phenylalaninamide | 635.2 |

TABLE 3-continued

| Ex # | Structure | IUPAC Name | Exact Mass [M + H]+ |
|---|---|---|---|
| 272 | 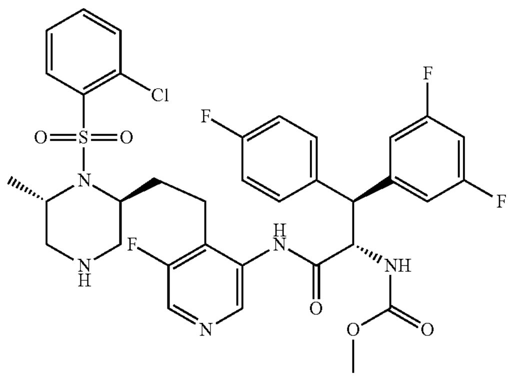 [SMILES: COC(=O)N[C@H](C(=O)Nc1cncc(F)c1CC[C@H]1CNC[C@H](C)N1S(=O)(=O)c1ccccc1Cl)[C@@H](c1ccc(F)cc1)c1cc(F)cc(F)c1] | (βS)-N-[4-(2-{(2S,6S)-1-[(2-chlorophenyl)sulfonyl]-6-methylpiperazin-2-yl}ethyl)-5-fluoropyridin-3-yl]-β-(3,5-difluorophenyl)-4-fluoro-Nα-(methoxycarbonyl)-L-phenylalaninamide | 748.2 |
| 273 | 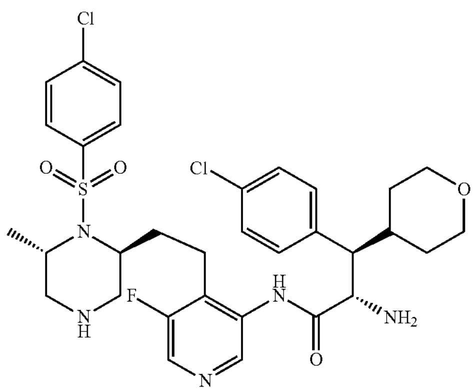 [SMILES: C[C@H]1CNC[C@H](CCc2c(F)cncc2NC(=O)[C@@H](N)[C@@H](c2ccc(Cl)cc2)C2CCOCC2)N1S(=O)(=O)c1ccc(Cl)cc1] | (βR)-4-chloro-N-[4-(2-{(2S,6S)-1-[(4-chlorophenyl)sulfonyl]-6-methylpiperazin-2-yl}ethyl)-5-fluoropyridin-3-yl]-β-(tetrahydro-2H-pyran-4-yl)-L-phenylalaninamide | 678.2 |
| 274 | 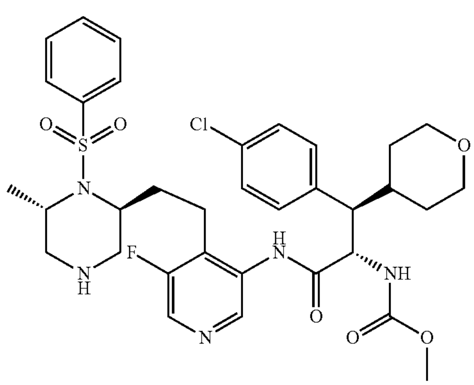 [SMILES: COC(=O)N[C@H](C(=O)Nc1cncc(F)c1CC[C@H]1CNC[C@H](C)N1S(=O)(=O)c1ccccc1)[C@@H](c1ccc(Cl)cc1)C1CCOCC1] | (βR)-4-chloro-N-(5-fluoro-4-{2-[(2S,6S)-6-methyl-1-(phenylsulfonyl)piperazin-2-yl]ethyl}pyridin-3-yl)-Nα-(methoxycarbonyl)-β-(tetrahydro-2H-pyran-4-yl)-L-phenylalaninamide | 702.3 |
| 275 | 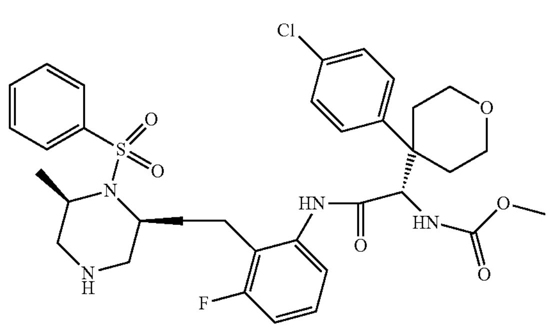 [SMILES: COC(=O)N[C@H](C(=O)Nc1cccc(F)c1CC[C@H]1CNC[C@@H](C)N1S(=O)(=O)c1ccccc1)C1(c2ccc(Cl)cc2)CCOCC1] | methyl {(1S)-1-[4-(4-chlorophenyl)tetrahydro-2H-pyran-4-yl]-2-[(3-fluoro-2-{2-[(2S,6R)-6-methyl-1-(phenylsulfonyl)piperazin-2-yl]ethyl}phenyl)amino]-2-oxoethyl}carbamate | 687.2 |

TABLE 3-continued

| Ex # | Structure | IUPAC Name | Exact Mass [M + H]+ |
|---|---|---|---|
| 276 | 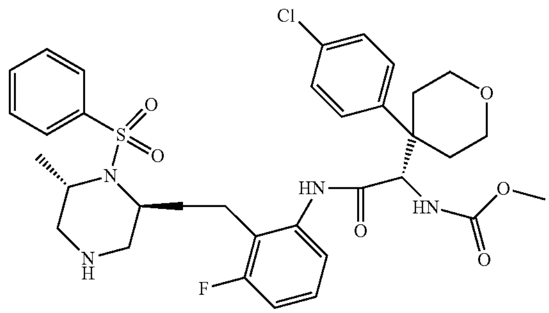 [SMILES: COC(=O)N[C@H](C(=O)Nc1cccc(F)c1CC[C@H]1CNC[C@H](C)N1S(=O)(=O)c1ccccc1)C1(c2ccc(Cl)cc2)CCOCC1] | methyl {(1S)-1-[4-(4-chlorophenyl)tetrahydro-2H-pyran-4-yl]-2-[(3-fluoro-2-{2-[(2S,6S)-6-methyl-1-(phenylsulfonyl)piperazin-2-yl]ethyl}phenyl)amino]-2-oxoethyl}carbamate | 687.2 |
| 277 | 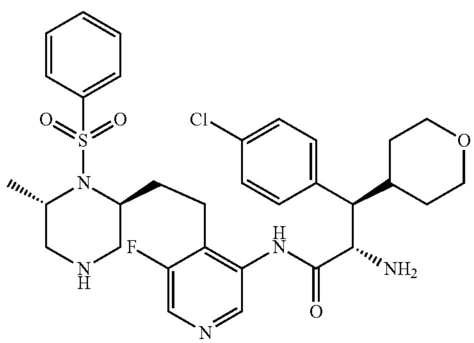 [SMILES: C[C@H]1CNC[C@H](CCc2c(F)cncc2NC(=O)[C@@H](N)[C@@H](c2ccc(Cl)cc2)C2CCOCC2)N1S(=O)(=O)c1ccccc1] | (βR)-4-chloro-N-(5-fluoro-4-{2-[(2S,6S)-6-methyl-1-(phenylsulfonyl)piperazin-2-yl]ethyl}pyridin-3-yl)-β-(tetrahydro-2H-pyran-4-yl)-L-phenylalaninamide | 644.2 |
| 278 | 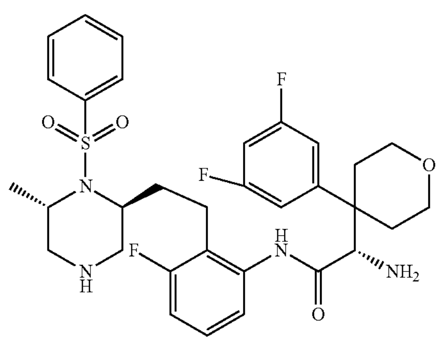 [SMILES: C[C@H]1CNC[C@H](CCc2c(F)cccc2NC(=O)[C@@H](N)C2(c3cc(F)cc(F)c3)CCOCC2)N1S(=O)(=O)c1ccccc1] | (2S)-2-amino-2-[4-(3,5-difluorophenyl)tetrahydro-2H-pyran-4-yl]-N-(3-fluoro-2-{2-[(2S,6S)-6-methyl-1-(phenylsulfonyl)piperazin-2-yl]ethyl}phenyl)ethanamide | 631.3 |
| 279 | 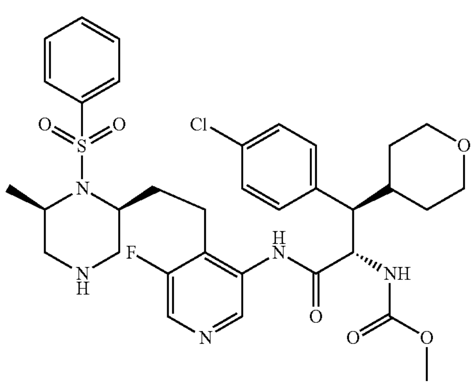 [SMILES: COC(=O)N[C@H](C(=O)Nc1cncc(F)c1CC[C@H]1CNC[C@@H](C)N1S(=O)(=O)c1ccccc1)[C@@H](c1ccc(Cl)cc1)C1CCOCC1] | (βR)-4-chloro-N-(5-fluoro-4-{2-[(2S,6R)-6-methyl-1-(phenylsulfonyl)piperazin-2-yl]ethyl}pyridin-3-yl)-Nα-(methoxycarbonyl)-β-(tetrahydro-2H-pyran-4-yl)-L-phenylalaninamide | 702.3 |

TABLE 3-continued

| Ex # | Structure | IUPAC Name | Exact Mass [M + H]+ |
|---|---|---|---|
| 280 | 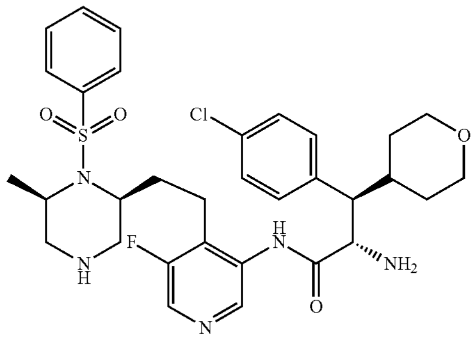 [SMILES: C[C@@H]1CNC[C@H](CCc2c(F)cncc2NC(=O)[C@@H](N)[C@@H](c2ccc(Cl)cc2)C2CCOCC2)N1S(=O)(=O)c1ccccc1] | (βR)-4-chloro-N-(5-fluoro-4-{2-[(2S,6R)-6-methyl-1-(phenylsulfonyl)piperazin-2-yl]ethyl}pyridin-3-yl)-β-(tetrahydro-2H-pyran-4-yl)-L-phenylalaninamide | 644.2 |
| 281 | 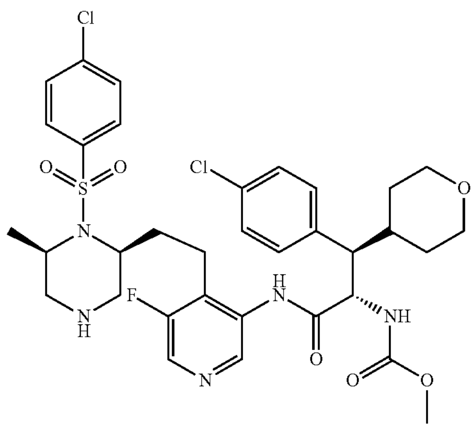 [SMILES: COC(=O)N[C@H](C(=O)Nc1cncc(F)c1CC[C@H]1CNC[C@@H](C)N1S(=O)(=O)c1ccc(Cl)cc1)[C@@H](c1ccc(Cl)cc1)C1CCOCC1] | (βR)-4-chloro-N-[4-(2-{(2S,6R)-1-[(4-chlorophenyl)sulfonyl]-6-methylpiperazin-2-yl}ethyl)-5-fluoropyridin-3-yl]-Nα-(methoxycarbonyl)-β-(tetrahydro-2H-pyran-4-yl)-L-phenylalaninamide | 736.2 |
| 282 | 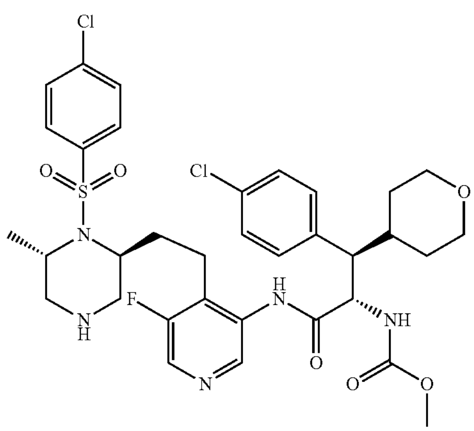 [SMILES: COC(=O)N[C@H](C(=O)Nc1cncc(F)c1CC[C@H]1CNC[C@H](C)N1S(=O)(=O)c1ccc(Cl)cc1)[C@@H](c1ccc(Cl)cc1)C1CCOCC1] | (βR)-4-chloro-N-[4-(2-{(2S,6S)-1-[(4-chlorophenyl)sulfonyl]-6-methylpiperazin-2-yl}ethyl)-5-fluoropyridin-3-yl]-Nα-(methoxycarbonyl)-β-(tetrahydro-2H-pyran-4-yl)-L-phenylalaninamide | 736.2 |
| 283 | 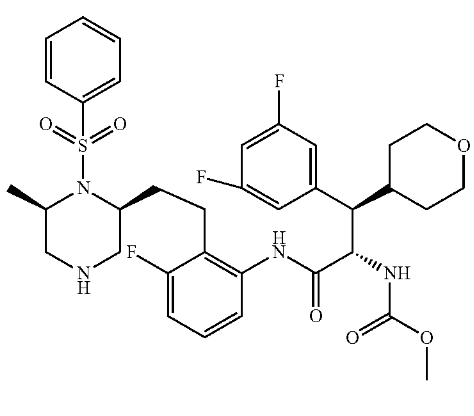 [SMILES: COC(=O)N[C@H](C(=O)Nc1cccc(F)c1CC[C@H]1CNC[C@@H](C)N1S(=O)(=O)c1ccccc1)[C@@H](c1cc(F)cc(F)c1)C1CCOCC1] | (βR)-3,5-difluoro-N-(3-fluoro-2-{2-[(2S,6R)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide | 703.3 |

TABLE 3-continued

| Ex # | Structure | IUPAC Name | Exact Mass [M + H]+ |
|---|---|---|---|
| 284 | 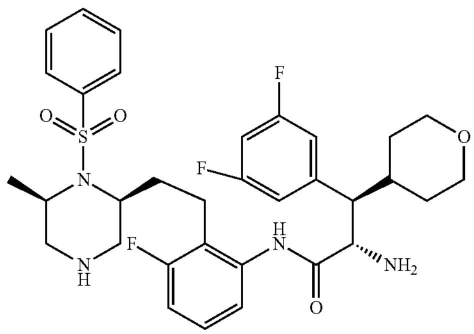 [SMILES: C[C@@H]1CNC[C@H](CCc2c(F)cccc2NC(=O)[C@@H](N)[C@@H](c2cc(F)cc(F)c2)C2CCOCC2)N1S(=O)(=O)c1ccccc1] | (βR)-3,5-difluoro-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide | 645.3 |
| 285 | 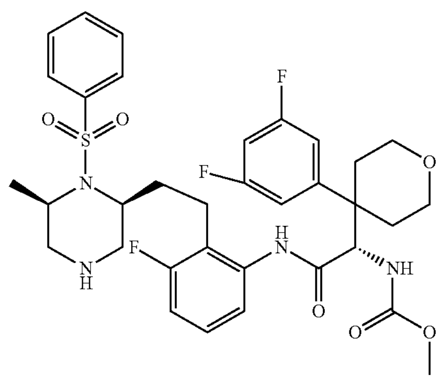 [SMILES: COC(=O)N[C@H](C(=O)Nc1cccc(F)c1CC[C@H]1CNC[C@@H](C)N1S(=O)(=O)c1ccccc1)C1(c2cc(F)cc(F)c2)CCOCC1] | methyl {(1S)-1-[4-{3,5-difluorophenyl)tetrahydro-2H-pyran-4-yl]-2-[(3-fluoro-2-{2-[(2S,6R)-6-methyl-1-(phenylsulfonyl)piperazin-2-yl]ethyl}phenyl)amino]-2-oxoethyl}carbamate | 689.3 |
| 286 | 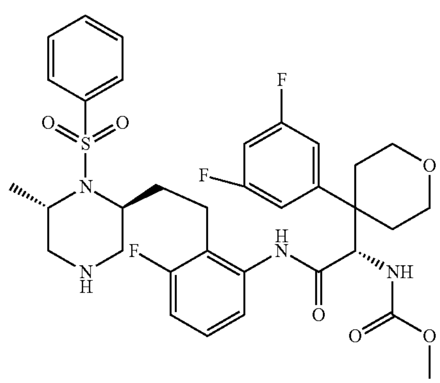 [SMILES: COC(=O)N[C@H](C(=O)Nc1cccc(F)c1CC[C@H]1CNC[C@H](C)N1S(=O)(=O)c1ccccc1)C1(c2cc(F)cc(F)c2)CCOCC1] | methyl {(1S)-1-[4-(3,5-difluorophenyl)tetrahydro-2H-pyran-4-yl]-2-[(3-fluoro-2-{2-[(2S,6S)-6-methyl-1-(phenylsulfonyl)piperazin-2-yl]ethyl}phenyl)amino]-2-oxoethyl}carbamate | 689.3 |
| 287 | 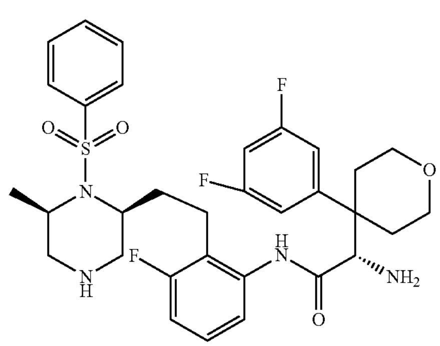 [SMILES: C[C@@H]1CNC[C@H](CCc2c(F)cccc2NC(=O)[C@@H](N)C2(c3cc(F)cc(F)c3)CCOCC2)N1S(=O)(=O)c1ccccc1] | (2S)-2-amino-2-[4-(3,5-difluorophenyl)tetrahydro-2H-pyran-4-yl]-N-(3-fluoro-2-{2-[(2S,6R)-6-methyl-1-(phenylsulfonyl)piperazin-2-yl]ethyl}phenyl)ethanamide | 631.3 |

TABLE 3-continued

| Ex # | Structure | IUPAC Name | Exact Mass [M + H]+ |
|---|---|---|---|
| 288 | 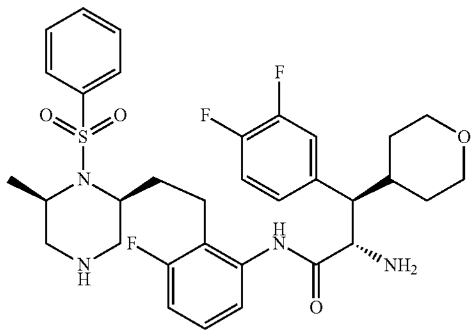 [SMILES: C[C@@H]1CNC[C@H](CCc2c(F)cccc2NC(=O)[C@@H](N)[C@@H](c2ccc(F)c(F)c2)C2CCOCC2)N1S(=O)(=O)c1ccccc1] | (βR)-3,4-difluoro-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide | 645.3 |
| 289 | 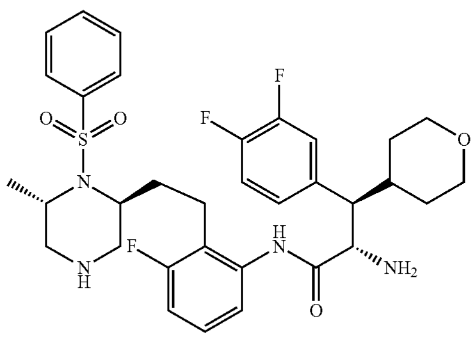 [SMILES: C[C@H]1CNC[C@H](CCc2c(F)cccc2NC(=O)[C@@H](N)[C@@H](c2ccc(F)c(F)c2)C2CCOCC2)N1S(=O)(=O)c1ccccc1] | (βR)-3,4-difluoro-N-(3-fluoro-2-{2-[(2S,6S)-6-methyl-1-(phenylsulfonyl)piperazin-2-yl]ethyl}phenyl)-β-(tetrahydro-2H-pyran-4-yl)-L-phenylalaninamide | 645.3 |
| 290 | 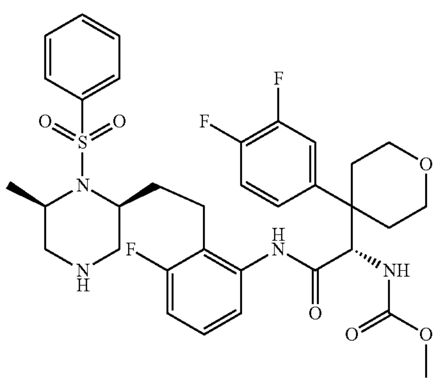 [SMILES: COC(=O)N[C@H](C(=O)Nc1cccc(F)c1CC[C@H]1CNC[C@@H](C)N1S(=O)(=O)c1ccccc1)C1(c2ccc(F)c(F)c2)CCOCC1] | methyl {(1S)-1-[4-(3,4-difluorophenyl)tetrahydro-2H-pyran-4-yl]-2-[(3-fluoro-2-{2-[(2S,6R)-6-methyl-1-(phenylsulfonyl)piperazin-2-yl]ethyl}phenyl)amino]-2-oxoethyl}carbamate | 689.3 |
| 291 | 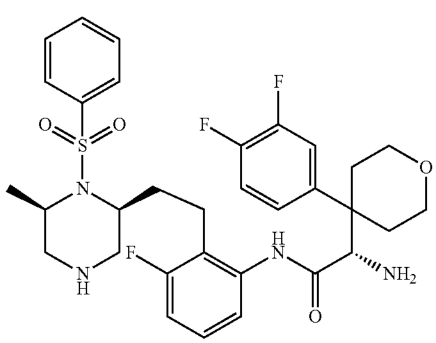 [SMILES: C[C@@H]1CNC[C@H](CCc2c(F)cccc2NC(=O)[C@@H](N)C2(c3ccc(F)c(F)c3)CCOCC2)N1S(=O)(=O)c1ccccc1] | (2S)-2-amino-2-[4-(3,4-difluorophenyl)tetrahydro-2H-pyran-4-yl]-N-(3-fluoro-2-{2-[(2S,6R)-6-methyl-1-(phenylsulfonyl)piperazin-2-yl]ethyl}phenyl)ethanamide | 631.3 |

TABLE 3-continued

| Ex # | Structure | IUPAC Name | Exact Mass [M + H]+ |
|---|---|---|---|
| 292 | 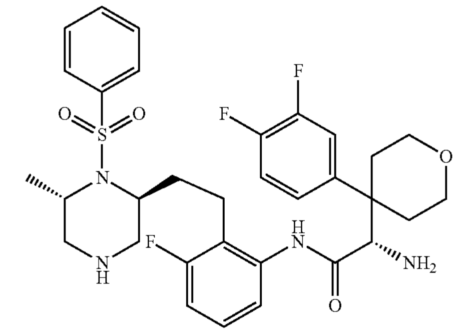 [SMILES: C[C@H]1CNC[C@H](CCc2c(F)cccc2NC(=O)[C@@H](N)C2(c3ccc(F)c(F)c3)CCOCC2)N1S(=O)(=O)c1ccccc1] | (2S)-2-amino-2-[4-(3,4-difluorophenyl)tetrahydro-2H-pyran-4-yl]-N-(3-fluoro-2-{2-[(2S,6S)-6-methyl-1-(phenylsulfonyl)piperazin-2-yl]ethyl}phenyl)ethanamide | 631.3 |
| 293 | 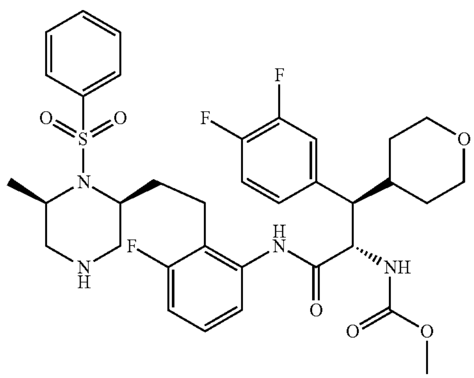 [SMILES: COC(=O)N[C@H](C(=O)Nc1cccc(F)c1CC[C@H]1CNC[C@@H](C)N1S(=O)(=O)c1ccccc1)[C@@H](c1ccc(F)c(F)c1)C1CCOCC1] | (βR)-3,4-difluoro-N-(3-fluoro-2-{2-[(2S,6R)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide | 703.3 |
| 294 | 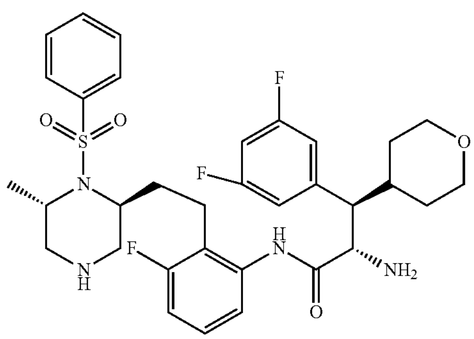 [SMILES: C[C@H]1CNC[C@H](CCc2c(F)cccc2NC(=O)[C@@H](N)[C@@H](c2cc(F)cc(F)c2)C2CCOCC2)N1S(=O)(=O)c1ccccc1] | (βR)-3,5-difluoro-N-(3-fluoro-2-{2-[(2S,6S)-6-methyl-1-(phenylsulfonyl)piperazin-2-yl]ethyl}phenyl)-β-(tetrahydro-2H-pyran-4-yl)-L-phenylalaninamide | 645.3 |
| 295 | 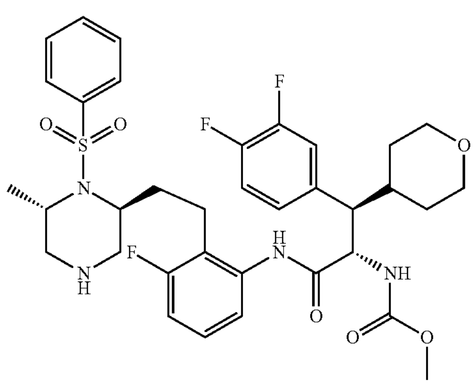 [SMILES: COC(=O)N[C@H](C(=O)Nc1cccc(F)c1CC[C@H]1CNC[C@H](C)N1S(=O)(=O)c1ccccc1)[C@@H](c1ccc(F)c(F)c1)C1CCOCC1] | (βR)-3,4-difluoro-N-(3-fluoro-2-{2-[(2S,6S)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide | 703.3 |

| Ex # | Structure | IUPAC Name | Exact Mass [M + H]+ |
|---|---|---|---|
| 296 | 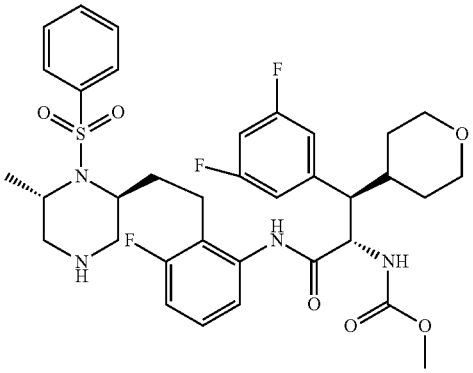 [SMILES: COC(=O)N[C@H](C(=O)Nc1cccc(F)c1CC[C@H]1CNC[C@H](C)N1S(=O)(=O)c1ccccc1)[C@@H](c1cc(F)cc(F)c1)C1CCOCC1] | (βR)-3,5-difluoro-N-(3-fluoro-2-{2-[(2S,6S)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide | 703.3 |
| 297 | 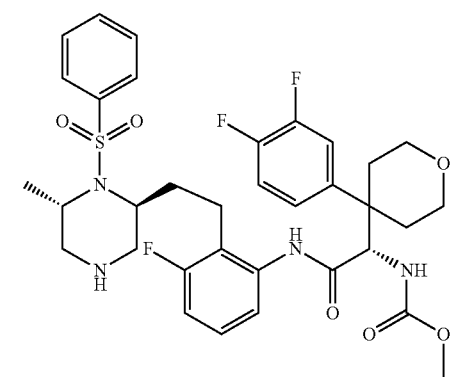 [SMILES: COC(=O)N[C@H](C(=O)Nc1cccc(F)c1CC[C@H]1CNC[C@H](C)N1S(=O)(=O)c1ccccc1)C1(c2ccc(F)c(F)c2)CCOCC1] | methyl {(1S)-1-[4-(3,4-difluorophenyl)tetrahydro-2H-pyran-4-yl]-2-[(3-fluoro-2-{2-[(2S,6S)-6-methyl-1-(phenylsulfonyl)piperazin-2-yl]ethyl}phenyl)amino]-2-oxoethyl}carbamate | 689.3 |
| 298 | 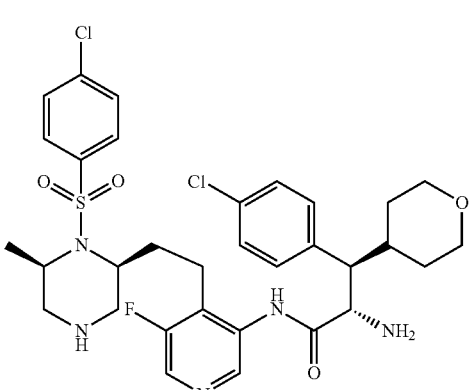 | (βR)-4-chloro-N-[4-(2-{(2S,6R)-1-[(4-chlorophenyl)sulfonyl]-6-methylpiperazin-2-yl}ethyl)-5-fluoropyridin-3-yl]-β-(tetrahydro-2H-pyran-4-yl)-L-phenylalaninamide | 678.2 |
| 299 | 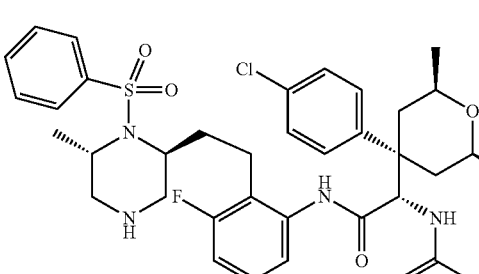 | methyl ((S)-1-((2R,4r,6S)-4-(4-chlorophenyl)-2,6-dimethyltetrahydro-2H-pyran-4-yl)-2-((3-fluoro-2-(2-((2S,6S)-6-methyl-1-(phenylsulfonyl)piperazin-2-yl)ethyl)phenyl)amino)-2-oxoethyl)carbamate | 716.3 |

TABLE 3-continued

| Ex # | Structure | IUPAC Name | Exact Mass [M + H]+ |
|---|---|---|---|
| 300 | 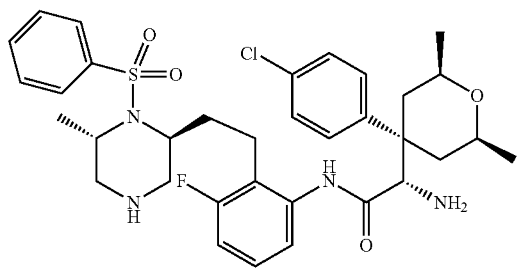 [SMILES: C[C@@H]1C[C@](c2ccc(Cl)cc2)([C@H](N)C(=O)Nc2cccc(F)c2CC[C@H]2CNC[C@H](C)N2S(=O)(=O)c2ccccc2)C[C@H](C)O1] | (S)-2-amino-2-((2R,4r,6S)-4-(4-chlorophenyl)-2,6-dimethyltetrahydro-2H-pyran-4-yl)-N-(3-fluoro-2-(2-((2S,6S)-6-methyl-1-(phenylsulfonyl)piperazin-2-yl)ethyl)phenyl)acetamide | 658.3 |
| 301 | 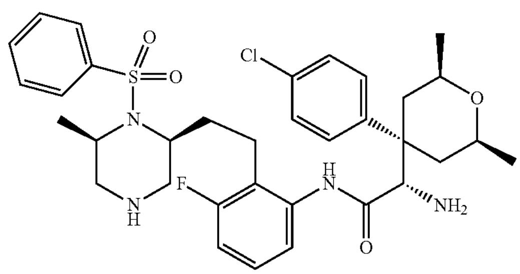 [SMILES: C[C@@H]1C[C@](c2ccc(Cl)cc2)([C@H](N)C(=O)Nc2cccc(F)c2CC[C@H]2CNC[C@@H](C)N2S(=O)(=O)c2ccccc2)C[C@H](C)O1] | (S)-2-amino-2-((2R,4r,6S)-4-(4-chlorophenyl)-2,6-dimethytetrahydro-2H-pyran-4-yl)-N-(3-fluoro-2-(2-((2S,6R)-6-methyl-1-(phenylsulfonyl)piperazin-2-yl)ethyl)phenyl)acetamide | 658.3 |

TABLE 4

| Ex # | Structure | IUPAC Name | Exact Mass [M + H]+ |
|---|---|---|---|
| 302 | 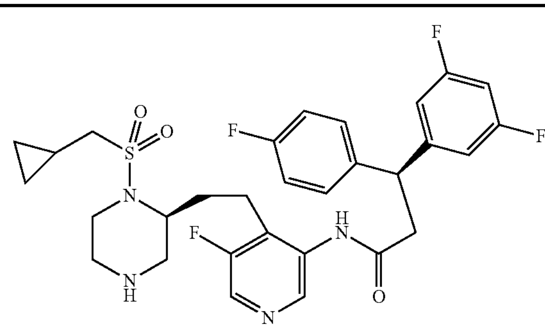 | (3S)-N-[4-(2-{(2S)-1-[(cyclopropylmethyl)sulfonyl]piperazin-2-yl}ethyl)-5-fluoropyridin-3-yl]-3-(3,5-difluorophenyl)-3-(4-fluorophenyl)propanamide | 605.2 |
| 303 | 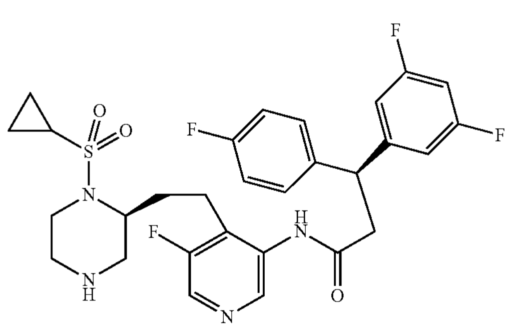 [SMILES: O=C(C[C@@H](c1ccc(F)cc1)c1cc(F)cc(F)c1)Nc1cncc(F)c1CC[C@H]1CNCCN1S(=O)(=O)C1CC1] | (3S)-N-(4-{2-[(2S)-1-(cyclopropylsulfonyl)piperazin-2-yl]ethyl}-5-fluoropyridin-3-yl)-3-(3,5-difluorophenyl)-3-(4-fluorophenyl)propanamide | 591.2 |

TABLE 4-continued

| Ex # | Structure | IUPAC Name | Exact Mass [M + H]+ |
|---|---|---|---|
| 304 | 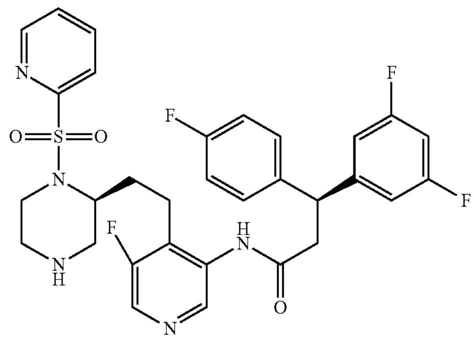 [SMILES: O=C(C[C@@H](c1ccc(F)cc1)c1cc(F)cc(F)c1)Nc1cncc(F)c1CC[C@H]1CNCCN1S(=O)(=O)c1ccccn1] | (3S)-3-(3,5-difluorophenyl)-3-(4-fluorophenyl)-N-(5-fluoro-4-{2-[(2S)-1-(pyridin-2-ylsulfonyl)piperazin-2-yl]ethyl}pyridin-3-yl)propanamide | 628.2 |
| 305 | 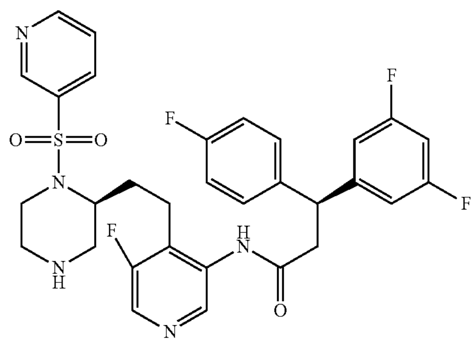 [SMILES: O=C(C[C@@H](c1ccc(F)cc1)c1cc(F)cc(F)c1)Nc1cncc(F)c1CC[C@H]1CNCCN1S(=O)(=O)c1cccnc1] | (3S)-3-(3,5-difluorophenyl)-3-(4-fluorophenyl)-N-(5-fluoro-4-{2-[(2S)-1-(pyridin-3-ylsulfonyl)piperazin-2-yl]ethyl}pyridin-3-yl)propanamide | 628.2 |
| 306 | 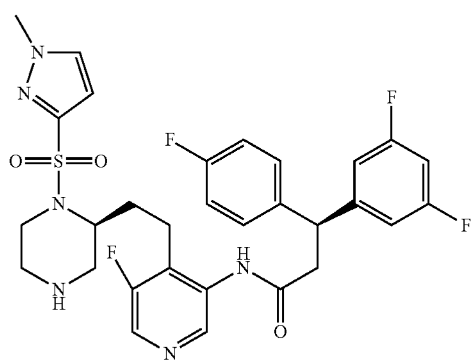 [SMILES: Cn1ccc(S(=O)(=O)N2CCNC[C@@H]2CCc2c(F)cncc2NC(=O)C[C@@H](c2ccc(F)cc2)c2cc(F)cc(F)c2)n1] | (3S)-3-(3,5-difluorophenyl)-N-[5-fluoro-4-(2-{(2S)-1-[(1-methyl-1H-pyrazol-3-yl)sulfonyl]piperazin-2-yl}ethyl)pyridin-3-yl]-3-(4-fluorophenyl)propanamide | 631.2 |
| 307 | 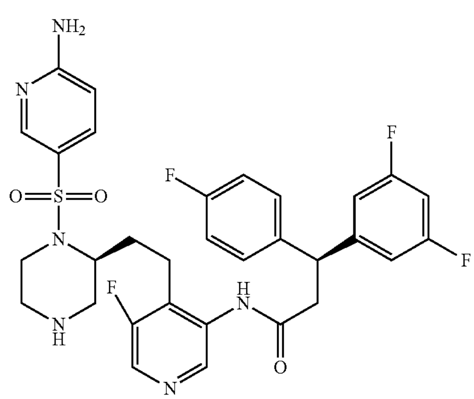 [SMILES: Nc1ccc(S(=O)(=O)N2CCNC[C@@H]2CCc2c(F)cncc2NC(=O)C[C@@H](c2ccc(F)cc2)c2cc(F)cc(F)c2)cn1] | (3S)-N-[4-(2-{(2S)-1-[(6-aminopyridin-3-yl)sulfonyl]piperazin-2-yl}ethyl)-5-fluoropyridin-3-yl]-3-(3,5-difluorophenyl)-3-(4-fluorophenyl)propanamide | 643.2 |

TABLE 4-continued

| Ex # | Structure | IUPAC Name | Exact Mass [M + H]+ |
|---|---|---|---|
| 308 | 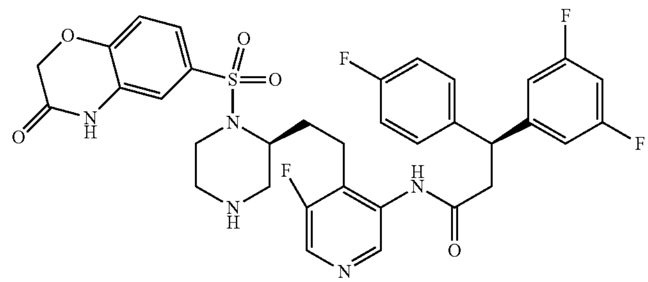 [SMILES: O=C1COc2ccc(S(=O)(=O)N3CCNC[C@@H]3CCc3c(F)cncc3NC(=O)C[C@@H](c3ccc(F)cc3)c3cc(F)cc(F)c3)cc2N1] | (3S)-3-(3,5-difluorophenyl)-N-[5-fluoro-4-(2-{(2S)-1-[(3-oxo-3,4-dihydro-2H-1,4-benzoxazin-6-yl)sulfonyl]piperazin-2-yl}ethyl)pyridin-3-yl]-3-(4-fluorophenyl)propanamide | 698.2 |
| 309 | 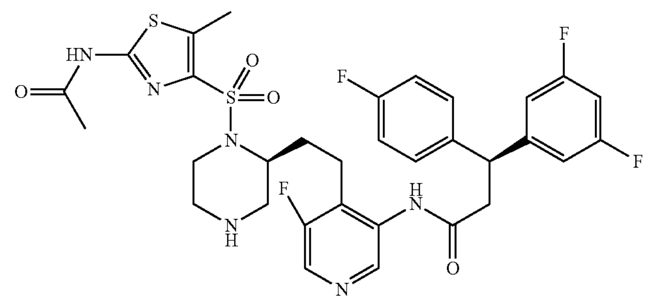 [SMILES: CC(=O)Nc1nc(S(=O)(=O)N2CCNC[C@@H]2CCc2c(F)cncc2NC(=O)C[C@@H](c2ccc(F)cc2)c2cc(F)cc(F)c2)c(C)s1] | (3S)-N-(4-{2-[(2S)-1-{[2-(acetylamino)-5-methyl-1,3-thiazol-4-yl]sulfonyl}piperazin-2-yl]ethyl}-5-fluoropyridin-3-yl)-3-(3,5-difluorophenyl)-3-(4-fluorophenyl)propanmide | 705.2 |
| 310 | 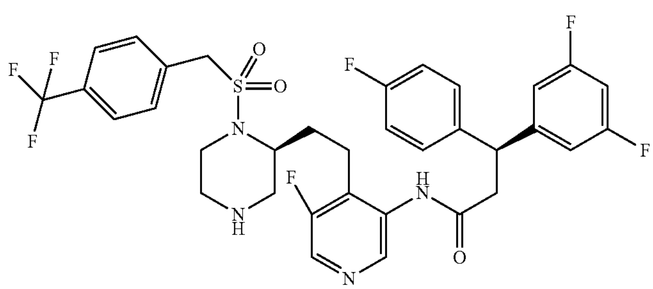 [SMILES: O=C(C[C@@H](c1ccc(F)cc1)c1cc(F)cc(F)c1)Nc1cncc(F)c1CC[C@H]1CNCCN1S(=O)(=O)Cc1ccc(C(F)(F)F)cc1] | (3S)-3-(3,5-difluorophenyl)-3-(4-fluorophenyl)-N-(5-fluoro-4-{2-[(2S)-1-{[4-(trifluoromethyl)benzyl]sulfonyl}piperazin-2-yl]ethyl}pyridin-3-yl)propanamide | 709.2 |
| 311 | 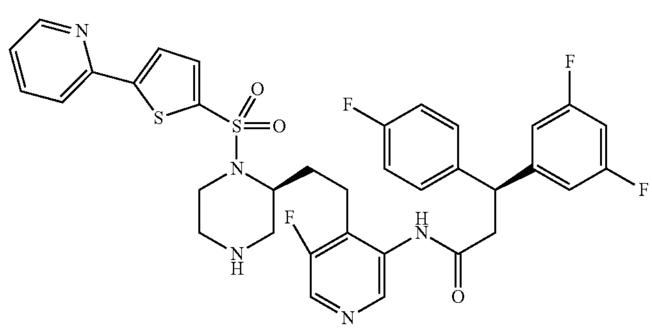 [SMILES: O=C(C[C@@H](c1ccc(F)cc1)c1cc(F)cc(F)c1)Nc1cncc(F)c1CC[C@H]1CNCCN1S(=O)(=O)c1ccc(-c2ccccn2)s1] | (3S)-3-(3,5-difluorophenyl)-3-(4-fluorophenyl)-N-[5-fluoro-4-(2-{(2S)-1-[(5-pyridin-2-ylthiophen-2-yl)sulfonyl]piperazin-2-yl}ethyl)pyridin-3-yl]propanamide | 710.2 |

TABLE 4-continued

| Ex # | Structure | IUPAC Name | Exact Mass [M + H]+ |
|---|---|---|---|
| 312 | 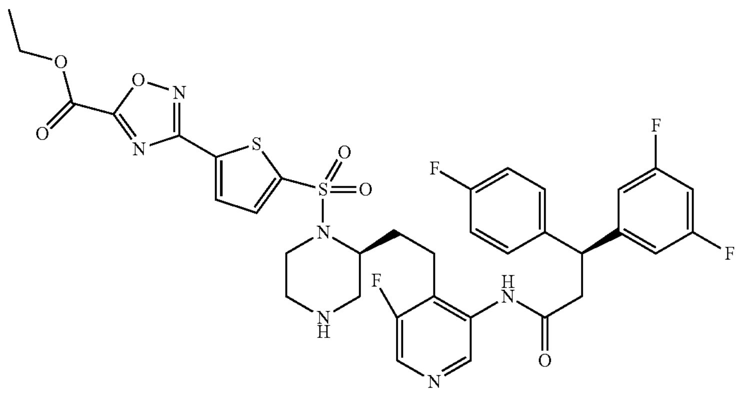 [SMILES: CCOC(=O)c1nc(-c2ccc(S(=O)(=O)N3CCNC[C@@H]3CCc3c(F)cncc3NC(=O)C[C@@H](c3ccc(F)cc3)c3cc(F)cc(F)c3)s2)no1] | ethyl 3-[5-({(2S)-2-[2-(3-{[(3S)-3-(3,5-difluorophenyl)-3-(4-fluorophenyl)propanoyl]amino}-5-fluoropyridin-4-yl)ethyl]piperazin-1-yl}sulfonyl)thiophen-2-yl]-1,2,4-oxadiazole-5-carboxylate | 773.2 |
| 313 | 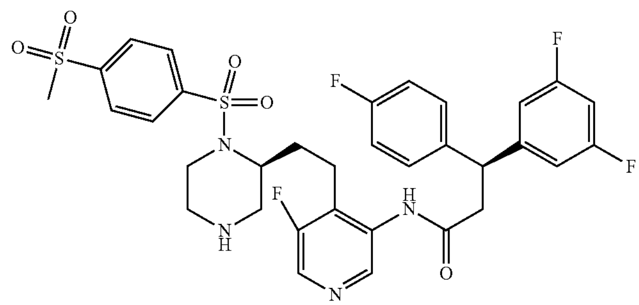 [SMILES: CS(=O)(=O)c1ccc(S(=O)(=O)N2CCNC[C@@H]2CCc2c(F)cncc2NC(=O)C[C@@H](c2ccc(F)cc2)c2cc(F)cc(F)c2)cc1] | (3S)-3-(3,5-difluorophenyl)-N-(5-fluoro-4-{2-[(2S)-1-{[4-(methylsulfonyl)phenyl]sulfonyl}piperazin-2-yl]ethyl}pyridin-3-yl)-3-(4-fluorophenyl)propanamide | 705.2 |
| 314 | 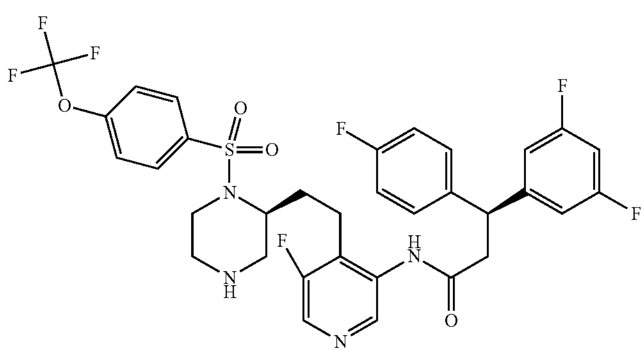 [SMILES: O=C(C[C@@H](c1ccc(F)cc1)c1cc(F)cc(F)c1)Nc1cncc(F)c1CC[C@H]1CNCCN1S(=O)(=O)c1ccc(OC(F)(F)F)cc1] | (3S)-3-(3,5-difluorophenyl)-3-(4-fluorophenyl)-N-(5-fluoro-4-{2-[(2S)-1-{[4-(trifluoromethoxy)phenyl]sulfonyl}piperazin-2-yl]ethyl}pyridin-3-yl)propanamide | 711.2 |
| 315 | 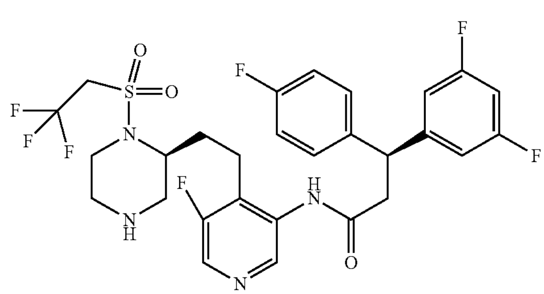 [SMILES: O=C(C[C@@H](c1ccc(F)cc1)c1cc(F)cc(F)c1)Nc1cncc(F)c1CC[C@H]1CNCCN1S(=O)(=O)CC(F)(F)F] | (3S)-3-(3,5-difluorophenyl)-3-(4-fluorophenyl)-N-[5-fluoro-4-(2-{(2S)-1-[(2,2,2-trifluoroethyl)sulfonyl]piperazin-2-yl}ethyl)pyridin-3-yl]propanamide | 633.2 |

TABLE 4-continued

| Ex # | Structure | IUPAC Name | Exact Mass [M + H]+ |
|---|---|---|---|
| 316 | 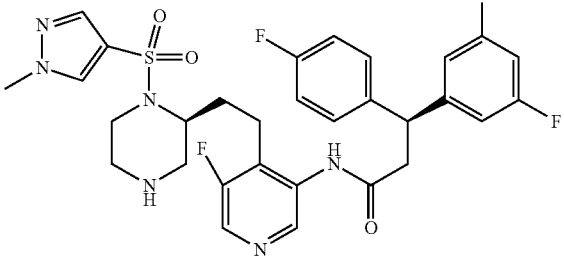 | (3S)-3-(3,5-difluorophenyl)-N-[5-fluoro-4-(2-{(2S)-1-[(1-methyl-1H-pyrazol-4-yl)sulfonyl]piperazin-2-yl}ethyl)pyridin-3-yl]-3-(4-fluorophenyl)propanamide | 631.2 |
| 317 | 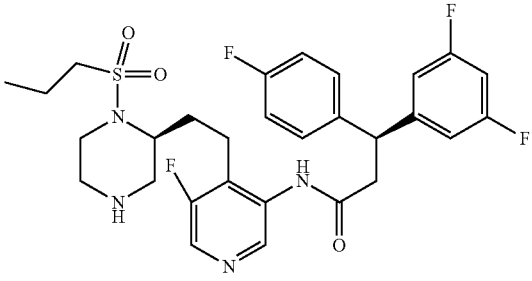 [SMILES: CCCS(=O)(=O)N1CCNC[C@@H]1CCc1c(F)cncc1NC(=O)C[C@@H](c1ccc(F)cc1)c1cc(F)cc(F)c1] | (3S)-3-(3,5-difluorophenyl)-3-(4-fluorophenyl)-N-(5-fluoro-4-{2-[(2S)-1-(propylsulfonyl)piperazin-2-yl]ethyl}pyridin-3-yl)propanamide | 593.2 |
| 318 | 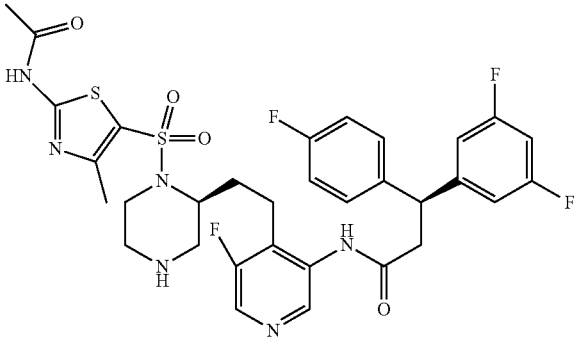 [SMILES: CC(=O)Nc1nc(C)c(S(=O)(=O)N2CCNC[C@@H]2CCc2c(F)cncc2NC(=O)C[C@@H](c2ccc(F)cc2)c2cc(F)cc(F)c2)s1] | (3S)-N-(4-{2-[(2S)-1-{[2-(acetylamino)-4-methyl-1,3-thiazol-5-yl]sulfonyl}piperazin-2-yl]ethyl}-5-fluoropyridin-3-yl)-3-(3,5-difluorophenyl)-3-(4-fluorophenyl)propanamide | 705.2 |
| 319 | 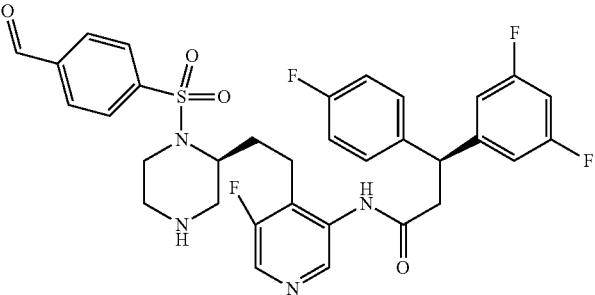 [SMILES: O=Cc1ccc(S(=O)(=O)N2CCNC[C@@H]2CCc2c(F)cncc2NC(=O)C[C@@H](c2ccc(F)cc2)c2cc(F)cc(F)c2)cc1] | (3S)-3-(3,5-difluorophenyl)-N-[5-fluoro-4-(2-{(2S)-1-[(4-formylphenyl)sulfonyl]piperazin-2-yl}ethyl)pyridin-3-yl]-3-(4-fluorophenyl)propanamide | 655.2 |
| 320 | 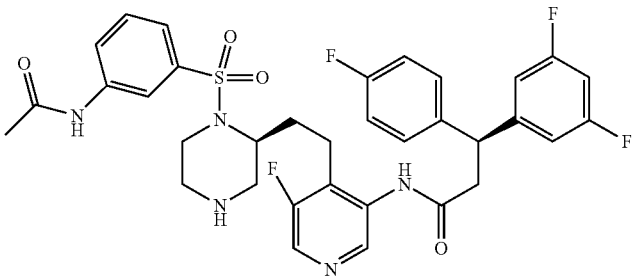 [SMILES: CC(=O)Nc1cccc(S(=O)(=O)N2CCNC[C@@H]2CCc2c(F)cncc2NC(=O)C[C@@H](c2ccc(F)cc2)c2cc(F)cc(F)c2)c1] | (3S)-N-(4-{2-[(2S)-1-{[3-(acetylamino)phenyl]sulfonyl}piperazin-2-yl]ethyl}-5-fluoropyridin-3-yl)-3-(3,5-difluorophenyl)-3-(4-fluorophenyl)propanamide | 684.2 |

TABLE 4-continued

| Ex # | Structure | IUPAC Name | Exact Mass [M + H]+ |
|---|---|---|---|
| 321 | 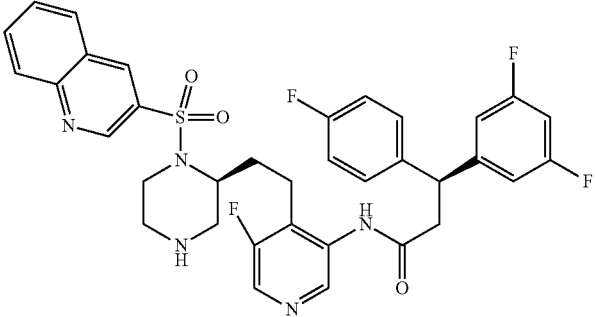 [SMILES: O=C(C[C@@H](c1ccc(F)cc1)c1cc(F)cc(F)c1)Nc1cncc(F)c1CC[C@H]1CNCCN1S(=O)(=O)c1cnc2ccccc2c1] | (3S)-3-(3,5-difluorophenyl)-3-(4-fluorophenyl)-N-(5-fluoro-4-{2-[(2S)-1-(quinolin-3-ylsulfonyl)piperazin-2-yl]ethyl}pyridin-3-yl)propanamide | 678.2 |
| 322 | 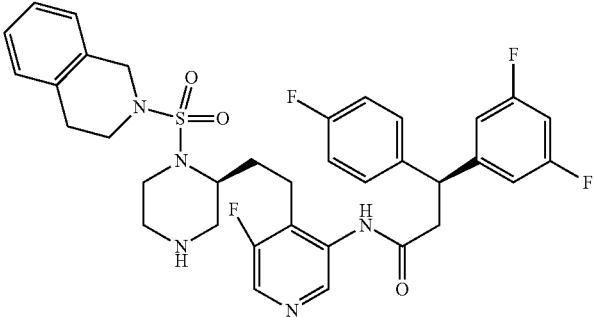 [SMILES: O=C(C[C@@H](c1ccc(F)cc1)c1cc(F)cc(F)c1)Nc1cncc(F)c1CC[C@H]1CNCCN1S(=O)(=O)N1CCc2ccccc2C1] | (3S)-3-(3,5-difluorophenyl)-N-(4-{2-[(2S)-1-(3,4-dihydroisoquinolin-2(1H)-ylsulfonyl)piperazin-2-yl]ethyl}-5-fluoropyridin-3-yl)-3-(4-fluorophenyl)propanamide | 682.2 |
| 323 | 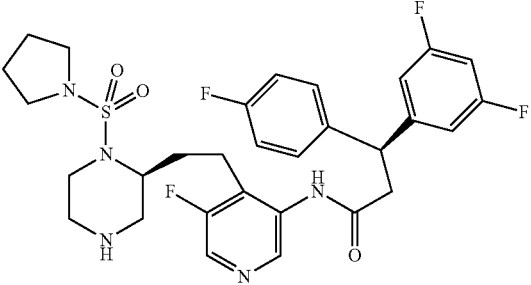 [SMILES: O=C(C[C@@H](c1ccc(F)cc1)c1cc(F)cc(F)c1)Nc1cncc(F)c1CC[C@H]1CNCCN1S(=O)(=O)N1CCCC1] | (3S)-3-(3,5-difluorophenyl)-3-(4-fluorophenyl)-N-(5-fluoro-4-{2-[(2S)-1-(pyrrolidin-1-ylsulfonyl)piperazin-2-yl]ethyl}pyridin-3-yl)propanamide | 620.2 |
| 324 | 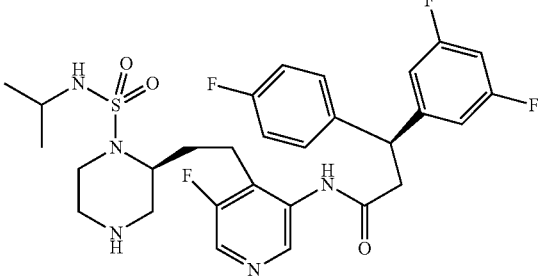 | (3S)-3-(3,5-difluorophenyl)-N-[5-fluoro-4-(2-{(2S)-1-[(1-methylethyl)sulfamoyl]piperazin-2-yl}ethyl)pyridin-3-yl]-3-(4-fluorophenyl)propanamide | 608.2 |

TABLE 4-continued

| Ex # | Structure | IUPAC Name | Exact Mass [M + H]+ |
|---|---|---|---|
| 325 | 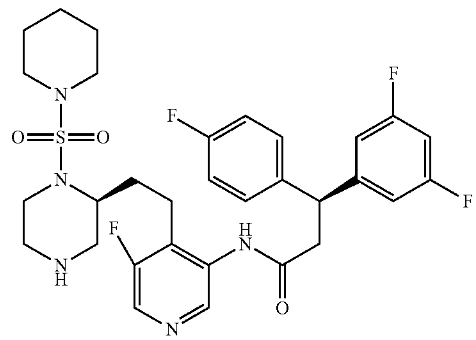 [SMILES: O=C(C[C@@H](c1ccc(F)cc1)c1cc(F)cc(F)c1)Nc1cncc(F)c1CC[C@H]1CNCCN1S(=O)(=O)N1CCCCC1] | (3S)-3-(3,5-difluorophenyl)-3-(4-fluorophenyl)-N-(5-fluoro-4-{2-[(2S)-1-(piperidin-1-ylsulfonyl)piperazin-2-yl]ethyl}pyridin-3-yl)propanamide | 634.2 |
| 326 | 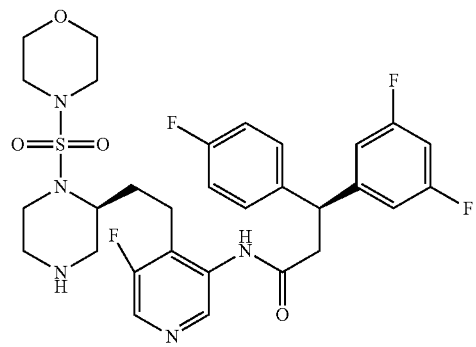 [SMILES: O=C(C[C@@H](c1ccc(F)cc1)c1cc(F)cc(F)c1)Nc1cncc(F)c1CC[C@H]1CNCCN1S(=O)(=O)N1CCOCC1] | (3S)-3-(3,5-difluorophenyl)-N-(5-fluoro-4-{2-[(2S)-1-(morpholin-4-ylsulfonyl)piperazin-2-yl]ethyl}pyridin-3-yl)-3-(4-fluorophenyl)propanamide | 636.2 |
| 327 | 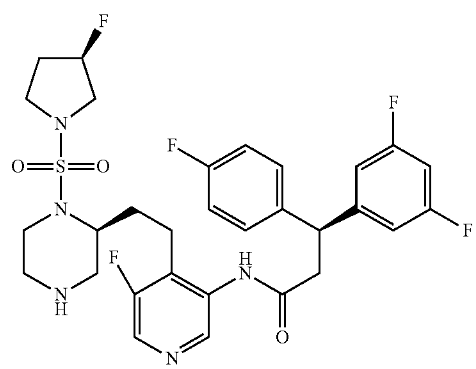 [SMILES: O=C(C[C@@H](c1ccc(F)cc1)c1cc(F)cc(F)c1)Nc1cncc(F)c1CC[C@H]1CNCCN1S(=O)(=O)N1CC[C@@H](F)C1] | (3S)-3-(3,5-difluorophenyl)-N-(5-fluoro-4-{2-[(2)S-1-{[(3R)-3-fluoropyrrolidin-1-yl]sulfonyl}piperazin-2-yl]ethyl}pyridin-3-yl)-3-(4-fluorophenyl)propanamide | 638.2 |
| 328 | 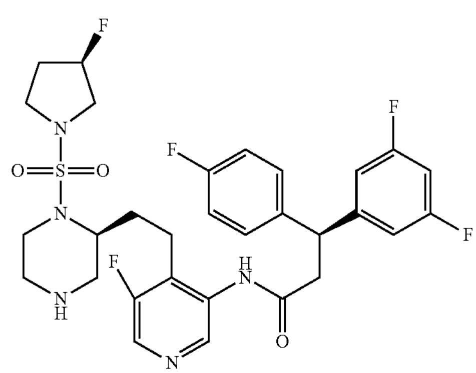 [SMILES: O=C(C[C@@H](c1ccc(F)cc1)c1cc(F)cc(F)c1)Nc1cncc(F)c1CC[C@H]1CNCCN1S(=O)(=O)N1CC[C@@H](F)C1] | (3S)-3-(3,5-difluorophenyl)-N-(5-fluoro-4-{2-[(2S)-1-{[(3S)-3-fluoropyrrolidin-1-yl]sulfonyl}piperazin-2-yl]ethyl}pyridin-3-yl)-3-(4-fluorophenyl)propanmide | 638.2 |

TABLE 4-continued

| Ex # | Structure | IUPAC Name | Exact Mass [M + H]+ |
|---|---|---|---|
| 329 | 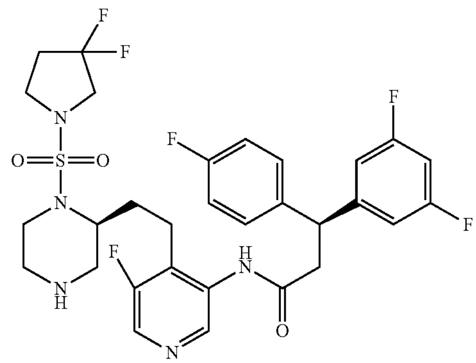 [SMILES: O=C(C[C@@H](c1ccc(F)cc1)c1cc(F)cc(F)c1)Nc1cncc(F)c1CC[C@H]1CNCCN1S(=O)(=O)N1CCC(F)(F)C1] | (3S)-3-(3,5-difluorophenyl)-N-[4-(2-{(2)S-1-[(3,3-difluoropyrrolidin-1-yl)sulfonyl]piperazin-2-yl}ethyl)-5-fluoropyridin-3-yl]-3-(4-fluorophenyl)propanamide | 656.2 |
| 330 | 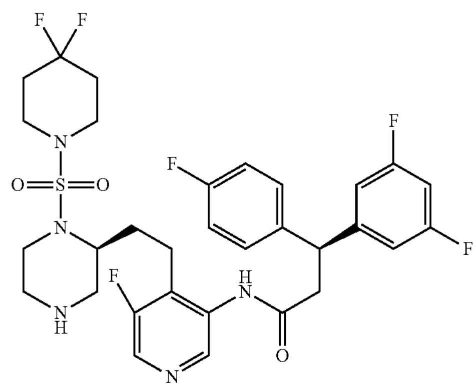 [SMILES: O=C(C[C@@H](c1ccc(F)cc1)c1cc(F)cc(F)c1)Nc1cncc(F)c1CC[C@H]1CNCCN1S(=O)(=O)N1CCC(F)(F)CC1] | (3S)-3-(3,5-difluorophenyl)-N-[4-(2-{(2S)-1-[(4,4-difluoropiperidin-1-yl)sulfonyl]piperazin-2-yl}ethyl)-5-fluoropyridin-3-yl]-3-(4-fluorophenyl)propanamide | 670.2 |
| 331 | 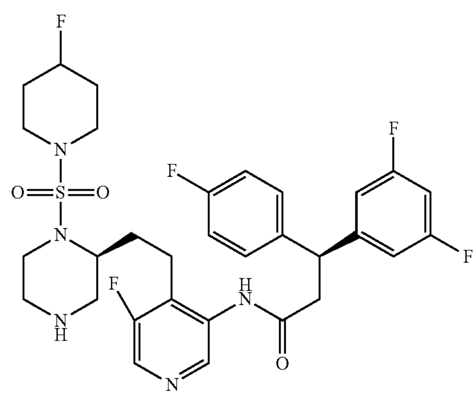 [SMILES: O=C(C[C@@H](c1ccc(F)cc1)c1cc(F)cc(F)c1)Nc1cncc(F)c1CC[C@H]1CNCCN1S(=O)(=O)N1CCC(F)CC1] | (3S)-3-(3,5-difluorophenyl)-N-[5-fluoro-4-(2-{(2S)-1-[(4-fluoropiperidin-1-yl)sulfonyl]piperazin-2-yl}ethyl)pyridin-3-yl]-3-(4-fluorophenyl)propanamide | 652.2 |
| 332 | 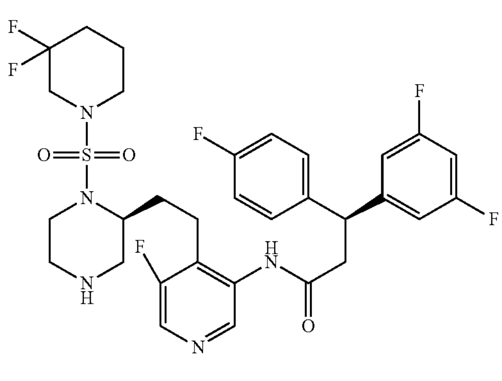 [SMILES: O=C(C[C@@H](c1ccc(F)cc1)c1cc(F)cc(F)c1)Nc1cncc(F)c1CC[C@H]1CNCCN1S(=O)(=O)N1CCCC(F)(F)C1] | (3S)-3-(3,5-difluorophenyl)-N-[4-(2-{(2S)-1-[(3,3-difluoropiperidin-1-yl)sulfonyl]piperazin-2-yl}ethyl)-5-fluoropyridin-3-yl]-3-(4-fluorophenyl)propanamide | 670.2 |

TABLE 4-continued

| Ex # | Structure | IUPAC Name | Exact Mass [M + H]+ |
|---|---|---|---|
| 333 | 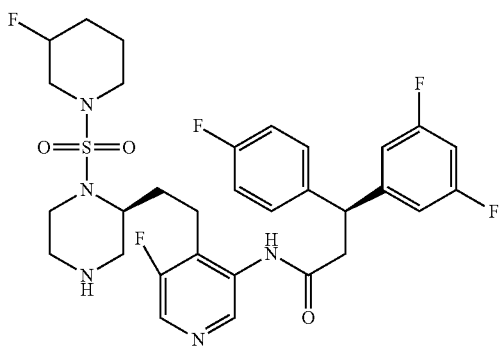 [SMILES: O=C(C[C@@H](c1ccc(F)cc1)c1cc(F)cc(F)c1)Nc1cncc(F)c1CC[C@H]1CNCCN1S(=O)(=O)N1CCCC(F)C1] | (3S)-3-(3,5-difluorophenyl)-N-[5-fluoro-4-(2-{(2S)-1-[(3-fluoropiperidin-1-yl)sulfonyl]piperazin-2-yl}ethyl)pyridin-3-yl]-3-(4-fluorophenyl)propanamide | 652.2 |
| 334 | 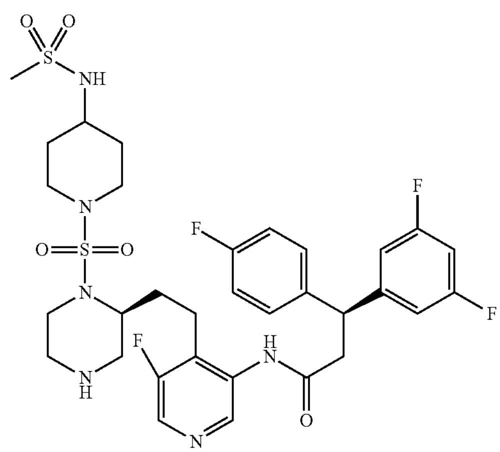 [SMILES: CS(=O)(=O)NC1CCN(S(=O)(=O)N2CCNC[C@@H]2CCc2c(F)cncc2NC(=O)C[C@@H](c2ccc(F)cc2)c2cc(F)cc(F)c2)CC1] | (3S)-3-(3,5-difluorophenyl)-N-(5-fluoro-4-{2-[(2S)-1-({4-[(methylsulfonyl)amino]piperidin-1-yl}sulfonyl)piperazin-2-yl]ethyl}pyridin-3-yl)-3-(4-fluorophenyl)propanamide | 727.2 |
| 335 | 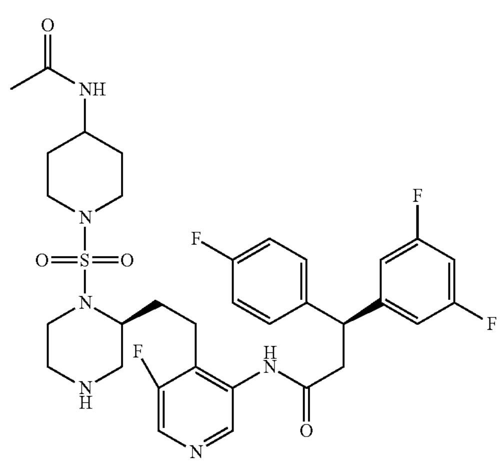 [SMILES: CC(=O)NC1CCN(S(=O)(=O)N2CCNC[C@@H]2CCc2c(F)cncc2NC(=O)C[C@@H](c2ccc(F)cc2)c2cc(F)cc(F)c2)CC1] | (3S)-N-(4-{2-[(2S)-1-{[4-(acetylamino)piperidin-1-yl]sulfonyl}piperazin-2-yl]ethyl}-5-fluoropyridin-3-yl)-3-(3,5-difluorophenyl)-3-(4-fluorophenyl)propanamide | 691.3 |

TABLE 4-continued

| Ex # | Structure | IUPAC Name | Exact Mass [M + H]+ |
|---|---|---|---|
| 336 | 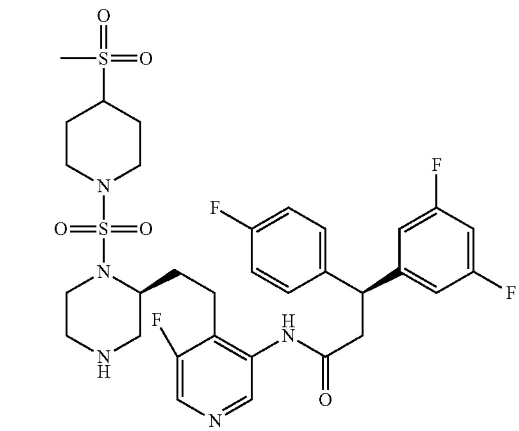 [SMILES: CS(=O)(=O)C1CCN(S(=O)(=O)N2CCNC[C@@H]2CCc2c(F)cncc2NC(=O)C[C@@H](c2ccc(F)cc2)c2cc(F)cc(F)c2)CC1] | (3S)-3-(3,5-difluorophenyl)-N-(5-fluoro-4-{2-[(2S)-1-{[4-(methylsulfonyl)piperidin-1-yl]sulfonyl}piperazin-2-yl]ethyl}pyridin-3-yl)-3-(4-fluorophenyl)propanamide | 712.2 |
| 337 | 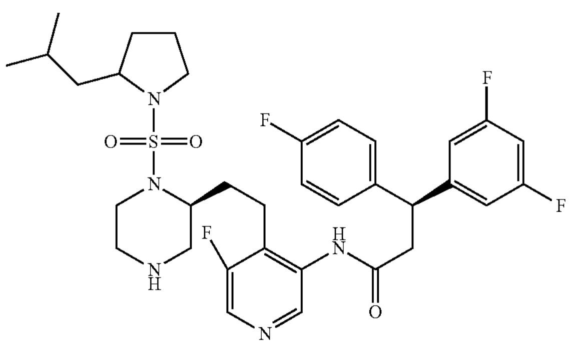 [SMILES: CC(C)CC1CCCN1S(=O)(=O)N1CCNC[C@@H]1CCc1c(F)cncc1NC(=O)C[C@@H](c1ccc(F)cc1)c1cc(F)cc(F)c1] | (3S)-3-(3,5-difluorophenyl)-N-(5-fluoro-4-{2-[(2S)-1-{[2-(2-methylpropyl)pyrrolidin-1-yl]sulfonyl}piperazin-2-yl]ethyl}pyridin-3-yl)-3-(4-fluorophenyl)propanamide | 676.3 |
| 338 | 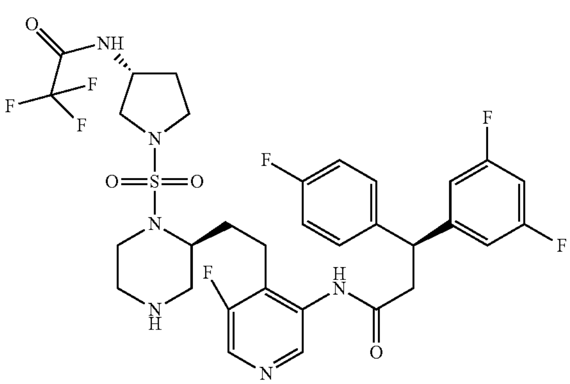 [SMILES: O=C(C[C@@H](c1ccc(F)cc1)c1cc(F)cc(F)c1)Nc1cncc(F)c1CC[C@H]1CNCCN1S(=O)(=O)N1CC[C@@H](NC(=O)C(F)(F)F)C1] | (3S)-3-(3,5-difluorophenyl)-3-(4-fluorophenyl)-N-(5-fluoro-4-{2-[(2S)-1-({(3R)-3-[(trifluoroacetyl)amino]pyrrolidin-1-yl}sulfonyl)piperazin-2-yl]ethyl}pyridin-3-yl)propanamide | 731.2 |
| 339 | 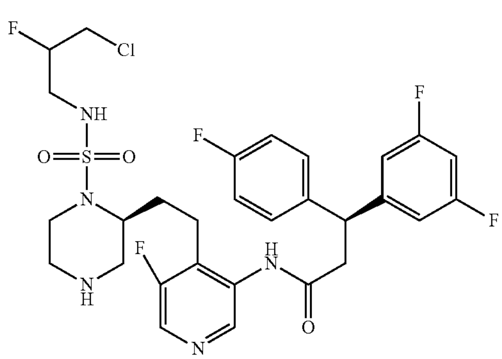 [SMILES: O=C(C[C@@H](c1ccc(F)cc1)c1cc(F)cc(F)c1)Nc1cncc(F)c1CC[C@H]1CNCCN1S(=O)(=O)NCC(F)CCl] | (3S)-N-[4-(2-{(2S)-1-[(3-chloro-2-fluoropropyl)sulfamoyl]piperazin-2-yl}ethyl)-5-fluoropyridin-3-yl]-3-(3,5-difluorophenyl)-3-(4-fluorophenyl)propanamide | 660.2 |

TABLE 4-continued

| Ex # | Structure | IUPAC Name | Exact Mass [M + H]+ |
|---|---|---|---|
| 340 | 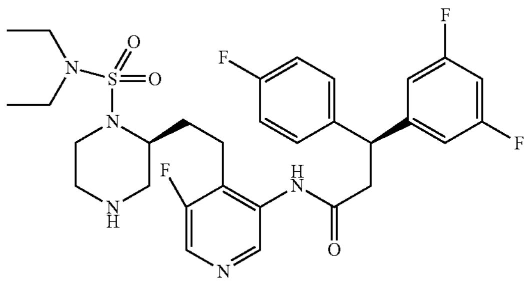 [SMILES: CCN(CC)S(=O)(=O)N1CCNC[C@@H]1CCc1c(F)cncc1NC(=O)C[C@@H](c1ccc(F)cc1)c1cc(F)cc(F)c1] | (3S)-N-(4-{2-[(2S)-1-(diethylsulfamoyl)piperazin-2-yl]ethyl}-5-fluoropyridin-3-yl)-3-(3,5-difluorophenyl)-3-(4-fluorophenyl)propanamide | 622.2 |
| 341 | 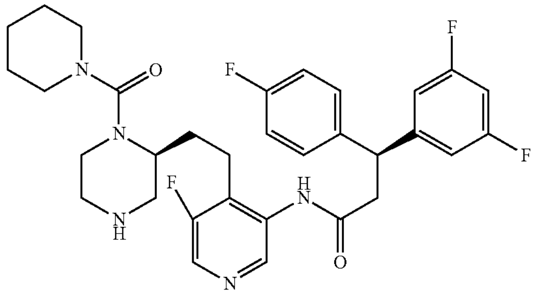 [SMILES: O=C(C[C@@H](c1ccc(F)cc1)c1cc(F)cc(F)c1)Nc1cncc(F)c1CC[C@H]1CNCCN1C(=O)N1CCCCC1] | (3S)-3-(3,5-difluorophenyl)-3-(4-fluorophenyl)-N-(5-fluoro-4-{2-[(2S)-1-(piperidin-1-ylcarbonyl)piperazin-2-yl]ethyl}pyridin-3-yl)propanamide | 598.3 |
| 342 | 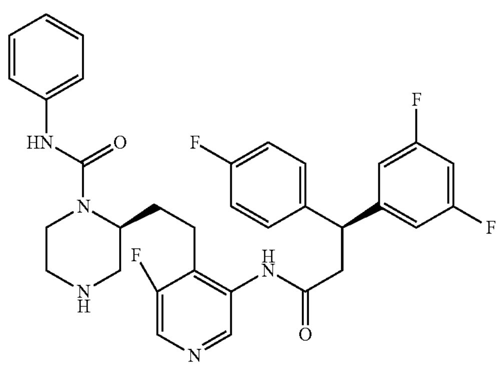 [SMILES: O=C(C[C@@H](c1ccc(F)cc1)c1cc(F)cc(F)c1)Nc1cncc(F)c1CC[C@H]1CNCCN1C(=O)Nc1ccccc1] | (2S)-2-[2-(3-{[(3S)-3-(3,5-difluorophenyl)-3-(4-fluorophenyl)propanoyl]amino}-5-fluoropyridin-4-yl)ethyl]-N-phenylpiperazine-1-carboxamide | 606.2 |
| 343 | 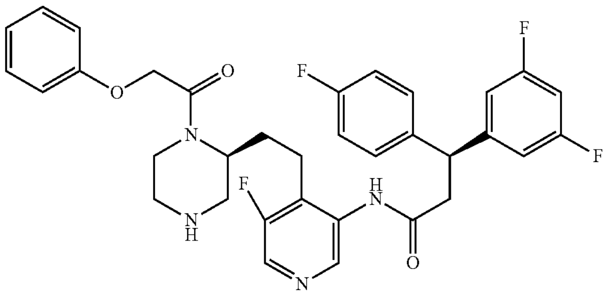 [SMILES: O=C(C[C@@H](c1ccc(F)cc1)c1cc(F)cc(F)c1)Nc1cncc(F)c1CC[C@H]1CNCCN1C(=O)COc1ccccc1] | (3S)-3-(3,5-difluorophenyl)-N-(5-fluoro-4-{2-[(2S)-1-(phenoxyacetyl)piperazin-2-yl]ethyl}pyridin-3-yl)-3-(4-fluorophenyl)propanamide | 621.2 |

TABLE 4-continued

| Ex # | Structure | IUPAC Name | Exact Mass [M + H]+ |
|---|---|---|---|
| 344 | 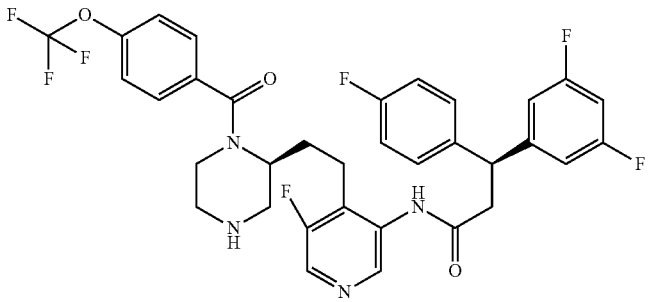 [SMILES: O=C(C[C@@H](c1ccc(F)cc1)c1cc(F)cc(F)c1)Nc1cncc(F)c1CC[C@H]1CNCCN1C(=O)c1ccc(OC(F)(F)F)cc1] | (3S)-3-(3,5-difluorophenyl)-3-(4-fluorophenyl)-N-(5-fluoro-4-{2-[(2S)-1-{[4-(trifluoromethoxy)phenyl]carbonyl}piperazin-2-yl]ethyl}pyridin-3-yl)propanamide | 675.2 |
| 345 | 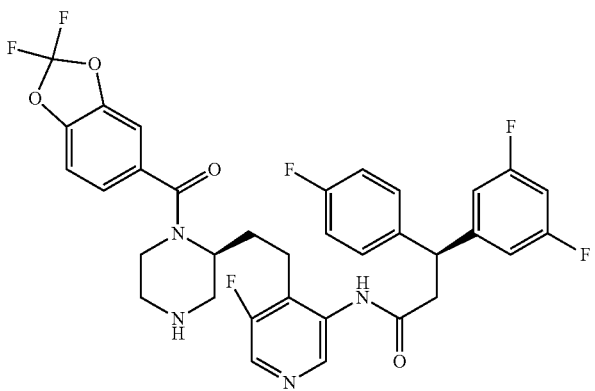 [SMILES: O=C(C[C@@H](c1ccc(F)cc1)c1cc(F)cc(F)c1)Nc1cncc(F)c1CC[C@H]1CNCCN1C(=O)c1ccc2c(c1)OC(F)(F)O2] | (3S)-N-[4-(2-{(2S)-1-[(2,2-difluoro-1,3-benzodioxol-5-yl)carbonyl]piperazin-2-yl}ethyl)-5-fluoropyridin-3-yl]-3-(3,5-difluorophenyl)-3-(4-fluorophenyl)propanamide | 671.2 |
| 346 | 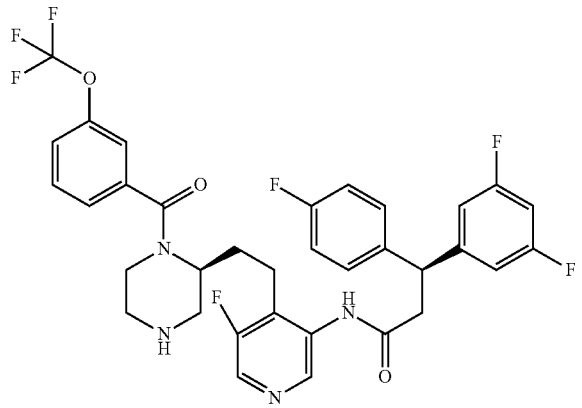 [SMILES: O=C(C[C@@H](c1ccc(F)cc1)c1cc(F)cc(F)c1)Nc1cncc(F)c1CC[C@H]1CNCCN1C(=O)c1cccc(OC(F)(F)F)c1] | (3S)-3-(3,5-difluorophenyl)-3-(4-fluorophenyl)-N-(5-fluoro-4-{2-[(2S)-1-{[3-(trifluoromethoxy)phenyl]carbonyl}piperazin-2-yl]ethyl}pyridin-3-yl)propanamide | 675.2 |
| 347 | 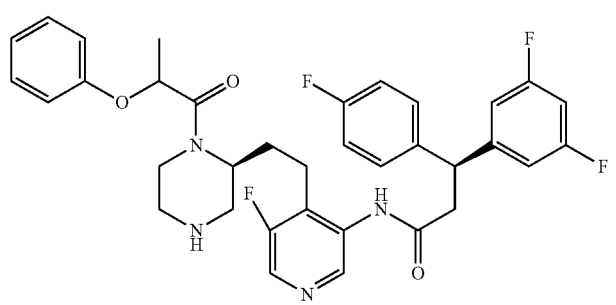 [SMILES: CC(Oc1ccccc1)C(=O)N1CCNC[C@@H]1CCc1c(F)cncc1NC(=O)C[C@@H](c1ccc(F)cc1)c1cc(F)cc(F)c1] | (3S)-3-(3,5-difluorophenyl)-N-(5-fluoro-4-{2-[(2S)-1-(2-phenoxypropanoyl)piperazin-2-yl]ethyl}pyridin-3-yl)-3-(4-fluorophenyl)propanamide | 635.3 |

TABLE 4-continued

| Ex # | Structure | IUPAC Name | Exact Mass [M + H]+ |
|---|---|---|---|
| 348 | 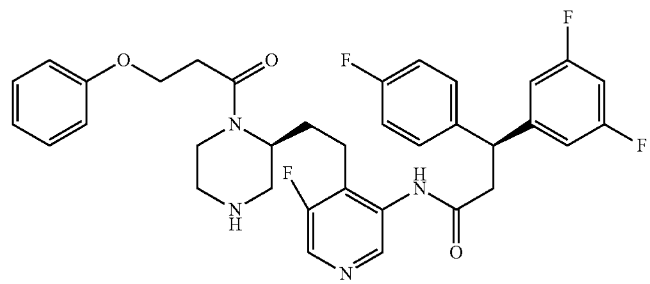 [SMILES: O=C(C[C@@H](c1ccc(F)cc1)c1cc(F)cc(F)c1)Nc1cncc(F)c1CC[C@H]1CNCCN1C(=O)CCOc1ccccc1] | (3S)-3-(3,5-difluorophenyl)-N-(5-fluoro-4-{2-[(2S)-1-(3-phenoxypropanoyl)piperazin-2-yl]ethyl}pyridin-3-yl)-3-(4-fluorophenyl)propanamide | 635.3 |
| 349 | 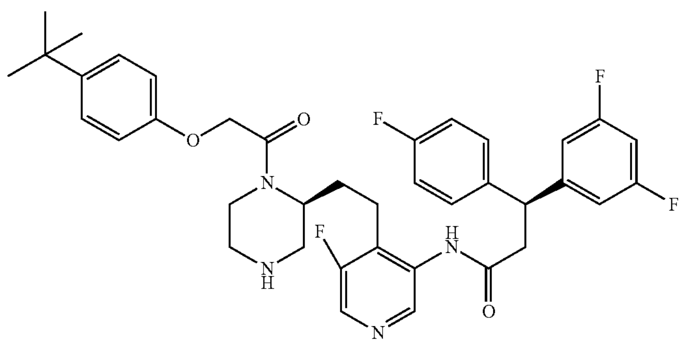 [SMILES: CC(C)(C)c1ccc(OCC(=O)N2CCNC[C@@H]2CCc2c(F)cncc2NC(=O)C[C@@H](c2ccc(F)cc2)c2cc(F)cc(F)c2)cc1] | (3S)-N-[4-(2-{(2S)-1-[(4-tert-butylphenoxy)acetyl]piperazin-2-yl}ethyl)-5-fluoropyridin-3-yl]-3-(3,5-difluorophenyl)-3-(4-fluorophenyl)propanamide | 677.3 |

EXAMPLE 350

Methyl ((S)-1,1-bis(4-fluorophenyl)-3-oxo-3-(((1S,2R)-2-(2-((S)-1-(phenylsulfonyl)piperazin-2-yl)ethyl)cyclopentyl)amino)propan-2-yl)carbamate

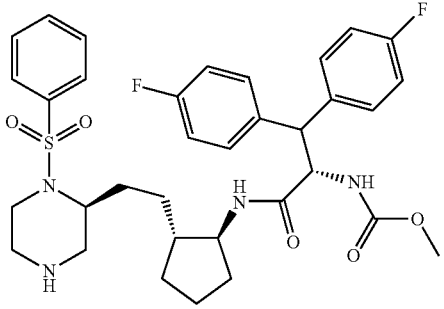 [SMILES: COC(=O)N[C@H](C(=O)N[C@H]1CCC[C@@H]1CC[C@H]1CNCCN1S(=O)(=O)c1ccccc1)C(c1ccc(F)cc1)c1ccc(F)cc1]

Step 1: (R)-1-benzyl 4-tert-butyl 2-(hydroxymethyl)piperazine-1,4-dicarboxylate

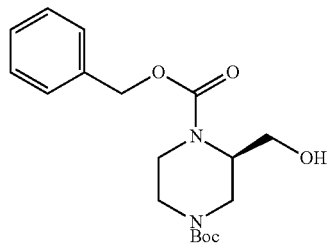 [SMILES: CC(C)(C)OC(=O)N1CCN(C(=O)OCc2ccccc2)[C@@H](CO)C1]

To a biphasic mixture of alcohol (9.9 g, 46 mmol) in CH$_2$Cl$_2$ (160 mL) and sat. aq. NaHCO$_3$ (160 mL) at rt was added benzyl chloroformate (6.5 mL, 46 mmol) in CH$_2$Cl$_2$ (15 mL) over ~10 minutes. The resulting biphasic mixture was stirred at rt overnight (12 h) whereupon the reaction was analyzed by both TLC and LC-MS to reveal consumption of starting material. The mixture was transferred to a separatory funnel where the layers were separated. The aqueous layer was extracted with CH$_2$Cl$_2$ (3×150 mL) and the organic layers were combined. The organic layer was dried (Na$_2$SO$_4$), filtered, concentrated under reduced pressure and placed under high vacuum to afford a thick yellow oil. The crude oil was dissolved in CH$_2$Cl$_2$ (15 mL) and was loaded onto a 220 g silica gel column. A gradient of 100% hexanes to 10% hexanes/90% EtOAc was run over 50 minutes whereupon the tubes containing the product were combined and concentrated under reduced pressure. The title compound was placed under high vacuum to afford 15.1 g of a light yellow oil. MS: m/z=351 (M+H$^+$).

Step 2: (R)-1-benzyl 4-tert-butyl 2-formylpiperazine-1,4-dicarboxylate

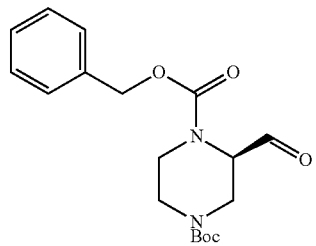 [SMILES: CC(C)(C)OC(=O)N1CCN(C(=O)OCc2ccccc2)[C@@H](C=O)C1]

To a mixture of (R)-1-benzyl 4-tert-butyl 2-(hydroxymethyl)piperazine-1,4-dicarboxylate (8.4 g, 24 mmol) in CH$_2$Cl$_2$ (120 mL) at 0° C. was added Dess-Martin Periodinane (12.2 g, 29 mmol) portionwise over ~5 minutes. The resulting milky solution was stirred for 3 h at 0° C. whereupon the mixture was deemed to be completed by TLC. Solid calcium hydroxide (~12 g) was added to the mixture and the resulting heterogenous mixture was stirred for 1 h at 0° C. The mixture was filtered thru a pad of Celite and the pad was washed with CH$_2$Cl$_2$ (3×100 mL). The resulting filtrate was concentrated under reduced pressure to afford 8.35 g of the title compound as a clear oil. This was taken on crude without further purification.

MS: m/z=349 (M+H$^+$).

Step 3: (S)-1-benzyl 4-tert-butyl 2-vinylpiperazine-1,4-dicarboxylate

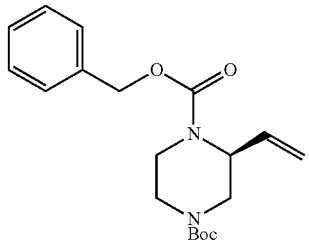 [SMILES: C=C[C@H]1CN(C(=O)OC(C)(C)C)CCN1C(=O)OCc1ccccc1]

To a solution of methyltriphenylphosphonium bromide (12.9 g, 36 mmol) in THF (30 mL) at rt was added a 0.5 M solution of KHMDS (72 ml, 36 mmol) dropwise to afford a yellow solution. The mixture was stirred for 1 h at rt and was cooled to −78° C. whereupon a solution of (R)-1-benzyl 4-tert-butyl 2-formylpiperazine-1,4-dicarboxylate (4.2 g, 12 mmol) in THF (30 mL) was added dropwise over ~20 minutes. The resulting solution was allowed to gradually warm to rt and stir for 3 h. TLC analysis revealed consumption of sm so the mixture was quenched with MeOH (~50 mL) and stirred for 15 min. Sat. aq. Rochelle's salt (30 mL) was added followed by Et$_2$O (100 mL) and the mixture was transferred to a separatory funnel. The layers were separated and the aqueous layer was extracted with Et$_2$O (3×75 mL) and the organic layers were combined. The organic layer was washed with brine (1×30 mL), dried (MgSO4), filtered, and concentrated under reduced pressure to afford a thick yellow oil. The crude material was taken up in CH$_2$Cl$_2$ (5 mL) and was loaded onto a 220 g silica gel column attached to an ISCO purification system. A gradient of 100% hexanes to 50% hexanes/50% EtOAc was run over 35 minutes whereupon the tubes containing the product were combined, concentrated under reduced pressure, and placed under high vacuum to afford 3.4 g of the title compound as a clear oil. MS: m/z=347 (M+H$^+$).

Step 4: (S)-tert-butyl 3-vinylpiperazine-1-carboxylate

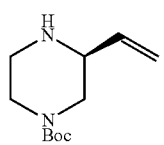

To a round bottom flask charged with a stir bar was added triethylsilane (1.59 mL, 9.9 mmol), Pd(OAc)$_2$ (51 mg, 0.225 mmol), and Et$_3$N (6 µL, 0.045 mmol) followed by addition of CH$_2$Cl$_2$ (21 mL). The resulting dark brown mixture was stirred for 15 min whereupon (S)-1-benzyl 4-tert-butyl 2-vinylpiperazine-1,4-dicarboxylate (1.56 g, 4.5 mmol) in CH$_2$Cl$_2$ (9 mL) was added dropwise to the mixture. The mixture was stirred for 12 h at rt whereupon LC-MS analysis and TLC revealed consumption of starting material. The mixture was diluted with sat. aq. NaHCO$_3$ (9 mL) and the mixture was transferred to a separatory funnel. The layers were separated and the aqueous layer was extracted with CH$_2$Cl$_2$ (3×20 mL) combining the organic layers. The organic layer was dried (Na$_2$SO$_4$), filtered, and concentrated under reduced pressure to afford a brown oil. The crude material was taken up in CH$_2$Cl$_2$ (6 mL) and was loaded onto an 120 g silica gel column attached to an ISCO purification system. A gradient of 100% CH$_2$Cl$_2$ to 90% CH$_2$Cl$_2$/10% MeOH over 35 minutes whereupon the tubes containing product were combined, concentrated under reduced pressure, and placed under high vacuum to afford 750 mg (78%) of the title compound as a brown oil. MS: m/z=213 (M+H$^+$) and 157 (M-t-butyl+H)$^+$.

Step 5: (S)-tert-butyl 4-(phenylsulfonyl)-3-vinylpiperazine-1-carboxylate

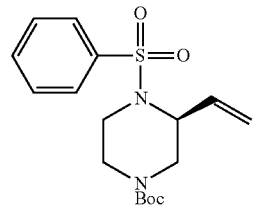 [SMILES: C=C[C@H]1CN(C(=O)OC(C)(C)C)CCN1S(=O)(=O)c1ccccc1]

To a solution of (S)-tert-butyl 3-vinylpiperazine-1-carboxylate (0.60 g, 2.82 mmol) in CH$_2$Cl$_2$ (18 mL) at 0° C. was added Et3N (0.60 mL, 4.2 mmol) followed by benzenesulfonyl chloride (0.48 mL, 3.6 mmol) to afford a brown, homogenous mixture. The resulting mixture was allowed to warm to room temperature and stir for 12 h whereupon TLC analysis revealed consumption of starting material. The mixture was diluted with CH$_2$Cl$_2$ (30 mL) and sat. aq. NaHCO3 (10 mL) and the layers were separated. The aqueous layer was extracted with CH$_2$Cl$_2$ (2×25 mL) and the organic layers were combined. The organic layer was washed with brine (15 mL), dried (Na2SO4), filtered, and concentrated under reduced pressure. The crude material was purified by preparative thin-layer chromatography (6×1000 uM) using a 2:1 mixture of hexanes/EtOAc as eluent. The lower band from each plate was scraped, combined, stirred with CH$_2$Cl$_2$, filtered, and concentrated under reduced pressure to afford 600 mg (63%) of the title compound as a light brown oil. MS: m/z=353 (M+H+).

Step 6: (5)-tert-butyl 3-((E)-2-((1R,2S)-2-(((benzyloxy)carbonyl)amino)cyclopentyl)vinyl)-4-(phenylsulfonyl)piperazine-1-carboxylate

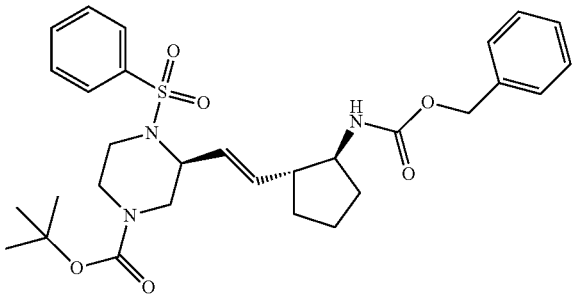 [SMILES: CC(C)(C)OC(=O)N1CCN(S(=O)(=O)c2ccccc2)[C@@H](/C=C/[C@H]2CCC[C@@H]2NC(=O)OCc2ccccc2)C1]

To a solution of (S)-tert-butyl 4-(phenylsulfonyl)-3-vinylpiperazine-1-carboxylate (350 mg, 1.141 mmol) and benzyl ((1S,2R)-2-vinylcyclopentyl)carbamate (200 mg, 0.815 mmol) in anhydrous dichloromethane (25 mL) was bubbled in nitrogen gas for 15 minutes. Zhan I catalyst (100 mg, 0.151 mmol) was then added and the resulting green solution was heated to 50° C. overnight under nitrogen atmosphere (reflux condensor set on round bottom flask). The reaction was filtered through a silica plug eluting with 100% ethyl acetate to remove some of the Zhan catalyst by-product. The filtrate was then concentrated to dryness and the residue was taken up into ether (12 mL) in which the residual catalyst crystallized. The solid was filtered off and washed with ether (1×10 mL). The ether solution was then concentrated under vacuum and the residue was purified via ISCO (40 g silica gel column) eluting with a gradient of 0-100% ethyl acetate in hexane over 12 CV. The tubes containing the product were collected and concentrated to dryness under reduced pressure to afford the product as a white foam solid (175 mg, 40.2%).

MS: m/z=570 (M+H+)

Step 7: (5)-tert-butyl 3-(2-((1R,2S)-2-aminocyclopentyl)ethyl)-4-(phenylsulfonyl)piperazine-1-carboxylate

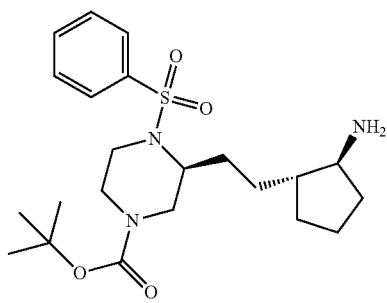 [SMILES: CC(C)(C)OC(=O)N1CCN(S(=O)(=O)c2ccccc2)[C@@H](CC[C@H]2CCC[C@@H]2N)C1]

To a solution of (S)-tert-butyl 3-((E)-2-((1R,2S)-2-(((benzyloxy)carbonyl)amino)cyclopentyl)vinyl)-4-(phenylsulfonyl)piperazine-1-carboxylate (170 mg, 0.30 mmol) in methanol (5 mL) was added 40 mg of 10% Pd—C and the resulting suspension set under hydrogen atmosphere, via balloon of hydrogen, and stirred at room temperature for 3 hours. LC-MS was checked and the reaction was deemed complete. The catalyst was filtered off using a Gilmen 0.45 PTFE syringe filter and washed with methanol (2×10 mL). The filtrate was then concentrated under reduced pressure to afford the product (110 mg, 86%). This compound was used without further purification. MS: m/z=438 (M+H+).

Step 8: (5)-tert-butyl 3-(2-((1R,2S)-2-((S)-3,3-bis(4-fluorophenyl)-2-((methoxycarbonyl)amino)propanamido)cyclopentyl)ethyl)-4-(phenylsulfonyl)piperazine-1-carboxylate

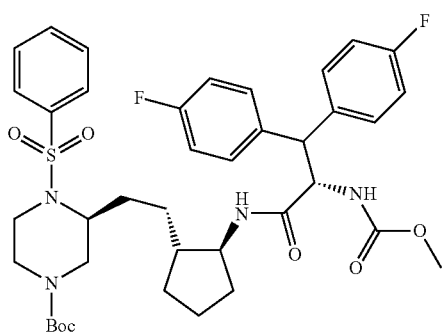

To a solution of (S)-tert-butyl 3-(2-((1R,2S)-2-aminocyclopentyl)ethyl)-4-(phenylsulfonyl)piperazine-1-carboxylate (30 mg, 0.07 mmol) in DCM (1 mL) under N2 at 0° C. was added (S)-3,3-bis(4-fluorophenyl)-2-((methoxycarbonyl)amino)propanoic acid (30 mg, 0.09 mmol) followed by dropwise addition of DIPEA (15.7 L, 0.08 mmol). HATU (42.5 mg, 0.112 mmol) was then added to the mixture in a single portion to afford a light yellow solution. The mixture was stirred overnight, allowing to warm to room temperature, whereupon the reaction was then deemed to be complete by LC-MS. The mixture was diluted with sat. aq. NaHCO3 (10 mL) and EtOAc (25 mL) and the layers were separated. The aqueous layer was extracted with EtOAc (3×10 mL) and the organic layers were combined. The organic layer was washed with brine (15 mL), dried (Na2SO4), filtered, and concentrated under reduced pressure to afford a light yellow semisolid. The crude material was taken up in CH2Cl2 (3 mL) and purified on a preparative TLC plates (2×1000 M, silica gel) developing with 50% ethyl acetate in hexane. The band containing the product was removed from the plates and the product eluded off the silica gel with ethyl acetate. The solvent was removed under reduced pressure to afford the product as a amorphous white solid (27 mg, 40%). MS: m/z=755 (M+H+).

317

Step 9. methyl ((S)-1,1-bis(4-fluorophenyl)-3-oxo-3-(((1S,2R)-2-(2-((S)-1-(phenylsulfonyl)piperazin-2-yl)ethyl)cyclopentyl)amino)propan-2-yl)carbamate To a solution of (S)-tert-butyl 3-(241R,2S)-2-((S)-3,3-bis(4-fluorophenyl)-2-((methoxycarbonyl)amino)propanamido)cyclopentyl)ethyl)-4-(phenylsulfonyl)piperazine-1-carboxylate (20 mg, 0.026 mmol) in 0.5 mL DCM was added TFA (0.1 mL) and the resulting solution stirred for 1 hour at room temperature. The solvent was removed under reduced pressure and the material taken up in 1:1 solution of acetonitrile/water. The mixture was purified via Gilsen reverse phase HPLC eluting with a gradient of 10-90% acetonitrile in water with 0.05% TFA as buffer. The tubes containing product were collected into a scintillation vial and frozen via dry ice/acetone bath. The frozen material was lyopholized overnight to afford a fluffy white solid as the product (9.7 mg, 57.3%). MS: m/z=655 (M+H+).

318

EXAMPLE 351

Methyl ((S)-1,1-bis(4-fluorophenyl)-3-oxo-3-(((1R,2S)-2-(2-((S)-1-(phenylsulfonyl)piperazin-2-yl)ethyl)cyclopentyl)amino)propan-2-yl)carbamate

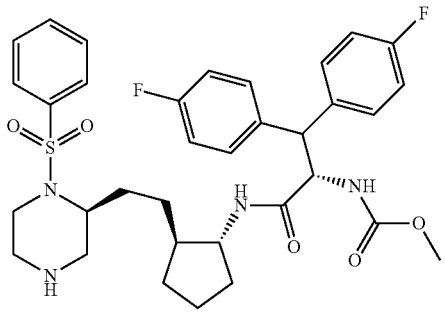 [SMILES: COC(=O)N[C@H](C(=O)N[C@@H]1CCC[C@H]1CC[C@H]1CNCCN1S(=O)(=O)c1ccccc1)C(c1ccc(F)cc1)c1ccc(F)cc1]

Example 351 was prepared using similar procedure for Example 1, using Intermediate I as starting material.

Examples shown in Table 5 were made in similar fashion as described in the prior experiment but with different substituents as follows:

TABLE 5

| Ex. | Structure | IUPAC Name | Exact Mass [M + H]+ |
|---|---|---|---|
| 352 | 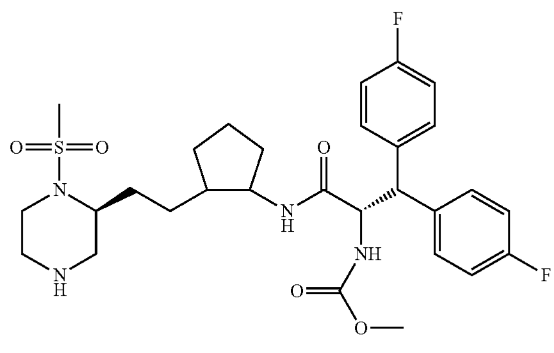 [SMILES: COC(=O)N[C@H](C(=O)NC1CCCC1CC[C@H]1CNCCN1S(C)(=O)=O)C(c1ccc(F)cc1)c1ccc(F)cc1] | 4-fluoro-beta-(4-fluorophenyl)-Nalpha-(methoxycarbonyl)-N-(2-{2-[(2S)-1-(methylsulfonyl)piperazin-2-yl]ethyl}cyclopentyl)-L-phenylalaninamide | 593.3 |
| 353 | 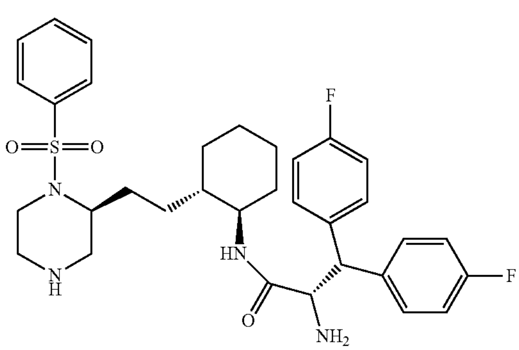 [SMILES: N[C@H](C(=O)N[C@@H]1CCCC[C@H]1CC[C@H]1CNCCN1S(=O)(=O)c1ccccc1)C(c1ccc(F)cc1)c1ccc(F)cc1] | 4-fluoro-beta-(4-fluorophenyl)-N-[(1R,2S)-2-{2-[(2S)-1-(phenylsulfonyl)piperazin-2-yl]ethyl}cyclohexyl]-L-phenylalaninamide | 611.3 |

TABLE 5-continued

| Ex. | Structure | IUPAC Name | Exact Mass [M + H]+ |
|---|---|---|---|
| 354 | 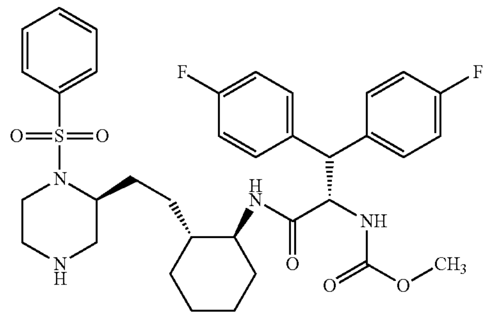 [SMILES: COC(=O)N[C@H](C(=O)N[C@H]1CCCC[C@@H]1CC[C@H]1CNCCN1S(=O)(=O)c1ccccc1)C(c1ccc(F)cc1)c1ccc(F)cc1] | methyl ((S)-1,1-bis(4-fluorophenyl)-3-oxo-3-(((1S,2R)-2-(2-((S)-1-(phenylsulfonyl)pipera-zin-2-yl)ethyl)cyclohexyl)amino)propan-2-yl)carbamate | 669.2 |
| 355 | 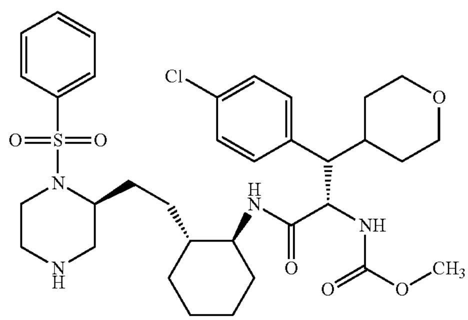 [SMILES: COC(=O)N[C@H](C(=O)N[C@H]1CCCC[C@@H]1CC[C@H]1CNCCN1S(=O)(=O)c1ccccc1)C(c1ccc(Cl)cc1)C1CCOCC1] | methyl ((1R,2S)-1-(4-chlorophenyl)-3-oxo-3-(((1S,2R)-2-(2-((S)-1-(phenylsulfonyl)pipera-zin-2-yl)ethyl)cyclohexyl)amino)-1-(tetrahydro-2H-pyran-4-yl)propan-2-yl)carbamate | 676.2 |
| 356 | 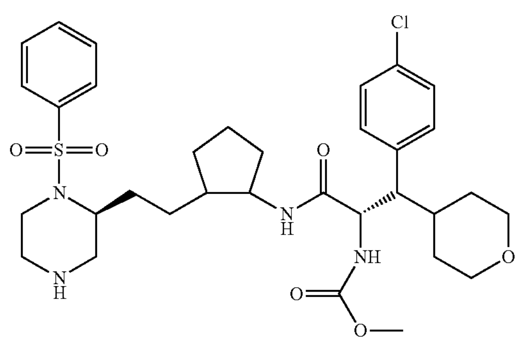 [SMILES: COC(=O)N[C@H](C(=O)NC1CCCC1CC[C@H]1CNCCN1S(=O)(=O)c1ccccc1)C(c1ccc(Cl)cc1)C1CCOCC1] | methyl ((1R,2S)-1-(4-chlorophenyl)-3-oxo-3-((2-(2-((S)-1-(phenylsulfonyl)pipera-zin-2-yl)ethyl)cyclopentyl)amino)-1-(tetrahydro-2H-pyran-4-yl)propan-2-yl)carbamate | 662.2 |

EXAMPLE 357

Methyl ((2R)-1,1-bis(4-fluorophenyl)-3-((4-hydroxy-2-(2-((S)-1-(phenylsulfonyl)piperazin-2-yl)ethyl)cyclopentyl)amino)-3-oxopropan-2-yl)carbamate

[trans of cyclopetane, R/S at OHCH position, mixture of isomers]

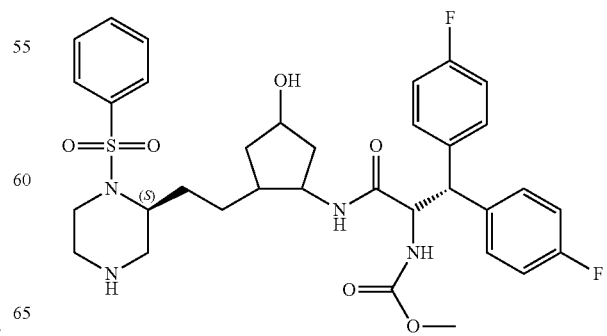

Step 1. (S)-benzyl 5-(benzyl(2-ethoxy-2-oxoethyl)amino)-4-((tert-butoxycarbonyl)amino)-5-oxopentanoate

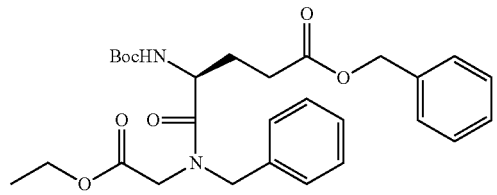 [SMILES: CCOC(=O)CN(Cc1ccccc1)C(=O)[C@H](CCC(=O)OCc1ccccc1)NC(=O)OC(C)(C)C]

To a solution of BOC-GLU(OBZL)-OH (22.56 g, 66.80 mmol) in 250 ml of DCM was added HOBt (11.28 g, 73.6 mmol) followed by 1 equivalent of EDC (12.8 g, 67.2 mmol) and the resulting mixture was stirred for 2 minutes at room temperature. Then, ethyl 2-(benzylamino)acetate (14.20 g, 73.6 mmol) was added dropwise over 5 minutes, and the resulting mixture stirred for 5 minutes. An addition equivalent of EDC (12.8 g, 67.2 mmol) was then added and the resulting mixture was stirred at rt for 3 hrs. The mixture was diluted with 200 ml of DCM and washed by sat'd aq. soln of $NaHCO_3$ (200 ml). The aqueous layer was extracted with DCM (2×100 ml) and the organic layers were combined, washed with $NaHCO_3$ and brine, dried over sodium sulfate, filtered, and concentrated in vacuo to afford 37.6 g of crude product. The material was purified by ISCO column (2×220 g silica gel) eluting with a gradient of 0-60% EtOAc in hexane (3000 ml). The tubes containing the product were collected and the solvent removed under reduced pressure to afford the title compound (25.6 g, 75%). MS: m/z=513 (M+H$^+$).

Step 2. (S)-benzyl 3-(4-benzyl-3,6-dioxopiperazin-2-yl)propanoate

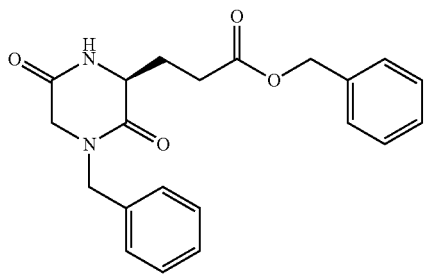 [SMILES: O=C1CN(Cc2ccccc2)C(=O)[C@H](CCC(=O)OCc2ccccc2)N1]

(S)-Benzyl 5-(benzyl(2-ethoxy-2-oxoethyl)amino)-4-((tert-butoxycarbonyl)amino)-5-oxopentanoate (25.6 g, 51.6 mmol) was treated with 320 ml of 4N HCl in 1,4-dioxane at room temperature for 45 minutes. The volatiles were removed in vacuo to afford the deBoc product as an intermediate. This material was then taken up in 300 ml of THF and 300 ml of a 1.0M aq. soln of $Na_2CO_3$ was added to the solution. The resulting mixture was stirred vigorously at room temperature overnight. LCMS showed the product with a small amount of starting de-Boc intermediate left. The mixture was diluted with 500 ml of EtOAc, and washed by water (300 mL), followed by brine (275 mL). The organics were then dried over sodium sulfate, filtered, and concentrated in vacuo to afford 24.0 g. of crude desired product. The material was purified by ISCO column (220 g, silica gel) eluting with a gradient of 0-20% MeOH in DCM (3000 ml) to afford (16.40 g, 87%) of desired product. MS: m/z=367 (M+H$^+$).

Step 3. (S)-3-(4-benzylpiperazin-2-yl)propan-1-ol

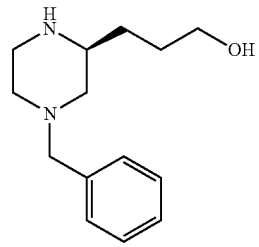 [SMILES: OCCC[C@H]1CN(Cc2ccccc2)CCN1]

LAH solution in THF (1M, 400 ml, 400 mmol) was added to an oven dried 1000 ml flask via syringe and cooled to 0° C. via ice/water bath. (S)-benzyl 3-(4-benzyl-3,6-dioxopiperazin-2-yl)propanoate (16.4 g, 44.8 mmol) in 100 ml of anhydrous THF was added via syringe over 5 minutes and the resulting mixture was stirred for 5 min. The reaction flask was then moved to a oil heating bath and fixed with a large water-cooling condensor. The mixture was stirred at reflux (80-82° C.) under nitrogen atmosphere for 3 hrs. The reaction was then cooled down in a ice/water bath and 120 mL of water was added carefully dropwise, followed by 120 mL of 1M aq solution of NaOH. After quenching, the mixture was placed in a 2000 mL separatory funnel and diluted with THF (600 ml). The mixture was separated and the organic layer was further diluted with EtOAc (300 ml). The solution was washed by brine (2×200 mL), dried over sodium sulfate, filtered through a silica gel pad (3×10 cm) and washed with EtOAc (400 ml). Unfortunately, it was observed that all the product was stuck on the silica gel. Therefore. The silica gel pad was then washed with 20% MeOH in DCM and filtrate was concentrated in vacuo to afford the desired product (9.76 g, 50%). MS: m/z=235 (M+H$^+$).

Step 4. (S)-1-benzyl-3-(3-((tert-butyldimethylsilyl)oxy)propyl)piperazine

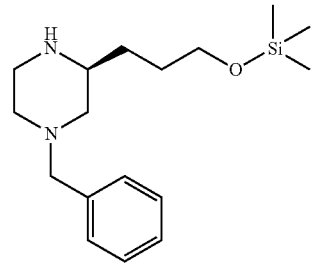 [SMILES: C[Si](C)(C)OCCC[C@H]1CN(Cc2ccccc2)CCN1]

To a solution of (S)-3-(4-benzylpiperazin-2-yl)propan-1-ol (9.76 g, 41 mmol) in 150 ml of DCM was added imidazole (3.20 g, 46.4 mmol) followed by TBS-Cl (8.0 g, 53.28 mmol) and the resulting mixture was stirred at room temperature overnight. The mixture was diluted with 400 mL of DCM, then washed by 300 ml of sat'd aq. solution of $NaHCO_3$ and brine. The organics were separated, dried over Na$_2$SO$_4$, filtered, and the filtrate was concentrated in vacuo to afford the desired product (11.36 g, 80%) to which was used as is for the next step. MS: m/z=349 (M+H$^+$).

Step 5. (5)-4-benzyl-2-(3-((tert-butyldimethylsilyl)oxy)propyl)-1-(phenylsulfonyl)piperazine

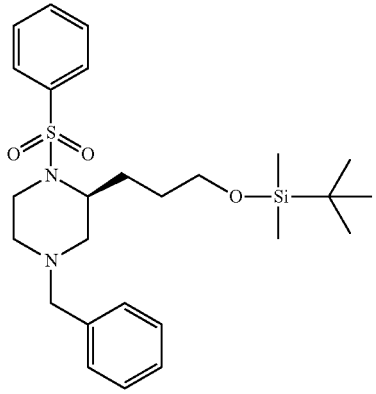 [SMILES: CC(C)(C)[Si](C)(C)OCCC[C@H]1CN(Cc2ccccc2)CCN1S(=O)(=O)c1ccccc1]

To a pre-cooled (0° C.) solution of (5)-1-benzyl-3-(3-((tert-butyldimethylsilyl)oxy)propyl)piperazine (7 g, 20.0 mmol) in 50 ml of DCM was added TEA (4.20 mL, 30.1 mmol) followed by benzenesulfonyl chloride (3.72 g, 21.1 mmol) in 10 ml of DCM, and the resulting mixture was stirred for 1 hr. The mixture was then diluted with 150 ml of DCM and quenched by saturated aq. solution of NaHCO3. The organics were separated and dried over Na$_2$SO$_4$, filtered and concentrated in vacuo. The residue was purified by ISCO column (220 g) using a gradient eluent of 0-35% EtOAc in hexane (3000 mL). The tubes containing the product were collected and the solvent removed under reduced pressure to afford 4.71 g (48%) of desired product. MS: m/z=489 (M+H$^+$).

Step 6: (5)-2-(3-((tert-butyldimethylsilyl)oxy)propyl)-1-(phenylsulfonyl)piperazine

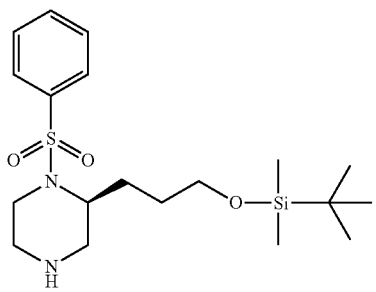 [SMILES: CC(C)(C)[Si](C)(C)OCCC[C@H]1CNCCN1S(=O)(=O)c1ccccc1]

A solution of (5)-4-benzyl-2-(3-((tert-butyldimethylsilyl)oxy)propyl)-1-(phenylsulfonyl)piperazine (3.80 g, 7.77 mmol) in 70 ml of MeOH was treated with 20% Pd(OH)$_2$ on carbon and stirred under hydrogen atmosphere, via balloon of hydrogen, for 20 hrs. LCMS shows all starting material was consumed. The catalyst was filtered off through a celite pad and washed with methanol (50 mL). The filtrate was concentrated in vacuo to afford the title compound (3.065 g, 99%) which was used without further purification. MS: m/z=399 (M+H$^+$).

Step 7. (5)-benzyl 3-(3-((tert-butyldimethylsilyl)oxy)propyl)-4-(phenylsulfonyl)piperazine-1-carboxylate

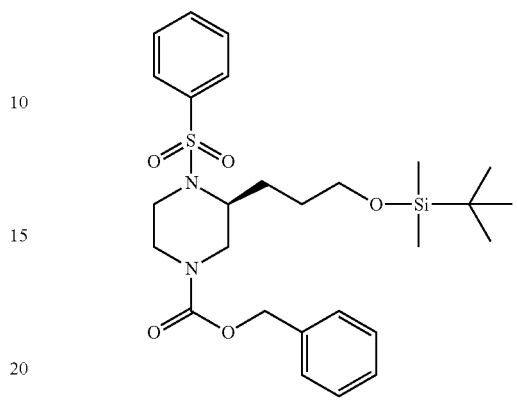

To a pre-cooled (0° C.) solution of (S)-2-(3-((tert-butyldimethylsilyl)oxy)propyl)-1-(phenylsulfonyl)piperazine (3.05 g, 7.65 mmol) in 30 ml of DCM was added TEA (1.39 mL, 9.95 mmol) followed by CBz-Cl (1.20 mL, 8.42 mmol) and the resulting mixture stirred for 2 hrs at 0° C. The reaction was quenched by sat'd aq. solution of NaHCO$_3$, and extracted with DCM (2×100 mL). The organics were combined, washed by brine (100 mL), dried over Na$_2$SO$_4$, filtered and concentrated in vacuo. The residue was purified by ISCO column (220 g silica gel) eluting with a gradient of 0-75% EtOAc in hexane over 10 column volumes (CV). The tubes containing the product were collected and the solvent removed under reduced pressure to afford the desired product (3.76 g, 92%). MS: m/z=533 (M+H$^+$).

Step 8. (S)-benzyl 3-(3-hydroxypropyl)-4-(phenylsulfonyl)piperazine-1-carboxylate

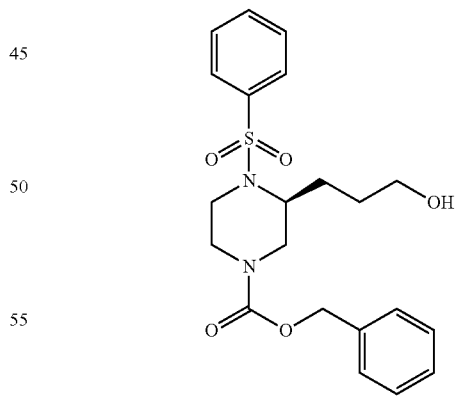

The solution of (S)-benzyl 3-(3-((tert-butyldimethylsilyl)oxy)propyl)-4-(phenylsulfonyl)piperazine-1-carboxylate (3.74 g, 7.02 mmol) in 20 ml of THF was treated with 1.0M solution of TBAF (8.8 mL, 8.80 mmol) which stirred at room temperature for 2 hrs under nitrogen atmosphere. LCMS shows deemed the reaction completed. The mixture was diluted with 100 mL of EtOAc and washed by water (50 mL) and brine (50 mL). The organic layer was then filtered through a pad of silica gel (6 cm) and washed with EtOAc (100 mL). The filtrate was concentrated in vacuo to afford the product (3.1 g, 100%) which was used without further purification. MS: m/z=419 (M+H⁺).

Step 9. (S)-benzyl 3-(3-oxopropyl)-4-(phenylsulfonyl)piperazine-1-carboxylate

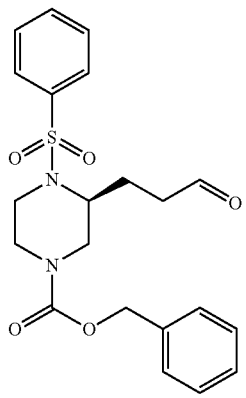 [SMILES: O=CCC[C@H]1CN(C(=O)OCc2ccccc2)CCN1S(=O)(=O)c1ccccc1]

To a pre-cooled (0° C.) solution of (S)-benzyl 3-(3-hydroxypropyl)-4-(phenylsulfonyl)piperazine-1-carboxylate (3.0 g, 6.20 mmol) in 25 ml of DCM was added Dess-Martin Periodinane (3.03 g, 7.15 mmol) in portions over 1 min, and the resulting mixture was then stirred for 45 minutes. The reaction was diluted with 120 mL of EtOAc and washed with 1 M aq. solution of $Na_2CO_3$ (100 ml). The organics were separated, washed by brine (50 mL), dried over sodium sulfate, filtered, and concentrated in vacuo. The residue was then purified by ISCO column (120 g silica gel) eluting with a gradient of 0-80% EtOAc in hexane (1600 ml). the tubes containing the product were collected and the solvent removed under reduced pressure to give the title product (2.49 g, 96%). MS: m/z=417 (M+H⁺).

Step 10. (S,E)-benzyl 3-(5-ethoxy-5-oxopent-3-en-1-yl)-4-(phenylsulfonyl)piperazine-1-carboxylate

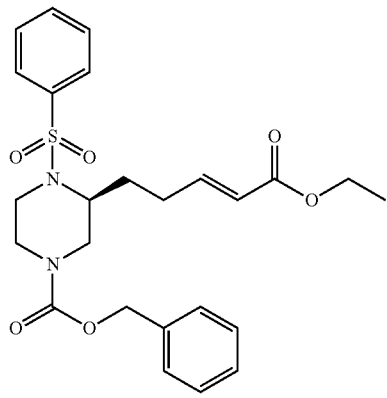 [SMILES: CCOC(=O)/C=C/CC[C@H]1CN(C(=O)OCc2ccccc2)CCN1S(=O)(=O)c1ccccc1]

To a pre-cooled (0° C.) solution of ethyl 2-(diethoxyphosphoryl)acetate (1.53 g, 6.82 mmol) in 15 ml of anhydrous THF was added NaH (0.25 g, 6.23 mmol) to which caused the solution to become a slurry. The mixture was stirred for 15 minutes at 0° C., then (S)-benzyl 3-(3-oxopropyl)-4-(phenylsulfonyl)piperazine-1-carboxylate (2.47 g, 5.93 mmol) in 10 ml of THF was added and the resulting mixture was stirred for 1 h at 0° C. LCMS and TLC showed that the rxn was complete. The mixture was quenched with sat'd aq. solution of $NH_4Cl$ and extracted with EtOAc (100 ml). The organics were separated, washed by brine, dried on $Na_2SO_4$, filtered, and concentrated in vacuo. The residue was purified by ISCO column (80 g silica gel) eluting with a gradient of 0-70% EtAOc in hexane (1500 ml). The tubes containing the product were collected and the solvent removed under reduced pressure to afford the title compound (2.31 g, 80). MS: m/z=487 (M+H⁺).

Step 11. (3S)-benzyl 3-(2-(2-(ethoxycarbonyl)-4-methylenecyclopentyl)ethyl)-4-(phenylsulfonyl)piperazine-1-carboxylate

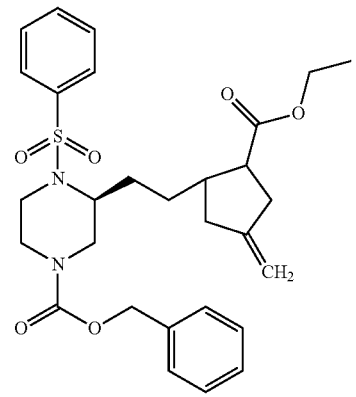 [SMILES: C=C1CC(CC[C@H]2CN(C(=O)OCc3ccccc3)CCN2S(=O)(=O)c2ccccc2)C(C(=O)OCC)C1]

To a solution of (S,E)-benzyl 3-(5-ethoxy-5-oxopent-3-en-1-yl)-4-(phenylsulfonyl)piperazine-1-carboxylate (2150 mg, 4.42 mmol) in 35 ml of toluene (which was degassed for 30 min by nitrogen gas) was added palladium acetate (99 mg, 0.442 mmol), followed by 2-((trimethylsilyl)methyl)allyl acetate (988 mg, 5.30 mmol) 1 minute later. After 10 minutes, triisopropyl phosphite (1.62 mL, 7.07 mmol) was added and the resulting mixture was then stirred for 5 minutes at room temperature and then set in a 95° C. oil bath (pre-heated to 95° C.) and stirred for 4 hrs. LCMS shows ~70% product and 30% starting material, therefore the reaction was allowed stir for 2 hrs longer. LCMS shows that the reaction has stalled with no further progress after the additional 2 hours. The volatiles were removed in vacuo and the residue was purified by ISCO column (120 g, silica gel) eluting with a gradient of 0-80% EtOAc in hexane (1200 mL). The tubes containing the product were collected and the solvent removed under reduced pressure to afford the title product (1210 mg, 54%). So starting material was also recovered from the reaction, (215 mg, 10%). MS of desired product: m/z=541 (M+H⁺).

Step 12. 2-(2-((S)-4-((benzyloxy)carbonyl)-1-(phenylsulfonyl)piperazin-2-yl)ethyl)-4-methylenecyclopentanecarboxylic acid

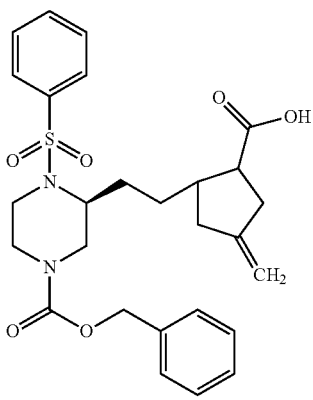 [SMILES: C=C1CC(CC[C@H]2CN(C(=O)OCc3ccccc3)CCN2S(=O)(=O)c2ccccc2)C(C(=O)O)C1]

The solution of (3S)-benzyl 3-(2-(2-(ethoxycarbonyl)-4-methylenecyclopentyl)ethyl)-4-(phenylsulfonyl)piperazine-1-carboxylate (1.25 g, 2.31 mmol) in 25 mL of EtOH was treated with 6 mL of 1.0M NaOH solution, which was stirred at 50° C. for 3 hrs. LCMS shows all starting material was consumed. The volatiles were removed in vacuo and the residue was taken up with 5 ml of water, and extracted with EtOAC (20 mL) to remove one impurity showing in LCMS. The water layer was then acidified with 4N HCl (~200 μL), and then extracted with EtOAc (2×15 mL). The organics were then combined, washed by brine (10 mL), dried over Na$_2$SO$_4$, filtered, and concentrated in vacuo to afford the title compound (0.91 g, 77%) which was used without further purification. MS: m/z=513 (M+H$^+$) and m/z=535 (M+Na$^+$).

Step 13. (3S)-benzyl 3-(2-(4-methylene-2-(((2-(trimethylsilyl)ethoxy)carbonyl)amino)cyclopentyl)ethyl)-4-(phenylsulfonyl)piperazine-1-carboxylate

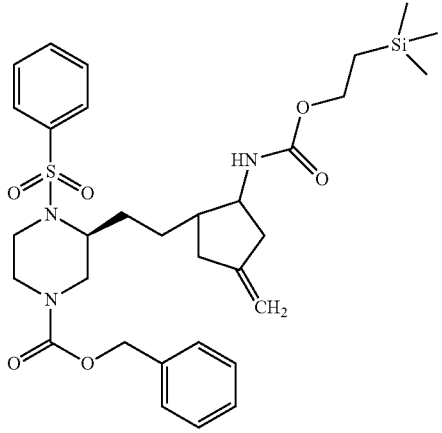 [SMILES: C=C1CC(CC[C@H]2CN(C(=O)OCc3ccccc3)CCN2S(=O)(=O)c2ccccc2)C(NC(=O)OCC[Si](C)(C)C)C1]

To solution of 2-(2-((S)-4-((benzyloxy)carbonyl)-1-(phenylsulfonyl)piperazin-2-yl)ethyl)-4-methylenecyclopentanecarboxylic acid (900 mg, 1.76 mmol) in 10 ml of toluene was added DPPA (628 mg, 2.28 mmol) followed by TEA (0.40 mL, 2.70 mmol). The resulting reaction mixture was then stirred at 85° C. for 25 minutes, then 2-(trimethylsilyl)ethanol (5190 mg, 43.2 mmol) was added and the resulting mixture stirred at 85° C. for 0.5 hours and then 70° C. overnight. The mixture was cooled to room temperature and then diluted with EtOAc (20 mL). The mixture washed by brine (10 mL), the organics separated, dried over Na$_2$SO$_4$, filtered, and concentrated in vacuo. The residue was then purified by ISCO column (120 g, silica gel) eluting with a gradient of 0-70% EtOAc in hexane (1500 ml). The tubes containing the product were collected and the solvent removed under reduced pressure to afford the title compound (641 mg, 58%). MS: m/z=628 (M+H$^+$).

Step 14. (3S)-benzyl 3-(2-(4-oxo-2-(((2-(trimethylsilyl)ethoxy)carbonyl)amino)cyclopentyl)ethyl)-4-(phenylsulfonyl)piperazine-1-carboxylate

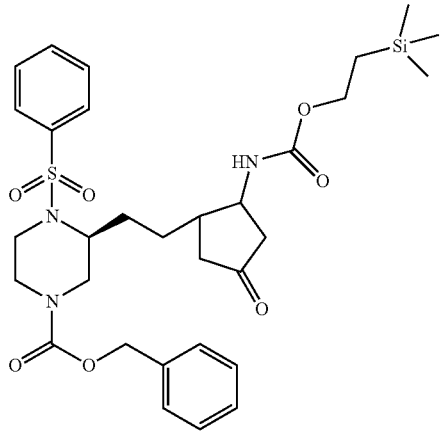 [SMILES: C[Si](C)(C)CCOC(=O)NC1CC(=O)CC1CC[C@H]1CN(C(=O)OCc2ccccc2)CCN1S(=O)(=O)c1ccccc1]

(3S)-benzyl 3-(2-(4-methylene-2-(((2-(trimethylsilyl)ethoxy)carbonyl)amino)cyclopentyl)ethyl)-4-(phenylsulfonyl)piperazine-1-carboxylate (450 mg, 0.72 mmol) was dissolved in 10 ml of DCM, cooled to −78° C. via dry ice/acetone bath, and then treated with O$_3$ gas (bubbling into the solution) for 5 min until a sky blue color persist. 2 ml of DMS was then added to the solution and the resulting mixture was stirred for 10 minutes at −78° C. The mixture was then aged for 1.5 hrs at room temperature. The volatiles were removed in vacuo to afford the title compound (450 mg, 99%) which was used without further purification. MS: m/z=630 (M+H$^+$).

Step 15. (3S)-benzyl 3-(2-(4-hydroxy-2-(((2-(trimethylsilyl)ethoxy)carbonyl)amino)cyclopentyl)ethyl)-4-(phenylsulfonyl)piperazine-1-carboxylate

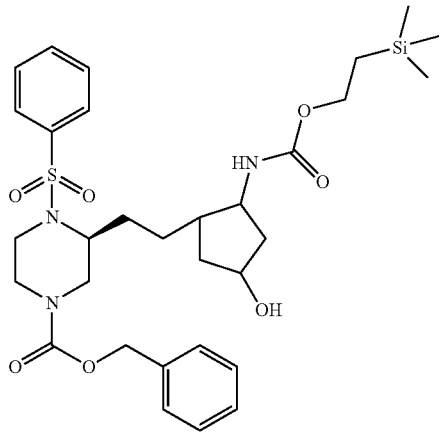 [SMILES: C[Si](C)(C)CCOC(=O)NC1CC(O)CC1CC[C@H]1CN(C(=O)OCc2ccccc2)CCN1S(=O)(=O)c1ccccc1]

To a pre-cooled (0° C.) solution of (3S)-benzyl 3-(2-(4-oxo-2-(((2-(trimethylsilyl)ethoxy)carbonyl)amino)cyclopentyl)ethyl)-4-(phenylsulfonyl)piperazine-1-carboxylate (45 mg, 0.071 mmol) in 2 ml of THF and 1 ml of MeOH was added NaBH$_4$ (13.52 mg, 0.357 mmol) and the resulting mixture stirred for 30 min. The reaction was quenched with 5 ml of sat'd aq. solution NH$_4$Cl, and extracted with EtOAc (2×30 mL), combined organic layers and washed by brine, dried over Na$_2$SO$_4$, filtered through a silica gel pad (3×2

Step 15. (3S)-benzyl 3-(2-(2-amino-4-hydroxycyclopentyl)ethyl)-4-(phenylsulfonyl)piperazine-1-carboxylate

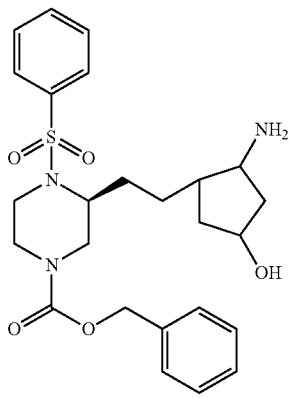 [SMILES: NC1CC(O)CC1CC[C@H]1CN(C(=O)OCc2ccccc2)CCN1S(=O)(=O)c1ccccc1]

To a solution of (3S)-benzyl 3-(2-(4-hydroxy-2-(((2-(trimethylsilyl)ethoxy)carbonyl)amino)cyclopentyl)ethyl)-4-(phenylsulfonyl)piperazine-1-carboxylate (40 mg, 0.063 mmol) in 2 ml of THF was added 1.3 eq. of 1.0M solution of TBAF in THF (0.20 mL, 0.20 mmol) and the resulting mixture stirred under nitrogen for 2 hrs at 50° C. LCMS shows all starting material was consumed. THF was removed in vacuo and the residue was partitioned between water and EtOAc. The organics were separated and water layer was back extracted with EA (2×5 mL). The combined organic layers were washed by brine (10 mL), dried over $Na_2SO_4$, filtered, and then concentrated in vacuo to afford the desired product (11 mg, 35.6%). MS: m/z=487 (M+H$^+$).

Step 16. (3S)-benzyl 3-(2-(2-((R)-3,3-bis(4-fluorophenyl)-2-((methoxycarbonyl)amino)propanamido)-4-hydroxycyclopentyl)ethyl)-4-(phenylsulfonyl)piperazine-1-carboxylate

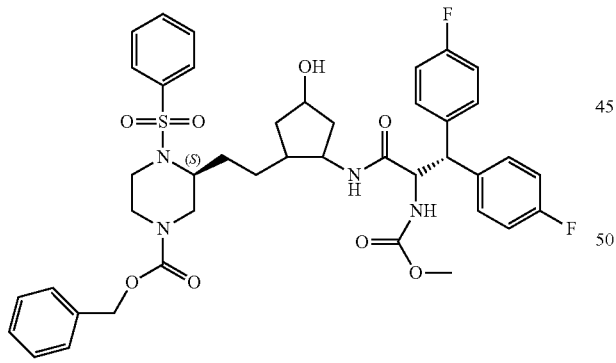

To a pre-cooled (0° C.) solution of 3,3-bis(4-fluorophenyl)-2-((methoxycarbonyl)amino)propanoic acid (11.35 mg, 0.034 mmol) and HATU (13 mg, 0.034 mmol) in 1 ml of acetonitrile was added (3S)-benzyl 3-(2-(2-amino-4-hydroxycyclopentyl)ethyl)-4-(phenylsulfonyl)piperazine-1-carboxylate (11 mg, 0.023 mmol) in 1.5 ml of acetonitrile and the resulting solution stirred for 5 minutes. Hunig's base (6 μL, 0.034 mmol) was then added and the resulting mixture was stirred for 4 hr allowing to warm to room temperature. The mixture was diluted with EtOAc (5 mL) and washed by brine (5 mL), separated, dried over $Na_2SO_4$, filtered and concentrated in vacuo. The crude product was purified by Gilson RP-HPLC (10-100% acetonitrile in water with 0.05% TFA as buffer, 12 min method) and the tube containing the product was collected into a scintillation vial, frozen by dry ice/acetone bath and lyophilized overnight to afford the product (5 mg, 28%) as a white fluffy solid. MS: m/z=806 (M+H$^+$).

Step 17. methyl ((2R)-1,1-bis(4-fluorophenyl)-3-((4-hydroxy-2-(2-((S)-1-(phenylsulfonyl)piperazin-2-yl)ethyl)cyclopentyl)amino)-3-oxopropan-2-yl)carbamate [trans of cyclopetane, R/S at OHCH position, mixture of isomers]

To a solution of (3S)-benzyl 3-(2-(2-((R)-3,3-bis(4-fluorophenyl)-2-((methoxycarbonyl)amino)propanamido)-4-hydroxycyclopentyl)ethyl)-4-(phenylsulfonyl)piperazine-1-carboxylate in 3 ml of MeOH was added 20% Pd(OH)$_2$ on carbon and the resulting suspension was evacuated via vacuum and then charged with hydrogen gas from a balloon of H$_2$ gas. The mixture was stirred vigorously under balloon of hydrogen for 2 hrs. LCMS show the starting material was consumed. The mixture was filtered through a celite pad and the filtrate was concentrated in vacuo. The crude product was purified by Gilson RP-HPLC (10-100% acetonitrile in water with 0.05% TFA as buffer, 12 min method) and the tube containing the product was collected into a scintillation vial, frozen by dry ice/acetone bath and lyopholized overnight to afford the product (mixture of diasteroisomers, 4.1 mg, 97%) as a white fluffy solid. MS: m/z=671 (M+H$^+$).

EXAMPLE 358 and EXAMPLE 359

Methyl ((2R)-1-((4,4-difluoro-2-(2-((S)-1-(phenylsulfonyl)piperazin-2-yl)ethyl)cyclopentyl)amino)-3,3-bis(4-fluorophenyl)-1-oxopropan-2-yl)carbamate

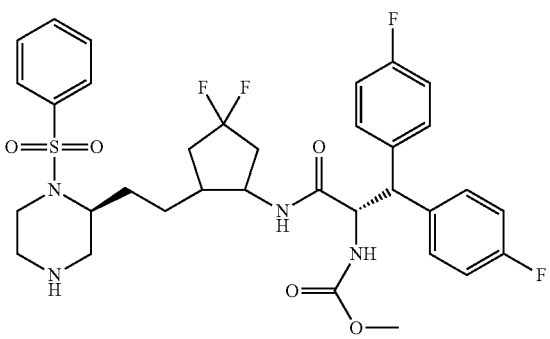 [SMILES: COC(=O)N[C@H](C(=O)NC1CC(F)(F)CC1CC[C@H]1CNCCN1S(=O)(=O)c1ccccc1)C(c1ccc(F)cc1)c1ccc(F)cc1]

Step 1. (3S)-benzyl 3-(2-(4,4-difluoro-2-(((2-(trimethylsilyl)ethoxy)carbonyl)amino)cyclo pentyl)ethyl)-4-(phenylsulfonyl)piperazine-1-carboxylate

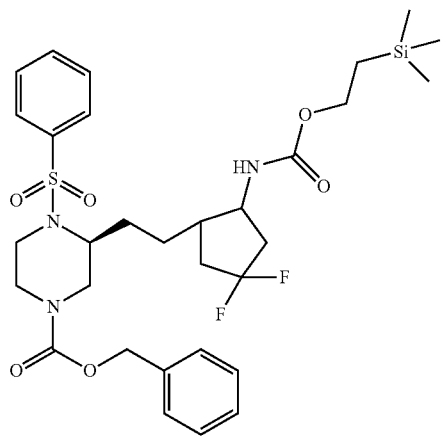 [SMILES: C[Si](C)(C)CCOC(=O)NC1CC(F)(F)CC1CC[C@H]1CN(C(=O)OCc2ccccc2)CCN1S(=O)(=O)c1ccccc1]

DAST (2.21 g, 13.73 mmol) was added to a stirring mixture of (3S)-benzyl 3-(2-(4-oxo-2-(((2-(trimethylsilyl)ethoxy)carbonyl)amino)cyclopentyl)ethyl)-4-(phenylsulfonyl)piperazine-1-carboxylate (1 g, 1.53 mmol) in 20 ml of DCM and 20 µL of MeOH, and the resulting mixture was stirred at room temperature for 2 hrs. LCMS shows a small peak of desired product and major peak of starting material, therefore the reaction was left stirring at room temperature overnight. The reaction mixture was quenched with water (30 mL) and the mixture was extracted with DCM (2×50 mL). The combined organic fractions were washed with brine (40 mL), dried (Na$_2$SO$_4$), filtered, and the solvent was evaporated under reduced pressure. The residue was purified by ISCO column (80 g silica gel) chromatography eluting with EtOAc/isohexane (0-80%, 2000 ml). The tubes containing the product were collected and the solvent removed under reduced pressure to afford the desired product (402 mg, 43.1%). MS: m/z=652 (M+H$^+$).

Step 2. (3S)-benzyl 3-(2-(2-amino-4,4-difluorocyclopentyl)ethyl)-4-(phenylsulfonyl)piperazine-1-carboxylate

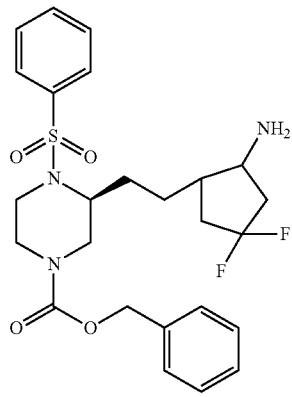 [SMILES: NC1CC(F)(F)CC1CC[C@H]1CN(C(=O)OCc2ccccc2)CCN1S(=O)(=O)c1ccccc1]

To a solution of (3S)-benzyl 3-(2-(4,4-difluoro-2-(((2-(trimethylsilyl)ethoxy)carbonyl)amino)cyclopentyl)ethyl)-4-(phenylsulfonyl)piperazine-1-carboxylate (120 mg, 0.189 mmol) in 6 ml of THF was added 1.3 eq. of 1.0M solution of TBAF in THF (0.60 mL, 0.60 mmol) and the resulting mixture stirred under nitrogen for 2 hrs at 50° C. LCMS shows all starting material was consumed. THF was removed in vacuo and the residue was partitioned between water and EtOAc. The organics were separated and water layer was back extracted with EA (2×10 mL). The combined organic layers were washed by brine (10 mL), dried over Na$_2$SO$_4$, filtered, and then concentrated in vacuo to afford the desired product (62 mg, 61%). MS: m/z=508 (M+H$^+$).

Step 3. (3S)-benzyl 3-(2-(2-((R)-3,3-bis(4-fluorophenyl)-2-((methoxycarbonyl)amino)propanamido)-4,4-difluorocyclopentyl)ethyl)-4-(phenylsulfonyl)piperazine-1-carboxylate

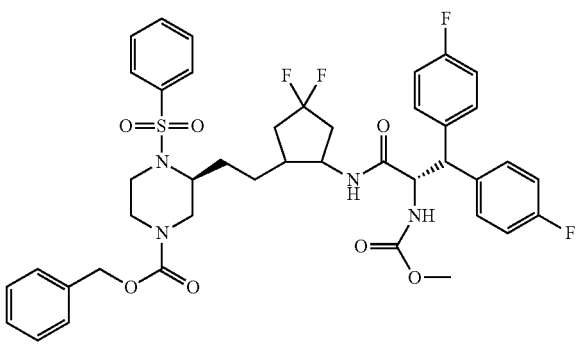 [SMILES: COC(=O)N[C@H](C(=O)NC1CC(F)(F)CC1CC[C@H]1CN(C(=O)OCc2ccccc2)CCN1S(=O)(=O)c1ccccc1)C(c1ccc(F)cc1)c1ccc(F)cc1]

To a pre-cooled (0° C.) solution of 3,3-bis(4-fluorophenyl)-2-((methoxycarbonyl)amino)propanoic acid (60 mg, 0.139 mmol) and HATU (70 mg, 0.40 mmol) in 1.5 ml of acetonitrile was added. (3S)-benzyl 3-(2-(2-amino-4,4-difluorocyclopentyl)ethyl)-4-(phenylsulfonyl)piperazine-1-carboxylate (60 mg, 0.135 mmol) in 1.5 ml of acetonitrile and the resulting solution stirred for 5 minutes. Hunig's base (58 µL, 0.417 mmol) was then added and the resulting mixture was stirred for 4 hr allowing to warm to room temperature. The mixture was diluted with EtOAc (10 mL) and washed by brine (10 mL), separated, dried over Na$_2$SO$_4$, filtered and concentrated in vacuo. The crude product was purified by Gilson RP-HPLC (10-100% acetonitrile in water with 0.05% TFA as buffer, 12 min method) and the tubes containing the product was collected into a large scintillation vial, frozen by dry ice/acetone bath and lyopholized overnight to afford the product (36.4 mg, 34.4%) as a white fluffy solid. MS: m/z=825 (M+H$^+$).

Step 4. Methyl ((2R)-1-((4,4-difluoro-2-(2-((S)-1-(phenylsulfonyl)piperazin-2-yl)ethyl)cyclopentyl)amino)-3,3-bis(4-fluorophenyl)-1-oxopropan-2-yl)carbamate (3S)-Benzyl 3-(2-(2-((R)-3,3-bis(4-fluorophenyl)-2-((methoxycarbonyl)amino)propanamido)-4,4-difluorocyclopentyl)ethyl)-4-(phenylsulfonyl)piperazine-1-carboxylate, mix of 2 trans cyclopentane isomers was taken up into 5 ml of MeOH and 20 mg of 20% Pd(OH)$_2$ was added. The reaction flask was evacuated under vacuum and purged by hydrogen gas from a balloon (repeated 3 times), then the mixture was stirred vigorously under hydrogen gas for 1 hr at room temperature. The catalyst was filtered off though a celite pad and washed with DCM. The filtrate was concentrated in vacuo and the residue was then purified by Gilson RP-HPLC (mobile phase: 0-75% acetonenitile in water with 0.1% TFA as buffer, 12 min method). The tube containing the product was collected into a scintilation vial, frozen via dry ice/acetone bath and then lyopholized overnight to afford (24 mg, 68%) of desired product as a mixture of 2 diastereomers (~1/1 ratio, due to 2 trans cyclopetane isomers) as the TFA salt form. This material was submitted for assays and then later it was separated into 2 pure diastereomers by COE group.
MS: m/z=691 (M+H$^+$).

Examples shown in Table 6 were made in similar fashion as described in the prior experiment but with different substituents as follows:

TABLE 6

| Ex# | Structure | IUPAC Name | Exact Mass [M + H]+ |
|---|---|---|---|
| 360 | 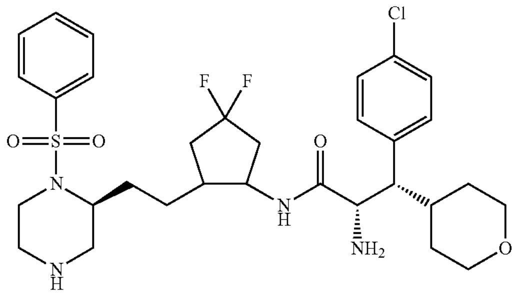 [SMILES: N[C@H](C(=O)NC1CC(F)(F)CC1CC[C@H]1CNCCN1S(=O)(=O)c1ccccc1)[C@H](c1ccc(Cl)cc1)C1CCOCC1] | (betaS)-4-chloro-N-(4,4-difluoro-2-{2-[(2S)-1-(phenylsulfonyl)piperazin-2-yl]ethyl}cyclopentyl)-beta-(tetrahydro-2H-pyran-4-yl)-L-phenylalaninamide | 639.3 |
| 361 | 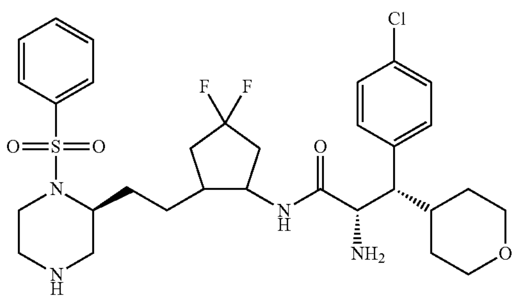 [SMILES: N[C@H](C(=O)NC1CC(F)(F)CC1CC[C@H]1CNCCN1S(=O)(=O)c1ccccc1)[C@H](c1ccc(Cl)cc1)C1CCOCC1] | (betaS)-4-hcloro-N-(4,4-difluoro-2-{2-[(2S)-1-(phenylsulfonyl)piperazin-2-yl]ethyl}cyclopentyl)-beta-(tetrahydro-2H-pyran-4-yl)-L-phenylalaninamide | 639.3 |

EXAMPLE 362 and EXAMPLE 363

Methyl ((2R)-1,1-bis(4-fluorophenyl)-3-oxo-3-((2-(2-((S)-1-(phenylsulfonyl)piperazin-2-yl)ethyl)cyclopropyl)amino)propan-2-yl)carbamate

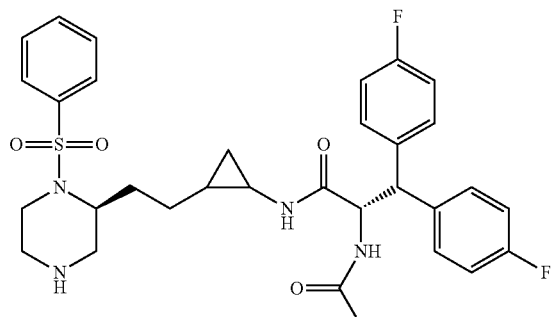

Step 1. (3S)-benzyl 3-(2-(2-(ethoxycarbonyl)cyclopropyl)ethyl)-4-(phenylsulfonyl)piperazine-1-carboxylate

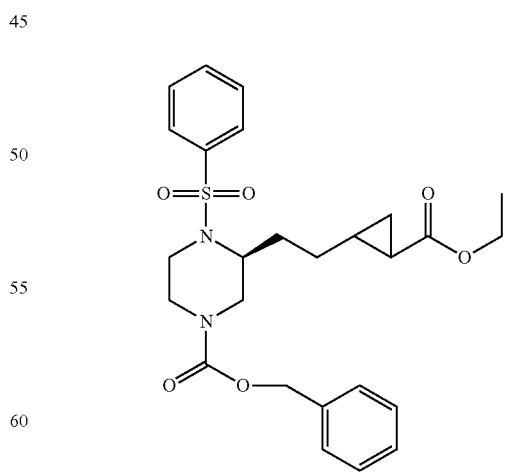

NaH (36.8 mg of 60% oil dispersed, 0.921 mmol) was suspended in 4 mL anhydrous DMSO in a oven dried flask under nitrogen atmosphere; then sulfoxonium (228 mg, 1.036 mmol) was added and the resulting mixture stirred for 1 hr at rt. (S,E)-Benzyl 3-(5-ethoxy-5-oxopent-3-en-1-yl)-4-(phenylsulfonyl)piperazine-1-carboxylate (280 mg, 0.575 mmol) in 2 ml of DMSO was added and the resulting mixture stirred for 1.5 hr at rt. LCMS showed rxn was complete. The mixture was diluted with ether (10 ml) and quenched with water (15 ml). The solution was extracted with ether (2×75 ml), separated, the combined organics dried with Na$_2$SO$_4$, filtered and concentrated in vacuo to afford (220 mg, 76%) of crude product used without further purification. MS: m/z=501 (M+H$^+$).

Step 2. 2-(2-((S)-4-((benzyloxy)carbonyl)-1-(phenylsulfonyl)piperazin-2-yl)ethyl)cyclopropanecarboxylic acid

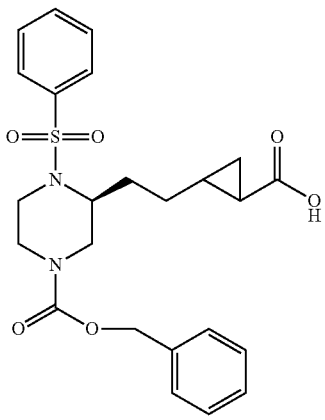 [SMILES: O=C(O)C1CC1CC[C@H]1CN(C(=O)OCc2ccccc2)CCN1S(=O)(=O)c1ccccc1]

The solution of (3S)-benzyl 3-(2-(2-(ethoxycarbonyl)cyclopropyl)ethyl)-4-(phenylsulfonyl)piperazine-1-carboxylate (200 mg, 0.40 mmol) in 4 mL of EtOH was treated with 1 mL of 1.0M NaOH solution, which was stirred at 50° C. for 3 hrs. LCMS shows all starting material was consumed. The volatiles were removed in vacuo and the residue was taken up with 5 ml of water, and extracted with EtOAC (10 mL) to remove impurities showing in LCMS. The water layer was then acidified with 4N HCl (~100 μL), and then extracted with EtOAc (2×15 mL). The organics were then combined, washed by brine (10 mL), dried over Na$_2$SO$_4$, filtered, and concentrated in vacuo to afford the title compound (133 mg, 77%) which was used without further purification. MS: m/z=573 (M+H$^+$) and m/z=595 (M+Na$^+$).

Step 3. (3S)-benzyl 4-(phenylsulfonyl)-3-(2-(2-(((2-(trimethylsilyl)ethoxy)carbonyl)amino)cyclopropyl)ethyl)piperazine-1-carboxylate

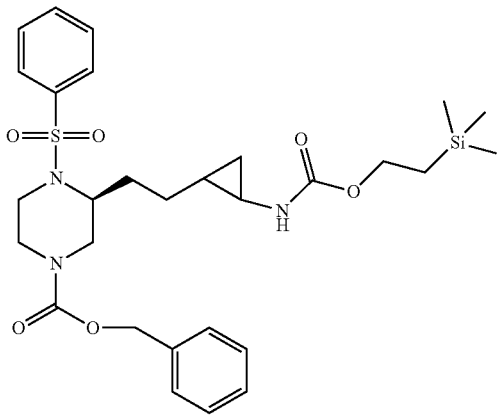 [SMILES: C[Si](C)(C)CCOC(=O)NC1CC1CC[C@H]1CN(C(=O)OCc2ccccc2)CCN1S(=O)(=O)c1ccccc1]

To solution of 2-(2-((S)-4-((benzyloxy)carbonyl)-1-(phenylsulfonyl)piperazin-2-yl)ethyl)cyclopropanecarboxylic acid (130 mg, 0.193 mmol) in 2 ml of toluene was added DPPA (60.9 mg, 0.221 mmol) followed by TEA (0.054 mL, 0.385 mmol). The resulting reaction mixture was then stirred at 85° C. for 25 minutes, then 2-(trimethylsilyl)ethanol (228 mg, 1.93 mmol) was added and the resulting mixture stirred at 85° C. for 0.5 hours and then 70° C. overnight. The mixture was cooled to room temperature and then diluted with EtOAc (10 mL). The mixture washed by brine (5 mL), the organics separated, dried over Na$_2$SO$_4$, filtered, and concentrated in vacuo. The residue was then purified by ISCO column (12 g, silica gel) eluting with a gradient of 0-70% EtOAc in hexane (600 ml). The tubes containing the product were collected and the solvent removed under reduced pressure to afford the title compound (41 mg, 36%). MS: m/z=588 (M+H$^+$).

Step 4. (3S)-benzyl 3-(2-(2-aminocyclopropyl)ethyl)-4-(phenylsulfonyl)piperazine-1-carboxylate

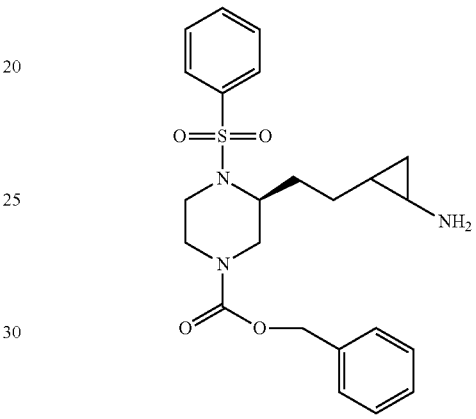

To a solution of (3S)-benzyl 4-(phenylsulfonyl)-3-(2-(2-(((2-(trimethylsilyl)ethoxy)carbonyl)amino)cyclopropyl)ethyl)piperazine-1-carboxylate (40 mg, 0.063 mmol) in 2 ml of THF was added 1.3 eq. of 1.0M solution of TBAF in THF (0.20 mL, 0.20 mmol) and the resulting mixture stirred under nitrogen for 2 hrs at 50° C. LCMS shows all starting material was consumed. THF was removed in vacuo and the residue was partitioned between water and EtOAc. The organics were separated and water layer was back extracted with EA (2×5 mL). The combined organic layers were washed by brine (10 mL), dried over Na$_2$SO$_4$, filtered, and then concentrated in vacuo to afford the desired product (21 mg, 69.6%). MS: m/z=444 (M+H$^+$).

Step 5. (3S)-benzyl 3-(2-(2-((R)-3,3-bis(4-fluorophenyl)-2-((methoxycarbonyl)amino)propanamido)cyclopropyl)ethyl)-4-(phenylsulfonyl)piperazine-1-carboxylate

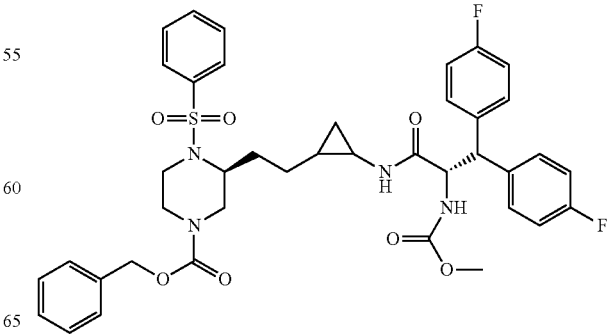

To a pre-cooled (0° C.) solution of 3,3-bis(4-fluorophenyl)-2-((methoxycarbonyl)amino)propanoic acid (22.7 mg, 0.068 mmol) and HATU (25.7 mg, 0.068 mmol) in 1.5 ml of acetonitrile was added (3S)-benzyl 3-(2-(2-aminocyclopropyl)ethyl)-4-(phenylsulfonyl)piperazine-1-carboxylate (20 mg, 0.045 mmol) in 1.5 ml of acetonitrile and the resulting solution stirred for 5 minutes. Hunig's base (20 µL, 0.135 mmol) was then added and the resulting mixture was stirred for 4 hr allowing to warm to room temperature. The mixture was diluted with EtOAc (10 mL) and washed by brine (10 mL), separated, dried over $Na_2SO_4$, filtered and concentrated in vacuo. The crude product was purified by Gilson RP-HPLC (using 30-100% CH3CN in water with 0.05% TFA as buffer, 12 min method) to give 25 mg of product as mixture of 2 isomers (2 isomers are not separable by Gilson). This material was then separated by silica gel TLC plate (2×1000 µM) using EtOAc/hexane (70/30) to give 5 mg of upper isomer (isomer 1) and 8 mg of lower isomer (isomer 2), (there are 2 trans diasteromers of the cyclopropane ring). MS of isomer 1: m/z=761 (M+H$^+$). MS of isomer 2: m/z=761 (M+H$^+$).

Step 6a. Methyl ((2R)-1,1-bis(4-fluorophenyl)-3-oxo-3-((2-(2-((S)-1-(phenylsulfonyl)piperazin-2-yl)ethyl)cyclopropyl)amino)propan-2-yl)carbamate First eluting isomer (3S)-Benzyl 3-(2-(2-((R)-3,3-bis(4-fluorophenyl)-2-((methoxycarbonyl)amino)propanamido)cyclopropyl)ethyl)-4-(phenylsulfonyl)piperazine-1-carboxylate (5 mg, 0.007 mmol) was taken into 3 ml of MeOH in a 50 ml flask, then 10 mg of Pd (5% o/c) was added. The reaction was then purged via vacuum/hydrogen gas from balloon and then was stirred vigorously under hydrogen balloon for 1 hr. LCMS shows all starting material was consumed. The reaction was diluted with EtOAc (5 mL) and filtered through a celite pad. The filtrate was concentrated in vacuo and the residue was purified by Gilson RP-HPLC (mobile phase: 10-80% CH3CN in water, both containing 0.05% TFA as buffer, 12 min method). The tube containing the product was collected into a scintilation vial, frozen via dry ice/acetone bath and then lyopholized overnight to afford (3.5 mg, 72%) of the desired product as the TFA salt form.
MS: m/z=627 (M+H$^+$).

Step 6b. Methyl ((2R)-1,1-bis(4-fluorophenyl)-3-oxo-3-((2-(2-((S)-1-(phenylsulfonyl)piperazin-2-yl)ethyl)cyclopropyl)amino)propan-2-yl)carbamate Second eluting isomer (3S)-Benzyl 3-(2-(2-((R)-3,3-bis(4-fluorophenyl)-2-((methoxycarbonyl)amino)propanamido)cyclopropyl)ethyl)-4-(phenylsulfonyl)piperazine-1-carboxylate (7 mg, 0.009 mmol) was taken into 3 ml of MeOH in a 50 ml flask, then 10 mg of Pd (5% o/c) was added. The reaction was then purged via vacuum/hydrogen gas from balloon and then was stirred vigorously under hydrogen balloon for 1 hr. LCMS shows all starting material was consumed. The reaction was diluted with EtOAc (5 mL) and filtered through a celite pad. The filtrate was concentrated in vacuo and the residue was purified by Gilson RP-HPLC (mobile phase: 10-80% CH3CN in water, both containing 0.05% TFA as buffer, 12 min method). The tube containing the product was collected into a scintilation vial, frozen via dry ice/acetone bath and then lyopholized overnight to afford (6.2 mg, 91%) of the desired product as the TFA salt form. MS: m/z=627 (M+H$^+$).

EXAMPLE 364 and EXAMPLE 365

(S)—N-(3-fluoro-2-(2-((S)-1-(phenylsulfonyl)piperazin-2-yl)ethyl)phenyl)-2-hydroxy-3,3-diphenylpropanamide and (R)—N-(3-fluoro-2-(2-((S)-1-(phenylsulfonyl)piperazin-2-yl)ethyl)phenyl)-2-hydroxy-3,3-diphenylpropanamide

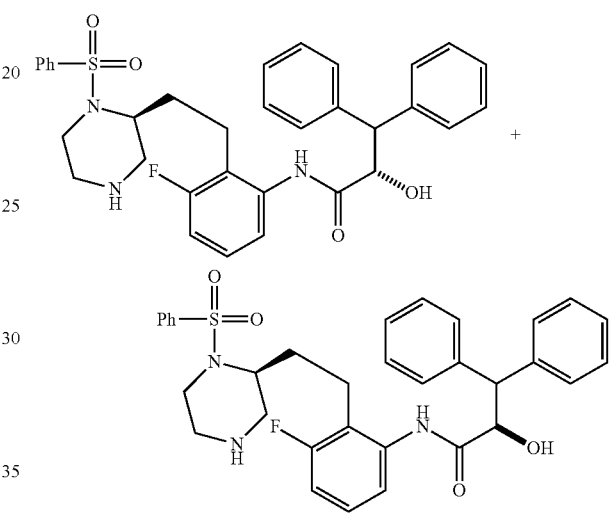

Step 1. Ethyl 2-(benzyloxy)-3,3-diphenylpropanoate

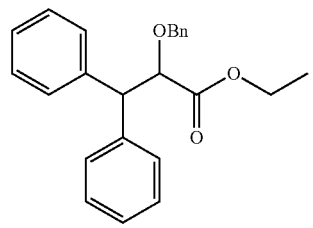 [SMILES: CCOC(=O)C(OCc1ccccc1)C(c1ccccc1)c1ccccc1]

60% NaH (222 mg, 5.55 mmol)) was added to a solution of Ethyl 2-hydroxy-3,3-diphenylpropanoate (500 mg, 1.85 mmol) in THF (10 mL) at 0° C. and the reaction stirred at rt for 30 min. Benzyl bromide (660 µl, 5.55 mmol) was added and the reaction heated at reflux for 1 hour. The reaction was quenched with aqueous potassium phosphate monobasic (saturated) and the mixture was extracted with ethyl acetate (×3). The combined organic fractions were dried (MgSO$_4$), filtered and the solvent was evaporated under reduced pressure. Purification on Silica (40 g), eluting with a gradient of 0-50% EtOAc/hexanes over 15 column volumes, afford the product (407 mg, 61.0% yield) as a white solid. MS: m/z=361 (M+H$^+$).

Step 2. 2-(Benzyloxy)-3,3-diphenylpropanoic acid

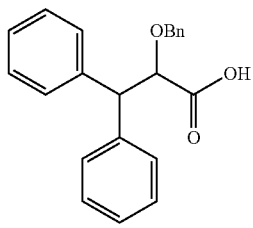 [SMILES: O=C(O)C(OCc1ccccc1)C(c1ccccc1)c1ccccc1]

Lithium hydroxide monohydrate (23.75 mg, 0.566 mmol) was added to a solution of ethyl 2-(benzyloxy)-3,3-diphenylpropanoate (51 mg, 0.141 mmol) in THF (1179 μl)/Water (236 μl), then MeOH was added dropwise until a clear solution resulted. The reaction was heated at 60° C. overnight. The solvent was evaporated under reduced pressure and the residue dissolved in water. 1M HCl (566 μl, 0.566 mmol) was added to neutralize the solution A few additional drops of 1M HCl were added to acidify the solution and the mixture was extracted with ethyl acetate (×3). The combined organic fractions were dried (MgSO$_4$), filtered and the solvent was evaporated under reduced pressure to afford the product (46.5 mg, 0.140 mmol, 99% yield) as a viscous gum. MS: m/z=333 (M+H$^+$).

Step 3. (4S)-tert-Butyl 4-(2-(2-(benzyloxy)-3,3-diphenylpropanamido)-6-fluorophenethyl)-2,2-dimethyloxazolidine-3-carboxylate

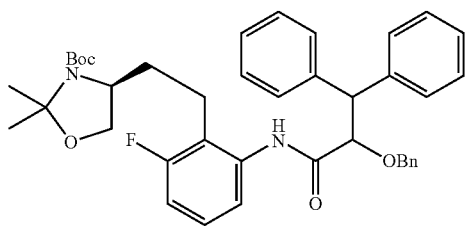 [SMILES: CC(C)(C)OC(=O)N1[C@@H](CCc2c(F)cccc2NC(=O)C(OCc2ccccc2)C(c2ccccc2)c2ccccc2)COC1(C)C]

POCl$_3$ (82 μl, 0.884 mmol) was added to a solution of (S)-tert-butyl 4-(2-amino-6-fluorophenethyl)-2,2-dimethyloxazolidine-3-carboxylate (299 mg, 0.884 mmol) and 2-(benzyloxy)-3,3-diphenylpropanoic acid (294 mg, 0.884 mmol) in Pyridine (4422 μl) at −15° C. The reaction was stirred at this temperature for 30 min, then warmed to 0° C. and stirred for 1 hour. The reaction was quenched with brine (saturated) and the mixture was extracted with ethyl acetate (×3). The combined organic fractions were dried (MgSO$_4$), filtered and the solvent was evaporated under reduced pressure. Purification on Silica (40 g), eluting with a gradient of 0-100% EtOAc/hexanes over 15 column volumes, afforded the product (317 mg, 0.486 mmol, 54.9% yield) as a viscous oil, LCMS shows the compound is 100% pure. MS: m/z=654 (M+H$^+$).

Step 4. N-(2-((S)-3-Amino-4-hydroxybutyl)-3-fluorophenyl)-2-(benzyloxy)-3,3-diphenylpropanamide

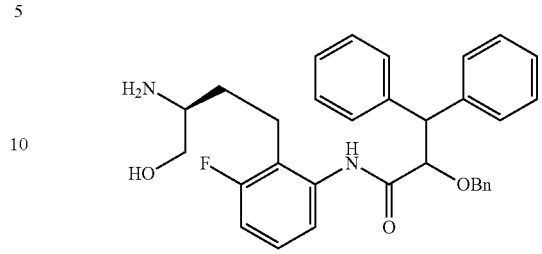

To a solution of (4S)-tert-butyl 4-(2-(2-(benzyloxy)-3,3-diphenylpropanamido)-6-fluorophenethyl)-2,2-dimethyloxazolidine-3-carboxylate (317 mg, 0.486 mmol) in DCM (2428 μl) at 0° C. is added TFA (1496 μl, 19.42 mmol) followed by water (350 μl, 19.42 mmol), the reaction was warmed to RT and stirred for 2 hours. The majority of the solvent was removed in vacuo and the residue is diluted with MeOH and the product is purified on a 5 g SCX column (1CV equilibration, material load, 2 CVs MeOH wash and 2 CVs NH$_3$ in MeOH) to afford the desired product (248 mg, 0.484 mmol, 100% yield) as a white foam. MS: m/z=514 (M+H$^+$).

Step 5. 2-(Benzyloxy)-N-(3-fluoro-2-((S)-4-hydroxy-3-(phenylsulfonamido)butyl)phenyl)-3,3-diphenylpropanamide

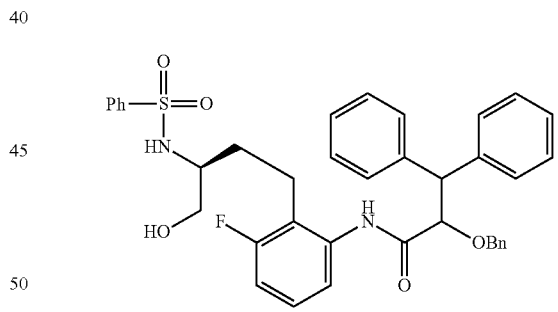

A solution of N-(2-((S)-3-amino-4-hydroxybutyl)-3-fluorophenyl)-2-(benzyloxy)-3,3-diphenylpropanamide (282 mg, 0.550 mmol) and TEA (153 μl, 1.100 mmol) in DMF (2751 μl) is cooled to 0° C. Benzenesulfonyl chloride (74.5 μl, 0.578 mmol) was added dropwise. The mixture was allowed to stir for 20 minutes at 0° C. The reaction was quenched with aqueous sodium hydrogen carbonate (saturated) and the mixture was extracted with ethyl acetate (×3). The combined organic fractions were dried (MgSO$_4$), filtered and the solvent was evaporated under reduced pressure to afford the desired product (359 mg, 0.550 mmol, 100% yield) as a vicsous oil. MS: m/z=654 (M+H$^+$).

Step 6. 2-(benzyloxy)-N-(3-fluoro-2-(2-((S)-1-(phenylsulfonyl)aziridin-2-yl)ethyl)phenyl)-3,3-diphenylpropanamide

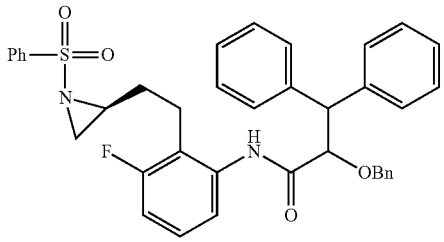 [SMILES: O=C(Nc1cccc(F)c1CC[C@H]1CN1S(=O)(=O)c1ccccc1)C(OCc1ccccc1)C(c1ccccc1)c1ccccc1]

DIAD (0.134 mL, 0.687 mmol) then triphenylphosphine (180 mg, 0.687 mmol) were added to a solution of 2-(benzyloxy)-N-(3-fluoro-2-((S)-4-hydroxy-3-(phenylsulfonamido)butyl)phenyl)-3,3-diphenylpropanamide (359 mg, 0.550 mmol) in THF (10 mL) at 0° C., LCMS after 20 min shows product and SM, LCMS after another 40 min is the same. Additional DIAD (0.134 mL, 0.687 mmol) followed by TRIPHENYLPHOSPHINE (180 mg, 0.687 mmol) were added, LCMS after 15 min shows the reaction is complete. The reaction was quenched with water and the mixture was extracted with ethyl acetate (×3). The combined organic fractions were dried (MgSO$_4$), filtered and the solvent was evaporated under reduced pressure. Purification on Silica (40 g), eluting with a gradient of 0-100% EtOAc/hexanes over 15 column volumes, afforded the desired product (349 mg, 0.550 mmol, 100% yield) as a colorless gum, LCMS looks ok. MS: m/z=636 (M+H$^+$).

Step 7. 2-(Benzyloxy)-N-(3-fluoro-2-((S)-4-((2-hydroxyethyl)amino)-3-(phenylsulfonamido)butyl)phenyl)-3,3-diphenylpropanamide

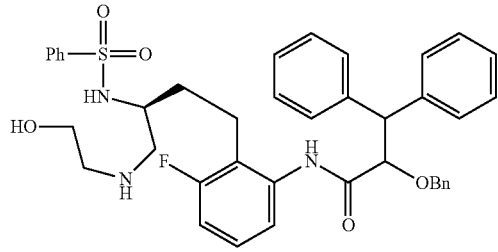 [SMILES: O=C(Nc1cccc(F)c1CC[C@@H](CNCCO)NS(=O)(=O)c1ccccc1)C(OCc1ccccc1)C(c1ccccc1)c1ccccc1]

Ethanolamine (332 µl, 5.50 mmol) was added to a solution of 2-(benzyloxy)-N-(3-fluoro-2-(2-((S)-1-(phenylsulfonyl)aziridin-2-yl)ethyl)phenyl)-3,3-diphenylpropanamide (349 mg, 0.550 mmol) in THF (5498 µl) and the reaction heated at 45° C. for 2 hours, LCMS shows no SM. The reaction was diluted with EtOAc and washed with water (×3), dried (MgSO$_4$), filtered and the solvent was evaporated under reduced pressure to afford the desired product (367 mg, 0.527 mmol, 96% yield) as a clear gum. MS: m/z=697 (M+H$^+$).

Step 8. 2-(Benzyloxy)-N-(3-fluoro-2-((S)-4-((2-hydroxyethyl)amino)-3-(phenylsulfonamido)butyl)phenyl)-3,3-diphenylpropanamide

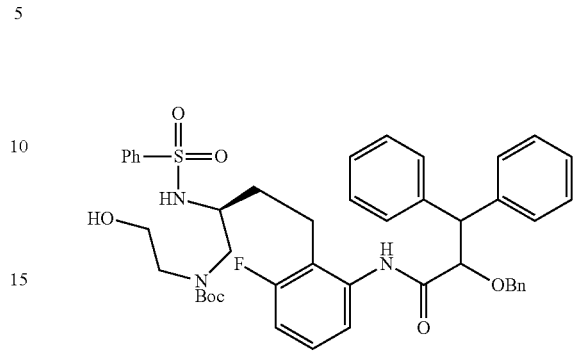

Boc$_2$O (196 µl, 0.844 mmol) was added to a solution of 2-(benzyloxy)-N-(3-fluoro-2-((S)-4-((2-hydroxyethyl)amino)-3-(phenylsulfonamido)butyl)phenyl)-3,3-diphenylpropanamide (367 mg, 0.527 mmol) and TEA (147 µl, 1.055 mmol) in Acetonitrile (5274 µl) at rt and the reaction stirred for 20 minutes at rt. The reaction was diluted with EtOAc, washed with water, then dried (MgSO$_4$), filtered and the solvent was evaporated under reduced pressure to afford the desired compound (420 mg, 0.528 mmol, 100% yield) as a clear gum. MS: m/z=797 (M+H$^+$).

Step 9. (3S)-tert-Butyl 3-(2-(2-(benzyloxy)-3,3-diphenylpropanamido)-6-fluorophenethyl)-4-(phenylsulfonyl)piperazine-1-carboxylate

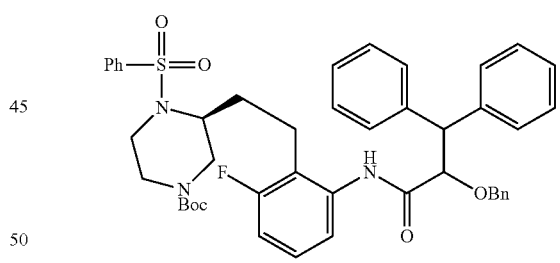

Tri-n-butylphosphine (195 µl, 0.791 mmol) was added to a solution of tert-butyl ((2S)-4-(2-(2-(benzyloxy)-3,3-diphenylpropanamido)-6-fluorophenyl)-2-(phenylsulfonamido)butyl)(2-hydroxyethyl)carbamate (420 mg, 0.528 mmol) and 1,1'-(Azodicarbonyl)dipiperidine (200 mg, 0.791 mmol) in THF (5277 µl) and the reaction stirred overnight at RT. The reaction was quenched with aqueous sodium hydrogen carbonate (saturated) and the mixture was extracted with ethyl acetate (×3). The combined organic fractions were dried (MgSO$_4$), filtered and the solvent was evaporated under reduced pressure. Purification by ISCO (40 g) 0-100% EtOAc/hexanes afford the desired product (289 mg, 0.371 mmol, 70.4% yield) as a white foam. MS: m/z=778 (M+H$^+$).

343

Step 10. (3S)-tert-Butyl 3-(2-fluoro-6-(2-hydroxy-3,3-diphenylpropanamido)phenethyl)-4-(phenylsulfonyl)piperazine-1-carboxylate

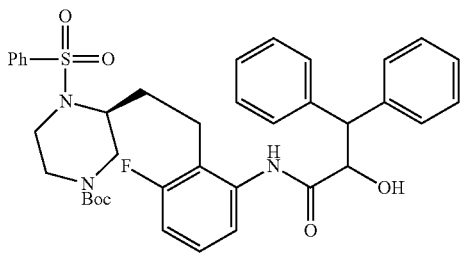 [SMILES: CC(C)(C)OC(=O)N1CCN(S(=O)(=O)c2ccccc2)[C@@H](CCc2c(F)cccc2NC(=O)C(O)C(c2ccccc2)c2ccccc2)C1]

Pearlman's Catalyst (111 mg, 0.159 mmol) was added to a nitrogen degassed solution of (3S)-tert-butyl 3-(2-(2-(benzyloxy)-3,3-diphenylpropanamido)-6-fluorophenethyl)-4-(phenylsulfonyl)piperazine-1-carboxylate (247 mg, 0.318 mmol) in Methanol (1588 µl) and the reaction evacuated and backfilled with hydrogen and was shaken on the Parr at 50 psi hydrogen overnight. The reaction was purged with nitrogen then filtered through a pad of celite and concentrated in vacuo. Purification on Silica (40 g), eluting with a gradient of 0-100% EtOAc/hexanes over 15 column volumes, afford (3S)-tert-butyl 3-(2-fluoro-6-(2-hydroxy-3,3-diphenylpropanamido)phenethyl)-4-(phenylsulfonyl)piperazine-1-carboxylate (113 mg, 0.164 mmol, 51.7% yield) as a white foam. MS: m/z=688 (M+H$^+$).

Step 11: (S)—N-(3-fluoro-2-(2-((S)-1-(phenylsulfonyl)piperazin-2-yl)ethyl)phenyl)-2-hydroxy-3,3-diphenylpropanamide and (R)—N-(3-fluoro-2-(2-((S)-1-(phenylsulfonyl)piperazin-2-yl)ethyl)phenyl)-2-hydroxy-3,3-diphenylpropanamide TFA (164 µl) was added to a solution of (3S)-tert-butyl 3-(2-fluoro-6-(2-hydroxy-3,3-diphenylpropanamido)phenethyl)-4-(phenylsulfonyl)piperazine-1-carboxylate (113 mg, 0.164 mmol) in DCM (657 µl) and the reaction stirred at rt for 2 hours, LCMS shows complete and no elimination. The solvent was removed in vacuo. The diastereoisomers were separated on an AD column 5×50 cm 20µ eluting at 50 mL/min with 60% EtOH 40% Hexanes (0.01% DEA), to afford (Peak 1 (first eluting) (S)—N-(3-fluoro-2-(2-((S)-1-(phenylsulfonyl)piperazin-2-yl)ethyl)phenyl)-2-hydroxy-3,3-diphenylpropanamide (41 mg, 0.070 mmol, 42.5% yield) MS: m/z=588 (M+H$^+$), and Peak 2 (second eluting) (R)—N-(3-fluoro-2-(2-((S)-1-(phenylsulfonyl)piperazin-2-yl)ethyl)phenyl)-2-hydroxy-3,3-diphenylpropanamide (24 mg, 0.041 mmol, 24.86% yield). MS: m/z=588 (M+H$^+$).

344

EXAMPLE 366

(S)-2-amino-N-(3-fluoro-2-(2-((S)-4-(phenylsulfonyl)-4,7-diazaspiro[2.5]octan-5-yl)ethyl)phenyl)-3,3-bis(4-fluorophenyl)propanamide

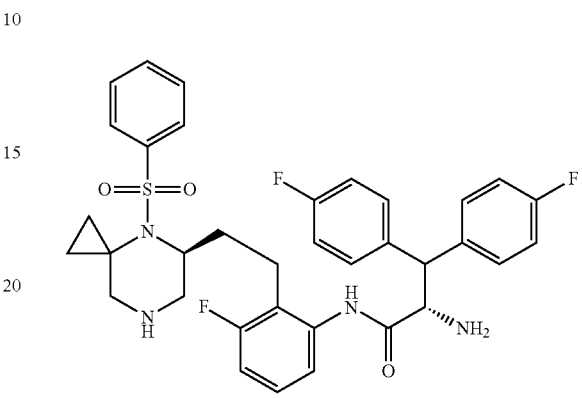

Step 1. (R)-1-benzyl-6-(((tert-butyldimethylsilyl)oxy)methyl)piperazin-2-one

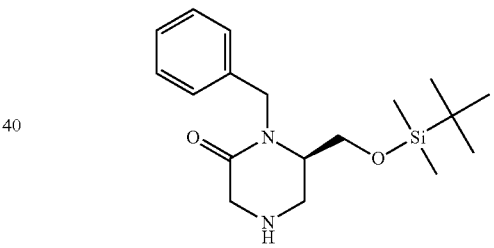

To a mixture of (R)-1-benzyl-6-(hydroxymethyl)piperazin-2-one (15 g, 68 mmol) in CH$_2$Cl$_2$ (340 mL) at rt was added triethylamine (14.2 mL, 0.10 mol) followed by DMAP (0.83 g, 6.8 mmol) to afford a yellow, homogenous mixture. TBDMSCl (12.3 g, 82 mmol) was added in one portion and the mixture was stirred under N$_2$ for 12 hr (overnight) at rt. The mixture was diluted with CH$_2$Cl$_2$ (300 mL) and water (30 mL) was added. The layers were separated and the water layer was extracted with CH$_2$Cl$_2$ (5×100 mL) whereupon the organic layers were combined. The organic layer was washed with sat. aq. NH$_4$Cl (3×25 mL), dried (Na$_2$SO$_4$), filtered, and concentrated under reduced pressure to afford a viscous oil. The crude oil taken up in CH$_2$Cl$_2$ (10 mL) was loaded onto a 330 g ISCO silica gel column. A gradient of 100% CH$_2$Cl$_2$ to 90% CH$_2$Cl$_2$/10% MeOH was run over 45 minutes to afford product (20.7 g, 89%) as a clear viscous oil. MS: m/z=335.3 (M+H$^+$).

Step 2. (R)-1,4-dibenzyl-6-(((tert-butyldimethylsilyl)oxy)methyl)piperazin-2-one

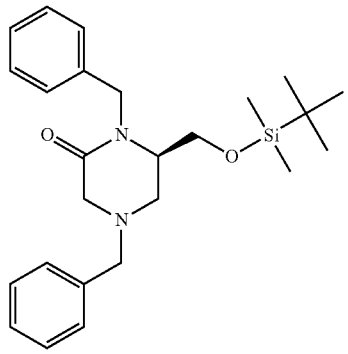 [SMILES: CC(C)(C)[Si](C)(C)OC[C@H]1CN(Cc2ccccc2)CC(=O)N1Cc1ccccc1]

To a solution of (R)-1-benzyl-6-(((tert-butyldimethylsilyl)oxy)methyl)piperazin-2-one (18.8 g, 56.2 mmol) in CH$_2$Cl$_2$ (260 mL)/HOAc (2 mL) under N$_2$ at rt was added benzaldehyde (6.9 mL, 67.4 mmol) dropwise. This resulting mixture was stirred for 30 minutes whereupon Na(OAc)$_3$BH (23.8 g, 0.11 mol) was added portionwise and the resulting mixture was then stirred at room temperature overnight. The entire reaction mixture was cooled to 0° C. in an ice-bath and then slowly quenched by adding sat. aq. NaHCO$_3$ (20 mL) and diluting the reaction with CH$_2$Cl$_2$ (150 mL). The layers were separated and the aqueous layer was extracted with CH$_2$Cl$_2$ (2×150 mL). The combined CH$_2$Cl$_2$ layers were washed with brine (3×15 mL), and then dried over anhydrous Na$_2$SO$_4$, filtered, and concentrated to yield a pale yellow viscous oil. The crude material was taken up in CH$_2$Cl$_2$ (20 mL) and was loaded on a RS ISCO 330 gm column. The column was eluted with a gradient of 100% hexanes to 60% hexanes/40% EtOAc over 40 minutes to afford product (23.5 g, 97%) as a light brown oil. MS: m/z=425.4 (M+H$^+$).

Step 3. (R)-4,7-dibenzyl-5-(((tert-butyldimethylsilyl)oxy)methyl)-4,7-diazaspiro[2.5]octane

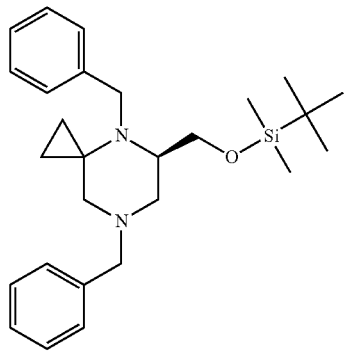 [SMILES: CC(C)(C)[Si](C)(C)OC[C@H]1CN(Cc2ccccc2)CC2(CC2)N1Cc1ccccc1]

To a 3-neck 500 mL flask charged with (R)-1,4-dibenzyl-6-(((tert-butyldimethylsilyl)oxy)methyl)piperazin-2-one (5.2 g, 12.3 mmol) in anhydrous THF (85 mL) under N$_2$ was added Ti(i-OPr)$_4$ (14.5 mL, 49 mmol) via a syringe. The reaction mixture was heated to reflux whereupon a 1M soln of EtMgBr in THF (122 mL, 0.12 mol) was added dropwise over 30 minutes via an addition funnel. The mixture was refluxed for 10-15 minutes after the addition was complete and was then cooled to rt. The entire reaction was cooled to 0° C. whereupon an ice-water solution (75 mL) was added carefully over 30 min. The resulting mixture was filtered thru a pad of Celite which was generously washed with CH$_2$Cl$_2$ (500 mL). The organic layer was washed with water (4×25 mL) followed by brine (2×20 mL). The combined CH$_2$Cl$_2$ layers were dried over anhydrous Na$_2$SO$_4$, filtered, and concentrated to yield a reddish brown viscous oil. This crude viscous oil was taken up in 15 mL CH$_2$Cl$_2$ and loaded on a RS ISCO 120 gm column. The column was eluted with a gradient of 100% hexanes to 60% hexanes/40% EtOAc over 40 minutes afforded the product (3.0 g, 56%) a clear oil. MS: m/z=437.5 (M+H$^+$).

Step 4. (R)-4-benzyl-5-(((tert-butyldimethylsilyl)oxy)methyl)-4,7-diazaspiro[2.5]octane hydrochloride

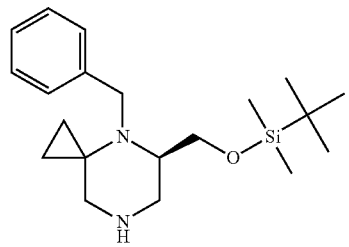 [SMILES: CC(C)(C)[Si](C)(C)OC[C@H]1CNCC2(CC2)N1Cc1ccccc1]

To a solution of (R)-4,7-dibenzyl-5-(((tert-butyldimethylsilyl)oxy)methyl)-4,7-diazaspiro[2.5]octane (3.0 g, 6.9 mmol) in DCE (35 mL) under N$_2$ at 0° C. was added a solution of 1-chloroethyl chloroformate (0.74 mL, 6.9 mmol) in DCE (4 mL). The reaction mixture was heated to reflux, stirred for 2.5 h, and was cooled to rt. The reaction mixture was concentrated to dryness under vacuum to yield a brown oil which was taken up in MeOH (15 mL) and was heated at reflux for 2 h. The solution was concentrated to dryness was taken up in Et$_2$O (15 mL) the resultant solid was filtered off. The solid was washed with washed with Et$_2$O (15 mL) and the resultant filtrate was concentrated to yield the product (2.1 g, 56%) as a brown oil. MS: m/z=347.3 (M+H$^+$). The product was used in the next step without purification.

Step 5. (R)-tert-butyl 4-benzyl-5-(((tert-butyldimethylsilyl)oxy)methyl)-4,7diazaspiro[2.5]octane-7-carboxylate

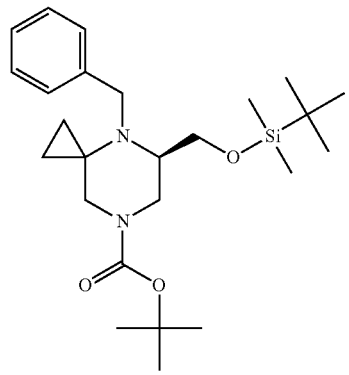 [SMILES: CC(C)(C)OC(=O)N1C[C@H](CO[Si](C)(C)C(C)(C)C)N(Cc2ccccc2)C2(CC2)C1]

To a solution of (R)-4-benzyl-5-(((tert-butyldimethylsilyl)oxy)methyl)-4,7-diazaspiro[2.5]octane hydrochloride (2.6 g, 4.8 mmol) in CH$_2$Cl$_2$ (35 mL) at rt under N$_2$ was added Boc$_2$O (1.3 g, 6.2 mmol) portionwise followed by dropwise addition of sat. aq. NaHCO$_3$ (5 mL). The reaction mixture was stirred at room temperature for 12 h and was diluted with water (3 mL) and CH$_2$Cl$_2$ (20 mL). The layers were separated and the aqueous layer was extracted with CH$_2$Cl$_2$ (2×20 mL). The organic layers were combined, washed with brine (2×5 mL), dried (Na$_2$SO$_4$), filtered and concentrated under reduced pressure to afford an oil. The crude product was taken up in CH$_2$Cl$_2$ (10 mL) and was loaded onto a RS ISCO 120 g column. The column was eluted with a gradient of 100% hexanes to 50% hexanes/50% EtOAc over 40 minutes to afford the product (2.3 g, 98%) as a clear oil. MS: m/z=447.3 (M+H$^+$).

Step 6. (R)-tert-butyl 4-benzyl-5-(hydroxymethyl)-4,7-diazaspiro[2.5]octane-7-carboxylate

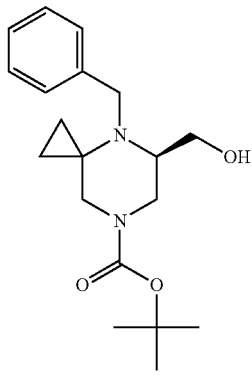 [SMILES: CC(C)(C)OC(=O)N1C[C@H](CO)N(Cc2ccccc2)C2(CC2)C1]

To a solution of (R)-tert-butyl 4-benzyl-5-(((tert-butyldimethylsilyl)oxy)methyl)-4,7diazaspiro[2.5]octane-7-carboxylate (1.5 g, 3.3 mmol) in anhydrous THF (15 mL) under N$_2$ at rt was added a 1M solution of TBAF in THF (6.5 mL, 6.5 mmol) dropwise. The resulting mixture was stirred for 2.5 h and was quenched by addition of sat. aq. KH$_2$PO$_4$ (3 mL). The mixture was diluted with EtOAc (40 mL) and the layers were separated. The aqueous layer was extracted with EtOAc (2×20 mL) and the organic layers were combined. The organic layer was washed with water (2×4 mL) and brine (2×4 mL) and was dried (Na$_2$SO$_4$). The organic layer was filtered and concentrated under reduced pressure to afford an oil. The crude material was dissolved in CH$_2$Cl$_2$ (5 mL) and was loaded onto RS ISCO 40 gm column attached to an ISCO purification system. The column was eluted with a gradient of 100% CH$_2$Cl$_2$ to 90% CH$_2$Cl$_2$/10% MeOH over 45 min to afford the product (1.1 g, 99%) as a clear oil. MS: m/z=333.2 (M+H$^+$)

Step 7. (R)-tert-butyl 5-(hydroxymethyl)-4,7-diazaspiro[2.5]octane-7-carboxylate

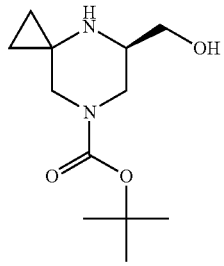 [SMILES: CC(C)(C)OC(=O)N1C[C@H](CO)NC2(CC2)C1]

To (R)-tert-butyl 4-benzyl-5-(hydroxymethyl)-4,7-diazaspiro[2.5]octane-7-carboxylate (0.80 g, 2.4 mmol) in EtOH (12 mL) under N$_2$ was added 10% Pd/C (0.33 g) in one portion. The mixture was stirred under a balloon of H$_2$ for 1.5 h whereupon the mixture was purged to N$_2$. The reaction mixture was filtered thru a pad of which was washed with EtOH (75 mL). The resultant filtrate was concentrated under reduced pressure to afford a pale viscous oil which was dissolved in CH$_2$Cl$_2$ and loaded on a RS ISCO 80 gm column. The column was eluted with a gradient of 100% CH$_2$Cl$_2$ to 70% CH$_2$Cl$_2$/30% MeOH over 40 minutes to afford the product (0.44 g, 75%) as a clear oil. MS: m/z=243.2 (M+H$^+$)

Step 8. (R)-4-((9H-fluoren-9-yl)methyl) 7-tert-butyl 5-(hydroxymethyl)-4,7-diazaspiro[2.5]octane-4,7-dicarboxylate

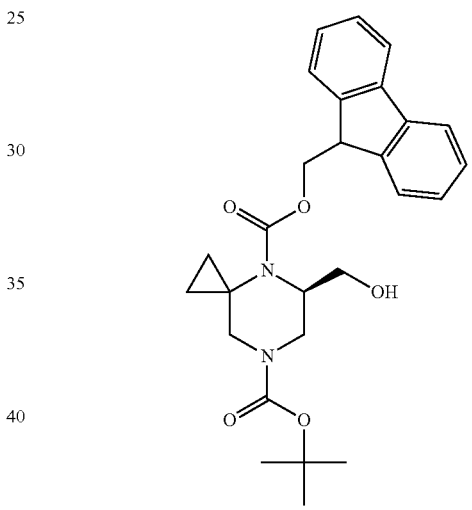

To a solution of (R)-tert-butyl 5-(hydroxymethyl)-4,7-diazaspiro[2.5]octane-7-carboxylate (0.55 g, 2.3 mmol) in Et$_2$O (10 mL) at rt was added solid NaHCO$_3$ (0.25 g, 3.0 mmol) followed by addition of water (2 mL). The mixture was cooled to 0° C. whereupon Fmoc-Cl (0.71 g, 2.7 mmol) was added portionwise. The mixture was stirred 3.5 hrs at 0° C. whereupon water (1 mL) and CH$_2$Cl$_2$ (10 mL) were added to the mixture. The layers were separated and the aqueous layer was extracted with CH$_2$Cl$_2$ (2×10 mL). The organic layers were combined and were washed with brine (2×5 mL). The organic layer was dried (Na$_2$SO$_4$), filtered, and concentrated under reduced pressure to afford an oil. The crude oil was dissolved in CH$_2$Cl$_2$ (7 mL) and was loaded onto a RS ISCO 40 gm column attached to an ISCO purification system. The column was eluted with a gradient of 100% CH$_2$Cl$_2$ to 90% CH$_2$Cl$_2$/10% MeOH over 60 minutes to afford the product (0.96 g, 90%) as a white solid. MS: m/z=465.3 (M+H$^+$).

Step 9. (R)-4-((9H-fluoren-9-yl)methyl) 7-tert-butyl 5-formyl-4,7-diazaspiro[2.5]octane-4,7-dicarboxylate

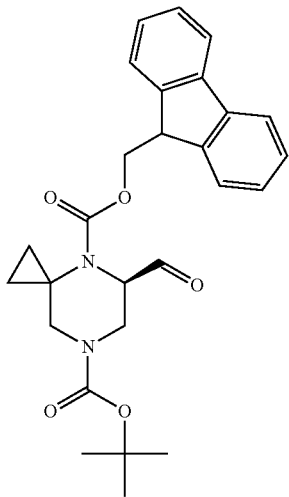 [SMILES: CC(C)(C)OC(=O)N1C[C@H](C=O)N(C(=O)OCC2c3ccccc3-c3ccccc32)C2(CC2)C1]

To a solution of (R)-4-((9H-fluoren-9-yl)methyl) 7-tert-butyl 5-(hydroxymethyl)-4,7-diazaspiro[2.5]octane-4,7-dicarboxylate (0.20 g, 0.43 mmol) in CH$_2$Cl$_2$ (3 mL) under N$_2$ at 0° C. was added Dess-Martin reagent (0.22 g, 0.52 mmol) in one portion. The mixture was stirred for 1.5 h at 0° C. whereupon an additional portion of Dess-Martin reagent (27 mg, 0.06 mmol) was added. The mixture was stirred for an additional 4 h at 0° C. whereupon Ca(OH)$_2$ (2 g) was added to the mixture which was stirred for 1.5 h. The mixture was filtered thru a pad of Celite which was washed with CH$_2$Cl$_2$ (40 mL). The resulting filtrate was concentrated under reduced pressure and placed under high vacuum to afford the product (0.20 g, 99%) as a white solid. MS: m/z=463.3 (M+H$^+$). This material was carried on directly to the next transformation without purification.

Step 10. (S,E)-4-((9H-fluoren-9-yl)methyl) 7-tert-butyl 5-(2-fluoro-6-nitrostyryl)-4,7-diazaspiro[2.5]octane-4,7-dicarboxylate

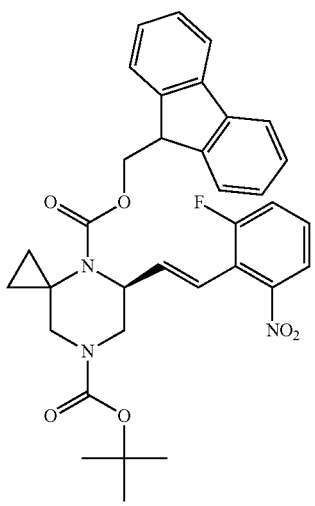 [SMILES: CC(C)(C)OC(=O)N1C[C@H](/C=C/c2c(F)cccc2[N+](=O)[O-])N(C(=O)OCC2c3ccccc3-c3ccccc32)C2(CC2)C1]

To a solution of bromo(2-fluoro-6-nitrobenzyl)triphenylphosphorane (0.26 g, 0.52 mmol) in DME (2 mL) under N$_2$ at rt was added K$_2$CO$_3$ (65 mg, 0.47 mmol) followed by 18-crown-6 (11 mg, 0.043 mmol). The resulting mixture was stirred for 30 min whereupon (R)-4-((9H-fluoren-9-yl)methyl) 7-tert-butyl 5-formyl-4,7-diazaspiro[2.5]octane-4,7-dicarboxylate (0.20 g, 0.43 mmol) in DME (1.5 mL) was added dropwise to the mixture. CH$_3$CN (1 mL) was added to the mixture to completely solubilize the mixture which was then stirred for 12 h. The reaction mixture was filtered thru a pad of Celite and the pad was washed with DME (2×50 mL). The resulting filtrate was concentrated under reduced pressure to afford a yellow oil. This yellow oil was dissolved in CH$_2$Cl$_2$ (4 mL) and was loaded onto several preparative TLC plates which were developed in a 2:1 mixture of hexanes/EtOAc to afford the product (94 mg, 36%) as a white solid. MS: m/z=600.4 (M+H$^+$).

Step 11. (S)-4-((9H-fluoren-9-yl)methyl) 7-tert-butyl 5-(2-amino-6-fluorophenethyl)-4,7-diazaspiro[2.5]octane-4,7-dicarboxylate

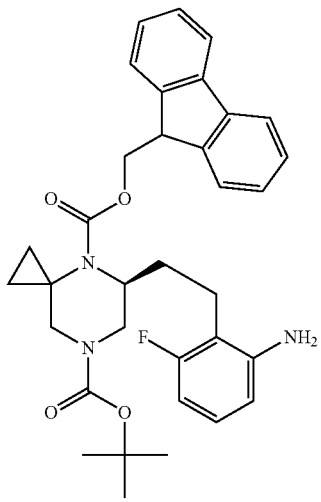 [SMILES: CC(C)(C)OC(=O)N1C[C@H](CCc2c(N)cccc2F)N(C(=O)OCC2c3ccccc3-c3ccccc32)C2(CC2)C1]

To a solution of (S,E)-4-((9H-fluoren-9-yl)methyl) 7-tert-butyl 5-(2-fluoro-6-nitrostyryl)-4,7-diazaspiro[2.5]octane-4,7-dicarboxylate (95 mg, 0.16 mmol) in EtOH (3 mL) at rt was added 20% Pd(OH)$_2$ (17 mg, 0.024 mmol) in one portion. The mixture was evacuated, purged to H$_2$, and stirred under a balloon of H$_2$ for 2.5 h. The reaction was evacuated and filled with N$_2$ and the mixture was filtered thru a pad of Celite. The pad of Celite was washed with EtOH (75 mL) and the resultant filtrated was concentrated under vacuum to yield the product (64 mg, 71%) as a pale brown solid. MS: m/z=572.8 (M+H$^+$). This material was taken on crude to the next transformation without purification.

Step 12. (S)-4-((9H-fluoren-9-yl)methyl) 7-tert-butyl 5-(2-((S)-2-((tert-butoxycarbonyl)amino)-3,3-bis(4-fluorophenyl)propanamido)-6-fluorophenethyl)-4,7-diazaspiro[2.5]octane-4,7-dicarboxylate

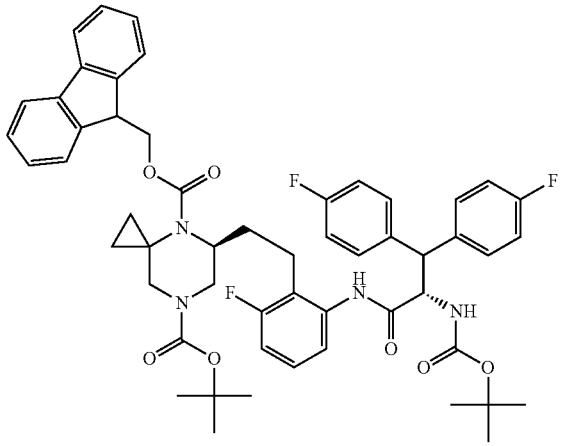 [SMILES: CC(C)(C)OC(=O)N[C@H](C(=O)Nc1cccc(F)c1CC[C@H]1CN(C(=O)OC(C)(C)C)CC2(CC2)N1C(=O)OCC1c2ccccc2-c2ccccc21)C(c1ccc(F)cc1)c1ccc(F)cc1]

To a round bottom flask charged with a stir bar at rt was added (S)-4-((9H-fluoren-9-yl)methyl) 7-tert-butyl 5-(2-amino-6-fluorophenethyl)-4,7-diazaspiro[2.5]octane-4,7-dicarboxylate (64 mg, 0.11 mmol) and (S)-2-((tert-butoxycarbonyl)amino)-3,3-bis(4-fluorophenyl)propanoic acid (0.051 g, 0.135 mmol) followed by anhydrous pyridine (1 mL). The mixture which was cooled to −15° C. whereupon POCl$_3$ (16 µL, 0.17 mmol) was added dropwise. The mixture was stirred for 30 min at −15° C., warmed to 0° C., and stirred for an additional 2.5 h at this temperature. The mixture was quenched with sat. aq. KH$_2$PO$_4$ (1 mL) and was diluted with EtOAc (10 mL). The layers were separated and the aqueous layer was extracted with EtOAc (3×10 mL). The organic layers were combined and were washed with brine (2×1 mL). The organic layer was dried (Na$_2$SO$_4$), filtered, and concentrated under reduced pressure. The crude material was dissolved in CH$_2$Cl$_2$ (3 mL) and was loaded onto 4×1000 uM preparative TLC plates. The plate were eluted in a 2:1 mixture of hexanes/EtOAc to afford the product (44 mg, 42%) as a white solid. MS: m/z=831.9 (M+H$^+$).

Step 13. (S)-tert-butyl 5-(2-((S)-2-((tert-butoxycarbonyl)amino)-3,3-bis(4-fluorophenyl)propanamido)-6-fluorophenethyl)-4,7-diazaspiro[2.5]octane-7-carboxylate

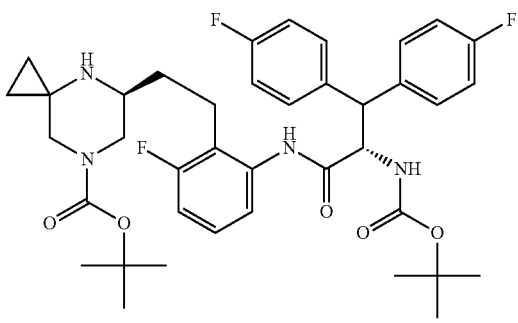 [SMILES: CC(C)(C)OC(=O)N[C@H](C(=O)Nc1cccc(F)c1CC[C@H]1CN(C(=O)OC(C)(C)C)CC2(CC2)N1)C(c1ccc(F)cc1)c1ccc(F)cc1]

To a solution of (S)-4-((9H-fluoren-9-yl)methyl) 7-tert-butyl 5-(2-((S)-2-((tert-butoxycarbonyl)amino)-3,3-bis(4-fluorophenyl)propanamido)-6-fluorophenethyl)-4,7-diazaspiro[2.5]octane-4,7-dicarboxylate (44 mg, 0.047 mmol) in CH$_2$Cl$_2$ (1 mL) under N$_2$ at rt was added piperidine (0.2 mL, 2.0 mmol) dropwise. The mixture was stirred for 1.5 hrs whereupon the mixture was concentrated to dryness. The resultant solid was azeotroped with CH$_2$Cl$_2$ (5×1 mL) to afford the product (33 mg, 98%) as a brown solid. MS: m/z=709.8 (M+H$^+$). This material was taken on crude to the next transformation without purification.

Step 14. (S)-tert-butyl 5-(2-((S)-2-((tert-butoxycarbonyl)amino)-3,3-bis(4-fluorophenyl)propanamido)-6-fluorophenethyl)-4-(phenylsulfonyl)-4,7-diazaspiro[2.5]octane-7-carboxylate

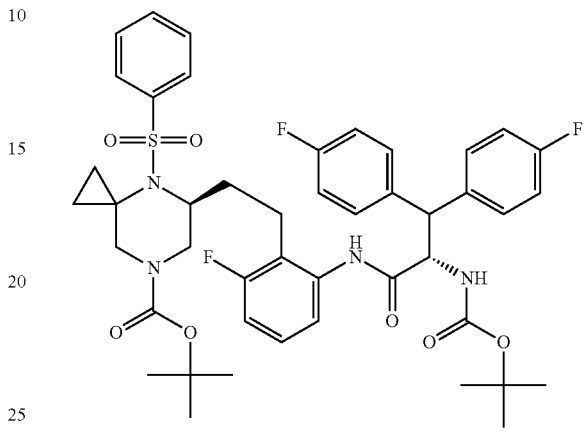

To a solution of (S)-tert-butyl 5-(2-((S)-2-((tert-butoxycarbonyl)amino)-3,3-bis(4-fluorophenyl)propanamido)-6-fluorophenethyl)-4,7-diazaspiro[2.5]octane-7-carboxylate (33 mg, 0.047 mmol) in CH$_2$Cl$_2$ (3 mL) under N$_2$ at rt was added DIPEA (9.8 uL, 0.056 mmol). The mixture was cooled to −78° C. whereupon a solution of PhSO$_2$Cl (5.4 uL, 0.042 mmol) in CH$_2$Cl$_2$ (0.5 mL). The resulting solution was stirred for 4.5 h at −78° C. whereupon an additional portion of PhSO$_2$Cl (2.7 uL, 0.021 mmol) and DIPEA (3 uL, 0.018 mmol). The mixture was allowed to warm to rt and stir for 12 h. An additional portion of PhSO$_2$Cl (31 uL, 0.24 mmol) and DIPEA (42 uL, 0.24 mmol) was added to the mixture which was stirred for an additional 12 h at rt. The mixture was quenced by adding sat. aq. NaHCO$_3$ (1 mL) and then extracted the aqueous layer with CH$_2$Cl$_2$ (3×15 mL). The organic layers were combined and were dried (Na$_2$SO$_4$), filtered, and concentrated under reduced pressure to afford a yellow oil. The crude product was dissolved in CH$_2$Cl$_2$ (2 mL) and was loaded onto 4×1000 uM preparative TLC plates. The plates were eluted with a 3:2 mixture of hexanes/EtOAc to afford the product (28 mg, 69%) as a white solid. MS: m/z=849.7 (M+H$^+$).

Step 15. (S)-2-amino-N-(3-fluoro-2-(2-((S)-4-(phenylsulfonyl)-4,7-diazaspiro[2.5]octan-5-yl)ethyl)phenyl)-3,3-bis(4-fluorophenyl)propanamide To a solution of (S)-tert-butyl 5-(2-((S)-2-((tert-butoxycarbonyl)amino)-3,3-bis(4-fluorophenyl)propanamido)-6-fluorophenethyl)-4-(phenylsulfonyl)-4,7-diazaspiro[2.5]octane-7-carboxylate (27.5 mg, 0.032 mmol) in CH$_2$Cl$_2$ (2 mL) under N$_2$ at rt was added TFA (24 µL, 0.32 mmol) dropwise. The mixture was stirred for 1.5 h at rt whereupon the mixture concentrated to dryness. The resulting solid was azeotroped with CH$_2$Cl$_2$ (4×5 mL) and placed under high vacuum to afford an off-white solid. The crude product was purified by reverse phase HPLC (Gilson, C18 column: gradient 10-90% acetonitrile in water with 0.05% TFA as buffer, 12 min method, detection=254 nM) to afford the product (17 mg, 58%) as a white solid after lyophilization in the bis TFA salt form. MS: m/z=649.5 (M+H$^+$).

The following Examples were prepared in an analogous fashion to Example KK1 except using different reagents in Step 12 to afford the following compounds:

| Ex. | Structure | Name | MS (M + H)+ |
|---|---|---|---|
| 367 | 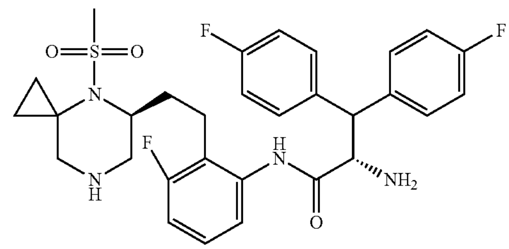 [SMILES: CS(=O)(=O)N1[C@@H](CCc2c(F)cccc2NC(=O)[C@@H](N)C(c2ccc(F)cc2)c2ccc(F)cc2)CNCC12CC2] | (S)-2-amino-N-(3-fluoro-2-(2-((S)-4-(methylsulfonyl)-4,7-diazaspiro[2.5]octan-5-yl)ethyl)phenyl)-3,3-bis(4fluorophenyl)propanamide | 587.5 |
| 368 | 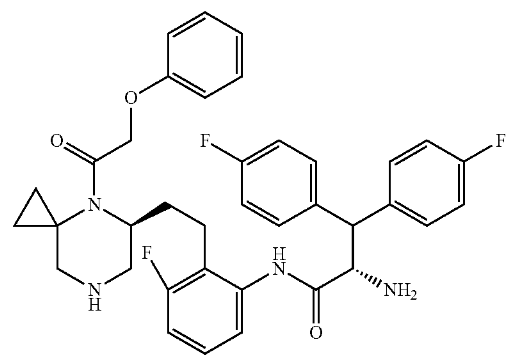 [SMILES: N[C@H](C(=O)Nc1cccc(F)c1CC[C@H]1CNCC2(CC2)N1C(=O)COc1ccccc1)C(c1ccc(F)cc1)c1ccc(F)cc1] | (S)-2-amino-N-(3-fluoro-2-(2-((S)-4-(2-phenoxyacetyl)-4,7-diazaspiro[2.5]octan-5-yl)ethyl)phenyl)-3,3-bis(4-fluorophenyl)propanamide | 643.6 |

EXAMPLE 369

((1R,2S)-1-(4-chlorophenyl)-3-((3-fluoro-2-(2-((S)-4-(phenylsulfonyl)-4,7-diazaspiro[2.5]octan-5-yl)ethyl)phenyl)amino)-3-oxo-1-(tetrahydro-2H-pyran-4-yl)propan-2-yl)carbamate

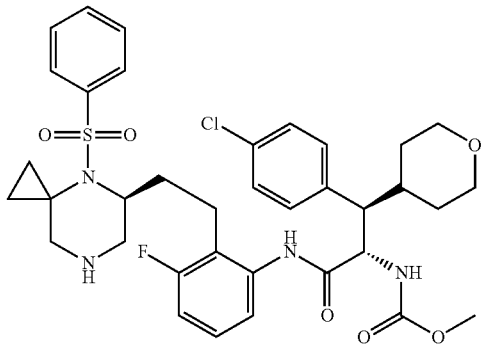 [SMILES: COC(=O)N[C@H](C(=O)Nc1cccc(F)c1CC[C@H]1CNCC2(CC2)N1S(=O)(=O)c1ccccc1)[C@@H](c1ccc(Cl)cc1)C1CCOCC1]

Step 1. (S,E)-tert-butyl 5-(2-fluoro-6-nitrostyryl)-4,7-diazaspiro[2.5]octane-7-carboxylate

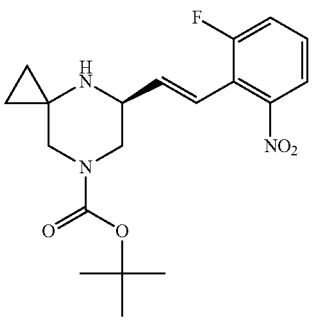 [SMILES: CC(C)(C)OC(=O)N1C[C@H](/C=C/c2c(F)cccc2[N+](=O)[O-])NC2(CC2)C1]

To a solution of (S,E)-4-((9H-fluoren-9-yl)methyl) 7-tert-butyl 5-(2-fluoro-6-nitrostyryl)-4,7-diazaspiro[2.5]octane-4,7-dicarboxylate (0.17 g, 0.28 mmol) in $CH_2Cl_2$ (3 mL) under $N_2$ at rt was added piperidine (0.42 mL, 0.84 mmol) dropwise. The mixture was stirred at rt for 1.5 h whereupon the mixture was concentrated to dryness. The resultant solid was azeotroped with a 1:1 ratio of $CH_2Cl_2$/hexanes (3×3 mL) to afford a brown solid. The crude residue was taken up in $CH_2Cl_2$ (2 mL) and was loaded onto 4×1000 uM preparative TLC plates. The plates were eluted with a 2:1 mixture of EtOAc/hexanes to afford the product (61 mg, 57%) as a pale yellow solid. MS: m/z=378.2 (M+H+).

Step 2. (S,E)-tert-butyl 5-(2-fluoro-6-nitrostyryl)-4-(phenylsulfonyl)-4,7-diazaspiro[2.5]octane-7-carboxylate

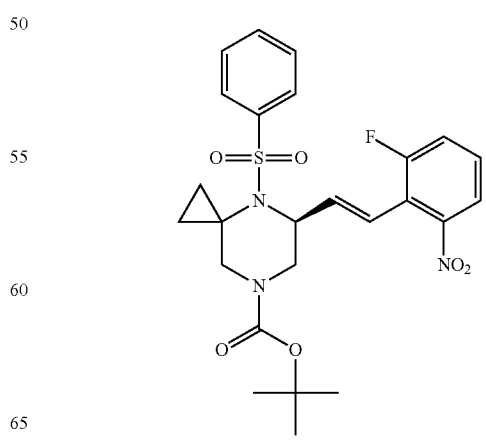

To a solution of (S,E)-tert-butyl 5-(2-fluoro-6-nitrostyryl)-4,7-diazaspiro[2.5]octane-7-carboxylate (61 mg, 0.16 mmol) in CH₂Cl₂ (3 mL) under N₂ at 0° C. was added Et₃N (0.12 mL, 0.81 mmol) followed by addition of PhSO₂Cl (62 µL, 0.48 mmol). The mixture was allowed to warm to rt and was heated to 45° C. An additional portion of PhSO₂Cl (62 µL, 0.48 mmol) and Et₃N (0.12 mL, 0.81 mmol) was added the mixture was heated at 55° C. for 2 h whereupon the reaction was complete. The mixture was cooled to room temperature and quenched by adding sat. NaHCO₃ (1.5 mL) and diluting with CH₂Cl₂ (15 mL). The aqueous was extracted with CH₂Cl₂ (3×10 mL) and the organic layers were combined. The organic layer was washed with sat. aq. NaHCO₃ (3×1 mL) and brine (3×1 mL). The organic layer was dried (Na₂SO₄), filtered, and concentrated under reduced pressure to afford an oil. The crude residue was dissolved in CH₂Cl₂ (2 mL) and was loaded onto 4×1000 uM preparative TLC plates. The plates were eluted with a 2:1 mixture of hexanes/EtOAc to afford the product (74 mg, 87%) as a clear oil. MS: m/z=518.2 (M+H⁺).

Step 3. (S)-tert-butyl 5-(2-amino-6-fluorophenethyl)-4-(phenylsulfonyl)-4,7-diazaspiro[2.5]octane-7-carboxylate

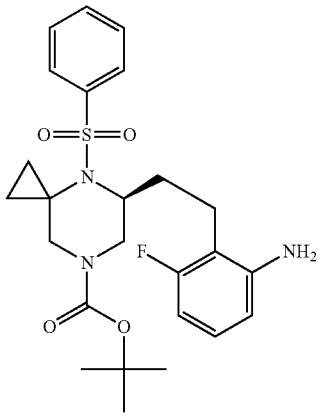 [SMILES: CC(C)(C)OC(=O)N1C[C@H](CCc2c(N)cccc2F)N(S(=O)(=O)c2ccccc2)C2(CC2)C1]

To a solution of (S,E)-tert-butyl 5-(2-fluoro-6-nitrostyryl)-4-(phenylsulfonyl)-4,7-diazaspiro[2.5]octane-7-carboxylate (74 mg, 0.14 mmol) in EtOH (3 mL) under N₂ at rt was added 20% Pd(OH)₂ (20 mg) to afford a heterogenous mixture. The mixture was evacuated under vacuum, filled with H₂, and the mixture was stirred under a H₂ balloon for 1 h. The mixture was purged to N₂ and the reaction mixture was filtered thru a pad of Celite. The pad of Celite was washed with EtOH (50 mL) and the resultant filtrate was concentrated under reduced pressure. The crude product was dissolved in CH₂Cl₂ (2 mL) and was loaded onto 4×1000 uM preparative TLC plates. The plates were eluted with a mixture of 1:1 hexanes/EtOAc to afford the product (50 mg, 71%) as a clear oil. MS: m/z=490.4 (M+H⁺).

Step 4. (S)-tert-butyl 5-(2-((2S,3R)-2-azido-3-(4-chlorophenyl)-3-(tetrahydro-2H-pyran-4-yl)propanamido)-6-fluorophenethyl)-4-(phenylsulfonyl)-4,7-diazaspiro[2.5]octane-7-carboxylate

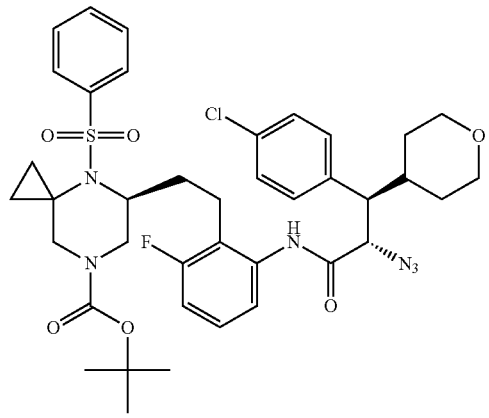 [SMILES: CC(C)(C)OC(=O)N1C[C@H](CCc2c(F)cccc2NC(=O)[C@@H](N=[N+]=[N-])[C@@H](c2ccc(Cl)cc2)C2CCOCC2)N(S(=O)(=O)c2ccccc2)C2(CC2)C1]

To a round bottom flask charged with a stir bar at rt was added (S)-tert-butyl 5-(2-amino-6-fluorophenethyl)-4-(phenylsulfonyl)-4,7-diazaspiro[2.5]octane-7-carboxylate (50 mg, 0.11 mmol) and (2S,3R)-2-azido-3-(4-chlorophenyl)-3-(tetrahydro-2H-pyran-4-yl)propanoic acid (38 mg, 0.12 mmol) was added anhydrous pyridine (1 mL). The mixture was cooled to −15° C. using whereupon POCl₃ (11 uL, 0.12 mmol) was added dropwise stir for 1 h. The mixture was warmed to 0° C., stirred for 2 h, and was treated with sat. aq. KH₂PO₄ (~1 mL). The reaction mixture was diluted with EtOAc (10 mL) and the layers were separated. The aqueous layer was extracted with EtOAc (3×5 mL) and the organic layers were combined. The organic layer was washed with brine (1×3 mL), dried (Na₂SO₄), filtered, and concentrated under reduced pressure. The crude material was dissolved in CH₂Cl₂ (2 mL) and was loaded onto 4×1000 uM preparative TLC plates. The plates were eluted with a 1:2 mixture of hexanes/EtOAc to afford the product (56 mg, 70%) as a pale yellow solid. MS: m/z=781.7 (M+H⁺).

Step 5. (S)-tert-butyl 5-(2-((2S,3R)-2-amino-3-(4-chlorophenyl)-3-(tetrahydro-2H-pyran-4-yl)propanamido)-6-fluorophenethyl)-4-(phenylsulfonyl)-4,7-diazaspiro[2.5]octane-7-carboxylate

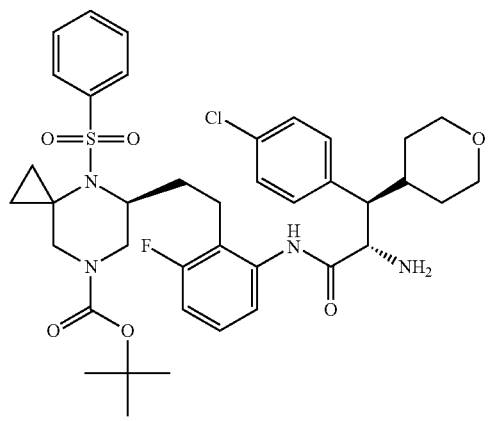 [SMILES: CC(C)(C)OC(=O)N1C[C@H](CCc2c(F)cccc2NC(=O)[C@@H](N)[C@@H](c2ccc(Cl)cc2)C2CCOCC2)N(S(=O)(=O)c2ccccc2)C2(CC2)C1]

To a solution of (S)-tert-butyl 5-(2-((2S,3R)-2-azido-3-(4-chlorophenyl)-3-(tetrahydro-2H-pyran-4-yl)propanamido)-6-fluorophenethyl)-4-(phenylsulfonyl)-4,7-diazaspiro[2.5]octane-7-carboxylate (54 mg, 0.069 mmol) in THF/water (2 mL/0.5 mL) under N$_2$ at rt was added PS—PPh$_3$ (54 mg, 0.11 mmol). The heterogenous mixture was affixed with a reflux condenser, heated to 70° C., and stirred for 12 h. The mixture was cooled to rt and the resin was filtered off on a disposable filter. The resin was washed with EtOAc (3×10 mL) and the resulting filtrate was concentrated under reduced pressure to afford product (51 mg, 96%) as a white solid. MS: m/z=755.6 (M+H$^+$). This material was taken on crude without purification to the next transformation.

Step 6. (S)-tert-butyl 5-(2-((2S,3R)-3-(4-chlorophenyl)-2-((methoxycarbonyl)amino)-3-(tetrahydro-2H-pyran-4-yl)propanamido)-6-fluorophenethyl)-4-(phenylsulfonyl)-4,7-diazaspiro[2.5]octane-7-carboxylate

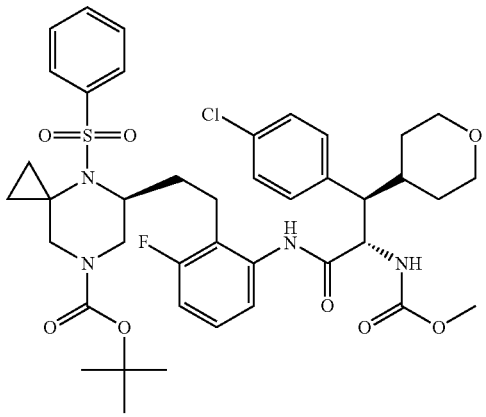 [SMILES: COC(=O)N[C@H](C(=O)Nc1cccc(F)c1CC[C@H]1CN(C(=O)OC(C)(C)C)CC2(CC2)N1S(=O)(=O)c1ccccc1)[C@@H](c1ccc(Cl)cc1)C1CCOCC1]

To a solution of (S)-tert-butyl 5-(2-((2S,3R)-2-amino-3-(4-chlorophenyl)-3-(tetrahydro-2H-pyran-4-yl)propanamido)-6-fluorophenethyl)-4-(phenylsulfonyl)-4,7-diazaspiro[2.5]octane-7-carboxylate (51 mg, 0.067 mmol) in CH$_2$Cl$_2$ (1 mL) under N$_2$ at rt was added 2,5-dioxopyrrolidin-1-yl methyl carbonate (14 mg, 0.081 mmol) to afford a light yellow, homogenous solution. The resulting mixture was stirred at rt for 12 h whereupon the reaction was complete. The reaction mixture was directly loaded onto 3×1000 uM preparative TLC plates chromatography plates. The plates were eluted with a 20:1 mixture of CH$_2$Cl$_2$/MeOH to afford the product (21 mg, 37%) as a white solid. MS: m/z=835.6 (M+H$^+$).

Step 7. ((1R,2S)-1-(4-chlorophenyl)-3-((3-fluoro-2-(2-((S)-4-(phenylsulfonyl)-4,7-diazaspiro[2.5]octan-5-yl)ethyl)phenyl)amino)-3-oxo-1-(tetrahydro-2H-pyran-4-yl)propan-2-yl)carbamate

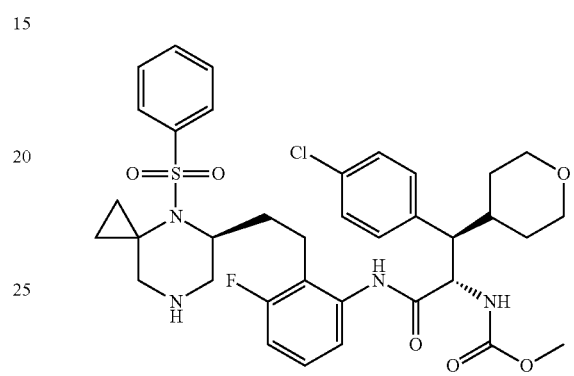

To a solution of (S)-tert-butyl 5-(2-((2S,3R)-3-(4-chlorophenyl)-2-((methoxycarbonyl)amino)-3-(tetrahydro-2H-pyran-4-yl)propanamido)-6-fluorophenethyl)-4-(phenylsulfonyl)-4,7-diazaspiro[2.5]octane-7-carboxylate (20.5 mg, 0.025 mmol) in CH$_2$Cl$_2$ (1 mL) at rt was added TFA (0.19 mL, 0.25 mmol) in one portion to afford a light yellow, homogenous mixture. The mixture was stirred at rt for 1 h whereupon the mixture was concentrated under reduced pressure. The resultant residue was azeotroped with CH$_2$Cl$_2$ (3×3 ml) multiple times and was concentrated to dryness to afford a off-white solid. The crude product was purified by reverse phase HPLC (Gilson, C18 column: gradient 10-100% acetonitrile in water with 0.05% TFA as buffer, 12 min method, detection=220 nM). The product (16 mg, 74%) was isolated after lyophilization as a white solid as the TFA salt. MS: m/z=713.6 (M+H$^+$).

Examples shown in Table 7 were made in similar fashion as described in Examples 3 and 10.

TABLE 7

| Ex. | Structure | Name | MS (M + H)+ |
|---|---|---|---|
| 370 | 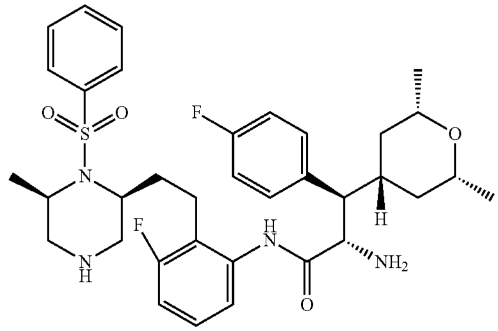 | (2S,3R)-2-amino-3-((2R,4r,6S)-2,6-dimethyltetrahydro-2H-pyran-4-yl)-N-(3-fluoro-2-(2-((2S,6R)-6-methyl-1-(phenylsulfonyl)piperazin-2-yl)ethyl)phenyl)-3-(4-fluorophenyl)propanamide | 655.3 |

TABLE 7-continued

| Ex. | Structure | Name | MS (M + H)+ |
|---|---|---|---|
| 371 | 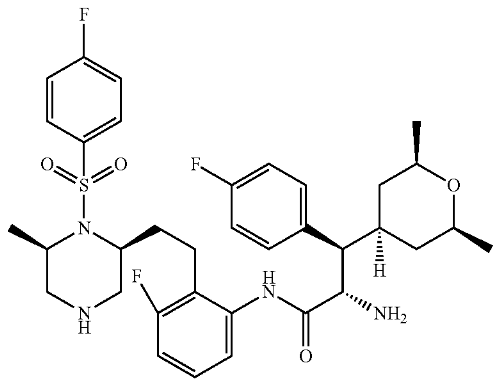 | (2S,3R)-2-amino-3-((2R,4r,6S)-2,6-dimethyltetrahydro-2H-pyran-4-yl)-N-(3-fluoro-2-(2-((2S,6S)-1-((4-fluorophenyl)sulfonyl)-6-methylpiperazin-2-yl)ethyl)phenyl)-3-(4-fluorophenyl)propanamide | 673.3 |
| 372 | 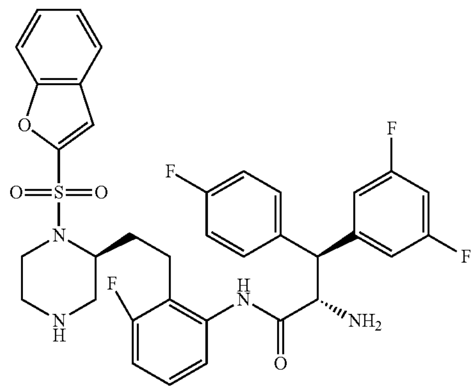 [SMILES: N[C@H](C(=O)Nc1cccc(F)c1CC[C@H]1CNCCN1S(=O)(=O)c1cc2ccccc2o1)[C@@H](c1ccc(F)cc1)c1cc(F)cc(F)c1] | (2S,3S)-2-amino-N-(2-(2-((S)-1-(benzofuran-2-ylsulfonyl)piperazin-2-yl)ethyl)-3-fluorophenyl)-3-(3,5-difluorophenyl)-3-(4-fluorophenyl)propanamide | 681.2 |
| 373 | 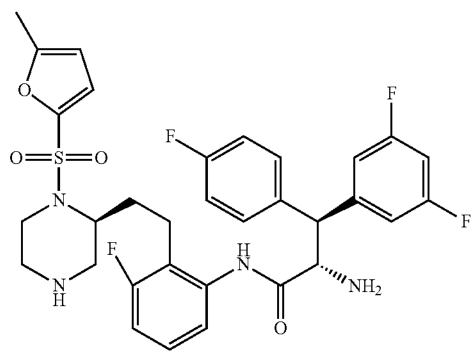 [SMILES: Cc1ccc(S(=O)(=O)N2CCNC[C@@H]2CCc2c(F)cccc2NC(=O)[C@@H](N)[C@@H](c2ccc(F)cc2)c2cc(F)cc(F)c2)o1] | (2S,3S)-2-amino-3-(3,5-difluorophenyl)-N-(3-fluoro-2-(2-((S)-1-((5-methylfuran-2-yl)sulfonyl)piperazin-2-yl)ethyl)phenyl)-3-(4-fluorophenyl)propanamide | 645.2 |

Assay for Inhibition of Microbial Expressed HIV Protease ("Pepcleav")

Studies of the inhibition of the wildtype HIV-1 protease (which was expressed in *Escherichia coli*) were carried out with a peptide substrate [Val-Ser-Gln-Asn-(βnaphtyl)Ala-Pro-Ile-Val]. The inhibitor is first preincubated with the HIV-1 protease (wild type) enzyme in assay buffer (50 mM sodium acetate, pH 5.5, 100 mM NaCl, and 0.1% BSA) for 30 minutes at room temperature. Substrate is added to 400 micromolar in a total volume of 20 microliters containing 20 picomolar HIV-1 protease (final) and the reaction is incubated for 1 hour at 30° C. The reaction is quenched with the addition of formic acid and indinavir to 0.012% and 150 nM final concentrations, respectively. The product formation is determined after separation of product and substrate on a Zorbax Eclipse XDB-C18 column connected to an API 4000 mass spectrometer (Applied Biosystems) with multiple reaction monitoring (transitions were 644.5/428.9 and 615.4/422.2 (M1/M3) for product and indinavir respectively). The extent of inhibition of the reaction is determined from the peak area of the products. Analysis of the products, independently synthesized, provided quantitation standards and confirmation of the product composition. Representative compounds in the Examples of the present invention exhibit inhibition of HIV-1 protease in this assay as shown in Table 8.

Cell-Based HIV Infection Assay Using a Reporter ("Cell-Based"):

MT4-GFP cells contain a stably integrated HIV long terminal repeat promoter directing the transcription of green fluorescent protein (GFP). When HIV infects the cell, GFP is produced and the cell becomes green. MT4-GFP cells (250,000 cells/ml) were bulk-infected with HIV-1 (H9IIIB strain) at low multiplicity of infection (MOI) in RPMI media, supplemented with 10% FBS for 24 hours. Cells were then washed once in RPMI plus 10% FBS and resuspended in RPMI plus 50% normal human serum (NHS). Test compounds were serial-diluted in DMSO using an ECHO liquid dispenser. A control well included a combination of three HIV drugs (an inhibitor of HIV protease, integrase strand transfer and a non-nucleoside reverse transcriptase inhibitor; triple drug). The infected MT4-GFP cells were added to a 384-well poly-D-lysine coated black plate with clear bottom in which the diluted test compounds were placed. The cells were seeded in the plate at 8,000 cells per well and the final DMSO concentration was 0.4%. Infected cells were quantified at both 24 and 48 hours post incubation using an Acumen eX3 plate reader. Viral reproductive ratio ($R_0$) was determined using the number of infected cells at 48 hours divided by the number of infected cells at 24 hours. Percent viral growth inhibition was calculated by $[1-(R-R_{tripledrug})/(R_{DMSO}-R_{tripledrug})]*100$. Compound potency IP or IC50 was determined with use of a 4-parameter dose response curve analysis.

Table 8 shows data obtained from the above described assays for the indicated examples. Data shown in the table reflects the mean of at least two independent experiments.

TABLE 8

| EXAMPLE number | Pepcleav IC$_{50}$ (nM) | Cell-based IP (nM) |
| --- | --- | --- |
| 1 | 9.7 | 67 |
| 2 | 1400 | |
| 3 | 0.48 | 4.0 |
| 4 | | 4.3 |
| 5 | | 5.9 |
| 6 | | 7.8 |
| 7 | | 6.0 |
| 8 | | 9.8 |
| 9 | | 7.1 |
| 10 | | 11 |
| 11 | | 11 |
| 12 | | 18 |
| 13 | | 20 |
| 14 | | 18 |
| 15 | | 18 |
| 16 | | 5.4 |
| 17 | | 4.4 |
| 18 | | 8.6 |
| 19 | | 16 |
| 20 | | 21 |
| 21 | 3.4 | |
| 22 | 0.2 | 10 |
| 23 | 10 | |
| 24 | 0.2 | |
| 25 | 1.3 | |
| 26 | 3.5 | |
| 28 | | 21 |
| 29 | | 520 |
| 30 | | 9.3 |
| 31 | | 850 |
| 32 | | 6.6 |
| 33 | | 25 |
| 34 | | 16 |
| 35 | | 13 |
| 36 | | 29 |
| 37 | | 46 |
| 38 | | 890 |
| 39 | | 12 |
| 40 | 0.03 | 4.8 |
| 41 | | 34 |
| 42 | | 60 |
| 43 | | 12 |
| 44 | | 15 |
| 45 | | 16 |
| 46 | | 12 |
| 47 | | 1200 |
| 48 | | 66 |
| 49 | | 1700 |
| 50 | | 21 |
| 51 | | 11 |
| 52 | | 9.2 |
| 53 | | 6.5 |
| 54 | | 9.8 |
| 55 | | 9.0 |
| 56 | | 13 |
| 57 | | 7.7 |
| 58 | | 42 |
| 59 | | 29 |
| 60 | | 27 |
| 61 | | 1200 |
| 62 | | 520 |
| 63 | 1300 | |
| 64 | 70 | 95 |
| 65 | | 120 |
| 66 | | 12 |
| 67 | | 5.8 |
| 68 | | 1800 |
| 69 | | 360 |
| 70 | | 27 |
| 71 | | 11 |
| 72 | | 21 |
| 73 | | 7.6 |
| 74 | | 24 |
| 75 | | 150 |
| 76 | | 9.4 |
| 77 | | 18 |
| 78 | | 110 |
| 79 | | 30 |
| 80 | | 66 |
| 81 | | 25 |
| 82 | | 34 |
| 83 | | 8.9 |
| 84 | | 8.4 |
| 85 | | 21 |
| 86 | | 13 |
| 87 | | 16 |
| 88 | | 520 |
| 89 | | 700 |
| 90 | | 66 |
| 91 | | 1700 |
| 92 | | 17 |
| 93 | | 120 |
| 94 | | 24 |
| 95 | | 20 |
| 96 | 6.1 | 24 |
| 97 | | 25 |
| 98 | | 350 |
| 99 | | 16 |
| 100 | | 30 |
| 101 | | 24 |
| 102 | | 19 |
| 103 | | 8.6 |
| 104 | | 37 |
| 105 | | 19 |
| 106 | | 30 |
| 107 | | 150 |
| 108 | | 32 |
| 109 | | 65 |
| 110 | | 74 |
| 111 | | 34 |
| 112 | | 19 |
| 113 | | 25 |
| 114 | | 100 |
| 115 | | 45 |
| 116 | | 24 |
| 117 | | 9.3 |
| 118 | | 12 |
| 119 | | 9.1 |
| 120 | | 19 |
| 121 | | 72 |
| 122 | | 360 |
| 123 | | 62 |
| 124 | | 63 |

TABLE 8-continued

| EXAMPLE number | Pepcleav IC$_{50}$ (nM) | Cell-based IP (nM) |
|---|---|---|
| 125 | | 18 |
| 126 | | 16 |
| 127 | | 300 |
| 128 | | 610 |
| 129 | | 210 |
| 130 | | 55 |
| 131 | | 17 |
| 132 | | 11 |
| 133 | | 55 |
| 134 | | 63 |
| 135 | | 23 |
| 136 | | 10 |
| 137 | | 240 |
| 138 | | 150 |
| 139 | | 36 |
| 140 | | 250 |
| 141 | | 77 |
| 142 | | 84 |
| 143 | | 570 |
| 144 | | 93 |
| 145 | | 170 |
| 146 | | 72 |
| 148 | | 8.8 |
| 150 | | 26 |
| 151 | | 17 |
| 152 | | 39 |
| 153 | | 28 |
| 154 | | 65 |
| 155 | | 67 |
| 156 | | 14 |
| 157 | | 7.3 |
| 158 | | 75 |
| 159 | | 42 |
| 160 | | 190 |
| 162 | | 22 |
| 163 | | 20 |
| 164 | | 37 |
| 165 | | 17 |
| 166 | | 29 |
| 167 | | 31 |
| 168 | | 19 |
| 169 | | 170 |
| 170 | | 60 |
| 171 | | 26 |
| 172 | | 180 |
| 173 | | 90 |
| 174 | | 99 |
| 175 | | 110 |
| 176 | | 190 |
| 177 | | 95 |
| 178 | | 340 |
| 179 | | 33 |
| 180 | | 69 |
| 181 | | 170 |
| 182 | | 130 |
| 183 | | 67 |
| 184 | | 25 |
| 185 | | 28 |
| 186 | | 86 |
| 187 | | 35 |
| 188 | | 55 |
| 189 | | 29 |
| 190 | | 13 |
| 191 | | 20 |
| 192 | | 36 |
| 193 | | 56 |
| 194 | | 34 |
| 195 | | 77 |
| 196 | | 49 |
| 197 | | 18 |
| 198 | | 21 |
| 199 | | 20 |
| 200 | | 16 |
| 201 | | 16 |
| 202 | | 620 |
| 203 | | 620 |
| 204 | | 80 |
| 205 | | 22 |
| 206 | | 480 |
| 207 | | 760 |
| 208 | | 42 |
| 209 | | 77 |
| 210 | | 13 |
| 211 | | 16 |
| 212 | | 13 |
| 213 | | 29 |
| 214 | | 44 |
| 215 | | 2500 |
| 216 | | 1300 |
| 217 | | 1800 |
| 218 | | 310 |
| 219 | | 25 |
| 220 | | 780 |
| 221 | | 230 |
| 222 | | 76 |
| 223 | | 36 |
| 224 | | 90 |
| 225 | | 23 |
| 226 | | 1100 |
| 227 | | 23 |
| 228 | | 15 |
| 229 | | 350 |
| 230 | | 290 |
| 231 | | 230 |
| 232 | | 190 |
| 233 | | 330 |
| 234 | | 49 |
| 235 | | 23 |
| 236 | | 8.2 |
| 237 | | 30 |
| 238 | | 110 |
| 239 | | 130 |
| 240 | | 71 |
| 241 | | 39 |
| 242 | | 220 |
| 243 | | 17 |
| 244 | | 5.9 |
| 245 | | 51 |
| 246 | | 5.9 |
| 247 | | 77 |
| 248 | | 45 |
| 249 | | 53 |
| 250 | | 34 |
| 251 | | 4.1 |
| 252 | | 7.9 |
| 253 | | 24 |
| 254 | | 16 |
| 255 | | 59 |
| 256 | | 73 |
| 257 | | 27 |
| 258 | | 31 |
| 259 | | 18 |
| 260 | | 140 |
| 261 | | 70 |
| 262 | | 25 |
| 263 | | 77 |
| 264 | | 69 |
| 265 | | 260 |
| 266 | | 26 |
| 267 | | 24 |
| 268 | | 14 |
| 269 | | 9.9 |
| 270 | | 24 |
| 271 | | 1200 |
| 272 | | 49 |
| 273 | | 11 |
| 274 | | 22 |
| 275 | | 19 |
| 276 | | 9.1 |
| 277 | | 15 |
| 278 | | 140 |
| 279 | | 16 |
| 280 | | 16 |
| 281 | | 13 |
| 282 | | 11 |
| 283 | | 14 |

TABLE 8-continued

| EXAMPLE number | Pepcleav IC$_{50}$ (nM) | Cell-based IP (nM) |
|---|---|---|
| 284 |  | 40 |
| 285 |  | 29 |
| 286 |  | 33 |
| 287 |  | 91 |
| 288 |  | 23 |
| 289 |  | 23 |
| 290 |  | 15 |
| 291 |  | 100 |
| 292 |  | 130 |
| 293 |  | 8.7 |
| 294 |  | 40 |
| 295 |  | 4.2 |
| 296 |  | 9.9 |
| 297 |  | 16 |
| 298 |  | 36 |
| 299 |  | 16 |
| 300 |  | 98 |
| 301 |  | 480 |
| 302 |  | 24 |
| 303 | 5.0 | 14 |
| 304 |  | 3.6 |
| 305 |  | 8.2 |
| 306 |  | 6.5 |
| 307 |  | 130 |
| 308 |  | 180 |
| 309 |  | 140 |
| 310 |  | 1700 |
| 311 |  | 20 |
| 312 |  | 140 |
| 313 |  | 48 |
| 314 |  | 9.2 |
| 315 |  | 1900 |
| 316 |  | 19 |
| 317 |  | 24 |
| 318 |  | 97 |
| 319 |  | 59 |
| 320 |  | 36 |
| 321 |  | 29 |
| 322 |  | 530 |
| 323 |  | 4.8 |
| 324 |  | 40 |
| 325 |  | 13 |
| 326 |  | 8.0 |
| 327 |  | 9.4 |
| 328 |  | 16 |
| 329 |  | 47 |
| 330 |  | 43 |
| 331 |  | 19 |
| 332 |  | 410 |
| 333 |  | 64 |
| 334 | 10 | 450 |
| 335 | 24 | 650 |
| 336 | 13 | 240 |
| 337 |  | 130 |
| 338 | 130 | 660 |
| 339 |  | 40 |
| 340 |  | 210 |
| 341 |  | 450 |
| 342 | 250 |  |
| 343 |  | 125 |
| 344 |  | 1800 |
| 345 |  | 1600 |
| 346 |  | 860 |
| 347 |  | 57 |
| 348 |  | 190 |
| 349 |  | 1500 |
| 350 |  | 12 |
| 351 |  | 360 |
| 352 |  | 190 |
| 353 |  | 540 |
| 354 |  | 22 |
| 355 |  | 14 |
| 356 |  | 28 |
| 357 |  | 820 |
| 358 |  | 160 |
| 359 |  | 530 |
| 360 |  | 610 |
| 361 |  | 880 |
| 362 |  | 76 |
| 363 |  | 370 |
| 364 |  | 34 |
| 365 |  | 68 |
| 366 |  | 13 |
| 367 |  | 47 |
| 368 |  | 1500 |
| 369 |  | 11 |
| 370 |  | 7.5 |
| 371 |  | 9.6 |
| 372 |  | 14 |
| 373 |  | 4.2 |

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A compound of Formula I

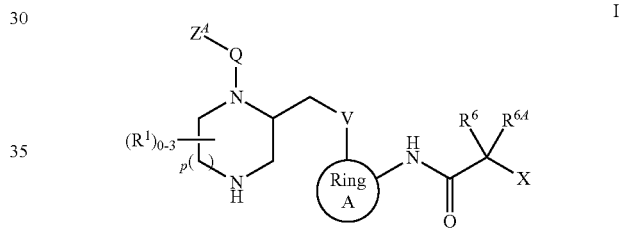

or a pharmaceutically acceptable salt thereof, wherein:

Q is —S(O)$_2$;

p is 1;

$R^1$ is not present or is one substituent selected from (i) —CH$_3$ unsubstituted or substituted with cyclopropyl, —OC$_{1-3}$alkyl or —O—CH$_2$phenyl, (ii) ethyl or (iii) spiro-cyclopropyl;

V is CH$_2$;

X is H, —OH, —NH$_2$ or —N(H)—C(O)—OC$_{1-4alkyl}$;

Ring A is

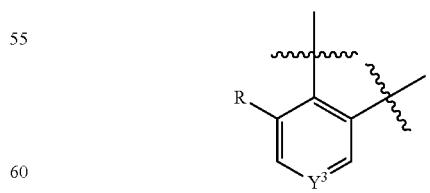

or C$_{3-6}$cycloalkyl;

$Y^3$ is CH or N;

R is H or F;

$R^{6a}$ is —H;

$R^6$ is

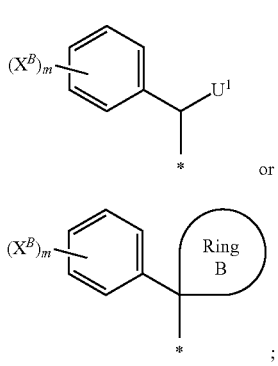

$X^B$ is independently selected at each occurrence from F, Cl, —OCH$_3$, —CF$_3$ or —OCF$_3$;
m is 0, 1 or 2;
Ring B is selected from tetrahydropyranyl or piperidinyl, each optionally substituted with 1 or 2 of methyl;
$U^1$ is selected from:

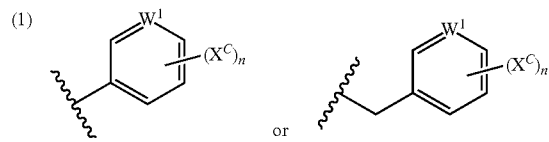

wherein
$W^1$ is CH or N,
$X^C$ is independently selected from F, Cl, —OCH$_3$, —CF$_3$ or —OCF$_3$, and
n is 0, 1 or 2,
(2) 1-methylethyl,
(3) tetrahydro-2H-pyran-4-yl unsubstituted or substituted with 1 or 2 of CH$_3$, or
(4) —CH$_2$-tetrahydro-2H-pyran-4-yl, wherein the tetrahydro-2H-pyran-4-yl is unsubstituted or substituted with 1 or 2 of CH$_3$; and
$Z^A$ is
methyl unsubstituted or substituted with cyclopropyl or —CF$_3$,
cyclopropyl,
phenyl or benzyl unsubstituted or substituted with F, Cl, NH$_2$, formyl, or —OCH$_3$ optionally substituted with 1-3 of F,
pyrrolidinyl unsubstituted or substituted with 1 to 3 of F,
piperidinyl unsubstituted or substituted with 1 or 2 of F, —NHC(O)CH$_3$, —NHC(O)CF$_3$, —NHSO$_2$CH$_3$, -SO$_2$CH$_3$, or C$_{1-4}$alkyl,
pyridinyl unsubstituted or substituted with NH$_2$,
pyrazolyl unsubstituted or substituted with methyl,
thiazolyl unsubstituted or substituted with —CH$_3$ or —NHC(O)CH$_3$,
oxadiazolyl unsubstituted or substituted with —COOC$_{1-3}$alkyl, or
furanyl unsubstituted or substituted with —CH$_3$.

2. The compound according to claim 1 or a pharmaceutically acceptable salt thereof wherein Ring A is

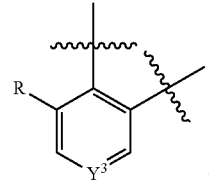

3. The compound according to claim 1 or a pharmaceutically acceptable salt thereof wherein Ring A is C$_{3-6}$cycloalkyl.

4. The compound according to claim 2 or a pharmaceutically acceptable salt thereof wherein $R^6$ is

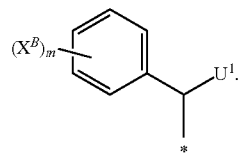

5. The compound according to claim 2 or a pharmaceutically acceptable salt thereof wherein $R^6$ is

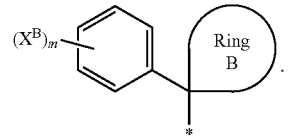

6. The compound according to claim 1 of Formula Ic

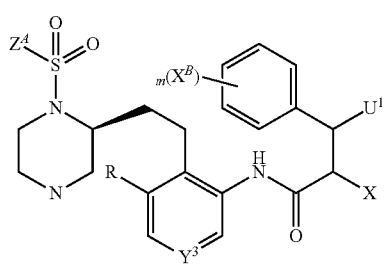

or a pharmaceutically acceptable salt thereof.

7. The compound according to claim 6 or a pharmaceutically acceptable salt thereof wherein:
$Z^A$ is
methyl unsubstituted or substituted with cyclopropyl or —CF$_3$,
cyclopropyl,
phenyl or benzyl unsubstituted or substituted with F, Cl, NH$_2$, formyl, or —OCH$_3$ optionally substituted with 1-3 of F,
pyrrolidinyl unsubstituted or substituted with 1 or 3 of F, or
pyridinyl unsubstituted or substituted with NH$_2$.

8. The compound according to claim 6 or a pharmaceutically acceptable salt thereof, wherein $U^1$ is

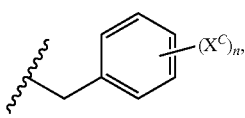

one X$^B$ group is present and substituted at the 4-position, one or two X$^C$ groups are present and substituted at the 3- or 3,5-positions respectively, and the X$^B$ group is a different group with respect to either X$^C$ group.

9. The compound according to claim 1 or a pharmaceutically acceptable salt thereof, wherein Z$^A$ is methyl unsubstituted or substituted with cyclopropyl or —CF$_3$.

10. The compound according to claim 1 or a pharmaceutically acceptable salt thereof, wherein Z$^A$ is cyclopropyl.

11. A compound selected from the group consisting of:
2S-Amino-3,3-di-(4-fluorophenyl)-N-(5-fluoro-4-(2-(1-methylsulfonylpiperazin-2-yl)ethyl)pyridin-3-yl)propanamide;
Methyl ((S)-1-((3-fluoro-2-(2-((S)-1-(phenylsulfonyl)piperazin-2-yl)ethyl)phenyl)amino)-3,3-bis(3-fluorophenyl)-1-oxopropan-2-yl)carbamate;
(S)-2-Amino-N-(5-fluoro-4-(2-((S)-1-(phenylsulfonyl)piperazin-2-yl)ethyl)pyridine-3-yl)-3,3-bis(3-fluorophenyl)propanamide;
Methyl ((1S,2S)-1-(4-chlorophenyl)-3-((3-fluoro-2-(2((S)-1-(phenylsulfonyl)piperizin-2-yl)ethyl)phenyl)amino)-1-(6-methoxypyridin-3-yl)-3-oxopropan-2-yl)carbamate;
(2S,3S)-2-amino-3-(4-chlorophenyl)-N-(3-fluoro-2-(2-((S)-1-(phenylsulfonyl)piperazin-2-yl)ethyl)phenyl)-3-(5-(trifluoromethyl)pyridine-3-yl)propanamide;
Methyl ((2S,3R)-1-((3-fluoro-2-(2-((2S,6S)-6-methyl-1-(phenylsulfonyl)piperazin-2-yl)ethyl)phenyl)amino)-3-(4-fluorophenyl)-1-oxo-3-(tetrahydro-2H-pyran-4-yl)propan-2-yl)carbamate;
Methyl ((2S,3R)-3-(4-chlorophenyl)-1-((5-fluoro-4-(2-((2S,6S)-6-methyl-1-(phenylsulfonyl)piperzin-2-yl)ethyl)pyridin-3-yl)amino)-4-methyl-1-oxopentan-2-yl)carbamate;
(2S,3R)-2-Amino-3-(4-chlorophenyl)-N-(5-fluoro-4-(2-((2S,6S)-1-((4-methoxyphenyl)sulfonyl)-6-methylpiperazin-2-yl)ethyl)pyridin-3-yl)-3-(tetrahydro-2H-pyran-4-yl)propanamide;
(S)-2-Amino-N-(3-fluoro-2-(2-((2S,6S)-6-methyl-1-(phenylsulfonyl)piperazin-2-yl)ethyl)phenyl)-3,3-bis(3-fluorophenyl)propanamide;
Methyl ((1S,2S)-1-(4-chlorophenyl)-3-((4-(2-((2S,6S)-1-(cyclopropylsulfonyl)-6-methylpiperazin-2-yl)ethyl)-5-fluoropyridin-3-yl)amino)-1-(3-fluorophenyl)-3-oxopropan-2-yl)carbamate;
Methyl (1R,2S)-1-(4-chlorophenyl)-3-(2-(2-((2S,6S)-1-(cyclopropylsulfonyl)-6-methylpiperazin-2-yl)ethyl)-3-fluorophenylamino)-3-oxo-1-(tetrahydro-2H-pyran-4-yl)propan-2-ylcarbamate;
(βS)-β-(3,5-difluorophenyl)-4-fluoro-N-(5-fluoro-4-{2-[(2S,6R)-6-methyl-1-(phenylsulfonyl)piperazin-2-yl]ethyl}pyridin-3-yl)-L-phenylalaninamide;
(βS)-4-chloro-N-(3-fluoro-2-{2-[(2S,6R)-6-methyl-1-(phenylsulfonyl)piperazin-2-yl]ethyl}phenyl)-β-(6-methoxypyridin-3-yl)-L-phenylalaninamide;
(βS)—N-(4-{2-[(2S,6R)-1-(cyclopropylsulfonyl)-6-methylpiperazin-2-yl]ethyl}-5-fluoropyridin-3-yl)-β-(3,5-difluorophenyl)-4-fluoro-L-phenylalaninamide;
(βS)-β-(3,5-difluorophenyl)-4-fluoro-N-[3-fluoro-2-(2-{(2S,6R)-1-[(4-methoxyphenyl)sulfonyl]-6-methylpiperazin-2-yl}ethyl)phenyl]-L-phenylalaninamide;
(βR)-4-chloro-N-(5-fluoro-4-{2-[(2S,6R)-6-methyl-1-(phenylsulfonyl)piperazin-2-yl]ethyl}pyridin-3-yl)-Nα-(methoxy carbonyl)-β-(1-methylethyl)-L-phenylalaninamide;
Methyl ((1R,2S)-1-(4-chlorophenyl)-3-((3-fluoro-2-(2-((2S,6R)-1-((4-fluorophenyl)sulfonyl)-6-methylpiperazin-2-yl)ethyl)phenyl)amino)-3-oxo-1-(tetrahydro-2H-pyran-4-yl)propan-2-yl)carbamate;
Methyl ((1S,2S)-1-(4-chlorophenyl)-3-((3-fluoro-2-(2-((S)-5-phenylsulfonyl)-5,8-diazaspiro[2.6]nonan-6-yl)ethyl)phenylamino)-1-(6-methoxypyridin-3-yl)-3-oxopropan-2-yl)carbamate;
Methyl ((2S,3R)-1-((3-fluoro-2-(2-((S)-5-(phenylsulfonyl)-5,8-diazaspiro[2.6]nonan-6-yl)ethyl)phenyl)amino)-3-(4-fluorophenyl)-1-oxo-3-(tetrahydro-2H-pyran-4-yl)propan-2-yl)carbamate;
N-(4-{2-[1-(benzylsulfonyl)piperazin-2-yl]ethyl}-5-fluoropyridin-3-yl)-4-fluoro-β-(4-fluorophenyl)-L-phenylalaninamide
(S)-2-amino-N-(5-fluoro-4-(2-((S)-1-(phenylsulfonyl)piperazin-2-yl)ethyl)pyridin-3-yl)-3,3-bis(4-fluorophenyl)propanamide
(S)-2-amino-N-(5-fluoro-4-(2-((R)-1-(phenylsulfonyl)piperazin-2-yl)ethyl)pyridin-3-yl)-3,3-bis(4-fluorophenyl)propanamide
(S)-2-amino-N-(4-(2-((S)-1-((4-aminophenyl)sulfonyl)piperazin-2-yl)ethyl)-5-fluoropyridin-3-yl)-3,3-bis(4-fluorophenyl)propanamide
(S)-2-amino-N-(4-(2-((R)-1-((4-aminophenyl)sulfonyl)piperazin-2-yl)ethyl)-5-fluoropyridin-3-yl)-3,3-bis(4-fluorophenyl)propanamide
(2S,3S)-2-amino-3-(3,5-difluorophenyl)-N-(5-fluoro-4-(2-((S)-1-(methylsulfonyl)piperazin-2-yl)ethyl)pyridin-3-yl)-3-(4-fluorophenyl)propanamide
(2S,3S)-2-amino-3-(3,5-difluorophenyl)-N-(5-fluoro-4-(2-((R)-1-(methylsulfonyl)piperazin-2-yl)ethyl)pyridin-3-yl)-3-(4-fluorophenyl)propanamide
(βS)-N-[4-(2-{(2S)-1-[(cyclopropylmethyl)sulfonyl]piperazin-2-yl}ethyl)-5-fluoropyridin-3-yl-]-3,5-difluoro-β-(4-fluorophenyl)-L-phenylalaninamide
(βS)-N-[4-(2-{(2S)-1-[(6-aminopyridin-3-yl)sulfonyl]piperazin-2-yl}ethyl)-5-fluoropyridin-3-yl]-3,5-difluoro-β-(4-fluorophenyl)-L-phenylalaninamide
(βS)-β-(3,5-difluorophenyl)-4-fluoro-N-(5-fluoro-4-{2-[(2S)-1-(phenylsulfonyl)piperazin-2-yl]ethyl}pyridin-3-yl)-L-phenylalaninamide
N-(4-{2-[1-(benzylsulfonyl)piperazin-2-yl]ethyl}-5-fluoropyridin-3-yl)-4-fluoro-β-(4-fluorophenyl)-L-phenylalaninamide
(S)-2-amino-N-(5-fluoro-4-(2-((S)-1-(phenylsulfonyl)piperazin-2-yl)ethyl)pyridin-3-yl)-3,3-bis(4-fluorophenyl)propanamide
(S)-2-amino-N-(5-fluoro-4-(2-((R)-1-(phenylsulfonyl)piperazin-2-yl)ethyl)pyridin-3-yl)-3,3-bis(4-fluorophenyl)propanamide
(S)-2-amino-N-(4-(2-((S)-1-((4-aminophenyl)sulfonyl)piperazin-2-yl)ethyl)-5-fluoropyridin-3-yl)-3,3-bis(4-fluorophenyl)propanamide
(S)-2-amino-N-(4-(2-((R)-1-((4-aminophenyl)sulfonyl)piperazin-2-yl)ethyl)-5-fluoropyridin-3-yl)-3,3-bis(4-fluorophenyl)propanamide
(2S,3S)-2-amino-3-(3,5-difluorophenyl)-N-(5-fluoro-4-(2-((S)-1-(methylsulfonyl)piperazin-2-yl)ethyl)pyridin-3-yl)-3-(4-fluorophenyl)propanamide (2S,3S)-2-amino-3-(3,5-difluorophenyl)-N-(5-fluoro-4-(2-((R)-1-(methylsulfonyl)piperazin-2-yl)ethyl)pyridin-3-yl)-3-(4-fluorophenyl)propanamide (βS)-N-[4-(2-{(2S)-1-[(cyclopropylmethyl)sulfonyl]piperazin-2-yl}ethyl)-5-fluoropyridin-3-yl]-3,5-difluoro-β-(4-fluorophenyl)-L-phenylalaninamide (βS)—N-[4-(2-{(2S)-1-[(6-aminopyridin-3-yl)sulfonyl]piperazin-2-yl}ethyl)-5-fluoropyridin-3-yl]-3,5-difluoro-β-(4-fluorophenyl)-L-phenylalaninamide (βS)-β-(3,5-difluorophenyl)-4-fluoro-N-(5-fluoro-4-{2-[(2S)-1-(phenylsulfonyl)piperazin-2-yl]ethyl}pyridin-3-yl)-L-phenylalaninamide (S)-2-amino-N-(3-fluoro-2-(2-((R)-1-(phenylsulfonyl)piperazin-2-yl)ethyl)phenyl)-3,3-bis(4-fluorophenyl)propanamide;

(S)-2-amino-N-(3-fluoro-2-(2-((S)-1-(phenylsulfonyl)piperazin-2-yl)ethyl)phenyl)-3,3-bis(4-fluorophenyl)propanamide;

(βS)-N-(4-{2-[(2S)-1-(cyclopropylsulfonyl)piperazin-2-yl]ethyl}-5-fluoropyridin-3-yl)-3,5-difluoro-β-(4-fluorophenyl)-L-phenylalaninamide;

β-(3,5-difluorophenyl)-3,5-difluoro-N-(3-fluoro-2-{2-[1-(phenylsulfonyl)piperazin-2-yl]ethyl}phenyl)-L-phenylalaninamide;

(βS)-4-chloro-β-(3-fluorophenyl)-N-(5-fluoro-4-{2-[(2S)-1-(phenylsulfonyl)piperazin-2-yl]ethyl}pyridin-3-yl)-L-phenylalaninamide;

(3R)-3-(4-chlorophenyl)-3-(1,1-dioxidotetrahydro-2H-thiopyran-4-yl)-N-(3-fluoro-2-{2-[(2S)-1-(phenylsulfonyl)piperazin-2-yl]ethyl}phenyl)propanamide;

(βR)-4-chloro-3-fluoro-N-(3-fluoro-2-{2-[(2S)-1-(phenylsulfonyl)piperazin-2-yl]ethyl}phenyl)-β-(tetrahydro-2H-pyran-4-yl)-L-phenylalaninamide;

(βR)-4-chloro-3-fluoro-N-(3-fluoro-2-{2-[(2R)-1-(phenylsulfonyl)piperazin-2-yl]ethyl}phenyl)-β-(tetrahydro-2H-pyran-4-yl)-L-phenylalaninamide;

(βS)-4-chloro-β-(3-fluorophenyl)-N-(3-fluoro-2-{2-[(2S)-1-(phenylsulfonyl)piperazin-2-yl]ethyl}phenyl)-L-phenylalaninamide;

3-fluoro-β-(3-fluorophenyl)-N-(3-fluoro-2-{2-[(2S)-1-(phenylsulfonyl)piperazin-2-yl]ethyl}phenyl)-L-phenylalaninamide;

(βR)-4-chloro-β-(1,1-dioxidotetrahydro-2H-thiopyran-4-yl)-N-(3-fluoro-2-{2-[(2S)-1-(phenylsulfonyl)piperazin-2-yl]ethyl}phenyl)-L-phenylalaninamide;

(βS)-4-chloro-N-(3-fluoro-2-{2-[(2S)-1-(phenylsulfonyl)piperazin-2-yl]ethyl}phenyl)-β-[3-(trifluoromethoxy)phenyl]-L-phenylalaninamide;

(βS)-4-chloro-β-(3,5-difluorophenyl)-N-(3-fluoro-2-{2-[(2S)-1-(phenylsulfonyl)piperazin-2-yl]ethyl}phenyl)-L-phenylalaninamide;

(βS)-4-chloro-N-(3-fluoro-2-{2-[(2S)-1-(phenylsulfonyl)piperazin-2-yl]ethyl}phenyl)-β-(5-fluoropyridin-3-yl)-L-phenylalaninamide;

(βS)-4-chloro-N-(5-fluoro-4-{2-[(2S)-1-(phenylsulfonyl)piperazin-2-yl]ethyl}pyridin-3-yl)-β-[3-(trifluoromethoxy)phenyl]-L-phenylalaninamide;

(βS)-4-chloro-β-(3,5-difluorophenyl)-N-(5-fluoro-4-{2-[(2S)-1-(phenylsulfonyl)piperazin-2-yl]ethyl}pyridin-3-yl)-L-phenylalaninamide;

N-(4-{2-[(2S)-1-(cyclopropylsulfonyl)piperazin-2-yl]ethyl}-5-fluoropyridin-3-yl)-4-fluoro-L-phenylalaninamide;

methyl ((1S,2S)-1-(3,5-difluorophenyl)-3-((5-fluoro-4-(2-((S)-1-(methylsulfonyl)piperazin-2-yl)ethyl)pyridin-3-yl)amino)-1-(4-fluorophenyl)-3-oxopropan-2-yl)carbamate;

methyl ((1S,2S)-1-(3,5-difluorophenyl)-3-((5-fluoro-4-(2-((R)-1-(methylsulfonyl)piperazin-2-yl)ethyl)pyridin-3-yl)amino)-1-(4-fluorophenyl)-3-oxopropan-2-yl)carbamate;

(βS)-N-(4-{2-[(2S)-1-(cyclopropylsulfonyl)piperazin-2-yl]ethyl}-5-fluoropyridin-3-yl)-3,5-difluoro-β-(4-fluorophenyl)-Nα-(methoxy carbonyl)-L-phenylalaninamide;

β-(3,5-difluorophenyl)-3,5-difluoro-N-(3-fluoro-2-{2-[(2S)-1-(phenylsulfonyl)piperazin-2-yl]ethyl}phenyl)-Nα-(methoxycarbonyl)-L-phenylalaninamide;

(βS)-4-chloro-β-(3-fluorophenyl)-N-(3-fluoro-2-{2-[(2S)-1-(phenylsulfonyl)piperazin-2-yl]ethyl}phenyl)-Nα-(methoxycarbonyl)-L-phenylalaninamide;

(βS)-4-chloro-β-(3-fluorophenyl)-N-(5-fluoro-4-{2-[(2S)-1-(phenylsulfonyl)piperazin-2-yl]ethyl}pyridin-3-yl)-Nα-(methoxycarbonyl)-L-phenylalaninamide;

3-fluoro-β-(3-fluorophenyl)-N-(5-fluoro-4-{2-[(2S)-1-(phenylsulfonyl)piperazin-2-yl]ethyl}pyridin-3-yl)-Nα-(methoxycarbonyl)-L-phenylalaninamide;

(βS)-4-chloro-N-(3-fluoro-2-{2-[(2S)-1-(phenylsulfonyl)piperazin-2-yl]ethyl}phenyl)-β-(5-fluoropyridin-3-yl)-Nα-(methoxy carbonyl)-L-phenylalaninamide;

(βS)-4-chloro-N-(5-fluoro-4-{2-[(2S)-1-(phenylsulfonyl)piperazin-2-yl]ethyl}pyridin-3-yl)-Nα-(methoxy carbonyl)-β-[3-(trifluoromethoxy)phenyl]-L-phenylalaninamide;

(βS)-4-chloro-β-(3,5-difluorophenyl)-N-(5-fluoro-4-{2-[(2S)-1-(phenylsulfonyl)piperazin-2-yl]ethyl}pyridin-3-yl)-Nα-(methoxycarbonyl)-L-phenylalaninamide;

(βS)-4-chloro-N-(3-fluoro-2-{2-[(2S)-1-(phenylsulfonyl)piperazin-2-yl]ethyl}phenyl)-Nα-(methoxy carbonyl)-β-[3-(trifluoromethoxy)phenyl]-L-phenylalaninamide;

(βS)-4-chloro-β-(3,5-difluorophenyl)-N-(3-fluoro-2-{2-[(2S)-1-(phenylsulfonyl)piperazin-2-yl]ethyl}phenyl)-Nα-(methoxycarbonyl)-L-phenylalaninamide;

3,3-bis(4-fluorophenyl)-N-(3-fluoro-2-{2-[(2S)-1-(phenylsulfonyl)piperazin-2-yl]ethyl}phenyl)propanamide;

3,3-bis(4-fluorophenyl)-N-(3-fluoro-2-{2-[(2R)-1-(phenylsulfonyl)piperazin-2-yl]ethyl}phenyl)propanamide;

2-[4-(4-chlorophenyl)tetrahydro-2H-pyran-4-yl]-N-(4-{2-[(2S)-1-(cyclopropylsulfonyl)piperazin-2-yl]ethyl}-5-fluoropyridin-3-yl)acetamide;

N-(4-{2-[(2S)-1-(cyclopropylsulfonyl)piperazin-2-yl]ethyl}-5-fluoropyridin-3-yl)-2-(3-phenylpiperidin-3-yl)acetamide;

(βR)-N-(4-{2-[(2S)-1-(cyclopropylsulfonyl)piperazin-2-yl]ethyl}-5-fluoropyridin-3-yl)-4-fluoro-β-(1-methylethyl)-L-phenylalaninamide;

(βR)-4-chloro-N-(3-fluoro-2-{2-[(2S)-1-(methylsulfonyl)piperazin-2-yl]ethyl}phenyl)-β-(tetrahydro-2H-pyran-4-yl)-L-phenylalaninamide;

(βS)-4-chloro-N-(3-fluoro-2-{2-[(2S)-1-(phenylsulfonyl)piperazin-2-yl]ethyl}phenyl)-Nα-(methoxy carbonyl)-β-[5-(trifluoromethyl)pyridin-3-yl]-L-phenylalaninamide;

(βS)-4-chloro-N-(3-fluoro-2-{2-[(2S)-1-(phenylsulfonyl)piperazin-2-yl]ethyl}phenyl)-β-(6-methoxypyridin-3-yl)-L-phenylalaninamide;

4-fluoro-N-[3-fluoro-2-(2-{(2S)-1-[methyl(2,2,2-trifluoroethyl)sulfamoyl]piperazin-2-yl}ethyl)phenyl]-β-(4-fluorophenyl)-L-phenylalaninamide;

N-[2-(2-{(2S)-1-[(cyclopropylmethyl)(methyl)sulfamoyl]piperazin-2-yl}ethyl)-3-fluorophenyl]-4-fluoro-β-(4-fluorophenyl)-L-phenylalaninamide;

(2S)-2-amino-2-[4-(4-chlorophenyl)tetrahydro-2H-pyran-4-yl]-N-(5-fluoro-4-{2-[(2S)-1-(phenylsulfonyl)piperazin-2-yl]ethyl}pyridin-3-yl)ethanamide;

methyl {(1S)-1-[4-(4-chlorophenyl)tetrahydro-2H-pyran-4-yl]-2-[(5-fluoro-4-{2-[(2S)-1-(phenylsulfonyl)piperazin-2-yl]ethyl}pyridin-3-yl)amino]-2-oxoethyl}carbamate;

(βR)-4-chloro-3-fluoro-N-(3-fluoro-2-{2-[(2S)-1-(phenylsulfonyl)piperazin-2-yl]ethyl}phenyl)-β-[2-(tetrahydro-2H-pyran-4-yl)ethyl]-L-phenylalaninamide;

(βR)-4-chloro-3-fluoro-N-(3-fluoro-2-{2-[(2S)-1-(phenylsulfonyl)piperazin-2-yl]ethyl}phenyl)-Nα-(methoxycarbonyl)-β-[2-(tetrahydro-2H-pyran-4-yl)ethyl]-L-phenylalaninamide;

(βR)-4-chloro-β-(2,2-dimethyltetrahydro-2H-pyran-4-yl)-N-(3-fluoro-2-{2-[(2S)-1-(phenylsulfonyl)piperazin-2-yl]ethyl}phenyl)-L-phenylalaninamide;

(βR)-4-chloro-N-(3-fluoro-2-{2-[(2S)-1-(phenylsulfonyl)piperazin-2-yl]ethyl}phenyl)-β-(2,2,6,6-tetramethyltetrahydro-2H-pyran-4-yl)-L-phenylalaninamide;

(βR)-4-chloro-β-(2,2-dimethyltetrahydro-2H-pyran-4-yl)-N-(3-fluoro-2-{2-[(2S)-1-(phenylsulfonyl)piperazin-2-yl]ethyl}phenyl)-Nα-(methoxycarbonyl)-L-phenylalaninamide;

(βR)-4-chloro-N-(3-fluoro-2-{2-[(2S)-1-(phenylsulfonyl)piperazin-2-yl]ethyl}phenyl)-Nα-(methoxy carbonyl)-β-(2,2,6,6-tetramethyltetrahydro-2H-pyran-4-yl)-L-phenylalaninamide;

(βR)-4-chloro-β-(2,2-dimethyltetrahydro-2H-pyran-4-yl)-N-(3-fluoro-2-{2-[(2S)-1-(methylsulfonyl)piperazin-2-yl]ethyl}phenyl)-L-phenylalaninamide;

(βR)-4-chloro-β-(2,2-dimethyltetrahydro-2H-pyran-4-yl)-N-(3-fluoro-2-{2-[(2S)-1-(methylsulfonyl)piperazin-2-yl]ethyl}phenyl)-Nα-(methoxy carbonyl)-L-phenylalaninamide;

(βS)-Nα-acetyl-N-(4-{2-[(2S)-1-(cyclopropylsulfonyl)piperazin-2-yl]ethyl}-5-fluoropyridin-3-yl)-3,5-difluoro-β-(4-fluorophenyl)-L-phenylalaninamide;

(βS)-Nα-(cyclopropylcarbonyl)-N-(4-{2-[(2S)-1-(cyclopropylsulfonyl)piperazin-2-yl]ethyl}-5-fluoropyridin-3-yl)-3,5-difluoro-β-(4-fluorophenyl)-L-phenylalaninamide;

(βS)—Nα-(cyclopropylacetyl)-N-(4-{2-[(2S)-1-(cyclopropylsulfonyl)piperazin-2-yl]ethyl}-5-fluoropyridin-3-yl)-3,5-difluoro-β-(4-fluorophenyl)-L-phenylalaninamide;

(βS)-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-L-phenylalaninamide;

(βS)-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-Nα-(methoxy carbonyl)-L-phenylalaninamide;

(βS)Nα-acetyl-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-L-phenylalaninamide;

(βS)-Nα-(cyclopropylcarbonyl)-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-L-phenylalaninamide;

(βS)-Nα-(cyclopropylacetyl)-3,5-difluoro-β-(4-fluorophenyl)-N-(5-fluoro-4-{2-[(2S)-1-(pyrrolidin-1-ylsulfonyl)piperazin-2-yl]ethyl}pyridin-3-yl)-L-phenylalaninamide;

N-(3-fluoro-2-{2-[(2S,5R)-5-methyl-1-(phenylsulfonyl)piperazin-2-yl]ethyl}phenyl)-3,3-bis(4-fluorophenyl)propanamide;

N-(3-fluoro-2-{2-[(2S,5S)-5-methyl-1-(phenylsulfonyl)piperazin-2-yl]ethyl}phenyl)-3,3-bis(4-fluorophenyl)propanamide;

N-(3-fluoro-2-{2-[(2S,6R)-6-methyl-1-(phenylsulfonyl)piperazin-2-yl]ethyl}phenyl)-3,3-bis(4-fluorophenyl)propanamide;

N-(3-fluoro-2-{2-[(2R,6R)-6-methyl-1-(phenylsulfonyl)piperazin-2-yl]ethyl}phenyl)-3,3-bis(4-fluorophenyl)propanamide;

N-(3-fluoro-2-{2-[(2S,6S)-6-methyl-1-(phenylsulfonyl)piperazin-2-yl]ethyl}phenyl)-3,3-bis(4-fluorophenyl)propanamide;

N-(3-fluoro-2-{2-[(2R,6S)-6-methyl-1-(phenylsulfonyl)piperazin-2-yl]ethyl}phenyl)-3,3-bis(4-fluorophenyl)propanamide;

(βS)-β-(3,5-difluorophenyl)-4-fluoro-N-(3-fluoro-2-{2-[(2S,6R)-6-methyl-1-(phenylsulfonyl)piperazin-2-yl]ethyl}phenyl)-L-phenylalaninamide;

(βS)-β-(3,5-difluorophenyl)-4-fluoro-N-(3-fluoro-2-{2-[(2S,6S)-6-methyl-1-(phenylsulfonyl)piperazin-2-yl]ethyl}phenyl)-Nα-(methoxycarbonyl)-L-phenylalaninamide;

(βS)-β-(3,5-difluorophenyl)-4-fluoro-N-(3-fluoro-2-{2-[(2S,6S)-6-methyl-1-(methylsulfonyl)piperazin-2-yl]ethyl}phenyl)-L-phenylalaninamide;

(βS)-β-(3,5-difluorophenyl)-4-fluoro-N-(3-fluoro-2-{2-[(2S,6S)-6-methyl-1-(phenylsulfonyl)piperazin-2-yl]ethyl}phenyl)-L-phenylalaninamide;

(βS)-4-chloro-N-(3-fluoro-2-{2-[(2S,5R)-5-methyl-1-(phenylsulfonyl)piperazin-2-yl]ethyl}phenyl)-β-[3-(trifluoromethoxy)phenyl]-L-phenylalaninamide;

(βS)-β-(3,5-difluorophenyl)-4-fluoro-N-(3-fluoro-2-{2-[(2S,6S)-6-methyl-1-(methylsulfonyl)piperazin-2-yl]ethyl}phenyl)-Nα-(methoxy carbonyl)-L-phenylalaninamide;

3-fluoro-N-(3-fluoro-2-{2-[(2S,6S)-6-methyl-1-(phenylsulfonyl)piperazin-2-yl]ethyl}phenyl)-β-(3-fluorophenyl)-Nα-(methoxy carbonyl)-L-phenylalaninamide;

(βS)-4-chloro-N-(3-fluoro-2-{2-[(2S,6S)-6-methyl-1-(phenylsulfonyl)piperazin-2-yl]ethyl}phenyl)-(3-(3-fluorophenyl)-L-phenylalaninamide;

(βR)-4-fluoro-N-(3-fluoro-2-{2-[(2S,6S)-6-methyl-1-(phenylsulfonyl)piperazin-2-yl]ethyl}phenyl)-β-(tetrahydro-2H-pyran-4-yl)-L-phenylalaninamide;

(βR)-4-fluoro-N-(3-fluoro-2-{2-[(2S,6R)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide;

(βR)-4-fluoro-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide;

(βS)-β-(3,5-difluorophenyl)-4-fluoro-N-(5-fluoro-4-{2-[(2S,6S)-6-methyl-1-(phenylsulfonyl)piperazin-2-yl]ethyl}pyridin-3-yl)-L-phenylalaninamide;

(βS)-β-(3,5-difluorophenyl)-4-fluoro-N-[3-fluoro-2-(2-{(2S,6S)-1-[(3-fluorophenyl)sulfonyl]-6-methylpiperazin-2-yl}ethyl)phenyl]-L-phenylalaninamide;

(βS)-β-(3,5-difluorophenyl)-4-fluoro-N-[3-fluoro-2-(2-{(2S,6S)-1-[(3-fluorophenyl)sulfonyl]-6-methylpiperazin-2-yl}ethyl)phenyl]-Nα-(methoxy carbonyl)-L-phenylalaninamide;

(βS)-4-chloro-N-(3-fluoro-2-{2-[(2S,6S)-6-methyl-1-(methylsulfonyl)piperazin-2-yl]ethyl}phenyl)-β-(3-fluorophenyl)-L-phenylalaninamide;
(βR)-4-chloro-N-(3-fluoro-2-{2-[(2S,6S)-6-methyl-1-(phenylsulfonyl)piperazin-2-yl]ethyl}phenyl)-β-(1-methylethyl)-L-phenylalaninamide;
(βR)-4-chloro-N-(3-fluoro-2-{2-[(2S,6R)-6-methyl-1-(phenylsulfonyl)piperazin-2-yl]ethyl}phenyl)-β-(1-methylethyl)-L-phenylalaninamide;
(βR)-4-chloro-N-(3-fluoro-2-{2-[(2S,6S)-6-methyl-1-(phenylsulfonyl)piperazin-2-yl]ethyl}phenyl)-Nα-(methoxycarbonyl)-β-(1-methylethyl)-L-phenylalaninamide;
(βR)-4-chloro-N-(3-fluoro-2-{2-[(2S,6R)-6-methyl-1-(phenylsulfonyl)piperazin-2-yl]ethyl}phenyl)-Nα-(methoxycarbonyl)-β-(1-methylethyl)-L-phenylalaninamide;
(βS)-β-(4-chlorophenyl)-3-fluoro-N-(5-fluoro-4-{2-[(2S,6S)-6-methyl-1-(phenylsulfonyl)piperazin-2-yl]ethyl}pyridin-3-yl)-L-phenylalaninamide;
(βR)-N-(2-{2-[(2S,6S)-1-(cyclopropylsulfonyl)-6-methylpiperazin-2-yl]ethyl}-3-fluorophenyl)-4-fluoro-β-(tetrahydro-2H-pyran-4-yl)-L-phenylalaninamide;
(βR)-N-(2-{2-[(2S,6S)-1-(cyclopropylsulfonyl)-6-methylpiperazin-2-yl]ethyl}-3-fluorophenyl)-4-fluoro-Nα-(methoxycarbonyl)-β-(tetrahydro-2H-pyran-4-yl)-L-phenylalaninamide;
(βR)-4-chloro-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide;
(βR)-4-chloro-N-(3-fluoro-2-{2-[(2S,6R)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide;
(βS)-4-chloro-N-(3-fluoro-2-{2-[(2S,6S)-6-methyl-1-(phenylsulfonyl)piperazin-2-yl]ethyl}phenyl)-β-(6-methoxypyridin-3-yl)-L-phenylalaninamide;
(βS)-4-chloro-N-(3-fluoro-2-{2-[(2S,6S)-6-methyl-1-(phenylsulfonyl)piperazin-2-yl]ethyl}phenyl)-Nα-(methoxycarbonyl)-β-(6-methoxypyridin-3-yl)-L-phenylalaninamide;
(βS)-4-chloro-N-(3-fluoro-2-{2-[(2S,6R)-6-methyl-1-(phenylsulfonyl)piperazin-2-yl]ethyl}phenyl)-Nα-(methoxycarbonyl)-β-(6-methoxypyridin-3-yl)-L-phenylalaninamide;
(βR)-4-chloro-N-(3-fluoro-2-{2-[(2S,6S)-6-methyl-1-(methylsulfonyl)piperazin-2-yl]ethyl}phenyl)-β-(tetrahydro-2H-pyran-4-yl)-L-phenylalaninamide;
(βR)-4-chloro-N-(3-fluoro-2-{2-[(2S,6S)-6-methyl-1-(methylsulfonyl)piperazin-2-yl]ethyl}phenyl)-β-(1-methylethyl)-L-phenylalaninamide;
(βR)-4-chloro-N-(3-fluoro-2-{2-[(2S,6S)-6-methyl-1-(methylsulfonyl)piperazin-2-yl]ethyl}phenyl)-Nα-(methoxycarbonyl)-β-(1-methylethyl)-L-phenylalaninamide;
(βR)-4-chloro-N-[3-fluoro-2-(2-{(2S,6S)-1-[(4-methoxyphenyl)sulfonyl]-6-methylpiperazin-2-yl}ethyl)phenyl]-β-(1-methylethyl)-L-phenylalaninamide;
(βR)-4-chloro-N-[3-fluoro-2-(2-{(2S,6S)-1-[(4-methoxyphenyl)sulfonyl]-6-methylpiperazin-2-yl}ethyl)phenyl]-Nα-(methoxycarbonyl)-β-(1-methylethyl)-L-phenylalaninamide;
(βR)-4-chloro-N-(5-fluoro-4-{2-[(2S,6S)-6-methyl-1-(phenylsulfonyl)piperazin-2-yl]ethyl}pyridin-3-yl)-β-(1-methylethyl)-L-phenylalaninamide;
(βR)-4-chloro-N-(2-{2-[(2S,6S)-1-(cyclopropylsulfonyl)-6-methylpiperazin-2-yl]ethyl}-3-fluorophenyl)-β-(1-methylethyl)-L-phenylalaninamide;
(βR)-4-chloro-N-(2-{2-[(2S,6R)-1-(cyclopropylsulfonyl)-6-methylpiperazin-2-yl]ethyl}-3-fluorophenyl)-β-(1-methylethyl)-L-phenylalaninamide;
(βR)-4-fluoro-N-(3-fluoro-2-{2-[(2S,6S)-6-methyl-1-(methylsulfonyl)piperazin-2-yl]ethyl}phenyl)-β-(tetrahydro-2H-pyran-4-yl)-L-phenylalaninamide;
(βR)-4-fluoro-N-(3-fluoro-2-{2-[(2S,6S)-6-methyl-1-(methylsulfonyl)piperazin-2-yl]ethyl}phenyl)-Nα-(methoxycarbonyl)-β-(tetrahydro-2H-pyran-4-yl)-L-phenylalaninamide;
(βR)-4-chloro-N-(3-fluoro-2-{2-[(2S,6S)-6-methyl-1-(phenylsulfonyl)piperazin-2-yl]ethyl}phenyl)-β-(tetrahydro-2H-pyran-4-yl)-L-phenylalaninamide;
(βR)-4-chloro-N-(3-fluoro-2-{2-[(2S,6S)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide;
3-fluoro-N-(3-fluoro-2-{2-[(2S,6R)-6-methyl-1-(phenylsulfonyl)piperazin-2-yl]ethyl}phenyl)-β-(3-fluorophenyl)-L-phenylalaninamide;
3-fluoro-N-(3-fluoro-2-{2-[(2S,6R)-6-methyl-1-(phenylsulfonyl)piperazin-2-yl]ethyl}phenyl)-β-(3-fluorophenyl)-Nα-(methoxy carbonyl)-L-phenylalaninamide;
(βS)-4-chloro-N-(5-fluoro-4-{2-[(2S,6R)-6-methyl-1-(phenylsulfonyl)piperazin-2-yl]ethyl}pyridin-3-yl)-β-(3-fluorophenyl)-L-phenylalaninamide;
(βR)-4-chloro-N-[5-fluoro-4-(2-{(2S,6S)-1-[(4-methoxyphenyl)sulfonyl]-6-methylpiperazin-2-yl}ethyl)pyridin-3-yl]-Nα-(methoxycarbonyl)-β-(tetrahydro-2H-pyran-4-yl)-L-phenylalaninamide;
N-[2-(2-{(2S,6S)-1-[(2-chlorophenyl)sulfonyl]-6-methylpiperazin-2-yl}ethyl)-3-fluorophenyl]-3-fluoro-β-(3-fluorophenyl)-L-phenylalaninamide;
N-[2-(2-{(2S,6S)-1-[(2-chlorophenyl)sulfonyl]-6-methylpiperazin-2-yl}ethyl)-3-fluorophenyl]-3-fluoro-β-(3-fluorophenyl)-Nα-(methoxycarbonyl)-L-phenylalaninamide;
(βR)-4-chloro-N-(3-fluoro-2-{2-[(2S,6S)-6-methyl-1-(methylsulfonyl)piperazin-2-yl]ethyl}phenyl)-Nα-(methoxycarbonyl)-β-(tetrahydro-2H-pyran-4-yl)-L-phenylalaninamide;
(βR)-4-chloro-N-(3-fluoro-2-{2-[(2S,6S)-6-methyl-1-{[4-(trifluoromethoxy)phenyl]sulfonyl}piperazin-2-yl]ethyl}phenyl)-β-(1-methylethyl)-L-phenylalaninamide;
(βR)-4-chloro-N-(2-{2-[(2S,6S)-1-(cyclopropylsulfonyl)-6-methylpiperazin-2-yl]ethyl}-3-fluorophenyl)-β-(tetrahydro-2H-pyran-4-yl)-L-phenylalaninamide;
(βR)-4-chloro-N-(3-fluoro-2-{2-[(2S,6S)-6-methyl-1-{[4-(trifluoromethoxy)phenyl]sulfonyl}piperazin-2-yl]ethyl}phenyl)-Nα-(methoxycarbonyl)-β-(1-methylethyl)-L-phenylalaninamide;
(βR)-4-chloro-N-[2-(2-{(2S,6S)-1-[(2-chlorophenyl)sulfonyl]-6-methylpiperazin-2-yl}ethyl)-3-fluorophenyl]-Nα-(methoxycarbonyl)-β-(1-methylethyl)-L-phenylalaninamide;
(βR)-4-chloro-N-(2-{2-[(2S,6S)-1-(cyclopropylsulfonyl)-6-methylpiperazin-2-yl]ethyl}-3-fluorophenyl)-Nα-(methoxycarbonyl)-β-(1-methylethyl)-L-phenylalaninamide;
(βR)-4-chloro-N-(2-{2-[(2S,6R)-1-(cyclopropylsulfonyl)-6-methylpiperazin-2-yl]ethyl}-3-fluorophenyl)-Nα-(methoxycarbonyl)-β-(1-methylethyl)-L-phenylalaninamide;

(βR)-4-fluoro-N-(3-fluoro-2-{2-[(2S,6R)-6-methyl-1-(methylsulfonyl)piperazin-2-yl]ethyl}phenyl)-Nα-(methoxycarbonyl)-β-(tetrahydro-2H-pyran-4-yl)-L-phenylalaninamide;

(βR)-4-fluoro-N-(3-fluoro-2-{2-[(2S,6R)-6-methyl-1-(methylsulfonyl)piperazin-2-yl]ethyl}phenyl)-β-(tetrahydro-2H-pyran-4-yl)-L-phenylalaninamide;

(βR)-4-chloro-Nα-(ethoxycarbonyl)-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide;

(βS)-4-chloro-N-(2-{2-[(2S,6S)-1-(cyclopropylsulfonyl)-6-methylpiperazin-2-yl]ethyl}-3-fluorophenyl)-β-(6-methoxypyridin-3-yl)-L-phenylalaninamide;

(βS)-4-chloro-N-(2-{2-[(2S,6S)-1-(cyclopropylsulfonyl)-6-methylpiperazin-2-yl]ethyl}-3-fluorophenyl)-Nα-(methoxycarbonyl)-β-(6-methoxypyridin-3-yl)-L-phenylalaninamide;

(βS)-4-chloro-N-(2-{2-[(2S,6R)-1-(cyclopropylsulfonyl)-6-methylpiperazin-2-yl]ethyl}-3-fluorophenyl)-β-(6-methoxypyridin-3-yl)-L-phenylalaninamide;

(βS)-4-chloro-N-(2-{2-[(2S,6R)-1-(cyclopropylsulfonyl)-6-methylpiperazin-2-yl]ethyl}-3-fluorophenyl)-Nα-(methoxycarbonyl)-β-(6-methoxypyridin-3-yl)-L-phenylalaninamide;

(βR)-3-chloro-N-(3-fluoro-2-{2-[(2S,6S)-6-methyl-1-(phenylsulfonyl)piperazin-2-yl]ethyl}phenyl)-(3-(3-fluorophenyl)-L-phenylalaninamide;

(βR)-3-chloro-N-(3-fluoro-2-{2-[(2S,6S)-6-methyl-1-(phenylsulfonyl)piperazin-2-yl]ethyl}phenyl)-β-(3-fluorophenyl)-Nα-(methoxycarbonyl)-L-phenylalaninamide;

3-fluoro-N-[3-fluoro-2-(2-{(2S,6S)-1-[(4-methoxyphenyl)sulfonyl]-6-methylpiperazin-2-yl}ethyl)phenyl]-β-(3-fluorophenyl)-L-phenylalaninamide;

3-fluoro-N-[3-fluoro-2-(2-{(2S,6S)-1-[(4-methoxyphenyl)sulfonyl]-6-methylpiperazin-2-yl}ethyl)phenyl]-β-(3-fluorophenyl)-Nα-(methoxycarbonyl)-L-phenylalaninamide;

N-(2-{2-[(2S,6S)-1-(cyclopropylsulfonyl)-6-methylpiperazin-2-yl]ethyl}-3-fluorophenyl)-3-fluoro-β-(3-fluorophenyl)-L-phenylalaninamide;

N-(2-{2-[(2S,6S)-1-(cyclopropylsulfonyl)-6-methylpiperazin-2-yl]ethyl}-3-fluorophenyl)-3-fluoro-β-(3-fluorophenyl)-Nα-(methoxycarbonyl)-L-phenylalaninamide;

(βR)-4-chloro-N-(3-fluoro-2-{2-[(2S,6R)-6-methyl-1-(methylsulfonyl)piperazin-2-yl]ethyl}phenyl)-β-(tetrahydro-2H-pyran-4-yl)-L-phenylalaninamide;

(βR)-3-chloro-N-[3-fluoro-2-(2-{(2S,6S)-1-[(4-methoxyphenyl)sulfonyl]-6-methylpiperazin-2-yl}ethyl)phenyl]-β-(3-fluorophenyl)-L-phenylalaninamide;

(βR)-3-chloro-N-[3-fluoro-2-(2-{(2S,6S)-1-[(4-methoxyphenyl)sulfonyl]-6-methylpiperazin-2-yl}ethyl)phenyl]-β-(3-fluorophenyl)-Nα-(methoxycarbonyl)-L-phenylalaninamide;

(βS)-4-chloro-N-(3-fluoro-2-{2-[(2S,6S)-6-methyl-1-(methylsulfonyl)piperazin-2-yl]ethyl}phenyl)-β-(6-methoxypyridin-3-yl)-L-phenylalaninamide;

(βS)-4-chloro-N-(3-fluoro-2-{2-[(2S,6S)-6-methyl-1-(methylsulfonyl)piperazin-2-yl]ethyl}phenyl)-Nα-(methoxycarbonyl)-β-(6-methoxypyridin-3-yl)-L-phenylalaninamide;

(βS)-4-chloro-N-(4-{2-[(2S,6S)-1-(cyclopropylsulfonyl)-6-methylpiperazin-2-yl]ethyl}-5-fluoropyridin-3-yl)-β-(3-fluorophenyl)-L-phenylalaninamide;

(βS)-4-chloro-N-(2-{2-[(2S,6S)-1-(cyclopropylsulfonyl)-6-methylpiperazin-2-yl]ethyl}-3-fluorophenyl)-β-(3-fluorophenyl)-L-phenylalaninamide;

(βS)-4-chloro-N-(2-{2-[(2S,6S)-1-(cyclopropylsulfonyl)-6-methylpiperazin-2-yl]ethyl}-3-fluorophenyl)-β-(3-fluorophenyl)-Nα-(methoxy carbonyl)-L-phenylalaninamide;

(βR)-3-chloro-N-(3-fluoro-2-{2-[(2S,6R)-6-methyl-1-(methylsulfonyl)piperazin-2-yl]ethyl}phenyl)-β-(3-fluorophenyl)-L-phenylalaninamide;

3-fluoro-N-(3-fluoro-2-{2-[(2S,6S)-6-methyl-1-(methylsulfonyl)piperazin-2-yl]ethyl}phenyl)-β-(3-fluorophenyl)-L-phenylalaninamide;

3-fluoro-N-(3-fluoro-2-{2-[(2S,6S)-6-methyl-1-(methylsulfonyl)piperazin-2-yl]ethyl}phenyl)-β-(3-fluorophenyl)-Nα-(methoxycarbonyl)-L-phenylalaninamide;

(βR)-3-chloro-N-(3-fluoro-2-{2-[(2S,6S)-6-methyl-1-(methylsulfonyl)piperazin-2-yl]ethyl}phenyl)-β-(3-fluorophenyl)-L-phenylalaninamide;

(βR)-3-chloro-N-(3-fluoro-2-{2-[(2S,6R)-6-methyl-1-(methylsulfonyl)piperazin-2-yl]ethyl}phenyl)-β-(3-fluorophenyl)-Nα-(methoxycarbonyl)-L-phenylalaninamide;

(βR)-3-chloro-N-(3-fluoro-2-{2-[(2S,6S)-6-methyl-1-(methylsulfonyl)piperazin-2-yl]ethyl}phenyl)-β-(3-fluorophenyl)-Nα-(methoxycarbonyl)-L-phenylalaninamide;

(βR)-3-chloro-N-(2-{2-[(2S,6S)-1-(cyclopropylsulfonyl)-6-methylpiperazin-2-yl]ethyl}-3-fluorophenyl)-β-(3-fluorophenyl)-Nα-(methoxy carbonyl)-L-phenylalaninamide;

(βR)-3-chloro-N-(2-{2-[(2S,6S)-1-(cyclopropylsulfonyl)-6-methylpiperazin-2-yl]ethyl}-3-fluorophenyl)-β-(3-fluorophenyl)-L-phenylalaninamide;

(βR)-4-chloro-N-(4-{2-[(2S,6S)-1-(cyclopropylsulfonyl)-6-methylpiperazin-2-yl]ethyl}-5-fluoropyridin-3-yl)-β-(1-methylethyl)-L-phenylalaninamide;

(βR)-4-chloro-N-(4-{2-[(2S,6R)-1-(cyclopropylsulfonyl)-6-methylpiperazin-2-yl]ethyl}-5-fluoropyridin-3-yl)-β-(1-methylethyl)-L-phenylalaninamide;

(βR)-4-chloro-N-(4-{2-[(2S,6S)-1-(cyclopropylsulfonyl)-6-methylpiperazin-2-yl]ethyl}-5-fluoropyridin-3-yl)-Nα-(methoxycarbonyl)-β-(1-methylethyl)-L-phenylalaninamide;

(βR)-4-chloro-N-(4-{2-[(2S,6R)-1-(cyclopropylsulfonyl)-6-methylpiperazin-2-yl]ethyl}-5-fluoropyridin-3-yl)-Nα-(methoxycarbonyl)-β-(1-methylethyl)-L-phenylalaninamide;

N-(2-{2-[(2S,6R)-1-(cyclopropylsulfonyl)-6-methylpiperazin-2-yl]ethyl}-3-fluorophenyl)-3-fluoro-β-(3-fluorophenyl)-L-phenylalaninamide;

(βR)-4-chloro-N-(5-fluoro-4-{2-[(2S,6R)-6-methyl-1-(methylsulfonyl)piperazin-2-yl]ethyl}pyridin-3-yl)-β-(tetrahydro-2H-pyran-4-yl)-L-phenylalaninamide;

(βR)-4-chloro-N-(3-fluoro-2-{2-[(2S,6R)-6-methyl-1-(methylsulfonyl)piperazin-2-yl]ethyl}phenyl)-Nα-(methoxycarbonyl)-β-(tetrahydro-2H-pyran-4-yl)-L-phenylalaninamide;

(βS)-4-chloro-N-(3-fluoro-2-{2-[(2S,6R)-6-methyl-1-(phenylsulfonyl)piperazin-2-yl]ethyl}phenyl)-β-(3-fluorophenyl)-Nα-(methoxycarbonyl)-L-phenylalaninamide;

(βS)-4-chloro-N-(3-fluoro-2-{2-[(2S,6S)-6-methyl-1-(phenylsulfonyl)piperazin-2-yl]ethyl}phenyl)-β-(3-fluorophenyl)-Nα-(methoxycarbonyl)-L-phenylalaninamide;

(βS)-4-chloro-β-(4-fluorobenzyl)-N-[3-fluoro-2-(2-{(2S,6S)-1-[(4-methoxyphenyl)sulfonyl]-6-methylpiperazin-2-yl}ethyl)phenyl]-L-phenylalaninamide;

(βS)-4-chloro-β-(4-fluorobenzyl)-N-[3-fluoro-2-(2-{(2S,6S)-1-[(4-methoxyphenyl)sulfonyl]-6-methylpiperazin-2-yl}ethyl)phenyl]-Nα-(methoxy carbonyl)-L-phenylalaninamide;

(βS)-4-chloro-N-(3-fluoro-2-{2-[(2S,6S)-6-methyl-1-{[4-(trifluoromethoxy)phenyl]sulfonyl}piperazin-2-yl]ethyl}phenyl)-(3-(6-methoxy pyridin-3-yl)-L-phenylalaninamide;

(βS)-4-chloro-N-(3-fluoro-2-{2-[(2S,6S)-6-methyl-1-{[4-(trifluoromethoxy)phenyl]sulfonyl}piperazin-2-yl]ethyl}phenyl)-Nα-(methoxycarbonyl)-β-(6-methoxypyridin-3-yl)-L-phenylalaninamide;

(βS)-β-(3,5-difluorophenyl)-4-fluoro-N-(5-fluoro-4-{2-[(2S,6S)-6-methyl-1-(methylsulfonyl)piperazin-2-yl]ethyl}pyridin-3-yl)-Nα-(methoxycarbonyl)-L-phenylalaninamide;

(βS)-β-(3,5-difluorophenyl)-4-fluoro-N-(5-fluoro-4-{2-[(2S,6S)-6-methyl-1-(methylsulfonyl)piperazin-2-yl]ethyl}pyridin-3-yl)-L-phenylalaninamide;

(βS)-N-(2-{2-[(2S,6R)-1-(cyclopropylsulfonyl)-6-methylpiperazin-2-yl]ethyl}-3-fluorophenyl)-β-(3,5-difluorophenyl)-4-fluoro-L-phenylalaninamide;

(βS)-4-chloro-β-(4-fluorobenzyl)-N-(3-fluoro-2-{2-[(2S,6S)-6-methyl-1-(phenylsulfonyl)piperazin-2-yl]ethyl}phenyl)-L-phenylalaninamide;

(βS)-4-chloro-β-(4-fluorobenzyl)-N-(3-fluoro-2-{2-[(2S,6S)-6-methyl-1-(phenylsulfonyl)piperazin-2-yl]ethyl}phenyl)-Nα-(methoxycarbonyl)-L-phenylalaninamide;

(βS)-4-chloro-β-(4-fluorobenzyl)-N-(3-fluoro-2-{2-[(2S,6R)-6-methyl-1-(phenylsulfonyl)piperazin-2-yl]ethyl}phenyl)-L-phenylalaninamide;

(βS)-4-chloro-β-(4-fluorobenzyl)-N-(3-fluoro-2-{2-[(2S,6R)-6-methyl-1-(phenylsulfonyl)piperazin-2-yl]ethyl}phenyl)-Nα-(methoxycarbonyl)-L-phenylalaninamide;

(βS)-N-(4-{2-[(2S,6S)-1-(cyclopropylsulfonyl)-6-methylpiperazin-2-yl]ethyl}-5-fluoropyridin-3-yl)-β-(3,5-difluorophenyl)-4-fluoro-L-phenylalaninamide;

(βS)-4-chloro-β-(3,5-difluorophenyl)-N-(3-fluoro-2-{2-[(2S,6S)-6-methyl-1-(methylsulfonyl)piperazin-2-yl]ethyl}phenyl)-L-phenylalaninamide;

(βS)-4-chloro-N-(2-{2-[(2S,6S)-1-(cyclopropylsulfonyl)-6-methylpiperazin-2-yl]ethyl}-3-fluorophenyl)-(3-(3,5-difluorophenyl)-L-phenylalaninamide;

(βS)-4-chloro-β-(3,5-difluorophenyl)-N-(3-fluoro-2-{2-[(2S,6S)-6-methyl-1-(methylsulfonyl)piperazin-2-yl]ethyl}phenyl)-Nα-(methoxy carbonyl)-L-phenylalaninamide;

(βS)-4-chloro-N-(2-{2-[(2S,6S)-1-(cyclopropylsulfonyl)-6-methylpiperazin-2-yl]ethyl}-3-fluorophenyl)-β-(3,5-difluorophenyl)-Nα-(methoxy carbonyl)-L-phenylalaninamide;

(βS)-4-chloro-β-(4-fluorobenzyl)-N-(3-fluoro-2-{2-[(2S,6S)-6-methyl-1-(methylsulfonyl)piperazin-2-yl]ethyl}phenyl)-L-phenylalaninamide;

(βR)-3-chloro-N-(2-{2-[(2S,6R)-1-(cyclopropylsulfonyl)-6-methylpiperazin-2-yl]ethyl}-3-fluorophenyl)-β-(3-chlorophenyl)-L-phenylalaninamide;

(βS)-4-chloro-N-(2-{2-[(2S,6R)-1-(cyclopropylsulfonyl)-6-methylpiperazin-2-yl]ethyl}-3-fluorophenyl)-β-(3-fluorophenyl)-L-phenylalaninamide;

(βS)-N-(2-{2-[(2S,6S)-6-cyclopropyl-1-(methylsulfonyl)piperazin-2-yl]ethyl}-3-fluorophenyl)-β-(3,5-difluorophenyl)-4-fluoro-L-phenylalaninamide;

(βR)-3-chloro-N-(3-fluoro-2-{2-[(2S,6R)-6-methyl-1-(phenylsulfonyl)piperazin-2-yl]ethyl}phenyl)-β-(1-methylethyl)-L-phenylalaninamide;

(βR)-3-chloro-N-(3-fluoro-2-{2-[(2S,6S)-6-methyl-1-(phenylsulfonyl)piperazin-2-yl]ethyl}phenyl)-(3-(1-methylethyl)-L-phenylalaninamide;

(βR)-3-chloro-N-(3-fluoro-2-{2-[(2S,6R)-6-methyl-1-(phenylsulfonyl)piperazin-2-yl]ethyl}phenyl)-Nα-(methoxycarbonyl)-β-(1-methylethyl)-L-phenylalaninamide;

(βR)-3-chloro-N-(3-fluoro-2-{2-[(2S,6S)-6-methyl-1-(phenylsulfonyl)piperazin-2-yl]ethyl}phenyl)-Nα-(methoxycarbonyl)-β-(1-methylethyl)-L-phenylalaninamide;

(βS)-N-(4-{2-[(2S,6S)-1-(cyclopropylsulfonyl)-6-methylpiperazin-2-yl]ethyl}-5-fluoropyridin-3-yl)-β-(3,5-difluorophenyl)-4-fluoro-Nα-(methoxycarbonyl)-L-phenylalaninamide;

(βS)-N-(4-{2-[(2S,6R)-1-(cyclopropylsulfonyl)-6-methylpiperazin-2-yl]ethyl}-5-fluoropyridin-3-yl)-β-(3,5-difluorophenyl)-4-fluoro-Nα-(methoxycarbonyl)-L-phenylalaninamide;

(βS)-N-(2-{2-[(2S,6S)-1-(cyclopropylsulfonyl)-6-methylpiperazin-2-yl]ethyl}-3-fluorophenyl)-β-(3,5-difluorophenyl)-4-fluoro-Nα-(methoxy carbonyl)-L-phenylalaninamide;

(βS)-4-chloro-N-(5-fluoro-4-{2-[(2S,6S)-6-methyl-1-(methylsulfonyl)piperazin-2-yl]ethyl}pyridin-3-yl)-(3-(3-fluorophenyl)-L-phenylalaninamide;

(βS)-β-(3,5-difluorophenyl)-4-fluoro-N-(3-fluoro-2-{2-[(2S,6S)-6-methyl-1-{[4-(trifluoromethoxy)phenyl]sulfonyl}piperazin-2-yl]ethyl}phenyl)-L-phenylalaninamide;

(βR)-3-chloro-N-(2-{2-[(2S,6S)-1-(cyclopropylsulfonyl)-6-methylpiperazin-2-yl]ethyl}-3-fluorophenyl)-β-(1-methylethyl)-L-phenylalaninamide;

(βR)-3-chloro-N-(2-{2-[(2S,6S)-1-(cyclopropylsulfonyl)-6-methylpiperazin-2-yl]ethyl}-3-fluorophenyl)-Nα-(methoxycarbonyl)-β-(1-methylethyl)-L-phenylalaninamide;

(βR)-3-chloro-N-(2-{2-[(2S,6R)-1-(cyclopropylsulfonyl)-6-methylpiperazin-2-yl]ethyl}-3-fluorophenyl)-Nα-(methoxycarbonyl)-β-(1-methylethyl)-L-phenylalaninamide;

(βR)-4-chloro-N-(3-fluoro-2-{2-[(2S)-6-(methoxy methyl)-1-(methylsulfonyl)piperazin-2-yl]ethyl}phenyl)-β-(tetrahydro-2H-pyran-4-yl)-L-phenylalaninamide;

(βS)-3-chloro-N-(3-fluoro-2-{2-[(2S,6S)-6-methyl-1-(phenylsulfonyl)piperazin-2-yl]ethyl}phenyl)-β-(5-fluoropyridin-3-yl)-L-phenylalaninamide;

(βS)-4-chloro-β-(4-fluorobenzyl)-N-(3-fluoro-2-{2-[(2S,6S)-6-methyl-1-{[4-(trifluoromethoxy)phenyl]sulfonyl}piperazin-2-yl]ethyl}phenyl)-L-phenylalaninamide;

(βS)-4-chloro-β-(4-fluorobenzyl)-N-(3-fluoro-2-{2-[(2S,6S)-6-methyl-1-{[4-(trifluoromethoxy)phenyl]sulfonyl}piperazin-2-yl]ethyl}phenyl)-Nα-(methoxycarbonyl)-L-phenylalaninamide;

(βR)-β-(3-chlorophenyl)-3-fluoro-N-(3-fluoro-2-{2-[(2S)-6-[(1-methylethoxy)methyl]-1-(methylsulfonyl)piperazin-2-yl]ethyl}phenyl)-Nα-(methoxy carbonyl)-L-phenylalaninamide;

(βS)-N-(2-{2-[(2S,6S)-1-(cyclopropylsulfonyl)-6-methylpiperazin-2-yl]ethyl}-3-fluorophenyl)-β-(3,5-difluorophenyl)-4-fluoro-L-phenylalaninamide;

(βR)-4-chloro-N-(2-{2-[(2S,6S)-6-ethyl-1-(methylsulfonyl)piperazin-2-yl]ethyl}-3-fluorophenyl)-β-(tetrahydro-2H-pyran-4-yl)-L-phenylalaninamide;

(βR)-4-chloro-N-(2-{2-[(2S,6S)-6-ethyl-1-(methylsulfonyl)piperazin-2-yl]ethyl}-3-fluorophenyl)-Nα-(methoxycarbonyl)-β-(tetrahydro-2H-pyran-4-yl)-L-phenylalaninamide;

(βS)-N-(2-{2-[(2S)-6-[(benzyloxy)methyl]-1-(methylsulfonyl)piperazin-2-yl]ethyl}-3-fluorophenyl)-4-chloro-β-(4-fluorobenzyl)-L-phenylalaninamide;

(βS)-β-(3,5-difluorophenyl)-4-fluoro-N-(5-fluoro-4-{2-[(2S,6R)-6-methyl-1-{[4-(trifluoromethoxy)phenyl]sulfonyl}piperazin-2-yl]ethyl}pyridin-3-yl)-L-phenylalaninamide;

(βS)-N-[2-(2-{(2S)-1-(cyclopropylsulfonyl)-6-[(1-methylethoxy)methyl]piperazin-2-yl}ethyl)-3-fluorophenyl]-β-(3,5-difluorophenyl)-4-fluoro-L-phenylalaninamide;

(βS)-N-[2-(2-{(2S,6S)-1-[(2-chlorophenyl)sulfonyl]-6-methylpiperazin-2-yl}ethyl)-3-fluorophenyl]-β-(3,5-difluorophenyl)-4-fluoro-L-phenylalaninamide;

(βS)-N-[2-(2-{(2S,6R)-1-[(2-chlorophenyl)sulfonyl]-6-methylpiperazin-2-yl}ethyl)-3-fluorophenyl]-β-(3,5-difluorophenyl)-4-fluoro-L-phenylalaninamide;

(βS)-N-[2-(2-{(2S,6S)-1-[(2-chlorophenyl)sulfonyl]-6-methylpiperazin-2-yl}ethyl)-3-fluorophenyl]-β-(3,5-difluorophenyl)-4-fluoro-Nα-(methoxycarbonyl)-L-phenylalaninamide;

(βS)-N-[2-(2-{(2S,6R)-1-[(2-chlorophenyl)sulfonyl]-6-methylpiperazin-2-yl}ethyl)-3-fluorophenyl]-β-(3,5-difluorophenyl)-4-fluoro-Nα-(methoxycarbonyl)-L-phenylalaninamide;

(βS)-4-chloro-β-(4-fluorobenzyl)-N-(3-fluoro-2-{2-[(2S,6S)-6-methyl-1-(methylsulfonyl)piperazin-2-yl]ethyl}phenyl)-Nα-(methoxy carbonyl)-L-phenylalaninamide;

(βS)-β-(3,5-difluorophenyl)-4-fluoro-N-(3-fluoro-2-{2-[(2S,6S)-6-methyl-1-{[4-(trifluoromethoxy)phenyl]sulfonyl}piperazin-2-yl]ethyl}phenyl)-Nα-(methoxycarbonyl)-L-phenylalaninamide;

(βS)-β-(3,5-difluorophenyl)-4-fluoro-N-[5-fluoro-4-(2-{(2S,6S)-1-[(2-methoxyphenyl)sulfonyl]-6-methylpiperazin-2-yl}ethyl)pyridin-3-yl]-L-phenylalaninamide;

(βS)-4-chloro-N-(3-fluoro-2-{2-[(2S,6S)-6-methyl-1-(phenylsulfonyl)piperazin-2-yl]ethyl}phenyl)-β-(5-fluoropyridin-3-yl)-L-phenylalaninamide;

(βS)-N-[2-(2-{(2S)-1-(cyclopropylsulfonyl)-6-[(1-methylethoxy)methyl]piperazin-2-yl}ethyl)-3-fluorophenyl]-β-(3,5-difluorophenyl)-4-fluoro-Nα-(methoxycarbonyl)-L-phenylalaninamide;

(βS)-β-(3,5-difluorophenyl)-4-fluoro-N-[3-fluoro-2-(2-{(2S,6S)-1-[(2-methoxyphenyl)sulfonyl]-6-methylpiperazin-2-yl}ethyl)phenyl]-L-phenylalaninamide;

(βS)-β-(3,5-difluorophenyl)-4-fluoro-N-[3-fluoro-2-(2-{(2S,6R)-1-[(2-methoxyphenyl)sulfonyl]-6-methylpiperazin-2-yl}ethyl)phenyl]-L-phenylalaninamide;

(βS)-β-(3,5-difluorophenyl)-4-fluoro-N-[3-fluoro-2-(2-{(2S,6S)-1-[(2-methoxyphenyl)sulfonyl]-6-methylpiperazin-2-yl}ethyl)phenyl]-Nα-(methoxy carbonyl)-L-phenylalaninamide;

(βS)-N-(2-{2-[(2S)-1-(cyclopropylsulfonyl)-6-(methoxymethyl)piperazin-2-yl]ethyl}-3-fluorophenyl)-β-(3,5-difluorophenyl)-4-fluoro-L-phenylalaninamide;

(βR)-β-(3-chlorophenyl)-3-fluoro-N-(3-fluoro-2-{2-[(2S)-6-[(1-methylethoxy)methyl]-1-(methylsulfonyl)piperazin-2-yl]ethyl}phenyl)-L-phenylalaninamide;

(βS)-β-(3,5-difluorophenyl)-4-fluoro-N-(5-fluoro-4-{2-[(2S,6S)-6-methyl-1-{[4-(trifluoromethoxy)phenyl]sulfonyl}piperazin-2-yl]ethyl}pyridin-3-yl)-L-phenylalaninamide;

(βS)-β-(3,5-difluorophenyl)-4-fluoro-N-[5-fluoro-4-(2-{(2S,6S)-1-[(4-methoxyphenyl)sulfonyl]-6-methylpiperazin-2-yl}ethyl)pyridin-3-yl]-L-phenylalaninamide;

(βS)-N-[4-(2-{(2S,6S)-1-[(2-chlorophenyl)sulfonyl]-6-methylpiperazin-2-yl}ethyl)-5-fluoropyridin-3-yl]-β-(3,5-difluorophenyl)-4-fluoro-L-phenylalaninamide;

(βS)-β-(3,5-difluorophenyl)-4-fluoro-N-[5-fluoro-4-(2-{(2S,6S)-1-[(4-methoxyphenyl)sulfonyl]-6-methylpiperazin-2-yl}ethyl)pyridin-3-yl]-Nα-(methoxycarbonyl)-L-phenylalaninamide;

(βS)-β-(3,5-difluorophenyl)-4-fluoro-N-(5-fluoro-4-{2-[(2S,6R)-6-methyl-1-{[4-(trifluoromethoxy)phenyl]sulfonyl}piperazin-2-yl]ethyl}pyridin-3-yl)-Nα-(methoxy carbonyl)-L-phenylalaninamide;

(βS)-β-(3,5-difluorophenyl)-4-fluoro-N-(3-fluoro-2-{2-[(2S,6R)-6-methyl-1-{[4-(trifluoromethoxy)phenyl]sulfonyl}piperazin-2-yl]ethyl}phenyl)-Nα-(methoxycarbonyl)-L-phenylalaninamide;

(βR)-3-chloro-N-[3-fluoro-2-(2-{(2S,6S)-1-[(4-methoxyphenyl)sulfonyl]-6-methylpiperazin-2-yl}ethyl)phenyl]-β-(1-methylethyl)-L-phenylalaninamide;

(βR)-3-chloro-N-[3-fluoro-2-(2-{(2S,6S)-1-[(4-methoxyphenyl)sulfonyl]-6-methylpiperazin-2-yl}ethyl)phenyl]-Nα-(methoxycarbonyl)-β-(1-methylethyl)-L-phenylalaninamide;

(βS)-β-(3,5-difluorophenyl)-4-fluoro-N-[3-fluoro-2-(2-{(2S,6S)-1-[(4-methoxyphenyl)sulfonyl]-6-methylpiperazin-2-yl}ethyl)phenyl]-L-phenylalaninamide;

(βS)-β-(3,5-difluorophenyl)-4-fluoro-N-[3-fluoro-2-(2-{(2S,6S)-1-[(4-methoxyphenyl)sulfonyl]-6-methylpiperazin-2-yl}ethyl)phenyl]-Nα-(methoxy carbonyl)-L-phenylalaninamide;

(βS)-3-chloro-N-(3-fluoro-2-{2-[(2S,6S)-6-methyl-1-(phenylsulfonyl)piperazin-2-yl]ethyl}phenyl)-β-(5-fluoropyridin-3-yl)-Nα-(methoxycarbonyl)-L-phenylalaninamide;

(βR)-4-chloro-N-(5-fluoro-4-{2-[(2S,6R)-6-methyl-1-(phenylsulfonyl)piperazin-2-yl]ethyl}pyridin-3-yl)-β-(1-methylethyl)-L-phenylalaninamide;

(βS)-β-(3,5-difluorophenyl)-4-fluoro-N-(3-fluoro-2-{2-[(2S,6R)-6-methyl-1-{[4-(trifluoromethoxy)phenyl]sulfonyl}piperazin-2-yl]ethyl}phenyl)-L-phenylalaninamide;

(βS)-N-[2-(2-{(2S)-1-(cyclopropylsulfonyl)-6-[(1-methylethoxy)methyl]piperazin-2-yl}ethyl)-3-fluorophenyl]-β-(3,5-difluorophenyl)-4-fluoro-L-phenylalaninamide;

(βS)-N-(2-{2-[(2S,6R)-1-(cyclopropylsulfonyl)-6-methylpiperazin-2-yl]ethyl}-3-fluorophenyl)-β-(3,5-difluorophenyl)-4-fluoro-Nα-(methoxy carbonyl)-L-phenylalaninamide;

(βS)-β-(3,5-difluorophenyl)-4-fluoro-N-(3-fluoro-2-{2-[(2S,6S)-6-methyl-1-(methylsulfonyl)piperazin-2-yl]ethyl}phenyl)-L-phenylalaninamide;

(βS)-β-(3,5-difluorophenyl)-4-fluoro-N-(3-fluoro-2-{2-[(2S,6S)-6-methyl-1-(methylsulfonyl)piperazin-2-yl]ethyl}phenyl)-Nα-(methoxy carbonyl)-L-phenylalaninamide;

(βR)-4-chloro-N-(3-fluoro-2-{2-[(2S)-6-(methoxymethyl)-1-(methylsulfonyl)piperazin-2-yl]ethyl}phenyl)-β-(tetrahydro-2H-pyran-4-yl)-L-phenylalaninamide;

(βS)-3-chloro-N-(3-fluoro-2-{2-[(2S,6R)-6-methyl-1-(phenylsulfonyl)piperazin-2-yl]ethyl}phenyl)-(3-(5-fluoropyridin-3-yl)-L-phenylalaninamide;

(βS)-β-(3,5-difluorophenyl)-N-(2-{2-[(2S,6S)-6-ethyl-1-(methylsulfonyl)piperazin-2-yl]ethyl}-3-fluorophenyl)-4-fluoro-L-phenylalaninamide;

(βS)-β-(3,5-difluorophenyl)-N-(2-{2-[(2S,6R)-6-ethyl-1-(methylsulfonyl)piperazin-2-yl]ethyl}-3-fluorophenyl)-4-fluoro-L-phenylalaninamide;

(βR)-4-chloro-N-(2-{2-[(2S,6R)-1-{[4-(difluoromethyl)phenyl]sulfonyl}-6-methylpiperazin-2-yl]ethyl}-3-fluorophenyl)-β-(tetrahydro-2H-pyran-4-yl)-L-phenylalaninamide;

(βR)-4-chloro-N-(2-{2-[(2S,6R)-6-ethyl-1-(methylsulfonyl)piperazin-2-yl]ethyl}-3-fluorophenyl)-β-(tetrahydro-2H-pyran-4-yl)-L-phenylalaninamide;

(βR)-4-chloro-N-(2-{2-[(2S,6R)-1-{[4-(difluoromethyl)phenyl]sulfonyl}-6-methylpiperazin-2-yl]ethyl}-3-fluorophenyl)-Nα-(methoxycarbonyl)-β-(tetrahydro-2H-pyran-4-yl)-L-phenylalaninamide;

methyl ((1R,2S)-1-(4-chlorophenyl)-3-((2-(2-((2S,6R)-6-ethyl-1-(phenylsulfonyl)piperazin-2-yl)ethyl)-3-fluorophenyl)amino)-3-oxo-1-(tetrahydro-2H-pyran-4-yl)propan-2-yl)carbamate;

methyl ((1R,2S)-1-(4-chlorophenyl)-3-((2-(2-((2S,6S)-6-ethyl-1-(phenylsulfonyl)piperazin-2-yl)ethyl)-3-fluorophenyl)amino)-3-oxo-1-(tetrahydro-2H-pyran-4-yl)propan-2-yl)carbamate;

(βS)-β-(3,5-difluorophenyl)-N-(2-{2-[(2S,6S)-6-ethyl-1-(methylsulfonyl)piperazin-2-yl]ethyl}-3-fluorophenyl)-4-fluoro-Nα-(methoxycarbonyl)-L-phenylalaninamide;

(βS)-β-(3,5-difluorophenyl)-N-(2-{2-[(2S,6R)-6-ethyl-1-(methylsulfonyl)piperazin-2-yl]ethyl}-3-fluorophenyl)-4-fluoro-Nα-(methoxycarbonyl)-L-phenylalaninamide;

(βR)-4-chloro-N-[2-(2-{(2S,6S)-1-[(2-chlorophenyl)sulfonyl]-6-methylpiperazin-2-yl}ethyl)-3-fluorophenyl]-β-(1-methylethyl)-L-phenylalaninamide;

(βS)-N-[4-(2-{(2S,6S)-1-[(2-chlorophenyl)sulfonyl]-6-methylpiperazin-2-yl}ethyl)-5-fluoropyridin-3-yl]-β-(3,5-difluorophenyl)-4-fluoro-Nα-(methoxycarbonyl)-L-phenylalaninamide;

(βR)-4-chloro-N-[4-(2-{(2S,6S)-1-[(4-chlorophenyl)sulfonyl]-6-methylpiperazin-2-yl}ethyl)-5-fluoropyridin-3-yl]-β-(tetrahydro-2H-pyran-4-yl)-L-phenylalaninamide;

(βR)-4-chloro-N-(5-fluoro-4-{2-[(2S,6S)-6-methyl-1-(phenylsulfonyl)piperazin-2-yl]ethyl}pyridin-3-yl)-Nα-(methoxycarbonyl)-β-(tetrahydro-2H-pyran-4-yl)-L-phenylalaninamide;

methyl {(1S)-1-[4-(4-chlorophenyl)tetrahydro-2H-pyran-4-yl]-2-[(3-fluoro-2-{2-[(2S,6R)-6-methyl-1-(phenylsulfonyl)piperazin-2-yl]ethyl}phenyl)amino]-2-oxoethyl}carbamate;

methyl {(1S)-1-[4-(4-chlorophenyl)tetrahydro-2H-pyran-4-yl]-2-[(3-fluoro-2-{2-[(2S,6S)-6-methyl-1-(phenylsulfonyl)piperazin-2-yl]ethyl}phenyl)amino]-2-oxoethyl}carbamate;

(βR)-4-chloro-N-(5-fluoro-4-{2-[(2S,6S)-6-methyl-1-(phenylsulfonyl)piperazin-2-yl]ethyl}pyridin-3-yl)-β-(tetrahydro-2H-pyran-4-yl)-L-phenylalaninamide;

(2S)-2-amino-2-[4-(3,5-difluorophenyl)tetrahydro-2H-pyran-4-yl]-N-(3-fluoro-2-{2-[(2S,6S)-6-methyl-1-(phenylsulfonyl)piperazin-2-yl]ethyl}phenyl)ethanamide;

(βR)-4-chloro-N-(5-fluoro-4-{2-[(2S,6R)-6-methyl-1-(phenylsulfonyl)piperazin-2-yl]ethyl}pyridin-3-yl)-Nα-(methoxycarbonyl)-β-(tetrahydro-2H-pyran-4-yl)-L-phenylalaninamide;

(βR)-4-chloro-N-(5-fluoro-4-{2-[(2S,6R)-6-methyl-1-(phenylsulfonyl)piperazin-2-yl]ethyl}pyridin-3-yl)-β-(tetrahydro-2H-pyran-4-yl)-L-phenylalaninamide;

(βR)-4-chloro-N-[4-(2-{(2S,6R)-1-[(4-chlorophenyl)sulfonyl]-6-methylpiperazin-2-yl}ethyl)-5-fluoropyridin-3-yl]-Nα-(methoxycarbonyl)-β-(tetrahydro-2H-pyran-4-yl)-L-phenylalaninamide;

(βR)-4-chloro-N-[4-(2-{(2S,6S)-1-[(4-chlorophenyl)sulfonyl]-6-methylpiperazin-2-yl}ethyl)-5-fluoropyridin-3-yl]-Nα-(methoxycarbonyl)-β-(tetrahydro-2H-pyran-4-yl)-L-phenylalaninamide;

(βR)-3,5-difluoro-N-(3-fluoro-2-{2-[(2S,6R)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide;

(βR)-3,5-difluoro-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide;

methyl {(1S)-1-[4-(3,5-difluorophenyl)tetrahydro-2H-pyran-4-yl]-2-[(3-fluoro-2-{2-[(2S,6R)-6-methyl-1-(phenylsulfonyl)piperazin-2-yl]ethyl}phenyl)amino]-2-oxoethyl}carbamate;

methyl {(1S)-1-[4-(3,5-difluorophenyl)tetrahydro-2H-pyran-4-yl]-2-[(3-fluoro-2-{2-[(2S,6S)-6-methyl-1-(phenylsulfonyl)piperazin-2-yl]ethyl}phenyl)amino]-2-oxoethyl}carbamate;

(2S)-2-amino-2-[4-(3,5-difluorophenyl)tetrahydro-2H-pyran-4-yl]-N-(3-fluoro-2-{2-[(2S,6R)-6-methyl-1-(phenylsulfonyl)piperazin-2-yl]ethyl}phenyl)ethanamide;

(βR)-3,4-difluoro-N-(3-fluoro-2-{2-[(2S,6R)-6-methyl-1-(phenylsulfonyl)piperazin-2-yl]ethyl}phenyl)-β-(tetrahydro-2H-pyran-4-yl)-L-phenylalaninamide;

(βR)-3,4-difluoro-N-(3-fluoro-2-{2-[(2S,6S)-6-methyl-1-(phenylsulfonyl)piperazin-2-yl]ethyl}phenyl)-β-(tetrahydro-2H-pyran-4-yl)-L-phenylalaninamide;

methyl {(1S)-1-[4-(3,4-difluorophenyl)tetrahydro-2H-pyran-4-yl]-2-[(3-fluoro-2-{2-[(2S,6R)-6-methyl-1-(phenylsulfonyl)piperazin-2-yl]ethyl}phenyl)amino]-2-oxoethyl}carbamate;

(2S)-2-amino-2-[4-(3,4-difluorophenyl)tetrahydro-2H-pyran-4-yl]-N-(3-fluoro-2-{2-[(2S,6R)-6-methyl-1-(phenylsulfonyl)piperazin-2-yl]ethyl}phenyl)ethanamide;

(2S)-2-amino-2-[4-(3,4-difluorophenyl)tetrahydro-2H-pyran-4-yl]-N-(3-fluoro-2-{2-[(2S,6S)-6-methyl-1-(phenylsulfonyl)piperazin-2-yl]ethyl}phenyl)ethanamide;

(βR)-3,4-difluoro-N-(3-fluoro-2-{2-[(2S,6R)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide;

(βR)-3,5-difluoro-N-(3-fluoro-2-{2-[(2S,6S)-6-methyl-1-(phenylsulfonyl)piperazin-2-yl]ethyl}phenyl)-β-(tetrahydro-2H-pyran-4-yl)-L-phenylalaninamide;

(βR)-3,4-difluoro-N-(3-fluoro-2-{2-[(2S,6S)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide;

(βR)-3,5-difluoro-N-(3-fluoro-2-{2-[(2S,6S)-6-methyl-1-(phenylsulfonyl)piperazin-2-yl]ethyl}phenyl)-Nα-(methoxycarbonyl)-β-(tetrahydro-2H-pyran-4-yl)-L-phenylalaninamide;
methyl {(1S)-1-[4-(3,4-difluorophenyl)tetrahydro-2H-pyran-4-yl]-2-[(3-fluoro-2-{2-[(2S,6S)-6-methyl-1-(phenylsulfonyl)piperazin-2-yl]ethyl}phenyl)amino]-2-oxoethyl}carbamate;
(βR)-4-chloro-N-[4-(2-{(2S,6R)-1-[(4-chlorophenyl)sulfonyl]-6-methylpiperazin-2-yl}ethyl)-5-fluoropyridin-3-yl]-β-(tetrahydro-2H-pyran-4-yl)-L-phenylalaninamide;
methyl ((S)-1-((2R,4r,6S)-4-(4-chlorophenyl)-2,6-dimethyltetrahydro-2H-pyran-4-yl)-2-((3-fluoro-2-(2-((2S,6S)-6-methyl-1-(phenylsulfonyl)piperazin-2-yl)ethyl)phenyl)amino)-2-oxoethyl)carbamate;
(S)-2-amino-2-((2R,4r,6S)-4-(4-chlorophenyl)-2,6-dimethyltetrahydro-2H-pyran-4-yl)-N-(3-fluoro-2-(2-((2S,6S)-6-methyl-1-(phenylsulfonyl)piperazin-2-yl)ethyl)phenyl)acetamide;
(S)-2-amino-2-((2R,4r,6S)-4-(4-chlorophenyl)-2,6-dimethyltetrahydro-2H-pyran-4-yl)-N-(3-fluoro-2-(2-((2S,6R)-6-methyl-1-(phenylsulfonyl)piperazin-2-yl)ethyl)phenyl)acetamide;
(3S)-N-[4-(2-{(2S)-1-[(cyclopropylmethyl)sulfonyl]piperazin-2-yl}ethyl)-5-fluoropyridin-3-yl]-3-(3,5-difluorophenyl)-3-(4-fluorophenyl)propanamide;
(3S)-N-(4-{2-[(2S)-1-(cyclopropylsulfonyl)piperazin-2-yl]ethyl}-5-fluoropyridin-3-yl)-3-(3,5-difluorophenyl)-3-(4-fluorophenyl)propanamide;
(3S)-3-(3,5-difluorophenyl)-3-(4-fluorophenyl)-N-(5-fluoro-4-{2-[(2S)-1-(pyridin-2-ylsulfonyl)piperazin-2-yl]ethyl}pyridin-3-yl)propanamide;
(3S)-3-(3,5-difluorophenyl)-3-(4-fluorophenyl)-N-(5-fluoro-4-{2-[(2S)-1-(pyridin-3-ylsulfonyl)piperazin-2-yl]ethyl}pyridin-3-yl)propanamide;
(3S)-3-(3,5-difluorophenyl)-N-[5-fluoro-4-(2-{(2S)-1-[(1-methyl-1H-pyrazol-3-yl)sulfonyl]piperazin-2-yl}ethyl)pyridin-3-yl]-3-(4-fluorophenyl)propanamide;
(3S)-N-[4-(2-{(2S)-1-[(6-aminopyridin-3-yl)sulfonyl]piperazin-2-yl}ethyl)-5-fluoropyridin-3-yl]-3-(3,5-difluorophenyl)-3-(4-fluorophenyl)propanamide;
(3S)-3-(3,5-difluorophenyl)-N-[5-fluoro-4-(2-{(2S)-1-[(3-oxo-3,4-dihydro-2H-1,4-benzoxazin-6-yl)sulfonyl]piperazin-2-yl}ethyl)pyridin-3-yl]-3-(4-fluorophenyl)propanamide;
(3S)-N-(4-{2-[(2S)-1-{[2-(acetylamino)-5-methyl-1,3-thiazol-4-yl]sulfonyl}piperazin-2-yl]ethyl}-5-fluoropyridin-3-yl)-3-(3,5-difluorophenyl)-3-(4-fluorophenyl)propanamide;
(3S)-3-(3,5-difluorophenyl)-3-(4-fluorophenyl)-N-(5-fluoro-4-{2-[(2S)-1-{[4-(trifluoromethyl)benzyl]sulfonyl}piperazin-2-yl]ethyl}pyridin-3-yl)propanamide;
(3S)-3-(3,5-difluorophenyl)-3-(4-fluorophenyl)-N-[5-fluoro-4-(2-{(2S)-1-[(5-pyridin-2-ylthiophen-2-yl)sulfonyl]piperazin-2-yl}ethyl)pyridin-3-yl]propanamide;
ethyl 3-[5-({(2S)-2-[2-(3-{[(3S)-3-(3,5-difluorophenyl)-3-(4-fluorophenyl)propanoyl]amino}-5-fluoropyridin-4-yl)ethyl]piperazin-1-yl}sulfonyl)thiophen-2-yl]-1,2,4-oxadiazole-5-carboxylate;
(3S)-3-(3,5-difluorophenyl)-N-(5-fluoro-4-{2-[(2S)-1-{[4-(methylsulfonyl)phenyl]sulfonyl}piperazin-2-yl]ethyl}pyridin-3-yl)-3-(4-fluorophenyl)propanamide;
(3S)-3-(3,5-difluorophenyl)-3-(4-fluorophenyl)-N-(5-fluoro-4-{2-[(2S)-1-{[4-(trifluoromethoxy)phenyl]sulfonyl}piperazin-2-yl]ethyl}pyridin-3-yl)propanamide;
(3S)-3-(3,5-difluorophenyl)-3-(4-fluorophenyl)-N-[5-fluoro-4-(2-{(2S)-1-[(2,2,2-trifluoroethyl)sulfonyl]piperazin-2-yl}ethyl)pyridin-3-yl]propanamide;
(3S)-3-(3,5-difluorophenyl)-N-[5-fluoro-4-(2-{(2S)-1-[(1-methyl-1H-pyrazol-4-yl)sulfonyl]piperazin-2-yl}ethyl)pyridin-3-yl]-3-(4-fluorophenyl)propanamide;
(3S)-3-(3,5-difluorophenyl)-3-(4-fluorophenyl)-N-(5-fluoro-4-{2-[(2S)-1-(propylsulfonyl)piperazin-2-yl]ethyl}pyridin-3-yl)propanamide;
(3S)-N-(4-{2-[(2S)-1-{[2-(acetylamino)-4-methyl-1,3-thiazol-5-yl]sulfonyl}piperazin-2-yl]ethyl}-5-fluoropyridin-3-yl)-3-(3,5-difluorophenyl)-3-(4-fluorophenyl)propanamide;
(3S)-3-(3,5-difluorophenyl)-N-[5-fluoro-4-(2-{(2S)-1-[(4-formylphenyl)sulfonyl]piperazin-2-yl}ethyl)pyridin-3-yl]-3-(4-fluorophenyl)propanamide;
(3S)-N-(4-{2-[(2S)-1-{[3-(acetylamino)phenyl]sulfonyl}piperazin-2-yl]ethyl}-5-fluoropyridin-3-yl)-3-(3,5-difluorophenyl)-3-(4-fluorophenyl)propanamide;
(3S)-3-(3,5-difluorophenyl)-3-(4-fluorophenyl)-N-(5-fluoro-4-{2-[(2S)-1-(quinolin-3-ylsulfonyl)piperazin-2-yl]ethyl}pyridin-3-yl)propanamide;
(3S)-3-(3,5-difluorophenyl)-N-(4-{2-[(2S)-1-(3,4-dihydroisoquinolin-2(1H)-ylsulfonyl)piperazin-2-yl]ethyl}-5-fluoropyridin-3-yl)-3-(4-fluorophenyl)propanamide;
(3S)-3-(3,5-difluorophenyl)-3-(4-fluorophenyl)-N-(5-fluoro-4-{2-[(2S)-1-(pyrrolidin-1-ylsulfonyl)piperazin-2-yl]ethyl}pyridin-3-yl)propanamide;
(3S)-3-(3,5-difluorophenyl)-N-[5-fluoro-4-(2-{(2S)-1-[(1-methylethyl)sulfamoyl]piperazin-2-yl}ethyl)pyridin-3-yl]-3-(4-fluorophenyl)propanamide;
(3S)-3-(3,5-difluorophenyl)-3-(4-fluorophenyl)-N-(5-fluoro-4-{2-[(2S)-1-(piperidin-1-ylsulfonyl)piperazin-2-yl]ethyl}pyridin-3-yl)propanamide;
(3S)-3-(3,5-difluorophenyl)-N-(5-fluoro-4-{2-[(2S)-1-(morpholin-4-ylsulfonyl)piperazin-2-yl]ethyl}pyridin-3-yl)-3-(4-fluorophenyl)propanamide;
(3S)-3-(3,5-difluorophenyl)-N-(5-fluoro-4-{2-[(2S)-1-{[(3R)-3-fluoropyrrolidin-1-yl]sulfonyl}piperazin-2-yl]ethyl}pyridin-3-yl)-3-(4-fluorophenyl)propanamide;
(3S)-3-(3,5-difluorophenyl)-N-(5-fluoro-4-{2-[(2S)-1-{[(3S)-3-fluoropyrrolidin-1-yl]sulfonyl}piperazin-2-yl]ethyl}pyridin-3-yl)-3-(4-fluorophenyl)propanamide;
(3S)-3-(3,5-difluorophenyl)-N-[4-(2-{(2S)-1-[(3,3-difluoropyrrolidin-1-yl)sulfonyl]piperazin-2-yl}ethyl)-5-fluoropyridin-3-yl]-3-(4-fluorophenyl)propanamide;
(3S)-3-(3,5-difluorophenyl)-N-[4-(2-{(2S)-1-[(4,4-difluoropiperidin-1-yl)sulfonyl]piperazin-2-yl}ethyl)-5-fluoropyridin-3-yl]-3-(4-fluorophenyl)propanamide;
(3S)-3-(3,5-difluorophenyl)-N-[5-fluoro-4-(2-{(2S)-1-[(4-fluoropiperidin-1-yl)sulfonyl]piperazin-2-yl}ethyl)pyridin-3-yl]-3-(4-fluorophenyl)propanamide;
(3S)-3-(3,5-difluorophenyl)-N-[4-(2-{(2S)-1-[(3,3-difluoropiperidin-1-yl)sulfonyl]piperazin-2-yl}ethyl)-5-fluoropyridin-3-yl]-3-(4-fluorophenyl)propanamide;
(3S)-3-(3,5-difluorophenyl)-N-[5-fluoro-4-(2-{(2S)-1-[(3-fluoropiperidin-1-yl)sulfonyl]piperazin-2-yl}ethyl)pyridin-3-yl]-3-(4-fluorophenyl)propanamide;

(3S)-3-(3,5-difluorophenyl)-N-(5-fluoro-4-{2-[(2S)-1-({4-[(methylsulfonyl)amino]piperidin-1-yl}sulfonyl)piperazin-2-yl]ethyl}pyridin-3-yl)-3-(4-fluorophenyl)propanamide;

(3S)-N-(4-{2-[(2S)-1-{[4-(acetylamino)piperidin-1-yl]sulfonyl}piperazin-2-yl]ethyl}-5-fluoropyridin-3-yl)-3-(3,5-difluorophenyl)-3-(4-fluorophenyl)propanamide;

(3S)-3-(3,5-difluorophenyl)-N-(5-fluoro-4-{2-[(2S)-1-{[4-(methylsulfonyl)piperidin-1-yl]sulfonyl}piperazin-2-yl]ethyl}pyridin-3-yl)-3-(4-fluorophenyl)propanamide;

(3S)-3-(3,5-difluorophenyl)-N-(5-fluoro-4-{2-[(2S)-1-{[2-(2-methylpropyl)pyrrolidin-1-yl]sulfonyl}piperazin-2-yl]ethyl}pyridin-3-yl)-3-(4-fluorophenyl)propanamide;

(3S)-3-(3,5-difluorophenyl)-3-(4-fluorophenyl)-N-(5-fluoro-4-{2-[(2S)-1-({(3R)-3-[(trifluoroacetyl)amino]pyrrolidin-1-yl}sulfonyl)piperazin-2-yl]ethyl}pyridin-3-yl)propanamide;

(3S)-N-[4-(2-{(2S)-1-[(3-chloro-2-fluoropropyl)sulfamoyl]piperazin-2-yl})-5-fluoropyridin-3-yl]-3-(3,5-difluorophenyl)-3-(4-fluorophenyl)propanamide;

(3S)-N-(4-{2-[(2S)-1-(diethylsulfamoyl)piperazin-2-yl]ethyl}-5-fluoropyridin-3-yl)-3-(3,5-difluorophenyl)-3-(4-fluorophenyl)propanamide;

(3S)-3-(3,5-difluorophenyl)-3-(4-fluorophenyl)-N-(5-fluoro-4-{2-[(2S)-1-(piperidin-1-ylcarbonyl)piperazin-2-yl]ethyl}pyridin-3-yl)propanamide;

(2S)-2-[2-(3-{[(3S)-3-(3,5-difluorophenyl)-3-(4-fluorophenyl)propanoyl]amino}-5-fluoropyridin-4-yl)ethyl]-N-phenylpiperazine-1-carboxamide;

(3S)-3-(3,5-difluorophenyl)-N-(5-fluoro-4-{2-[(2S)-1-(phenoxyacetyl)piperazin-2-yl]ethyl}pyridin-3-yl)-3-(4-fluorophenyl)propanamide;

(3S)-3-(3,5-difluorophenyl)-3-(4-fluorophenyl)-N-(5-fluoro-4-{2-[(2S)-1-{[4-(trifluoromethoxy)phenyl]carbonyl}piperazin-2-yl]ethyl}pyridin-3-yl)propanamide;

(3S)-N-[4-(2-{(2S)-1-[(2,2-difluoro-1,3-benzodioxol-5-yl)carbonyl]piperazin-2-yl}ethyl)-5-fluoropyridin-3-yl]-3(3,5-difluorophenyl)-3-(4-fluorophenyl)propanamide;

(3S)-3-(3,5-difluorophenyl)-3-(4-fluorophenyl)-N-(5-fluoro-4-{2-[(2S)-1-{[3-(trifluoromethoxy)phenyl]carbonyl}piperazin-2-yl]ethyl}pyridin-3-yl)propanamide;

(3S)-3-(3,5-difluorophenyl)-N-(5-fluoro-4-{2-[(2S)-1-(2-phenoxypropanoyl)piperazin-2-yl]ethyl}pyridin-3-yl)-3-(4-fluorophenyl)propanamide;

(3S)-3-(3,5-difluorophenyl)-N-(5-fluoro-4-{2-[(2S)-1-(3-phenoxypropanoyl)piperazin-2-yl]ethyl}pyridin-3-yl)-3-(4-fluorophenyl)propanamide;

(3S)-N-[4-(2-{(2S)-1-[(4-tert-butylphenoxy)acetyl]piperazin-2-yl})-5-fluoropyridin-3-yl]-3-(3,5-difluorophenyl)-3-(4-fluorophenyl)propanamide;

Methyl ((S)-1,1-bis(4-fluorophenyl)-3-oxo-3-(((1S,2R)-2-(2-((S)-1-(phenylsulfonyl)piperazin-2-yl)ethyl)cyclopentyl)amino)propan-2-yl)carbamate;

Methyl ((S)-1,1-bis(4-fluorophenyl)-3-oxo-3-(((1R,2S)-2-(2-((S)-1-(phenylsulfonyl)piperazin-2-yl)ethyl)cyclopentyl)amino)propan-2-yl)carbamate;

4-fluoro-beta-(4-fluorophenyl)-Nalpha-(methoxycarbonyl)-N-(2-{2-[(2S)-1-(methylsulfonyl)piperazin-2-yl]ethyl}cyclopentyl)-L-phenylalaninamide;

4-fluoro-beta-(4-fluorophenyl)-N-[(1R,2S)-2-{2-[(2S)-1-(phenylsulfonyl)piperazin-2-yl]ethyl}cyclohexyl]-L-phenylalaninamide;

methyl ((S)-1,1-bis(4-fluorophenyl)-3-oxo-3-(((1S,2R)-2-(2-((S)-1-(phenylsulfonyl)piperazin-2-yl)ethyl)cyclohexyl)amino)propan-2-yl)carbamate;

methyl ((1R,2S)-1-(4-chlorophenyl)-3-oxo-3-(((1S,2R)-2-(2-((S)-1-(phenylsulfonyl)piperazin-2-yl)ethyl)cyclohexyl)amino)-1-(tetrahydro-2H-pyran-4-yl)propan-2-yl)carbamate;

methyl ((1R,2S)-1-(4-chlorophenyl)-3-oxo-3-((2-(2-((S)-1-(phenylsulfonyl)piperazin-2-yl)ethyl)cyclopentyl)amino)-1-(tetrahydro-2H-pyran-4-yl)propan-2-yl)carbamate;

Methyl ((2R)-1,1-bis(4-fluorophenyl)-3-((4-hydroxy-2-(2-((S)-1-(phenylsulfonyl)piperazin-2-yl)ethyl)cyclopentyl)amino)-3-oxopropan-2-yl)carbamate;

Methyl ((2R)-1-((4,4-difluoro-2-(2-((S)-1-(phenylsulfonyl)piperazin-2-yl)ethyl)cyclopentyl)amino)-3,3-bis(4-fluorophenyl)-1-oxopropan-2-yl)carbamate;

(betaS)-4-chloro-N-(4,4-difluoro-2-{2-[(2S)-1-(phenylsulfonyl)piperazin-2-yl]ethyl}cyclopentyl)-beta-(tetrahydro-2H-pyran-4-yl)-L-phenylalaninamide;

(betaS)-4-chloro-N-(4,4-difluoro-2-{2-[(2S)-1-(phenylsulfonyl)piperazin-2-yl]ethyl}cyclopentyl)-beta-(tetrahydro-2H-pyran-4-yl)-L-phenylalaninamide;

Methyl ((2R)-1,1-bis(4-fluorophenyl)-3-oxo-3-((2-(2-((S)-1-(phenylsulfonyl)piperazin-2-yl)ethyl)cyclopropyl)amino)propan-2-yl)carbamate;

(S)-N-(3-fluoro-2-(2-((S)-1-(phenylsulfonyl)piperazin-2-yl)ethyl)phenyl)-2-hydroxy-3,3-diphenylpropanamide;

(R)-N-(3-fluoro-2-(2-((S)-1-(phenylsulfonyl)piperazin-2-yl)ethyl)phenyl)-2-hydroxy-3,3-diphenylpropanamide;

(S)-2-amino-N-(3-fluoro-2-(2-((S)-4-(phenylsulfonyl)-4,7-diazaspiro[2.5]octan-5-yl)ethyl)phenyl)-3,3-bis(4-fluorophenyl)propanamide;

(S)-2-amino-N-(3-fluoro-2-(2-((S)-4-(methylsulfonyl)-4,7-diazaspiro[2.5]octan-5-yl)ethyl)phenyl)-3,3-bis(4-fluorophenyl)propanamide;

(S)-2-amino-N-(3-fluoro-2-(2-((S)-4-(2-phenoxyacetyl)-4,7-diazaspiro[2.5]octan-5-yl)ethyl)phenyl)-3,3-bis(4-fluorophenyl)propanamide;

((1R,2S)-1-(4-chlorophenyl)-3-((3-fluoro-2-(2-((S)-4-(phenylsulfonyl)-4,7-diazaspiro[2.5]octan-5-yl)ethyl)phenyl)amino)-3-oxo-1-(tetrahydro-2H-pyran-4-yl)propan-2-yl)carbamate;

(2S,3R)-2-amino-3-((2R,4r,6S)-2,6-dimethyltetrahydro-2H-pyran-4-yl)-N-(3-fluoro-2-(2-((2S,6R)-6-methyl-1-(phenylsulfonyl)piperazin-2-yl)ethyl)phenyl)-3-(4-fluorophenyl)propanamide;

(2S,3R)-2-amino-3-((2R,4r,6S)-2,6-dimethyltetrahydro-2H-pyran-4-yl)-N-(3-fluoro-2-(2-((2S,6S)-1-((4-fluorophenyl)sulfonyl)-6-methylpiperazin-2-yl)ethyl)phenyl)-3-(4-fluorophenyl)propanamide;

(2S,3S)-2-amino-N-(2-(2-((S)-1-(benzofuran-2-ylsulfonyl)piperazin-2-yl)ethyl)-3-fluorophenyl)-3-(3,5-difluorophenyl)-3-(4-fluorophenyl)propanamide;

(2S,3S)-2-amino-3-(3,5-difluorophenyl)-N-(3-fluoro-2-(2-((S)-1-((5-methylfuran-2-yl)sulfonyl)piperazin-2-yl)ethyl)phenyl)-3-(4-fluorophenyl)propanamide;

or a pharmaceutically acceptable salt of any of the foregoing compounds.

12. A pharmaceutical composition comprising an effective amount of a compound according to claim 1 or a pharmaceutically acceptable salt thereof, and a pharmaceutically acceptable carrier, and optionally further comprising an effective amount of an anti-HIV agent selected from the group consisting of HIV antiviral agents, immunomodulators, and anti-infective agents.

13. A method for the treatment or prophylaxis of infection by HIV or for the treatment, prophylaxis, or delay in the onset of AIDS in a subject in need thereof, which comprises administering to the subject an effective amount of the compound according to claim 1 or a pharmaceutically acceptable salt thereof.

* * * * *